US009999641B2

(12) United States Patent
Schneider et al.

(10) Patent No.: US 9,999,641 B2
(45) Date of Patent: Jun. 19, 2018

(54) TREATMENT OF CLOSTRIDIUM DIFFICILE INFECTION

(71) Applicant: Vedanta Biosciences, Inc., Cambridge, MA (US)

(72) Inventors: Jessica Schneider, Cambridge, MA (US); Yun-Gi Kim, Watertown, MA (US); Bernat Olle, Cambridge, MA (US); Shilpa Reddy, Watertown, MA (US); Jason Norman, North Weymouth, MA (US); Juan Patarroyo, Lexington, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 0 days. days.

(21) Appl. No.: 15/630,088

(22) Filed: Jun. 22, 2017

(65) Prior Publication Data
US 2017/0354697 A1 Dec. 14, 2017

Related U.S. Application Data

(63) Continuation of application No. PCT/US2017/037498, filed on Jun. 14, 2017.

(60) Provisional application No. 62/349,914, filed on Jun. 14, 2016.

(51) Int. Cl.
| A61K 35/747 | (2015.01) |
| A61K 9/00 | (2006.01) |
| A61K 9/48 | (2006.01) |
| A61K 35/742 | (2015.01) |
| A61K 35/74 | (2015.01) |

(52) U.S. Cl.
CPC .......... *A61K 35/747* (2013.01); *A61K 9/0053* (2013.01); *A61K 9/48* (2013.01); *A61K 35/74* (2013.01); *A61K 35/742* (2013.01)

(58) Field of Classification Search
None
See application file for complete search history.

(56) References Cited

U.S. PATENT DOCUMENTS

| 6,635,260 B1 | 10/2003 | Gerding | |
| 8,460,648 B2 * | 6/2013 | Borody ................ | A61K 35/741 424/184.1 |
| 9,386,793 B2 | 7/2016 | Blaser et al. | |
| 2010/0074872 A1 | 3/2010 | Blaser et al. | |
| 2014/0199281 A1 * | 7/2014 | Henn ..................... | A61K 38/13 424/93.46 |
| 2014/0328803 A1 | 11/2014 | McKenzie et al. | |
| 2014/0341921 A1 * | 11/2014 | Honda .................. | A61K 35/74 424/141.1 |
| 2015/0037476 A1 | 2/2015 | Dhingra et al. | |
| 2015/0079209 A1 | 3/2015 | Kameyama et al. | |
| 2016/0022745 A1 | 1/2016 | Wang | |
| 2016/0022746 A1 | 1/2016 | Lawley et al. | |
| 2016/0040215 A1 | 2/2016 | Henn et al. | |
| 2016/0113971 A1 | 4/2016 | Kaplan et al. | |
| 2016/0228476 A1 | 8/2016 | Cutcliffe et al. | |
| 2017/0143772 A1 | 5/2017 | Mulder et al. | |

FOREIGN PATENT DOCUMENTS

| WO | WO 2002/007741 A1 | 1/2002 |
| WO | WO 2006/050479 A1 | 5/2006 |
| WO | WO 2011/152566 A1 | 12/2011 |
| WO | WO 2013/037067 A1 | 3/2013 |
| WO | WO 2013/037068 A1 | 3/2013 |
| WO | WO 2013/080561 A1 | 6/2013 |
| WO | WO 2013/182038 A1 | 12/2013 |
| WO | WO 2014/082050 A1 | 5/2014 |
| WO | WO 2014/121298 A1 | 8/2014 |
| WO | WO 2014/121301 A1 | 8/2014 |
| WO | WO 2014/121302 A1 | 8/2014 |
| WO | WO 2014/145958 A2 | 9/2014 |
| WO | WO 2014/153194 A2 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/156419 A1 | 10/2015 |
| WO | WO 2015/164555 A1 | 10/2015 |
| WO | WO 2015/179437 A1 | 11/2015 |
| WO | WO 2016/086161 A1 | 6/2016 |
| WO | WO 2016/086205 A2 | 6/2016 |
| WO | WO 2016/086206 A1 | 6/2016 |
| WO | WO 2016/086208 A1 | 6/2016 |
| WO | WO 2016/086209 A1 | 6/2016 |
| WO | WO 2016/086210 A1 | 6/2016 |
| WO | WO 2016/185469 A1 | 11/2016 |
| WO | WO 2016/201053 A1 | 12/2016 |
| WO | WO 2016/203217 A1 | 12/2016 |
| WO | WO 2016/203218 A1 | 12/2016 |

(Continued)

OTHER PUBLICATIONS

Drancourt et al. 2000; 16S Ribosomal DNA Sequence Analysis of a Large Collection of Environmental and Clinical Unidentifiable Bacterial Isolates; Journal of Clinical Microbiology; 38(10): 3623-3630. (Year: 2000).*
Marvola et al. 1999 (Enteric polymers as binders and coating material in multiple-unit site-specific drug delivery systems; European Journal of Pharmaceutical Sciences 7:259-267). (Year: 1999).*
Alang et al., Weight gain after fecal microbiota transplantation. Open Forum Infect Dis. Feb. 4, 2015;2(1):ofv004. doi: 10.1093/ofid/ofv004. eCollection Jan. 2015.
Blaser, The microbiome revolution. J Clin Invest. Oct. 2014;124(10):4162-5. doi: 10.1172/JCI78366. Epub Oct. 1, 2014.
Borody et al., Therapeutic faecal microbiota transplantation: current status and future developments. Curr Opin Gastroenterol.Jan. 2014;30(1):97-105. doi: 10.1097/MOG.0000000000000027.
Buffie et al., Precision microbiome reconstitution restores bile acid mediated resistance to Clostridium difficile. Nature. Jan. 8, 2015;517(7533):205-8. doi: 10.1038/nature13828. Epub Oct. 22, 2014.

(Continued)

*Primary Examiner* — Mary Maille Lyons
(74) *Attorney, Agent, or Firm* — Wolf, Greenfield & Sacks, P.C.

(57) ABSTRACT

Provided herein are compositions and methods for the treatment or prevention of pathogenic infections.

8 Claims, 41 Drawing Sheets

(56) References Cited

FOREIGN PATENT DOCUMENTS

| WO | WO 2016/203220 A1 | 12/2016 |
|---|---|---|
| WO | WO 2016/203221 A1 | 12/2016 |
| WO | WO 2016/203223 A1 | 12/2016 |
| WO | WO 2016/209806 A1 | 12/2016 |
| WO | WO 2017/008026 A1 | 1/2017 |
| WO | WO 2017/035188 A1 | 3/2017 |
| WO | WO 2017/075098 A1 | 5/2017 |
| WO | WO 2017/085518 A1 | 5/2017 |
| WO | WO 2017/085520 A1 | 5/2017 |
| WO | WO 2017/089794 A1 | 6/2017 |
| WO | WO 2017/089795 A1 | 6/2017 |
| WO | WO 2017/091783 A2 | 6/2017 |
| WO | WO 2017/148596 A1 | 9/2017 |

OTHER PUBLICATIONS

Burns et al., Donor Recruitment and Eligibility for Fecal Microbiota Transplantation: Results From an International Public Stool Bank. Gastro. Apr. 2015;148(4):S96-S97.

Calfee, Clostridium difficile: a reemerging pathogen. Geriatrics. Sep. 1, 2008;63(9):10-21.

Cammarota et al., Randomised clinical trial: faecal microbiota transplantation by colonoscopy vs. vancomycin for the treatment of recurrent Clostridium difficile infection. Aliment Pharmacol Ther. May 2015;41(9):835-43. doi: 10.1111/apt.13144. Epub Mar. 1, 2015.

Eyre et al., Whole-genome sequencing demonstrates that fidaxomicin is superior to vancomycin for preventing reinfection and relapse of infection with Clostridium difficile. J Infect Dis. May 1, 2014;209(9):1446-51. doi:10.1093/infdis/jit598. Epub Nov. 11, 2013.

Hooper et al., Interactions between the microbiota and the immune system. Science. Jun. 8, 2012;336(6086):1268-73. doi:10.1126/science.1223490. Epub Jun. 6, 2012.

Hughes et al., Immune activation in irritable bowel syndrome: can neuroimmune interactions explain symptoms? Am J Gastroenterol. Jul. 2013;108(7):1066-74. doi: 10.1038/ajg.2013.120. Epub May 7, 2013.

Kassam et al., Fecal microbiota transplantation for Clostridium difficile infection: systematic review and meta-analysis. Am J Gastroenterol. Apr. 2013;108(4):500-8. doi: 10.1038/ajg.2013.59. Epub Mar. 19, 2013.

Khoruts et al., Emergence of fecal microbiota transplantation as an approach to repair disrupted microbial gut ecology. Immunol Lett. Dec. 2014;162(2 Pt A):77-81. doi: 10.1016/j.imlet.2014.07.016. Epub Aug. 10, 2014.

Leblanc et al., Bacteria as vitamin suppliers to their host: a gut microbiota perspective. Curr Opin Biotechnol. Apr. 2013;24(2):160-8. doi: 10.1016/j.copbio.2012.08.005. Epub Aug. 30, 2012.

Lessa et al., Burden of Clostridium difficile infection in the United States. N Engl J Med. Feb. 26, 2015;372(9):825-34. doi:10.1056/NEJMoa1408913.

Louie et al., Fidaxomicin preserves the intestinal microbiome during and after treatment of Clostridium difficile infection (CDI) and reduces both toxin reexpression and recurrence of CDI. Clin Infect Dis. Aug. 2012;55 Suppl 2:S132-42. doi: 10.1093/cid/cis338.

Miller, Fidaxomicin (OPT-80) for the treatment of Clostridium difficile infection. Expert Opin Pharmacother. Jun. 2010;11(9):1569-78. doi:10.1517/14656566.2010.485614.

Mullane, Fidaxomicin in Clostridium difficile infection: latest evidence and clinical guidance. Ther Adv Chronic Dis. Mar. 2014;5(2):69-84. doi:10.1177/2040622313511285.

Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.

Paramsothy et al., Donor Recruitment for Fecal Microbiota Transplantation. Inflamm Bowel Dis. Jul. 2015;21(7):1600-6. doi: 10.1097/MIB.0000000000000405.

Rossi-Tamisier et al., Cautionary tale of using 16S rRNA gene sequence similarity values in identification of human-associated bacterial species. Int J Syst Evol Microbiol. Jun. 2015;65(Pt 6):1929-34. doi:10.1099/ijs.0.000161. Epub Mar. 3, 2015.

Shannon-Lowe et al., Prevention and medical management of Clostridium difficile infection. BMJ. Mar. 12, 2010;340:c1296. doi:10.1136/bmj.c1296.

Surawicz, Fecal microbiota transplantation: what we know and what we need to know. Ann Intern Med. May 5, 2015;162(9):662-3. doi: 10.7326/M15-0609.

Tannock et al., A new macrocyclic antibiotic, fidaxomicin (OPT-80), causes less alteration to the bowel microbiota of Clostridium difficile-infected patients than does vancomycin. Microbiology. Nov. 2010;156(Pt 11):3354-9. doi: 10.1099/mic.0.042010-0. Epub Aug. 19, 2010.

Van Nood et al., Duodenal infusion of donor feces for recurrent Clostridium difficile. N. Engl J Med. Jan. 31, 2013;368(5):407-15. doi: 10.1056/NEJMoa1205037. Epub Jan. 16, 2013.

Youngster et al., Fecal microbiota transplant for relapsing Clostridium difficile infection using a frozen inoculum from unrelated donors: a randomized, open-label, controlled pilot study. Clin Infect Dis. Jun. 2014;58(11):1515-22. doi: 10.1093/cid/ciu135. Epub Apr. 23, 2014.

Genbank Accession No. NR_104687.1. NCBI. Sakamoto. Feb. 3, 2015.

* cited by examiner

Figure 1

| Composition A | Composition B | Composition C | Composition D |
|---|---|---|---|
| SEQ_03 - 5 - Clostridium_hathewayi (XIVa)* | SEQ_10 - 211 - Flavonifractor_plautii (IV) | SEQ_12 - VE202-26 - Clostridium_scindens (XIVa)* | SEQ_12 - VE202-26 - Clostridium_scindens (XIVa)* |
| SEQ_04 - 7 - Blautia_hansenii (XIVa)* | SEQ_14 - VE202-13 - Anaerotruncus_colihominis (IV) | SEQ_03 - 5 - Clostridium_hathewayi (XIVa)* | SEQ_03 - 5 - Clostridium_hathewayi (XIVa)* |
| SEQ_05 - 10 - Blautia_hansenii (XIVa)* | SEQ_15 - VE202-14 - Eubacterium_fissicatena (XIVa) | SEQ_05 - 10 - Blautia_hansenii (XIVa)* | SEQ_05 - 10 - Blautia_hansenii (XIVa)* |
| SEQ_07 - 59 - Blautia_producta / Blautia_coccoides (XIVa) | SEQ_16 - VE202-16 - Clostridium_symbiosum (XIVa) | SEQ_01 - 71 - Blautia_wexlerae (XIVa)* | SEQ_01 - 71 - Blautia_wexlerae (XIVa)* |
| SEQ_08 - 79 - Blautia_hansenii (XIVa)* | SEQ_17 - VE202-7 - Clostridium_bolteae (XIVa) | SEQ_07 - 59 - Blautia_producta/Blautia_coccoides (XIVa)* | SEQ_14 - VE202-13 - Anaerotruncus_colihominis (IV) |
| SEQ_09 - VE202-21 - Eubacterium_contortum / Eubacterium_fissicatena (XIVa)* | SEQ_20 – 170 – Dorea longicatena (XIVa) | SEQ_18 - 148 - Dorea_longicatena (XIVa) | SEQ_18 - 148 - Dorea_longicatena (XIVa) |
| SEQ_11 - VE202-9 - Anaerostipes_caccae (XIVa)* | SEQ_19 - 16 - Blautia_producta (XIVa) | SEQ_21 - 189 - Clostridium_innocuum (XVII) | SEQ_21 - 189 - Clostridium_innocuum (XVII) |
| SEQ_12 - VE202-26 - Clostridium_scindens (XIVa)* | SEQ_21 - 189 - Clostridium_innocuum (XVII) | SEQ_10 - 211 - Flavonifractor_plautii (IV) / | SEQ_10 - 211 - Flavonifractor_plautii (IV) / |
| SEQ_13 - 136 - Marvinbryantia_formatexigens (XIVa)* | | SEQ_14 - VE202-13 - Anaerotruncus_colihominis (IV) | SEQ_02 - 102 - Turicibacter_sanguinis (non-Clostridium) |
| SEQ_23 - VE202-29 - Eisenbergiella_tayi (XIVa)* | | SEQ_16 - VE202-16 - Clostridium_symbiosum (XIVa) | SEQ_06 - 40 - Lactobacillus_mucosae (non-Clostridium) |

*bolding indicates strains other than Clostridium cluster XIVa*

* = BaiCD+

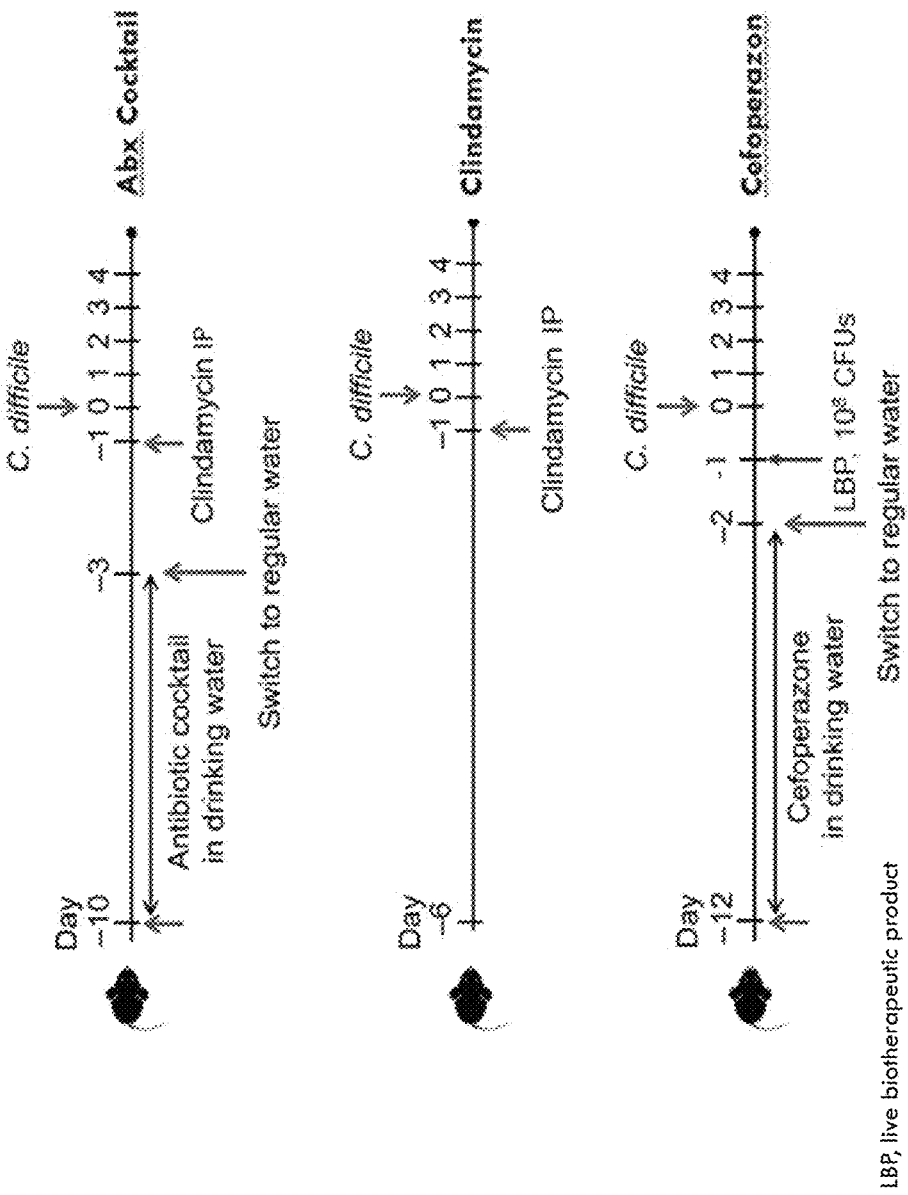

Figure 3

| Groups | # of animals | Abx | C. difficile Spores |
|---|---|---|---|
| (1) Control | 5 | - | $10^1$ |
| (2) Control | 5 | - | $10^4$ |
| (3) Abx cocktail | 5 | + | $10^1$ |
| (4) Abx cocktail | 5 | + | $10^4$ |
| (5) Clindamycin | 5 | + | $10^1$ |
| (6) Clindamycin | 5 | + | $10^4$ |
| (7) Cefoperazone | 5 | + | $10^1$ |
| (8) Cefoperazone | 5 | + | $10^4$ |

Figure 5

| Groups | # of animals | Abx | CFUs (Spores) |
|---|---|---|---|
| (1) Control- | 5 | - | $10^4$ |
| (2) Control+ | 5 | + | $10^4$ |
| (3) Van | 5 | + | $10^4$ |
| (4) Composition E | 5 | + | $10^4$ |
| (5) Composition I | 5 | + | $10^4$ |
| (6) Composition A | 5 | + | $10^4$ |
| (7) Composition B | 5 | + | $10^4$ |
| (8) Composition C | 5 | + | $10^4$ |
| (9) Composition D | 5 | + | $10^4$ |

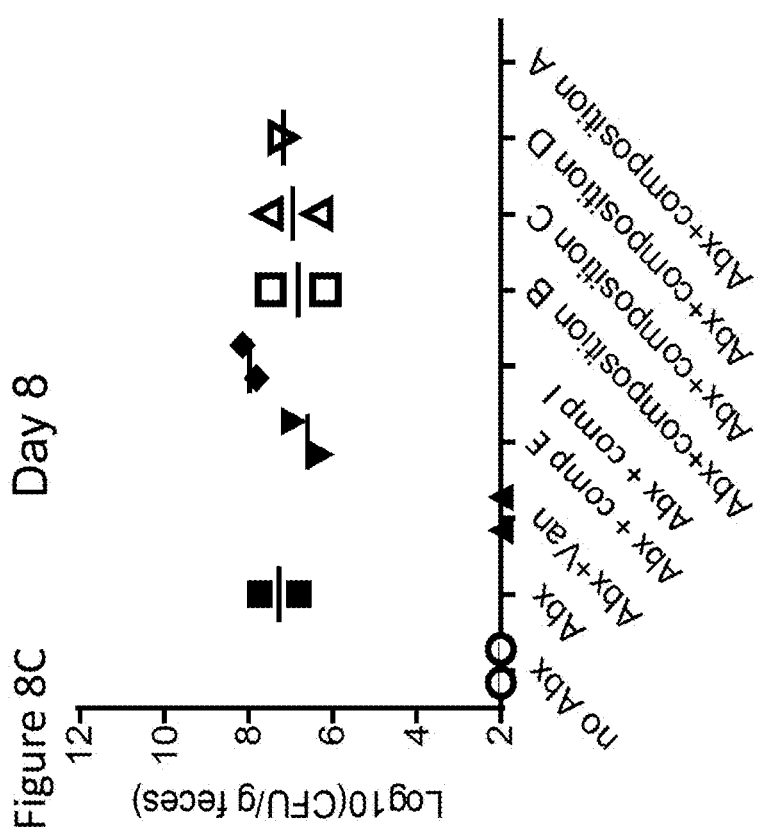

Figure 9

| Groups | # of animals | Abx | C. difficile spore | CFUs LBPs |
|---|---|---|---|---|
| (1) Control | 7 | + | $10^4$ | - |
| (2) Composition B | 8 | + | $10^4$ | $10^8$/mouse |

Figure 13

Composition F

| SEQ_NO | StrainID | Genus_species | SEQ_NO | StrainID | Genus_species |
|---|---|---|---|---|---|
| SEQ_24 | YK96 | Dorea_longicatena | SEQ_52 | YK51 | Eubacterium_rectale |
| SEQ_25 | YK101 | Ruminococcus_obeum | SEQ_53 | YK52 | Eubacterium_rectale |
| SEQ_26 | YK110 | Megasphaera_elsdenii | SEQ_54 | YK54 | Anaerostipes_hadrus |
| SEQ_27 | YK149 | Acidaminococcus_fermentans / Acidaminococcus_intestini | SEQ_55 | YK56 | Ruminococcus_faecis |
| SEQ_28 | YK154 | Megasphaera_elsdenii | SEQ_56 | YK57 | Ruminococcus_faecis |
| SEQ_29 | YK36 | Ruminococcus_faecis | SEQ_57 | YK58 | Dorea_longicatena |
| SEQ_30 | YK95 | Bacteroides_cellulosilyticus | SEQ_58 | YK65 | Roseburia_faecis |
| SEQ_31 | YK32 | Anaerostipes_hadrus | SEQ_59 | YK67 | Blautia_luti |
| SEQ_32 | YK64 | Ruminococcus_obeum | SEQ_60 | YK69 | Fusicatenibacter_saccharivorans |
| SEQ_33 | YK73 | Flavonifractor_plautii | SEQ_61 | YK70 | Fusicatenibacter_saccharivorans |
| SEQ_34 | YK87 | Eubacterium_rectale | SEQ_62 | YK71 | Roseburia_faecis |
| SEQ_35 | YK105 | Flavonifractor_plautii | SEQ_63 | YK74 | Megasphaera_elsdenii |
| SEQ_36 | YK153 | Megasphaera_elsdenii | SEQ_64 | YK88 | Eubacterium_rectale |
| SEQ_37 | YK163 | Eubacterium_rectale | SEQ_65 | YK89 | Eubacterium_rectale |
| SEQ_38 | YK191 | Ruminococcus_albus | SEQ_66 | YK97 | Roseburia_faecis |
| SEQ_39 | YK99 | Ruminococcus_champanellensis | SEQ_67 | YK98 | Blautia_faecis |
| SEQ_40 | YK55 | Ruminococcus_faecis | SEQ_68 | YK139 | Fusicatenibacter_saccharivorans |
| SEQ_41 | YK75 | Bifidobacterium_bifidum | SEQ_69 | YK141 | Dorea_formicigenerans |
| SEQ_42 | YK90 | Anaerostipes_hadrus | SEQ_70 | YK142 | Ruminococcus_faecis |
| SEQ_43 | YK30 | Anaerostipes_hadrus | SEQ_71 | YK152 | Blautia_hansenii |
| SEQ_44 | YK31 | Anaerostipes_hadrus | SEQ_72 | YK155 | Blautia_hansenii |
| SEQ_45 | YK12 | Eubacterium_rectale | SEQ_73 | YK157 | Eubacterium_rectale |
| SEQ_46 | YK27 | Ruminococcus_faecis | SEQ_74 | YK160 | Roseburia_faecis |
| SEQ_47 | YK28 | Blautia_luti | SEQ_75 | YK166 | Eubacterium_rectale |
| SEQ_48 | YK29 | Ruminococcus_faecis | SEQ_76 | YK168 | Eubacterium_rectale |
| SEQ_49 | YK33 | Anaerostipes_hadrus | SEQ_77 | YK169 | Eubacterium_rectale |
| SEQ_50 | YK34 | Anaerostipes_hadrus | SEQ_78 | YK171 | Eubacterium_rectale |
| SEQ_51 | YK35 | Ruminococcus_faecis | SEQ_79 | YK192 | Roseburia_faecis |

Figure 14

| Cluster | Composition F | SCFAs |
|---|---|---|
| XIVa | Eubacterium rectale 12 | A, B, L |
| | Ruminococcus faecis 8 | A, L |
| | Ruminococcus obeum 2 | A, L |
| | Blautia faecis 1 | A, L |
| | Blautia hansenii 2 | A, L |
| | Blautia luti 2 | A, L |
| | Anaerostipes hadrus 7 | B |
| | Roseburia faecis 5 | A, B |
| | Fusicatenibacter saccharivorans 3 | A, L |
| | Dorea formicigenerans 1 | A |
| | Dorea longicatena 2 | A |
| IV | Flavonifractor plautii 2 | A, B |
| | Ruminococcus champanellensis 2 | A |
| IX | Acidaminococcus fermentans 1 | A, B, P |
| | Megasphaera elsdeni 4 | P |
| other | Bacteroides cellulosilyticus 1 | A, S |
| | Bifiidobacterium Bifidum | L, A |

A, acetate;
B, Butyrate;
L, lactate;
P, propionate;
S, succinate

Figure 15

| Groups | # of animals | Abx | C. difficile spore | CFUs LBPs |
|---|---|---|---|---|
| (1) Control | 10 | + | $10^4$ | - |
| (2) Composition B dosed at day -1 | 10 | + | $10^4$ | $10^8$/mouse |
| (3) Composition B dosed at day -2 and -1 | 10 | + | $10^4$ | $10^8$/mouse |
| (4) Composition B dosed at day -2, -1, 1, 2, and 3 | 10 | + | $10^4$ | $10^8$/mouse |
| (5) Composition F dosed at day -1 | 5 | + | $10^4$ | OD Normalized |
| (6) Composition F dosed at day -2, -1, 1, 2, and 3 | 5 | + | $10^4$ | OD Normalized |
| (7) FMT mouse | 5 | + | $10^4$ | 200ul of 10% fecal samples/mouse |
| (8) FMT human | 5 | + | $10^4$ | 200ul of 10% fecal samples/mouse |

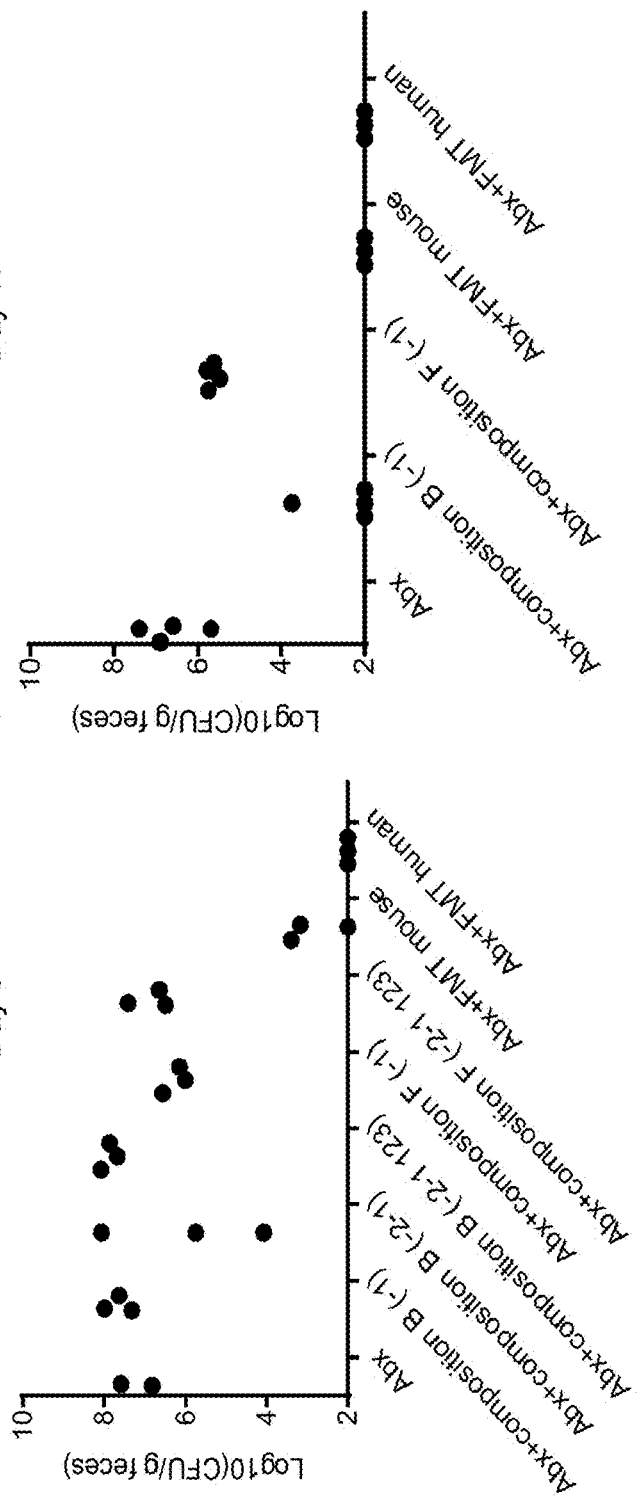

Figure 19

Composition G

| | | |
|---|---|---|
| SEQ_27 | YK149 | Acidaminococcus_fermentans/Acidaminococcus_intesti |
| SEQ_43 | YK90 | Anaerostipes_hadrus |
| SEQ_44 | YK30 | Anaerostipes_hadrus |
| SEQ_51 | YK34 | Anaerostipes_hadrus |
| SEQ_55 | YK54 | Anaerostipes_hadrus |
| SEQ_68 | YK98 | Blautia_faecis |
| SEQ_72 | YK152 | Blautia_hansenii |
| SEQ_70 | YK141 | Dorea_formicigenerans |
| SEQ_24 | YK96 | Dorea_longicatena |
| SEQ_34 | YK87 | Eubacterium_rectale |
| SEQ_37 | YK163 | Eubacterium_rectale |
| SEQ_46 | YK12 | Eubacterium_rectale |
| SEQ_76 | YK166 | Eubacterium_rectale |
| SEQ_77 | YK168 | Eubacterium_rectale |
| SEQ_35 | YK105 | Flavonifractor_plautii |
| SEQ_62 | YK70 | Fusicatenibacter_saccharivorans |
| SEQ_26 | YK110 | Megasphaera_elsdenii |
| SEQ_63 | YK71 | Roseburia_faecis |
| SEQ_67 | YK97 | Roseburia_faecis |
| SEQ_40 | YK99 | Ruminococcus_champanellensis |
| SEQ_38 | YK191 | Ruminococcus_champanellensis/Ruminococcus_albus |
| SEQ_47 | YK27 | Ruminococcus_faecis |
| SEQ_56 | YK56 | Ruminococcus_faecis |
| SEQ_25 | YK101 | Ruminococcus_obeum |
| SEQ_32 | YK64 | Ruminococcus_obeum |

Figure 20

| Groups | N | Abx | CFUs *C. difficile* | CFUs LBPs |
|---|---|---|---|---|
| (1) Vehicle | 7 | + | $10^4$ | 200ul of PBS |
| (2) Composition B | 8 | + | $10^4$ | $10^8$/mouse |
| (3) Composition B1 | 8 | + | $10^4$ | $10^8$/mouse |
| (4) Composition B2 | 8 | + | $10^4$ | $10^8$/mouse |
| (5) Composition F | 7 | + | $10^4$ | OD Normalized |
| (6) Composition G | 7 | + | $10^4$ | OD Normalized |
| (7) EtOH treated Human fecal samples | 5 | + | $10^4$ | 200ul of 10% fecal samples/mouse |
| (8) EtOH treated Composition B | 5 | + | $10^4$ | $10^8$/mouse |
| (9) Frozen Composition B | 5 | + | $10^4$ | $10^8$/mouse |
| (10) EtOH treated Composition J | 5 | + | $10^4$ | colony scrapes |

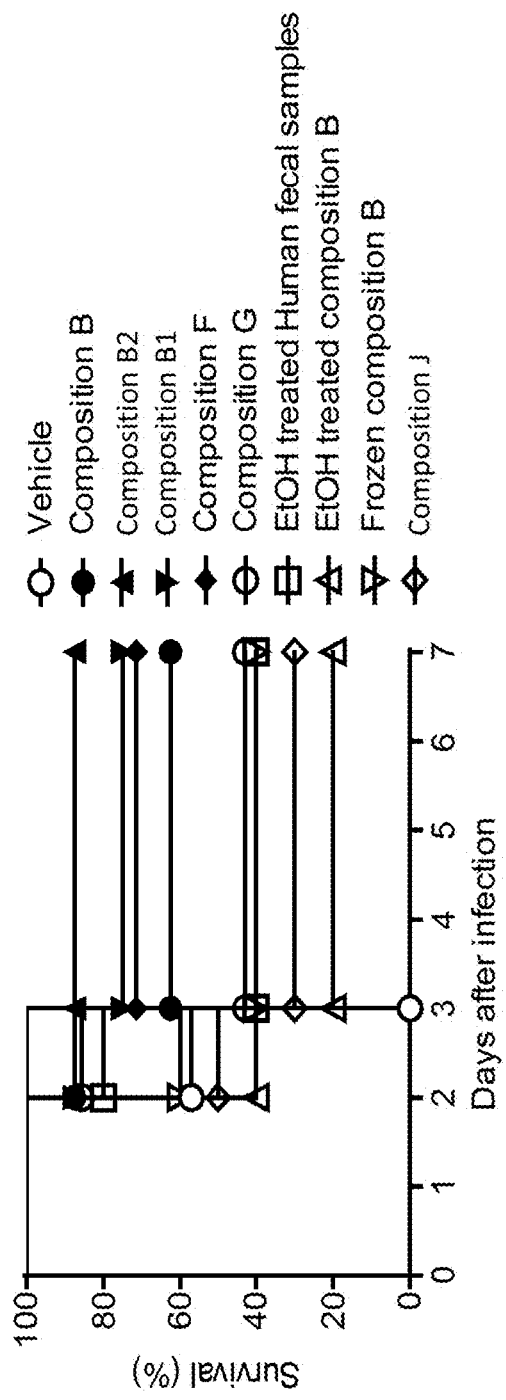

Figure 25

| Groups | N | Abx | CFUs C. difficile | CFUs LBPs |
|---|---|---|---|---|
| (1) Vehicle | 10 | + | $10^4$ | 200ul of PBS |
| (2) human FMT | 10 | + | $10^4$ | 200ul of 10% fecal samples/mouse |
| (3) Composition B | 10 | + | $10^4$ | $10^8$/mouse |
| (4) Composition B + 4 spores* | 10 | + | $10^4$ | $10^8$ live bacteria+spores/mouse |
| (5) Composition H** | 10 | + | $10^4$ | $10^8$/mouse |

*Composition B + 4 spores = The strains of Composition B plus the following four strains in spore form: *Clostrodium bolteae, Anaerotruncus colihominis, Clostridium symbiosum,* and *Clostridium innocuum*

**Composition H contains the following six strains in spore form: *Clostrodium bolteae, Anaerotruncus colihominis, Clostridium symbiosum, Clostridium innocuum, Clostridium disporicum,* and *Erysipelatoclostridium ramosum*

Figure 26
Composition H

**Composition H = The following six strains in spore form Clostridium bolteae, Anaerotru

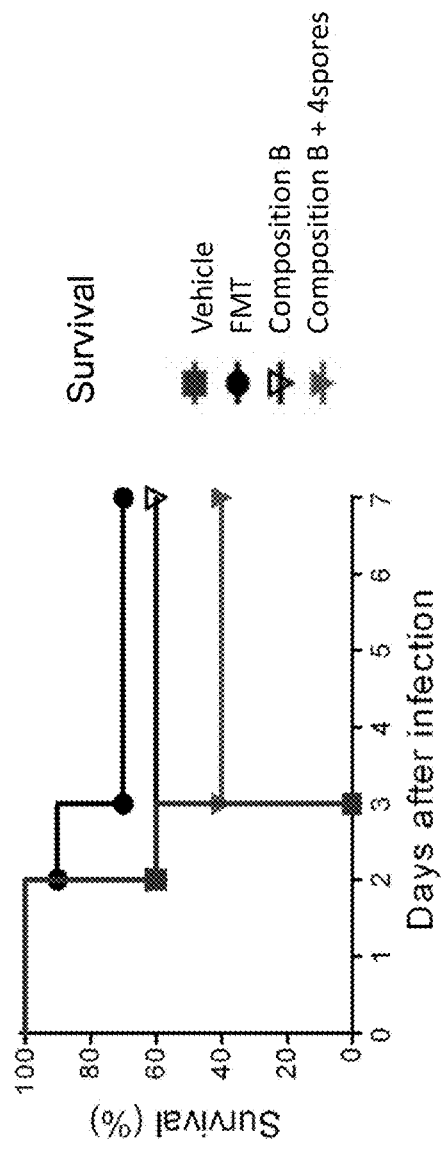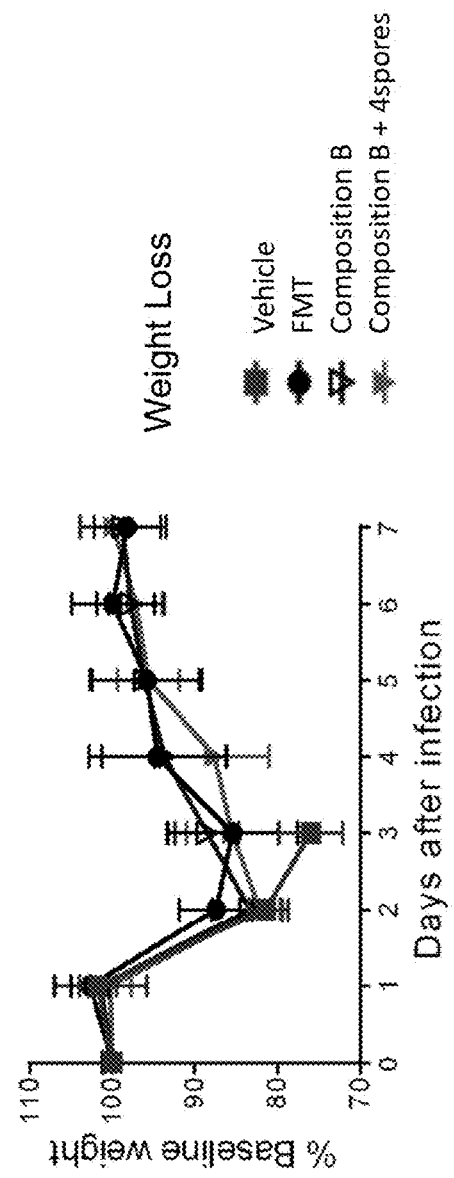
Figure 27A
Figure 27B

SEQUENCE LISTING

```
<160> NUMBER OF SEQ ID NOS: 159

<210> SEQ ID NO 1
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 1
gcccggagca gttgatgtga aggatgggtc acctgtggac tgcattggaa ctgtcatact    60
tgagtgccgg agggtaagcg gaattcctag tgtagcggtg aaatgcgtag atattaggag   120
gaacaccagt ggcgaaggcg gcttactgga cggtaactga cgttgaggct cgaaagcgtg   180
gggagcaaac aggattagat accctggtaa                                     210

<210> SEQ ID NO 2
<211> LENGTH: 184
<212> TYPE: DNA
<213> ORGANISM: Artificial Sequence
<220> FEATURE:
<223> OTHER INFORMATION: Synthetic Polynucleotide

<400> SEQUENCE: 2
ctaaccgtgg aggtcattgg aaactggtca acttgagtgc agaagaggga agtggaattc    60
catgtgtagc ggtgaaatgc gtagagatat ggaggaacac cagtggcgaa ggcggcttcc   120
tggtctgtaa ctgacactga ggcgcgaaag cgtgggggc aaacaggatt agatcccccg    180
gtaa                                                                184

<210> SEQ ID NO 3
<211> LENGTH: 196
<212> TYPE: DNA
<213> ORGANISM: Artificial Sequence
<220> FEATURE:
```

<223> OTHER INFORMATION: Synthetic Polynucleotide

<400> SEQUENCE: 3

```
atgaaagccg gggctcaacc ccggtactgc tttggaaact gtttgacttg agtgcttgag      60
aggtaagtgg aattcctagt gtagcgggaa atgtttagat attaggagga caccagtggc     120
gaaggcggct tactggactg taactgacgt tgtggctcga tttgtgggga gcaaacagga     180
ttatatcccc tggtaa                                                     196
```

<210> SEQ ID NO 4
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 4

```
cggaaggtct gatgtgaagg ttggggctta ccccggactg cattggaaac tgtttttcta      60
gagtgcccga gaggtaagcg gaattcctag tgtagcggtg aaatgcttta gatattagga     120
ggaacaccag tggcgaaggc ggcttactgg acggtaactg acgttgaggc tcgaaagcgt     180
ggggagcaaa caggattaga taccctggta a                                    211
```

<210> SEQ ID NO 5
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 5

```
cgatgtctga gtgaaggctg gggcttaccc caggactgca ttggaactgt ttttctagag      60
tgccggagag gtaagcggaa ttcctagtgt agcggtgaaa tgcgtagata ttaggaggaa     120
caccagtggc gaaggcggct tactggacgg taactgacgt tgaggctcga aagcgtgggg     180
agcaaacagg attagatacc ctggtaa                                         207
```

<210> SEQ ID NO 6
<211> LENGTH: 179
<212> TYPE: DNA
<213> ORGANISM: Artificial Sequence
<220> FEATURE:
<223> OTHER INFORMATION: Synthetic Polynucleotide

<400> SEQUENCE: 6

```
ttaaccaaga agtgcattgg aactgtcaga cttgggggaa aaaagacag tgcaactcca       60
tgtgtagcgg tggaatgctc catatatatg gaagaacacc agtggcgaag gcggctgtct     120
ggtctgcaac tgacgctgag gctcgaattc atgggtaaga agtattagt cccttgtaa       179
```

<210> SEQ ID NO 7
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 7

```
acccgcttgg tctgaggtga ggctggggct taaccccagg actgcattgg aaactgttgt      60
tctagagtgc cggagaggta agcggaattc ctagtgtagc ggtgaaatgc gtagatatta     120
ggaggaacac cagtggcgaa ggcggcttac tggacggtaa ctgacgttga ggctcgaaag     180
```

```
cgtggggagc aaacaggatt agataccctg gtaa                          214
```

<210> SEQ ID NO 8
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 8

```
taggctgggg cttaacccca ggactgcatt ggaaactgtt tttctagagt gccggagagg    60
taagcggaat tcctagtgta gcggtgaaat gcgtagatat taggaggaac accagtggcg   120
aaggcggctt actggacggt aactgacgtt gaggctcgaa agcgtgggga gcaaacagga   180
ttagataccc tggtaa                                                  196
```

<210> SEQ ID NO 9
<211> LENGTH: 297
<212> TYPE: DNA
<213> ORGANISM: Artificial Sequence
<220> FEATURE:
<223> OTHER INFORMATION: Synthetic Polynucleotide

<400> SEQUENCE: 9

```
ttgcattgga cactatgtca gctgagtgtc ggagaggtaa gtggaattcc tagtgtagcg    60
gtgaaatgcg tagatattag gaggaacacc agtggcgaag gcggcttact gcacgttttc   120
tgacgttgag gctcgaaatc gtggggagca aacaaaaata gatccctgg tagtccacgc    180 cgtaaacgat gcatactagg tgtcgggtgg caaagccatt cggtgccgca gcaaacgcaa   240
taagtatgcc acctggggag tacgttcgca agaatgaaac tcaaataaat tgacgga      297
```

<210> SEQ ID NO 10
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 10

```
cccgtcgtag atgtgaactg ggggctcacc tccagcctgc atttgaaact gtagttcttg    60
agtgctggag aggcaatcgg aattccgtgt gtagcggtga aatgcgtaga tatacggagg   120
aacaccagtg gcgaaggcgg attgctggac agtaactgac gctgaggcgc gaaagcgtgg   180
ggagcaaaca ggattagata ccctcataa                                    209
```

<210> SEQ ID NO 11
<211> LENGTH: 401
<212> TYPE: DNA
<213> ORGANISM: Artificial Sequence
<220> FEATURE:
<223> OTHER INFORMATION: Synthetic Polynucleotide

<400> SEQUENCE: 11

```
acctgatgca gcgacgccgc gtgagtgaag aagtatttcg gtatgtaaag ctctatcagc    60
agggaagaaa aaagacggta cctgactaag aagccccggc taactacgtg ccagcagccg   120
cggtaatacg tagggggcaa gcgttatccg gaattactgg gtgtaaaggg tgcgtaggtg   180
gcatggtaag tcagaagtga aagcccgggg cttaaccccg gactgctttt gaaactgtc    240 atgctggagt gcaggagagg taagcggaat tcctagtgta gcggtgaaat gcgtagatat   300
```

```
taggaggaac accagtggcg aaggcggctt actggactgt cactgacact gatgcacgaa    360
agcgtgggga gcaaacagga ttagataccc tggaagtcca t                        401
```

```
<210> SEQ ID NO 12
<211> LENGTH: 355
<212> TYPE: DNA
<213> ORGANISM: Artificial Sequence
<220> FEATURE:
<223> OTHER INFORMATION: Synthetic Polynucleotide

<400> SEQUENCE: 12
atgggagcgt agatggcgac tgggccatat gtgacagccc tggtctcaac cccttaactg     60
catttggaac tgagtggctg gagtgtcgga gaggcaggcg gaattcctag tgtagcggtg    120
aaatgcgtag atattaggag gaacaccagt ggcgaaggcg gcctgctgga cgatgactga    180
cgttgaggct cgaaagcgtg gggagcaaac aggattagat accctggtag tccacgccgt    240
aaacgatgac tactaggtgt cgggtggcaa ggacattcgg tgccgcagca aacgcaataa    300
gtagtccacc tggggagtac gttcgcaaga atgaaactca aaggaaattg acgga         355
```

```
<210> SEQ ID NO 13
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 13
cgcagcggag tgtatcctag gctcacctgg ctgctttcga actggttttc tagatcgtgt     60 agaggggag attcctggtg tagcgtgaaa tgcgtagata tctggaggaa caccagtggc    120
gaaggcggcc tcctggacgg caactgacgt tgaggctcga agtgtgggg agcaaacagg    180 attagatacc ctggtaa                                                   197
```

```
<210> SEQ ID NO 14
<211> LENGTH: 1522
<212> TYPE: DNA
<213> ORGANISM: Artificial Sequence
<220> FEATURE:
<223> OTHER INFORMATION: Synthetic Polynucleotide

<400> SEQUENCE: 14
tcaaagagtt tgatcctggc tcaggacgaa cgctggcggc gcgcctaaca catgcaagtc     60
gaacggagct tacgttttga agttttcgga tggacgaatg taagcttagt ggcggacggg    120
tgagtaacac gtgagcaacc tgcctttcag aggggggataa cagccggaaa cggctgctaa    180
taccgcatga tgttgcgggg gcacatgccc ctgcaaccaa aggagcaatc cgctgaaaga    240
tgggctcgcg tccgattagc cagttggcgg ggtaacggcc caccaaagcg acgatcggta    300
gccggactga gaggttgaac ggccacattg ggactgagac acggcccaga ctcctacggg    360
aggcagcagt gggggatatt gcacaatggg cgaaagcctg atgcagcgac gccgcgtgag    420
ggaagacggt cttcggattg taaacctctg tctttgggga agaaaatgac ggtacccaaa    480
gaggaagctc cggctaacta cgtgccagca gccgcggtaa tacgtaggga gcaagcgttg    540
tccggaatta ctgggtgtaa agggagcgta ggcgggatgg caagtagaat gttaaatcca    600
tcggctcaac cggtggctgc gttctaaact gccgttcttg agtgaagtag aggcaggcgg    660
aattcctagt gtagcggtga aatgcgtaga tattaggagg aacaccagtg gcgaaggcgg    720
cctgctgggc tttaactgac gctgaggctc gaaagcgtgg ggagcaaaca ggattagata    780
```

```
cctggtagt ccacgccgta aacgatgatt actaggtgtg gggggactga ccccttccgt    840
gccgcagtta acacaataag taatccacct ggggagtacg gccgcaaggt tgaaactcaa    900
aggaattgac gggggcccgc acaagcagtg gagtatgtgg tttaattcga agcaacgcga    960
agaaccttac caggtcttga catcggatgc atagcctaga gataggtgaa gcccttcggg   1020
gcatccagac aggtggtgca tggttgtcgt cagctcgtgt cgtgagatgt tgggttaagt   1080
cccgcaacga gcgcaacccet tattattagt tgctacgcaa gagcactcta atgagactgc   1140
cgttgacaaa acggaggaag gtggggatga cgtcaaatca tcatgcccct tatgacctgg   1200
gctacacacg tactacaatg gcactaaaac agagggcggc gacaccgcga ggtgaagcga   1260
atcccgaaaa agtgtctcag ttcagattgc aggctgcaac ccgcctgcat gaagtcggaa   1320
ttgctagtaa tcgcggatca gcatgccgcg gtgaatacgt tcccgggcct tgtacacacc   1380
gcccgtcaca ccatgggagt cggtaacacc cgaagccagt agcctaaccg caaggggggc   1440
gctgtcgaag gtgggattga tgactggggt gaagtcgtaa caaggtagcc gtatcggaag   1500
gtgcggctgg atcacctcct tt                                            1522
```

<210> SEQ ID NO 15
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 15

```
tacgagagtt tgatcctggc tcaggatgaa cgctggcggc gtgcctaaca catgcaagtc     60
gagcgaagcg ctgttttcag aatcttcgga ggaagaggac agtgactgag cggcggacgg    120
gtgagtaacg cgtgggcaac ctgcctcata caggggdata acagttagaa atgactgcta    180
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga    360
ggcagcagtg gggaatattg cacaatgggg gaaaccctga tgcagcgacg ccgcgtgaag    420
gaagaagtat ttcggtatgt aaacttctat cagcagggaa gaagatgacg gtacctgagt    480
aagaagcacc ggctaaatac gtgccagcag ccgcggtaat acgtatggtg caagcgttat    540
ccggatttac tgggtgtaaa gggagcgtag acggataggc aagtctggag tgaaaaccca    600
gggctcaacc ctgggactgc tttggaaact gcagatctgg agtgccggag aggtaagcgg    660
aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcatccgaga caggtggtgc atggttgtcg tcagctcgtg tcgtgagatg ttgggttaag   1080
tcccgcaacg agcgcaaccc ttatcttcag tagccagcat ataaggtggg cactctggag   1140
agactgccag ggagaacctg gaggaaggtg gggatgacgt caaatcatca tgccccttat   1200
ggccagggct acacacgtgc tacaatggcg taaacaaagg gaagcgagag ggtgacctgg   1260
```

```
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc caaccttaga   1440
ggagggagct gtcgaaggcg ggacggataa ctggggtgaa gtcgtaacaa ggtagccgta   1500
tcggaaggtg cggctggatc acctcctttt                                    1529
```

<210> SEQ ID NO 16
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 16

```
atgagagttt gatcctggct caggatgaac gctggcggcg tgcctaacac atgcaagtcg    60
aacgaagcga tttaacggaa gttttcggat ggaagttgaa ttgactgagt ggcggacggg   120
tgagtaacgc gtgggtaacc tgccttgtac tggggggacaa cagttagaaa tgactgctaa   180
taccgcataa gcgcacagta tcgcatgata cagtgtgaaa aactccggtg gtacaagatg   240
gacccgcgtc tgattagcta gttggtaagg taacggctta ccaaggcgac gatcagtagc   300
cgacctgaga gggtgaccgg ccacattggg actgagacac ggcccaaact cctacgggag   360
gcagcagtgg ggaatattgc acaatgggcg aaagcctgat gcagcgacgc cgcgtgagtg   420
aagaagtatt tcggtatgta aagctctatc agcagggaag aaaatgacgg tacctgacta   480 agaagcccg gctaactacg tgccagcagc cgcggtaata cgtagggggc aagcgttatc   540
cggatttact gggtgtaaag ggagcgtaga cggtaaagca agtctgaagt gaaagcccgc   600
ggctcaactg cgggactgct ttggaaactg tttaactgga gtgtcggaga ggtaagtgga   660
attcctagtg tagcggtgaa atgcgtagat attaggagga acaccagtgg cgaaggcgac   720
ttactggacg ataactgacg ttgaggctcg aaagcgtggg gagcaaacag gattagatac   780
cctggtagtc cacgccgtaa acgatgaata ctaggtgttg gggagcaaag ctcttcggtg   840
ccgtcgcaaa gcagtaagt attccacctg gggagtacgt tcgcaagaat gaaactcaaa   900
ggaattgacg gggacccgca caagcggtgg agcatgtggt ttaattcgaa gcaacgcgaa   960
gaaccttacc aggtcttgac atcgatccga cggggagta acgtcccctt cccttcgggg  1020
cggagaagac aggtggtgca tggttgtcgt cagctcgtgt cgtgagatgt tgggttaagt  1080
cccgcaacga gcgcaaccct tattctaagt agccagcggt tcggccggga actcttggga  1140
gactgccagg gataacctgg aggaaggtgg ggatgacgtc aaatcatcat gccccttatg  1200
atctgggcta cacacgtgct acaatggcgt aaacaaagag aagcaagacc gcgaggtgga  1260
gcaaatctca aaaataacgt ctcagttcgg actgcaggct gcaactcgcc tgcacgaagc  1320
tggaatcgct agtaatcgcg aatcagaatg tcgcggtgaa tacgttcccg gtcttgtac   1380 acaccgcccg tcacaccatg ggagtcagta acgcccgaag tcagtgaccc aaccgcaagg  1440
agggagctgc cgaaggcggg accgataact ggggtgaagt cgtaacaagg tagccgtatc  1500
ggaaggtgcg gctggatcac ctccttt                                     1527
```

<210> SEQ ID NO 17
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 17

```
atgagagttt gatcctggct caggatgaac gctggcggcg tgcctaacac atgcaagtcg      60
aacgaagcaa ttaaaatgaa gttttcggat ggattttga ttgactgagt ggcggacggg      120
tgagtaacgc gtggataacc tgcctcacac tggggataa cagttagaaa tgactgctaa     180
taccgcataa gcgcacagta ccgcatggta cggtgtgaaa aactccggtg gtgtgagatg     240
gatccgcgtc tgattagcca gttggcgggg taacggccca ccaaagcgac gatcagtagc     300
cgacctgaga gggtgaccgg ccacattggg actgagacac ggcccaaact cctacgggag     360
gcagcagtgg ggaatattgc acaatgggcg aaagcctgat gcagcgacgc cgcgtgagtg     420
aagaagtatt tcggtatgta aagctctatc agcagggaag aaaatgacgg tacctgacta     480
agaagcccg gctaactacg tgccagcagc cgcggtaata cgtaggggc aagcgttatc      540
cggatttact gggtgtaaag ggagcgtaga cggcgaagca agtctgaagt gaaaacccag     600
ggctcaaccc tgggactgct ttggaaactg ttttgctaga gtgtcggaga ggtaagtgga     660
attcctagtg tagcggtgaa atgcgtagat attaggagga acaccagtgg cgaaggcggc     720
ttactggacg ataactgacg ttgaggctcg aaagcgtggg gagcaaacag gattagatac     780
cctggtagtc cacgccgtaa acgatgaatg ctaggtgttg gggggcaaag cccttcggtg     840
ccgtcgcaaa gcagtaagc attccacctg gggagtacgt tcgcaagaat gaaactcaaa     900
ggaattgacg gggacccgca caagcggtgg agcatgtggt ttaattcgaa gcaacgcgaa     960
gaaccttacc aagtcttgac atcctcttga ccggcgtgta acggcgcctt cccttcgggg    1020
caagagagac aggtggtgca tggttgtcgt cagctcgtgt cgtgagatgt tgggttaagt    1080
cccgcaacga gcgcaaccct tatccttagt agccagcagg taaagctggg cactctaggg    1140
agactgccag ggataacctg gaggaaggtg gggatgacgt caaatcatca tgcccttat    1200
gatttgggct acacacgtgc tacaatggcg taaacaagg gaagcaagac agtgatgtgg    1260
agcaaatccc aaaaataacg tcccagttcg gactgtagtc tgcaacccga ctacacgaag    1320
ctggaatcgc tagtaatcgc gaatcagaat gtcgcggtga atacgttccc gggtcttgta    1380
cacaccgccc gtcacaccat gggagtcagc aacgcccgaa gtcagtgacc caactcgcaa    1440
gagagggagc tgccgaaggc ggggcaggta actggggtga agtcgtaaca aggtagccgt    1500
atcggaaggt gcggctggat cacctccttt                                     1530
```

<210> SEQ ID NO 18
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 18

```
aacgagagtt tgatcctggc tcaggatgaa cgctggcggc gtgcttaaca catgcaagtc      60
gagcgaagca ctttggaaga ttcttcggat gaagactttt gtgactgagc ggcggacggg    120
tgagtaacgc gtgggtaacc tgcctcatac aggggataa cagttagaaa tgactgctaa    180
taccgcataa gaccacggta ccgcatggta cagtggtaaa aactccggtg gtatgagatg    240
gacccgcgtc tgattaggta gttggtgggg taacggccta ccaagccgac gatcagtagc    300
cgacctgaga gggtgaccgg ccacattggg actgagacac ggcccagact cctacgggag    360
gcagcagtgg ggaatattgc acaatggagg aaactctgat gcagcgacgc cgcgtgaagg    420
```

```
atgaagtatt tcggtatgta aacttctatc agcagggaag aaaatgacgg tacctgacta    480
agaagccccg gctaactacg tgccagcagc cgcggtaata cgtaggggc aagcgttatc    540 cggatttact gggtgtaaag ggagcgtaga cggcacggca agccagatgt gaaagcccgg    600
ggctcaaccc cgggactgca tttggaactg ctgagctaga gtgtcggaga ggcaagtgga    660
attcctagtg tagcggtgaa atgcgtagat attaggagga acaccagtgg cgaaggcggc    720
ttgctggacg atgactgacg ttgaggctcg aaagcgtggg gagcaaacag gattagatac    780
cctggtagtc cacgccgtaa acgatgactg ctaggtgtcg ggtggcaaag ccattcggtg    840
ccgcagctaa cgcaataagc agtccacctg gggagtacgt tcgcaagaat gaaactcaaa    900
ggaattgacg gggacccgca caagcggtgg agcatgtggt ttaattcgaa gcaacgcgaa    960
gaaccttacc tgatcttgac atcccgatga ccgcttcgta atggaagctt ttcttcggaa   1020
catcggtgac aggtggtgca tggttgtcgt cagctcgtgt cgtgagatgt tgggttaagt   1080
cccgcaacga gcgcaacccc tatcttcagt agccagcagg ttaagctggg cactctggag   1140
agactgccag gataacctg gaggaaggtg gggatgacgt caaatcatca tgccccttat   1200
gaccagggct acacacgtgc tacaatggcg taaacaaaga gaagcgaact cgcgagggta   1260
agcaaatctc aaaaataacg tctcagttcg gattgtagtc tgcaactcga ctacatgaag   1320
ctggaatcgc tagtaatcgc agatcagaat gctgcggtga atacgttccc gggtcttgta   1380
cacaccgccc gtcacaccat gggagtcagt aacgcccgaa gtcagtgacc caaccgtaag   1440
gagggagctg ccgaaggtgg gaccgataac tggggtgaag tcgtaacaag gtagccgtat   1500
cggaaggtgc ggctggatca cctcctttt                                     1528

<210> SEQ ID NO 19
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 19
atcagagagt tgatcctgg ctcaggatga acgctggcgg cgtgcttaac acatgcaagt     60
cgagcgaagc acttaagtgg atctcttcgg attgaaactt atttgactga gcggcggacg   120
ggtgagtaac gcgtgggtaa cctgcctcat acaggggggat aacagttaga aatggctgct   180
aataccgcat aagcgcacag gaccgcatgg tctggtgtga aaaactccgg tggtatgaga   240
tggacccgcg tctgattagc tagttggagg ggtaacggcc caccaaggcg acgatcagta   300
gccggcctga gagggtgaac ggccacattg ggactgagac acggcccaga ctcctacggg   360
aggcagcagt ggggaatatt gcacaatggg ggaaaccctg atgcagcgac gccgcgtgaa   420
ggaagaagta tctcggtatg taaacttcta tcagcaggga agaaaatgac ggtacctgac   480
taagaagccc cggctaacta cgtgccagca gccgcggtaa tacgtagggg caagcgttta   540
tccggattta ctgggtgtaa agggagcgta gacggaagag caagtctgat gtgaaaggct   600
ggggcttaac cccaggactg cattggaaac tgttttttcta gagtgccgga gaggtaagcg   660
gaattcctag tgtagcggtg aaatgcgtag atattaggag gaacaccagt ggcgaaggcg   720
gcttactgga cggtaactga cgttgaggct cgaaagcgtg gggagcaaac aggattagat   780
accctggtag tccacgccgt aaacgatgaa tactaggtgt cgggtggcaa agccattcgg   840
tgccgcagca aacgcaataa gtattccacc tgggagtac gttcgcaaga atgaaactca   900
aaggaattga cggggacccg cacaagcggt ggagcatgtg gtttaattcg aagcaacgcg   960
```

```
aagaaccta ccaagtcttg acatccctct gaccggcccg taacgggccc ttcccttcgg    1020
ggcagaggag acaggtggtg catggttgtc gtcagctcgt gtcgtgagat gttgggttaa    1080
gtcccgcaac gagcgcaacc cctatcctta gtagccagca ggtgaagctg gcactctag    1140 ggagactgcc ggggataacc cggaggaagg cggggacgac gtcaaatcat catgcccctt    1200
atgatttggg ctacacacgt gctacaatgg cgtaaacaaa gggaagcgag acagcgatgt    1260
tgagcaaatc ccaaaaataa cgtcccagtt cggactgcag tctgcaactc gactgcacga    1320
agctggaatc gctagtaatc gcgaatcaga atgtcgcggt gaatacgttc ccgggtcttg    1380
tacacaccgc ccgtcacacc atgggagtca gtaacgcccg aagtcagtga cccaaccta    1440 caggagggag ctgccgaagg cgggaccgat aactggggtg aagtcgtaac aaggtagccg    1500
tatcggaagg tgcggctgga tcacctcctt t                                    1531

<210> SEQ ID NO 20
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 20
aacgagagtt tgatcctggc tcaggatgaa cgctggcggc gtgcttaaca catgcaagtc      60
gagcgaagca cttggaaga ttcttcggat gatttccttt gtgactgagc ggcggacggg     120
tgagtaacgc gtgggtaacc tgcctcatac aggggataa cagttagaaa tgactgctaa     180
taccgcataa gaccacggta ccgcatggta cagtggtaaa aactccggtg gtatgagatg     240
gacccgcgtc tgattaggta gttggtgggg taacggccta ccaagccgac gatcagtagc     300
cgacctgaga gggtgaccgg ccacattggg actgagacac ggcccagact cctacgggag     360
gcagcagtgg ggaatattgc acaatggagg aaactctgat gcagcgacgc cgcgtgaagg     420
atgaagtatt tcggtatgta aacttctatc agcagggaag aaaatgacgg tacctgacta     480 agaagcccg gctaactacg tgccagcagc cgcggtaata cgtaggggc aagcgttatc     540 cggatttact gggtgtaaag ggagcgtaga cggcacggca agccagatgt gaaagcccgg     600
ggctcaaccc cgggactgca tttggaactg ctgagctaga gtgtcggaga ggcaagtgga     660
attcctagtg tagcggtgaa atgcgtagat attaggagga acaccagtgg cgaaggcggc     720
ttgctggacg atgactgacg ttgaggctcg aaagcgtggg gagcaaacag gattagatac     780
cctggtagtc cacgccgtaa acgatgactg ctaggtgtcg ggtggcaaag ccattcggtg     840
ccgcagctaa cgcaataagc agtccacctg gggagtacgt tcgcaagaat gaaactcaaa     900
ggaattgacg ggacccgca caagcggtgg agcatgtggt ttaattcgaa gcaacgcgaa     960
gaaccttacc tgatcttgac atcccgatga ccgcttcgta atggaagctt tcttcggaa    1020 catcggtgac aggtggtgca tggttgtcgt cagctcgtgt cgtgagatgt tgggttaagt    1080
cccgcaacga gcgcaacccc tatcttcagt agccagcagg ttaagctggg cactctggag    1140
agactgccag ggataacctg gaggaaggtg gggatgacgt caaatcatca tgcccttat    1200 gacccagggct acacacgtgc tacaatgcg taaacaaaga gaagcgaact cgcgaggta    1260 agcaaatctc aaaaataacg tctcagttcg gattgtagtc tgcaactcga ctacatgaag    1320
ctggaatcgc tagtaatcgc agatcagaat gctgcggtga atacgttccc gggtcttgta    1380
cacaccgccc gtcacaccat gggagtcagt aacgcccgaa gtcagtgacc caaccgtaag    1440
```

```
gagggagctg ccgaaggtgg gaccgataac tggggtgaag tcgtaacaag gtagccgtat    1500
cggaaggtgc ggctggatca cctcctttt                                     1528

<210> SEQ ID NO 21
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 21
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca    120
cgtaggtaac ctgcccatgt gtccgggata actgctggaa acggtagcta aaaccggata    180
ggtatacaga gcgcatgctc agtatattaa agcgcccatc aaggcgtgaa catggatgga    240
cctgcggcgc attagctagt tggtgaggta acggcccacc aaggcgatga tgcgtagccg    300
gcctgagagg gtaaacggcc acattgggac tgagacacgg cccaaactcc tacgggaggc    360
agcagtaggg aattttcgtc aatggggaa acccctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatggaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
agtgtgaaac tcaaaggaat tgacgggggc ccgcacaagc ggtggagtat gtggtttaat    960
tcgaagcaac gcgaagaacc ttaccaggcc ttgacatgga aacaaatacc ctagagatag   1020 gggataatt atggatcaca caggtggtgc atggttgtcg tcagctcgtg tcgtgagatg    1080
ttgggttaag tcccgcaacg agcgcaaccc ttgtcgcatg ttaccagcat caagttgggg    1140
actcatgcga gactgccggt gacaaaccgg aggaaggtgg ggatgacgtc aaatcatcat    1200
gccccttatg gcctgggcta cacacgtact acaatggcgg ccacaaagag cagcgacaca   1260
gtgatgtgaa gcgaatctca taaaggtcgt ctcagttcgg attgaagtct gcaactcgac    1320
ttcatgaagt cggaatcgct agtaatcgca gatcagcatg ctgcggtgaa tacgttctcg    1380
ggccttgtac acaccgcccg tcaaaccatg ggagtcagta atacccgaag ccggtggcat    1440
aaccgtaagg agtgagccgt cgaaggtagg accgatgact ggggttaagt cgtaacaagg    1500
tatccctacg ggaacgtggg gatggatcac ctccttt                             1537

<210> SEQ ID NO 22
<211> LENGTH: 476
<212> TYPE: DNA
<213> ORGANISM: Artificial Sequence
<220> FEATURE:
<223> OTHER INFORMATION: Synthetic Polynucleotide

<400> SEQUENCE: 22
agtaacgcgt gggtaacctg cctcatacag ggggataaca gttagaaatg actgctaata     60
ccgcataaga ccacggtacc gcatggtaca gtggtaaaaa ctccggtggt atgagatgga    120
```

```
cccgcgtctg attaggtagt tggtggggta acggcctacc aagccgacga tcagtagccg      180
acctgagagg gtgaccggcc acattgggac tgagacacgg cccagactcc tacgggaggc      240
agcagtgggg aatattgcac aatggaggaa actctgatgc agcgacgccg cgtgaaggat      300
gaagtatttc ggtatgtaaa cttctatcag cagggaagaa aatgacggta cctgactaag      360
aagccccggc taactacgtg ccagcagccg cggtaatacg tagggggcaa gcgttatccg      420
gatttactgg gtgtaaaggg agcgtagacg gcacggcaag ccagatgtga aagccc         476
```

<210> SEQ ID NO 23
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 23

```
caggctggag tgcaggagag gtaagcggaa ttcctagtgt agcggtgaaa tgcgtagata       60
ttaggaggaa caccagtggc gaaggcggct tactggactg taactgacgt tgaggctcga      120
aagcgtgggg agcaaacagg attagatacc ctggtagtcc acgcggtaaa cgatgattgc      180
taggtgtagg tgggtatgga cccatcggtg ccgcagctaa cgcaataagc aatccacctg      240
gggagtacgt tcgcaagaat gaaactcaaa ggaattgacg ggacccgca caagcggtgg       300 agcatgtggt ttaattcgaa gcaacgcgaa gaaccttacc aagtcttgac atcc            354
```

<210> SEQ ID NO 24
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 24

```
ccggggctca ccccgggact gcatttggaa ctgctgagct agagtgtcgg agaggcaagt       60
ggaattccta gtgtagcggt gaaatgcgta gatattagga ggaacaccag tggcgaaggc      120
ggcttgctgg acgatgactg acgttgaggc tcgaaagcgt ggggagcaaa caggattaga      180
taccctggta                                                             190
```

<210> SEQ ID NO 25
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 25

```
agggtcaacc cctggactgc attggaaact gtcaggctgg agtgccggag aggtaagcgg       60
aattcctagt gtagcggtga aatgcgtaga tattaggagg aacaccagtg gcgaaggcgg      120
cttactggac ggtaactgac gttgatgctc gaaagcgtgg ggagcaaaca ggattagata      180
acctggtaaa                                                             190
```

<210> SEQ ID NO 26
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 26

```
gggaagtcgg tcttaagtgc ggggcttaac cccgtgaggg gaccgaaact gtgaagctcg      60
agtgtcggag aggaaagcgg aattcctagt gtagcggtga aatgcgtaga tattaggagg     120
aacaccagtg gcgaaagcgg cttttctgga cgacaactgac gctgaggcgc gaaagccagg    180
ggagcaaacg ggattagata ccccagtaa                                       209
```

<210> SEQ ID NO 27
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 27

```
tagtctgagt gatgcggggc ttaaccccgt atggcgttgg atactggaag tcttgagtgc      60
aggagaggaa aggggaattc ccagtgtagc ggtgaaatgc gtagatattg ggaggaacac     120
cagtggcgaa ggcgcctttc tggactgtgt ctgacgctga gatgcgaaag ccagggtagc    180
aaacgggatt agataccacg gta                                             203
```

<210> SEQ ID NO 28
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 28

```
gatagtcggt cttaagtgcg gggcttaccc cgtgagggga ccgaaactgt gaagctcgag      60
tgtcggagag gaaagcggaa ttcctagtgt agcggtgaaa tgcgtagata ttaggaggaa     120
caccagtggc gaaagcggct ttctggacga caactgacgc tgaggcgcga aagccagggg    180
agcaaacggg attagatacc acggtaa                                         207
```

<210> SEQ ID NO 29
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 29

```
cgtttgctcc acgctttcga gcctcacgtc agttaccgtc cagtaagccg ccttcgccac      60
tggtgttcct cctaatatct acgcatttca ccgctacact aggaattccg cttacctctc     120
cggtactcta gattgacagt ttccaatgca gtcccgggt tgagcccgg gttttcacat      180
cagacttgcc actccgtcta cgctcccttt acacccagta aatccggata acgcttgcac    240
catacgtatt accgcggctg ctggcacgta tttagccggt gcttcttagt caggtaccgt    300
cattttcttc cctgctgata gagctttaca taccgaaata cttcatcgct cacgcggcgt    360
cgctgcatca gggtttcccc cattgtgcaa tattccccac tgctgcctcc cgtaggagtt    420
tgga                                                                  424
```

<210> SEQ ID NO 30
<211> LENGTH: 441
<212> TYPE: DNA
<213> ORGANISM: Artificial Sequence
<220> FEATURE:
<223> OTHER INFORMATION: Synthetic Polynucleotide

<400> SEQUENCE: 30

```
tgtcacactt tcgagcatca gcgtcagtta cagtccagta agctgccttc gcaatcggag    60
ttcttcgtga tatctaagca tttcaccgct acaccacgaa ttccgcctac ctctactgca   120
ctcaagacga ccagtatcaa ctgcaatttt acggttgagc cgcaaacttt cacagctgac   180
ttaatagtcc gcctacgctc cctttaaacc caataaatcc ggataacgct tggatcctcc   240
gtattaccgc ggctgctggc acggagttag ccgatcctta ttcgtatggt acatacaaaa   300
agccacacgt ggctcacttt attcccatat aaaagaagtt tacaacccat agggcagtca   360
tccttcacgc tacttggctg gttcagactc tcgtccattg accaatattc ctcactgctg   420
cctcccgtag gtagtttgga a                                            441
```

<210> SEQ ID NO 31
<211> LENGTH: 422
<212> TYPE: DNA
<213> ORGANISM: Artificial Sequence
<220> FEATURE:
<223> OTHER INFORMATION: Synthetic Polynucleotide

<400> SEQUENCE: 31

```
ccgttgtcac gctttcgtgc tcagtgtcag tttcagtcca gtaagccgcc ttcgccactg    60
atgttcctcc taatatctac gcatttcacc gctacactag gaattccgct tacctctcct   120
gcactccagt ctgacagttt caaaagcagt cccagagtta agccctgggt tttcacttct   180
gacttgccat accacctacg cacccattac acccagtaat tccggataac gcttgccccc   240
tacgtattac cgcggctgct ggcacgtagt tagccggggc ttcttagtca ggtaccgtca   300
ttttcttccc tgctgataga gctttacata ccgaaatact tcttcactca cgcggcgtcg   360
ctgcatcagg gttccccca ttgtgcaata ttccccactg ctgcctcccg tggaagtttg   420
ga                                                                 422
```

<210> SEQ ID NO 32
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 32

```
gcgaatgtca cgcattcgag cctcacgtca gttaccgtcc agtaagccgc cttcgccact    60
ggtgttcctc ctaatatcta cgcatttcac cgctacacta ggaattccgc ttacctctcc   120
ggcactcaag actaacagtt tccaatgcag tccaggggtt gagccccgc ctttcacatc   180
agacttgcca gtccgtctac gctcccttta cacccagtaa atccggataa cgcttgcccc   240
ctacgtatta ccgcggctgc tggcacgtag ttagccgggg cttcttagtc aggtaccgtc   300
actatcttcc ctgctgatag aagtttacat accgagatac ttcttccttc acgcggcgtc   360
gctgcatcag ggtttccccc attgtgcaat attccccact gctgcctccc gtgggagttt   420
ggaa                                                               424
```

<210> SEQ ID NO 33
<211> LENGTH: 422
<212> TYPE: DNA
<213> ORGANISM: Artificial Sequence
<220> FEATURE:
<223> OTHER INFORMATION: Synthetic Polynucleotide

<400> SEQUENCE: 33

```
tgctcacgct tcgcgctca gcgtcagtta ctgtccagca atccgccttc gccactggtg    60
ttcctccgta tatctacgca tttcaccgct acacacggaa ttccgattgc ctctccagca   120
ctcaagaact acagtttcaa atgcaggctg gaggttgagc ccccagtttt cacatctgac   180
ttgcaatccc gcctacacgc cctttacacc cagtaaatcc ggataacgct tgccacctac   240
gtattaccgc ggctgctggc acgtagttag ccgtggctta ttcgtcaggt accgtcattt   300
gtttcgtccc tgacaaaaga agtttacaac ccgaaagcct tcttccttca cgcggcgttg   360
ctgggtcagg cttgcgccca ttgcccaata ttccccactg ctgcctcccg tggtagtttg   420
ga                                                                  422
```

<210> SEQ ID NO 34
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 34

```
tgtccacgct tcgagctca gcgtcagtta tcgtccagta agccgccttc gccactggtg    60
ttcctcctaa tatctacgca tttcaccgct acactaggaa ttccgcttac ccctccgaca   120
ctctagtacg acagtttcca atgcagtacc ggggttgagc cccgggcttt cacatcagac   180
ttgccgcacc gcctgcgctc cctttacacc cagtaaatcc ggataacgct tgcaccatac   240
gtattaccgc ggctgctggc acgtatttag ccggtgcttc ttagtcaggt accgtcatta   300
tcttccctgc tgatagagct ttacataccg aaatacttct tcgctcacgc ggcgtcgctg   360
catcaggctt tcgcccattg tgcaatattc cccactgctg actccgtag gagtttgga    419
```

<210> SEQ ID NO 35
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 35

```
cgtttctcca cgcttcgcgc tcagcgtcag ttactgtcca gcaatccgcc ttcgccactg    60
gtgttcctcc gtatatctac gcatttcacc gctacacacg gaattccgat tgcctctcca   120
gcactcaaga actacagttt caaatgcagg ctggaggttg agcccccagt tttcacatct   180
gacttgcaat cccgcctaca cgcccttac acccagtaaa tccggataac gcttgccacc   240
tacgtattac cgcggctgct ggcacgtagt tagccgtggc ttattcgtca ggtaccgtca   300
tttgtttcgt ccccgacaaa agaagtttac aacccgaaag ccttcttcct tcacgcggcg   360
ttgctgggtc aggcttgcgc ccattgccca atattcccca ctgctgcctc cctgggaagt   420
ttgg                                                                424
```

<210> SEQ ID NO 36
<211> LENGTH: 445
<212> TYPE: DNA
<213> ORGANISM: Artificial Sequence
<220> FEATURE:
<223> OTHER INFORMATION: Synthetic Polynucleotide

<400> SEQUENCE: 36

```
atgtcctgac ttcgcgcctc agcgtcagtt gtcgtccaga aagccgcttt cgccactggt    60
```

```
gttcctccta atatctacgc atttcaccgc tacactagga attccgcttt cctctccgac    120
actcgagctt cacagtttcg gtccctcac ggggttaagc cccgcacttt taagaccgac    180
ttgcgatgcc gcctgcgcgc cctttacgcc caataattcc ggacaacgct tgccacctac    240
gtattaccgc ggctgctggc acgtagttag ccgtggcttt ctcttacggt accgtcaggg    300
ataacgggta ttgaccgcta tcctgttcgt cccatataac agaactttac aacccgaagg    360
ccgtcatcgt tcacgcggcg ttgctccgtc agactttcgt ccattgcgga agattcccca    420
ctgctgcctc cctgggaagt ttgga                                          445

<210> SEQ ID NO 37
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 37
gtttgctcac gctttcgagc tcagcgtcag ttatcgtcca gtaagccgcc ttcgccactg     60
gtgttcctcc taatatctac gcatttcacc gctacactag gaattccgct taccccctccg    120 acactctagt acgacagttt ccaatgcagt accggggttg agccccgggc tttcacatca    180
gacttgccgc accgcctgcg ctcccttac acccagtaaa tccggataac gcttgcacca    240
tacgtattac cgcggctgct ggcacgtatt tagccggtgc ttcttagtca ggtaccgtca    300
ttatcttccc tgctgataga gctttacata ccgaaatact tcttcgctca cgcggcgtcg    360
ctgcatcagg ctttcgccca ttgtgcaata ttccccactg ctgcctcccg taggagtttg    420
g                                                                    421

<210> SEQ ID NO 38
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 38
cgttgctcac gcattcgagc ctcagcgtca gttaagccca gtaagccgcc ttcgccactg     60
atgttcctcc taatatctac gcatttcacc gctacactag gaattccgct tacctctact    120
tcactcaaga accacagttt caaatgcagt ttatgggtta agcccatagt tttcacatct    180
gacttgcgat cccgcctacg ctcccttac acccagtaat tccggacaac gctcgctccc    240
tacgtattac cgcggctgct ggcacgtagt tagccggagc ttcctcctca ggtaccgtct    300
tttttcgtcc ctgaagacag aggtttacaa tcctaaaacc ttcttccctc acgcggcatc    360
gctgcatcag agtttcctcc attgtgcaat attccccact gctgcctccc gtaggagttt    420
ggaa                                                                 424

<210> SEQ ID NO 39
<211> LENGTH: 189
<212> TYPE: DNA
<213> ORGANISM: Artificial Sequence
<220> FEATURE:
<223> OTHER INFORMATION: Synthetic Polynucleotide

<400> SEQUENCE: 39
tgggcttacc cataaactgc atttgaaact gtggttcttg agtgaagtag aggtaagcgg     60
```

```
aattcctagt gtagcggtga aatgcgtaga tattaggagg aacatcagtg gcgaaggcgg    120
cttactgggc tttaactgac gctgaggctc gaaagcgtgg ggagcaaaca ggattagata    180
cccaagtaa                                                            189

<210> SEQ ID NO 40
<211> LENGTH: 414
<212> TYPE: DNA
<213> ORGANISM: Artificial Sequence
<220> FEATURE:
<223> OTHER INFORMATION: Synthetic Polynucleotide

<400> SEQUENCE: 40
gtcagcatcg agctcacgtc agttaccgtc cagtaagccg ccttcgccac tggtgttcct     60
cctaatatct acgcatttca ccgctacact aggaattccg cttacctctc cggtactcta    120
gattgacagt ttccaatgca gtcccggggt tgagccccgg gttttcacat cagacttgcc    180
actccgtcta cgctccctt  acacccagta atccggata  acgcttgcac catacgtatt    240
accgcggctg ctggcacgta tttagccggt gcttcttagt caggtaccgt cattttcttc    300
cctgctgata gagctttaca taccgaaata cttcatcgct cacgcggcgt cgctgcatca    360
gggtttcccc cattgtgcaa tattccccac tgctgcctcc cgagggagtt tgga          414

<210> SEQ ID NO 41
<211> LENGTH: 191
<212> TYPE: DNA
<213> ORGANISM: Artificial Sequence
<220> FEATURE:
<223> OTHER INFORMATION: Synthetic Polynucleotide

<400> SEQUENCE: 41
tcatcgctta cggtggatct gcgccgggta cgggcgggct ggagtgcggt aggggagact     60
ggaattcccg gtgtaacggt ggaatgtgta gatatcggga agaacaccga tggcgaaggc    120
aggtctctgg gccgtcactg acgctgagga gcgaaagcgt ggggagcgaa caggattaga    180
tacaacggta a                                                         191

<210> SEQ ID NO 42
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 42
tgaacccagg gcttaactct gggactgctt ttgaactgtc agactggagt gcaggagagg     60
taagcggaat tcctagtgta gcggtgaaat gcgtagatat taggaggaac atcagtggcg    120
aaggcggctt actggactga aactgacact gaggcacgaa agcgtgggga gcaaacagga    180
ttagatacca tggtaa                                                    196

<210> SEQ ID NO 43
<211> LENGTH: 192
<212> TYPE: DNA
<213> ORGANISM: Artificial Sequence
<220> FEATURE:
<223> OTHER INFORMATION: Synthetic Polynucleotide

<400> SEQUENCE: 43
accagggctt aactctggga ctgcttttga actgtcagac tggagtgcag gagaggtaag     60
cggaattcct agtgtagcgg tgaaatgcgt agatattagg aggaacatca gtggcgaagg    120
```
cggcttactg gactgaaact gacactgagg cacgaaagcg tggggagcaa acaggattag    180 atacccctggt aa    192

<210> SEQ ID NO 44
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 44
gaacccaggg cttaactctg ggactgcttt tgaactgtca gactggagtg caggagaggt    60
aagcggaatt cctagtgtag cggtgaaatg cgtagatatt aggaggaaca tcagtggcga    120
aggcggctta ctggactgaa actgacactg aggcacgaaa gcgtggggag caaacaggat    180 tagataccccc ggtaa    195

<210> SEQ ID NO 45
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 45
gagtcagctt tcgagctcag cgtcagttat cgtccagtaa gccgccttcg ccactggtgt    60
tcctcctaat atctacgcat ttcaccgcta cactaggaat tccgcttacc cctccgacac    120
tctagtacga cagtttccaa tgcagtaccg gggttgagcc ccgggctttc acatcagact    180
tgccgcaccg cctgcgctcc ctttacaccc agtaaatccg gataacgctt gcaccatacg    240
tattaccgcg gctgctggca cgtatttagc cggtgcttct tagtcaggta ccgtcattat    300
cttccctgct gatagagctt tacataccga aatacttctt cgctcacgcg cgtcgctgc    360 atcaggcttt cgcccattgt gcaatattcc ccactgctgc ctcccgaggg agtttgga    418

<210> SEQ ID NO 46
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 46
tgtcagcttt cgagctcacg tcagttaccg tccagtaagc cgccttcgcc actggtgttc    60
ctcctaatat ctacgcattt caccgctaca ctaggaattc cgcttacctc tccggtactc    120
tagattgaca gtttccaatg cagtcccggg gttgagcccc gggttttcac atcagacttg    180
ccactccgtc tacgctccct ttacacccag taaatccgga taacgcttgc accatacgta    240
ttaccgcggc tgctggcacg tatttagccg gtgcttctta gtcaggtacc gtcattttct    300
tccctgctga tagagcttta cataccgaaa tacttcatcg ctcacgcggc gtcgctgcat    360
cagggtttcc cccattgtgc aatattcccc actgctgcct cccgtaggag tttgga    416

<210> SEQ ID NO 47
<211> LENGTH: 400
<212> TYPE: DNA
<213> ORGANISM: Artificial Sequence
<220> FEATURE:
<223> OTHER INFORMATION: Synthetic Polynucleotide

<400> SEQUENCE: 47

```
cacgtcagtt accgtccagt aagccgcctt cgccactggt gttcctccta atatctacgc    60
atttcaccgc tacactagga attccgctta cctctccggc actcaagacg ggcagtttcc   120
aatgcagtcc cggggttgag ccccagcctt tcacatcaga cttgtccatc cgtctacgct   180
ccctttacac ccagtaaatc cggataacgc ttgcccccta cgtattaccg cggctgctgg   240
cacgtagtta gccggggctt cttagtcagg taccgtcatt ttcttccctg ctgatagaag   300
tttacatacc gagatacttc ttccttcacg cggcgtcgct gcatcagggt ttcccccatt   360
gtgcaatatt ccccactgct gcctcccgta ggagtttggg                         400
```

<210> SEQ ID NO 48
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 48

```
gtcagctttc gagctcacgt cagttaccgt ccagtaagcc gccttcgcca ctggtgttcc    60
tcctaatatc tacgcatttc accgctacac taggaattcc gcttacctct ccggtactct   120
agattgacag tttccaatgc agtcccgggg ttgagccccg gttttcaca tcagacttgc    180
cactccgtct acgctccctt tacacccagt aaatccggat aacgcttgca ccatacgtat   240
taccgcggct gctggcacgt atttagccgg tgcttcttag tcaggtaccg tcattttctt   300
ccctgctgat agagctttac ataccgaaat acttcatcgc tcacgcggcg tcgctgcatc   360
agggtttccc ccattgtgca atattcccca ctgctgcctc ccgtggggag tttgga       416
```

<210> SEQ ID NO 49
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 49

```
gatgctcagc tttcgtgctc agtgtcagtt tcagtccagt aagccgcctt cgccactgat    60
gttcctccta atatctacgc atttcaccgc tacactagga attccgctta cctctcctgc   120
actccagtct gacagtttca aaagcagtcc cagagttaag ccctgggttt tcacttctga   180
cttgccatac cacctacgca ccctttacac ccagtaattc cggataacgc ttgccccta   240
cgtattaccg cggctgctgg cacgtagtta gccggggctt cttagtcagg taccgtcatt   300
ttcttccctg ctgatagagc tttacatacc gagatacttc ttcactcacg cggcgtcgct   360
gcatcagggt ttcccccatt gtgcaatatt ccccactgct gcctcccgaa ggaagtttgg   420
a                                                                    421
```

<210> SEQ ID NO 50
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 50

```
gtgtcagctt cgtgctcagt gtcagtttca gtccagtaag ccgccttcgc cactgatgtt    60
cctcctaata tctacgcatt tcaccgctac actaggaatt ccgcttacct ctcctgcact   120
```

```
ccagtctgac agtttcaaaa gcagtcccag agttaagccc tgggttttca cttctgactt    180
gccataccac ctacgcaccc tttacaccca gtaattccgg ataacgcttg ccccctacgt    240
attaccgcgg ctgctggcac gtagttagcc ggggcttctt agtcaggtac cgtcattttc    300
ttccctgctg atagagcttt acataccgag atacttcttc actcacgcgg cgtcgctgca    360
tcagggtttc ccccattgtg caatattccc cactgctgcc tcccgtaggg agtttgga     418
```

<210> SEQ ID NO 51
<211> LENGTH: 415
<212> TYPE: DNA
<213> ORGANISM: Artificial Sequence
<220> FEATURE:
<223> OTHER INFORMATION: Synthetic Polynucleotide

<400> SEQUENCE: 51

```
gtcagcttcg agcctcacgt cagttaccgt ccagtaagcc gccttcgcca ctggtgttcc     60
tcctaatatc tacgcatttc accgctacac taggaattcc gcttacctct ccggtactct    120
agattgacag tttccaatgc agtcccgggg ttgagcccg gttttcaca tcagacttgc     180 cactccgtct acgctccctt tacacccagt aaatccggat aacgcttgca ccatacgtat    240
taccgcggct gctggcacgt atttagccgg tgcttcttag tcaggtaccg tcattttctt    300
ccctgctgat agagctttac ataccgaaat acttcatcgc tcacgcggcg tcgctgcatc    360
agggtttccc ccattgtgca atattcccca ctgctgcctc gcgtaggagt ttgga          415
```

<210> SEQ ID NO 52
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 52

```
tgtcagcttt cgagctcagc gtcagttatc gtccagtaag ccgccttcgc cactggtgtt     60
cctcctaata tctacgcatt tcaccgctac actaggaatt ccgcttaccc ctccgacact    120
ctagtacgac agtttccaat gcagtaccgg ggttgagccc cggctttca catcagactt    180 gccgcaccgc ctgcgctccc tttacaccca gtaaatccgg ataacgcttg caccatacgt    240
attaccgcgg ctgctggcac gtatttagcc ggtgcttctt agtcaggtac cgtcattatc    300
ttccctgctg atagagcttt acataccgaa atacttcttc gctcacgcgg cgtcgctgca    360
tcaggctttc gcccattgtg caatattccc cactgctgcc tcccgaaggg agtttgga     418
```

<210> SEQ ID NO 53
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 53

```
ttcagctttc gagctcagcg tcagttatcg tccagtaagc cgccttcgcc actggtgttc     60
ctcctaatat ctacgcattt caccgctaca ctaggaattc cgcttacccc tccgacactc    120
tagtacgaca gtttccaatg cagtaccggg gttgagcccc gggctttcac atcagacttg    180
ccgcaccgcc tgcgctccct ttacacccag taaatccgga taacgcttgc accatacgta    240
ttaccgcggc tgctggcacg tatttagccg gtgcttctta gtcaggtacc gtcattatct    300
```

```
tccctgctga tagagctttta cataccgaaa tacttcttcg ctcacgcggc gtcgctgcat    360
caggctttcg cccattgtgc aatattcccc actgctgcct cccgagggga gtttgg         416
```

<210> SEQ ID NO 54
<211> LENGTH: 435
<212> TYPE: DNA
<213> ORGANISM: Artificial Sequence
<220> FEATURE:
<223> OTHER INFORMATION: Synthetic Polynucleotide

<400> SEQUENCE: 54

```
ttcggtctgc tttcccttc tcgcgcctca gtgtcagttt ctgtctagta agccgccttc      60
gccactgatg ttcctcctaa tatctacgca cttcaccgct ccacaatgaa ttccgcttac    120
ccctcccgcg ctctagtctg acagttttaa aaaaactccc cgagagaaac cctgggtttt    180
ttcttctgac atgcgatatc ccaccccac cctttataca cccaaaaatc ggataaaagg     240
tgcgacctac gtattatacc ggctgctggg gcgtagatag ccgggggttc ttatacaggg    300
accgtcattt tctttccgc tgatacagct ttacataccg aaatacttct ttctcacgcg     360
gcgtcgctgc atcagggttt cccccattgt gcaatattcc ccactgctgc ctcccgaagg    420
ggaagttggg ggaaa                                                      435
```

<210> SEQ ID NO 55
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 55

```
gttcagcttt cgagcctcac gtcagttacc gtccagtaag ccgccttcgc cactggtgtt     60
cctcctaata tctacgcatt tcaccgctac actaggaatt ccgcttacct ctccggtact    120
ctagattgac agtttccaat gcagtcccgg ggttgagccc cgggttttca catcagactt    180
gccactccgt ctacgctccc tttacacca gtaaatccgg ataacgcttg caccatacgt     240
attaccgcgg ctgctggcac gtatttagcc ggtgcttctt agtcaggtac cgtcattttc    300
ttccctgctg atagagcttt acataccgaa atacttcatc gctcacgcgg cgtcgctgca    360
tcagggtttc ccccattgtg caatattccc cactgctgcc tcccgagggg agtttgga      418
```

<210> SEQ ID NO 56
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 56

```
gtcagctttc gagctcacgt cagttaccgt ccagtaagcc gccttcgcca ctggtgttcc     60
tcctaatatc tacgcatttc accgctacac taggaattcc gcttacctct ccggtactct    120
agattgacag tttccaatgc agtcccgggg ttgagccccg gttttcaca tcagacttgc     180 cactccgtct acgctccctt tacacccagt aaatccggat aacgcttgca ccatacgtat    240
taccgcggct gctggcacgt atttagccgg tgcttcttag tcaggtaccg tcattttctt    300
ccctgctgat agagctttac ataccgaaat acttcatcgc tcacgcgcg tcgctgcatc     360 agggtttccc ccattgtgca atattcccca ctgctgcctc cgaggggag tttgga         416
```

<210> SEQ ID NO 57
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 57

```
tctcacgctt tcgagctcac gtcagtcatc gtccagcaag ccgccttcgc cactggtgtt      60
cctcctaata tctacgcatt tcaccgctac actaggaatt ccacttgcct ctccgacact     120
ctagctcagc agttccaaat gcagtcccgg ggttgagccc cgggctttca catctggctt     180
gccgtgccgt ctacgctccc tttacaccca gtaaatccgg ataacgcttg cccccctacgt    240 attaccgcgg ctgctggcac gtagttagcc ggggcttctt agtcaggtac cgtcattttc     300
ttccctgctg atagaagttt acataccgaa atacttcatc cttcacgcgg cgtcgctgca     360
tcagagtttc ctccattgtg caatattccc cactgctgcc tcccgtaggg agtttgg        417
```

<210> SEQ ID NO 58
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 58

```
gtcagctttc gagctcagcg tcagttatcg tccagtaagc cgccttcgcc actggtgttc      60
ctcctaatat ctacgcattt caccgctaca ctaggaattc acttacccc tccgacactc     120 tagtacgaca gtttccaatg cagtaccggg gttgagcccc gggctttcac atcagacttg     180
ccgcaccgcc tgcgctccct ttacacccag taaatccgga taacgcttgc accatacgta     240
ttaccgcggc tgctggcacg tatttagccg gtgcttctta gtcaggtacc gtcattcttc     300
ttccctgctg atagagcttt acataccgaa atacttcttc gctcacgcgg cgtcgctgca     360
tcagggtttc ccccattgtg caatattccc cactgctgcc tcccgaggga gtttgga        417
```

<210> SEQ ID NO 59
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 59

```
agccccgctt tcgagcctca cgtcagttac cgtccagtaa gccgccttcg ccactggtgt      60
tcctcctaat atctacgcat ttaccgcta cactaggaat tccgcttacc tctccggcac     120
tcaagacggg cagtttccaa tgcagtcccg gggttgagcc ccagcctttc acatcagact     180
tgtccatccg tctacgctcc ctttacaccc agtaaatccg gataacgctt gccccctacg     240
tattaccgcg gctgctggca cgtagttagc cggggcttct tagtcaggta ccgtcatttt     300
cttccctgct gatagaagtt tacataccga gatacttctt ccttcacgcg cgtcgctgc      360 atcagggttt ccccattgt gcaatattcc ccactgctgc ctcccgaagg aagtttgga       419
```

<210> SEQ ID NO 60
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 60

```
tgctcagctt tcgagcctca cgtcagttac cgtccagtaa gccgccttcg ccactggtgt      60
tcttcctaat atctacgcat ttcaccgcta cactaggaat tccgcttacc tctccggcac     120
tcgagccaga cagtttccaa tgcagtccca gggttaagcc ctgggttttc acatcagact     180
tgccttgccg tctacgctcc ctttacaccc agtaaatccg ataacgctt gcccctacg      240
tattaccgcg gctgctggca cgtagttagc cggggcttct tagtcaggta ccgtcattat     300
cttccctgct gatagagctt tacataccga aatacttctt cgctcacgcg cgtcgctgc     360
atcagggttt cccccattgt gcaatattcc ccactgctgc ctcccgaagg gagtttgga     419
```

<210> SEQ ID NO 61
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 61

```
gttgctcagc tttcgagctc acgtcagtta ccgtccagta agccgccttc gccactggtg      60
ttcttcctaa tatctacgca tttcaccgct acactaggaa ttccgcttac ctctccggca     120
ctcgagccag acagtttcca atgcagtccc agggttaagc cctgggtttt cacatcagac     180
ttgccttgcc gtctacgctc cctttacacc cagtaaatcc ggataacgct tgcccctac     240
gtattaccgc ggctgctggc acgtagttag ccggggcttc ttagtcaggt accgtcatta     300
tcttccctgc tgatagagct ttacataccg aaatacttct tcgctcacgc ggcgtcgctg     360
catcagggtt tcccccattg tgcaatattc cccactgctg cctcccgaag gaaagtttgg     420
a                                                                    421
```

<210> SEQ ID NO 62
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 62

```
tgctcagctt tcgagctcag cgtcagttat cgtccagtaa gccgccttcg ccactggtgt      60
tcctcctaat atctacgcat ttcaccgcta cactaggaat tccacttacc cctccgacac     120
tctagtacga cagtttccaa tgcagtaccg gggttgagcc ccgggctttc acatcagact     180
tgccgcaccg cctgcgctcc ctttacaccc agtaaatccg ataacgctt gcaccatacg     240
tattaccgcg gctgctggca cgtatttagc cggtgcttct tagtcaggta ccgtcattct     300
tcttccctgc tgatagagct ttacataccg aaatacttct cgctcacgc ggcgtcgctg     360
catcagggtt tcccccattg tgcaatattc cccactgctg cctcccgaag ggagtttgga     420
```

<210> SEQ ID NO 63
<211> LENGTH: 446
<212> TYPE: DNA
<213> ORGANISM: Artificial Sequence
<220> FEATURE:
<223> OTHER INFORMATION: Synthetic Polynucleotide

<400> SEQUENCE: 63

```
gatgccctgg cttcgcgctc agcgtcagtt gtcgtccaga aagccgcttt cgccactggt      60
gttcctccta atatctacgc atttcaccgc tacactagga attccgcttt cctctccgac     120
```

```
actcgagctt cacagtttcg gtcccctcac ggggttaagc cccgcacttt taagaccgac    180
ttgcgatgcc gcctgcgcgc cctttacgcc caataattcc ggacaacgct tgccacctac    240
gtattaccgc ggctgctggc acgtagttag ccgtggcttt ctcttacggt accgtcaggg    300
ataacgggta ttgaccgcta tcctgttcgt cccatataac agaactttac aacccgaagg    360
ccgtcatcgt tcacgcggcg ttgctccgtc agactttcgt ccattgcgga agattcccca    420
ctgctgcctc ccgggggggag tttgga                                        446

<210> SEQ ID NO 64
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 64
gtcccgcttt cgagcctcag cgtcagttat cgtccagtaa gccgccttcg ccactggtgt     60
tcctcctaat atctacgcat ttcaccgcta cactaggaat tccgcttacc cctccgacac    120
tctagtacga cagtttccaa tgcagtaccg gggttgagcc ccgggctttc acatcagact    180
tgccgcaccg cctgcgctcc ctttacaccc agtaaatccg gataacgctt gcaccatacg    240
tattaccgcg gctgctggca cgtatttagc cggtgcttct tagtcaggta ccgtcattat    300
cttccctgct gatagagctt tacataccga aatacttctt cgctcacgcg cgtcgctgc    360 atcaggcttt cgcccattgt gcaatattcc ccactgctgc ctcccgaagg gaagtttgg    419

<210> SEQ ID NO 65
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 65
tgtcagcttt cgagctcagc gtcagttatc gtccagtaag ccgccttcgc cactggtgtt     60
cctcctaata tctacgcatt tcaccgctac actaggaatt ccgcttaccc ctccgacact    120
ctagtacgac agtttccaat gcagtaccgg ggttgagccc gggctttca catcagactt    180 gccgcaccgc ctgcgctccc tttacaccca gtaaatccgg ataacgcttg caccatacgt    240
attaccgcgg ctgctggcac gtatttagcc ggtgcttctt agtcaggtac cgtcattatc    300
ttccctgctg atagagcttt ataccgaa atacttcttc gctcacgcgg cgtcgctgca    360
tcaggctttc gcccattgtg caatattccc cactgctgcc tcccgaaggg agtttgga    418

<210> SEQ ID NO 66
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 66
tgctcagctt tcgagctcag cgtcagttat cgtccagtaa gccgccttcg ccactggtgt     60
tcctcctaat atctacgcat ttcaccgcta cactaggaat tccacttacc cctccgacac    120
tctagtacga cagtttccaa tgcagtaccg gggttgagcc ccgggctttc acatcagact    180
tgccgcaccg cctgcgctcc ctttacaccc agtaaatccg gataacgctt gcaccatacg    240
```

| | |
|---|---|
| tattaccgcg gctgctggca cgtatttagc cggtgcttct tagtcaggta ccgtcattct | 300 |
| tcttccctgc tgatagagct ttacataccg aaatacttct tcgctcacgc ggcgtcgctg | 360 |
| catcagggtt tcccccattg tgcaatattc cccactgctg cctcccgaag ggagtttgga | 420 |

<210> SEQ ID NO 67
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 67

| | |
|---|---|
| attcagcttt cgagctcacg tcagttaccg tccagtaagc cgccttcgcc actggtgttc | 60 |
| ctcctaatat ctacgcattt caccgctaca ctaggaattc cgcttacccc tccggcactc | 120 |
| aagcatacca gtttccaatg cagtccaggg gttaagcccc tgcctttcac atcagacttg | 180 |
| atacgccgtc tacgctccct ttacacccag taaatccgga taacgctcgc ccctacgta | 240 |
| ttaccgcggc tgctggcacg tagttagccg gggcttctta gtcaggtacc gtcattatct | 300 |
| tccctgctga tagaagttta cataccgaga tacttcttcc ttcacgcggc gtcgctgcat | 360 |
| cagggttttcc cccattgtgc aatattcccc actgctgcct cccgagggaa gtttgga | 417 |

<210> SEQ ID NO 68
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 68

| | |
|---|---|
| gtgtcagctt tcgagctcac gtcagttacc gtccagtaag ccgccttcgc cactggtgtt | 60 |
| cttcctaata tctacgcatt tcaccgctac actaggaatt ccgcttacct ctccggcact | 120 |
| cgagccagac agtttccaat gcagtccag ggttaagccc tgggttttca catcagactt | 180 |
| gccttgccgt ctacgctccc tttacaccca gtaaatccgg ataacgcttg cccctacgt | 240 |
| attaccgcgg ctgctggcac gtagttagcc ggggcttctt agtcaggtac cgtcattatc | 300 |
| ttccctgctg atagagcttt acataccgaa atacttcttc gctcacgcgg cgtcgctgca | 360 |
| tcagggtttc cccattgtg caatattccc cactgctgcc tcccgaggga gtttgg | 416 |

<210> SEQ ID NO 69
<211> LENGTH: 416
<212> TYPE: DNA
<213> ORGANISM: Artificial Sequence
<220> FEATURE:
<223> OTHER INFORMATION: Synthetic Polynucleotide

<400> SEQUENCE: 69

| | |
|---|---|
| gccagcttcg agcctcacgt cagtcatcgt ccagtaagcc gccttcgcca ctggtgttcc | 60 |
| tcctaatatc tacgcatttc accgctacac taggaattcc acttacctct ccgacactct | 120 |
| agctgcacag tttccaaagc agtccacagg ttgagcccat gcctttcact tcagacttgc | 180 |
| acagccgtct acgctccctt tacacccagt aaatccggat aacgcttgcc ccctacgtat | 240 |
| taccgcggct gctggcacgt agttagccgg ggcttcttag tcaggtaccg tcatttttctt | 300 |
| ccctgctgat agaagtttac ataccgaaat acttcatcct tcacgcggcg tcgctgcatc | 360 |
| aggctttcgc ccattgtgca atattcccca ctgctgcctc cgagggaag tttgga | 416 |

<210> SEQ ID NO 70
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 70

```
tgatcagctt tcgagctcac gtcagttacc gtccagtaag ccgccttcgc cactggtgtt      60
cctcctaata tctacgcatt tcaccgctac actaggaatt ccgcttacct ctccggtact     120
ctagattgac agtttccaat gcagtcccgg ggttgagccc cgggttttca catcagactt     180
gccactccgt ctacgctccc tttacaccca gtaaatccgg ataacgcttg caccatacgt     240
attaccgcgg ctgctggcac gtatttagcc ggtgcttctt agtcaggtac cgtcattttc     300
ttccctgctg atagagcttt acataccgaa atacttcatc gctcacgcgg cgtcgctgca     360
tcagggtttc ccccattgtg caatattccc cactgctgcc tcccgggggg agtttgga      418
```

<210> SEQ ID NO 71
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 71

```
gatgatcagc tttcgagctc acgtcagtta ccgtccagta agccgccttc gccactggtg      60
ttcctcctaa tatctacgca tttcaccgct acactaggaa ttccgcttac ctctccggca     120
ctctagaaaa acagtttcca atgcagtcct ggggttaagc cccagccttt cacatcagac     180
ttgctcttcc gtctacgctc cctttacacc cagtaaatcc ggataacgct tgcccccctac     240
gtattaccgc ggctgctggc acgtagttag ccggggcttc ttagtcaggt accgtcattt     300
tcttccctgc tgatagaagt ttacataccg agatacttct tccttcacgc ggcgtcgctg     360
catcagggtt tccccccattg tgcaatattc cccactgctg cctcccgggg gaagtttgga    420
```

<210> SEQ ID NO 72
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 72

```
ttgatcagct ttcgagctca cgtcagttac cgtccagtaa gccgccttcg ccactggtgt      60
tcctcctaat atctacgcat ttcaccgcta cactaggaat tccgcttacc tctccggcac     120
tctagaaaaa cagtttccaa tgcagtcctg gggttaagcc ccagcctttc acatcagact     180
tgctcttccg tctacgctcc ctttacaccc agtaaatccg gataacgctt gccccctacg     240
tattaccgcg gctgctggca cgtagttagc cggggcttct tagtcaggta ccgtcatttt     300
cttccctgct gatagaagtt tacataccga gatacttctt ccttcacgcg cgtcgctgc      360
atcagggttt cccccattgt gcaatattcc ccactgctgc ctcccgaagg gagtttgg       418
```

<210> SEQ ID NO 73
<211> LENGTH: 421
<212> TYPE: DNA
<213> ORGANISM: Artificial Sequence
<220> FEATURE:
<223> OTHER INFORMATION: Synthetic Polynucleotide

<400> SEQUENCE: 73

```
gtatttcagc tttcgagctc agcgtcagtt atcgtccagt aagccgcctt cgccactggt    60
gttcctccta atatctacgc atttcaccgc tacactagga attccgctta ccctccgac    120
actctagtac gacagtttcc aatgcagtac cggggttgag ccccgggctt cacatcaga    180
cttgccgcac cgcctgcgct ccctttacac ccagtaaatc cggataacgc ttgcaccata    240
cgtattaccg cggctgctgg cacgtattta gccggtgctt cttagtcagg taccgtcatt    300
atcttccctg ctgatagagc tttacatacc gaaatacttc ttcgctcacg cggcgtcgct    360
gcatcaggct ttcgcccatt gtgcaatatt ccccactgct gcctcccgaa gggagtttgg    420
a                                                                    421
```

<210> SEQ ID NO 74
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 74

```
gctcagcttt cgagctcagc gtcagttatc gtccagtaag ccgccttcgc cactggtgtt    60
cctcctaata tctacgcatt tcaccgctac actaggaatt ccacttaccc ctccgacact    120
ctagtacgac agtttccaat gcagtaccgg ggttgagccc cgggctttca catcagactt    180
gccgcaccgc ctgcgctccc tttacaccca gtaaatccgg ataacgcttg caccatacgt    240
attaccgcgg ctgctggcac gtatttagcc ggtgcttctt agtcaggtac cgtcattctt    300
cttccctgct gatagagctt acataccgaa atacttcttc gctcacgcg cgtcgctgc    360
atcagggttt cccccattgt gcaatattcc ccactgctgc ctcccgaggg gagtttgga    419
```

<210> SEQ ID NO 75
<211> LENGTH: 417
<212> TYPE: DNA
<213> ORGANISM: Artificial Sequence
<220> FEATURE:
<223> OTHER INFORMATION: Synthetic Polynucleotide

<400> SEQUENCE: 75

```
tttcagcttc gagcctcagc gtcagttatc gtccagtaag ccgccttcgc cactggtgtt    60
cctcctaata tctacgcatt tcaccgctac actaggaatt ccgcttaccc ctccgacact    120
ctagtacgac agtttccaat gcagtaccgg ggttgagccc cgggctttca catcagactt    180
gccgcaccgc ctgcgctccc tttacaccca gtaaatccgg ataacgcttg caccatacgt    240
attaccgcgg ctgctggcac gtatttagcc ggtgcttctt agtcaggtac cgtcattatc    300
ttccctgctg atagagcttt acataccgaa atacttcttc gctcacgcgg cgtcgctgca    360
tcaggctttc gcccattgtg caatattccc cactgctagc tcccgaagga gtttgga       417
```

<210> SEQ ID NO 76
<211> LENGTH: 419
<212> TYPE: DNA
<213> ORGANISM: Artificial Sequence
<220> FEATURE:
<223> OTHER INFORMATION: Synthetic Polynucleotide

<400> SEQUENCE: 76

```
agctcagctt tcgagctcag cgtcagttat cgtccagtaa gccgccttcg ccactggtgt    60
tcctcctaat atctacgcat ttcaccgcta cactaggaat tccgcttacc cctccgacac    120
```

```
tctagtacga cagtttccaa tgcagtaccg gggttgagcc ccgggctttc acatcagact    180
tgccgcaccg cctgcgctcc ctttacaccc agtaaatccg gataacgctt gcaccatacg    240
tattaccgcg gctgctggca cgtatttagc cggtgcttct tagtcaggta ccgtcattat    300
cttccctgct gatagagctt tacataccga aatacttctt cgctcacgcg cgtcgctgc     360 atcaggcttt cgcccattgt gcaatattcc ccactgctgc ctcccgaagg gagtttgga     419
```

<210> SEQ ID NO 77
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 77

```
gtccagcttt cgagcctcag cgtcagttat cgtccagtaa gccgccttcg ccactggtgt    60
tcctcctaat atctacgcat ttcaccgcta cactaggaat tccgcttacc cctccgacac   120
tctagtacga cagtttccaa tgcagtaccg gggttgagcc ccgggctttc acatcagact   180
tgccgcaccg cctgcgctcc ctttacaccc agtaaatccg gataacgctt gcaccatacg   240
tattaccgcg gctgctggca cgtatttagc cggtgcttct tagtcaggta ccgtcattat   300
cttccctgct gatagagctt tacataccga aatacttctt cgctcacgcg cgtcgctgc    360 atcaggcttt cgcccattgt gcaatattcc ccactgctgc ctcccgaggg agtttgga     418
```

<210> SEQ ID NO 78
<211> LENGTH: 193
<212> TYPE: DNA
<213> ORGANISM: Artificial Sequence
<220> FEATURE:
<223> OTHER INFORMATION: Synthetic Polynucleotide

<400> SEQUENCE: 78

```
tgagccgggc tcaccccggt actgcattgg aactgtcgta ctagagtgtc ggagggtaa     60 gcggaattcc tagtgtagcg gtgaaatgcg tagatattag gaggaacacc agtggcgaag   120
gcggcttact ggacgataac tgacgctgag gctcgaaagc gtggggagca aacaggatta   180 gataccaccgg taa                                                      193
```

<210> SEQ ID NO 79
<211> LENGTH: 424
<212> TYPE: DNA
<213> ORGANISM: Artificial Sequence
<220> FEATURE:
<223> OTHER INFORMATION: Synthetic Polynucleotide

<400> SEQUENCE: 79

```
cacgatgtca gctttcgagc tcagcgtcag ttatcgtcca gtaagccgcc ttcgccactg     60
gtgttcctcc taatatctac gcatttcacc gctacactag gaattccact acccctccg    120 acactctagt acgacagttt ccaatgcagt accggggttg agccccgggc tttcacatca   180
gacttgccgc accgcctgcg ctccctttac acccagtaaa tccggataac gcttgcacca   240
tacgtattac cgcggctgct ggcacgtatt tagccggtgc ttcttagtca ggtaccgtca   300
ttcttcttcc ctgctgatag agctttacat accgaaatac ttcttcgctc acgcggcgtc   360
gctgcatcag ggtttccccc attgtgcaat attccccact gctgcctccc gagggagtt   420 tgga                                                                424
```

<210> SEQ ID NO 80
<211> LENGTH: 1524
<212> TYPE: DNA
<213> ORGANISM: Artificial Sequence
<220> FEATURE:
<223> OTHER INFORMATION: Synthetic Polynucleotide

<400> SEQUENCE: 80

| | | | | | |
|---|---|---|---|---|---|
| atggagagtt | tgatcctggc | tcaggatgaa | cgctggcggc | gtgcctaata | catgcaagtc | 60 |
| gaacgcgagc | acttgtgctc | gagtggcgaa | cgggtgagta | atacataagt | aacctgccct | 120 |
| agacaggggg | ataactattg | gaaacgatag | ctaagaccgc | ataggtacgg | acactgcatg | 180 |
| gtgaccgtat | taaaagtgcc | tcaaagcact | ggtagaggat | ggacttatgg | cgcattagct | 240 |
| ggttggcggg | gtaacggccc | accaaggcga | cgatgcgtag | ccgacctgag | agggtgaccg | 300 |
| gccacactgg | gactgagaca | cggcccagac | tcctacggga | ggcagcagta | gggaattttc | 360 |
| ggcaatgggg | gaaaccctga | ccgagcaacg | ccgcgtgaag | gaagaaggtt | ttcggattgt | 420 |
| aaacttctgt | tataaaggaa | gaacggcggc | tacaggaaat | ggtagccgag | tgacggtact | 480 |
| ttattagaaa | gccacggcta | actacgtgcc | agcagccgcg | gtaatacgta | ggtggcaagc | 540 |
| gttatccgga | attattgggc | gtaaagaggg | agcaggcggc | agcaagggtc | tgtggtgaaa | 600 |
| gcctgaagct | taacttcagt | aagccataga | aaccaggcag | ctagagtgca | ggagaggatc | 660 |
| gtggaattcc | atgtgtagcg | gtgaaatgcg | tagatatatg | gaggaacacc | agtggcgaag | 720 |
| gcgacgatct | ggcctgcaac | tgacgctcag | tcccgaaagc | gtgggagca | aataggatta | 780 |
| gataccctag | tagtccacgc | cgtaaacgat | gagtactaag | tgttggatgt | caaagttcag | 840 |
| tgctgcagtt | aacgcaataa | gtactccgcc | tgagtagtac | gttcgcaaga | atgaaactca | 900 |
| aaggaattga | cggggcccg | cacaagcggt | ggagcatgtg | gtttaattcg | aagcaacgcg | 960 |
| aagaaccta | ccaggtcttg | acatactcat | aaaggctcca | gagatggaga | gatagctata | 1020 |
| tgagatacag | gtggtgcatg | gttgtcgtca | gctcgtgtcg | tgagatgttg | ggttaagtcc | 1080 |
| cgcaacgagc | gcaaccctta | tcgttagtta | ccatcattaa | gttggggact | ctagcgagac | 1140 |
| tgccagtgac | aagctggagg | aaggcgggga | tgacgtcaaa | tcatcatgcc | ccttatgacc | 1200 |
| tgggctacac | acgtgctaca | atggatggtg | cagagggaag | cgaagccgcg | aggtgaagca | 1260 |
| aaacccataa | aaccattctc | agttcggatt | gtagtctgca | actcgactac | atgaagttgg | 1320 |
| aatcgctagt | aatcgcgaat | cagcatgtcg | cggtgaatac | gttctcgggc | cttgtacaca | 1380 |
| ccgcccgtca | caccacgaga | gttgataaca | cccgaagccg | gtggcctaac | cgcaaggaag | 1440 |
| gagctgtcta | aggtgggatt | gatgattggg | gtgaagtcgt | aacaaggtat | ccctacggga | 1500 |
| acgtggggat | ggatcacctc | cttt | | | | 1524 |

<210> SEQ ID NO 81
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 81

| | | | | | |
|---|---|---|---|---|---|
| atgagagttt | gatcctggct | caggatgaac | gctggcggcg | tgcctaacac | atgcaagtcg | 60 |
| aacgaagcaa | ttgaaggaag | ttttcggatg | gaattcgatt | gactgagtgg | cggacgggtg | 120 |
| agtaacgcgt | ggataacctg | cctcacactg | ggggataaca | gttagaaatg | actgctaata | 180 |
| ccgcataagc | gcacagtacc | gcatggtaca | gtgtgaaaaa | ctccggtggt | gtgagatgga | 240 |

```
tccgcgtctg attagccagt tggcggggta acggcccacc aaagcgacga tcagtagccg        300
acctgagagg gtgaccggcc acattgggac tgagacacgg cccaaactcc tacgggaggc        360
agcagtgggg aatattgcac aatgggcgaa agcctgatgc agcgacgccg cgtgagtgaa        420
gaagtatttc ggtatgtaaa gctctatcag cagggaagaa aatgacggta cctgactaag        480
aagccccggc taactacgtg ccagcagccg cggtaatacg tagggggcaa gcgttatccg        540
gatttactgg gtgtaaaggg agcgtagacg gcgaagcaag tctgaagtga aaacccaggg        600
ctcaaccctg ggactgcttt ggaaactgtt ttgctagagt gtcggagagg taagtggaat        660
tcctagtgta gcggtgaaat gcgtagatat taggaggaac accagtggcg aaggcggctt        720
actggacgat aactgacgtt gaggctcgaa agcgtgggga gcaaacagga ttagataccc        780
tggtagtcca cgccgtaaac gatgaatgct aggtgttggg gggcaaagcc ttcggtgcc         840 gtcgcaaacg cagtaagcat tccacctggg gagtacgttc gcaagaatga aactcaaagg        900
aattgacggg gacccgcaca agcggtggag catgtggttt aattcgaagc aacgcgaaga        960
accttaccaa gtcttgacat cctcttgacc ggcgtgtaac ggcgccttcc cttcggggca       1020
agagagacag gtggtgcatg gttgtcgtca gctcgtgtcg tgagatgttg ggttaagtcc       1080
cgcaacgagc gcaacccttta tccttagtag ccagcaggta aagctgggca ctctagggag       1140
actgccaggg ataacctgga ggaaggtggg gatgacgtca aatcatcatg ccccttatga       1200
tttgggctac acacgtgcta caatggcgta acaaaggga agcaagacag tgatgtggag       1260
caaatcccaa aaataacgtc ccagttcgga ctgtagtctg caacccgact acacgaagct       1320
ggaatcgcta gtaatcgcga atcagaatgt cgcggtgaat acgttcccgg gtcttgtaca       1380
caccgcccgt cacaccatgg gagtcagcaa cgcccgaagt cagtgaccca actcgcaaga       1440
gagggagctg ccgaaggcgg ggcaggtaac tggggtgaag tcgtaacaag gtagccgtat       1500
cggaaggtgc ggctggatca cctcctttt                                          1528
```

<210> SEQ ID NO 82
<211> LENGTH: 385
<212> TYPE: DNA
<213> ORGANISM: Artificial Sequence
<220> FEATURE:
<223> OTHER INFORMATION: Synthetic Polynucleotide

<400> SEQUENCE: 82

```
aattcgacgt tgtccggatt actgggcgta aagggagcgt aggcggactt ttaagtgaga         60
tgtgaaatac ccgggctcaa cttgggtgct gcatttcaaa ctggaagtct agagtgcagg        120
agaggagaat ggaattccta gtgtagcggt gaaatgcgta gagattagga agaaccccag        180
tggcgaaggc gattctctgg actgtaactg acgctgaggc tcgaaagcgt ggggagcaaa        240
caggattaga taccctggta gtccacgccg taaacgatga atactaggtg taggggttgt        300 catgaccctct gtgccgccgc taacgcatta agtattccgc ctggggagta cggtcgcaag       360
attaaaactc aaagaaattg acgga                                              385
```

<210> SEQ ID NO 83
<211> LENGTH: 434
<212> TYPE: DNA
<213> ORGANISM: Artificial Sequence
<220> FEATURE:
<223> OTHER INFORMATION: Synthetic Polynucleotide

<400> SEQUENCE: 83

```
acgagcgtat cggattattg ggtttaaggg agcgtaggtg gattgttaag tcagttgtga    60
aagtttgcgg ctcaaccgta aaattgcagt tgaaactggc agtcttgagt acagtagagg   120
tgggcggaat tcgtggtgta gcggtgaaat gcttagatat cacgaagaac tccgattgcg   180
aaggcagctc actagactgt cactgacact gatgctcgaa agtgtgggta tcaaacagga   240
ttagataccc tggtagtcca cacagtaaac gatgaatact cgctgtttgc gatatacagt   300
aagcggccaa gcgaaagcat taagtattcc acctggggag tacgccggca acggtgaaac   360
tcaaagaaat tgacggaagc ccgcccaggg gggaaaaaca tggggtttag ttggatgata   420
cggggaggaa cctc                                                     434

<210> SEQ ID NO 84
<211> LENGTH: 1457
<212> TYPE: DNA
<213> ORGANISM: Ruminococcus obeum
<220> FEATURE:
<221> NAME/KEY: misc_feature
<222> LOCATION: (65)..(66)
<223> OTHER INFORMATION: n is a, c, g, t or u
<220> FEATURE:
<221> NAME/KEY: misc_feature
<222> LOCATION: (960)..(960)
<223> OTHER INFORMATION: n is a, c, g, t or u

<400> SEQUENCE: 84
ggcggcgtgc ttaacacatg caagtcgaac gggaaacctt tcattgaagc ttcggcagat    60
ttggnntgtt tctagtggcg gacgggtgag taacgcgtgg gtaacctgcc ttatacaggg   120
ggataacaac cagaaatggt tgctaatacc gcataagcgc acaggaccgc atggtctggt   180
gtgaaaaact ccggtggtat aagatggacc cgcgttggat tagctagttg gcagggtaac   240
ggcctaccaa ggcgacgatc catagccggc ctgagagggt gaacggccac attgggactg   300
agacacggcc cagactccta cgggaggcag cagtggggaa tattgcacaa tgggggaaac   360
cctgatgcag cgacgccgcg tgaaggaaga agtatctcgg tatgtaaact tctatcagca   420
gggaagatag tgacggtacc tgactaagaa gccccggcta actacgtgcc agcagccgcg   480
gtaatacgta gggggcaagc gttatccgga tttactgggt gtaaagggag cgtagacgga   540
ctggcaagtc tgatgtgaaa ggcggggct caacccctgg actgcattgg aaactgttag   600
tcttgagtgc cggagaggta agcggaattc ctagtgtagc ggtgaaatgc gtagatatta   660
ggaggaacac cagtggcgaa ggcggcttac tggacggtaa ctgacgttga ggctcgaaag   720
cgtggggagc aaacaggatt agataccctg gtagtccacg ccgtaaacga tgattactag   780
gtgttgggga gcaaagctct tcggtgccgc cgcaaacgca ttaagtattc cacctgggga   840
gtacgttcgc aagaatgaaa ctcaaaggaa ttgacgggga cccgcacaag cggtggagca   900
tgtggtttaa ttcgaagcaa cgcgaagaac cttaccaagt cttgacatcc ctctgaccgn   960
cccttaaccg gatctttcct tcgggacagg ggagacaggt ggtgcatggt tgtcgtcagc  1020
tcgtgtcgtg agatgttggg ttaagtcccg caacgagcgc aacccctatc ccagtagcc   1080 agcagtccgg ctgggcactc tgaggagact gccaggata acctggagga aggcgggat   1140 gacgtcaaat catcatgccc cttatgattt gggctacaca cgtgctacaa tggcgtaaac  1200
aaagggaagc aagcctgcga aggtaagcaa atcccaaaaa taacgtccca gttcggactg  1260
cagtctgcaa ctcgactgca cgaagctgga atcgctagta atcgcggatc agaatgccgc  1320
ggtgaatacg ttcccgggtc ttgtacacac cgcccgtcac accatgggag tcagtaacgc  1380
ccgaagtcag tgacctaact gcaaagaagg agctgccgaa ggcgggaccg atgactgggg  1440
```
tgaagtcgta acaaggt        1457

<210> SEQ ID NO 85
<211> LENGTH: 1398
<212> TYPE: DNA
<213> ORGANISM: Ruminococcus obeum
<220> FEATURE:
<221> NAME/KEY: misc_feature
<222> LOCATION: (1083)..(1083)
<223> OTHER INFORMATION: n is a, c, g, t or u
<220> FEATURE:
<221> NAME/KEY: misc_feature
<222> LOCATION: (1207)..(1207)
<223> OTHER INFORMATION: n is a, c, g, t or u
<220> FEATURE:
<221> NAME/KEY: misc_feature
<222> LOCATION: (1233)..(1233)
<223> OTHER INFORMATION: n is a, c, g, t or u

<400> SEQUENCE: 85
ggcgtgctta acacatgcaa gtcgaacggg aaacttttca ttgaagcttc ggcagatttg        60
gtctgtttct agtggcggac gggtgagtaa cgcgtgggta acctgcctta tacaggggga       120
taacaaccag aaatggttgc taataccgca taagcgcaca ggaccgcatg gtctggtgtg       180
aaaaactccg gtggtataag atggacccgc gttggattag ctagttggca gggtaacggc       240
ctaccaaggc gacgatccat agccggcctg agagggtgaa cggccacatt gggactgaga       300
cacgcccag actcctcggg aggcagcagt ggggaatatt gcacaatggg ggaaaccctg       360
atgcagcgac gccgcgtgaa ggaagaagta tctcggtatg taaacttcta tcagcaggga       420
agatagtgac ggtacctgac taagaagccc cgkctaacta cgtgccagca gccgcggtaa       480
tacgtagggg gcaagcgtta tccggattta ctgggtgtaa agggagcgta gacggactgg       540
caagtctgat gtgaaaggcg ggggctcaac ccctggactg cattggaaac tgttagtctt       600
gagtgccgga gaggtaagcg gaattcctag tgtagcggtg aaatgcgtag atattaggag       660
gaacaccagt ggcgaaggcg gcttactgga cggtaactga cgttgaggct cgaaagcgtg       720
gggagcaaac aggattagat accctggtag tccacgccgc aaacgatgaa tactaggtgt       780
tggggagcaa agctcttcgg tgccgccgca aacgcattaa gtattccacc tggggagtac       840
gttcgcaaga atgaaactca aaggaattga cggggacccg cacaagcggt ggagcatgtg       900
gtttaattcg aagcaacgcg aagaaccttac caagtcttg acatccctct gaccgtccct       960
taaccggatc tttccttcgg gacaggggag acaggtggtg catggttgtc gtcagctcgt      1020
gtcgtgagat gttgggttaa gtcccgcaac gagcgcaacc cctatcccca gtagccagca      1080
gtncggctgg gcactctgag gagactgcca gggataacct ggaggaaggc ggggatgacg      1140
tcaaatcatc atgccccta tgatttgggc tacacacgtg ctacaatggc gtaaacaaag      1200
ggaagcnagc ctkcgraggt aagcaaatcc canaataac gtcccagttc ggactgcagt      1260
ctgcaactcg actgcacgaa gctggaatcg ctagtaatcg cggatcagaa tgccgcggtg      1320
aatacgttcc cgggtcttgt acacaccgcc cgtcacacca tgggagtcag taacgcccga      1380
agtcagtgac ctaactgc        1398

<210> SEQ ID NO 86
<211> LENGTH: 1472
<212> TYPE: DNA
<213> ORGANISM: Clostridium disporicum

<400> SEQUENCE: 86

```
gctcaggacg aacgctggcg gcgtgcctaa cacatgcaag tcgagcgagt tgattctctt    60
cggagatgaa gctagcggcg gacgggtgag taacacgtgg gcaacctgcc tcatagaggg   120
gaatagcctc ccgaaaggga gattaatacc gcataagatt gtagcttcgc atgaagtagc   180
aattaaagga gcaatccgct atgagatggg cccgcggcgc attagctagt tggtgaggta   240
acggctcacc aaggcgacga tgcgtagccg acctgagagg gtgatcggcc acattgggac   300
tgagacacgg cccagactcc tacgggaggc agcagtgggg aatattgcac aatgggggaa   360
accctgatgc agcaacgccg cgtgagtgat gacggccttc gggttgtaaa gctctgtctt   420
cagggacgat aatgacggta cctgaggagg aagccacggc taactacgtg ccagcagccg   480
cggtaatacg taggtggcga gcgttgtccg gatttactgg gcgtaaaggg agcgtaggcg   540 gactttaag tgagatgtga atacccggg ctcaacttgg gtgctgcatt tcaaactgga    600
agtctagagt gcaggagagg agaatggaat tcctagtgta gcggtgaaat gcgtagagat   660
taggaagaac accagtggcg aaggcgattc tctggactgt aactgacgct gaggctcgaa   720
agcgtgggga gcaaacagga ttagataccc tggtagtcca cgccgtaaac gatgaatact   780
aggtgtaggg gttgtcatga cctctgtgcc gccgctaacg cattaagtat tccgcctggg   840
gagtacggtc gcaagattaa aactcaaagg aattgacggg ggcccgcaca agcagcggag   900
catgtggttt aattcgaagc aacgcgaaga accttaccta gacttgacat ctcctgaatt   960 accgtaact ggggaagcca cttcggtggc aggaagacag tggtgcatg gttgtcgtca    1020 gctcgtgtcg tgagatgttg ggttaagtcc cgcaacgagc gcaaccctta ttgttagttg   1080
ctaccattta gttgagcact ctagcgagac tgcccgggtt aaccgggagg aaggtgggga   1140
tgacgtcaaa tcatcatgcc ccttatgtct agggctacac acgtgctaca atggcaagta   1200
caaagagaag caagaccgcg aggtggagca aaactcaaaa acttgtctca gttcggattg   1260
taggctgaaa ctcgcctaca tgaagctgga gttgctagta atcgcgaatc agcatgtcgc   1320
ggtgaatacg ttcccgggcc ttgtacacac cgcccgtcac accatgagag ttggcaatac   1380
ccaacgtacg tgatctaacc cgcaagggag gaagcgtcct aaggtagggt cagcgattgg   1440
ggtgaagtcg taacaaggta gccgtaggag aa                                 1472
```

<210> SEQ ID NO 87
<211> LENGTH: 1529
<212> TYPE: DNA
<213> ORGANISM: Clostridium scindens

<400> SEQUENCE: 87

```
gagagtttga tcctggctca ggatgaacgc tggcggcgtg cctaacacat gcaagtcgaa    60
cgaagcgcct ggccccgact tcttcggaac gaggagcctt gcgactgagt ggcggacggg   120
tgagtaacgc gtgggcaacc tgccttgcac tgggggataa cagccagaaa tggctgctaa   180
taccgcataa gaccgaagcg ccgcatggcg cggcggccaa agccccggcg gtgcaagatg   240
ggcccgcgtc tgattaggta gttggcgggg taacggccca ccaagccgac gatcagtagc   300
cgacctgaga gggtgaccgg ccacattggg actgagacac ggcccagact cctacgggag   360
gcagcagtgg ggaatattgc acaatggggg aaaccctgat gcagcgacgc cgcgtgaagg   420
atgaagtatt tcggtatgta aacttctatc agcagggaag aagatgacgg tacctgacta   480 agaagcccg gctaactacg tgccagcagc cgcggtaata cgtaggggc aagcgttatc    540 cggatttact gggtgtaaag ggagcgtaga cggcgatgca agccagatgt gaaagcccgg   600
ggctcaaccc cgggactgca tttggaactg cgtggctgga gtgtcggaga ggcaggcgga   660
```

```
attcctagtg tagcggtgaa atgcgtagat attaggagga acaccagtgg cgaaggcggc      720
ctgctggacg atgactgacg ttgaggctcg aaagcgtggg gagcaaacag gattagatac      780
cctggtagtc cacgccgtaa acgatgacta ctaggtgtcg ggtggcaagg ccattcggtg      840
ccgcagcaaa cgcaataagt agtccacctg gggagtacgt tcgcaagaat gaaactcaaa      900
ggaattgacg gggacccgca caagcggtgg agcatgtggt ttaattcgaa gcaacgcgaa      960
gaaccttacc tgatcttgac atcccgatgc caaagcgcgt aacgcgctct tcttcggaa      1020 catcggtgac aggtggtgca tggttgtcgt cagctcgtgt cgtgagatgt tgggttaagt     1080
cccgcaacga gcgcaacccc tatcttcagt agccagcatt ttggatgggc actctggaga     1140
gactgccagg gagaacctgg aggaaggtgg ggatgacgtc aaatcatcat gccccttatg     1200
accagggcta cacacgtgct acaatggcgt aaacaaaggg aggcgaaccc gcgaggtgg     1260 gcaaatccca aaataacgt ctcagttcgg attgtagtct gcaactcgac tacatgaagt     1320
tggaatcgct agtaatcgcg aatcagaatg tcgcggtgaa tacgttcccg ggtcttgtac     1380
acaccgcccg tcacaccatg ggagtcagta acgcccgaag ccggtgaccc aacccgtaag    1440
ggagggagcc gtcgaaggtg ggaccgataa ctggggtgaa gtcgtaacaa ggtagccgta    1500
tcggaaggtg cggctggatc acctcctc                                      1529

<210> SEQ ID NO 88
<211> LENGTH: 1456
<212> TYPE: DNA
<213> ORGANISM: Anaerostipes caccae

<400> SEQUENCE: 88
gcgcttaata catgtcaagt cgaacgaagc atttaggatt gaagttttcg gatggatttc       60
ctatatgact gagtggcgga cgggtgagta acgcgtgggg aacctgccct atacaggggg      120
ataacagctg gaaacggctg ctaataccgc ataagcgcac agaatcgcat gattcagtgt      180
gaaaagccct ggcagtatag gatggtcccg cgtctgatta gctggttggt gaggtaacgg      240
ctcaccaagg cgacgatcag tagccggctt gagagagtga acggccacat tgggactgag      300
acacggccca aactcctacg ggaggcagca gtggggaata ttgcacaatg ggggtaaacc     360
ctgatgcagc gacgccgcgt gagtgaagaa gtatttcggt atgtaaagct ctatcagcag     420
ggaagaaaac agacggtacc tgactaagaa gccccggcta actacgtgcc agcagccgcg     480
gtaatacgta gggggcaagc gttatccgga attactgggt gtaaagggtg cgtaggtggc     540
atggtaagtc agaagtgaaa gcccggggct taacccggg actgcttttg aaactgtcat     600
gctggagtgc aggagaggta agcggaattc ctagtgtagc ggtgaaatgc gtagatatta     660
ggaggaacac cagtggcgaa ggcggcttac tggactgtca ctgacactga tgcacgaaag     720
cgtggggagc aaacaggatt agataccctg gtagtccacg ccgtaaacga tgaatactag     780
gtgtcggggc gtagaggct tcggtgccgc agcaaacgca gtaagtattc cacctgggga    840
gtacgttcgc aagaatgaaa ctcaaaggaa ttgacgggga cccgcacaag cggtggagca    900
tgtggtttaa ttcgaagcaa cgcgaagaac cttacctggt cttgacatcc caatgaccga    960
accttaaccg gttttttctt tcgagacatt ggagacaggt ggtgcatggt tgtcgtcagc   1020
tcgtgtcgtg agatgttggg ttaagtcccg caacgagcgc aacccctatc tttagtagcc   1080
agcatttaag gtgggcactc tagagagact gccaggata acctgagga aggtggggac   1140 gacgtcaaat catcatgccc cttatggcca gggctacaca cgtgctacaa tggcgtaaac   1200
```

```
aaagggaagc gaagtcgtga ggcgaagcaa atcccagaaa taacgtctca gttcggattg    1260
tagtctgcaa ctcgactaca tgaagctgga atcgctagta atcgtgaatc agaatgtcac    1320
ggtgaatacg ttcccgggtc ttgtacacac cgcccgtcac accatgggag tcagtaacgc    1380
ccgaagtcag tgacccaacc gcaaggaggg agctgccgaa ggtgggaccg ataactgggg    1440
tgaagtcgta acaagg                                                    1456

<210> SEQ ID NO 89
<211> LENGTH: 1456
<212> TYPE: DNA
<213> ORGANISM: Marvinbryantia formatexigens

<400> SEQUENCE: 89
tggcggcgtg cttaacacat gcaagtcgag cgaagcattt taaatgaagt tttcggacgg      60
aatttaaaat gactgagcgg cggacgggtg agtaacgcgt ggataacctg ccttatacag     120
ggggataaca gccagaaatg gctgctaata ccgcataagc gcacggtacc gcatggtaca     180
gtgtgaaaaa ctccggtggt ataagatggg tccgcgttgg attaggcagt tggcggggta     240
aaggcccacc aaaccgacga tccatagccg gcctgagagg gtggacggcc acattgggac     300
tgagacacgg cccagactcc tacgggaggc agcagtgggg aatattgcac aatggggga     360 accctgatgc agcgacgccg cgtgggtgaa gaagtatttc ggtatgtaaa gccctatcag     420
cagggaagaa aatgacggta cctgaccaag aagccccggc taactacgtg ccagcagccg     480
cggtaatacg taggggcaa gcgttatccg gatttactgg gtgtaaaggg agcgtagacg     540
gccatgcaag tctggtgtga aaggcggggg ctcaaccccc ggactgcatt ggaaactgta     600
tggcttgagt gccggagagg taagcggaat tcctggtgta gcggtgaaat gcgtagatat     660
caggaggaac accagtggcg aaggcggctt actggacggt aactgacgtt gaggctcgaa     720
agcgtgggga gcaaacagga ttagataccc tggtagtcca cgccgtaaac gatgaatacc     780
aggtgtcggg ggacacggtc cttcggtgcc gcagcaaacg cactaagtat tccacctggg     840
gagtacgttc gcaagaatga aactcaaagg aattgacggg gacccgcaca agcggtggag     900
catgtggttt aattcgaagc aacgcgaaga accttaccag gtcttgacat ccggacgacc     960
ggacagtaac gtgtccttcc cttcggggcg tccgagacag gtggtgcatg gttgtcgtca    1020
gctcgtgtcg tgagatgttg ggttaagtcc cgcaacgagc gcaacccctg ttcccagtag    1080
ccagcattca ggatgggcac tctggggaga ctgccaggga taacctggag gaaggcgggg    1140
atgacgtcaa atcatcatgc cccttatgat ctgggctaca cacgtgctac aatggcgtga    1200
acagagggaa gcgaacccgc gaggggagc aaatcccaga ataacgtcc cagttcggat    1260 tgtagtctgc aacccggcta catgaagctg gaatcgctag taatcgcgga tcagcatgcc    1320
gcggtgaata cgttcccggg tcttgtacac accgcccgtc acaccatggg agtcggaaat    1380
gcccgaagtc agtgacccaa ccggaaggag ggagctgccg aaggcgggc cggtaactgg    1440 ggtgaagtcg taacaa                                                    1456

<210> SEQ ID NO 90
<211> LENGTH: 1568
<212> TYPE: DNA
<213> ORGANISM: Lactobacillus mucosae

<400> SEQUENCE: 90
agagtttgat cctggctcag gatgaacgcc ggcggtgtgc ctaatacatg caagtcgaac      60
gcgttggccc aactgattga acgtgcttgc acggacttga cgttggttta ccagcgagtg     120
```

```
gcggacgggt gagtaacacg taggtaacct gccccaaagc ggggggataac atttggaaac      180 agatgctaat accgcataac aatttgaatc gcatgattca aatttaaaag atggcttcgg      240
ctatcacttt gggatggacc tgcggcgcat tagcttgttg gtagggtaac ggcctaccaa      300
ggctgtgatg cgtagccgag ttgagagact gatcggccac aatggaactg agacacggtc      360
catactccta cgggaggcag cagtagggaa tcttccacaa tgggcgcaag cctgatggag      420
caacaccgcg tgagtgaaga agggtttcgg ctcgtaaagc tctgttgtta gagaagaacg      480
tgcgtgagag caactgttca cgcagtgacg gtatctaacc agaaagtcac ggctaactac      540
gtgccagcag ccgcggtaat acgtaggtgg caagcgttat ccggatttat tgggcgtaaa      600
gcgagcgcag gcggtttgat aagtctgatg tgaaagcctt tggcttaacc aaagaagtgc      660
atcggaaact gtcagacttg agtgcagaag aggacagtgg aactccatgt gtagcggtgg      720
aatgcgtaga tatatggaag aacaccagtg gcgaaggcgg ctgtctggtc tgcaactgac      780
gctgaggctc gaaagcatgg gtagcgaaca ggattagata ccctggtagt ccatgccgta      840
aacgatgagt gctaggtgtt ggagggtttc cgcccttcag tgccgcagct aacgcattaa      900
gcactccgcc tggggagtac gaccgcaagg ttgaaactca aaggaattga cgggggcccg      960
cacaagcggt ggagcatgtg gtttaattcg aagctacgcg aagaacctta ccaggtcttg     1020
acatcttgcg ccaaccctag agataggggcg tttccttcgg gaacgcaatg acaggtggtg     1080
catggtcgtc gtcagctcgt gtcgtgagat gttgggttaa gtcccgcaac gagcgcaacc     1140
cttgttacta gttgccagca ttcagttggg cactctagtg agactgccgg tgacaaaccg     1200
gaggaaggtg gggacgacgt cagatcatca tgccccttat gacctgggct acacacgtgc     1260
tacaatggac ggtacaacga gtcgcgaact cgcgagggca agctaatctc ttaaaaccgt     1320
tctcagttcg gactgcaggc tgcaactcgc ctgcacgaag tcggaatcgc tagtaatcgc     1380
ggatcagcat gccgcggtga atacgttccc gggccttgta cacaccgccc gtcacaccat     1440
gagagtttgc aacacccaaa gtcggtgggg taacccttcg gggagctagc cgcctaaggt     1500
ggggcagatg attagggtga agtcgtaaca aggtagccgt aggagaacct gcggctggat     1560
cacctcct                                                              1568

<210> SEQ ID NO 91
<211> LENGTH: 1508
<212> TYPE: DNA
<213> ORGANISM: Turicibacter sanguinis

<400> SEQUENCE: 91
agagtttgat catggctcag gatgaacgct ggcggcgtgc ctaatacatg caagtcgagc       60
gaaccacttc ggtggtgagc ggcgaacggg tgagtaacac gtaggttatc tgcccatcag      120
acggggacaa cgattggaaa cgatcgctaa taccggatag gacgaaagtt taaaggtgct      180
tcggcaccac tgatggatga gcctgcggcg cattagctag ttggtagggt aaaggcctac      240
caaggcgacg atgcgtagcc gacctgagag ggtgaacggc cacactggga ctgagacacg      300
gcccagactc ctacggggagg cagcagtagg gaatcttcgg caatgggcga aagcctgacc      360
gagcaacgcc gcgtgaatga tgaaggcctt cgggttgtaa aattctgtta taagggaaga      420
atggctctag taggaaatgg ctagagtgtg acggtacctt atgagaaagc cacggctaac      480
tacgtgccag cagccgcggt aatacgtagg tggcagcgtt atccggaat tattgggcgt      540 aaagagcgcg caggtggttg attaagtctg atgtgaaagc ccacggctta accgtggagg      600
```

| | |
|---|---|
| gtcattggaa actggtcaac ttgagtgcag aagagggaag tggaattcca tgtgtagcgg | 660 |
| tgaaatgcgt agagatatgg aggaacacca gtggcgaagg cggcttcctg gtctgtaact | 720 |
| gacactgagg cgcgaaagcg tggggagcaa acaggattag ataccctggt agtccacgcc | 780 |
| gtaaacgatg agtgctaagt gttgggggtc gaacctcagt gctgaagtta acgcattaag | 840 |
| cactccgcct ggggagtacg gtcgcaagac tgaaactcaa aggaattgac ggggacccgc | 900 |
| acaagcggtg gagcatgtgg tttaattcga agcaacgcga agaaccttac caggtcttga | 960 |
| cataccagtg accgtcctag agataggatt ttcccttcgg ggacaatgga tacaggtggt | 1020 |
| gcatggttgt cgtcagctcg tgtcgtgaga tgttgggtta agtcccgcaa cgagcgcaac | 1080 |
| ccctgtcgtt agttgccagc attcagttgg ggactctaac gagactgcca gtgacaaact | 1140 |
| ggaggaaggt ggggatgacg tcaaatcatc atgcccctta tgacctgggc tacacacgtg | 1200 |
| ctacaatggt tggtacaaag agaagcgaag cggtgacgtg gagcaaacct cataaagcca | 1260 |
| atctcagttc ggattgtagg ctgcaactcg cctacatgaa gttggaatcg ctagtaatcg | 1320 |
| cgaatcagca tgtcgcggtg aatacgttcc cgggtcttgt acacaccgcc cgtcacacca | 1380 |
| cgagagttta caacccccga agtcagtggc ctaaccgcaa ggagggagct gcctaaggtg | 1440 |
| gggtagatga ttggggtgaa gtcgtaacaa ggtatcccta ccggaaggtg gggttggatc | 1500 |
| acctcctt | 1508 |

<210> SEQ ID NO 92
<211> LENGTH: 1456
<212> TYPE: DNA
<213> ORGANISM: Roseburia faecis

<400> SEQUENCE: 92

| | |
|---|---|
| gatgaacgct ggcggcgtgc ttaacacatg caagtcgaac gaagcactct atttgatttt | 60 |
| cttcggaaat gaagattttg tgactgagtg gcggacgggt gagtaacgcg tgggtaacct | 120 |
| gcctcataca gggggataac agttggaaac gactgctaat accgcataag cgcacaggat | 180 |
| cgcatgatcc ggtgtgaaaa actccggtgg tatgagatgg acccgcgtct gattagccag | 240 |
| ttggcagggt aacggcctac caaagcgacg atcagtagcc gacctgagag ggtgaccggc | 300 |
| cacattggga ctgagacacg gcccaaactc ctacgggagg cagcagtggg gaatattgca | 360 |
| caatggggga acccctgatg cagcgacgcc gcgtgagcga agaagtattt cggtatgtaa | 420 |
| agctctatca gcagggaaga agaatgacgg tacctgacta agaagcaccg gctaaatacg | 480 |
| tgccagcagc cgcggtaata cgtatggtgc aagcgttatc cggatttact gggtgtaaag | 540 |
| ggagcgcagg cggtgcggca agtctgatgt gaaagcccgg ggctcaaccc cggtactgca | 600 |
| ttggaaactg tcgtactaga gtgtcggagg ggtaagtgga attcctagtg tagcggtgaa | 660 |
| atgcgtagat attaggagga acaccagtgg cgaaggcggc ttactggacg ataactgacg | 720 |
| ctgaggctcg aaagcgtggg gagcaaacag gattagatac cctggtagtc cacgccgtaa | 780 |
| acgatgaata ctaggtgtcg gggagcattg ctcttcggtg ccgcagcaaa cgcaataagt | 840 |
| attccacctg gggagtacgt tcgcaagaat gaaactcaaa ggaattgacg ggacccgca | 900 |
| caagcggtgg agcatgtggt ttaattcgaa gcaacgcgaa gaaccttacc aagtcttgac | 960 |
| atcccgatga cagagtatgt aatgtacytt ctcttcggag catcggtgac aggtggtgca | 1020 |
| tggttgtcgt cagctcgtgt cgtgagatgt tgggttaagt cccgcaacga gcgcaacccc | 1080 |
| tgtccttagt agccagcggt tcggccgggc actctaggga gactgccagg ataacctgg | 1140 |
| aggaaggcgg ggatgacgtc aaatcatcat gccccttatg acttgggcta cacacgtgct | 1200 |

```
acaatggcgt aaacaaaggg aagcggagcc gtgaggccga gcaaatctca aaaataacgt    1260
ctcagttcgg actgtagtct gcaacccgac tacacgaagc tggaatcgct agtaatcgca    1320
gatcagaatg ctgcggtgaa tacgttcccg ggtcttgtac acaccgcccg tcacaccatg    1380
ggagttggaa atgcccgaag tcagtgaccc aaccgcaagg agggagctgc cgaaggcagg    1440
ttcgataact ggggtg                                                   1456
```

<210> SEQ ID NO 93
<211> LENGTH: 1465
<212> TYPE: DNA
<213> ORGANISM: Flavonifractor plautii

<400> SEQUENCE: 93

```
cgctggcggc gtgcttaaca catgcaagtc gaacggggtg ctcatgacgg aggattcgtc      60
caatggattg agttacctag tggcggacgg gtgagtaacg cgtgaggaac ctgccttgga     120
gaggggaata acactccgaa aggagtgcta ataccgcatg aagcagttgg gtcgcatggc     180
tctgactgcc aaagatttat cgctctgaga tggcctcgcg tctgattagc tagtaggcgg     240
ggtaacggcc cacctaggcg acgatcagta gccggactga gaggttgacc ggccacattg     300
ggactgagac acggcccaga ctcctacggg aggcagcagt ggggaatatt gggcaatggg     360
cgcaagcctg acccagcaac gccgcgtgaa ggaagaaggc tttcggttg taaacttctt     420 ttgtcgggga cgaaacaaat gacggtaccc gacgaataag ccacggctaa ctacgtgcca     480
gcagccgcgg taatacgtag gtggcaagcg ttatccggat ttactgggtg taaagggcgt     540
gtaggcggga ttgcaagtca gatgtgaaaa ctgggggctc aacctccagc ctgcatttga     600
aactgtagtt cttgagtgct ggagaggcaa tcggaattcc gtgtgtagcg gtgaaatgcg     660
tagatatacg gaggaacacc agtggcgaag gcggattgct ggacagtaac tgacgctgag     720
gcgcgaaagc gtggggagca aacaggatta gataccctgg tagtccacgc cgtaaacgat     780
ggatactagg tgtgggggt ctgaccccct ccgtgccgca gttaacacaa taagtatccc     840
acctggggag tacgatcgca aggttgaaac tcaaaggaat tgacggggc ccgcacaagc     900 ggtggagtat gtggtttaat tcgaagcaac gcgaagaacc ttaccaggc ttgacatccc     960 actaacgagg cagagatgcg ttaggtgccc ttcggggaaa gtggagacag gtggtgcatg    1020
gttgtcgtca gctcgtgtcg tgagatgttg ggttaagtcc cgcaacgagc gcaaccctta    1080
ttgttagttg ctacgcaaga gcactctagc gagactgccg ttgacaaaac ggaggaaggt    1140
ggggacgacg tcaaatcatc atgccccta tgtcctgggc cacacacgta ctacaatggt    1200
ggttaacaga gggaggcaat accgcgaggt ggagcaaatc cctaaaagcc atcccagttc    1260
ggattgcagg ctgaaacccg cctgtatgaa gttggaatcg ctagtaatcg cggatcagca    1320
tgccgcggtg aatacgttcc cgggccttgt acacaccgcc cgtcacacca tgagagtcgg    1380
gaacacccga agtccgtagc ctaaccgcaa ggagggcgcg ccgaaggtg ggttcgataa    1440 ttggggtgaa gtcgtaacaa ggtag                                        1465
```

<210> SEQ ID NO 94
<211> LENGTH: 1438
<212> TYPE: DNA
<213> ORGANISM: Blautia wexlerae
<220> FEATURE:
<221> NAME/KEY: misc_feature
<222> LOCATION: (19)..(19)
<223> OTHER INFORMATION: n is a, c, g, t or u

<400> SEQUENCE: 94

```
caagtcgaac gggaattant ttattgaaac ttcggtcgat ttaatttaat tctagtggcg    60
gacgggtgag taacgcgtgg gtaacctgcc ttatacaggg ggataacagt cagaaatggc   120
tgctaatacc gcataagcgc acagagctgc atggctcagt gtgaaaaact ccggtggtat   180
aagatggacc cgcgttggat tagcttgttg gtggggtaac ggcccaccaa ggcgacgatc   240
catagccggc ctgagagggt gaacggccac attgggactg agacacgcc cagactccta    300
cgggaggcag cagtggggaa tattgcacaa tgggggaaac cctgatgcag cgacgccgcg   360
tgaaggaaga agtatctcgg tatgtaaact tctatcagca gggaagatag tgacggtacc   420
tgactaagaa gccccggcta actacgtgcc agcagccgcg gtaatacgta gggggcaagc   480
gttatccgga tttactgggt gtaaaggag cgtagacggt gtggcaagtc tgatgtgaaa    540
ggcatgggct caacctgtgg actgcattgg aaactgtcat acttgagtgc cggagggta    600
agcggaattc ctagtgtagc ggtgaaatgc gtagatatta ggaggaacac cagtggcgaa   660
ggcggcttac tggacggtaa ctgacgttga ggctcgaaag cgtggggagc aaacaggatt   720
agataccctg gtagtccacg ccgtaaacga tgaataacta ggtgtcgggt ggcaaagcca   780
ttcggtgccg tcgcaaacgc agtaagtatt ccacctgggg agtacgttcg caagaatgaa   840
actcaaagga attgacgggg acccgcacaa gcggtggagc atgtggttta attcgaagca   900
acgcgaagaa ccttaccaag tcttgacatc cgcctgaccg atccttaacc ggatctttcc   960
ttcgggacag gcgagacagg tggtgcatgg ttgtcgtcag ctcgtgtcgt gagatgttgg  1020
gttaagtccc gcaacgagcg caaccccctat cctcagtagc cagcatttaa ggtgggcact  1080
ctggggagac tgccagggat aacctggagg aaggcgggga tgacgtcaaa tcatcatgcc  1140
ccttatgatt tgggctacac acgtgctaca atggcgtaaa caagggaag cgagattgtg   1200
agatggagca atcccaaaa ataacgtccc agttcggact gtagtctgca acccgactac  1260
acgaagctgg aatcgctagt aatcgcggat cagaatgccg cggtgaatac gttcccgggt  1320
cttgtacaca ccgcccgtca ccatgggag tcagtaacg cccgaagtca gtgacctaac    1380
tgcaaagaag gagctgccga aggcgggacc gatgactggg gtgaagtcgt aacaaggt   1438
```

<210> SEQ ID NO 95
<211> LENGTH: 1365
<212> TYPE: DNA
<213> ORGANISM: Anaerotruncus colihominis

<400> SEQUENCE: 95

```
aacggagctt acgttttgaa gttttcggat ggatgaatgt aagcttagtg gcggacgggt    60
gagtaacacg tgagcaacct gccttttcaga gggggataac agccggaaac ggctgctaat   120
accgcatgat gttgcggggg cacatgcccc tgcaaccaaa ggagcaatcc gctgaaagat   180
gggctcgcgt ccgattagcc agttggcggg gtaacggccc accaaagcga cgatcggtag   240
ccggactgag aggttgaacg gccacattgg gactgagaca cggcccagac tcctacggga   300
ggcagcagtg ggggatattg cacaatgggc gaaagcctga tgcagcgacg ccgcgtgagg   360
gaagacggtc ttcggattgt aaacctctgt ctttggggaa gaaaatgacg gtacccaaag   420
aggaagctcc ggctaactac gtgccagcag ccgcggtaat acgtagggag caagcgttgt   480
ccggaattac tgggtgtaaa gggagcgtag gcgggatggc aagtagaatg ttaaatccat   540
cggctcaacc ggtggctgcg ttctaaactg ccgttcttga gtgaagtaga ggcaggcgga   600
attcctagtg tagcggtgaa atgcgtagat attaggagga acaccagtgg cgaaggcggc   660
```

| | |
|---|---:|
| ctgctgggct taactgacg ctgaggctcg aaagcgtggg gagcaaacag gattagatac | 720 |
| cctggtagtc cacgccgtaa acgatgatta ctaggtgtgg ggggactgac cccttccgtg | 780 |
| ccgcagttaa cacaataagt aatccacctg gggagtacgg ccgcaaggtt gaaactcaaa | 840 |
| ggaattgacg ggggcccgca caagcagtgg agtatgtggt ttaattcgaa gcaacgcgaa | 900 |
| gaaccttacc aggtcttgac atcggcgtaa tagcctagag agtaggtgaa gcccttcggg | 960 |
| gcatccagac aggtggtgca tggttgtcgt cagctcgtgt cgtgagatgt tgggttaagt | 1020 |
| cccgcaacga gcgcaaccct tattattagt tgctacgcaa gagcactcta atgagactgc | 1080 |
| cgttgacaaa acgaggaag gtggggatga cgtcaaatca tcatgcccct tatgacctgg | 1140 |
| gctacacacg tactacaatg gcactaaaac agagggcggc gacaccgcga ggtgaagcga | 1200 |
| atcccagaaa aagtgtctca gttcagattg caggctgcaa cccgcctgca tgaagtcgga | 1260 |
| attgctagta atcgcggatc agcatgccgc ggtgaatacg ttcccgggcc ttgtacacac | 1320 |
| cgcccgtcac accatgggag tccgggtaac acccgaagcc agtag | 1365 |

<210> SEQ ID NO 96
<211> LENGTH: 1404
<212> TYPE: DNA
<213> ORGANISM: Ruminococcus faecis

<400> SEQUENCE: 96

| | |
|---|---:|
| atgcaagtcg aacgaagcac cttgatttga ttcttcggat gaagatcttg gtgactgagt | 60 |
| ggcggacggg tgagtaacgc gtgggtaacc tgcctcatac aggggataa cagttagaaa | 120 |
| tgactgctaa taccgcataa gaccacagca ccgcatggtg caggggtaaa aactccggtg | 180 |
| gtatgagatg gacccgcgtc tgattaggta gttggtgggg taacggccta ccaagccgac | 240 |
| gatcagtagc cgacctgaga gggtgaccgg ccacattggg actgagacac ggcccaaact | 300 |
| cctacgggag gcagcagtgg ggaatattgc acaatggggg aaaccctgat gcagcgacgc | 360 |
| cgcgtgagcg atgaagtatt tcggtatgta aagctctatc agcagggaag aaaatgacgg | 420 |
| tacctgacta agaagcaccg gctaaatacg tgccagcagc cgcggtaata cgtatggtgc | 480 |
| aagcgttatc cggatttact gggtgtaaag ggagcgtaga cggagtggca agtctgatgt | 540 |
| gaaaacccgg ggctcaaccc cgggactgca ttggaaactg tcaatctaga gtaccggaga | 600 |
| ggtaagcgga attcctagtg tagcggtgaa atgcgtagat attaggagga acaccagtgg | 660 |
| cgaaggcggc ttactggacg gtaactgacg ttgaggctcg aaagcgtggg gagcaaacag | 720 |
| gattagatac cctggtagtc cacgccgtaa acgatgacta ctaggtgtcg ggcagcaaag | 780 |
| ctgttcggtg ccgcagcaaa cgcaataagt agtccacctg gggagtacgt tcgcaagaat | 840 |
| gaaactcaaa ggaattgacg gggacccgca caagcggtgg agcatgtggt ttaattcgaa | 900 |
| gcaacgcgaa gaaccttacc tgctcttgac atctccctga ccggcaagta atgttgcctt | 960 |
| tccttcggga cagggatgac aggtggtgca tggttgtcgt cagctcgtgt cgtgagatgt | 1020 |
| tgggttaagt cccgcaacga gcgcaacccc tatctttagt agccagcggt ttggccgggc | 1080 |
| actctagaga gactgccagg gataacctgg aggaaggtgg ggatgacgtc aaatcatcat | 1140 |
| gccccttatg agcagggcta cacacgtgct acaatgcgct aaacaaaggg aggcagaacc | 1200 |
| gcgaggtcga gcaaatccca aaaataacgt ctcagttcgg attgtagtct gcaactcgac | 1260 |
| tacatgaagc tggaatcgct agtaatcgcg aatcagaatg tcgcggtgaa tacgttcccg | 1320 |
| ggtcttgtac acaccgcccg tcacaccatg ggagtcagta acgcccgaag tcagtgaccc | 1380 |

```
                                              -continued
aaccgtaagg aggagctgcc gaag                                      1404

<210> SEQ ID NO 97
<211> LENGTH: 1316
<212> TYPE: DNA
<213> ORGANISM: Dorea longicatena

<400> SEQUENCE: 97
taacgcgtgg gtaacctgcc tcatacaggg ggataacagt tagaaatgac tgctaatacc   60
gcataagacc acgtaccgca tggtacagtg gtaaaaactc cggtggtatg agatggaccc  120
gcgtctgatt aggtagttgg tgggtaacg gcctaccaag ccgacgatca gtagccgacc   180
tgagagggtg accggccaca ttgggactga gacacggccc agactcctac gggaggcagc   240
agtggggaat attgcacaat ggaggaaact ctgatgcagc gacgccgcgt gaaggatgaa   300
gtatttcggt atgtaaactt ctatcagcag ggaagaaaat gacggtacct gactaagaag   360
ccccggctaa ctacgtgcca gcagccgcgg taatacgtag gggcaagcg ttatccggat    420 ttactgggtg taaagggagc gtagacggca cggcaagcca gatgtgaaaa gcccggggct   480
caaccccggg actgcatttg aactgctga gctagagtgt cggagaggca agtggaattc    540
ctagtgtagc ggtgaaatgc gtagatatta ggaggaacac cagtggcgaa ggcggcttgc   600
tggacgatga ctgacgttga ggctcgaaag cgtgggagc aaacaggatt agataccctg    660
gtagtccacg ccgtaaacga tgactgctag gtgtcgggtg gcaaagccat cggtgccgc    720 agctaacgca ataagcagtc cacctgggga gtacgttcgc aagaatgaaa ctcaaaggaa   780
ttgacgggga cccgcacaag cggtggagca tgtggtttaa ttcgaagcaa cgcgaagaac   840
cttacctgat cttgacatcc cgatgaccgc ttcgtaatgg aagttttct tcggaacatc    900 ggtgacaggt ggtgcatggt tgtcgtcagc tcgtgtcgtg agatgttggg ttaagtcccg   960
caacgagcgc aaccctatc ttcagtagcc agcaggttaa gctgggcact ctggagagac   1020
tgccagggat aacctggagg aaggtgggga tgacgtcaaa tcatcatgcc ccttatgacc   1080
agggctacac acgtgctaca atggcgtaaa caaagagaag cgaactcgcg agggtaagca   1140
aatctcaaaa ataacgtctc agttcggatt gtagtctgca actcgactac atgaagctgg   1200
aatcgctagt aatcgcagat cagaatgctg cggtgaatac gttcccgggt cttgtacaca   1260
ccgcccgtca caccatggga gtcataacgc ccgaagtcag tgacccaacc gtaagg       1316

<210> SEQ ID NO 98
<211> LENGTH: 1475
<212> TYPE: DNA
<213> ORGANISM: Clostridium innocuum
<220> FEATURE:
<221> NAME/KEY: misc_feature
<222> LOCATION: (905)..(905)
<223> OTHER INFORMATION: n is a, c, g, t or u
<220> FEATURE:
<221> NAME/KEY: misc_feature
<222> LOCATION: (942)..(942)
<223> OTHER INFORMATION: n is a, c, g, t or u

<400> SEQUENCE: 98
atggagagtt tgatcctggc tcaggatgaa cgctggcggc atgcctaata catgcaagtc    60
gaacgaagtc ttcaggaagc ttgcttccaa aaagacttag tggcgaacgg gtgagtaaca   120
cgtaggtaac ctgcccatgt gtccgggata actgctggaa acggtagcta aaaccggata   180
ggtatacgga gcgcatgctc tgtatattaa agcgcccttc aaggcgtgaa catggatgga   240
cctgcgacgc attagctagt tggtgaggta acggcccacc aaggcgatga tgcgtagccg   300
```

```
gcctgagagg gtaaacggcc acattgggac tgagacacgg cccaaactcc tacgggaggc      360
agcagtaggg aattttcgtc aatgggggaa accctgaacg agcaatgccg cgtgagtgaa      420
gaaggtcttc ggatcgtaaa gctctgttgt aagtgaagaa cggctcatag aggaaatgct      480
atgggagtga cggtagctta ccagaaagcc acggctaact acgtgccagy agccgcggta      540
atacgtaggt ggcaagcgtt atccggaatc attgggcgta aaggtgcgt aggtggcgta      600 ctaagtctgt agtaaaaggc aatggctcaa ccattgtaag ctatggaaac tggtatgctg      660
gagtgcagaa gagggcgatg gaattccatg tgtagcggta aaatgcgtag atatatggag      720
gaacaccagt ggcgaaggcg gtcgcctggt ctgtaactga cactgaggca cgaaagcgtg      780
gggagcaaat aggattagat accctagtag tccacgccgt aaacgatgag aactaagtgt      840
tggagaaatt cagtgctgca gttaacgcaa taagttctcc gcctgggag tatgcacgca      900 agttngaaac tcaaaggaat tgacgggggc ccgcacaagc gntggagtat gtggtttaat      960
tcgaagcaac gcgaagaacc ttaccaggcc ttgacatgga aacaaatacc ctagagatag     1020
ggggataatt atggatcaca caggtggtgc atggttgtcg tcagctcgtg tcgtgagatg     1080
ttgggttaag tcccgcaacg agcgcaaccc ttgtcgcatg ttaccagcat caagttgggg     1140
actcatgcga gactgccggt gacaaaccgg aggaaggtgg ggatgacgtc aaatcatcat     1200
gccccttatg gcctgggcta cacacgtact acaatggcga ccacaaagag cagcgacttg     1260
gtgacaagaa gcgaatctca taaagatcgt ctcagttcgg attgaagtct gcaactcgac     1320
ttcatgaagt cggaatcgct agtaatcgca gatcagcatg ctgcggtgaa tacgttctcg     1380
ggccttgtac acaccgcccg tcaaaccatg ggagtcagta atacccgaag ccggtggcat     1440
aaccgtaagg agtgagccgt cgaaggtagg accga                                1475

<210> SEQ ID NO 99
<211> LENGTH: 1492
<212> TYPE: DNA
<213> ORGANISM: Blautia hansenii

<400> SEQUENCE: 99
agagtttgat cctggctcag gatgaacgct ggcggcgtgc ttaacacatg caagtcgagc       60
gaagcactta tcattgactc ttcggaagat ttgatatttg actgagcggc ggacgggtga      120
gtaacgcgtg ggtaacctgc ctcatacagg ggaataacag ttagaaatgg ctgctaatgc      180
cgcataagcg cacaggaccg catggtctgg tgtgaaaaac tgaggtggta tgagatggac      240
ccgcgtctga ttaggtagtt ggtggggtaa cggcctacca agccgacgat cagtagccgg      300
cctgagaggg tgaacggcca cattgggact gagacacggc ccagactcct acgggaggca      360
gcagtgggga atattgcaca atgggggaaa ccctgatgca gcgacgccgc gtgaaggaag      420
aagtatctcg gtatgtaaac ttctatcagc agggaagaaa atgacggtac ctgactaaga      480
agccccggct aactacgtgc cagcagccgc ggtaatacgt aggggcaag cgttatccgg      540 atttactggg tgtaaaggga gcgtagacgg aagagcaagt ctgatgtgaa aggctggggc      600
ttaaccccag gactgcattg gaaactgttt ttctagagtg ccggagaggt aagcggaatt      660
cctagtgtag cggtgaaatg cgtagatatt aggaggaaca ccagtggcga aggcggctta      720
ctggacggta actgacgttg aggctcgaaa gcgtgggag caaacaggat tagataccct      780
ggtagtccac gccgtaaacg atgaatacta ggtgtcgggg tgcaaagcag ttcggtgccg      840
cagcaaacgc aataagtatt ccacctgggg agtacgttcg caagaatgaa actcaaagga      900
```

-continued

| | | |
|---|---|---|
| attgacgggg acccgcacaa gcggtggagc atgtggttta attcgaagca acgcgaagaa | 960 | |
| ccttaccaag tcttgacatc tgcctgaccg ttccttaacc ggagctttcc ttcgggacag | 1020 | |
| gcaagacagg tggtgcatgg ttgtcgtcag ctcgtgtcgt gagatgttgg gttaagtccc | 1080 | |
| gcaacgagcg caaccccta t ccttagtagc cagcagtccg gctgggcact ctagggagac | 1140 | |
| tgccggggat aacccggagg aaggcgggga cgacgtcaaa tcatcatgcc ccttatgatt | 1200 | |
| tgggctacac acgtgctaca atggcgtaaa caaagggaag cgaagcggtg acgcttagca | 1260 | |
| aatctcaaaa ataacgtccc agttcggact gcagtctgca actcgactgc acgaagctgg | 1320 | |
| aatcgctagt aatcgcgaat cagaatgtcg cggtgaatac gttcccgggt cttgtacaca | 1380 | |
| ccgcccgtca caccatggga gtcagtaacg cccgaagtca gtgacccaac cttatggagg | 1440 | |
| gagctgccga aggcgggacc gataactggg gtgaagtcgt aacaaggtaa cc | 1492 | |

<210> SEQ ID NO 100
<211> LENGTH: 1473
<212> TYPE: DNA
<213> ORGANISM: Bacteroides cellulosilyticus

<400> SEQUENCE: 100

| | | |
|---|---|---|
| agagtttgat cctggctcag gatgaacgct agctacaggc ttaacacatg caagtcgagg | 60 | |
| ggcagcatga cctagcaata ggttgatggc gaccggcgca cgggtgagta acacgtatcc | 120 | |
| aacctaccgg ttattccggg atagcctttc gaaagaaaga ttaataccgg atagtataac | 180 | |
| gagaaggcat cttttgtta ttaaagaatt tcgataaccg atgggatgc gttccattag | 240 | |
| tttgttggcg gggtaacggc ccaccaagac atcgatggat aggggttctg agaggaaggt | 300 | |
| cccccacatt ggaactgaga cacggtccaa actcctacgg gaggcagcag tgaggaatat | 360 | |
| tggtcaatgg acgagagtct gaaccagcca agtagcgtga aggatgactg ccctatgggt | 420 | |
| tgtaaacttc ttttatatgg gaataaagtg agccacgtgt ggcttttgt atgtaccata | 480 | |
| cgaataagga tcggctaact ccgtgccagc agccgcggta atacggagga tccgagcgtt | 540 | |
| atccggattt attgggttta aagggagcgt aggcggacta ttaagtcagc tgtgaaagtt | 600 | |
| tgcggctcaa ccgtaaaatt gcagttgata ctggtcgtct tgagtgcagt agaggtaggc | 660 | |
| ggaattcgtg gtgtagcggt gaaatgctta gatatcacga agaactccga ttgcgaaggc | 720 | |
| agcttactgg actgtaactg acgctgatgc tcgaaagtgt gggtatcaaa caggattaga | 780 | |
| taccctggta gtccacacag taaacgatga atactcgctg tttgcgatat acagcaagcg | 840 | |
| gccaagcgaa agcattaagt attccacctg gggagtacgc cggcaacggt gaaactcaaa | 900 | |
| ggaattgacg ggggcccgca caagcggagg aacatgtggt ttaattcgat gatacgcgag | 960 | |
| gaaccttacc cgggcttaaa ttgcatctga ataatttgga aacagattag ccgcaaggca | 1020 | |
| gatgtgaagg tgctgcatgg ttgtcgtcag ctcgtgccgt gaggtgtcgg cttaagtgcc | 1080 | |
| ataacgagcg caacccttat ctttagttac taacaggtca tgctgaggac tctagagaga | 1140 | |
| ctgccgtcgt aagatgtgag gaaggtgggg atgacgtcaa atcagcacgg cccttacgtc | 1200 | |
| cggggctaca cacgtgttac aatgggggt acagaaggca gctacacagc gatgtgatgc | 1260 | |
| taatcccaaa agcctctctc agttcggatt ggagtctgca acccgactcc atgaagctgg | 1320 | |
| attcgctagt aatcgcgcat cagccacggc gcggtgaata cgttcccggg ccttgtacac | 1380 | |
| accgcccgtc aagccatgaa agccgggggt acctgaagtc cgtaaccgca aggagcggcc | 1440 | |
| tagggtaaaa ctggtaattg ggctaagtc gta | 1473 | |

```
<210> SEQ ID NO 101
<211> LENGTH: 1459
<212> TYPE: DNA
<213> ORGANISM: Bacteroides ovatus

<400> SEQUENCE: 101
ggctcaggat gaacgctagc tacaggctta acacatgcaa gtcgagggc agcattttag      60 tttgcttgca aactgaagat ggcgaccggc gcacgggtga gtaacacgta tccaacctgc     120
cgataactcc ggaatagcct ttcgaaagaa agattaatac cggatagcat acgaatatcg     180
catgatattt ttattaaaga atttcggtta tcgatgggga tgcgttccat tagtttgttg     240
gcggggtaac ggcccaccaa gactacgatg dataggggtt ctgagaggaa ggtccccac      300 attggaactg agacacggtc caaactccta cgggaggcag cagtgaggaa tattggtcaa     360
tgggcgagag cctgaaccag ccaagtagcg tgaaggatga aggctctatg ggtcgtaaac     420 ttctttttata tgggaataaa gttttccacg tgtggaattt tgtatgtacc atatgaataa     480
ggatcggcta actccgtgcc agcagccgcg gtaatacgga ggatccgagc gttatccgga     540
tttattgggt ttaaagggag cgtaggtgga ttgttaagtc agttgtgaaa gtttgcggct     600
caaccgtaaa attgcagttg aaactggcag tcttgagtac agtagaggtg gcggaattc      660 gtggtgtagc ggtgaaatgc ttagatatca cgaagaactc cgattgcgaa ggcagctcac     720
tagactgtta ctgacactga tgctcgaaag tgtgggtatc aaacaggatt agataccctg     780
gtagtccaca cagtaaacga tgaatactcg ctgtttgcga tatacagtaa gcggccaagc     840
gaaagcatta agtattccac ctggggagta cgccggcaac ggtgaaactc aaaggaattg     900
acgggggccc gcacaagcgg aggaacatgt ggtttaattc gatgatacgc gaggaacctt     960
acccgggctt aaattgcaac agaatatatt ggaaacagta tagccgtaag gctgttgtga    1020
aggtgctgca tggttgtcgt cagctcgtgc cgtgaggtgt cggcttaagt gccataacga    1080
gcgcaaccct tatctttagt tactaacagg ttatgctgag gactctagag agactgccgt    1140
cgtaagatgt gaggaaggtg gggatgacgt caaatcagca cggcccttac gtccggggct    1200
acacacgtgt tacaatgggg ggtacagaag gcagctacct ggcgacagga tgctaatccc    1260
aaaaacctct ctcagttcgg atcgaagtct gcaacccgac ttcgtgaagc tggattcgct    1320
agtaatcgcg catcagccat ggcgcggtga atacgttccc gggccttgta cacaccgccc    1380
gtcaagccat gaaagccggg ggtacctgaa gtacgtaacc gcaaggagcg tcctagggta    1440
aaactggtaa ttggggcta                                                1459

<210> SEQ ID NO 102
<211> LENGTH: 1526
<212> TYPE: DNA
<213> ORGANISM: Eubacterium fissicatena

<400> SEQUENCE: 102
tagagtttga tcctggctca ggatgaacgc tggcggcgtg cttaacacat gcaagtcgag      60
cgaagcgctt tacttagatt tcttcggatt gaagagtttt gcgactgagc ggcggacggg     120
tgagtaacgc gtgggtaacc tgcctcatac aggggataa cagttagaaa tgactgctaa     180
taccgcataa gaccacagta ccgcatggta cagtgggaaa aactccggtg gtatgagatg     240
gacccgcgtc tgattagcta gttggtaagg taacggctta ccaaggcgac gatcagtagc     300
cgacctgaga gggtgaccgg ccacattggg actgagacac ggcccaaact cctacgggag     360
gcagcagtgg ggaatattgc acaatggggg aaaccctgat gcagcgacgc cgcgtgaagg     420
```

```
atgaagtatt tcggtatgta aacttctatc agcagggaag aaaatgacgg tacctgacta      480
agaagccccg gctaactacg tgccagcagc cgcggtaata cgtaggggc aagcgttatc       540 cggatttact gggtgtaaag ggagcgtaga cggttatgta agtctgatgt gaaaacccgg      600
ggctcaaccc cgggactgca ttggaaacta tgtaactaga gtgtcggaga ggtaagtgga     660
attcctagtg tagcggtgaa atgcgtagat attaggagga acaccagtgg cgaaggcggc     720
ttactggacg atcactgacg ttgaggctcg aaagcgtggg gagcaaacag gattagatac      780
cctggtagtc cacgccgtaa acgatgaata ctaggtgtcg ggtggcaaag ccattcggtg      840
ccgcagcaaa cgcaataagt attccacctg gggagtacgt tcgcaagaat gaaactcaaa      900
ggaattgacg gggacccgca caagcggtgg agcatgtggt ttaattcgaa gcaacgcgaa      960
gaaccttacc tgctcttgac atcccactga ccggcgtgta atggcgcctt cccttcgggg     1020
cagtggagac aggtggtgca tggttgtcgt cagctcgtgt cgtgagatgt tgggttaagt    1080
cccgcaacga gcgcaaccct tatctttagt agccagcggt ttggccgggc actctagaga     1140
gactgccagg gataacctgg aggaaggtgg ggatgacgtc aaatcatcat gccccttatg     1200
agcagggcta cacacgtgct acaatggcgt aaacaaaggg aggcaatacc gcgaggttga     1260
gcaaatccca aaaataacgt ctcagttcgg attgtagtct gcaactcgac tacatgaagc     1320
tggaatcgct agtaatcgcg aatcagaatg tcgcggtgaa tacgttcccg ggtcttgtac     1380
acaccgcccg tcacaccatg ggagttggta acgcccgaag tcagtgaccc aaccgtaagg    1440
agggagctgc cgaaggcggg atcgataact ggggtgaagt cgtaacaagg tagccgtatc     1500
ggaaggtgcg gctggatcac ctcctt                                          1526
```

<210> SEQ ID NO 103
<211> LENGTH: 1493
<212> TYPE: DNA
<213> ORGANISM: Blautia coccoides

<400> SEQUENCE: 103

```
agagtttgat cctggctcag gatgaacgct ggcggcgtgc ttaacacatg caagtcgagc       60
gaagcgctaa gacagatttc ttcggattga agtctttgtg actgagcggc ggacgggtga     120
gtaacgcgtg ggtaacctgc ctcatacagg gggataacag ttagaaatga ctgctaatac     180
cgcataagcg cacaggaccg catggtctgg tgtgaaaaac tccggtggta tgagatggac     240
ccgcgtctga ttagctagtt ggaggggtaa cggcccacca aggcgacgat cagtagccgg     300
cctgagaggg tgaacggcca cattgggact gagacacggc ccagactcct acgggaggca     360
gcagtgggga atattgcaca atgggggaaa ccctgatgca gcgacgccgc gtgaaggaag     420
aagtatctcg gtatgtaaac ttctatcagc agggaagaaa atgacggtac ctgactaaga     480
agccccggct aactacgtgc cagcagccgc ggtaatacgt aggggggcaag cgttatccgg      540 atttactggg tgtaaaggga gcgtagacgg aagagcaagt ctgatgtgaa aggctggggc      600
taacccccag gactgcattg gaaactgttg ttctagagtg ccgagaggt aagcggaatt       660 cctagtgtag cggtgaaatg cgtagatatt aggaggaaca ccagtggcga aggcggctta     720
ctggacggta actgacgttg aggctcgaaa gcgtggggag caaacaggat tagataccct     780
ggtagtccac gccgtaaacg atgaatacta ggtgtcgggt ggcaaagcca ttcggtgccg     840
cagcaaacgc aataagtatt ccacctgggg agtacgttcg caagaatgaa actcaaagga     900
attgacgggg acccgcacaa gcggtggagc atgtggttta attcgaagca acgcgaagaa     960
ccttaccaag tcttgacatc cctctgaccg tcccgtaacg ggggcttccc ttcggggcag    1020
```

```
aggagacagg tggtgcatgg ttgtcgtcag ctcgtgtcgt gagatgttgg gttaagtccc    1080
gcaacgagcg caacccttat ccttagtagc cagcacatga tggtgggcac tctagggaga    1140
ctgccgggga taacccggag gaaggcgggg acgacgtcaa atcatcatgc cccttatgat    1200
ttgggctaca cacgtgctac aatggcgtaa acaaagggaa gcgagacagc gatgttgagc    1260
gaatcccaaa aataacgtcc cagttcggac tgcagtctgc aactcgactg cacgaagctg    1320
gaatcgctag taatcgcgga tcagaatgcc gcggtgaata cgttcccggg tcttgtacac    1380
accgcccgtc acaccatggg agtcagtaac gcccgaagtc agtgacctaa ccgaaaggaa    1440
ggagctgccg aaggcgggac cgataactgg ggtgaagtcg taacaaggta acc           1493

<210> SEQ ID NO 104
<211> LENGTH: 1262
<212> TYPE: DNA
<213> ORGANISM: Blautia faecis

<400> SEQUENCE: 104
ataacagcca gaaatgactg ctaataccgc ataagcgcac agaaccgcat ggttcggtgt      60
gaaaaactcc ggtggtataa gatggacccg cgttggatta gctagttggc agggcagcgg    120
cctaccaagg cgacgatcca tagccggcct gagagggtga acggccacat tgggactgag    180
acacggccca gactcctacg ggaggcagca gtggggaata ttgcacaatg ggggaaaccc    240
tgatgcagcg acgccgcgtg aaggaagaag tatctcggta tgtaaacttc tatcagcagg    300
gaagataatg acggtacctg actaagaagc cccggctaac tacgtgccag cagccgcggt    360
aatacgtagg gggcaagcgt tatccggatt tactgggtgt aaagggagcg tagacggcgc    420
agcaagtctg atgtgaaagg caggggctta acccctggac tgcattggaa actgctgtgc    480
ttgagtgccg gaggggtaag cggaattcct agtgtagcgg tgaaatgcgt agatattagg    540
aggaacacca gtggcgaagg cggcttactg gacggtaact gacgttgagg ctcgaaagcg    600
tggggagcaa acaggattag ataccctggt agtccacgcc gtaaacgatg aatactaggt    660
gtcagggagc acagctcttt ggtgccgccg caaacgcatt aagtattcca cctggggagt    720
acgttcgcaa gaatgaaact caaaggaatt gacgggaccc gcacaagcg gtggagcatg     780 tggtttaatt cgaagcaacg cgaagaacct taccaaatct tgacatccct ctgaccggga    840
cttaaccgtc cctttccttc gggacagggg agacaggtgg tgcatggttg tcgtcagctc    900
gtgtcgtgag atgttgggtt aagtcccgca acgagcgcaa ccctatcct tagtagccag     960 cacgcartgg tgggcactct gaggagactg ccagggataa cctggaggaa ggcggggatg    1020
acgtcaaatc atcatgcccc ttatgatttg gctacacac gtgctacaat ggcgtaaaca    1080
aagggaagcg aacccgcgag ggtgggcaaa tctcaaaaat aacgtcccag ttcggactgc    1140
agtctgcaac tcgactgcac gaagctggaa tcgctagtaa tcgcggatca gaatgccgcg    1200
gtgaatacgt tcccgggtct tgtacacacc gcccgtcaca ccatgggagt cagtaacgcc    1260
cg                                                                   1262

<210> SEQ ID NO 105
<211> LENGTH: 1431
<212> TYPE: DNA
<213> ORGANISM: Clostridium hathewayi
<220> FEATURE:
<221> NAME/KEY: misc_feature
<222> LOCATION: (191)..(191)
<223> OTHER INFORMATION: n is a, c, g, t or u
<220> FEATURE:
```

```
<221> NAME/KEY: misc_feature
<222> LOCATION: (211)..(211)
<223> OTHER INFORMATION: n is a, c, g, t or u
<220> FEATURE:
<221> NAME/KEY: misc_feature
<222> LOCATION: (248)..(248)
<223> OTHER INFORMATION: n is a, c, g, t or u
<220> FEATURE:
<221> NAME/KEY: misc_feature
<222> LOCATION: (979)..(979)
<223> OTHER INFORMATION: n is a, c, g, t or u

<400> SEQUENCE: 105
ctcaggatga acgctggcgg cgtgcttaac acatgcaagt cgagcgaagc ggtttcaatg      60
aagttttcgg atggatttga aattgactta gcggcggacg ggtgagtaac gcgtgggtaa     120
cctgccttac actgggggat aacagttaga aatgactgct aataccgcat aagcgcacag     180
ggccgcatgg nctggtgtga aaaactccgg nggtgtaaga tggacccgcg tctgattagg     240
tagttggngg ggtaacggcc caccaagccg acgatcagta gccgacctga gagggtgacc     300
ggccacattg ggactgagac acggcccaaa ctcctacggg aggcagcagt ggggaatatt     360
ggacaatggg cgaaagcctg atccagcgac gccgcgtgag tgaagaagta tttcggtatg     420
taaagctcta tcagcaggga agaaaatgac ggtacctgac taagaagccc ggctaacta      480
cgtgccagca gccgcggtaa tacgtagggg gcaagcgtta tccggattta ctgggtgtaa     540
agggagcgta gacggtttag caagtctgaa gtgaaagccc ggggctcaac cccggtactg     600
ctttggaaac tgttagactt gagtgcagga gaggtaagtg gaattcctag tgtagcggtg     660
aaatgcgtag atattaggag gaacaccagt ggcgaaggcg gcttactgga ctgtaactga     720
cgttgaggct cgaaagcgtg gggagcaaac aggattagat accctggtag tccacgccgt     780
aaacgatgaa tactaggtgt cggggggcaa agcccttcgg tgccgccgca aacgcaataa     840
gtattccacc tggggagtac gttcgcaaga atgaaactca aaggaattga cggggacccg     900
cacaagcggt ggagcatgtg gtttaattcg aagcaacgcg aagaaccta ccaagtcttg      960
acatcccact gaaaacacnt taaccgtgat ccctcttcgg agcagtggag acaggtggtg     1020
catggttgtc gtcagctcgt gtcgtgagat gttgggttaa gtcccgcaac gagcgcaacc     1080
cttatcctta gtagccagcg agtagagtcg ggcactctgg ggagactgcc agggataacc     1140
tggaggaagg tggggatgac gtcaaatcat catgcccctt atgatttggg ctacacacgt     1200
gctacaatgg cgtaaacaaa gggaggcaaa ggagcgatct ggagcaaacc ccaaaaataa     1260
cgtctcagtt cggattgcag gctgcaactc gcctgcatga agctggaatc gctagtaatc     1320
gcgaatcaga atgtcgcggt gaatacgttc ccgggtcttg tacacaccgc ccgtcacacc     1380
atgggagttg gtaacgcccg aagtcagtga cccaaccgaa aggagggagc t              1431

<210> SEQ ID NO 106
<211> LENGTH: 1493
<212> TYPE: DNA
<213> ORGANISM: Blautia producta

<400> SEQUENCE: 106
agagtttgat cctggctcag gatgaacgct ggcggcgtgc ttaacacatg caagtcgagc      60
gaagcactaa gacggatttc ttcggattga agtctttgtg actgagcggc ggacgggtga     120
gtaacgcgtg gtaacctgc ctcatacagg gggataacag ttagaaatga ctgctaatac     180
cgcataagcg cacaggaccg catggtctgg tgtgaaaaac tccggtggta tgagatggac     240
ccgcgtctga ttagctagtt ggaggggtaa cggcccacca aggcgacgat cagtagccgg     300
```

-continued

```
cctgagaggg tgaacggcca cattgggact gagacacggc ccagactcct acgggaggca    360
gcagtgggga atattgcaca atgggggaaa ccctgatgca gcgacgccgc gtgaaggaag    420
aagtatctcg gtatgtaaac ttctatcagc agggaagaaa atgacggtac ctgactaaga    480
agccccggct aactacgtgc cagcagccgc ggtaatacgt aggggggcaag cgttatccgg    540 atttactggg tgtaaaggga gcgtagacgg aagagcaagt ctgatgtgaa aggctggggc    600
ttaaccccag gactgcattg gaaactgttg ttctagagtg ccgagaggt aagcggaatt     660 cctagtgtag cggtgaaatg cgtagatatt aggaggaaca ccagtggcga aggcggctta    720
ctggacggta actgacgttg aggctcgaaa gcgtggggag caaacaggat tagataccct    780
ggtagtccac gccgtaaacg atgaatacta ggtgtcgggt ggcaaagcca ttcggtgccg    840
cagcaaacgc aataagtatt ccacctgggg agtacgttcg caagaatgaa actcaaagga    900
attgacgggg acccgcacaa gcggtggagc atgtggttta attcgaagca acgcgaagaa    960
ccttaccaag tcttgacatc cctctgaccg tcccgtaacg ggacttccc ttcggggcag     1020 aggagacagg tggtgcatgg ttgtcgtcag ctcgtgtcgt gagatgttgg gttaagtccc    1080
gcaacgagcg caacccttat ccttagtagc cagcacatga tggtgggcac tctagggaga    1140
ctgccgggga taacccggag gaaggcgggg acgacgtcaa atcatcatgc cccttatgat    1200
ttgggctaca cacgtgctac aatggcgtaa acaaagggaa gcgagacagc gatgttgagc    1260
gaatcccaaa ataacgtcc cagttcggac tgcagtctgc aactcgactg cacgaagctg     1320
gaatcgctag taatcgcgga tcagaatgcc gcggtgaata cgttcccggg tcttgtacac    1380
accgcccgtc acaccatggg agtcagtaac gcccgaagtc agtgacctaa ccgaaaggaa    1440
ggagctgccg aaggcgggac cgataactgg ggtgaagtcg taacaaggta acc           1493
```

<210> SEQ ID NO 107
<211> LENGTH: 1515
<212> TYPE: DNA
<213> ORGANISM: Anaerostipes hadrus

<400> SEQUENCE: 107

```
tggctcagga tgaacgctgg cggcgtgctt aacacatgca agtcgaacga agctgcttaa     60
ctgatcttct tcggaattga cgttttgtag actgagtggc ggacgggtga gtaacgcgtg    120
ggcaacctgc cctgtacagg gggataacag tcagaaatga ctgctaatac cgcataagac    180
cacagcaccg catggtgcag gggtaaaaac tccggtggta caggatggac ccgcgtctga    240
ttagctggtt ggtgaggtaa cggctcacca aggcgacgat cagtagccgg cttgagagag    300
tgaacggcca cattgggact gagacacggc ccaaactcct acgggaggca gcagtgggga    360
atattgcaca atgggggaaa ccctgatgca gcgacgccgc gtgagtgaag aagtatctcg    420
gtatgtaaag ctctatcagc agggaagaaa atgacggtac ctgactaaga agccccggct    480
aactacgtgc cagcagccgc ggtaatacgt aggggcaag cgttatccgg aattactggg     540
tgtaaagggt gcgtaggtgg tatggcaagt cagaagtgaa acccagggc ttaactctgg     600 gactgctttt gaaactgtca gactggagtg caggagaggt aagcggaatt cctagtgtag    660
cggtgaaatg cgtagatatt aggaggaaca tcagtggcga aggcggctta ctggactgaa    720
actgacactg aggcacgaaa gcgtggggag caaacaggat tagataccct ggtagtccac    780
gccgtaaacg atgaatacta ggtgtcgggg ccgtagaggc ttcggtgccg cagccaacgc    840
agtaagtatt ccacctgggg agtacgttcg caagaatgaa actcaaagga attgacgggg    900
```

| | |
|---|---|
| acccgcacaa gcggtggagc atgtggttta attcgaagca acgcgaagaa ccttacctgg | 960 |
| tcttgacatc cttctgaccg gtccttaacc ggacctttcc ttcgggacag gagagacagg | 1020 |
| tggtgcatgg ttgtcgtcag ctcgtgtcgt gagatgttgg gttaagtccc gcaacgagcg | 1080 |
| caacccctat ctttagtagc cagcatttca ggtgggcact ctagagagac tgccagggat | 1140 |
| aacctggagg aaggtgggga cgacgtcaaa tcatcatgcc ccttatgacc agggctacac | 1200 |
| acgtgctaca atggcgtaaa cagagggaag cagcctcgtg agagtgagca atcccaaaa | 1260 |
| ataacgtctc agttcggatt gtagtctgca actcgactac atgaagctgg aatcgctagt | 1320 |
| aatcgcgaat cagaatgtcg cggtgaatac gttcccgggt cttgtacaca ccgcccgtca | 1380 |
| caccatggga gtcagtaacg cccgaagtca gtgacccaac cgtaaggagg gagctgccga | 1440 |
| aggcgggacc gataactggg gtgaagtcgt aacaaggtag ccgtatcgga aggtgcggct | 1500 |
| ggatcacctc ctttc | 1515 |

<210> SEQ ID NO 108
<211> LENGTH: 1523
<212> TYPE: DNA
<213> ORGANISM: Eubacterium fissicatena

<400> SEQUENCE: 108

| | |
|---|---|
| gtttgatcct ggctcaggat gaacgctggc ggcgtgctta acacatgcaa gtcgagcgaa | 60 |
| gcgctttact tagatttctt cggattgaag agttttgcga ctgagcggcg gacgggtgag | 120 |
| taacgcgtgg gtaacctgcc tcatacaggg ggataacagt tagaaatgac tgctaatacc | 180 |
| gcataagacc acagtaccgc atggtacagt gggaaaaact ccggtggtat gagatggacc | 240 |
| cgcgtctgat tagctagttg gtaaggtaac ggcttaccaa ggcaacgatc agtagccgac | 300 |
| ctgagagggt gaccggccac attgggactg agacacggcc caaactccta cgggaggcag | 360 |
| cagtggggaa tattgcacaa tgggggaaac cctgatgcag cgacgccgcg tgaaggatga | 420 |
| agtatttcgg tatgtaaact tctatcagca gggaagaaaa tgacggtacc tgactaagaa | 480 |
| gccccggcta actacgtgcc agcagccgcg gtaatacgta gggggcaagc gttatccgga | 540 |
| tttactgggt gtaaagggag cgtagacggt tatgtaagtc tgatgtgaaa acccggggct | 600 |
| caaccccggg actgcattgg aaactatgta actagagtgt cggagaggta agtggaattc | 660 |
| ctagtgtagc ggtgaaatgc gtagatatta ggaggaacac cagtggcgaa ggcggcttac | 720 |
| tggacgatca ctgacgttga ggctcgaaag cgtggggagc aaacaggatt agataccctg | 780 |
| gtagtccacg ccgtaaacga tgaatactag gtgtcgggtg gcaaagccat tcggtgccgc | 840 |
| agcaaacgca ataagtattc cacctgggga gtacgttcgc aagaatgaaa ctcaaaggaa | 900 |
| ttgacgggga cccgcacaag cggtggagca tgtggtttaa ttcgaagcaa cgcgaagaac | 960 |
| cttacctgct cttgacatcc cactgaccgg cgtgtaatgg cgcttccct tcggggcagt | 1020 |
| ggagacaggt ggtgcatggt tgtcgtcagc tcgtgtcgtg agatgttggg ttaagtcccg | 1080 |
| caacgagcgc aaccccttatc tttagtagcc agcggtttgg ccgggcactc tagagagact | 1140 |
| gccagggata acctggagga aggtgggggat gacgtcaaat catcatgccc cttatgagca | 1200 |
| gggctacaca cgtgctacaa tggcgtaaac aaagggaggc aataccgcga ggttgagcaa | 1260 |
| atcccaaaaa taacgtctca gttcggattg tagtctgcaa ctcgactaca tgaagctgga | 1320 |
| atcgctagta atcgcgaatc agaatgtcgc ggtgaatacg ttcccgggtc ttgtacacac | 1380 |
| cgcccgtcac accatgggag ttggtaacgc ccgaagtcag tgacccaacc gtaaggaggg | 1440 |
| agctgccgaa ggcgggatcg ataactgggg tgaagtcgta acaaggtagc cgtatcggaa | 1500 | ggtgcggctg gatcacctcc ttt    1523

<210> SEQ ID NO 109
<211> LENGTH: 1524
<212> TYPE: DNA
<213> ORGANISM: Eubacterium contortum

<400> SEQUENCE: 109
tttgatcctg gctcaggatg aacgctggcg acgtgcttaa cacatgcaag tcgagcgaag      60
cactttactt tgatttcttc ggaatgaaag gttttgtgac tgagcggcgg acgggtgagt     120
aacgcgtggg taacctgcct catacagggg gataacagtt agaaatgact gctaataccg     180
cataagacca cagtaccgca tggtacagtg ggaaaaactc cggtggtatg agatggaccc     240
gcgtctgatt agctagttgg taaggtaacg gcttaccaag cgacgatca gtagccgacc      300 tgagagggtg accggccaca ttgggactga dacacggccc aaactcctac gggaggcagc     360
agtggggaat attgcacaat gggggaaacc ctgatgcagc gacgccgcgt gaaggatgaa     420
gtatttcggt atgtaaactt ctatcagcag ggaagaaaat gacggtacct gactaagaag     480
ccccggctaa ctacgtgcca gcagccgcgg taatacgtag gggcaagcg ttatccggat      540 ttactgggtg taagggagc gtagacggtt atgtaagtct gatgtgaaaa cccggggctc     600
aaccccggga ctgcattgga aactatgtaa ctagagtgtc ggagaggtaa gtggaattcc     660
tagtgtagcg gtgaaatgcg tagatattag gaggaacacc agtggcgaag gcggcttact     720
ggacgatgac tgacgttgag gctcgaaagc gtggggagca acaggatta gatacctgg      780 tagtccacgc cgtaaacgat gaatactagg tgtcgggtgg caaagccatt cggtgccgca     840
gcaaacgcaa taagtattcc acctggggag tacgttcgca agaatgaaac tcaaaggaat     900
tgacggggac ccgcacaagc ggtggagcat gtggtttaat tcgaagcaac gcgaagaacc     960
ttacctgctc ttgacatccc cctgaccggc gtgtaatggt gcctttcctt cgggacaggg    1020
gagacaggtg gtgcatggtt gtcgtcagct cgtgtcgtga gatgttgggt taagtcccgc    1080
aacgagcgca accttatct ttagtagcca gcggtttggc cgggcactct agagagactg     1140
ccagggataa cctggaggaa ggtggggatg acgtcaaatc atcatgcccc ttatgagcag    1200
ggctacacac gtgctacaat ggcgtaaaca aagggaggcg aagccgtgag gtggagcaaa    1260
tcccaaaaat aacgtctcag ttcggattgt agtctgcaac tcgactacat gaagctggaa    1320
tcgctagtaa tcgcgaatca gaatgtcgcg gtgaatacgt tcccgggtct tgtacacacc    1380
gcccgtcaca ccatgggagt tggtaacgcc cgaagtcagt gacccaaccg caaggaggga    1440
gctgccgagg gtgggaccga taactggggt gaagtcgtaa caaggtagcc gtatcggaag    1500
gtgcggctgg atcacctcct ttct                                          1524

<210> SEQ ID NO 110
<211> LENGTH: 1390
<212> TYPE: DNA
<213> ORGANISM: Clostridium bolteae

<400> SEQUENCE: 110
ttttaattga ctgagtggcg gacgggtgag taacgcgtgg ataacctgcc tcacactggg      60
ggataacagt tagaaatgac tgctaatacc gcataagcgc acagtaccgc atggtacagt     120
gtgaaaaact ccgtggtgt gagatggatc cgcgtctgat tagccagttg gcggggtaac     180
ggcccaccaa agcgacgatc agtagccgac ctgagagggt gaccggccac attgggactg     240

```
agacacggcc caaactccta cgggaggcag cagtgggaa tattgcacaa tgggcgaaag      300
cctgatgcag cgacgccgcg tgagtgaaga agtatttcgg tatgtaaagc tctatcagca      360
gggaagaaaa tgacggtacc tgactaagaa gccccggcta actacgtgcc agcagccgcg      420
gtaatacgta gggggcaagc gttatccgga tttactgggt gtaaagggag cgtagacggc      480
gaagcaagtc tgaagtgaaa acccagggct caaccctggg actgctttgg aaactgtttt      540
gctagagtgt cggagaggta agtggaattc ctagtgtagc ggtgaaatgc gtagatatta      600
ggaggaacac cagtggcgaa ggcggcttac tggacgataa ctgacgttga ggctcgaaag      660
cgtgggagc aaacaggatt agataccctg gtagtccacg ccgtaaacga tgaatgctag      720
gtgttggggg gcaaagccct tcggtgccgt cgcaaacgca gtaagcattc cacctgggga      780
gtacgttcgc aagaatgaaa ctcaaaggaa ttgacgggga cccgcacaag cggtggagca      840
tgtggtttaa ttcgaagcaa cgcgaagaac cttaccaagt cttgacatcc tcttgaccgg      900
cgtgtaacgg cgccttccct cggggcaag agagacaggt ggtgcatggt tgtcgtcagc      960
tcgtgtcgtg agatgttggg ttaagtcccg caacgagcgc aacccttatc cttagtagcc     1020
agcaggtaaa gctgggcact ctagggagac tgccagggat aacctggagg aaggtgggga     1080
tgacgtcaaa tcatcatgcc ccttatgatt tgggctacac acgtgctaca atggcgtaaa     1140
caaagggaag caagacagtg atgtggagca atcccaaaa ataacgtccc agttcggact     1200
gtagtctgca acccgactac acgaagctgg aatcgctagt aatcgcgaat cagaatgtcg     1260
cggtgaatac gttcccgggt cttgtacaca ccgcccgtca ccatgggga gtcagcaacg     1320
cccgaagtca gtgacccaac tcgcaagaga gggagctgcc gaaggcgggg caggtaactg     1380
gggtgaagtc                                                             1390
```

<210> SEQ ID NO 111
<211> LENGTH: 1308
<212> TYPE: DNA
<213> ORGANISM: Blautia luti
<220> FEATURE:
<221> NAME/KEY: misc_feature
<222> LOCATION: (702)..(705)
<223> OTHER INFORMATION: n is a, c, g, t or u

<400> SEQUENCE: 111

```
gtgggtaacc tgccttatac aggggataa cagtcagaaa tgactgctaa taccgcataa       60
gcgcacagag ctgcatggct ccggtgtgaa aaactccggt ggtataagat ggacccgcgt      120
tggattagct agttggtgag gtaacggccc accaaggcga cgatccatag ccggcctgag      180
agggtgaacg gccacattgg gactgagaca cggcccagac tcctacggga ggcagcagtg      240
gggaatattg cacaatgggg gaaaccctga tgcagcgacg ccgcgtgaag gaagaagtat      300
ctcggtatgt aaacttctat cagcagggaa gaaaatgacg gtacctgact aagaagcccc      360
ggctaactac gtgccagcag ccgcggtaat acgtagggggg caagcgttat ccggatttac      420
tgggtgtaaa gggagcgtag acggcatgga caagtctgat gtgaaaggct ggggctcaac      480
cccgggactg cattggaaac tgcccgtctt gagtgccgga gaggtaagcg gaattcctag      540
tgtagcggtg aaatgcgtag atattaggag gaacaccagt ggcgaaggcg cttactgga      600
cggtaactga cgttgaggct cgaaagcgtg gggagcaaac aggattagat accctggtag      660
tccacgcgt aaacgatgaa tcctaggtgt cggggagcaa annnnttcgg tgccgccgca      720
aacgcattaa gcattccacc tggggagtac gttcgcaaga atgaaactca aggaattga      780
cggggacccg cacaagcggt ggagcatgtg gtttaattcg aagcaacgcg aagaaccttaa     840
```

-continued

```
ccaagtcttg acatccctct gaccgagtat gtatggtact tttccttcgg gagagagagg    900
agacaggtgg tgcatggttg tcgtcagctc gtgtcgtgag atgttgggtt aagtcccgca    960
acgagcgcaa ccctatccc cagtagccag cggttcggcc gggcactctg aggagactgc    1020
cagggataac ctggaggaag gcggggatga cgtcaaatca tcatgcccct tatgatttgg    1080
gctacacacg tgctacaatg gcgtaaacaa agggaagcaa gcctgcgagg gtgggcaaat    1140
cccaaaaata acgtcccagt tcggactgta gtctgcaacc cgactacacg aagctggaat    1200
cgctagtaat cgcggatcag aatgccgcgg tgaatacgtt cccgggtctt gtacacaccg    1260
cccgtcacac catgggagtc agtaacgccc gaagtcagtg acctaact                 1308

<210> SEQ ID NO 112
<211> LENGTH: 1489
<212> TYPE: DNA
<213> ORGANISM: Acidaminococcus intestini

<400> SEQUENCE: 112
ctggcggcgt gcttaacaca tgcaagtcga acggagaact tatttcggta agttcttagt    60
ggcgaacggg tgagtaacgc gtgggcaacc tgccctccag ttggggacaa cattccgaaa    120
gggatgctaa taccgaatgt cctccctcct ccgcatggag gagggaggaa agatggcctc    180
tgcttgcaag ctatcgctgg aagatgggcc cgcgtctgat tagctagttg gtggggtaac    240
ggctcaccaa ggcgatgatc agtagccggt ctgagaggat gaacggccac attgggactg    300
agacacggcc caaactccta cgggaggcag cagtggggaa tcttccgcaa tggacgaaag    360
tctgacggag caacgccgcg tgagtgatga aggtcttcgg attgtaaaac tctgttgtta    420
gggacgaaag caccgtgttc gaacaggtca tggtgttgac ggtacctaac gaggaagcca    480
cggctaacta cgtgccagca gccgcggtaa tacgtaggtg gcaagcgttg tccggaatta    540
ttgggcgtaa agagcatgta ggcgggcttt taagtctgac gtgaaaatgc ggggcttaac    600
cccgtatggc gttggatact ggaagtcttg agtgcaggag aggaaagggg aattcccagt    660
gtagcggtga aatgcgtaga tattgggagg aacaccagtg gcgaaggcgc ctttctggac    720
tgtgtctgac gctgagatgc gaaagccagg gtagcaaacg ggattagata ccccggtagt    780
cctggccgta aacgatggat actaggtgta ggaggtatcg accccttctg tgccggagtt    840
aacgcaataa gtatcccgcc tggggactac gatcgcaaga ttgaaactca aaggaattga    900
cgggggcccg cacaagcggt ggagtatgtg gtttaattcg acgcaacgcg aagaaccttg    960
ccaaggcttg acattgagtg aaagaccttag agataggtcc ctcccttcgg ggacacgaaa    1020
acaggtggtg catggctgtc gtcagctcgt gtcgtgagat gttgggttaa gtcccgcaac    1080
gagcgcaacc cctatcctat gttaccagcc gtaaaggcg gggactcata ggagactgcc    1140
agggataact ggaggaagg cggggatgac gtcaagtcat catgcccctt atgtcttggg    1200
ctacacacgt actacaatgg tcggcaacaa agggcagcga accgcgagg tggagcaaat    1260
cccagaaacc cgaccccagt tcggatcgta ggctgcaacc cgcctacgtg aagttggaat    1320
cgctagtaat cgcaggtcag catactgcgg tgaatacgtt cccgggcctt gtacacaccg    1380
cccgtcacac cacgaaagtt ggtaacaccc gaagccggtg agataacctt ttaggagtca    1440
gctgtctaag gtggggccga tgattggggt gaagtcgtaa caaggtagc                1489

<210> SEQ ID NO 113
<211> LENGTH: 1500
<212> TYPE: DNA
```

<213> ORGANISM: Ruminococcus albus

<400> SEQUENCE: 113

```
agagtttgat cctggctcag gacgaacgct ggcggcacgc ttaacacatg caagtcgaac    60
gagcgaaaga gtgcttgcac tctctagcta gtggcggacg ggtgagtaac acgtgagcaa   120
tctgcctttc ggagagggat accaattgga aacgattgtt aatacctcat aacataacga   180
agccgcatga ctttgttatc aaatgaattt cgccgaaaga tgagctcgcg tctgattagg   240
tagttggtga ggtaacggcc caccaagccg acgatcagta gccggactga gaggttgaac   300
ggccacattg ggactgagac acggcccaga ctcctacggg aggcagcagt ggggaatatt   360
gcacaatggg cgaaagcctg atgcagcgat gccgcgtgag ggaagaaggt tttaggattg   420
taaacctctg tctttgggga cgataatgac ggtacccaag gaggaagctc cggctaacta   480
cgtgccagca gccgcggtaa tacgtaggga gcgagcgttg tccggaatta ctgggtgtaa   540
agggagcgta ggcgggattg caagtcaggt gtgaaattta ggggcttaac ccctgaactg   600
cacttgaaac tgtagttctt gagtgaagta gaggtaagcg gaattcctag tgtagcggtg   660
aaatgcgtag atattaggag gaacatcagt ggcgaaggcg gcttactggg ctttaactga   720
cgctgaggct cgaaagcgtg gggagcaaac aggattagat accctggtag tccacgccgt   780
aaacgatgat tactaggtgt gggggactg accccttccg tgccgcagtt aacacaataa   840
gtaatccacc tggggagtac ggccgcaagg ctgaaactca aaggaattga cggggacccg   900
cacaagcagt ggagtatgtg gtttaattcg aagcaacgcg aagaaccta ccaggtcttg   960
acatcgtacg catagcatag agatatgtga aatcccttcg gggacgtata gacaggtggt  1020
gcatggttgt cgtcagctcg tgtcgtgaga tgttggggtt aagtcccgca acgagcgcaa  1080
cccttactgt tagttgctac gcaagagcac tctagcagga ctgccgttga caaaacggag  1140
gaaggtgggg atgacgtcaa atcatcatgc cccttatgac ctgggctaca cacgtactac  1200
aatggctgtt aacagaggga agcaaaacag tgatgtggag caaaacccta aaagcagtct  1260
tagttcggat tgtaggctgc aacccgccta catgaagtcg gaattgctag taatcgcgga  1320
tcagcatgcc gcggtgaata cgttcccggg ccttgtacac accgcccgtc acgccatggg  1380
agtcggtaac acccgaagcc tgtgttctaa ccgcaaggag gaagcagtcg aaggtgggat  1440
tgatgactgg ggtgaagtcg taacaaggta gccgtatcgg aaggtgcggc tggatcacct  1500
```

<210> SEQ ID NO 114
<211> LENGTH: 1521
<212> TYPE: DNA
<213> ORGANISM: Eubacterium rectale

<400> SEQUENCE: 114

```
agagtttgat cctggctcag gatgaacgct ggcggcgtgc ttaacacatg caagtcgaac    60
gaagcacttt atttgatttc cttcgggact gattattttg tgactgagtg gcggacgggt   120
gagtaacgcg tgggtaacct gccttgtaca ggggataac agttggaaac ggctgctaat   180
accgcataag cgcacggcat cgcatgatgc agtgtgaaaa actccggtgg tataagatgg   240
acccgcgttg gattagctag ttggtgaggt aacggcccac caaggcgacg atccatagcc   300
gacctgagag ggtgaccggc cacattggga ctgagacacg gcccaaactc ctacgggagg   360
cagcagtggg gaatattgca caatgggcga aagcctgatg cagcgacgcc gcgtgagcga   420
agaagtattt cggtatgtaa agctctatca gcagggaaga taatgacggt acctgactaa   480
gaagcaccgg ctaaatacgt gccagcagcc gcggtaatac gtatggtgca agcgttatcc   540
```

```
ggatttactg ggtgtaaagg gagcgcaggc ggtgcggcaa gtctgatgtg aaagcccggg     600
gctcaacccc ggtactgcat tggaaactgt cgtactagag tgtcggaggg gtaagcggaa     660
ttcctagtgt agcggtgaaa tgcgtagata ttaggaggaa caccagtggc gaaggcggct     720
tactggacga taactgacgc tgaggctcga aagcgtgggg agcaaacagg attagatacc     780
ctggtagtcc acgccgtaaa cgatgaatac taggtgttgg gaagcattgc ttctcggtgc     840
cgtcgcaaac gcagtaagta ttccacctgg ggagtacgtt cgcaagaatg aaactcaaag     900
gaattgacgg ggacccgcac aagcggtgga gcatgtggtt taattcgaag caacgcgaag     960
aaccttacca agtcttgaca tccttctgac cggtacttaa ccgtaccttc tcttcggagc    1020
aggagtgaca ggtggtgcat ggttgtcgtc agctcgtgtc gtgagatgtt gggttaagtc    1080
ccgcaacgag cgcaacccct tatctttagta gccagcggtt cggccgggca ctctagagag    1140
actgccaggg ataacctgga ggaaggcggg gatgacgtca atcatcatg ccccttatga    1200 cttgggctac acacgtgcta caatggcgta aacaaaggga agcaaagctg tgaagccgag    1260
caaatctcaa aaataacgtc tcagttcgga ctgtagtctg caacccgact acacgaagct    1320
ggaatcgcta gtaatcgcag atcagaatgc tgcggtgaat acgttcccgg gtcttgtaca    1380
caccgcccgt cacaccatgg gagttgggaa tgcccgaagc cagtgaccta accgaaagga    1440
aggagctgtc gaaggcaggc tcgataactg gggtgaagtc gtaacaaggt agccgtatcg    1500
gaaggtgcgg ctggatcacc t                                              1521

<210> SEQ ID NO 115
<211> LENGTH: 1545
<212> TYPE: DNA
<213> ORGANISM: Acidaminococcus fermentans

<400> SEQUENCE: 115
agagtttgat cctggctcag gacgaacgct ggcggcgtgc ttaacacatg caagtcgaac      60
ggagaacttt cttcggaatg ttcttagtgg cgaacgggtg agtaacgcgt aggcaacctg     120
ccctctggtt ggggacaaca ttccgaaagg gatgctaata ccgaatgaga tcctcttttcc    180 gcatggagag aggatgaaag atggcctcta cttgtaagct atcgccagaa gatgggcctg     240
cgtctgatta gctagtaggt gaggtaacgg ctcacctagg cgatgatcag tagccggtct     300
gagaggatga acggccacat tgggactgag acacggccca aactcctacg ggaggcagca     360
gtggggaatc ttccgcaatg gacgaaagtc tgacggagca acgccgcgtg agtgatgaag     420
gccttcgggt tgtaaaactc tgttgtcagg gacgaaagca ccgatctata atacattttg     480
gtgttgacgg tacctgacga ggaagccacg gctaactacg tgccagcagc cgcggtaata     540
cgtaggtggc aagcgttgtc cggaattatt gggcgtaaag agcatgtagg cgggcttttta    600 agtccgacgt gaaaatgcgg ggcttaaccc cgtatggcgt tggatactgg aagtcttgag     660
tgcaggagag gaaaggggaa ttcccagtgt agcggtgaaa tgcgtagata ttgggaggaa     720
caccagtggc gaaggcgcct ttctggactg tgtctgacgc tgagatgcga aagccagggt     780
agcaaacggg attagatacc ccggtagtcc tggccgtaaa cgatgggtac taggtgtagg     840
aggtatcgac ccctctgtg ccggagttaa cgcaataagt accccgcctg gggactacga    900
tcgcaagatt gaaactcaaa ggaattgacg gggcccgca caagcggtgg agtatgtggt      960
ttaattcgac gcaacgcgaa gaaccttacc aaggcttgac attgagtgaa agacccagag    1020
atgggtcccc ttcttcggaa gcacgaaaac aggtggtgca tggctgtcgt cagctcgtgt    1080
```

```
cgtgagatgt tgggttaagt cccgcaacga gcgcaaccct tatcctatgt taccagcacg    1140
taatggtggg gactcatagg agactgccag ggataacctg gaggaaggcg gggatgacgt    1200
caagtcatca tgccccttat gtcttgggct acacacgtac tacaatggtc ggcaacaaag    1260
ggcagcgaag ccgcgaggcg gagccaatcc cagaaacccg accccagttc ggatcgcagg    1320
ctgcaacccg cctgcgtgaa gttggaatcg ctagtaatcg caggtcagca tactgcggtg    1380
aatacgttcc cgggccttgt acacaccgcc cgtcacacca cgaaagttgg taacacccga    1440
agccggtgag ataacctttt aggagtcagc tgtctaaggt ggggccgatg attggggtga    1500
agtcgtaaca aggtagccgt tcgagaacga gcggctggat cacct                   1545
```

<210> SEQ ID NO 116
<211> LENGTH: 1423
<212> TYPE: DNA
<213> ORGANISM: Fusicatenibacter saccharivorans

<400> SEQUENCE: 116

```
tggctcagga tgaacgctgg cggcgtgctt aacacatgca agtcgagcga agcagttaag     60
aagattyttc ggatgattct tgactgactg agcggcggac gggtgagtaa cgcgtgggtg    120
acctgcccca taccggggga taacagctgg aaacggctgc taataccgca taagcgcaca    180
gagctgcatg gctcggtgtg aaaaactccg gtggtatggg atgggcccgc gtctgattag    240
gcagttggcg gggtaacggc ccaccaaacc gacgatcagt agccggcctg agagggcgac    300
cggccacatt gggactgaga cacggcccaa actcctacgg gaggcagcag tggggaatat    360
tgcacaatgg gggaaaccct gatgcagcga cgccgcgtga cgaagaagt atttcggtat    420 gtaaagctct atcagcaggg aagataatga cggtacctga ctaagaagcc ccggctaact    480
acgtgccagc agccgcggta atacgtaggg gcaagcgtt atccggattt actgggtgta    540
aagggagcgt agacggcaag gcaagtctga tgtgaaaacc cagggcttaa ccctgggact    600
gcattggaaa ctgtctggct cgagtgccgg agaggtaagc ggaattccta gtgtagcggt    660
gaaatgcgta gatattagga agaacaccag tggcgaaggc ggcttactgg acggtaactg    720
acgttgaggc tcgaaagcgt ggggagcaaa caggattaga taccctggta gtccacgccg    780
taaacgatga atgctaggtg ttggggagca agctcttcg gtgccgccgc aaacgcatta    840
agcattccac ctggggagta cgttcgcaag aatgaaactc aaaggaattg acggggaccc    900
gcacaagcgg tggagcatgt ggtttaattc gaagcaacgc gaagaacctt accaggtctt    960
gacatcccga tgaccggccc gtaacgggc cttctcttcg gagcattgga gacaggtggt    1020
gcatggttgt cgtcagctcg tgtcgtgaga tgttgggtta agtcccgcaa cgagcgcaac    1080
ccttatcctc agtagccagc aggtaaagct gggcactctg tggagactgc cagggataac    1140
ctggaggaag gtggggatga cgtcaaatca tcatgcccct tatgatctgg gctacacacg    1200
tgctacaatg gcgtaaacaa agggaggcaa agccgcgagg tggagcaaat cccaaaaata    1260
acgtctcagt tcggactgca gtctgcaact cgactgcacg aagctggaat cgctagtaat    1320
cgcgaatcag aatgtcgcgg tgaatacgtt cccgggtctt gtacacaccg cccgtcacac    1380
catgggagtt ggtaacgccc gaagtcagtg acccaacctt tta                    1423
```

<210> SEQ ID NO 117
<211> LENGTH: 1494
<212> TYPE: DNA
<213> ORGANISM: Ruminococcus champanellensis

<400> SEQUENCE: 117

-continued

| | |
|---|---|
| agagtttgat cctggctcag gacgaacgct ggcggcacgc ctaacacatg caagtcgaac | 60 |
| ggagataaag acttcggttt ttatcttagt ggcggacggt gagtaacac gtgagcaacc | 120 |
| tgcctctgag agaggatag cttctggaaa cggatggtaa tacctcataa catagcggta | 180 |
| ccgcatgata ctgctatcaa agatttatcg ctcagagatg ggctcgcgtc tgattagcta | 240 |
| gatggtgagg taacggctca ccatggcgac gatcagtagc cggactgaga ggttgaacgg | 300 |
| ccacattggg actgagacac ggcccagact cctacgggag gcagcagtgg ggaatattgc | 360 |
| acaatgggcg caagcctgat gcagcgatgc cgcgtggagg aagaaggttt tcggattgta | 420 |
| aactcctgtc ttaagggacg ataatgacgg taccttagga ggaagctccg gctaactacg | 480 |
| tgccagcagc cgcggtaata cgtagggagc gagcgttgtc cggaattact gggtgtaaag | 540 |
| ggagcgtagg cgggattgca agtcagatgt gaaaactatg ggcttaaccc atagactgca | 600 |
| tttgaaactg tagttcttga gtgaagtaga ggtaagcgga attcctagtg tagcggtgaa | 660 |
| atgcgtagat attaggagga acatcggtgg cgaaggcggc ttactgggct tttactgacg | 720 |
| ctgaggctcg aaagcgtggg gagcaaacag gattagatac cctggtagtc cacgctgtaa | 780 |
| acgatgatta ctaggtgtgg ggggactgac cccttccgtg ccgcagttaa cacaataagt | 840 |
| aatccacctg gggagtacgg ccgcaaggtt gaaactcaaa ggaattgacg ggggcccgca | 900 |
| caagcagtgg agtatgtggt ttaattcgaa gcaacgcgaa aaaccttacc aggtcttgac | 960 |
| atcgagtgaa tgatctagag atagatcagt ccttcgggac acaaagacag gtggtgcatg | 1020 |
| gttgtcgtca gctcgtgtcg tgagatgttg ggttaagtcc cgcaacgagc gcaacccttg | 1080 |
| cctttagttg ctacgcaaga gcactctaga gggactgccg ttgacaaaac ggaggaaggt | 1140 |
| ggggatgacg tcaaatcatc atgcccctta tgacctgggc tacacacgta ctacaatggc | 1200 |
| aatgaacaga gggaagcaat acagtgatgt ggagcaaatc cccaaaaatt gtcccagttc | 1260 |
| agattgtagg ctgcaactcg cctacatgaa gtcggaattg ctagtaatcg cagatcagca | 1320 |
| tgctgcggtg aatacgttcc cgggccttgt acacaccgcc cgtcacacca tgggagtcgg | 1380 |
| taacacccga agccagtagc ctaaccgcaa ggagggcgct gtcgaaggtg ggattgatga | 1440 |
| ctggggtgaa gtcgtaacaa ggtagccgta tcggaaggtg cggctggatc acct | 1494 |

<210> SEQ ID NO 118
<211> LENGTH: 1533
<212> TYPE: DNA
<213> ORGANISM: Bifidobacterium bifidum

<400> SEQUENCE: 118

| | |
|---|---|
| tttttgtgga gggttcgatt ctggctcagg atgaacgctg gcggcgtgct taacacatgc | 60 |
| aagtcgaacg ggatccatcg ggctttgctt ggtggtgaga gtggcgaacg ggtgagtaat | 120 |
| gcgtgaccga cctgccccat gctccggaat agctcctgga aacgggtggt aatgccggat | 180 |
| gttccacatg atcgcatgtg attgtgggaa agattctatc ggcgtgggat ggggtcgcgt | 240 |
| cctatcagct tgttggtgag gtaacggctc accaaggctt cgacgggtag ccggcctgag | 300 |
| agggcgaccg gccacattgg gactgagata cggcccagac tcctacggga ggcagcagtg | 360 |
| gggaatattg cacaatgggc gcaagcctga tgcagcgacg ccgcgtgagg gatggaggcc | 420 |
| ttcgggttgt aaacctcttt tgtttgggag caagccttcg ggtgagtgta cctttcgaat | 480 |
| aagcgccggc taactacgtg ccagcagccg cggtaatacg tagggcgcaa gcgttatccg | 540 |
| gatttattgg gcgtaaaggg ctcgtaggcg gctcgtcgcg tccggtgtga agtccatcg | 600 |

| | |
|---|---|
| cttaacggtg gatctgcgcc gggtacgggc gggctggagt gcggtagggg agactggaat | 660 |
| tcccggtgta acggtggaat gtgtagatat cgggaagaac accgatggcg aaggcaggtc | 720 |
| tctgggccgt cactgacgct gaggagcgaa agcgtgggga gcgaacagga ttagataccc | 780 |
| tggtagtcca cgccgtaaac ggtggacgct ggatgtgggg cacgttccac gtgttccgtg | 840 |
| tcggagctaa cgcgttaagc gtcccgcctg gggagtacgg ccgcaaggct aaaactcaaa | 900 |
| gaaattgacg ggggcccgca caagcggcgg agcatgcgga ttaattcgat gcaacgcgaa | 960 |
| gaaccttacc tgggcttgac atgttcccga cgacgccaga gatggcgttt cccttcgggg | 1020 |
| cgggttcaca ggtggtgcat ggtcgtcgtc agctcgtgtc gtgagatgtt gggttaagtc | 1080 |
| ccgcaacgag cgcaaccctc gccccgtgtt gccagcacgt tatggtggga actcacgggg | 1140 |
| gaccgccggg gttaactcgg aggaaggtgg ggatgacgtc agatcatcat gccccttacg | 1200 |
| tccagggctt cacgcatgct acaatggccg gtacagcggg atgcgacatg gcgacatgga | 1260 |
| gcggatccct gaaaaccggt ctcagttcgg atcggagcct gcaacccggc tccgtgaagg | 1320 |
| cggagtcgct agtaatcgcg gatcagcaac gccgcgtgta atgcgttccc gggccttgta | 1380 |
| cacaccgccc gtcaagtcat gaaagtgggc agcacccgaa gccggtggcc taacccctcg | 1440 |
| tgggatggag ccgtctaagg tgaggctcgt gattgggact aagtcgtaac aaggtagccg | 1500 |
| taccggaagg tgcggctgga tcacctcctt tct | 1533 |

<210> SEQ ID NO 119
<211> LENGTH: 1552
<212> TYPE: DNA
<213> ORGANISM: Megasphaera elsdenii

<400> SEQUENCE: 119

| | |
|---|---|
| agagtttgat cctggctcag gacgaacgct ggcggcgtgc ttaacacatg caagtcgaac | 60 |
| gagaagagat gagaagcttg cttcttatca attcgagtgg caaacgggtg agtaacgcgt | 120 |
| aagcaacctg cccttcagat ggggacaaca gctggaaacg gctgctaata ccgaatacgt | 180 |
| tcttttttgtc gcatggcaga gggaagaaag ggaggctctt cggagctttc gctgaaggag | 240 |
| gggcttgcgt ctgattagct agttggaggg gtaacggccc accaaggcga cgatcagtag | 300 |
| ccggtctgag aggatgaacg gccacattgg gactgagaca cggcccagac tcctacggga | 360 |
| ggcagcagtg gggaatcttc cgcaatggac gaaagtctga cggagcaacg ccgcgtgaac | 420 |
| gatgacggcc ttcgggttgt aaagttctgt tatacgggac gaatggcgta gcggtcaata | 480 |
| cccgttacga gtgacggtac cgtaagagaa agccacggct aactacgtgc cagcagccgc | 540 |
| ggtaatacgt aggtggcaag cgttgtccgg aattattggg cgtaaagggc gcgcaggcgg | 600 |
| cgtcgtaagt cggtcttaaa agtgcggggc ttaacccgt gaggggaccg aaactgcgat | 660 |
| gctagagtat cggagaggaa agcggaattc ctagtgtagc ggtgaaatgc gtagatatta | 720 |
| ggaggaacac cagtggcgaa agcggctttc tggacgacaa ctgacgctga ggcgcgaaag | 780 |
| ccaggggagc aaacgggatt agataccccg gtagtcctgg ccgtaaacga tggatactag | 840 |
| gtgtaggagg tatcgacccc ttctgtgccg gagttaacgc aataagtatc cgcctgggg | 900 |
| agtacgccg caaggctgaa actcaaagga attgacgggg gcccgcacaa gcggtggagt | 960 |
| atgtggttta attcgacgca acgcgaagaa ccttaccaag ccttgacatt gattgctatg | 1020 |
| gatagagata tccagttcct cttcggagga caagaaaaca ggtggtgcac ggctgtcgtc | 1080 |
| agctcgtgtc gtgagatgtt gggttaagtc ccgcaacgag cgcaacccct atcttctgtt | 1140 |
| accagcggtt cggccgggga ctcaggagag actgccgcag acaatgcgga ggaaggcggg | 1200 |

```
gatgacgtca agtcatcatg ccccttatgg cttgggctac acacgtacta caatggctct    1260
taatagaggg aagcgaagga gcgatccgga gcaaacccca aaaacagagt cccagttcgg    1320
attgcaggct gcaactcgcc tgcatgaagc aggaatcgct agtaatcgca ggtcagcata    1380
ctgcggtgaa tacgttcccg ggccttgtac acaccgcccg tcacaccacg aaagtcattc    1440
acacccgaag ccggtgaggt aacctttttgg agccagccgt cgaaggtggg ggcgatgatt    1500
ggggtgaagt cgtaacaagg tagccgtatc ggaaggtgcg gctggatcac ct           1552
```

<210> SEQ ID NO 120
<211> LENGTH: 1479
<212> TYPE: DNA
<213> ORGANISM: Dorea formicigenerans
<220> FEATURE:
<221> NAME/KEY: misc_feature
<222> LOCATION: (123)..(125)
<223> OTHER INFORMATION: n is a, c, g, t or u
<220> FEATURE:
<221> NAME/KEY: misc_feature
<222> LOCATION: (220)..(222)
<223> OTHER INFORMATION: n is a, c, g, t or u
<220> FEATURE:
<221> NAME/KEY: misc_feature
<222> LOCATION: (287)..(287)
<223> OTHER INFORMATION: n is a, c, g, t or u
<220> FEATURE:
<221> NAME/KEY: misc_feature
<222> LOCATION: (349)..(350)
<223> OTHER INFORMATION: n is a, c, g, t or u
<220> FEATURE:
<221> NAME/KEY: misc_feature
<222> LOCATION: (517)..(517)
<223> OTHER INFORMATION: n is a, c, g, t or u
<220> FEATURE:
<221> NAME/KEY: misc_feature
<222> LOCATION: (534)..(535)
<223> OTHER INFORMATION: n is a, c, g, t or u
<220> FEATURE:
<221> NAME/KEY: misc_feature
<222> LOCATION: (725)..(725)
<223> OTHER INFORMATION: n is a, c, g, t or u
<220> FEATURE:
<221> NAME/KEY: misc_feature
<222> LOCATION: (918)..(918)
<223> OTHER INFORMATION: n is a, c, g, t or u
<220> FEATURE:
<221> NAME/KEY: misc_feature
<222> LOCATION: (921)..(921)
<223> OTHER INFORMATION: n is a, c, g, t or u
<220> FEATURE:
<221> NAME/KEY: misc_feature
<222> LOCATION: (955)..(956)
<223> OTHER INFORMATION: n is a, c, g, t or u
<220> FEATURE:
<221> NAME/KEY: misc_feature
<222> LOCATION: (1184)..(1185)
<223> OTHER INFORMATION: n is a, c, g, t or u

<400> SEQUENCE: 120

```
ttaaacgaga gtttgatcct ggctcaggat gaacgctggc ggcgtgctta acacatgcaa      60
gtcgagcgaa gcacataagt ttgattcttc ggatgaagac ttttgtgact gagcggcgga     120
cgnnngagta acgcgtgggt aacctgcctc atacagggggg ataacagyta gaaatggctg    180
ctaataccgc ataagaccac agtactgcat ggtacagtgn nnaaaactcc ggtggtatga    240
gatggacccg cgtctgatta ggtagttggt gaggtaacgg cccaccnagc cgacgatcag    300
tagccgacct gagagggtga ccggccacat tgggactgag acacggccnn gactcctacg    360
ggaggcagca gtggggaata ttgcacaatg ggcgaaagcc tgatgcagcg acgccgcgtg    420
```

| | |
|---|---|
| aaggatgaag tatttcggta tgtaaacttc tatcagcagg gaagaaaatg acggtacctg | 480 |
| actaagaagc cccggctaac tacgtgccag cagccgnggt aatacgtagg gggnnagcgt | 540 |
| tatccggatt tactgggtgt aaagggagcg tagacggctg tgcaagtctg aagtgaaagg | 600 |
| catgggctca acctgtggac tgctttggaa actgtgcagc tagagtgtcg gagaggtaag | 660 |
| tggaattcct agtgtagcgg tgaaatgcgt agatattagg aggaacacca gtggcgaagg | 720 |
| cggcntactg gacgatgact gacgttgagg ctcgaaagcg tggggagcaa acaggattag | 780 |
| ataccctggt agtccacgcc gtaaacgatg actgctaggt gtcgggtagc aaagctattc | 840 |
| ggtgccgcag ctaacgcaat aagcagtcca cctggggagt acgttcgcaa gaatgaaact | 900 |
| caaaggaatt gacggggncc ngcacaagcg gtggagcatg tggtttaatt cgaannaacg | 960 |
| cgaagaacct tacctgatct tgacatcccg atgaccgctt cgtaatggaa gyttttcttc | 1020 |
| ggaacatcgg tgacaggtgg tgcatggttg tcgtcagctc gtgtcgtgag atgttgggtt | 1080 |
| aagtcccgca acgagcgcaa cccttatctt cagtagccag catttaggat gggcactctg | 1140 |
| gagagactgc cagggataac ctggaggaag gtggggatga cgtnnaatca tcatgcccct | 1200 |
| tatgaccagg gctacacacg tgctacaatg gcgtaaacag agggaggcag agccgcgagg | 1260 |
| ccgagcaaat ctcaaaaata acgtctcagt tcggattgta gtctgcaact cgactacatg | 1320 |
| aagctggaat cgctagtaat cgcagatcag aatgctgcgg tgaatacgtt cccgggtctt | 1380 |
| gtacacaccg cccgtcacac catgggagtc agtaacgccc gaagtcagtg acccaaccga | 1440 |
| aaggagggag ctgccgaagg tgggaccgat aactggggt | 1479 |

<210> SEQ ID NO 121
<211> LENGTH: 1390
<212> TYPE: DNA
<213> ORGANISM: Eisenbergiella tayi

<400> SEQUENCE: 121

| | |
|---|---|
| ggtataactt agtggcggac gggtgagtaa cgcgtgggaa acctgccctg taccggggga | 60 |
| taacacttag aaataggtgc taataccgca taagcgcacg gaaccgcatg gttccgtgtg | 120 |
| aaaaactccg gtggtacagg atggtcccgc gtctgattag ccagttggca gggtaacggc | 180 |
| ctaccaaagc gacgatcagt agccggcctg agagggtgaa cggccacatt gggactgaga | 240 |
| cacggcccaa actcctacgg gaggcagcag tggggaatat tgcacaatgg gggaaaccct | 300 |
| gatgcagcga cgccgcgtga gtgaagaagt atttcggtat gtaaagctct atcagcaggg | 360 |
| aagaaaatga cggtacctga ctaagaagcc ccggctaact acgtgccagc agccgcggta | 420 |
| atacgtaggg ggcaagcgtt atccggattt actgggtgta aagggagcgt agacggcatg | 480 |
| gcaagccaga tgtgaaaacc cagggctcaa ccttgggatt gcatttggaa ctgccaggct | 540 |
| ggagtgcagg agaggtaagc ggaattccta gtgtagcggt gaaatgcgta gatattagga | 600 |
| ggaacaccag tggcgaaggc ggcttactgg actgtaactg acgttgaggc tcgaaagcgt | 660 |
| ggggagcaaa caggattaga taccctggta gtccacgccg taaacgatga ttgctaggtg | 720 |
| taggtgggta tggacccatc ggtgccgcag ctaacgcaat aagcaatcca cctggggagt | 780 |
| acgttcgcaa gaatgaaact caaaggaatt gacggggacc cgcacaagcg gtggagcatg | 840 |
| tggtttaatt cgaagcaacg cgaagaacct taccaagtct tgacatccca atgacgcacc | 900 |
| tgtaaagagg tgttcccttc ggggcattgg agacaggtgg tgcatggttg tcgtcagctc | 960 |
| gtgtcgtgag atgttgggtt aagtcccgca acgagcgcaa cccttatctt tagtagccag | 1020 |
| caggtaaagc tgggcactct aaggagactg ccggggataa cccggaggaa ggcggggatg | 1080 |

```
acgtcaaatc atcatgcccc ttatgatttg ggctacacac gtgctacaat ggcgtaaaca    1140
aagggaagcg agacagtgat gtggagcaaa tcycagaaat aacgtctcag ttcggattgt    1200
agtctgcaac tcgactacat gaagctggaa tcgctagtaa tcgcgaatca gcatgtcgcg    1260
gtgaatacgt tcccgggtct tgtacacacc gcccgtcaca ccatgggagt tggaaatgcc    1320
cgaagtctgt gacctaaccg aaagggagga gcagccgaag gcaggtctga taactggggt    1380
gaagtcgtaa                                                           1390
```

<210> SEQ ID NO 122
<211> LENGTH: 1478
<212> TYPE: DNA
<213> ORGANISM: Clostridium symbiosum
<220> FEATURE:
<221> NAME/KEY: misc_feature
<222> LOCATION: (349)..(350)
<223> OTHER INFORMATION: n is a, c, g, t or u
<220> FEATURE:
<221> NAME/KEY: misc_feature
<222> LOCATION: (534)..(535)
<223> OTHER INFORMATION: n is a, c, g, t or u
<220> FEATURE:
<221> NAME/KEY: misc_feature
<222> LOCATION: (606)..(606)
<223> OTHER INFORMATION: n is a, c, g, t or u
<220> FEATURE:
<221> NAME/KEY: misc_feature
<222> LOCATION: (618)..(619)
<223> OTHER INFORMATION: n is a, c, g, t or u
<220> FEATURE:
<221> NAME/KEY: misc_feature
<222> LOCATION: (709)..(709)
<223> OTHER INFORMATION: n is a, c, g, t or u
<220> FEATURE:
<221> NAME/KEY: misc_feature
<222> LOCATION: (921)..(921)
<223> OTHER INFORMATION: n is a, c, g, t or u
<220> FEATURE:
<221> NAME/KEY: misc_feature
<222> LOCATION: (955)..(956)
<223> OTHER INFORMATION: n is a, c, g, t or u
<220> FEATURE:
<221> NAME/KEY: misc_feature
<222> LOCATION: (1012)..(1013)
<223> OTHER INFORMATION: n is a, c, g, t or u
<220> FEATURE:
<221> NAME/KEY: misc_feature
<222> LOCATION: (1015)..(1015)
<223> OTHER INFORMATION: n is a, c, g, t or u
<220> FEATURE:
<221> NAME/KEY: misc_feature
<222> LOCATION: (1081)..(1081)
<223> OTHER INFORMATION: n is a, c, g, t or u
<220> FEATURE:
<221> NAME/KEY: misc_feature
<222> LOCATION: (1185)..(1185)
<223> OTHER INFORMATION: n is a, c, g, t or u
<220> FEATURE:
<221> NAME/KEY: misc_feature
<222> LOCATION: (1240)..(1240)
<223> OTHER INFORMATION: n is a, c, g, t or u
<220> FEATURE:
<221> NAME/KEY: misc_feature
<222> LOCATION: (1391)..(1392)
<223> OTHER INFORMATION: n is a, c, g, t or u
<220> FEATURE:
<221> NAME/KEY: misc_feature
<222> LOCATION: (1470)..(1470)
<223> OTHER INFORMATION: n is a, c, g, t or u
<220> FEATURE:
<221> NAME/KEY: misc_feature
<222> LOCATION: (1474)..(1475)
<223> OTHER INFORMATION: n is a, c, g, t or u

<400> SEQUENCE: 122

```
aaacatgaga gtttgatcct ggctcaggat gaacgctggc ggcgtgccta acacatgcaa    60
gtcgaacgaa gcgatttaac ggaagttttc ggatggaagt tgaattgact gagtggcgga   120
cgggtgagta acgcgtgggt aacctgcctt gtactggggg acaacagtta gaaatgactg   180
ctaataccgc ataagcgcac agtattgcat gatacagtgt gaaaaactcc ggtggtacaa   240
gatggacccg cgtctgatta gctagttggt aaggtaacgg cttaccaagg cgacgatcag   300
tagccgacct gagagggtga ccggccacat tgggactgag acacggccnn aactcctacg   360
ggaggcagca gtggggaata ttgcacaatg ggcgaaagcc tgatgcagcg acgccgcgtg   420
agtgaagaag tatttcggta tgtaaagctc tatcagcagg aagaaaatg acggtacctg    480
actaagaagc cccggctaac tacgtgccag cagccgcggt aatacgtagg gggnnagcgt   540
tatccggatt tactgggtgt aaagggagcg tagacggtaa agcaagtctg aagtgaaagc   600
ccgcgnctca actgcggnnc tgctttggaa actgtttaac tggagtgtcg gagaggtaag   660
tggaattcct agtgtagcgg tgaaatgcgt agatattagg aggaacacna gtggcgaagg   720
cgacttactg gacgataact gacgttgagg ctcgaaagcg tggggagcaa acaggattag   780
ataccctggt agtccacgcc gtaaacgatg aatactaggt gttggggagc aaagctcttc   840
ggtgccgtcg caaacgcagt aagtattcca cctggggagt acgttcgcaa gaatgaaact   900
caaaggaatt gacgggggacc ngcacaagcg gtggagcatg tggtttaatt cgaannaacg   960
cgaagaacct taccaggtct tgacatcgac tcgacggggg agtaacgtcc cnntnccttc  1020
ggggcggaga agacaggtgg tgcatggttg tcgtcagctc gtgtcgtgag atgttgggtt  1080
nagtcccgca acgagcgcaa cccttattct aagtagccag cggttcggcc gggaactctt  1140
gggagactgc cagggataac ctggaggaag gtggggatga cgtcnaatca tcatgcccct  1200
tatgatctgg gctacacacg tgctacaatg gcgtaaacan agagaagcaa gaccgcgagg  1260
tggagcaaat ctcaaaaata acgtctcagt tcggactgca ggctgcaact cgcctgcacg  1320
aagctggaat cgctagtaat cgcgaatcag aatgtcgcgg tgaatacgtt cccgggtctt  1380
gtacacaccg nncgtcacac catgggagtc agtaacgccc gaagtcagtg acccaaccgc  1440
aaggagggag ctgccgaagg cgggaccgan aacnnggg                          1478
```

<210> SEQ ID NO 123
<211> LENGTH: 1488
<212> TYPE: DNA
<213> ORGANISM: Erysipelatoclostridium ramosum

<400> SEQUENCE: 123

```
agagtttgat cctggctcag gatgaacgct ggcggcgtgc ctaatacatg caagtcgaac    60
gcgagcactt gtgctcgagt ggcgaacggg tgagtaatac ataagtaacc tgccctagac   120
agggggataa ctattggaaa cgatagctaa gaccgcatag gtacgacac tgcatggtga    180
ccgtattaaa agtgcctcaa agcactggta gaggatggac ttatggcgca ttagctggtt   240
ggcggggtaa cggcccacca aggcgacgat gcgtagccga cctgagaggg tgaccggcca   300
cactgggact gagacacggc ccagactcct acggagagca gcagtaggga atttcggca    360
atggggaaa ccctgaccga gcaacgccgc gtgaaggaag aaggttttcg gattgtaaac    420
ttctgttata aaggaagaac ggcggctaca ggaaatggta gccgagtgac ggtactttat   480
tagaaagcca cggctaacta cgtgccagca gccgcggtaa tacgtaggtg gcaagcgtta   540
tccggaatta ttgggcgtaa agagggagca ggcggcagca agggtctgtg gtgaaagcct   600
```

```
gaagcttaac ttcagtaagc catagaaacc aggcagctag agtgcaggag aggatcgtgg    660
aattccatgt gtagcggtga aatgcgtaga tatatggagg aacaccagtg gcgaaggcga    720
cgatctggcc tgcaactgac gctcagtccc gaaagcgtgg ggagcaaata ggattagata    780
ccctagtagt ccacgccgta acgatgagt actaagtgtt ggatgtcaaa gttcagtgct    840
gcagttaacg caataagtac tccgcctgag tagtacgttc gcaagaatga aactcaaagg    900
aattgacggg ggcccgcaca agcggtggag catgtggttt aattcgaagc aacgcgaaga    960
accttaccag gtcttgacat actcataaag gctccagaga tggagagata gctatatgag   1020
atacaggtgt gcatggttg tcgtcagctc gtgtcgtgag atgttgggtt aagtcccgca   1080
acgagcgcaa cccttatcgt tagttaccat cattaagttg gggactctag cgagactgcc   1140
agtgacaagc tggaggaagg cggggatgac gtcaaatcat catgcccctt atgacctggg   1200
ctacacacgt gctacaatgg atggtgcaga gggaagcgaa gccgcgaggt gaagcaaaac   1260
ccataaaacc attctcagtt cggattgtag tctgcaactc gactacatga gttggaatc    1320 gctagtaatc gcgaatcagc atgtcgcggt gaatacgttc tcgggccttg tacacaccgc   1380
ccgtcacacc acgagagttg ataacacccg aagccggtgg cctaaccgca aggaaggagc   1440
tgtctaaggt gggattgatg attggggtga agtcgtaaca aggtaacc                1488

<210> SEQ ID NO 124
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 124
atgagagttt gatcctggct caggatgaac gctggcggcg tgcctaacac atgcaagtcg     60
aacgaagcaa ttaaaggaag ttttcggatg gaatttgatt gactgagtgg cggacgggtg    120
agtaacgcgt ggataaccctg cctcacactg ggggataaca gttagaaatg actgctaata    180
ccgcataagc gcacagtacc gcatggtacg gtgtgaaaaa ctccggtggt gtgagatgga    240
tccgcgtctg attagccagt tggcggggta acggcccacc aaagcgacga tcagtagccg    300
acctgagagg gtgaccggcc acattgggac tgagacacgg cccaaactcc tacgggaggc    360
agcagtgggg aatattgcac aatgggcgaa agcctgatgc agcgacgccg cgtgagtgaa    420
gaagtatttc ggtatgtaaa gctctatcag cagggaagaa aatgacggta cctgactaag    480
aagccccggc taactacgtg ccagcagccg cggtaatacg tagggggcaa gcgttatccg    540
gattcactgg gtgtaaaggg agcgtagacg gcgaagcaag tctgaagtga aaacccaggg    600
ctcaaccctg ggactgcttt ggaaactgtt ttgctagagt gtcggagagg taagtggaat    660
tcctagtgta gcggtgaaat gcgtagatat taggaggaac accagtggcg aaggcggctt    720
actggacgat aactgacgtt gaggctcgaa agcgtgggga gcaaacagga ttagataccc    780
tggtagtcca cgccgtaaac gatgaatgct aggtgttggg gggcaaagcc ttcggtgcc    840 gtcgcaaacg cagtaagcat tccacctggg gagtacgttc gcaagaatga aactcaaagg    900
aattgacggg gacccgcaca agcggtggag catgtggttt aattcgaagc aacgcgaaga    960
accttaccaa gtcttgacat cctcttgacc ggcgtgtaac ggcgccttcc cttcggggca   1020
agagagacag gtggtgcatg gttgtcgtca gctcgtgtcg tgagatgttg ggttaagtcc   1080
cgcaacgagc gcaacccctta tccttagtag ccagcaggta gagctgggca ctctagggag   1140
```

| | |
|---|---|
| actgccaggg ataacctgga ggaaggtggg gatgacgtca atcatcatg cccttatga | 1200 |
| tttgggctac acacgtgcta caatggcgta acaaaggga agcaagacag tgatgtggag | 1260 |
| caaatcccaa aaataacgtc ccagttcgga ctgtagtctg caacccgact acacgaagct | 1320 |
| ggaatcgcta gtaatcgcga atcagaatgt cgcggtgaat acgttccgg gtcttgtaca | 1380 |
| caccgcccgt cacaccatgg gagtcagcaa cgcccgaagt cagtgaccca actcgcaaga | 1440 |
| gagggagctg ccgaaggcgg ggcaggtaac tggggtgaag tcgtaacaag gtagccgtat | 1500 |
| cggaaggtgc ggctggatca cctcctttt | 1528 |

<210> SEQ ID NO 125
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 125

| | |
|---|---|
| atgagagttt gatcctggct caggatgaac gctggcggcg tgcctaacac atgcaagtcg | 60 |
| aacgaagcaa ttaaaatgaa gtttcggat ggattttga ttgactgagt ggcggacggg | 120 |
| tgagtaacgc gtggataacc tgcctcacac tgggggataa cagttagaaa tgactgctaa | 180 |
| taccgcataa gcgcacagta ccgcatggta cggtgtgaaa aactccggtg gtgtgggatg | 240 |
| gatccgcgtc tgattagcca gttggcgggg taacggccca ccaaagcgac gatcagtagc | 300 |
| cgacctgaga gggtgaccgg ccacattggg actgagacac ggcccaaact cctacgggag | 360 |
| gcagcagtgg ggaatattgc acaatgggcg aaagcctgat gcagcgacgc cgcgtgagtg | 420 |
| aagaagtatt tcggtatgta aagctctatc agcagggaag aaaatgacgg tacctgacta | 480 |
| agaagccccg gctaactacg tgccagcagc cgcggtaata cgtaggggc aagcgttatc | 540 |
| cggatttact gggtgtaaag ggagcgtaga cggcgaagca agtctgaagt gaaaacccag | 600 |
| ggctcaaccc tgggactgct ttggaaactg ttttgctaga gtgtcggaga ggtaagtgga | 660 |
| attcctagtg tagcggtgaa atgcgtagat attaggagga acaccagtgg cgaaggcggc | 720 |
| ttactggacg ataactgacg ttgaggctcg aaagcgtggg gagcaaacag gattagatac | 780 |
| cctggtagtc cacgccgtaa acgatgaatg ctaggtgttg gggggcaaag cccttcggtg | 840 |
| ccgtcgcaaa gcagtaagc attccacctg gggagtacgt tcgcaagaat gaaactcaaa | 900 |
| ggaattgacg gggacccgca caagcggtgg agcatgtggt ttaattcgaa gcaacgcgaa | 960 |
| gaaccttacc aagtcttgac atcctcttga ccggcgtgta acggcgcctt cccttcgggg | 1020 |
| caagagagac aggtggtgca tggttgtcgt cagctcgtgt cgtgagatgt tgggttaagt | 1080 |
| cccgcaacga gcgcaaccct tatccttagt agccagcagg taaagctggg cactctaggg | 1140 |
| agactgccag gataacctg gaggaaggtg gggatgacgt caaatcatca tgcccctat | 1200 |
| gatttgggct acacacgtgc tacaatggcg taaacaaagg gaagcaagac agtgatgtgg | 1260 |
| agcaaatccc aaaaataacg tcccagttcg gactgtagtc tgcaacccga ctacacgaag | 1320 |
| ctggaatcgc tagtaatcgc gaatcagaat gtcgcggtga atacgttccc gggtcttgta | 1380 |
| cacaccgccc gtcacaccat gggagtcagc aacgcccgaa gtcagtgacc caactcgcaa | 1440 |
| gagagggagc tgccgaaggc ggggcaggta actggggtga agtcgtaaca aggtagccgt | 1500 |
| atcggaaggt gcggctggat cacctccttt | 1530 |

<210> SEQ ID NO 126
<211> LENGTH: 1528

```
<212> TYPE: DNA
<213> ORGANISM: Artificial Sequence
<220> FEATURE:
<223> OTHER INFORMATION: Synthetic Polynucleotide

<400> SEQUENCE: 126
atgagagttt gatcctggct caggatgaac gctggcggcg tgcctaacac atgcaagtcg      60
aacgaagcaa ttaaaatgaa gttttcggat ggattttga ttgactgagt ggcggacggg     120
tgagtaacgc gtggataacc tgcctcacac tggggataa cagttagaaa tgactgctaa     180
taccgcataa gcgcacagta ccgcatggta cggtgtgaaa actccggtg gtgtgagatg     240 gatccgcgtc tgattagcca gttggcgggg taacggccca ccaaagcgac gatcagtagc    300
cgacctgaga gggtgaccgg ccacattggg actgagacac ggcccaaact cctacgggag    360
gcagcagtgg ggaatattgc acaatgggcg aaagcctgat gcagcgacgc cgcgtgagtg    420
aagaagtatt tcggtatgta aagctctatc agcagggaag aaatgacggt acctgactaa    480
gaagccccgg ctaactacgt gccagcagcc gcggtaatac gtaggggca agcgttatcc     540 ggatttactg ggtgtaaagg gagcgtagac ggcgaagcaa gtctgaagtg aaaacccagg    600
gctcaaccct gggactgctt tggaaactgt tttgctagag tgtcggagag gtaagtggaa    660
ttcctagtgt agcggtgaaa tgcgtagata ttaggaggaa caccagtggc gaaggcggct    720
tactggacga taactgacgt tgaggctcga aagcgtgggg agcaaacagg attagatacc    780
ctggtagtcc acgccgtaaa cgatgaatgc taggtgttgg gggcaaagcc cttcggtgcc    840
gtcgcaaacg cagtaagcat tccacctggg gagtacgttc gcaagaatga aactcaaagg    900
aattgacggg gacccgcaca gcggtggag catgtggttt aattcgaagc aacgcgaaga    960
accttaccaa gtcttgacat cctcttgacc ggcgtaac ggcgccttcc cttcgggcca    1020
agagagacag gtggtgcatg gttgtcgtca gctcgtgtcg tgagatgttg ggttaagtcc    1080
cgcaacgagc gcaaccctta tccttagtag ccagcaggta agctgggca ctctagggag    1140 actgccaggg ataacctgga ggaaggtggg gatgacgtca atcatcatg ccccttatga    1200 tttgggctac acacgtgcta caatggcgta acaaaggga agcaagacag tgatgtggag    1260
caaatcccaa aaataacgtc ccagttcgga ctgtagtctg caacccgact acacgaagct    1320
ggaatcgcta gtaatcgcga atcagaatgt cgcggtgaat acgttccgg gtcttgtaca    1380 caccgcccgt cacaccatgg gagtcagcaa cgcccgaagt cagtgaccca actcgcaaga    1440
gagggagctg ccgaaggcgg ggcaggtaac tggggtgaag tcgtaacaag gtagccgtat    1500
cggaaggtgc ggctggatca cctcctttt                                     1528

<210> SEQ ID NO 127
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 127
atgagagttt gatcctggct caggatgaac gctggcggcg tgcctaacac atgcaagtcg     60
aacgaagcaa ttaaaatgaa gttttcggat ggattttga ttgactgagt ggcggacggg    120
tgagtaacgc gtggataacc tgcctcacac tggggataa cagttagaaa tgactgctaa    180
taccgcataa gcgcacagta ccgcatggta cggtgtgaaa actccggtg gtgtgagatg    240 gatccgcgtc tgattagcca gttggcgggg taacggccca ccaaagcgac gatcagtagc   300
```

```
cgacctgaga gggtgaccgg ccacattggg actgagacac ggcccaaact cctacgggag    360
gcagcagtgg ggaatattgc acaatgggcg aaagcctgat gcagcgacgc cgcgtgagtg    420
aagaagtatt tcggtatgta aagctctatc agcagggaag aaaatgacgg tacctgacta    480 agaagcccccg gctaactacg tgccagcagc cgcggtaata cgtagggggc aagcgttatc    540
cggatttact gggtgtaaag ggagcgtaga cggcgaagca agtctgaagt gaaaacccag    600
ggctcaaccc tgggactgct ttggaaactg ttttgctaga gtgtcggaga ggtaagtgga    660
attcctagtg tagcggtgaa atgcgtagat attaggagga acaccagtgg cgaaggcggc    720
ttactggacg ataactgacg ttgaggctcg aaagcgtggg gagcaaacag gattagatac    780
cctggtagtc cacgccgtaa acgatgaatg ctaggtgttg ggggcaaagc ccttcggtgc    840
cgtcgcaaac gcagtaagca ttccacctgg ggagtacgtt cgcaagaatg aaactcaaag    900
gaattgacgg ggacccgcac aagcggtgga gcatgtggtt taattcgaag caacgcgaag    960
aaccttacca agtcttgaca tcctcttgac cggcgtgtaa cggcgccttc ccttcggggc   1020
aggagagaca ggtggtgcat ggttgtcgtc agctcgtgtc gtgagatgtt gggttaagtc   1080
ccgcaacgag cgcaacccctt atccttagta gccagcaggt agagctgggc actctaggga   1140
gactgccagg gataacctgg aggaaggtgg ggatgacgtc aaatcatcat gccccttatg   1200
atttgggcta cacacgtgct acaatggcgt aaacaaaggg aagcaagaca gtgatgtgga   1260
gcaaatccca aaataacgtc ccagttcgga ctgtagtctg caacccgact acacgaagct   1320
ggaatcgcta gtaatcgcga atcagaatgt cgcggtgaat acgttcccgg gtcttgtaca   1380
caccgcccgt cacaccatgg gagtcagcaa cgcccgaagt cagtgaccca actcgcaaga   1440
gagggagctg ccgaaggcgg ggcaggtaac tgggggtgaag tcgtaacaag gtagccgtat   1500
cggaaggtgc ggctggatca cctcctttt                                     1528

<210> SEQ ID NO 128
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 128
atgagagttt gatcctggct caggatgaac gctggcggcg tgcctaacac atgcaagtcg     60
aacgaagcaa ttaaaatgaa gttttcggat ggatttaat tgactgagtg gcggacgggt    120
gagtaacgcg tggataacct gcctcacact ggggggataac agttagaaat gactgctaat    180
accgcataag cgcacagtac cgcatggtac ggtgtgaaaa actccggtgg tgtgagatgg    240
atccgcgtct gattagccag ttggcggggt aacggcccac caaagcgacg atcagtagcc    300
gacctgagag ggtgaccggc cacattggga ctgagacacg gcccaaactc ctacgggagg    360
cagcagtggg gaatattgca caatgggcga aagcctgatg cagcgacgcc gcgtgagtga    420
agaagtattt cggtatgtaa agctctatca gcagggaaga aaatgacggt acctgactaa    480 gaagcccccgg ctaactacgt gccagcagcc gcggtaatac gtagggggca agcgttatcc    540
ggatttactg ggtgtaaagg gagcgtagac ggcgaagcaa gtctgaagtg aaaacccagg    600
gctcaaccct gggactgctt tggaaactgt tttgctagag tgtcggagag gtaagtggaa    660
ttcctagtgt agcggtgaaa tgcgtagata ttaggaggaa caccagtggc gaaggcggct    720
tactggacga taactgacgt tgaggctcga aagcgtgggg agcaaacagg attagatacc    780
ctggtagtcc acgccgtaaa cgatgaatgc taggtgttgg ggggcaaagc ccttcggtgc    840
```

```
cgtcgcaaac gcagtaagca ttccacctgg ggagtacgtt cgcaagaatg aaactcaaag      900
gaattgacgg ggacccgcac aagcggtgga gcatgtggtt taattcgaag caacgcgaag      960
aaccttacca agtcttgaca tcctcttgac cggcgtgtaa cggcgccttc ccttcggggc     1020
aagagagaca ggtggtgcat ggttgtcgtc agctcgtgtc gtgagatgtt gggttaagtc     1080
ccgcaacgag cgcaacccct atccttagta gccagcaggt aaagctgggc actctaggga     1140
gactgccagg gataacctgg aggaaggtgg ggatgacgtc aaatcatcat gccccttatg     1200
atttgggcta cacacgtgct acaatggcgt aaacaaaggg aagcaagaca gtgatgtgga     1260
gcaaatccca aaataacgtc ccagttcgga ctgtagtctg caacccgact acacgaagct     1320
ggaatcgcta gtaatcgcga atcagaatgt cgcggtgaat acgttcccgg tcttgtaca     1380 caccgcccgt cacaccatgg gagtcagcaa cgcccgaagt cagtgaccca actcgcaaga     1440
gagggagctg ccgaaggcgg ggcaggtaac tggggtgaag tcgtaacaag gtagccgtat     1500
cggaaggtgc ggctggatca cctcctttt                                      1528
```

<210> SEQ ID NO 129
<211> LENGTH: 1522
<212> TYPE: DNA
<213> ORGANISM: Artificial Sequence
<220> FEATURE:
<223> OTHER INFORMATION: Synthetic Polynucleotide

<400> SEQUENCE: 129

```
tcaaagagtt tgatcctggc tcaggacgaa cgctggcggc gcgcctaaca catgcaagtc       60
gaacggagct tacgttttga agttttcgga tggatgaatg taagcttagt ggcggacggg      120
tgagtaacac gtgagcaacc tgcctttcag aggggggataa cagccggaaa cggctgctaa     180
taccgcatga tgttgcgggg gcacatgccc ctgcaaccaa aggagcaatc cgctgaaaga     240
tgggctcgcg tccgattagc cagttggcgg ggtaacggcc caccaaagcg acgatcggta     300
gccggactga gaggttgaac ggccacattg gactgagaca cggcccaga ctcctacggg      360 aggcagcagt gggggatatt gcacaatggg cgaaagcctg atgcagcgac gccgcgtgag     420
ggaagacggt cttcggattg taaacctctg tctttgggga agaaaatgac ggtacccaaa     480
gaggaagctc cggctaacta cgtgccagca gccgcggtaa tacgtaggga gcaagcgttg     540
tccggaatta ctgggtgtaa agggagcgta ggcgggatgg caagtagaat gttaaatcca     600
tcggctcaac cggtggctgc gttctaaact gccgttcttg agtgaagtag aggcaggcgg     660
aattcctagt gtagcggtga aatgcgtaga tattaggagg aacaccagtg gcgaaggcgg     720
cctgctgggc tttaactgac gctgaggctc gaaagcgtgg ggagcaaaca ggattagata     780
ccctggtagt ccacgccgta aacgatgatt actaggtgtg ggggactga ccccttccgt      840 gccgcagtta acacaataag taatccacct ggggagtacg ccgcaaggt tgaaactcaa     900 aggaattgac gggggcccgc acaagcagtg gagtatgtgt ttaattcga agcaacgcga      960 agaaccttac caggtcttga catcggatgc ataggtaga gataggtgaa gcccttcggg     1020
gcatccagac aggtggtgca tggttgtcgt cagctcgtgt cgtgagatgt tgggttaagt    1080
cccgcaacga gcgcaacccct tattattagt tgctacgcaa gagcactcta atgagactgc    1140
cgttgacaaa acggaggaag gtggggatga cgtcaaatca tcatgcccct tatgacctgg    1200
gctacacacg tactacaatg gcactaaaac agagggcggc gacaccgcga ggtgaagcga    1260
atcccgaaaa agtgtctcag ttcagattgc aggctgcaac ccgcctgcat gaagtcggaa    1320
```

```
ttgctagtaa tcgcggatca gcatgccgcg gtgaatacgt tcccgggcct tgtacacacc   1380
gcccgtcaca ccatgggagt cggtaacacc cgaagccagt agcctaaccg caagggggc    1440 gctgtcgaag gtgggattga tgactggggt gaagtcgtaa caaggtagcc gtatcggaag   1500
gtgcggctgg atcacctcct tt                                            1522

<210> SEQ ID NO 130
<211> LENGTH: 1521
<212> TYPE: DNA
<213> ORGANISM: Artificial Sequence
<220> FEATURE:
<223> OTHER INFORMATION: Synthetic Polynucleotide

<400> SEQUENCE: 130
tcaaagagtt tgatcctggc tcaggacgaa cgctggcggc gcgcctaaca catgcaagtc     60
gaacggagct tacgttttga agttttcgga tggacgaatg taagcttagt ggcggacggg   120
tgagtaacac gtgagcaacc tgcctttcag aggggataac agccgaaaac ggctgctaat   180
accgcatgat gttgcggggg cacatgcccc tgcaaccaaa ggagcaatcc gctgaaagat   240
gggctcgcgt ccgattagcc agttggcggg gtaacggccc accaaagcga cgatcggtag   300
ccggactgag aggttgaacg gccacattgg gactgagaca cggcccagac tcctacggga   360
ggcagcagtg ggggatattg cacaatgggc gaaagcctga tgcagcgacg ccgcgtgagg   420
gaagacggtc ttcggattgt aaacctctgt ctttggggaa gaaaatgacg gtacccaaag   480
aggaagctcc ggctaactac gtgccagcag ccgcggtaat acgtagggag caagcgttgt   540
ccggaattac tgggtgtaaa gggagcgtag gcgggatggc aagtagaatg ttaaatccat   600
cggctcaacc ggtggctgcg ttctaaactg ccgttcttga gtgaagtaga ggcaggcgga   660
attcctagtg tagcggtgaa atgcgtagat attaggagga acaccagtgg cgaaggcggc   720
ctgctgggct ttaactgacg ctgaggctcg aaagcgtggg gagcaaacag gattagatac   780
cctggtagtc cacgccgtaa acgatgatta ctaggtgtgg ggggactgac cccttccgtg   840
ccgcagttaa cacaataagt aatccacctg gggagtacgg ccgcaaggtt gaaactcaaa   900
ggaattgacg gggccccgca caagcagtgg agtatgtggt ttaattcgaa gcaacgcgaa   960
gaaccttacc aggtcttgac atcggatgca tagcctagag ataggtgaag cccttcgggg   1020
catccagaca ggtggtgcat ggttgtcgtc agctcgtgtc gtgagatgtt gggttaagtc   1080
ccgcaacgag cgcaacccct attattagtt gctacgcaag agcactctaa tgagactgcc   1140
gttgacaaaa cggaggaagg tggggatgac gtcaaatcat catgcccctt atgacctggg   1200
ctacacacgt actacaatgg cactaaaaca gagggcggcg acaccgcgag gtgaagcgaa   1260
tcccgaaaaa gtgtctcagt tcagattgca ggctgcaacc cgcctgcatg aagtcggaat   1320
tgctagtaat cgcggatcag catgccgcgg tgaatacgtt cccgggcctt gtacacaccg   1380
cccgtcacac catgggagtc ggtaacaccc gaagccagta gcctaaccgc aagggggcg    1440 ctgtcgaagg tgggattgat gactggggtg aagtcgtaac aaggtagccg tatcggaagg   1500
tgcggctgga tcacctcctt t                                             1521

<210> SEQ ID NO 131
<211> LENGTH: 1522
<212> TYPE: DNA
<213> ORGANISM: Artificial Sequence
<220> FEATURE:
<223> OTHER INFORMATION: Synthetic Polynucleotide

<400> SEQUENCE: 131
```

```
tcaaagagtt tgatcctggc tcaggacgaa cgctggcggc gcgcctaaca catgcaagtc      60
gaacggagct tacgttttga agttttcgga tggatgaatg taagcttagt ggcggacggg     120
tgagtaacac gtgagcaacc tgcctttcag aggggggataa cagccggaaa cggctgctaa    180
taccgcatga tgttgcgggg gcacatgccc ctgcaaccaa aggagcaatc cgctgaaaga    240
tgggctcgcg tccgattagc cagttggcgg ggtaacggcc caccaaagcg acgatcggta    300
gccggactga gaggttgaac ggccacattg gactgagac acggcccaga ctcctacggg     360
aggcagcagt gggggatatt gcacaatggg cgaaagcctg atgcagcgac gccgcgtgag    420
ggaagacggt cttcggattg taaacctctg tctttgggga gaaaatgac ggtacccaaa     480 gaggaagctc cggctaacta cgtgccagca gccgcggtaa tacgtaggga gcaagcgttg    540
tccggaatta ctgggtgtaa agggagcgta ggcgggatgg caagtagaat gttaaatcca    600
tcggctcaac cggtggctgc gttctaaact gccgttcttg agtgaagtag aggcaggcgg    660
aattcctagt gtagcggtga aatgcgtaga tattaggagg aacaccagtg gcgaaggcgg    720
cctgctgggc tttaactgac gctgaggctc gaaagcgtgg ggagcaaaca ggattagata    780
ccctggtagt ccacgccgta aacgatgatt actaggtgtg gggggactga ccccttccgt    840
gccgcagtta acacaataag taatccacct ggggagtacg ccgcaaggt tgaaactcaa     900 aggaattgac gggggcccgc acaagcagtg gagtatgtgg tttaattcga agcaacgcga    960
agaaccttac caggtcttga catcggatgc atagcctaga gataggtgaa gcccttcggg   1020
gcatccagac aggtggtgca tggttgtcgt cagctcgtgt cgtgagatgt tgggttaagt   1080
cccgcaacga gcgcaaccct tattattagt tgctacgcaa gagcactcta atgagactgc    1140
cgttgacaaa acgaggaag gtggggatga cgtcaaatca tcatgcccct tatgacctgg    1200
gctacacacg tactacaatg gcactaaaac agagggcggc gacaccgcga ggtgaagcga   1260
atcccgaaaa agtgtctcag ttcagattgc aggctgcaac ccgcctgcat gaagtcggaa   1320
ttgctagtaa tcgcggatca gcatgccgcg gtgaatacgt tcccgggcct tgtacacacc    1380
gcccgtcaca ccatgggagt cggtaacacc cgaagccagt agcctaaccg caagggggc   1440 gctgtcgaag gtgggattga tgactggggt gaagtcgtaa caaggtagcc gtatcggaag   1500
gtgcggctgg atcacctcct tt                                              1522
```

<210> SEQ ID NO 132
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 132

```
tacgagagtt tgatcctggc tcaggatgaa cgctggcggc gtgcctaaca catgcaagtc     60
gagcgaagcg ctgttttcag aatcttcgga ggaagaggac agtgactgag cggcggacgg    120
gtgagtaacg cgtgggcaac ctgcctcata caggggggata acagttagaa atgactgcta   180
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga   360
ggcagcagtg ggaatattg cacaatgggg gaaaccctga tgcagcgacg ccgcgtgaag   420
gaagaagtat ttcggtatgt aaacttctat cagcagggaa gaaaatgacg gtacctgagt    480
```

```
aagaagcacc ggctaaatac gtgccagcag ccgcggtaat acgtatggtg caagcgttat    540
ccggatttac tgggtgtaaa gggagcgtag acgataggc aagtctggag tgaaaaccca     600
gggctcaacc ctgggactgc tttggaaact gcagatctgg agtgccggag aggtaagcgg    660
aattcctagt gtagcggtga atgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcgt     840 gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcgtccgaga caggtggtgc atggttgtcg tcagctcgtg tcgtgagatg ttgggttaag   1080
tcccgcaacg agcgcaaccc ttatcttcag tagccagcat ataaggtggg cactctggag   1140
agactgccag ggagaacctg gaggaaggtg gggatgacgt caaatcatca tgccccttat   1200
ggccagggct acacacgtgc tacaatggcg taaacaaagg gaagcgagag ggtgacctgg   1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc aaccttaga   1440 ggagggagct gtcgaaggcg ggacggataa ctggggtgaa gtcgtaacaa ggtagccgta   1500
tcggaaggtg cggctggatc acctccttt                                     1529
```

<210> SEQ ID NO 133
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 133

```
tacgagagtt tgatcctggc tcaggatgaa cgctggcggc gtgcctaaca catgcaagtc     60
gagcgaagcg ctgtttttcag aatcttcgga ggaagaggac agtgactgag cggcggacgg   120
gtgagtaacg cgtgggcaac ctgcctcata caggggata acagttagaa atgactgcta    180
ataccgcata agcgcacagg accgcatggt gtagtgtgaa aaactccggt ggtatgagat   240
ggacccgcgt ctgattaggt agttggtggg gtaaaggcct accaagccga cgatcagtag   300
ccgacctgag agggtgaccg gccacattgg gactgagaca cggcccaaac tcctacggga   360
ggcagcagtg gggaatattg cacaatgggg gaaaccctga tgcagcgacg ccgcgtgaag   420
gaagaagtat ttcggtatgt aaacttctat cagcagggaa gaagatgacg gtacctgagt   480
aagaagcacc ggctaaatac gtgccagcag ccgcggtaat acgtatggtg caagcgttat    540
ccggatttac tgggtgtaaa gggagcgtag acgataggc aagtctggag tgaaaaccca    600
gggctcaacc ctgggactgc tttggaaact gcagatctgg agtgccggag aggtaagcgg   660
aattcctagt gtagcggtga atgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcgt    840 gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
```

```
gcatccgaga caggtggtgc atggttgtcg tcagctcgtg tcgtgagatg ttgggttaag    1080
tcccgcaacg agcgcaaccc ttatcttcag tagccagcat ataaggtggg cactctggag    1140
agactgccag ggagaacctg gaggaaggtg gggatgacgt caaatcatca tgccccttat    1200
ggccagggct acacacgtgc tacaatggcg taaacaaagg gaagcgagag ggtgacctga    1260
agcgaatccc aaaaataacg tctcagttcg gattgtagtc tgcaactcga ctacatgaag    1320
ctggaatcgc tagtaatcgc ggatcagcat gccgcggtga atacgttccc gggtcttgta    1380
cacaccgccc gtcacaccat gggagtcagt aacgcccgaa gccagtgacc caaccttaga    1440
ggagggagct gtcgaaggcg ggacggataa ctggggtgaa gtcgtaacaa ggtagccgta    1500
tcggaaggtg cggctggatc acctcctttt                                     1529
```

<210> SEQ ID NO 134
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 134

```
tacgagagtt tgatcctggc tcaggatgaa cgctggcggc gtgcctaaca catgcaagtc      60
gagcgaagcg ctgttttcag aatcttcgga ggaagaggac agtgactgag cggcggacgg     120
gtgagtaacg cgtgggcaac ctgcctcata caggggata acagttagaa atgactgcta      180
ataccgcata agcgcacagg accgcatggt gtagtgtgaa aaactccggt ggtatgagat     240
ggacccgcgt ctgattaggt agttggtggg gtaaaggcct accaagccga cgatcagtag     300
ccgacctgag agggtgaccg gccacattgg gactgagaca cggcccaaac tcctacggga     360
ggcagcagtg gggaatattg cacaatgggg gaaaccctga tgcagcgacg ccgcgtgaag     420
gaagaagtat ttcggtatgt aaacttctat cagcagggaa gaagatgacg gtacctgagt     480
aagaagcacc ggctaaatac gtgccagcag ccgcggtaat acgtatggtg caagcgttat     540
ccggatttac tgggtgtaaa gggagcgtag acggataggc aagtctgagt gaaaaccca      600 gggctcaacc ctgggactgc tttggaaact gcagatctgg agtgccggag aggtaagcgg     660
aattcctagt gtagcggtga aatgcgtaga tattaggagg aacaccagtg gcgaaggcgg     720
cttactggac ggtgactgac gttgaggctc gaaagcgtgg ggagcaaaca ggattagata     780
ccctggtagt ccacgccgta acgatgact actaggtgtc ggtgtgcaaa gcacatcgt      840 gccgcagcaa acgcaataag tagtccacct ggggagtacg ttcgcaagaa tgaaactcaa     900
aggaattgac ggggacccgc acaagcggtg gagcatgtgg tttaattcga gcaacgcga      960 agaaccttac ctggtcttga catccggatg acgggcgagt aatgtcgccg tcccttcggg    1020
gcatccgaga caggtggtgc atggttgtcg tcagctcgtg tcgtgagatg ttgggttaag    1080
tcccgcaacg agcgcaaccc ttatcttcag tagccagcat ataaggtggg cactctggag    1140
agactgccag ggagaacctg gaggaaggtg gggatgacgt caaatcatca tgccccttat    1200
ggccagggct acacacgtgc tacaatggcg taaacaaagg gaagcgagag ggtgacctgg    1260
agcgaatccc aaaaataacg tctcagttcg gattgtagtc tgcaactcga ctacatgaag    1320
ctggaatcgc tagtaatcgc ggatcagcat gccgcggtga atacgttccc gggtcttgta    1380
cacaccgccc gtcacaccat gggagtcagt aacgcccgaa gccagtgacc caaccttaga    1440
ggagggagct gtcgaaggcg ggacggataa ctggggtgaa gtcgtaacaa ggtagccgta    1500
```

```
tcggaaggtg cggctggatc acctcctttt                                    1529

<210> SEQ ID NO 135
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 135
tacgagagtt tgatcctggc tcaggatgaa cgctggcggc gtgcctaaca catgcaagtc     60
gagcgaagcg ctgttttcag aatcttcgga ggaagaggac agtgactgag cggcggacgg    120
gtgagtaacg cgtgggcaac ctgcctcata caggggata acagttagaa atgactgcta     180
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga    360
ggcagcagtg gggaatattg cacaatgggg gaaaccctga tgcagcgacg ccgcgtgaag    420
gaagaagtat ttcggtatgt aaacttctat cagcagggaa gaagatgacg gtacctgagt    480
aagaagcacc ggctaaatac gtgccagcag ccgcggtaat acgtatggtg caagcgttat    540
ccggatttac tgggtgtaaa gggagcgtag acggataggc aagtctggag tgaaaaccca    600
gggctcaacc ctgggactgc tttggaaact gcagatctgg agtgccgag aggtaagcgg     660 aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta acgatgact actaggtgtc ggtgtgcaaa gcacatcgt     840 gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcatccgaga caggtggtgc atggttgtcg tcagctcgtg tcgtgagatg ttgggttaag   1080
tcccgcaacg agcgcaaccc ttatcttcag tagccagcat ataaggtggg cactctggag   1140
agactgccag ggagaacctg gaggaaggtg gggatgacgt caaatcatca tgccccttat   1200
ggccagggct acacacgtgc tacaatggcg taaacaaagg gaagcgagag ggtgacctga   1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc caaccttaga   1440
ggagggagct gtcgaaggcg ggacggataa ctgggtgaa gtcgtaacaa ggtagccgta    1500
tcggaaggtg cggctggatc acctcctttt                                    1529

<210> SEQ ID NO 136
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 136
tacgagagtt tgatcctggc tcaggatgaa cgctggcggc gtgcctaaca catgcaagtc     60
gagcgaagcg ctgttttcag aatcttcgga ggaagaggac agtgactgag cggcggacgg    120
gtgagtaacg cgtgggcaac ctgcctcata caggggata acagttagaa atgactgcta     180
```

```
ataccgcata agcgcacagg accgcatggt gtagtgtgaa aaactccggt ggtatgagat        240
ggacccgcgt ctgattaggt agttggtggg gtaaaggcct accaagccga cgatcagtag        300
ccgacctgag agggtgaccg gccacattgg gactgagaca cggcccaaac tcctacggga        360
ggcagcagtg gggaatattg cacaatgggg gaaaccctga tgcagcgacg ccgcgtgaag        420
gaagaagtat ttcggtatgt aaacttctat cagcagggaa gaagatgacg gtacctgagt        480
aagaagcacc ggctaaatac gtgccagcag ccgcggtaat acgtatggtg caagcgttat        540
ccggatttac tgggtgtaaa gggagcgtag acggataggc aagtctggag tgaaaaccca        600
gggctcaacc ctgggactgc tttggaaact gcagatctgg agtgccggag aggtaagcgg        660
aattcctagt gtagcggtga atgcgtaga tattaggagg aacaccagtg gcgaaggcgg        720
cttactggac ggtgactgac gttgaggctc gaaagcgtgg ggagcaaaca ggattagata        780
ccctggtagt ccacgccgta acgatgact actaggtgtc ggtgtgcaaa gcacatcggt        840
gccgcagcaa acgcaataag tagtccacct ggggagtacg ttcgcaagaa tgaaactcaa        900
aggaattgac ggggacccgc acaagcggtg gagcatgtgg tttaattcga agcaacgcga        960
agaaccttac ctggtcttga catccggatg acgggcgagt aatgtcgccg tcccttcggg       1020
gcatccgaga caggtggtgc atggttgtcg tcagctcgtg tcgtgagatg ttgggttaag       1080
tcccgcaacg agcgcaaccc ttatcttcag tagccagcat ataaggtggg cactctggag       1140
agactgccag ggagaacctg gaggaaggtg gggatgacgt caaatcatca tgccccttat       1200
ggccagggct acacacgtgc tacaatggcg taaacaaagg gaagcgagag ggtgacctgg       1260
agcgaatccc aaaaataacg tctcagttcg gattgtagtc tgcaactcga ctacatgaag       1320
ctggaatcgc tagtaatcgc ggatcagcat gccgcggtga atacgttccc gggtcttgta       1380
cacaccgccc gtcacaccat gggagtcagt aacgcccgaa gccagtgacc caaccttaga       1440
ggagggagct gtcgaaggcg ggacggataa ctggggtgaa gtcgtaacaa ggtagccgta       1500
tcggaaggtg cggctggatc acctccttt                                          1529
```

<210> SEQ ID NO 137
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 137

```
atgagagttt gatcctagct caggatgaac gctggcggcg tgcctaacac atgcaagtcg         60
aacgaagcaa tttaacggaa gttttcggat ggaagttgaa ttgactgagt ggcggacggg        120
tgagtaacgc gtgggtaacc tgccttgtac tggggacaa cagttagaaa tgactgctaa        180
taccgcataa gcgcacagta tcgcatgata cagtgtgaaa actccggtg gtacaagatg        240 gacccgcgtc tgattagcta gttggtaagg taacggctta ccaaggcgac gatcagtagc        300
cgacctgaga gggtgaccgg ccacattggg actgagacac ggcccaaact cctacgggag       360
gcagcagtgg ggaatattgc acaatgggcg aaagcctgat gcagcgacgc cgcgtgagtg        420
aagaagtatt tcggtatgta aagctctatc agcagggaag aaaatgacgg tacctgacta        480
agaagccccg gctaactacg tgccagcagc cgcggtaata cgtaggggc aagcgttatc        540 cggatttact gggtgtaaag ggagcgtaga cggtaaagca agtctgaagt gaaagcccgc        600
ggctcaactg cgggactgct ttggaaactg tttaactgga gtgtcggaga ggtaagtgga       660
```

| | |
|---|---|
| attcctagtg tagcggtgaa atgcgtagat attaggagga acaccagtgg cgaaggcgac | 720 |
| ttactggacg ataactgacg ttgaggctcg aaagcgtggg gagcaaacag gattagatac | 780 |
| cctggtagtc cacgccgtaa acgatgaata ctaggtgttg gggagcaaag ctcttcggtg | 840 |
| ccgtcgcaaa cgcagtaagt attccacctg gggagtacgt tcgcaagaat gaaactcaaa | 900 |
| ggaattgacg gggacccgca caagcggtgg agcatgtggt ttaattcgaa gcaacgcgaa | 960 |
| gaaccttacc aggtcttgac atcgatccga cgggggagta acgtcccctt cccttcgggg | 1020 |
| cggagaagac aggtggtgca tggttgtcgt cagctcgtgt cgtgagatgt tgggttaagt | 1080 |
| cccgcaacga gcgcaaccct tattctaagt agccagcggt tcggccggga actcttggga | 1140 |
| gactgccagg gataacctgg aggaaggtgg ggatgacgtc aaatcatcat gccccttatg | 1200 |
| atctgggcta cacacgtgct acaatggcgt aaacaaagag aagcaagacc gcgaggtgga | 1260 |
| gcaaatctca aaaataacgt ctcagttcgg actgcaggct gcaactcgcc tgcacgaagc | 1320 |
| tggaatcgct agtaatcgcg aatcagaatg tcgcggtgaa tacgttcccg ggtcttgtac | 1380 |
| acaccgcccg tcacaccatg ggagtcagta acgcccgaag tcagtgaccc aaccgcaagg | 1440 |
| agggagctgc cgaaggcggg accgataact ggggtgaagt cgtaacaagg tagccgtatc | 1500 |
| ggaaggtgcg gctggatcac ctcctttt | 1527 |

<210> SEQ ID NO 138
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 138

| | |
|---|---|
| atgagagttt gatcctggct caggatgaac gctggcggcg tgcctaacac atgcaagtcg | 60 |
| aacgaagcga tttaacggaa attttcggat ggaagttgaa ttgactgagt ggcggacggg | 120 |
| tgagtaacgc gtgggtaacc tgccttgtac tggggacaa cagttagaaa tgactgctaa | 180 |
| taccgcataa gcgcacagta tcgcatgata cagtgtgaaa aactccggtg gtacaagatg | 240 |
| gacccgcgtc tgattagcta gttggtaagg taacggctta ccaaggcgac gatcagtagc | 300 |
| cgacctgaga gggtgaccgg ccacattggg actgagacac ggcccaaact cctacgggag | 360 |
| gcagcagtgg ggaatattgc acaatgggcg aaagcctgat gcagcgacgc cgcgtgagtg | 420 |
| aagaagtatt tcggtatgta aagctctatc agcagggaag aaaatgacgg tacctgacta | 480 |
| agaagccccg gctaactacg tgccagcagc cgcggtaata cgtaggggc aagcgttatc | 540 |
| cggatttact gggtgtaaag ggagcgtaga cggtaaagca agtctgaagt gaaagcccgc | 600 |
| ggctcaactg cgggactgct ttggaaactg tttaactgga gtgtcggaga ggtaagtgga | 660 |
| attcctagtg tagcggtgaa atgcgtagat attaggagga acaccagtgg cgaaggcgac | 720 |
| ttactggacg ataactgacg ttgaggctcg aaagcgtggg gagcaaacag gattagatac | 780 |
| cctggtagtc cacgccgtaa acgatgaata ctaggtgttg gggagcaaag ctcttcggtg | 840 |
| ccgtcgcaaa cgcagtaagt attccacctg gggagtacgt tcgcaagaat gaaactcaaa | 900 |
| ggaattgacg gggacccgca caagcggtgg agcatgtggt ttaattcgaa gcaacgcgaa | 960 |
| gaaccttacc aggtcttgac atcgatccga cgggggagta acgtcccctt cccttcgggg | 1020 |
| cggagaagac aggtggtgca tggttgtcgt cagctcgtgt cgtgagatgt tgggttaagt | 1080 |
| cccgcaacga gcgcaaccct tattctaagt agccagcggt tcggccggga actcttggga | 1140 |
| gactgccagg gataacctgg aggaaggtgg ggatgacgtc aaatcatcat gccccttatg | 1200 |

| atctgggcta cacacgtgct acaatggcgt aaacaaagag aagcaagacc gcgaggtgga | 1260 |
| gcaaatctca aaataacgt ctcagttcgg actgcaggct gcaactcgcc tgcacgaagc | 1320 |
| tggaatcgct agtaatcgcg aatcagaatg tcgcggtgaa tacgttcccg ggtcttgtac | 1380 |
| acaccgcccg tcacaccatg ggagtcagta acgcccgaag tcagtgaccc aaccgcaagg | 1440 |
| agggagctgc cgaaggcggg accgataact ggggtgaagt cgtaacaagg tagccgtatc | 1500 |
| ggaaggtgcg gctggatcac ctccttt | 1527 |

<210> SEQ ID NO 139
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 139

| atgagagttt gatcctggct caggatgaac gctggcggcg tgcctaacac atgcaagtcg | 60 |
| aacgaagcga tttaacggaa gttttcggat ggaagttgaa ttgactgagt ggcggacggg | 120 |
| tgagtaacgc gtgggtaacc tgccttgtac tgggggacaa cagttagaaa tgactgctaa | 180 |
| taccgcataa gcgcacagta tcgcatgata cagtgtgaaa actccggtg gtacaagatg | 240 |
| gacccgcgtc tgattagcta gttggtaagg taacggctta ccaaggcgac gatcagtagc | 300 |
| cgacctgaga gggtgaccgg ccacattggg actgagacac ggcccaaact cctacgggag | 360 |
| gcagcagtgg ggaatattgc acaatgggcg aaagcctgat gcagcgacgc cgcgtgagtg | 420 |
| aagaagtatt tcggtatgta agctctatc agcagggaag aaaatgacgg tacctgacta | 480 |
| agaagcccg gctaactacg tgccagcagc cgcggtaata cgtagggggc aagcgttatc | 540 |
| cggatttact gggtgtaaag ggagcgtaga cggtaaagca agtctgaagt gaaagcccgc | 600 |
| ggctcaactg cgggactgct ttggaaactg tttaactgga gtgtcggaga ggtaagtgga | 660 |
| attcctagtg tagcggtgaa atgcgtagat attaggagga caccagtgg cgaaggcgac | 720 |
| ttactggacg ataactgacg ttgaggctcg aaagcgtggg gagcaaacag gattagatac | 780 |
| cctggtagtc cacgccgtaa acgatgaata ctaggtgttg gggagcaaag ctcttcggtg | 840 |
| ccgtcgcaaa cgcagtaagt attccacctg gggagtacgt tcgcaagaat gaaactcaaa | 900 |
| ggaattgacg gaacccgca caagcggtgg agcatgtggt ttaattcgaa gcaacgcgaa | 960 |
| gaaccttacc aggtcttgac atcgatccga cggggagta acgtcccctt cccttcgggg | 1020 |
| cggagaagac aggtggtgca tggttgtcgt cagctcgtgt cgtgagatgt tgggttaagt | 1080 |
| cccgcaacga gcgcaaccct tattctaagt agccagcggt tcggccggga actcttggga | 1140 |
| gactgccagg gataacctgg aggaaggtgg ggatgacgtc aaatcatcat gccccttatg | 1200 |
| atctgggcta cacacgtgct acaatggcgt aaacaaagag aagcaagacc gcgaggtgga | 1260 |
| gcaaatctca aaataacgt ctcagttcgg actgcaggct gcaactcgcc tgcacgaagc | 1320 |
| tggaatcgct agtaatcgcg aatcagaatg tcgcggtgaa tacgttcccg ggtcttgtac | 1380 |
| acaccgcccg tcacaccatg ggagtcagta acgcccgaag tcagtgaccc aaccgcaagg | 1440 |
| agggagctgc cgaaggcggg accgataact ggggtgaagt cgtaacaagg tagccgtatc | 1500 |
| ggaaggtgcg gctggatcac ctccttt | 1527 |

<210> SEQ ID NO 140
<211> LENGTH: 1527
<212> TYPE: DNA

<213> ORGANISM: Artificial Sequence
<220> FEATURE:
<223> OTHER INFORMATION: Synthetic Polynucleotide

<400> SEQUENCE: 140

```
atgagagttt gatcctggct caggatgaac gctggcggcg tgcctaacac atgcaagtcg      60
aacgaagcga tttaacggaa gttttcggat ggaagttgga ttgactgagt ggcggacggg     120
tgagtaacgc gtgggtaacc tgccttgtac tgggggacaa cagttagaaa tgactgctaa     180
taccgcataa gcgcacagta tcgcatgata cagtgtgaaa aactccggtg gtacaagatg     240
gacccgcgtc tgattagcta gttggtaagg taacggctta ccaaggcgac gatcagtagc     300
cgacctgaga gggtgaccgg ccacattggg actgagacac ggcccaaact cctacgggag     360
gcagcagtgg ggaatattgc acaatgggcg aaagcctgat gcagcgacgc cgcgtgagtg     420
aagaagtatt tcggtatgta aagctctatc agcagggaag aaaatgacgg tacctgacta     480
agaagccccg gctaactacg tgccagcagc cgcggtaata cgtaggggc aagcgttatc     540
cggatttact gggtgtaaag ggagcgtaga cggtaaagca agtctgaagt gaaagcccgc     600
ggctcaactg cgggactgct ttggaaactg tttaactgga gtgtcggaga ggtaagtgga     660
attcctagtg tagcggtgaa atgcgtagat attaggagga caccagtgg cgaaggcgac     720
ttactggacg ataactgacg ttgaggctcg aaagcgtggg gagcaaacag gattagatac     780
cctggtagtc cacgccgtaa acgatgaata ctaggtgttg gggagcaaag ctcttcggtg     840
ccgtcgcaaa cgcagtaagt attccacctg gggagtacgt tcgcaagaat gaaactcaaa     900
ggaattgacg gggacccgca caagcggtgg agcatgtggt ttaattcgaa gcaacgcgaa     960
gaaccttacc aggtcttgac atcgatccga cgggggagta acgtcccctt cccttcgggg    1020
cggagaagac aggtggtgca tggttgtcgt cagctcgtgt cgtgagatgt tgggttaagt    1080
cccgcaacga gcgcaacct tattctaagt agccagcggt tcggccggga actcttggga    1140
gactgccagg gataacctgg aggaaggtgg ggatgacgtc aaatcatcat gccccttatg    1200
atctgggcta cacacgtgct acaatggcgt aaacaaagag aagcaagacc gcgaggtgga    1260
gcaaatctca aaaataacgt ctcagttcgg actgcaggct gcaactcgcc tgcacgaagc    1320
tggaatcgct agtaatcgcg aatcagaatg tcgcggtgaa tacgttcccg ggtcttgtac    1380
acaccgcccg tcacaccatg ggagtcagta acgcccgaag tcagtgaccc aaccgcaagg    1440
agggagctgc cgaaggcggg accgataact ggggtgaagt cgtaacaagg tagccgtatc    1500
ggaaggtgcg gctggatcac ctccttt                                       1527
```

<210> SEQ ID NO 141
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 141

```
atcagagagt ttgatcctgg ctcaggatga acgctggcgg cgtgcttaac acatgcaagt      60
cgagcgaagc acttaagtgg atctcttcgg attgaaactt atttgactga gcggcggacg     120
ggtgagtaac gcgtgggtaa cctgcctcat acaggggat aacagttaga aatggctgct     180
aataccgcat aagcgcacag gaccgcatgg tctggtgtga aaaactccgg tggtatgaga     240
tggacccgcg tctgattagc tagttggagg ggtaacggcc caccaaggcg acgatcagta     300
gccggcctga gagggtgaac ggccacattg ggactgagac acggcccaga ctcctacggg     360
```

```
aggcagcagt gggaatatt gcacaatggg ggaaaccctg atgcagcgac gccgcgtgaa    420
ggaagaagta tctcggtatg taaacttcta tcagcaggga agaaaatgac ggtacctgac    480
taagaagccc cggctaacta cgtgccagca gccgcggtaa tacgtagggg caagcgtta     540 tccggattta ctgggtgtaa agggagcgta gacggaagag caagtctgat gtgaaaggct    600
ggggcttaac cccaggactg cattggaaac tgttttcta gagtgccgga gaggtaagcg    660
gaattcctag tgtagcggtg aaatgcgtag atattaggag gaacaccagt ggcgaaggcg    720
gcttactgga cggtaactga cgttgaggct cgaaagcgtg gggagcaaac aggattagat    780
accctggtag tccacgccgt aaacgatgaa tactaggtgt cgggtggcaa agccattcgg    840
tgccgcagca aacgcaataa gtattccacc tggggagtac gttcgcaaga atgaaactca    900
aaggaattga cggggacccg cacaagcggt ggagcatgtg gtttaattcg aagcaacgcg    960
aagaacctta ccaagtcttg acatccctct gaccggcccg taacgggcc ttcccttcgg   1020 ggcagaggag acaggtggtg catggttgtc gtcagctcgt gtcgtgagat gttgggttaa   1080
gtcccgcaac gagcgcaacc cctatcctta gtagccagca ggtgaagctg gcactctag   1140 ggagactgcc ggggataacc cggaggaagg cgggacgac gtcaaatcat catgcccctt   1200
atgatttggg ctacacacgt gctacaatgg cgtaaacaaa gggaagcgag acagcgatgt   1260
tgagcaaatc ccaaaaataa cgtcccagtt cggactgcag tctgcaactc gactgcacga   1320
agctggaatc gctagtaatc gcgaatcaga atgtcgcggt gaatacgttc ccgggtcttg   1380
tacacaccgc ccgtcacacc atgggagtca gtaacgcccg aagtcagtga cccaacctttt  1440 taggagggag ctgccgaagg cgggaccgat aactggggtg aagtcgtaac aaggtagccg   1500
tatcggaagg tgcggctgga tcacctcctt t                                  1531
```

<210> SEQ ID NO 142
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 142

```
atcagagagt ttgatcctgg ctcaggatga acgctggcgg cgtgcttaac acatgcaagt     60
cgagcgaagc acttaagtgg atctcttcgg attgaaactt atttgactga gcggcggacg    120
ggtgagtaac gcgtgggtaa cctgcctcat acagggggat aacagttaga atggctgct    180 aataccgcat aagcgcacag gaccgcatgg tctggtgtga aaaactccgg tggtatgaga    240
tggacccgcg tctgattagc tagttggagg ggtaacggcc caccaaggcg acgatcagta    300
gccggcctga gagggtgaac ggccacattg gactgagaca cggcccaga ctcctacggg    360 aggcagcagt gggaatatt gcacaatggg ggaaaccctg atgcagcgac gccgcgtgaa    420
ggaagaagta tctcggtatg taaacttcta tcagcaggga agaaaatgac ggtacctgac    480
taagaagccc cggctaacta cgtgccagca gccgcggtaa tacgtagggg caagcgtta     540 tccggattta ctgggtgtaa agggagcgta gacggaagag caagtctgat gtgaaaggct    600
ggggcttaac cccaggactg cattggaaac tgttttcta gagtgccgga gaggtaagtg    660
gaattcctag tgtagcggtg aaatgcgtag atattaggag gaacaccagt ggcgaaggcg    720
gcttactgga cggtaactga cgttgaggct cgaaagcgtg gggagcaaac aggattagat    780
accctggtag tccacgccgt aaacgatgaa tactaggtgt cgggtggcaa agccattcgg    840
```

| tgccgcagca aacgcaataa gtattccacc tggggagtac gttcgcaaga atgaaactca | 900 |
| aaggaattga cggggacccg cacaagcggt ggagcatgtg gtttaattcg aagcaacgcg | 960 |
| aagaacctta ccaagtcttg acatccctct gaccggcccg taacgggcc ttcccttcgg | 1020 |
| ggcagaggag acaggtggtg catggttgtc gtcagctcgt gtcgtgagat gttgggttaa | 1080 |
| gtcccgcaac gagcgcaacc cctatcctta gtagccagca ggtgaagctg gcactctag | 1140 |
| ggagactgcc ggggataacc cggaggaagg cggggacgac gtcaaatcat catgcccctt | 1200 |
| atgatttggg ctacacacgt gctacaatgg cgtaaacaaa gggaagcggg acagcgatgt | 1260 |
| tgagcaaatc ccaaaaataa cgtcccagtt cggactgcag tctgcaactc gactgcacga | 1320 |
| agctggaatc gctagtaatc gcgaatcaga atgtcgcggt gaatacgttc ccgggtcttg | 1380 |
| tacacaccgc ccgtcacacc atgggagtca gtaacgcccg aagtcagtga cccaaccta | 1440 |
| caggagggag ctgccgaagg cgggaccgat aactggggtg aagtcgtaac aaggtagccg | 1500 |
| tatcggaagg tgcggctgga tcacctcctt t | 1531 |

<210> SEQ ID NO 143
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 143

| atcagagagt ttgatcctgg ctcaggatga acgctggcgg cgtgcttaac acatgcaagt | 60 |
| cgagcgaagc acttaagtgg atctcttcgg attgaagctt atttgactga gcggcggacg | 120 |
| ggtgagtaac gcgtgggtaa cctgcctcat acaggggggat aacagttaga aatggctgct | 180 |
| aataccgcat aagcgcacag gaccgcatgg tctggtgtga aaaactccgg tggtatgaga | 240 |
| tggacccgcg tctgattagc tagttggagg ggtaacggcc caccaaggcg acgatcagta | 300 |
| gccggcctga gagggtgaac ggccacattg gactgagac acggcccaga ctcctacggg | 360 |
| aggcagcagt ggggaatatt gcacaatggg ggaaaccctg atgcagcgac gccgcgtgaa | 420 |
| ggaagaagta tctcggtatg taaacttcta tcagcaggga agaaaatgac ggtacctgac | 480 |
| taagaagccc cggctaacta cgtgccagca gccgcggtaa tacgtagggg gcaagcgtta | 540 |
| tccggattta ctgggtgtaa agggagcgta gacggaagag caagtctgat gtgaaaggct | 600 |
| ggggcttaac cccaggactg cattggaaac tgttttttcta gagtgccgga gaggtaagcg | 660 |
| gaattcctag tgtagcggtg aaatgcgtag atattaggag gaacaccagt ggcgaaggcg | 720 |
| gcttactgga cggtaactga cgttgaggct cgaaagcgtg gggagcaaac aggattagat | 780 |
| accctggtag tccacgccgt aaacgatgaa tactaggtgt cgggtggcaa agccattcgg | 840 |
| tgccgcagca aacgcaataa gtattccacc tggggagtac gttcgcaaga atgaaactca | 900 |
| aaggaattga cggggacccg cacaagcggt ggagcatgtg gtttaattcg aagcaacgcg | 960 |
| aagaacctta ccaagtcttg acatccctct gaccggcccg taacgggcc ttcccttcgg | 1020 |
| ggcagaggag acaggtggtg catggttgtc gtcagctcgt gtcgtgagat gttgggttaa | 1080 |
| gtcccgcaac gagcgcaacc cctatcctta gtagccagca ggtgaagctg gcactctag | 1140 |
| ggagactgcc ggggataacc cggaggaagg cggggacgac gtcaaatcat catgcccctt | 1200 |
| atgatttggg ctacacacgt gctacaatgg cgtaaacaaa gggaagcgag acagcgatgt | 1260 |
| tgagcaaatc ccaaaaataa cgtcccagtt cggactgcag tctgcaactc gactgcacga | 1320 |
| agctggaatc gctagtaatc gcgaatcaga atgtcgcggt gaatacgttc ccgggtcttg | 1380 |

```
tacacaccgc ccgtcacacc atgggagtca gtaacgcccg aagtcagtga cccaaccta      1440 caggagggag ctgccgaagg cgggaccgat aactggggtg aagtcgtaac aaggtagccg     1500
tatcggaagg tgcggctgga tcacctcctt t                                    1531
```

<210> SEQ ID NO 144
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 144

```
atcagagagt ttgatcctgg ctcaggatga acgctggcgg cgtgcttaac acatgcaagt      60
cgagcgaagc acttaagcgg atctcttcgg attgaaactt atttgactga gcggcggacg    120
ggtgagtaac gcgtgggtaa cctgcctcat acaggggggat aacagttaga aatggctgct   180
aataccgcat aagcgcacag gaccgcatgg tctggtgtga aaaactccgg tggtatgaga    240
tggacccgcg tctgattagc tagttggagg ggtaacggcc caccaaggcg acgatcagta    300
gccggcctga gagggtgaac ggccacattg ggactgagac acggcccaga ctcctacggg    360
aggcagcagt ggggaatatt gcacaatggg ggaaaccctg atgcagcgac gccgcgtgaa    420
ggaagaagta tctcggtatg taaacttcta tcagcaggga agaaaatgac ggtacctgac    480
taagaagccc cggctaacta cgtgccagca gccgcggtaa tacgtagggg gcaagcgtta    540
tccggattta ctgggtgtaa agggagcgta gacggaagag caagtctgat gtgaaaggct    600
ggggcttaac cccaggactg cattggaaac tgttttctta gagtgccgga gaggtaagcg    660
gaattcctag tgtagcggtg aaatgcgtag atattaggag gaacaccagt ggcgaaggcg    720
gcttactgga cggtaactga cgttgaggct cgaaagcgtg gggagcaaac aggattagat    780
accctggtag tccacgccgt aaacgatgaa tactaggtgt cgggtggcaa agccattcgg    840
tgccgcagca aacgcaataa gtattccacc tggggagtac gttcgcaaga atgaaactca    900
aaggaattga cggggacccg cacaagcggt ggagcatgtg gtttaattcg aagcaacgcg    960 aagaaccta ccaagtcttg acatccctct gaccggcccg taacgggccc ttcccttcgg   1020
ggcagaggag acaggtggtg catggttgtc gtcagctcgt gtcgtgagat gttgggttaa   1080
gtcccgcaac gagcgcaacc cctatcctta gtagccagca ggtgaagctg ggcactctag   1140
ggagactgcc ggggataacc cggaggaagg cggggacgac gtcaaatcat catgcccctt   1200
atgatttggg ctacacacgt gctacaatgg cgtaaacaaa gggaagcgag acagcgatgt   1260
tgagcaaatc ccaaaaataa cgtcccagtt cggactgcag tctgcaactc gactgcacga   1320
agctggaatc gctagtaatc gcgaatcaga atgtcgcggt gaatacgttc ccgggtcttg   1380
tacacaccgc ccgtcacacc atgggagtca gtaacgcccg aagtcagtga cccaaccta    1440 caggagggag ctgccgaagg cgggaccgat aactggggtg aagtcgtaac aaggtagccg    1500
tatcggaagg tgcggctgga tcacctcctt t                                  1531
```

<210> SEQ ID NO 145
<211> LENGTH: 1531
<212> TYPE: DNA
<213> ORGANISM: Artificial Sequence
<220> FEATURE:
<223> OTHER INFORMATION: Synthetic Polynucleotide

<400> SEQUENCE: 145

| | |
|---|---:|
| atcagagagt tgatcctgg ctcaggatga acgctggcgg cgtgcttaac acatgcaagt | 60 |
| cgagcgaagc acttaagtgg atctcttcgg attgaaactt atttgactga gcggcggacg | 120 |
| ggtgagtaac gcgtgggtaa cctgcctcat acaggggat aacagttaga aatggctgct | 180 |
| aataccgcat aagcgcacag gaccgcatgg tctggtgtga aaaactccgg tggtatgaga | 240 |
| tggacccgcg tctgattagc tagttggagg ggtaacggcc caccaaggcg acgatcagta | 300 |
| gccggcctga gagggtgaac ggccacattg gactgagac acggcccaga ctcctacggg | 360 |
| aggcagcagt ggggaatatt gcacaatggg ggaaaccctg atgcagcgac gccgcgtgaa | 420 |
| ggaagaagta tctcggtatg taaacttcta tcagcaggga agaaaatgac ggtacctgac | 480 |
| taagaagccc cggctaacta cgtgccagca gccgcggtaa tacgtagggg gcaagcgtta | 540 |
| tccggattta ctgggtgtaa agggagcgta gacggaagag caagtctgat gtgaaaggct | 600 |
| ggggcttaac cccaggactg cattggaaac tgttttttcta gagtgccgga gaggtaagcg | 660 |
| gaattcctag tgtagcggtg aaatgcgtag atattaggag gaacatcagt ggcgaaggcg | 720 |
| gcttactgga cggtaactga cgttgaggct cgaaagcgtg gggagcaaac aggattagat | 780 |
| accctggtag tccacgccgt aaacgatgaa tactaggtgt cgggtggcaa agccattcgg | 840 |
| tgccgcagca aacgcaataa gtattccacc tggggagtac gttcgcaaga atgaaactca | 900 |
| aaggaattga cggggacccg cacaagcggt ggagcatgtg gtttaattcg aagcaacgcg | 960 |
| aagaacctta ccaagtcttg acatccctct gaccggcccg taacgggcc ttcccttcgg | 1020 |
| ggcagaggag acaggtggtg catggttgtc gtcagctcgt gtcgtgagat gttgggttaa | 1080 |
| gtcccgcaac gagcgcaacc cctatcctta gtagccagca ggtgaagctg gcactctag | 1140 |
| ggagactgcc ggggataacc cggaggaagg cggggacgac gtcaaatcat catgcccctt | 1200 |
| atgatttggg ctacacacgt gctacaatgg cgtaaacaaa gggaagcgag acagcgatgt | 1260 |
| tgagcaaatc ccaaaaataa cgtcctagtt cggactgcag tctgcaactc gactgcacga | 1320 |
| agctggaatc gctagtaatc gcgaatcaga atgtcgcggt gaatacgttc ccgggtcttg | 1380 |
| tacacaccgc ccgtcacacc atgggagtca gtaacgcccg aagtcagtga cccaacctta | 1440 |
| caggagggag ctgccgaagg cgggaccgat aactggggtg aagtcgtaac aaggtagccg | 1500 |
| tatcggaagg tgcggctgga tcacctcctt t | 1531 |

<210> SEQ ID NO 146
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 146

| | |
|---|---:|
| aacgagagtt tgatcctggc tcaggatgaa cgctggcggc gtgcttaaca catgcaagtc | 60 |
| gagcgaagca cttaagtttg attcttcgga tgaagacttt tgtgactgag cggcggacgg | 120 |
| gtgagtaacg cgtgggtaac ctgcctcata caggggata acagttagaa atgactgcta | 180 |
| ataccgcata agaccacggt accgcatggt acagtggtaa aaactccggt ggtatgagat | 240 |
| ggacccgcgt ctgattaggt agttggtggg gtaacggcct accaagccga cgatcagtag | 300 |
| ccgacctgag agggtgaccg ccacattgg gactgagaca cggcccagac tcctacggga | 360 |
| ggcagcagtg gggaatattg cacaatggag gaaactctga tgcagcgacg ccgcgtgaag | 420 |
| gatgaagtat ttcggtatgt aaacttctat cagcagggaa gaaaatgacg gtacctgact | 480 |
| aagaagcccc ggctaactac gtgccagcag ccgcggtaat acgtaggggg caagcgttat | 540 |

```
ccggatttac tgggtgtaaa gggagcgtag acggcacggc aagccagatg tgaaagcccg      600
gggctcaacc ccgggactgc atttggaact gctgagctag agtgtcggag aggcaagtgg      660
aattcctagt gtagcggtga aatgcgtaga tattaggagg aacaccagtg gcgaaggcgg      720
cttgctggac gatgactgac gttgaggctc gaaagcgtgg ggagcaaaca ggattagata      780
ccctggtagt ccacgccgta acgatgact gctaggtgtc gggtggcaaa gccattcggt      840
gccgcagcta acgcaataag cagtccacct ggggagtacg ttcgcaagaa tgaaactcaa      900
aggaattgac ggggacccgc acaagcggtg gagcatgtgg tttaattcga agcaacgcga      960
agaaccttac ctgatcttga catcccgatg accgcttcgt aatggaagtt tttcttcgga     1020
acatcggtga caggtggtgc atggttgtcg tcagctcgtg tcgtgagatg ttgggttaag     1080
tcccgcaacg agcgcaaccc ctatcttcag tagccagcag gttaagctgg gcactctgga     1140
gagactgcca gggataacct ggaggaaggt ggggatgacg tcaaatcatc atgccccta     1200 tgaccagggc tacacacgtg ctacaatggc gtaaacaaag agaagcgaac tcgcgagggt     1260
aagcaaatct caaaaataac gtctcagttc ggattgtagt ctgcaactcg actacatgaa     1320
gctggaatcg ctagtaatcg cagatcagaa tgctgcggtg aatacgttcc cgggtcttgt     1380
acacaccgcc cgtcacacca tgggagtcag taacgcccga agtcagtgac caaccgtaa     1440 ggagggagct gccgaaggtg ggaccgataa ctggggtgaa gtcgtaacaa ggtagccgta     1500
tcggaaggtg cggctggatc acctccttt                                       1529
```

<210> SEQ ID NO 147
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 147

```
aacgagagtt tgatcctggc tcaggatgaa cgctggcggc gtgcttaaca catgcaagtc       60
gagcgaagca ctttggaaag attcttcgga tgatttcctt tgtgactgag cggcggacgg      120
gtgagtaacg cgtgggtaac ctgcctcata caggggata acagttagaa atgactgcta       180
ataccgcata agaccacggt accgcatggt acagtggtaa aaactccggt ggtatgagat      240
ggacccgcgt ctgattaggt agttggtggg gtaacggcct accaagccga cgatcagtag      300
ccgacctgag agggtgaccg gccacattgg gactgagaca cggcccagac tcctacggga      360
ggcagcagtg gggaatattg cacaatggag gaaactctga tgcagcgacg ccgcgtgaag      420
gatgaagtat ttcggtatgt aaacttctat cagcagggaa gaaaatgacg gtacctgact      480
aagaagcccc ggctaactac gtgccagcag ccgcggtaat acgtaggggg caagcgttat      540
ccggatttac tgggtgtaaa gggagcgtag acggcacggc aagccagatg tgaaagcccg      600
gggctcaacc ccggactgca tttggaactg ctgagctaga gtgtcggaga ggcaagtgga      660
attcctagtg tagcggtgaa atgcgtagat attaggagga acaccagtgg cgaaggcggc      720
ttgctggacg atgactgacg ttgaggctcg aaagcgtggg gagcaaacag gattagatac      780
cctggtagtc cacgccgtaa acgatgactg ctaggtgtcg ggtggcaaag ccattcggtg      840
ccgcagctaa cgcaataagc agtccacctg gggagtacgt tcgcaagaat gaaactcaaa      900
ggaattgacg gggacccgca caagcggtgg agcatgtggt ttaattcgaa gcaacgcgaa      960
gaaccttacc tgatcttgac atcccgatga ccgcttcgta atggaagctt ttcttcggaa     1020
```

```
catcggtgac aggtggtgca tggttgtcgt cagctcgtgt cgtgagatgt tgggttaagt    1080
cccgcaacga gcgcaacccc tatcttcagt agccagcagg ttaagctggg cactctggag    1140
agactgccag ggataacctg gaggaaggtg gggatgacgt caaatcatca tgccccttat    1200
gaccagggct acacacgtgc tacaatggcg taaacaaaga gaagcgaact cgcgagggta    1260
agcaaatctc aaaaataacg tctcagttcg gattgtagtc tgcaactcga ctacatgaag    1320
ctggaatcgc tagtaatcgc agatcagaat gctgcggtga atacgttccc gggtcttgta    1380
cacaccgccc gtcacaccat gggagtcagt aacgcccgaa gtcagtgacc caaccgtaag    1440
gagggagctg ccgaaggtgg gaccgataac tggggtgaag tcgtaacaag gtagccgtat    1500
cggaaggtgc ggctggatca cctcctttt                                     1528
```

<210> SEQ ID NO 148
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 148

```
aacgagagtt tgatcctggc tcaggatgaa cgctggcggc gtgcttaaca catgcaagtc      60
gagcgaagca cttaagtttg attcttcgga tgaagacttt tgtgactgag cggcggacgg     120
gtgagtaacg cgtgggtaac ctgcctcata caggggata acagttagaa atgactgcta     180
ataccgcata agaccacggt accgcatggt acagtggtaa aaactccggt ggtatgagat     240
ggacccgcgt ctgattaggt agttggtggg gtaacggcct accaagccga cgatcagtag     300
ccgacctgag agggtgaccg gccacattgg gactgagaca cggcccagac tcctacggga     360
ggcagcagtg gggaatattg cacaatggag gaaactctga tgcagcgacg ccgcgtgaag     420
gatgaagtat ttcggtatgt aaacttctat cagcagggaa gaaaatgacg gtacctgact     480
aagaagcccc ggctaactac gtgccagcag ccgcggtaat acgtaggggg caagcgttat     540
ccggatttac tgggtgtaaa gggagcgtag acggcacggc aagccagatg tgaaagcccg     600
gggctcaacc ccgggactgc atttggaact gctgagctag agtgtcggag aggcaagtgg     660
aattcctagt gtagcggtga aatgcgtaga tattaggagg aacaccagtg gcgaaggcgg     720
cttgctggac gatgactgac gttgaggctc gaaagcgtgg ggagcaaaca ggattagata     780
ccctggtagt ccacgccgta acgatgact gctaggtgtc gggtggcaaa gccattcggt     840
gccgcagcta acgcaataag cagtccacct ggggagtacg ttcgcaagaa tgaaactcaa     900
aggaattgac ggggacccgc acaagcggtg gagcatgtgg tttaattcga agcaacgcga     960
agaaccttac ctgatcttga catcccgatg accgcttcgt aatggaagct tttcttcgga    1020
acatcggtga caggtggtgc atggttgtcg tcagctcgtg tcgtgagatg ttgggttaag    1080
tcccgcaacg agcgcaaccc ctatcttcag tagccagcag gttaagctgg gcactctgga    1140
gagactgcca gggataacct ggaggaaggt ggggatgacg tcaaatcatc atgcccctta    1200
tgaccagggc tacacacgtg ctacaatggc gtaaacaaag agaagcgaac tcgcgagggt    1260
aagcaaatct caaaaataac gtctcagttc ggattgtagt ctgcaactcg actacatgaa    1320
gctggaatcg ctagtaatcg cagatcagaa tgctgcggtg aatacgttcc gggtcttgt    1380 acacaccgcc gtcacacca tgggagtcag taacgcccga agtcagtgac ccaaccgtaa    1440
ggagggagct gccgaaggtg ggaccgataa ctggggtgaa gtcgtaacaa ggtagccgta    1500
tcggaaggtg cggctggatc acctcctttt                                    1529
```

<210> SEQ ID NO 149
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 149

```
aacgagagtt tgatcctggc tcaggatgaa cgctggcggc gtgcttaaca catgcaagtc      60
gagcgaagca ctttggaaag attcttcgga tgatttcctt tgtgactgag cggcggacgg     120
gtgagtaacg cgtgggtaac ctgcctcata caggggata acagttagaa atgactgcta     180
ataccgcata agaccacggt accgcatggt acagtggtaa aaactccggt ggtatgagat     240
ggacccgcgt ctgattaggt agttggtggg gtaacggcct accaagccga cgatcagtag     300
ccgacctgag agggtgaccg gccacattgg gactgagaca cggcccagac tcctacggga     360
ggcagcagtg gggaatattg cacaatggag gaaactctga tgcagcgacg ccgcgtgaag     420
gatgaagtat ttcggtatgt aaacttctat cagcagggaa gaaaatgacg gtacctgact     480
aagaagcccc ggctaactac gtgccagcag ccgcggtaat acgtaggggg caagcgttat     540
ccggatttac tgggtgtaaa gggagcgtag acggcacggc aagccagatg tgaaagcccg     600
gggctcaacc ccgggactgc atttggaact gctgagctag agtgtcggag aggcaagtgg     660
aattcctagt gtagcggtga aatgcgtaga tattaggagg aacaccagtg gcgaaggcgg     720
cttgctggac gatgactgac gttgaggctc gaaagcgtgg ggagcaaaca ggattagata     780
ccctggtagt ccacgccgta acgatgact gctaggtgtc gggtggcaaa gccattcggt     840
gccgcagcta acgcaataag cagtccacct ggggagtacg ttcgcaagaa tgaaactcaa     900
aggaattgac ggggacccgc acaagcggtg gagcatgtgg tttaattcga agcaacgcga     960
agaaccttac ctgatcttga catcccgatg accgcttcgt aatggaagct tttcttcgga    1020
acatcggtga caggtggtgc atggttgtcg tcagctcgtg tcgtgagatg ttgggttaag    1080
tcccgcaacg agcgcaaccc ctatcttcag tagccagcag gttaagctgg cactctgga    1140
gagactgcca gggataacct ggaggaaggt ggggatgacg tcaaatcatc atgcccctta    1200
tgaccagggc tacacacgtg ctacaatggc gtaaacaaag agaagcgaac tcgcgagggt    1260
aagcaaatct caaaaataac gtctcagttc ggattgtagt ctgcaactcg actacatgaa    1320
gctggaatcg ctagtaatcg cagatcagaa tgctgcggtg aatacgttcc cgggtcttgt    1380
acacaccgcc cgtcacacca tgggagtcag taacgcccga agtcagtgac caaccgtaa    1440
ggagggagct gccgaaggtg ggaccgataa ctggggtgaa gtcgtaacaa ggtagccgta    1500
tcggaaggtg cggctggatc acctccttt                                      1529
```

<210> SEQ ID NO 150
<211> LENGTH: 1528
<212> TYPE: DNA
<213> ORGANISM: Artificial Sequence
<220> FEATURE:
<223> OTHER INFORMATION: Synthetic Polynucleotide

<400> SEQUENCE: 150

```
aacgagagtt tgatcctggc tcaggatgaa cgctggcggc gtgcttaaca catgcaagtc      60
gagcgaagcg cttaagtttg attcttcgga tgaagacttt tgtgactgag cggcggacgg     120
gtgagtaacg cgtgggtaac ctgcctcata caggggata acagttagaa atgactgcta     180
```

| | |
|---|---|
| ataccgcata agaccacggt accgcatggt acagtggtaa aaactccggt ggtatgagat | 240 |
| ggacccgcgt ctgattaggt agttggtggg gtaacggcct accaagccga cgatcagtag | 300 |
| ccgacctgag agggtgaccg gccacattgg gactgagaca cggcccagac tcctacggga | 360 |
| ggcagcagtg gggaatattg cacaatggag gaaactctga tgcagcgacg ccgcgtgaag | 420 |
| gatgaagtat ttcggtatgt aaacttctat cagcagggaa gaaaatgacg gtacctgact | 480 |
| aagaagcccc ggctaactac gtgccagcag ccgcggtaat acgtaggggg caagcgttat | 540 |
| ccggatttac tgggtgtaaa gggagcgtag acggcacggc aagccagatg tgaaagcccg | 600 |
| ggctcaaccc cgggactgca tttggaactg ctgagctaga gtgtcggaga ggcaagtgga | 660 |
| attcctagtg tagcggtgaa atgcgtagat attaggagga acaccagtgg cgaaggcggc | 720 |
| ttgctggacg atgactgacg ttgaggctcg aaagcgtggg gagcaaacag gattagatac | 780 |
| cctggtagtc cacgccgtaa acgatgactg ctaggtgtcg ggtggcaaag ccattcggtg | 840 |
| ccgcagctaa cgcaataagc agtccacctg gggagtacgt tcgcaagaat gaaactcaaa | 900 |
| ggaattgacg gggacccgca caagcggtgg agcatgtggt ttaattcgaa gcaacgcgaa | 960 |
| gaaccttacc tgatcttgac atcccgatga ccgcttcgta atggaagttt tcttcggaa | 1020 |
| catcggtgac aggtggtgca tggttgtcgt cagctcgtgt cgtgagatgt tgggttaagt | 1080 |
| cccgcaacga gcgcaacccc tatcttcagt agccagcagg ttaagctggg cactctggag | 1140 |
| agactgccag gataacctg gaggaaggtg gggatgacg caaatcatca tgcccttat | 1200 |
| gaccagggct acacacgtgc tacaatggcg taaacaaaga gaggcaaact cgcgagggta | 1260 |
| agcaaatctc aaaaataacg tctcagttcg gattgtagtc tgcaactcga ctacatgaag | 1320 |
| ctggaatcgc tagtaatcgc agatcagaat gctgcggtga atacgttccc gggtcttgta | 1380 |
| cacaccgccc gtcacaccat gggagtcagt aacgcccgaa gtcagtgacc caaccgtaag | 1440 |
| gagggagctg ccgaaggtgg gaccgataac tggggtgaag tcgtaacaag gtagccgtat | 1500 |
| cggaaggtgc ggctggatca cctcctttt | 1528 |

<210> SEQ ID NO 151
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 151

| | |
|---|---|
| aacgagagtt tgatcctggc tcaggatgaa cgctggcggc gtgcttaaca catgcaagtc | 60 |
| gagcgaagcg cttgggaag attcttcgga tgatttcctt tgtgactgag cggcggacgg | 120 |
| gtgagtaacg cgtgggtaac ctgcctcata caggggata acagttagaa atgactgcta | 180 |
| ataccgcata agaccacggt accgcatggt acagtggtaa aaactccggt ggtatgagat | 240 |
| ggacccgcgt ttgattaggt agttggtggg gtaacggcct accaagccga cgatcagtag | 300 |
| ccgacctgag agggtgaccg gccacattgg gactgagaca cggcccagac tcctacggga | 360 |
| ggcagcagtg gggaatattg cacaatggag gaaactctga tgcagcgacg ccgcgtgaag | 420 |
| gatgaagtat ttcggtatgt aaacttctat cagcagggaa gaaaatgacg gtacctgact | 480 |
| aagaagcccc ggctaactac gtgccagcag ccgcggtaat acgtaggggg caagcgttat | 540 |
| ccggatttac tgggtgtaaa gggagcgtag acggcacggc aagccagatg tgaaagcccg | 600 |
| gggctcaacc ccgggactgc atttggaact gctgagctag agtgtcggag aggcaagtgg | 660 |
| aattcctagt gtagcggtga aatgcgtaga tattaggagg aacaccagtg gcgaaggcgg | 720 |

```
cttgctggac gatgactgac gttgaggctc gaaagcgtgg ggagcaaaca ggattagata      780
ccctggtagt ccacgccgta aacgatgact gctaggtgtc gggtggcaaa gccattcggt      840
gccgcagcta acgcaataag cagtccacct ggggagtacg ttcgcaagaa tgaaactcaa      900
aggaattgac ggggacccgc acaagcggtg gagcatgtgt tttaattcga agcaacgcga      960
agaaccttac ctgatcttga catcccgatg actgcttcgt aatggaagtt tttcttcgga     1020
acatcggtga caggtggtgc atggttgtcg tcagctcgtg tcgtgagatg ttgggttaag     1080
tcccgcaacg agcgcaaccc ctatcttcag tagccagcag gttaagctgg cactctgga      1140 gagactgcca gggataacct ggaggaaggt ggggatgacg tcaaatcatc atgcccctta     1200
tgaccagggc tacacacgtg ctacaatggc gtaaacaaag agaagcgaac tcgcgagggt     1260
aagcaaatct caaaaataac gtctcagttc ggattgtagt ctgcaactcg actacatgaa     1320
gctggaatcg ctagtaatcg cagatcagaa tgctgcggtg aatacgttcc cgggtcttgt     1380
acacaccgcc cgtcacacca tgggagtcag taacgcccga agtcagtgac caaccgtaa      1440 ggagggagct gccgaaggtg ggaccgataa ctggggtgaa gtcgtaacaa ggtagccgta     1500
tcggaaggtg cggctggatc acctcctttt                                      1529
```

<210> SEQ ID NO 152
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 152

```
atggagagtt tgatcctggc tcaggatgaa cgctggcggc atgcctaata catgcaagtc       60
gaacgaagtt tcgaggaagc ttgcttccaa agagacttag tggcgaacgg gtgagtaaca      120
cgtaggtaac ctgcccatgt gtccgggata actgctggaa acggtagcta aaaccggata      180
ggtatacaga gcgcatgctc agtatattaa agcgcccatc aaggcgtgaa catggatgga     240
cctgcggcgc attagctagt tggtgaggta acggctcacc aaggcgatga tgcgtagccg      300
gcctgagagg gtaaacggcc acattgggac tgagacacgg cccaaactcc tacgggaggc      360
agcagtaggg aattttcgtc aatggggga accctgaacg agcaatgccg cgtgagtgaa      420
gaaggtcttc ggatcgtaaa gctctgttgt aagtgaagaa cggctcatag aggaaatgct      480
atgggagtga cggtagctta ccagaaagcc acggctaact acgtgccagc agccgcggta      540
atacgtaggt ggcaagcgtt atccggaatc attgggcgta aagggtgcgt aggtggcgta      600
ctaagtctgt agtaaaaggc aatggctcaa ccattgtaag ctatggaaac tggtatgctg      660
gagtgcagaa gagggcgatg gaattccatg tgtagcggta aaatgcgtag atatatggag      720
gaacaccagt ggcgaaggcg gtcgcctggt ctgtaactga cactgaggca cgaaagcgtg      780
gggagcaaat aggattagat accctagtag tccacgccgt aaacgatgag aactaagtgt      840
tggaggaatt cagtgctgca gttaacgcaa taagttctcc gcctggggag tatgcacgca      900
agtgtgaaac tcaaaggaat tgacgggggc ccgcacaagc ggtggagtat gtggtttaat      960
tcgaagcaac gcgaagaacc ttaccaggcc ttgacatgga aacaaatacc ctagagatag     1020 gggataatt atggatcaca caggtggtgc atggttgtcg tcagctcgtg tcgtgagatg     1080
ttgggttaag tcccgcaacg agcgcaaccc ttgtcgcatg ttaccagcat caagttgggg     1140
actcatgcga gactgccggt gacaaaccgg aggaaggtgg ggatgacgtc aaatcatcat     1200
```

| | |
|---|---|
| gccccttatg gcctgggcta cacacgtact acaatggcgg ccacaaagag cagcgacaca | 1260 |
| gtgatgtgaa gcgaatctca taaaggtcgt ctcagttcgg attgaagtct gcaactcgac | 1320 |
| ttcatgaagt cggaatcgct agtaatcgca gatcagcatg ctgcggtgaa tacgttctcg | 1380 |
| ggccttgtac acaccgcccg tcaaaccatg ggagtcagta atacccgaag ccggtggcat | 1440 |
| aaccgtaagg agtgagccgt cgaaggtagg accgatgact ggggttaagt cgtaacaagg | 1500 |
| tatccctacg ggaacgtggg gatggatcac ctcctttt | 1537 |

<210> SEQ ID NO 153
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 153

| | |
|---|---|
| atggagagtt tgatcctggc tcaggatgaa cgctggcggc atgcctaata catgcaagtc | 60 |
| gaacgaagtt tcgaggaagc ttgcttccaa agagacttag tggcgaacgg gtgagtaaca | 120 |
| cgtaggtaac ctgcccatgt gtccgggata actgctggaa acggtagcta aaaccggata | 180 |
| ggtatacaga gcgcatgctc agtatattaa agcgcccatc aaggcgtgaa catggatgga | 240 |
| cctgcggcgc attagctagt tggtgaggta acggcccacc aaggcgatga tgcgtagccg | 300 |
| gcctgagagg gtaaacggcc acattgggac tgagacacgg cccaaactcc tacgggaggc | 360 |
| agcagtaggg aattttcgtc aatggggaa accctgaacg agcaatgccg cgtgagtgaa | 420 |
| gaaggtcttc ggatcgtaaa gctctgttgt aagtgaagaa cggctcatag aggaaatgct | 480 |
| atgggagtga cggtagctta ccagaaagcc acggctaact acgtgccagc agccgcggta | 540 |
| atacgtaggt ggcaagcgtt atccggaatc attgggcgta aagggtgcgt aggtggcgta | 600 |
| ctaagtctgt agtaaaaggc aatggctcaa ccattgtaag ctatggaaac tggtatgctg | 660 |
| gagtgcagaa gagggcgatg gaattccatg tgtagcggta aaatgcgtag atatatggag | 720 |
| gaacaccagt ggcgaaggcg gtcgcctggt ctgtaactga cactgaggca cgaaagcgtg | 780 |
| gggagcaaat aggattagat accctagtag tccacgccgt aaacgatgag aactaagtgt | 840 |
| tggaggaatt cagtgctgca gttaacgcaa taagttctcc gcctggggag tatgcacgca | 900 |
| agtgtgaaac tcaaaggaat tgacgggggc ccgcacaagc ggtggagtat gtggtttaat | 960 |
| tcgaagcaac gcgaagaacc ttaccaggcc ttgacatgga acaaataccc tagagatag | 1020 |
| gggataatt atggatcaca caggtggtgc atggttgtcg tcagctcgtg tcgtgagatg | 1080 |
| ttgggttaag tcccgcaacg agcgcaaccc ttgtcgcatg ttaccagcat caagttgggg | 1140 |
| actcatgcga gactgccggt gacaaaccgg aggaaggtgg ggatgacgtc aaatcatcat | 1200 |
| gccccttatg gcctgggcta cacacgtact acaatggcgg ccacaaagag cagcgacaca | 1260 |
| gtgatgtgaa gcgaatctca taaaggtcgt ctcagttcgg attgaagtct gcaactcgac | 1320 |
| ttcatgaagt cggaatcgct agtaatcgca gatcagcatg ctgcggtgaa tacgttctcg | 1380 |
| ggccttgtac acaccgcccg tcaaaccatg ggagtcagta atacccgaag ccggtggcat | 1440 |
| aaccgtaagg agtgagccgt cgaaggtagg accgatgact ggggttaagt cgtaacaagg | 1500 |
| tatccctacg ggaacgtggg gatggatcac ctcctttt | 1537 |

<210> SEQ ID NO 154
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 154

```
atggagagtt tgatcctggc tcaggatgaa cgctggcggc atgcctaata catgcaagtc      60
gaacgaagtt tcgaggaagc ttgcttccaa agagacttag tggcgaacgg gtgagtaaca     120
cgtaggtaac ctgcccatgt gtccgggata actgctggaa acggtagcta aaaccggata     180
ggtatacaga gcgcatgctc agtatattaa agcgcccatc aaggcgtgaa catggatgga     240
cctgcggcgc attagctagt tggtgaggta acggctcacc aaggcgatga tgcgtagccg     300
gcctgagagg gtaaacggcc acattgggac tgagacacgg cccaaactcc tacgggaggc     360
agcagtaggg aattttcgtc aatggggggaa accctgaacg agcaatgccg cgtgagtgaa     420
gaaggtcttc ggatcgtaaa gctctgttgt aagtgaagaa cggctcatag aggaaatgct     480
atgggagtga cggtagctta ccagaaagcc acggctaact acgtgccagc agccgcggta     540
atacgtaggt ggcaagcgtt atccggaatc attgggcgta aagggtgcgt aggtggcgta     600
ctaagtctgt agtaaaaggc aatggctcaa ccattgtaag ctatggaaac tggtatgctg     660
gagtgcagaa gagggcgatg gaattccatg tgtagcggta aaatgcgtag atatatggag     720
gaacaccagt ggcgaaggcg gtcgcctggt ctgtaactga cactgaggca cgaaagcgtg     780
gggagcaaat aggattagat accctagtag tccacgccgt aaacgatgag aactaagtgt     840
tggaggaatt cagtgctgca gttaacgcaa taagttctcc gcctggggag tatgcacgca     900
agtgtgaaac tcaaaggaat tgacgggggc ccgcacaagc ggtggagtat gtggtttaat     960
tcgaagcaac gcgaagaacc ttaccaggcc ttgacatgga aacaaatacc ctagagatag    1020
ggggataatt atgatcaca caggtggtgc atggttgtcg tcagctcgtg tcgtgagatg    1080
ttgggttaag tcccgcaacg agcgcaaccc ttgtcgcatg ttaccagcat caagttgggg    1140
actcatgcga gactgccggt gacaaaccgg aggaaggtgg ggatgacgtc aaatcatcat    1200
gccccttatg gcctgggcta cacacgtact acaatggcgg ccacaaagag cagcgacaca    1260
gtgatgtgaa gcgaatctca taaaggtcgt ctcagttcgg attgaagtct gcaactcgac    1320
ttcatgaagt cggaatcgct agtaatcgca gatcagcatg ctgcggtgaa tacgttctcg    1380
ggccttgtac acaccgcccg tcaaaccatg ggagtcagta atacccgaag ccggtggcat    1440
aaccgtaagg agtgagccgt cgaaggtagg accgatgact ggggttaagt cgtaacaagg    1500
tatccctacg ggaacgtggg gatggatcac ctcctttt                            1537
```

<210> SEQ ID NO 155
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 155

```
atggagagtt tgatcctggc tcaggatgaa cgctggcggc atgcctaata catgcaagtc      60
gaacgaagtt tcgaggaagc ttgcttccaa agagacttag tggcgaacgg gtgagtaaca     120
cgtaggtaac ctgcccatgt gtccgggata actgctggaa acggtagcta aaaccggata     180
ggtatacaga gcgcatgctc agtatattaa agcgcccatc aaggcgtgaa catggatgga     240
cctgcggcgc attagctagt tggtgaggta acggcccacc aaggcgatga tgcgtagccg     300
gcctgagagg gtaaacggcc acattgggac tgagacacgg cccaaactcc tacgggaggc     360
```

```
agcagtaggg aattttcgtc aatgggggaa accctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatggaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
agtgtgaaac tcaaaggaat tgacggggc ccgcacaagc ggtggagtat gtggtttaat    960
tcgaagcaac gcgaagaacc ttaccaggcc ttgacatgga aacaaatacc ctagagatag   1020 gggataatt atggatcaca caggtggtgc atggttgtcg tcagctcgtg tcgtgagatg   1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat   1200
gccccttatg gcctgggcta cacacgtact acaatggcga ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaaccatg ggagtcagta atacccgaag ccggtggcat   1440
aaccgcaagt agtgagccgt cgaaggtagg accgatgact ggggttaagt cgtaacaagg   1500
tatccctacg ggaacgtggg gatggatcac ctccttt                            1537
```

<210> SEQ ID NO 156
<211> LENGTH: 1537
<212> TYPE: DNA
<213> ORGANISM: Artificial Sequence
<220> FEATURE:
<223> OTHER INFORMATION: Synthetic Polynucleotide

<400> SEQUENCE: 156

```
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca    120
cgtaggtaac ctgcccatgt gtccgggata actgctggaa acggtagcta aaaccggata    180
ggtatacaga gcgcatgctc agtatattaa agcgcccatc aaggcgtgaa catggatgga    240
cctgcggcgc attagctagt tggtgaggta acggcccacc aaggcgatga tgcgtagccg    300
gcctgagagg gtaaacggcc acattgggac tgagacacgg cccaaactcc tacgggaggc    360
agcagtaggg aattttcgtc aatgggggaa accctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatggaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
```

```
agtgtgaaac tcaaaggaat tgacggggc ccgcacaagc ggtggagtat gtggtttaat        960
tcgaagcaac gcgaagaacc ttaccaggcc ttgacatgga acaaatacc ctagagatag       1020 ggggataatt atggatcaca caggtggtgc atggttgtcg tcagctcgtg tcgtgagatg      1080
ttgggttaag tcccgcaacg agcgcaaccc ttgtcgcatg ttaccagcat caagttgggg      1140
actcatgcga gactgccggt gacaaaccgg aggaaggtgg ggatgacgtc aaatcatcat      1200
gccccttatg gcctgggcta cacacgtact acaatggcgg ccacaaagag cagcgacaca      1260
gtgatgtgaa gcgaatctca taaaggtcgt ctcagttcgg attgaagtct gcaactcgac      1320
ttcatgaagt cggaatcgct agtaatcgca gatcagcatg ctgcggtgaa tacgttctcg      1380
ggccttgtac acaccgcccg tcaaaccatg ggagtcagta atacccgaag ccggtggcat      1440
aaccgtaagg agtgagccgt cgaaggtagg accgatgact ggggttaagt cgtaacaagg      1500
tatccctacg ggaacgtggg gatggatcac ctccttt                               1537
```

<210> SEQ ID NO 157
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 157

```
tattgagagt ttgatcctgg ctcaggatga acgctggcgg cgtgcttaac acatgcaagt       60 cgaacgggt gctcatgacg gaggattcgt ccaacggatt gagttaccta gtggcggacg       120
ggtgagtaac gcgtgaggaa cctgccttgg agaggggaat aacactccga aaggagtgct      180
aataccgcat gatgcagttg ggtcgcatgg ctctgactgc caaagattta tcgctctgag      240
atggcctcgc gtctgattag ctagtaggcg gggtaacggc ccacctaggc gacgatcagt      300
agccggactg agaggttgac cggccacatt gggactgaga cacggcccag actcctacgg      360
gaggcagcag tggggaatat tgggcaatgg gcgcaagcct gacccagcaa cgccgcgtga      420
aggaagaagg ctttcgggtt gtaaacttct tttgtcgggg acgaaacaaa tgacggtacc      480
cgacgaataa gccacggcta actacgtgcc agcagccgcg gtaatacgta ggtggcaagc      540
gttatccgga tttactgggt gtaaagggcg tgtaggcggg attgcaagtc agatgtgaaa      600
actgggggct caacctccag cctgcatttg aaactgtagt tcttgagtgc tggagaggca      660
atcggaattc cgtgtgtagc ggtgaaatgc gtagatatac ggaggaacac cagtggcgaa      720
ggcggattgc tggacagtaa ctgacgctga gcgcgaaag cgtggggagc aaacaggatt      780
agataccctg gtagtccacg ccgtaaacga tggatactag gtgtgggggt ctgaccccct      840
ccgtgccgca gttaacacaa taagtatccc acctggggag tacgatcgca aggttgaaac      900
tcaaaggaat tgacggggc ccgcacaagc ggtggagtat gtggtttaat tcgaagcaac      960
gcgaagaacc ttaccaggc ttgacatccc actaacgaag cagagatgca ttaggtgccc      1020
ttcggggaaa gtggagacag gtggtgcatg gttgtcgtca gctcgtgtcg tgagatgttg     1080
ggttaagtcc cgcaacgagc gcaaccctta ttgttagttg ctacgcaaga gcactctagc     1140
gagactgccg ttgacaaaac ggaggaaggt ggggacgacg tcaaatcatc atgccccctta    1200 tgtcctgggc cacacacgta ctacaatggt ggttaacaga gggaggcaat accgcgaggt     1260
ggagcaaatc cctaaaagcc atcccagttc ggattcagg ctgaaacccg cctgtatgaa      1320
gttggaatcg ctagtaatcg cggatcagca tgccgcggtg aatacgttcc cgggccttgt     1380
```

```
acacaccgcc cgtcacacca tgagagtcgg gaacacccga agtccgtagc ctaaccgcaa    1440
ggagggcgcg gccgaaggtg ggttcgataa ttggggtgaa gtcgtaacaa ggtagccgta    1500
tcggaaggtg cggctggatc acctccttt                                      1529
```

<210> SEQ ID NO 158
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 158

```
tattgagagt ttgatcctgg ctcaggatga acgctggcgg cgtgcttaac acatgcaagt      60
cgaacgggt gctcatgacg gaggattcgt ccaacggatt gagttaccta gtggcggacg     120
ggtgagtaac gcgtgaggaa cctgccttgg agaggggaat aacactccga aaggagtgct    180
aataccgcat gatgcagttg ggtcgcatgg ctctgactgc caaagattta tcgctctgag    240
atggcctcgc gtctgattag ctagtaggcg ggtaacggc ccacctaggc gacgatcagt     300
agccggactg agaggttgac cggccacatt gggactgaga cacggcccag actcctacgg    360
gaggcagcag tggggaatat tgggcaatgg gcgcaagcct gacccagcaa cgccgcgtga    420
aggaagaagg ctttcgggtt gtaaacttct tttgtcgggg acgaaacaaa tgacggtacc    480
cgacgaataa gccacggcta actacgtgcc agcagccgcg gtaatacgta ggtggcaagc    540
gttatccgga tttactgggt gtaaaggcg tgtaggcggg attgcaagtc agatgtgaaa     600
actgggggct caacctccag cctgcatttg aaactgtagt tcttgagtgc tggagaggca    660
atcggaattc cgtgtgtagc ggtgaaatgc gtagatatac ggaggaacac cagtggcgaa    720
ggcggattgc tggacagtaa ctgacgctga gcgcgaaag cgtggggagc aaacaggatt     780
agataccctg gtagtccacg ccgtaaacga tggatactag gtgtgggggg tctgaccccc    840
tccgtgccgc agttaacaca ataagtatcc cacctgggga gtacgatcgc aaggttgaaa    900
ctcaaaggaa ttgacggggg cccgcacaag cggtggagta tgtggtttaa ttcgaagcaa    960
cgcgaagaac cttaccaggg cttgacatcc cactaacgaa gcagagatgc attaggtgcc    1020
cttcggggaa agtggagaca ggtggtgcat ggttgtcgtc agctcgtgtc gtgagatgtt    1080
gggttaagtc ccgcaacgag cgcaacccctt attgttagtt gctacgcaag agcactctag    1140
cgagactgcc gttgacaaaa cggaggaagg tggggacgac gtcaaatcat catgcccctt    1200
atgtcctggg ccacacacgt actacaatgg tggttaacag agggaggcaa taccgcgagg    1260
tggagcaaat ccctaaaagc catcccagtt cggattgcag gctgaaaccc gcctgtatga    1320
agttggaatc gctagtaatc gcggatcagc atgccgcggt gaatacgttc ccgggccttg    1380
tacacaccgc ccgtcacacc atgagagtcg ggaacacccg aagtccgtag cctaaccgca    1440
aggagggcgc ggccgaaggt gggttcgata ttggggtga agtcgtaaca aggtagccgt     1500
atcggaaggt gcggctggat cacctccttt                                     1530
```

<210> SEQ ID NO 159
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 159

```
tattgagagt ttgatcctgg ctcaggatga acgctggcgg cgtgcttaac acatgcaagt      60
```

```
cgaacggggt gctcatgacg gaggattcgt ccaacggatt gagttaccta gtggcggacg    120
ggtgagtaac gcgtgaggaa cctgccttgg agaggggaat aacactccga aaggagtgct    180
aataccgcat aatgcagttg ggtcgcatgg ctctgactgc caaagattta tcgctctgag    240
atggcctcgc gtctgattag ctagtaggcg gggtaacggc ccacctaggc gacgatcagt    300
agccggactg agaggttgac cggccacatt gggactgaga cacggcccag actcctacgg    360
gaggcagcag tggggaatat tgggcaatgg gcgcaagcct gacccagcaa cgccgcgtga    420
aggaagaagg ctttcgggtt gtaaacttct tttgtcaggg acgaaacaaa tgacggtacc    480
tgacgaataa gccacggcta actacgtgcc agcagccgcg gtaatacgta ggtggcaagc    540
gttatccgga tttactgggt gtaaagggcg tgtaggcggg attgcaagtc agatgtgaaa    600
actgggggct caacctccag cctgcatttg aaactgtagt tcttgagtgc tggagaggca    660
atcggaattc cgtgtgtagc ggtgaaatgc gtagatatac ggaggaacac cagtggcgaa    720
ggcggattgc tggacagtaa ctgacgctga ggcgcgaaag cgtggggagc aaacaggatt    780
agataccctg gtagtccacg ccgtaaacga tggatactag gtgtgggggg tctgacccct    840
ccgtgccgca gttaacacaa taagtatccc acctggggag tacgatcgca aggttgaaac    900
tcaaaggaat tgacgggggc ccgcacaagc ggtggagtat gtggtttaat tcgaagcaac    960
gcgaagaacc ttaccaggqc ttgacatccc actaacgaag cagagatgca ttaggtgccc   1020
ttcggggaaa gtggagacag gtggtgcatg gttgtcgtca gctcgtgtcg tgagatgttg   1080
ggttaagtcc cgcaacgagc gcaaccctta ttgttagttg ctacgcaaga gcactctagc   1140
gagactgccg ttgacaaaac ggaggaaggt ggggacgacg tcaaatcatc atgcccctta   1200
tgtcctgggc cacacacgta ctacaatggt ggttaacaga gggaggcaat accgcgaggt   1260
ggagcaaatc cctaaaagcc atcccagttc ggattgcagg ctgaaacccg cctgtatgaa   1320
gttggaatcg ctagtaatcg cggatcagca tgccgcggtg aatacgttcc cgggccttgt   1380
acacaccgcc cgtcacacca tgagagtcgg gaacacccga agtccgtagc ctaaccgcaa   1440
ggagggcgcg gccgaaggtg ggttcgataa ttgggqtgaa gtcgtaacaa ggtagccgta   1500
tcggaaggtg cggctggatc acctcctttt                                    1529
```

TREATMENT OF CLOSTRIDIUM DIFFICILE INFECTION

RELATED APPLICATIONS

This application is a continuation of international application number PCT/US2017/037498, filed Jun. 14, 2017, which claims the benefit under 35 U.S.C. § 119(e) of U.S. provisional application No. 62/349,914, filed Jun. 14, 2016, each of which is incorporated by reference herein in its entirety.

FIELD OF INVENTION

The disclosure relates to compositions of purified bacterial strains, and methods for treating pathogenic infections, such as *Clostridium difficile* infections, by administering the compositions to a subject having a pathogenic infection.

BACKGROUND OF THE INVENTION

The collection of bacterial, viral, and fungal commensal microorganisms that reside within and on the human body are collectively known as the human microbiome. The bacterial subset of the human microbiome plays an important role in host nutrient acquisition, development, immunological homeostasis, neurological health, and protection against pathogens (LeBlanc et al. *Curr. Opin. Biotechnol.* (2013) 24(2): 160-168; Hooper et al. *Science* (2012) 336 (6086): 1268-1273; Hughes et al. *Am. J. Gastroenterol.* (2013) 108(7): 1066-1074). As the largest reservoir of mammalian commensals, bacteria residing in the gastrointestinal (GI) tract influence nearly all of these aspects of human biology (Blaser *J. Clin. Invest.* (2014) 124(10): 4162-4165). Consequently, perturbation of the normal bacterial populations within the GI niche, a state known as dysbiosis, can predispose humans to a variety of diseases.

*Clostridium difficile* infection (CDI) arises after intestinal colonization by the anaerobic spore-forming Gram-positive pathogen *Clostridium difficile*. Upon colonization of the GI tract, *C. difficile* produces toxins which causes diarrhea and may ultimately lead to death. This illness is the most common identifiable cause of nosocomial diarrhea and is thought to arise as a direct result of dysbiosis (Calfee *Geriatrics* (2008) 63: 10-21; Shannon-Lowe et al *BMJ* (2010) 340: c1296). Not surprisingly, usage of nearly all classes of antibiotics has been associated with CDI, presumably by inducing dysbiosis in the GI tract and thereby enabling *C. difficile* outgrowth. The Center for Disease Control currently classifies CDI as a public health threat requiring immediate and aggressive action because of its natural resistance to many drugs and the emergence of a fluoroquinolone-resistant strain that is now prevalent throughout North America and Europe. *C. difficile* was responsible for almost half a million infections and was associated with approximately 29,000 deaths in 2011 (Lessa et al. *NEJM* 2015, 372: 825-834).

The antibiotics metronidazole, vancomycin, and fidaxomicin are the current therapeutic options for treatment of CDI. However, metronidazole is inadequate because of decreased response rates and neither metronidazole nor vancomycin prevent disease recurrence, with up to 30% of patients initially responding experiencing a clinical recurrence after antibiotic cessation (Miller *Expert Opin. Pharmacother.* (2010) 11: 1569-1578). Fidaxomicin has been shown to be superior to vancomycin in preventing recurrent CDI (Mullane *Ther. Adv. Chronic Dis.* (2014) 5(2): 69-84). Because of its narrow spectrum of activity, fidaxomicin is thought to enable normal microbiome repopulation of the gut following dysbiosis and CDI, thereby lowering the likelihood of recurrent disease (Tannock et al. *Microbiology* (2010) 156 (Pt 11): 3354-3359; Louie et al. *Clin. Infect. Dis.* (2012) 55 Suppl. 2: S132-142). Nonetheless, 14% of fidaxomicin-treated patients experience CDI relapse and mutations conferring reduced sensitivity have already been reported (Eyre et al. *J. Infect. Dis.* (2014) 209(9): 1446-1451).

Because the risk of recurrent CDI is heightened by antibiotic use and *C. difficile* spores are inherently recalcitrant to the available chemotherapeutic arsenal, alternative therapeutic modalities are being pursued for the treatment of CDI. Fecal microbiota transplantation (FMT) is one such modality that has shown efficacy against CDI (Khoruts et al. *Immunol. Lett.* (2014) 162(2): 77-81; van Nood et al. *N. Engl. J. Med.* (2013) 368(5): 407-415). To date, results of FMT studies for the treatment of CDI, have reported cure rates up to 90% in three randomized controlled studies (Cammarota et al. *Alimen. Pharmacol. Therap.* (2015) 41(9): 835-843; Kassam et al. *Am. J. Gastroenterol.* (2013) 108(4): 500-508; van Nood et al. *N. Engl. J. Med.* (2013) 368(5): 407-415; Youngster et al. *Infec. Dis. Soc. Am.* (2014) 58(11): 1515-1522).

Despite the success of FMT, this therapeutic approach is not without risks and logistical concerns. Selection of FMT donors is critical and challenging. When FMT donor recruitment is performed with stringent screening and standardization protocols, most prospective donors fail this process. Only 6-10% of prospective FMT donors qualify, with the majority of failures arising from asymptomatic carriage of GI pathogens (Paramsothy et al. *Inflamm. Bowel Dis.* (2015) 21(7): 1600-1606; Borody et al. *Curr. Opin. Gastroenterol.* (2014) 30(10): 97-105; Burns et al. *Gastroenterology* (2015) 148: S96-S97; Surawicz *Ann. Intern. Med.* (2015) 162(9): 662-663). Furthermore, variation between donors may lead to variation in FMT efficacy. In addition, the risk of transmission of even non-infectious illnesses may be heightened by FMT. Indeed, significant weight gain has been reported in a patient who received an FMT from an overweight stool donor (Alang et al. *Open Forum Infect. Dis.* (Winter 2015) 2(1)).

SUMMARY OF THE INVENTION

Provided herein are compositions and methods for the treatment or prevention of pathogenic infections including *C. difficile*.

In one aspect, the disclosure provides compositions comprising two or more purified bacterial strains of species selected from the group consisting of: *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimonas intestinalis, Dracourtella massiliensis, Dracourtella massilinesis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostridium bolteae* 90A9, *Dorea longicatena, Dorea longicatena* CAG:42, *Clostridium innocuum, Erysipelotrichaceae_bacterium* 21-3, *Blautia wexlerae, Clostridium disporicum, Erysip-* elatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellnsis, Ruminococcus albus, Bifidobacterium bifidum, Blautia luti, Roseburia faecis, Fusicatenibacter saccharivorans, Roseburia faecis, Blautia faecis, Dorea formicigenerans and Bacteroides ovatus.

In some embodiments of the compositions provided herein, the composition comprises two or more purified bacterial strains of species selected from the group consisting of: Clostridium hathewayi, Blautia hansenii, Blautia producta, Blautia producta ATCC 27340, Clostridium bacterium UC5.1-1D4, Blautia coccoides, Eubacterium contortum, Eubacterium fissicatena, Sellimonas intestinalis, Dracourtella massiliensis, Dracourtella massilinesis GD1, Ruminococcus torques, Anaerostipes caccae, Clostridium scindens, Marvinbryanta formatexigens, Eisenbergiella tayi, Flavinofractor plautii, Clostridium orbiscindens 1_3_50AFAA, Lachnospiraceae bacterium 7_1_58FAA, Subdoligranulum, Anaerotruncus colihominis, Anaerotruncus colihominis DSM 17241, Clostridium symbiosum, Clostridium symbiosum WAL-14163, Clostridium bolteae, Clostridium bolteae 90A9, Dorea longicatena, Dorea longicatena CAG:42, Clostridium innocuum, Erysipelotrichaceae_bacterium_21-3, Blautia wexlerae, Turicibacter sanguinis, Lactobacillus mucosae, and Bacteroides ovatus.

In some embodiments of the compositions provided herein, the composition comprises two or more purified bacterial strains of species selected from the group consisting of: Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens, and Eisenbergiella tayi.

In some embodiments of the compositions provided herein, the composition comprises two or more purified bacterial strains of species selected from the group consisting of: Flavinofractor plautii, Clostridium orbiscindens 1_3_50AFAA, Lachnospiraceae bacterium 7_1_58FAA, Subdoligranulum, Anaerotruncus colihominis, Anaerotruncus colihominis DSM 17241, Eubacterium fissicatena, Sellimonas intestinalis, Dracourtella massiliensis, Dracourtella massilinesis GD1, Ruminococcus torques, Clostridium symbiosum, Clostridium symbiosum WAL-14163, Clostridium bolteae, Clostridium bolteae 90A9, Dorea longicatena, Dorea longicatena CAG:42, Blautia producta, Blautia producta ATCC 27340, Clostridium bacterium UC5.1-1D4, Clostridium innocuum, and Erysipelotrichaceae_bacterium_21-3.

In some embodiments of the compositions provided herein, the composition comprises two or more purified bacterial strains of species selected from the group consisting of: Clostridium orbiscindens 1_3_50AFAA, Anaerotruncus colihominis DSM 17241, Dracourtella massilinesis GD1, Clostridium symbiosum WAL-14163, Clostridium bolteae 90A9, Dorea longicatena CAG:42, Clostridium bacterium UC5.1-1D4, and Erysipelotrichaceae_bacterium_21-3.

In some embodiments of the compositions provided herein, the composition comprises two or more purified bacterial strains of species selected from the group consisting of: Clostridium orbiscindens 1_3_50AFAA, Anaerotruncus colihominis DSM 17241, Sellimonas intestinalis, Clostridium symbiosum WAL-14163, Clostridium bolteae 90A9, Dorea longicatena CAG:42, Clostridium bacterium UC5.1-1D4, and Erysipelotrichaceae_bacterium_21_3.

In some embodiments of the compositions provided herein, the composition comprises purified bacterial strains Clostridium orbiscindens 1_3_50AFAA, Anaerotruncus colihominis DSM 17241, Dracourtella massilinesis GD1, Clostridium symbiosum WAL-14163, Clostridium bolteae 90A9, Dorea longicatena CAG:42, Clostridium bacterium UC5.1-1D4, and Erysipelotrichaceae_bacterium_21-3.

In some embodiments of the compositions provided herein, the composition comprises purified bacterial strains Clostridium orbiscindens 1_3_50AFAA, Anaerotruncus colihominis DSM 17241, Sellimonas intestinalis GD1, Clostridium symbiosum WAL-14163, Clostridium bolteae 90A9, Dorea longicatena CAG:42, Clostridium bacterium UC5.1-1D4, and Erysipelotrichaceae_bacterium_21_3.

In some embodiments of the compositions provided herein, the composition comprises two or more purified bacterial strains of species selected from the group consisting of: Flavinofractor plautii, Anaerotruncus colihominis, Dracourtella massiliensis, Clostridium symbiosum, Clostridium bolteae, Dorea longicatena, Blautia producta, and Clostridium innocuum.

In some embodiments of the compositions provided herein, the composition comprises purified bacterial strains Flavinofractor plautii, Anaerotruncus colihominis, Dracourtella massiliensis, Clostridium symbiosum, Clostridium bolteae, Dorea longicatena, Blautia producta, and Clostridium innocuum.

In some embodiments of the compositions provided herein, the composition comprises two or more purified bacterial strains of species selected from the group consisting of: Flavinofractor plautii, Anaerotruncus colihominis, Eubacterium fissicatena, Clostridium symbiosum, Clostridium bolteae, Dorea longicatena, Blautia producta, and Clostridium innocuum.

In some embodiments of the compositions provided herein, the composition comprises purified bacterial strains Flavinofractor plautii, Anaerotruncus colihominis, Eubacterium fissicatena, Clostridium symbiosum, Clostridium bolteae, Dorea longicatena, Blautia producta, and Clostridium innocuum.

In some embodiments of the compositions provided herein, the composition comprises two or more purified bacterial strains of species selected from the group consisting of: Flavinofractor plautii, Lachnospiraceae bacterium 7_1_58FAA, Subdoligranulum, Anaerotruncus colihominis, Eubacterium fissicatena, Ruminococcus torques, Clostridium symbiosum, Clostridium bolteae, Dorea longicatena, Blautia producta, Clostridium innocuum, Erysipelotrichaceae_bacterium_21-3, and Bacteroides ovatus.

In some embodiments of the compositions provided herein, the composition comprises two or more purified bacterial strains of species selected from the group consisting of: Clostridium orbiscindens 1_3_50 AFAA, Anaerotruncus colihominis DSM 17241, Dracourtella massiliensis GD1, Clostridium symbiosum WAL-14163, Clostridium bolteae 90A9, Dorea longicatena CAG:42, Clostridium bacterium UC5.1-1D4, Erysipelotrichaceae_bacterium_21-3, and Bacteroides ovatus.

In some embodiments of the compositions provided herein, the composition comprises two or more purified bacterial strains of species selected from the group consisting of: Clostridium orbiscindens 1_3_50AFAA, Anaerotruncus colihominis DSM 17241, Sellimonas intestinalis, Clostridium symbiosum WAL-14163, Clostridium

*bolteae* 90A9, *Dorea longicatena* CAG:42, *Clostridium bacterium* UC5.1-1D4, *Erysipelotrichaceae_bacterium_21-3*, and *Bacteroides ovatus*.

In some embodiments of the compositions provided herein, the composition does not include a bacterial strain of the species *Flavinofractor plautii*, *Subdoligranulum*, or *Lachnospiraceae bacterium* 7_1_58FAA. In some embodiments of the compositions provided herein, the composition does not include a bacterial strain of the species *Bacteroides ovatus*. The composition of any one of claims 4-12, wherein the composition does not include a bacterial strain of the species *Flavinofractor plautii*, *Subdoligranulum*, *Clostridium orbiscindens* 1_3_50AFAA, or *Lachnospiraceae bacterium* 7¬_1_58 FAA.

In some embodiments of the compositions provided herein, the composition comprises two or more purified bacterial strains of species selected from the group consisting of: *Clostridium scindens*, *Clostridium hathewayi*, *Blautia hansenii*, *Blautia wexlerae*, *Blautia producta*, *Blautia coccoides*, *Dorea longicatena*, *Clostridium innocuum*, *Erysipelotrichaceae_bacterium_21-3*, *Flavinofractor plautii*, *Lachnospiraceae bacterium* 7-_1_58FAA, *Subdoligranulum*, *Anaerotruncus colihominis*, and *Clostridium symbiosum*. In some embodiments of the compositions provided herein, the composition does not include a bacterial strain of the species *Flavinofractor plautii*, *Subdoligranulum*, or *Lachnospiraceae bacterium* 7_1_58FAA.

In some embodiments of the compositions provided herein, the composition comprises two or more purified bacterial strains of species selected from the group consisting of: *Clostridium scindens*, *Clostridium hathewayi*, *Blautia hansenii*, *Blautia wexlerae*, *Anaerotruncus colihominis*, *Dorea longicatena*, *Clostridium innocuum*, *Erysipelotrichaceae_bacterium_21-3*, *Flavinofractor plautii*, *Lachnospiraceae bacterium* 7-_1_58FAA, *Subdoligranulum*, *Turicibacter sanguinis*, and *Lactobacillus mucosae*. In some embodiments of the compositions provided herein, the composition does not include a bacterial strain of the species *Flavinofractor plautii*, *Subdoligranulum* or *Lachnospiraceae bacterium* 7_1_58FAA.

In some embodiments of the compositions provided herein, the composition comprises two or more purified bacterial strains of species selected from the group consisting of: *Dorea longicatena*, *Ruminococcus obeum*, *Megasphaera elsdenii*, *Acidaminococcus fermentans*, *Acidaminococcus intestine*, *Ruminococcus faecis*, *Bacteroides cellulosilyticus*, *Anaerostipes hadrus*, *Flavinofractor plautii*, *Eubacterium rectale*, *Ruminococcus champanellensis*, *Ruminococcus albus*, *Bifidobacterium bifidum*, *Ruminococcus faecis*, *Blautia luti*, *Roseburia faecis*, *Fusicatenibacter saccharivorans*, *Blautia faecis*, *Dorea formicigenerans*, and *Blautia hansenii*.

In some embodiments of the compositions provided herein, the composition comprises two or more purified bacterial strains of species selected from the group consisting of: *Acidaminococcus fermentans*, *Acidaminococcus intestine*, *Anaerostipes hadrus*, *Blautia faecis*, *Blautia hansenii*, *Dorea formicigenerans*, *Dorea longicatena*, *Eubacterium rectale*, *Flavinofractor plautii*, *Fusicatenibacter saccharivorans*, *Megasphaera elsdenii*, *Roseburia faecis*, *Ruminococcus champanellensis*, *Ruminococcus albus*, *Ruminococcus faecis*, and *Ruminococcus obeum*.

In one aspect the disclosure provides compositions comprising two or more purified bacterial strains, wherein the two or more purified bacterial strains comprise 16S rDNA sequences having at least 97% homology with nucleic acid sequences selected from the group consisting of SEQ ID NOs:1-83 and 124-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:1-23, SEQ ID NO:83, SEQ ID NOs: 124-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21. In some embodiments of the compositions provided herein, the composition comprises purified bacterial strains that comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124, SEQ ID NO: 129, SEQ ID NO: 132, SEQ ID NO: 137, SEQ ID NO: 141, SEQ ID NO: 146, SEQ ID NO: 152, and SEQ ID NO: 157. In some embodiments of the compositions provided herein, the composition comprises purified bacterial strains that comprise 16S rDNA sequences having at least 97% homology with nucleic acid sequences selected from the group consisting of SEQ ID NO: 124, SEQ ID NO: 129, SEQ ID NO: 132, SEQ ID NO: 137, SEQ ID NO: 141, SEQ ID NO: 146, SEQ ID NO: 152, and SEQ ID NO: 157.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20 and SEQ ID NO:21, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:124-156, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21 and SEQ ID NO:22. In some embodiments of the compositions provided herein, the composition comprises two or more purified bacterial strains, wherein the two or more purified bacterial strains comprise 16S rDNA sequences having at least 97% homology with nucleic acid sequence selected from the group consisting of SEQ ID NO: 124-145, SEQ ID NO: 152-159, SEQ ID NO: 18, and SEQ ID NO: 22.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21 and SEQ ID NO:22, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124-145 and SEQ ID NO: 152-156, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10 and SEQ ID NOs:14-22. In some embodiments of the compositions provided herein, the composition comprises two or more purified bacterial strains, wherein the two or more purified bacterial strains comprise 16S rDNA sequences having at least 97% homology with nucleic acid sequence selected from the group consisting of SEQ ID NOs: 124-159, SEQ ID NO: 18, and SEQ ID NO: 22.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:14-22 and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 129-156, SEQ ID NO: 18, SEQ ID NO: 22, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21 and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID Nos: 124-159 and SEQ ID NO: 83.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-156 and SEQ ID NO: 83, and wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22 and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159, SEQ ID NO: 22, and SEQ ID NO: 83, In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-145, SEQ ID NOs: 152-156, SEQ ID NO: 22, and SEQ ID NO: 83, wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NOs:14-22, and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159, SEQ ID NO: 18, SEQ ID NO:22, and SEQ ID NO: 83.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:14-22 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124-15, SEQ ID NO: 18, SEQ ID NO:22, and SEQ ID NO: 83, wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:1, SEQ ID NO:3, SEQ ID NO:5, SEQ ID NO:7, SEQ ID NO:10, SEQ ID NO:12, SEQ ID NO:14, SEQ ID NO:16, SEQ ID NO:18, and SEQ ID NO:21.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:1, SEQ ID NO:2, SEQ ID NO:3, SEQ ID NO:5, SEQ ID NO:6, SEQ ID NO:10, SEQ ID NO:12, SEQ ID NO:14, SEQ ID NO:18, and SEQ ID NO:21.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:24-79.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:24-27, SEQ ID NO:32, SEQ ID NO:34, SEQ ID NO:35, SEQ ID NO:37, SEQ ID NO:38, SEQ ID NO:40, SEQ ID NO:43, SEQ ID NO:44, SEQ ID NO:46, SEQ ID NO:47, SEQ ID NO:51, SEQ ID NO:55, SEQ ID NO:56, SEQ ID NO:62, SEQ ID NO:63, SEQ ID NO:67, SEQ ID NO:68, SEQ ID NO:70, SEQ ID NO:72, SEQ ID NO:76 and SEQ ID NO:77.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:16, SEQ ID NO:21, and SEQ ID NOs:80-82.

In one aspect the disclosure provides compositions comprising two or more purified bacterial strains, wherein the two or more purified bacterial strains comprise 16S rDNA sequences having at least 97% homology with nucleic acid sequences selected from the group consisting of SEQ ID NOs:84-123.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:97, SEQ ID NO:98, SEQ ID NO:99, SEQ ID NO:101, SEQ ID NO:102, SEQ ID NO:103, SEQ ID NO:105, SEQ ID NO:106, SEQ ID NO:108, SEQ ID NO:109, SEQ ID NO:110, SEQ ID NO:121, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:88, SEQ ID NO:89, SEQ ID NO:99, SEQ ID NO:103, SEQ ID NO:105, SEQ ID NO:106, SEQ ID NO:108, SEQ ID NO:109, and SEQ ID NO:121.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:102, SEQ ID NO:106, SEQ ID NO:110, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:95, SEQ ID NO:97, SEQ ID NO:98, SEQ ID NO:102, SEQ ID NO:106, SEQ ID NO:110, and SEQ ID NO:122, and wherein the composition does not include a bacterial strain comprising a 16S rDNA sequence having at least 97% homology with a nucleic acid sequence of SEQ ID NO:93.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:101, SEQ ID NO:102, SEQ ID NO:106, SEQ ID NO:110, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:95, SEQ ID NO:97, SEQ ID NO:98, SEQ ID NO:101, SEQ ID NO:102, SEQ ID NO:106, SEQ ID NO:110, and SEQ ID NO:122, and wherein the composition does not include a bacterial strain comprising a 16S rDNA sequence having at least 97% homology with a nucleic acid sequence of SEQ ID NO:93.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:93, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:90, SEQ ID NO:91, SEQ ID NO:93, SEQ ID NO:94, SEQ ID NO:95, SEQ ID NO:97, SEQ ID NO:98, SEQ ID NO:99, and SEQ ID NO:105.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:100, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, and SEQ ID NO:120.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, and SEQ ID NO:119.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:86, SEQ ID NO:95, SEQ ID NO:98, SEQ ID NO:110, SEQ ID NO:122, and SEQ ID NO:123.

In some embodiments of the compositions provided herein, the composition comprises at least one bacterial strain from *Clostridium* cluster XIVa and at least one bacterial strain from *Clostridium* cluster XVII. In some embodiments of the compositions provided herein, the composition comprises at least one bacterial strain from *Clostridium* cluster IV and at least one bacterial strain from *Clostridium* cluster XVII. In some embodiments of the compositions provided herein, the composition comprises at least one bacterial strain from *Clostridium* cluster XIVa, at least one strain from *Clostridium* cluster IV and at least one bacterial strain from *Clostridium* cluster XVII.

In some embodiments of the compositions provided herein, the composition comprises at least one *Bacteroides* strain. In some embodiments of the compositions provided herein, the composition does not include *Clostridium scindens*.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 purified bacterial strains.

In some embodiments of the compositions provided herein, one or more of the bacterial strains are spore formers. In some embodiments of the compositions provided herein, one or more of the bacterial strains are in spore form. In some embodiments of the compositions provided herein, each of the bacterial strains is in spore form.

In some embodiments of the compositions provided herein, one or more of the bacterial strains is in vegetative form. In some embodiments of the compositions provided herein, each of the bacterial strains is in vegetative form.

In some embodiments of the compositions provided herein, the composition comprises only obligate anaerobic bacterial strains. In some embodiments of the compositions provided herein, the composition comprises bacterial strains that originate from more than one human donor.

In some embodiments of the compositions provided herein, one or more of the bacterial strains are baiCD–. In some embodiments of the compositions provided herein, each of the bacterial strains is baiCD–. In some embodiments of the compositions provided herein, the composition does not mediate bile acid 7-alpha-dehydroxylation. In some embodiments of the compositions provided herein, the composition inhibits *C. difficile* toxin production. In some embodiments of the compositions provided herein, the composition inhibits *C. difficile* replication and/or survival.

In some embodiments of the compositions provided herein, the bacterial strains are lyophilized.

In some embodiments of the compositions provided herein, the composition induces the proliferation and/or accumulation of regulatory T cells (Tregs).

In one aspect, the disclosure provides compositions comprising two or more purified bacterial strains, wherein the composition comprises at least one bacterial strain from *Clostridium* cluster XIVa and at least one bacterial strain from *Clostridium* cluster XVII. In one aspect, the disclosure provides compositions comprising two or more purified bacterial strains, wherein the composition comprises at least one bacterial strain from *Clostridium* cluster IV and at least one bacterial strain from *Clostridium* cluster XVII. In one aspect, the disclosure provides compositions comprising two or more purified bacterial strains, wherein the composition comprises at least one bacterial strain from *Clostridium* cluster IV, at least one bacterial strain from *Clostridium* cluster XIVa and at least one bacterial strain from *Clostridium* cluster XVII.

In some embodiments of the compositions provided herein, the composition comprises at least one *Bacteroides* strain. In some embodiments of the compositions provided herein, the composition does not include *Clostridium scindens*.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 purified bacterial strains.

In some embodiments of the compositions provided herein, one or more of the bacterial strains are spore formers. In some embodiments of the compositions provided herein, one or more of the bacterial strains are in spore form. In some embodiments of the compositions provided herein, each of the bacterial strains is in spore form.

In some embodiments of the compositions provided herein, one or more of the bacterial strains is in vegetative form. In some embodiments of the compositions provided herein, each of the bacterial strains is in vegetative form.

In some embodiments of the compositions provided herein, the composition comprises only obligate anaerobic bacterial strains.

In some embodiments of the compositions provided herein, the composition comprises bacterial strains that originate from more than one human donor.

In some embodiments of the compositions provided herein, one or more of the bacterial strains are baiCD−. In some embodiments of the compositions provided herein, each of the bacterial strains is baiCD−. In some embodiments of the compositions provided herein, the composition does not mediate bile acid 7-alpha-dehydroxylation. In some embodiments of the compositions provided herein, the composition inhibits *C. difficile* toxin production. In some embodiments of the compositions provided herein, the composition inhibits *C. difficile* replication and/or survival.

In some embodiments of the compositions provided herein, the bacterial strains are lyophilized.

In some embodiments of the compositions provided herein, the composition induces the proliferation and/or accumulation of regulatory T cells (Tregs).

In one aspect, the disclosure provides a pharmaceutical composition comprising any of the compositions provided herein further comprising a pharmaceutically acceptable excipient. In some embodiments of the pharmaceutical compositions provided herein, the pharmaceutical composition is formulated for oral delivery. In some embodiments of the pharmaceutical compositions provided herein, the pharmaceutical composition is formulated for rectal delivery. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon.

In one aspect, the disclosure provides a food product comprising any of the compositions provided herein further comprising a nutrient.

In one aspect, the disclosure provides a method of treating a pathogenic infection in a subject, comprising administering to the subject a therapeutically effective amount of any of the compositions or food products provided herein to treat the pathogenic infection.

In some embodiments of the methods provided herein, the pathogenic infection is *C. difficile*, Vancomycin Resistant Enterococci (VRE), Carbapenem Resistant Enterobacteriaceae (CRE), *Neisseria gonorrheae*, Multidrug Resistant *Acinetobacter*, *Campylobacter*, Extended spectrum beta-lactamese (ESBL) producing Enterobacteriaceae, Multidrug Resistant *Pseudomonas aeruginosa*, *Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, Clindamycin resistant Group B *Streptococcus*, and combinations thereof. In some embodiments of the methods provided herein, the pathogenic infection is *C. difficile*. In some embodiments of the methods provided herein, the pathogenic infection is Vancomycin-Resistant Enterococci.

In some embodiments of the methods provided herein, the subject is human. In some embodiments of the methods provided herein, the subject is an asymptotic carrier.

In some embodiments of the methods provided herein, the subject is administered a dose of an antibiotic prior to administration of the composition. In some embodiments of the methods provided herein, the subject is administered more than one dose of the antibiotic prior to administration of the composition. In some embodiments of the methods provided herein, the subject has not been administered an antibiotic prior to administration of the composition.

In some embodiments of the methods provided herein, the composition is administered to the subject by oral administration. In some embodiments of the methods provided herein, the composition is administered to the subject by rectal administration.

In some embodiments of the methods provided herein, the administering results in proliferation and/or accumulation of regulatory T cells (Tregs).

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 1 shows the strains of Compositions A-D. Each entry includes the SEQ ID NO of the 16S rDNA sequence of the strain, a strain identifier, and the species with the closest known homology (can be more than one species). The bracketed roman numeral indicates the *Clostridium* cluster classification of each strain based on the closest species homology. Strains that are not classified in Cluster XIVa are highlighted in bold. The two non-clostridial strains (SEQ ID NO:2, closest known species *Turicibacter sanguinis*, and SEQ ID NO:6, closest known species *Lactobacillus mucosae*) do not belong to the *Clostridium* genus.

FIG. 2 shows various *Clostridium difficile* infection models. Timelines indicate antibiotic type, duration of treatment, as well as exposure to *C. difficile* spores. The top panel shows an antibiotic cocktail treatment model in which the antibiotic cocktail is provided in the drinking water from day −10 to day −3 followed by intraperitoneal clindamycin on day −1. The middle panel shows a clindamycin IP injection model, in which clindamycin is administered by intraperitoneal injection on day −1. The bottom panel shows the cefoperazone treatment model, in which cefoperazone is provided in the drinking water from day −12 to day −2, followed by administration of a live biotherapeutic product (LBP) on day −1.

FIG. 3 shows the experimental conditions described in Example 1. The groups of mice were divided based on the antibiotic regimen received prior to administration of the indicated amount of *C. difficile* spores. "Abx" refers to treatment with any of the antibiotic regimens.

FIGS. 4A-4D show survival of mice that received no treatment (FIG. 4A), antibiotic cocktail (FIG. 4B), clindamycin (FIG. 4C), or cefoperazone (FIG. 4D) prior to *C. difficile* infection. FIGS. 4E-4H show body weight of mice that received no treatment (FIG. 4E), antibiotic cocktail (FIG. 4F), clindamycin (FIG. 4G), or cefoperazone (FIG. 4H) prior to *C. difficile* infection. FIGS. 4I-4L show *C. difficile* burden (CFU) per gram of feces from mice that received no treatment (FIG. 4I), antibiotic cocktail (FIG. 4J), clindamycin (FIG. 4K), or cefoperazone (FIG. 4L) prior to *C. difficile* infection. Open circles indicate infection with 10 *C. difficile* spores; closed squares indicate infection with 10,000 *C. difficile* spores. Black triangles in FIG. 4J indicate an additional experimental arm in which mice were treated with vancomycin following *C. difficile* infection.

FIG. 5 shows experimental conditions evaluated in Example 2, the results for which are presented in FIGS. 7-9. Composition E corresponds to a mixture of 17 bacterial strains (See e.g., Narushima et al., Gut Microbes 5: 3, 333-339). Composition I corresponds to a mixture of *Clostridium scindens, Pseudoflavonifractor capillosus,* and *Blautia hansenii*. "Abx" refers to treatment with any of the antibiotic regimens.

FIG. 7A shows weight of the mice that received no antibiotic treatment. FIG. 7B shows weight of the mice that received cefoperazone treatment. FIG. 7C shows weight of the mice that received cefoperazone treatment followed by vancomycin. FIG. 7D shows weight of the mice that received cefoperazone treatment followed by Composition I. FIG. 7E shows weight of the mice that received cefoperazone treatment followed by Composition E. FIG. 7F shows weight of the mice that received cefoperazone treatment followed by composition A. FIG. 7G shows weight of the mice that received cefoperazone treatment followed by composition B. FIG. 7H shows weight of the mice that received cefoperazone treatment followed by composition C. FIG. 7I shows weight of the mice that received cefoperazone treatment followed by composition D.

FIGS. 8A-8C show the load of *C. difficile* in colony forming units (CFUs) in fecal pellets at various times post infection with *C. difficile*. FIG. 8A shows *C. difficile* CFU/g feces one-day post infection. FIG. 8B shows *C. difficile* CFU/g feces 3 days post infection. FIG. 8C shows *C. difficile* CFU/g feces 8 days post infection.

FIG. 9 shows experimental conditions evaluated in Example 3, the results for which are presented in FIGS. 10-12.

FIG. 13 shows the strains of Composition F. The genus-species notation indicates the closest species based on the sequence of the isolated strain.

FIG. 14 shows the classification by *Clostridium* cluster of the strains in Composition F and their short-chain fatty acid producing abilities.

FIG. 15 shows experimental conditions evaluated in Example 4, the results for which are presented in FIGS. 16-18. The dosing days are relative to *C. difficile* infection. FMT refers to Fecal Matter Transplant with fecal matter isolated from mice or from humans.

FIG. 17A shows weight of the mice that received cefoperazone treatment. FIG. 17B shows weight of the mice that received cefoperazone treatment followed by FMT with fecal matter from a human. FIG. 17C shows weight of the mice that received cefoperazone treatment followed by FMT with fecal matter from a mouse. FIG. 17D shows weight of the mice that received cefoperazone treatment followed by Composition B on day −1. FIG. 17E shows weight of the mice that received cefoperazone treatment followed by Composition B on days −2 and −1. FIG. 17F shows weight of the mice that received cefoperazone treatment followed by Composition B on days −2, −1, 1, 2, and 3. FIG. 17G shows weight of the mice that received cefoperazone treatment followed by Composition F on day −1. FIG. 17H shows weight of the mice that received cefoperazone treatment followed by Composition F on days −2, −1, 1, 2, and 3.

FIGS. 18A-18B show the load of *C. difficile* in colony forming units (CFUs) in fecal pellets at various times post infection with *C. difficile*. FIG. 18A shows *C. difficile* CFU/g feces 8 days post infection. FIG. 18B shows *C. difficile* CFU/g feces 17 days post infection.

FIG. 19 shows the strains of Composition G. The genus-species notation indicates the closest species based on the sequence of the isolated strain.

FIG. 20 shows experimental conditions evaluated in Example 5, the results for which are presented in FIGS. 21-23. Composition B1=Composition B with *Bacteroides*; Composition B2=Composition B with *Bacteroides* but without *Flavonifractor plautii*.

FIG. 21 shows survival of the mice over time post infection with *C. difficile* spores, according to the experimental conditions shown in FIG. 20. Mice losing >20% body weight of baseline were included in mortality numbers in survival curves.

FIG. 22A shows weight of the mice that received vehicle control. FIG. 22B shows weight of the mice that received Composition F. FIG. 22C shows weight of the mice that received Composition G. FIG. 22D shows weight of the mice that received cefoperazone treatment followed by Composition B. FIG. 22E shows weight of the mice that received cefoperazone treatment followed by Composition B2 (=Composition B without *Flavonifractor plautii* and with added *Bacteroides*). FIG. 22F shows weight of the mice that received cefoperazone treatment followed by Composition B1 (=Composition B with *Bacteroides* added). FIG. 22G shows weight of the mice that received cefoperazone treatment followed by frozen Composition B. FIG. 22H shows weight of the mice that received cefoperazone treatment followed by ethanol treated human fecal samples. FIG. 22I shows weight of the mice that received cefoperazone treatment followed by ethanol treated Composition B. FIG. 22J shows weight of the mice that received cefoperazone treatment followed by Composition J.

FIG. 25 shows experimental conditions evaluated in Example 6, the results of which are presented in FIGS. 27-29.

FIG. 26 shows the strains in Composition H (SEQ ID NO:14-VE202-13-*Anaerotruncus colihominis* (Cluster IV); SEQ ID NO:16-VE202-16-*Clostridium symbiosum* (Cluster XIVa); SEQ ID NO:21-189-*Clostridium innocuum* (Cluster XVII); SEQ ID NO:82-PE9-*Clostridium disporicum* (Cluster I); SEQ ID NO:81-PE5-*Clostridium bolteae* (Cluster XIVa); SEQ ID NO:80-VE202-18-*Erysipelatoclostridium ramosum* (Cluster XVIII).

FIGS. 27A and 27B shows survival and weight loss of the mice over time post infection with *C. difficile* spores, according to the experimental conditions shown in FIG. 25. Mice losing >20% body weight of baseline were included in mortality numbers in survival curves.

FIG. 28A shows survival/mortality of mice that received the indicated treatment prior to *C. difficile* infection. FIG. 28B shows the weight over time of mice that received the indicated treatment prior to *C. difficile* infection.

FIGS. 29A and 29B show the *C. difficile* burden in CFU/gram feces collected from mice that received the indicated treatment prior to *C. difficile*. FIG. 29A shows *C. difficile* burden at one-day post *C. difficile* infection. FIG. 29B shows *C. difficile* burden at 4 days post *C. difficile* infection.

DETAILED DESCRIPTION OF THE INVENTION

Figure 4A:
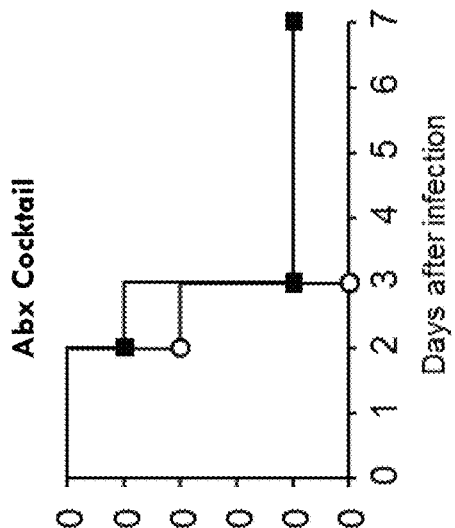
FIGS. 4A-4L show data obtained in Example 1.
Figure 4B:
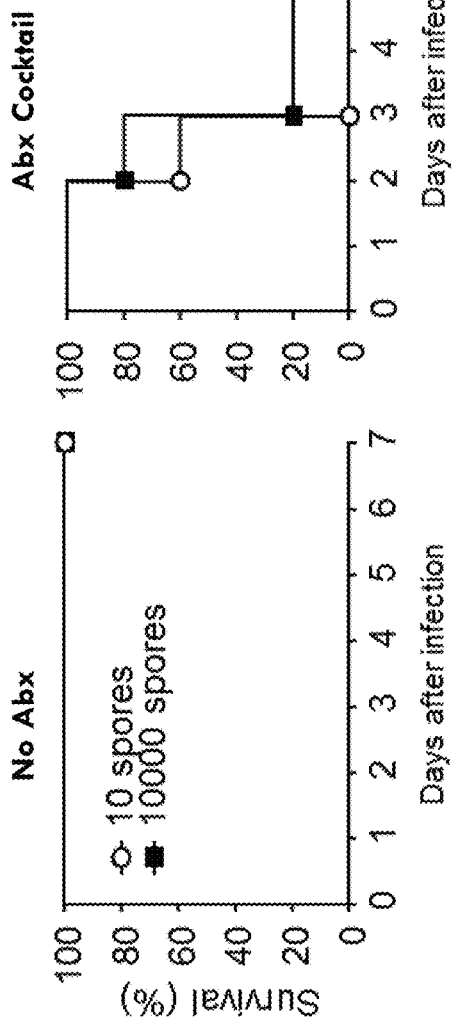
Figure 4D:
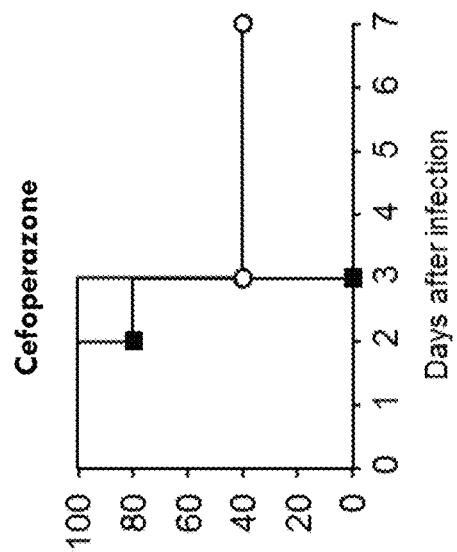
Figure 4C:
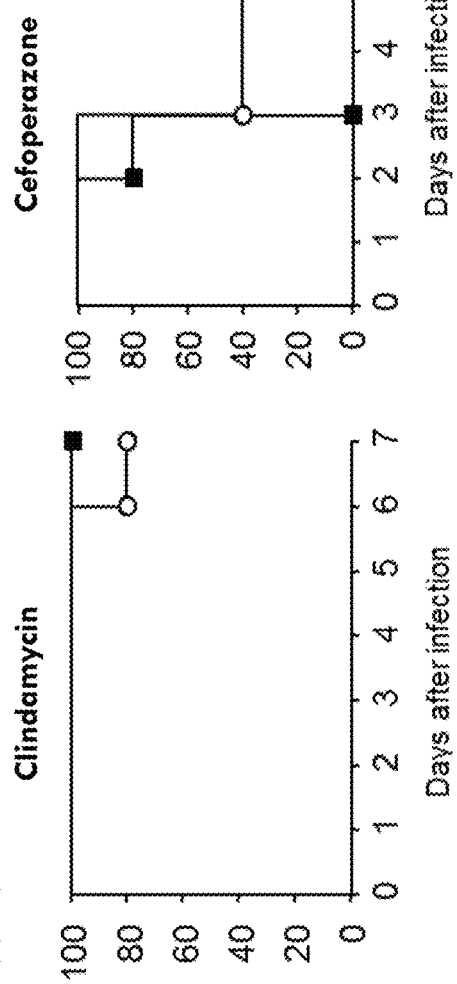

Disclosed herein are compositions comprising purified bacterial strains and pharmaceutical compositions and food products containing such compositions and bacterial strains. Also disclosed are methods of treating a pathogenic infection, such as *Clostridium difficile* (*C. difficile*) infection, in a subject by administering said compositions to the subject.

Various factors including antibiotic usage can induce dysbiosis of the gastrointestinal tract, which may allow for colonization by pathogenic microorganisms, such as *C. difficile*. Such colonization or pathogenic infection can lead to a variety of adverse effects in the subject including diarrhea, which is one of the primary symptoms characteristic of *C. difficile* infection (CDI). In the case of CDI, diarrhea is thought to be a result of *C. difficile* production of Toxin B (also referred to as cytotoxin TcdB), which results in opening of the tight junctions between intestinal epithelial cells, increasing vascular permeability, hemorrhage, and inflammation.

The compositions described herein are effective in the treatment of *C. difficile* infection. As shown herein, the disclosed compositions are effective in suppressing the pathogenic effects of *C. difficile* infection. The compositions provided herein reduce the amount of *C. difficile* after infection and thereby provide an effective method for eliminating *C. difficile* from the body (e.g., the gut). The compositions provided herein induce the proliferation and/or accumulation of regulatory T cells (Tregs), for example when administered to a subject. Remarkably, the compositions disclosed herein have been found to reduce or inhibit production or activity of *C. difficile* Toxin B and thereby represent effective compositions for the treatment or prevention of CDI. The compositions disclosed herein have also been found to inhibit the growth and/or survival of *C. difficile*.

The present disclosure provides compositions comprising purified bacterial strains that can be administered to subjects experiencing or having experienced a pathogenic infection to treat the infection. In some embodiments, the compositions may be administered to subjects who may be at risk for a pathogenic infection. Such subjects include subjects who previously had pathogenic infections, subjects who have been treated with antibiotics and subjects who will undergo a procedure that will put them at an increased risk for a pathogenic infection (e.g., surgery and/or hospitalization). In some embodiments, the pathogenic infection, is infection by a pathogen that is present predominantly in the gut or the intestine. In some embodiments, the pathogen that is present predominantly in the gut or the intestine is *Clostridium difficile*.

In some embodiments, the one or more of the bacterial strains of the compositions provided herein colonize or recolonize the intestinal tract or parts of the intestinal tract (e.g., the colon or the cecum) of the subject. Such colonization or recolonization may also be referred to as grafting. In some embodiments, the one or more of the bacterial strains of the compositions recolonize the intestinal tract (e.g., the colon or the cecum) of the subject after the naturally present microbiome has been partially or completely removed, e.g., because of administration of antibiotics. In some embodiments, the one or more of the bacterial strains of the compositions colonize a dysbiotic gastrointestinal tract.

In some embodiments, the one or more of the bacterial strains of the compositions can "outgrow" a pathogen, such as *C. difficile*. Thus, in some embodiments, if a pathogen (e.g., *C. difficile*) and one or more bacteria of compositions provided herein are both present in the intestinal tract (e.g., the colon or the cecum), the one or more bacteria of compositions provided herein grow faster (e.g., have a shorter doubling time) than the pathogen, thereby preventing the pathogen from accumulating in the intestinal tract (e.g., the colon or the cecum). In some embodiments, the faster growth results because the one or more bacteria of the compositions provided herein are better at grafting in the intestinal tract (e.g., the colon or the cecum). In some embodiments, the faster growth results because the one or more bacteria of the compositions provided herein are better at metabolizing nutrients present in the intestinal tract (e.g., the colon or the cecum). In some embodiments, the compositions of bacterial strains provided herein prevent or inhibit production of bacterial toxins by the pathogenic infection, or prevent or inhibit the cytopathic or cytotoxic effects of such bacterial toxins. In some embodiments, the bacterial strains of the compositions provided herein can treat pathogenic infections, because of the synergy between the bacterial strains. Thus, without being limiting, in some embodiments, the combination of the bacterial strains of the compositions provided herein act synergistically because the combination of the strains is particularly well-suited to use nutrients in the intestinal tract (e.g., the colon or the cecum), or instance through metabolic interactions, and/or because the combination is superior in grafting (e.g., by providing a favorable microenvironment).

In some embodiments, a pathogenic infection such as *C. difficile* is treated because the combination of bacterial strains of the compositions provided herein is superior in the use of nutrients when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in the use of nutrients and in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein inhibits the growth and/or survival of the pathogen such as *C. difficile*. In some embodiments, a pathogenic infection such as *C. difficile* is treated because the combination of bacterial strains of the compositions provided herein induces regulatory T cells (Tregs) in the subject that results in reduction or elimination of the pathogen such as *C. difficile*. In some embodiments, a pathogenic infection such as *C. difficile* is treated because the combination of bacterial strains of the compositions provided herein inhibits the growth and/or survival of the pathogen and induces regulatory T cells (Tregs) in the subject that results in reduction or elimination of the pathogen such as *C. difficile*.

In some embodiments, the synergistic effect is provided by the capacity of the combination to colonize specific niches in the intestinal tract (e.g., the colon or the cecum). In some embodiments, the synergistic effect is provided by the capacity of the combination to metabolize specific nutrients. In some embodiments, the synergistic effect is provided by the capacity of the combination to provide specific metabolites to the environment. Such specific metabolites may suppress growth of the pathogen and/or stimulate growth of non-pathogens. In some embodiments, the synergistic effect is provided by the capacity of the combination to provide short-chain fatty acids to the environment. In some embodiments, the synergistic effect is provided by the capacity of the combination to provide specific short-chain fatty acids to the environment. In some embodiments, the synergistic effect is provided by the capacity of the combination to produce butyrate. In some embodiments, the synergistic effect is provided by the capacity of the combination to produce acetate. In some embodiments, the synergistic effect is provided by the capacity of the combination to produce lactate. In some embodiments, the synergistic effect is provided by the capacity of the combination to produce propionate. In some embodiments, the synergistic effect is provided by the capacity of the combination to produce succinate. In some embodiments, the synergistic effect is provided by the capacity of the combination to produce multiple metabolites. In some embodiments, the synergistic effect is provided by the capacity of the combination to produce multiple short-chain fatty acids. In some embodiments, the synergistic effect is provided by the capacity of the combination to produce both butyrate and acetate. In some embodiments, the synergistic effect is provided by the capacity of the combination to produce both butyrate and lactate. In some embodiments, the synergistic effect is provided by the capacity of the combination to produce both butyrate and propionate. In some embodiments, the synergistic effect is provided by the capacity of the combination to produce both butyrate and succinate. In some embodiments, the synergistic effect is provided by the capacity of the combination to produce butyrate, acetate and additional short-chain fatty acids.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the bacteria of the compositions provided herein are anaerobic bacteria. In some embodiments, the bacteria of the compositions provided herein are obligate anaerobic bacteria. In some embodiments, the bacteria of the compositions provided herein are *clostridia*. *Clostridia* may be classified into phylogenetic clusters with other closely related strains and species. (See e.g., Rajilic-Stojanovic, M., and de Vos, W. M. *FEMS Microbiol Rev* 38, (2014) 996-1047). In general, *clostridia* are classified as belonging to a specific cluster based on their 16S rRNA (or 16S rDNA) nucleic acid sequence. Methods for determining the identity of specific bacterial species based on their 16S rRNA (or 16S rDNA) nucleic acid sequence are well known in the art (See e.g., *Jumpstart Consortium Human Microbiome Project Data Generation Working, G. PLoS One* (2012) 7, e39315).

Provided herein are compositions comprising bacterial strains belonging to specific *Clostridium* clusters that have been found to be effective in treating and/or preventing pathogenic infection (e.g., *C. difficile* infection). In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster XVII. In some embodiments, at least one of the bacterial strains of the composition belongs to *Clostridium* cluster I. In some embodiments, at least one of the bacterial strains of the composition belongs to *Clostridium* cluster IX. In some embodiments, at least one of the bacterial strains of the composition belongs to *Clostridium* cluster XIVa and at least one of the bacterial strains belongs to *Clostridium* cluster XVII. In some embodiments, at least one of the bacterial strains of the composition belongs to *Clostridium* cluster IV and at least one of the bacterial strains belongs to *Clostridium* cluster XVII. In some embodiments, at least one of the bacterial strains of the composition belongs to *Clostridium* cluster IV, at least one of the bacterial strains belongs to *Clostridium* cluster XIVa, and at least one of the bacterial strains belongs to *Clostridium* cluster XVII.

In some embodiments, the composition has at least twice as many bacterial strains that belong to *Clostridium* cluster XIVa when compared to the bacterial strains that belong to *Clostridium* cluster IV. In some embodiments, at least two of the bacterial strains of the composition belong to *Clostridium* cluster IV and at least five of the bacterial strains belong to *Clostridium* cluster XIVa. In some embodiments, the composition has at least twice as many bacterial strains that belong to *Clostridium* cluster XIVa when compared to the bacterial strains that belong to *Clostridium* cluster IV, and the composition has at least one strain that belongs to *Clostridium* cluster XVII. In some embodiments, at least two of the bacterial strains of the composition belong to *Clostridium* cluster IV, at least five of the bacterial strains belongs to *Clostridium* cluster XIVa, and at least one of the bacterial strains belongs to *Clostridium* cluster XVII.

In some embodiments, the compositions provided herein do not include bacterial strains belonging to *Clostridium* cluster XVIII. In some embodiments, the compositions provided herein do not include bacterial strains belonging to *Clostridium* cluster XVI. In some embodiments, the compositions provided herein do not include bacterial strains belonging to *Clostridium* cluster XI. In some embodiments, the compositions provided herein do not include bacterial strains belonging to *Clostridium* cluster I.

In one aspect, the disclosure provides bacterial strains comprising a 16S rDNA sequence with a nucleic acid sequence selected from the group consisting of SEQ ID NOs: 1-83 and 124-159. It should be appreciated that SEQ ID NOs: 1-83 and 124-159 may include both full length and partial 16S rDNA sequences.

In one aspect, the disclosure provides compositions comprising a bacterial strain comprising a 16S rDNA sequence with a nucleic acid sequence selected from the group consisting of SEQ ID NOs: 1-83 and 124-159. In one aspect, the disclosure provides compositions comprising as an active ingredient a bacterial strain comprising a 16S rDNA sequence with a nucleic acid sequence selected from the group consisting of SEQ ID NOs: 1-83 and 124-159. It should be appreciated that for all compositions provided herein, in some embodiments, the bacterial strain or the bacterial strains are the active ingredient of the composition.

It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs: 1-83 and 124-159. In addition, for example, the disclosure provides compositions comprising purified bacterial strains comprising a 16S rDNA sequence with a nucleic acid sequence selected from the group consisting of SEQ ID NOs: 1-83 and 124-159. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more bacterial strains, wherein the one or more bacterial strains comprise a 16S rDNA sequence with a nucleic acid sequence selected from the group consisting of SEQ ID NOs:1-83 and 124-159. In one aspect, the disclosure provides compositions comprising one or more bacterial strains wherein the one or more bacterial strains comprise 16S rDNA sequences having at least 97% homology with nucleic acid sequences selected from the group consisting of SEQ ID NOs:1-83 and 124-159. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% homology with nucleic acid sequences selected from the group consisting of SEQ ID NOs:1-83 and 124-159.

In one aspect, the disclosure provides compositions comprising two or more purified bacterial strains wherein the two or more purified bacterial strains comprise 16S rDNA sequences having at least 97% homology with nucleic acid sequences selected from the group consisting of SEQ ID NOs:1-83 and 124-159. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% homology with nucleic acid sequences selected from the group consisting of SEQ ID NOs:1-83 and 124-159.

In one aspect, the disclosure provides bacterial strains and combinations of bacterial strains that are homologous or have a high percent of homology with bacterial strains comprising 16S rDNA sequences selected from the group consisting of SEQ ID NOs:1-83 and 124-159. As discussed previously, in some embodiments, the bacterial strains are purified. The bacterial strains disclosed herein that have a 16S rDNA sequence with a nucleic acid sequence selected from the group consisting of SEQ ID NOs:1-83 and 124-159 have a high percent of homology (e.g., greater than 90%) with 16S rDNA sequences of bacterial strains that have been described in various databases (See e.g., the National Center for Biotechnology Information). Table 1 and Table 3 provides the closest known species by homology when the 16S rDNA sequences comprising SEQ ID NOs:1-83 and 124-159 are compared to 16S rDNA sequences of bacterial species available in public databases. By way of example, the bacterial strain comprising a 16S rDNA sequence with SEQ ID NO:1 (also referred to herein as "Strain 71") disclosed herein has the highest homology with a bacterial strain of the species *Blautia wexlerae* as defined by Accession # NR_044054 (having 16S rDNA sequence SEQ ID NO:94). While the bacterial strain with SEQ ID NO:1 has homology with other published bacterial strains as well, the highest homology is with a bacterial strain of the species *Blautia wexlerae* as defined by Accession # NR_044054. In this particular example the homology of SEQ ID NO:1 is 96.6% with SEQ ID NO:94 (corresponding to *Blautia wexlerae*). It should be appreciated that multiple bacterial strains disclosed herein may have the highest homology with the same species. (e.g., both SEQ ID NO:4 and SEQ ID NO:5 have the highest homology with a 16S rDNA sequence of a strain of the species *Blautia hansenii*).

It should further be appreciated that the bacterial strains disclosed herein that have a 16S rDNA sequence with a nucleic acid sequence selected from the group consisting of SEQ ID NOs:1-83 and 124-159, are also homologous to other strains based on their whole genome sequence, or subset of their whole genome sequence. Homologies based on whole genome analysis are provided in Table 2 and Table 3.

In one aspect, the disclosure provides compositions comprising one or more bacterial strains wherein the one or more bacterial strains are of species selected from the group consisting of *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium_21-3, Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus*.

In some embodiments, the disclosure provides compositions comprising two or more bacterial strains, wherein the two or more bacterial strains are of species selected from the group consisting of *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium_21-3, Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus*.

It should be appreciated that the compositions may include multiple strains of a particular species. Thus, for illustration, a non-limiting example of the compositions disclosed herein, comprises one strain of *Clostridium hathewayi* and two strains of *Blautia hansenii*.

The invention also encompasses compositions comprising bacterial strains that are close in homology to and/or fall within the species *Clostridium hathewayi, Blautia hansenii, Blautia producta, Blautia producta* ATCC 27340, *Clostridia bacteria* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium_21-3, Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifi-* dobacterium bifidum, Blautia luti, Roseburia faecis, Fusicatenibacter saccharivorans, Roseburia faecis, Blautia faecis, Dorea formicigenerans and Bacteroides ovatus. Thus, in one embodiment, the compositions of the disclosure include one or more bacterial strains comprising 16S rDNA sequences having at least 97% homology with nucleic acid sequences selected from the group consisting of SEQ ID NOs: 84-123. In some embodiments, the compositions of the disclosure include two or more bacterial strains comprising 16S rDNA sequences having at least 97% homology with nucleic acid sequences selected from the group consisting of SEQ ID NOs:84-123.

In one aspect, the compositions of the disclosure include two or more purified bacterial strains comprising 16S rDNA sequences having at least 97% homology with nucleic acid sequences selected from the group consisting of SEQ ID NOs:1-23 and 124-159. In some embodiments, the compositions of the disclosure include two or more bacterial strains of species selected from the group consisting of *Clostridium hathewayi, Blautia hansenii, Blautia producta, Blautia producta* ATCC 27340, *Clostridia bacteria* UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50AFAA, *Lachnospiraceae bacterium* 7_1_58FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium_*21-3, *Blautia wexlerae, Turicibacter sanguinis, Lactobacillus mucosae*, and *Bacteroides ovatus*. In some embodiments, the compositions of the disclosure include two or more purified bacterial strains comprising 16S rDNA sequences having at least 97% homology with nucleic acid sequences selected from the group consisting of SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:97, SEQ ID NO:98, SEQ ID NO:99, SEQ ID NO:102, SEQ ID NO:103, SEQ ID NO:105, SEQ ID NO:106, SEQ ID NO:108, SEQ ID NO:109, SEQ ID NO:110, SEQ ID NO:121, and SEQ ID NO:122.

In one aspect, the disclosure provides Composition A (See e.g., FIG. 1, Table A). As shown in FIG. 1, Composition A contains bacterial strains that comprise 16S rDNA sequences with nucleic acid sequences: SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with two or more purified bacterial strains that comprise 16S rDNA sequences with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with five or more purified bacterial strains that comprise 16S rDNA sequences with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with at least ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition consisting of ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition essentially consisting of ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. As used herein, essentially consisting of refers to a composition that includes no additional bacterial strains.

In some embodiments, the disclosure provides compositions with bacterial strains that comprise 16S rDNA sequences having at least 97% homology with nucleic acid sequences selected from the group consisting of: SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with two or more purified bacterial strains that comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with five or more purified bacterial strains that comprise 16S rDNA having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with at least ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition consisting of ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition essentially consisting of ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively.

The bacterial strains in Composition A are related to the following bacterial species: *Clostridium hathewayi, Blautia* hansenii, *Blautia* producta, *Blautia coccoides, Eubacterium contortum, Eubacterium fissicatena, Anaerostipes caccae, Clostridium scindens, Marvinbryanta formatexigens*, and *Eisenbergiella tayi* (See e.g., Table 1). It should be appreciated that multiple bacterial strains of the compositions disclosed herein can have the same related bacterial species.

For instance, the bacterial strains having 16S rDNA sequences with nucleic acid sequences SEQ ID NO:4, SEQ ID NO:5 and SEQ ID NO:7 all have *Blautia hansenii* as related species. In some embodiments, the disclosure provides compositions with two or more bacteria of species selected from the group consisting of *Clostridium hathewayi*, *Blautia* hansenii, *Blautia* producta, *Blautia coccoides*, *Eubacterium contortum*, *Eubacterium fissicatena*, *Anaerostipes caccae*, *Clostridium scindens*, *Marvinbryanta formatexigens*, and *Eisenbergiella tayi*. In some embodiments, the disclosure provides compositions with two or more purified bacterial strains comprising 16S rDNA sequences having at least 97% homology with nucleic acid sequences selected from the group consisting of SEQ ID NO:87, SEQ ID NO:88, SEQ ID NO:89, SEQ ID NO:99, SEQ ID NO:103, SEQ ID NO:105, SEQ ID NO:106, SEQ ID NO:108, SEQ ID NO:109, and SEQ ID NO:121.

In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:5, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:5; SEQ ID NO:7, SEQ ID NO:8, and SEQ ID NO:13.

Each of the bacterial strains of Composition A are BaiCD+, meaning that the bacterial strains encode, or are predicted to encode, the bile inducible operon gene BaiCD and/or a protein with stereospecific NAD(H)-dependent 3-oxo-$\Delta^4$-cholenoic acid oxidoreductase activity. The BaiCD status of a bacterial strain can be determined for instance by PCR (See e.g., Wells et al. *Clin Chim Acta* (2003) May; 331(1-2):127-34). Furthermore, each of the strains of Composition A are classified as belonging to *Clostridium* cluster XIVa. In some embodiments, the disclosure provides compositions comprising two or more bacterial strains, wherein the bacterial strains are BaiCD+ strains. In some embodiments, the disclosure provides compositions comprising two or more bacterial strains, wherein the bacterial strains are BaiCD+ and belong to *Clostridium* cluster XIVa. In some embodiments of the compositions comprising two or more bacterial strains that are BaiCD+ strains and that belong to *Clostridium* cluster XIVa, the compositions do not include bacterial strains that belong to *Clostridium* cluster IV.

In some embodiments, the disclosure provides compositions with two or more purified bacterial strains that comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, wherein all the bacterial strains belong to *Clostridium* cluster XIVa.

TABLE A

Composition A

SEQ_03 - 5 - *Clostridium_hathewayi* (XIVa)*
SEQ_04 - 7 - *Blautia_hansenii* (XIVa)*
SEQ_05 - 10 - *Blautia_hansenii* (XIVa)*
SEQ_07 - 59 - *Blautia_producta/Blautia_coccoides* (XIVa)
SEQ_08 - 79 - *Blautia_hansenii* (XIVa)*
SEQ_09 - VE202-21 - *Eubacterium_contortum/Eubacterium_fissicatena* (XIVa)*
SEQ_11 - VE202-9 - *Anaerostipes_caccae* (XIVa)*
SEQ_12 - VE202-26 - *Clostridium_scindens* (XIVa)*
SEQ_13 - 136 - *Marvinbryantia_formatexigens* (XIVa)*
SEQ_23 - VE202-29 - *Eisenbergiella_tayi* (XIVa)*

*= BaiCD⁺

In one aspect, the disclosure provides Composition B (See e.g., FIG. 1, Table B). As shown in FIG. 1, Composition B contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include two or more purified bacterial strains comprising 16S rDNA sequences with nucleic acid sequences selected from the group consisting of SEQ ID NOs: 124-159. In some embodiments, the compositions include two or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include five or more purified bacterial strains comprising 16S rDNA sequences with nucleic acid sequences selected from the group consisting of SEQ ID NOs: 124-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include at least eight purified bacterial strains comprising 16S rDNA sequences with nucleic acid sequences selected from the group consisting of SEQ ID NOs: 124-159, respectively. In some embodiments, the compositions include at least eight purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of eight purified bacterial strains comprising 16S rDNA sequences with nucleic acid sequences selected from the group consisting of SEQ ID NOs:124-159, respectively. In some embodiments, the compositions consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition essentially consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of at least eight purified bacterial strains comprising 16S rDNA sequences with nucleic acid sequences selected from the group consisting of SEQ ID NOs:124-159, respectively. In some embodiments, the composition essentially consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the compositions include eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include eight purified bacterial strains comprising 16S rDNA sequences with nucleic acid sequences selected from the group consisting of SEQ ID NOs: 124-159, respectively. In some embodiments, the compositions include eight purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of eight purified bacterial strains comprising 16S rDNA sequences with nucleic acid sequences selected from the group consisting of SEQ ID NOs:124-159, respectively. In some embodiments, the compositions consists of eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition essentially consists of eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of eight purified bacterial strains comprising 16S rDNA sequences with nucleic acid sequences selected from the group consisting of SEQ ID NOs:124-159, respectively. In some embodiments, the composition essentially consists of eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-159. In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In one aspect, the disclosure provides a composition that contains bacterial strains that comprise 16S rDNA sequences with nucleic acid sequences: SEQ ID NOs: 124-159. In one aspect, the disclosure provides a composition that contains bacterial strains that comprise 16S rDNA sequences with nucleic acid sequences: SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include two or more purified bacterial strains comprising 16S rDNA sequences with nucleic acid sequences selected from the group consisting of SEQ ID NO:22, SEQ ID NOs: 124-145, and SEQ ID NOs: 152-159. In some embodiments, the compositions include two or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include five or more purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the compositions include at least eight purified bacterial strains comprising 16S rDNA sequences with nucleic acid sequences selected from the group consisting of SEQ ID NO:22, SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the composition consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition consists of at least eight purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the composition consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the composition essentially consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition essentially consists of at least eight purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the composition essentially consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In one aspect, the disclosure provides compositions that contain bacterial strains that comprise 16S rDNA sequences having at least 97% homology with nucleic acid sequences selected from the group consisting of: SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159. In one aspect, the disclosure provides compositions that contain bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In one aspect, the disclosure provides compositions that contain bacterial strains that comprise 16S rDNA sequences having at least 97% homology with nucleic acid sequences selected from the group consisting of: SEQ ID NOs: 124-159. In one aspect, the disclosure provides compositions that contain bacterial strains that comprise 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include two or more purified bacterial strains comprising 16S rDNA sequences having at least 97% homology with nucleic acid sequences selected from the group consisting of SEQ ID NOs: 124-159. In some embodiments, the compositions include two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include five or more purified bacterial strains comprising 16S rDNA sequences having at least 97% homology with nucleic acid sequences selected from the group consisting of SEQ ID NOs: 124-159. In some embodiments, the compositions include five or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159, respectively. In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include at least eight purified bacterial strains comprising 16S rDNA sequences having at least 97% homology with nucleic acid sequences selected from the group consisting of SEQ ID NOs: 124-159. In some embodiments, the compositions include at least eight purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of at least eight purified bacterial strains comprising 16S rDNA sequences having at least 97% homology with nucleic acid sequences selected from the group consisting of SEQ ID NOs:124-159, respectively. In some embodiments, the composition consists of at least eight purified bacterial strains comprising 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159, respectively. In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of at least eight purified bacterial strains comprising 16S rDNA sequences having at least 97% homology with nucleic acid sequences selected from the group consisting of SEQ ID NOs: 124-159, respectively. In some embodiments, the composition essentially consists of at least eight purified bacterial strains comprising 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In one aspect, the disclosure provides a composition that contains bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159. In one aspect, the disclosure provides a composition that contains bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In one aspect, the disclosure provides a composition that contains bacterial strains that comprise 16S rDNA sequences having at least 97% homology with nucleic acid sequences: SEQ ID NO:22, SEQ ID NO: 124-145, and SEQ ID NOs: 152-159.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO: 124-145, and SEQ ID NOs: 152-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include two or more purified bacterial strains comprising 16S rDNA sequences having at least 97% homology with nucleic acid sequences selected from the group consisting of SEQ ID NO: 22, SEQ ID NO: 124-145, and SEQ ID NOs: 152-159.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include five or more purified bacterial strains comprising 16S rDNA sequences having at least 97% homology with nucleic acid sequences selected from the group consisting of SEQ ID NO: 20, SEQ ID NO: 124-145, and SEQ ID NOs: 152-159.

In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the compositions include at least eight purified bacterial strains comprising 16S rDNA sequences having at least 97% homology with nucleic acid sequences selected from the group consisting of SEQ ID NO: 22, SEQ ID NO: 124-145, and SEQ ID NOs: 152-159.

In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition consists of at least eight purified bacterial strains comprising 16S rDNA sequences having at least 97% homology with nucleic acid sequences SEQ ID NO: 22, SEQ ID NO: 124-145, and SEQ ID NOs: 152-159.

In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition essentially consists of at least eight purified bacterial strains comprising 16S rDNA sequences having at least 97% homology with nucleic acid sequences SEQ ID NO: 22, SEQ ID NO: 124-145, and SEQ ID NOs: 152-159.

In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159. In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In one aspect, the disclosure provides a composition that contains bacterial strains that comprise 16S rDNA sequences with nucleic acid sequences: SEQ ID NO:18, SEQ ID NO:22, and SEQ ID NO: 124-159.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In some embodiments, the compositions include two or more purified bacterial strains comprising 16S rDNA sequences having at least 97% homology with nucleic acid sequences selected from the group consisting of SEQ ID NO:18, SEQ ID NO:22, and SEQ ID NO: 124-159.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In some embodiments, the compositions include five or more purified bacterial strains comprising 16S rDNA sequences having at least 97% homology with nucleic acid sequences selected from the group consisting of SEQ ID NO:18, SEQ ID NO:22, and SEQ ID NOs: 124-159.

In some embodiments, the compositions include at least ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-159, respectively. In some embodiments, the compositions include at least ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the compositions include at least ten purified bacterial strains comprising 16S rDNA sequences having at least 97% homology with nucleic acid sequences selected from the group consisting of SEQ ID NO: 18, SEQ ID NO: 22, and SEQ ID NOs: 124-159.

In some embodiments, the composition consists of ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159, respectively. In some embodiments, the composition consists of ten purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the composition consists of ten purified bacterial strains comprising 16S rDNA sequences having at least 97% homology with nucleic acid sequences selected from the group consisting of SEQ ID NO:18, SEQ ID NO:22, SEQ ID NOs: 124-159, respectively.

In some embodiments, the composition essentially consists of ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159, respectively. In some embodiments, the composition essentially consists of ten purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the composition essentially consists of ten purified bacterial strains comprising 16S rDNA sequences having at least 97% homology with nucleic acid sequences selected from the group consisting of SEQ ID NO:18, SEQ ID NO:22, and SEQ ID NO: 124-159, respectively.

The bacterial strains in Composition B are related to the following bacterial species: *Flavinofractor plautii, Lachnospiraceae, bacterium 7_1_58FAA, Subdoligranulum Anaerotruncus colihominis, Eubacterium fissicatena, Ruminococcus torques Clostridium symbiosum, Clostridium bolteae, Dorea longicatena, Blautia producta, Clostridium innocuum*, and *Erysipelotrichaceae_bacterium_21-3* (See e.g., Table 2).

Selected strains were subjected to whole genome sequencing using a PacBio Biosciences platform (Menlo Park, Calif.) and sequences were assembled into whole genomes (Table 3). The 16S rDNA sequences were identified using Prokka and Barrnap. It was found that several strains contained more than one 16S sequence. All identified 16S rRNA gene nucleotide sequences for each strain were then clustered at 97% identity using the usearch (v 5.2.236) algorithm and the cluster seed sequence was selected as the representative sequence for each Composition B strain (The Consensus 16S sequence: column labeled "*Consensus SEQ ID # of 16S region as determined by WGS" in Table 3). Table 3 provides identification of the indicated strains included in Composition B based on Sanger sequencing of the 16S region as well as on whole genome sequencing (WGS). The closest species of the bacterial strains were identified both by comparison to a 16S database (column labeled: "Closest species based on Consensus SEQ ID # of 16S region as compared with 16S database") and to whole genome databases (column labeled: "Closest species based on WGS compared versus WG databases).

Based on identification of 16S sequences through whole genome sequencing, and by comparing these sequences with 16S databases, the bacterial strains in Composition B are related to the following bacterial species: *Clostridium bolteae, Anaerotruncus colihominis, Dracourtella massiliensis, Clostridium symbiosum Blautia producta, Dorea longicatena Clostridium innocuum* and *Flavinofractor plautii* (see, e.g., Table 3).

Based on whole genome sequencing and comparing of the whole genome to whole genome databases, the bacterial strains in Composition B are most closely related to the following bacterial species: *Clostridium bolteae* 90A9, *Anaerotruncus colihominis* DSM 17241, *Dracourtella massiliensis* GD1, *Clostridium symbiosum* WAL-14163, *Clostridium bacterium* UC5.1-1D4, *Dorea longicatena* CAG:42, *Erysipelotrichaceae_bacterium_21_3*, and *Clostridium orbiscindens* 1_3_50AFAA (see, e.g., Table 3).

It should be appreciated that multiple strains of the compositions disclosed herein can have the same related bacterial species. For instance, the bacterial strains comprising 16S rDNA sequences with nucleic acid sequences SEQ ID NO 18, SEQ ID NO:20 and SEQ ID NO:22 all have *Dorea longicatena* as related bacterial species. In some embodiments, the disclosure provides compositions with two or more bacteria selected from the group consisting of *Flavinofractor plautii, Lachnospiraceae, bacterium 7_1_58FAA, Subdoligranulum Anaerotruncus colihominis, Eubacterium fissicatena, Ruminococcus torques Clostridium symbiosum, Clostridium bolteae, Dorea longicatena, Blautia producta, Clostridium innocuum* and *Erysipelotrichaceae_bacterium_21-3*. In some embodiments, the disclosure provides compositions with two or more bacteria selected from the group consisting of *Flavinofractor plautii, Anaerotruncus colihominis, Eubacterium fissicatena, Clostridium symbiosum, Clostridium bolteae, Dorea longicatena, Blautia producta,* and *Clostridium innocuum*. In some embodiments, the disclosure provides compositions that include two or more purified bacterial strains comprising 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:102, SEQ ID NO:106, SEQ ID NO:110, and SEQ ID NO:122.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, SEQ ID NO:22, and SEQ ID NOs: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NOs: 124-159. In some embodiments, the composition comprises two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, SEQ ID NO:22, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:18, SEQ ID NO:22, and SEQ ID NO: 124-159. In some embodiments, the composition comprises two or more purified bacterial strains comprising 16S rDNA sequences having at least 97% homology with nucleic acid sequences selected from the group consisting of SEQ ID NO:18, SEQ ID NO:22, SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments, the composition comprises two or more purified bacterial strains comprising 16S rDNA sequences having at least 97% homology with nucleic acid sequences selected from the group consisting of SEQ ID NO:18 and SEQ ID NO: 124-159. In some embodiments, the composition comprises two or more purified bacterial strains comprising 16S rDNA sequences having at least 97% homology with nucleic acid sequences selected from the group consisting of SEQ ID NO:18, SEQ ID NO: 124, SEQ ID NO:129, SEQ ID NO:132, SEQ ID NO:137, SEQ ID NO:141, SEQ ID NO:146, SEQ ID NO:152, and SEQ ID NO:157

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO: 124-145, and SEQ ID NO: 151-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:22, SEQ ID NO: 124-145, and SEQ ID NO: 151-159. In some embodiments, the composition comprises two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:152, and SEQ ID NO:157

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the composition comprises two or more purified bacterial strains comprising 16S rDNA sequences having at least 97% homology with nucleic acid sequences selected from the group consisting of SEQ ID NOs: 124-159.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, SEQ ID NOs: 124-145, and SEQ ID NOs: 152-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, and SEQ ID NO:21. In some embodiments, the composition comprises two or more purified bacterial strains comprising 16S rDNA sequences having at least 97% homology with nucleic acid sequences selected from the group consisting of SEQ ID NO: 18, SEQ ID NOs: 124-145, and SEQ ID NOs: 152-159.

In some embodiments, the composition comprises two or more purified bacterial strains comprising 16S rDNA sequences having at least 97% homology with nucleic acid sequences selected from the group consisting of SEQ ID NO:10, SEQ ID NO:18, SEQ ID NO:19, SEQ ID NO:20, SEQ ID NO:21, SEQ ID NO:22, SEQ ID NOs: 157-159, and SEQ ID NOs:141-156. In some embodiments, the composition comprises two or more purified bacterial strains comprising 16S rDNA sequences having at least 97% homology with nucleic acid sequences selected from the group consisting of SEQ ID NO:10, SEQ ID NO:18, SEQ ID NO:19, SEQ ID NO:20, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:18, SEQ ID NO:22, SEQ ID NOs: 157-159, and SEQ ID NO:141-156.

Each of the bacteria of Composition B are BaiCD– strains, meaning that the strains do not encode and/or are not predicted to encode the bile inducible operon gene baiCD and/or a protein with stereospecific NAD(H)-dependent 3-oxo-$\Delta^4$-cholenoic acid oxidoreductase activity. In some embodiments, the disclosure provides compositions comprising two or more bacteria, wherein the bacteria are BaiCD– strains. The strains of Composition B are classified as belonging to *Clostridium* clusters IV, XIVa, and XVII. In some embodiments, the disclosure provides two or more bacterial strains, wherein the bacteria are BaiCD– strains and belong to *Clostridium* clusters IV, XIVa, or XVII. In some embodiments, the disclosure provides two or more bacterial strains, wherein the bacteria are BaiCD– strains and belong to *Clostridium* clusters IV or XVII. In some embodiments, the disclosure provides two or more bacterial strains, wherein the bacteria are BaiCD– strains and belong to *Clostridium* clusters XIVa or XVII. In some embodiments, the disclosure provides two or more bacterial strains, wherein the bacteria are BaiCD– strains and belong to *Clostridium* clusters IV or XIVa. In some embodiments, the disclosure provides two or more bacterial strains, wherein the bacteria are BaiCD– strains and belong to *Clostridium* cluster IV. In some embodiments, the disclosure provides two or more bacterial strains, wherein the bacteria are BaiCD– strains and belong to *Clostridium* cluster XIVa. In some embodiments, the disclosure provides two or more bacterial strains, wherein the bacteria are BaiCD– strains and belong to *Clostridium* clusters XVII. In some embodiments, the disclosure provides two or more bacterial strains, wherein the bacteria are BaiCD– strains and belong to *Clostridium* clusters IV, XIVa, and XVII and do not belong to *Clostridium* clusters XVI or XVIII.

In some embodiments, the disclosure provides two or more bacterial strains wherein the bacterial strains are spore forming bacterial strains. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NO:14, SEQ ID NO:16, SEQ ID NO:17, SEQ ID NO:21, SEQ ID NOs 124-140, and SEQ ID NO: 152-156. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NO:14, SEQ ID NO:16, SEQ ID NO:17, and SEQ ID NO:21. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NOs: 124-140, and SEQ ID NOs: 152-156.

In some embodiments, the disclosure provides two or more bacterial strains wherein the bacteria include both spore formers and non-spore formers. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NO:14, SEQ ID NO:16, SEQ ID NO:17, SEQ ID NO:21, SEQ ID NOs: 124-140, and SEQ ID NOs: 152-156. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NO:14, SEQ ID NO:16, SEQ ID NO:17, and SEQ ID NO:21. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NOs: 124-140 and SEQ ID NO: 152-156.

TABLE B

Composition B

SEQ_10 - 211 - *Flavonifractor_plautii* (IV)
SEQ_14 - VE202-13 - *Anaerotruncus_colihominis* (IV)
SEQ_15 - VE202-14 - *Eubacterium_fissicatena* (XIVa)
SEQ_16 - VE202-16 - *Clostridium_symbiosum* (XIVa)
SEQ_17 - VE202-7 - *Clostridium_bolteae* (XIVa)
SEQ_19 - 16 - *Blautia_producta* (XIVa)
SEQ_20 - 170 - *Dorea_longicatena* (XIVa)
SEQ_21 - 189 - *Clostridium_innocuum* (XVII)

In some embodiments, the compositions include one or more bacterial species from the *Bacteroides* genus. In some embodiments, the compositions include one or more bacterial species selected from the group consisting of *B. acidifaciens, B. caccae, B. coprocola, B. coprosuis, B. eggerthii, B. finegoldii, B. fragilis, B. helcogenes, B. intestinalis, B. massiliensis, B. nordii, B. ovatus, B. thetaiotaomicron, B. vulgatus, B. plebeius, B. uniformis B. salyersai, B. pyogenes, B. goldsteinii, B. dorei,* and *B. johnsonii*. In some embodiments, the compositions include *Bacteroides ovatus*. In some embodiments, the *Bacteroides ovatus* has a 16S rDNA sequence comprising SEQ ID NO:83. In some embodiments, the *Bacteroides ovatus* has a 16S rDNA sequence having at least 97% homology with a nucleic acid sequence comprising SEQ ID NO:83. In some embodiments, the *Bacteroides ovatus* has a 16S rDNA sequence having at least 97% homology with a nucleic acid sequence comprising SEQ ID NO:101.

While not being limited to a specific mechanism it is thought that the inclusion of a *Bacteroides* species in the bacterial compositions disclosed herein increases the ability to sense and adapt to nutrient availability or influence the host immune system so that it becomes more effective in fighting pathogens (e.g., *C. difficile*). In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, SEQ ID NO: 124-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO:83. (Composition B1, See e.g., Table B1). In some embodiments, the composition comprises two or more purified bacterial strains comprising 16S rDNA sequences having at least 97% homology with nucleic acid sequences selected from the group consisting of SEQ ID NOs: 124-159, and SEQ ID NO: 83.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, SEQ ID NO: 152-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO:83. In some embodiments, the composition comprises two or more purified bacterial strains comprising 16S rDNA sequences having at least 97% homology with nucleic acid sequences selected from the group consisting of SEQ ID NOs: 124-145, SEQ ID NO: 152-159, and SEQ ID NO: 83.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO: 124-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:83. In some embodiments, the composition comprises two or more purified bacterial strains comprising 16S rDNA sequences having at least 97% homology with nucleic acid sequences selected from the group consisting of SEQ ID NOs: 124-159, SEQ ID NO: 18, SEQ ID NO: 22, and SEQ ID NO: 83.

In some embodiments, the composition comprises two or more purified bacterial strains comprising 16s rDNA sequences having at least 97% homology with nucleic acid sequences selected from the group consisting of SEQ ID NO:93, SEQ ID NO:95, SEQ ID NO:97, SEQ ID NO:98, SEQ ID NO:101, SEQ ID NO:102, SEQ ID NO:106, SEQ ID NO:110, and SEQ ID NO:122. It should also be appreciated that in some embodiments, the compositions disclosed herein do not include bacterial species from the *Bacteroides* genus.

TABLE B1

Composition B1

SEQ_10 - 211 - *Flavonifractor_plautii* (IV)
SEQ_14 - VE202-13 - *Anaerotruncus_colihominis* (IV)
SEQ_15 - VE202-14 - *Eubacterium_fissicatena* (XIVa)
SEQ_16 - VE202-16 - *Clostridium_symbiosum* (XIVa)
SEQ_17 - VE202-7 - *Clostridium_bolteae* (XIVa)
SEQ_20 - 170 - *Dorea_longicatena* (XIVa)
SEQ_19 - 16 - *Blautia_producta* (XIVa)
SEQ_21 - 189 - *Clostridium_innocuum* (XVII)
SEQ_83 *Bacteroides ovatus*

In some embodiments, the compositions disclosed herein do not include *Clostridium orbiscindens* 1_3_50AFAA, *Flavinofractor plautii, Subdoligranulum* or *Lachnospiraceae bacterium* 7_1_58FAA. In some embodiments, the compositions disclosed herein do not include *Clostridium orbiscindens* 1_3_50AFAA. In some embodiments, the compositions disclosed herein do not include *Flavinofractor plautii*. In some embodiments, the compositions disclosed herein do not include *Subdoligranulum*. In some embodiments, the compositions disclosed herein do not include *Lachnospiracae bacterium 7_1_58FAA*.

In some embodiments, the composition comprises two or more purified bacterial strains comprising 16S rDNA sequences having at least 97% homology with nucleic acid sequences selected from the group consisting of SEQ ID NO:14, SEQ ID NO: 15, SEQ ID NO:16, SEQ ID NO:17, SEQ ID NO:19, SEQ ID NO:20, SEQ ID NO:21, and SEQ ID NO: 124-156, wherein the composition does not include a bacterial strain comprising a 16s rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO: 15, SEQ ID NO:16, SEQ ID NO:17, SEQ ID NO:19, SEQ ID NO:20, and SEQ ID NO:21, wherein the composition does not include a bacterial strain comprising a 16s rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NOs: 124-156, wherein the composition does not include a bacterial strain comprising a 16S rDNA sequence having at least 97% homology with a nucleic acid sequence of SEQ ID NOs:157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-146 and SEQ ID NO: 152-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, and SEQ ID NO:22, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22, SEQ ID NOs: 124-146, and SEQ ID NOs: 152-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:18, SEQ ID NO:22, and SEQ ID NOs: 124-159, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:95, SEQ ID NO:97, SEQ ID NO:98, SEQ ID NO:102, SEQ ID NO:106, SEQ ID NO:110, and SEQ ID NO:122, wherein the composition does not include a bacterial strain comprising a 16S rDNA sequence having at least 97% homology with a nucleic acid sequence of SEQ ID NO:93.

In some embodiments, the compositions include one or more bacterial species from the *Bacteroides* genus and do not include *Clostridium orbiscindens 1_3_50AFAA*, *Flavinofractor plautii*, *Subdoligranulum* or *Lachnospiraceae bacterium 7_1_58FAA*. (Composition B2, See e.g., Table B2). In some embodiments, the compositions include *Bacteroides ovatus* and do not include *Clostridium orbiscindens 1_3_50AFAA*, *Flavinofractor plautii*, *Subdoligranulum* or *Lachnospiraceae bacterium 7_1_58FAA*.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 SEQ ID NO:83, and SEQ ID NOs: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:83 and SEQ ID NOs: 124-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22, SEQ ID NO:83, SEQ ID NOs: 124-145, and SEQ ID NOs: 152-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22 SEQ ID NO:83, SEQ ID NOs: 124-145, and SEQ ID NOs: 152-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:83, and SEQ ID NO: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22, SEQ ID NO:83, and SEQ ID NO: 124-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:95, SEQ ID NO:97, SEQ ID NO:98, SEQ ID NO:101, SEQ ID NO:102, SEQ ID NO:106, SEQ ID NO:110, and SEQ ID NO:122, wherein the composition does not include a bacterial strain comprising a 16S rDNA sequence having at least 97% homology with a nucleic acid sequence of SEQ ID NO:93.

TABLE B2

| Composition B2 |
| --- |
| SEQ_14 - VE202-13 - *Anaerotruncus_colihominis* (IV) |
| SEQ_15 - VE202-14 - *Eubacterium_fissicatena* (XIVa) |
| SEQ_16 - VE202-16 - *Clostridium_symbiosum* (XIVa) |
| SEQ_17 - VE202-7 - *Clostridium_bolteae* (XIVa) |
| SEQ_20 - 170 - *Dorea_longicatena* (XIVa) |
| SEQ_19 - 16 - *Blautia_producta* (XIVa) |
| SEQ_21 - 189 - *Clostridium_innocuum* (XVII) |
| SEQ_83 *Bacteroides ovatus* |

In one aspect, the disclosure provides Composition C (See e.g., FIG. 1, Table C). As shown in FIG. 1, Composition C contains bacteria that have the following 16S rDNA sequences: SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the disclosure provides compositions with two or more purified bacterial strains that have 16S rDNA sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include four or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include at least ten purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the composition consists of ten purified bacterial strains comprising 16S rDNA sequences with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively. In some embodiments, the composition consists essentially of ten purified bacterial strains comprising 16S rDNA sequences with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively.

In some embodiments, the compositions include two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include four or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include at least ten purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the composition consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively. In some embodiments, the composition essentially consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively.

The bacterial strains in Composition C are related to the following species: Clostridium scindens, Clostridium hathewayi, Blautia hansenii, Blautia wexlerae, Blautia producta, Blautia coccoides, Dorea longicatena, Clostridium innocuum, Flavonifractor plautii, Lachnospiraceae bacterium 7_1_58FAA, Subdoligranulum, Anaerotruncus colihominis, and Clostridium symbiosum. In some embodiments, the disclosure provides compositions with two or more bacterial strains of species selected from the group consisting of Clostridium scindens, Clostridium hathewayi, Blautia hansenii, Blautia wexlerae, Blautia product, Blautia coccoides, Dorea longicatena, Clostridium innocuum, Flavonifractor plautii, Lachnospiraceae bacterium 7_1_58FAA, Subdoligranulum, Anaerotruncus colihominis, and Clostridium symbiosum. In some embodiments, the disclosure provides compositions that include two or more purified bacterial strains comprising 16S rDNA sequences having at least 97% homology with nucleic acid sequences selected from the group consisting of SEQ ID NO:87, SEQ ID NO:93, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122.

In some embodiments, the compositions disclosed herein do not include Flavinofractor plautii, Subdoligranulum or Lachnospiraceae bacterium 7_1_58FAA. In some embodiments, the composition comprises two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:14, and SEQ ID NO:16, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:87, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122, wherein the composition does not include a bacterial strain comprising a 16S rDNA sequence having at least 97% homology with a nucleic acid sequence of SEQ ID NO:93.

The strains of Composition C include both BaiCD$^+$ strains and Bai CD– strains. In some embodiments, the disclosure provides compositions comprising two or more bacteria, wherein one or more bacteria are BaiCD+ strains and one or more bacteria are BaiCD– strains. In some embodiments of the one or more bacteria that are BaiCD+ strains are selected from bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, and SEQ ID NO:7. In some embodiments the one or more bacteria that are BaiCD– strains are selected from bacterial strains comprising 16S rDNA sequences having at least 97% homology with nucleic acid sequences selected from the group consisting of SEQ ID NO:18, SEQ ID NO:21, SEQ ID NO:10, SEQ ID NO:14, and SEQ ID NO:16. In some embodiments of the one or more bacteria that are BaiCD+ strains are selected from the bacterial species Clostridium scindens, Clostridium hathewayi, Blautia hansenii, Blautia wexlerae, Blautia product, and Blautia coccoides. In some embodiments of the one or more bacteria that are BaiCD– strains are selected from the bacterial species Dorea longicatena, Clostridium innocuum, Flavonifractor plautii, or Lachnospiraceae bacterium 7_1_58FAA, Anaerotruncus colihominis, and Clostridium symbiosum. The clostridial strains of Composition C are classified as belonging to Clostridium clusters IV, XIVa, and XVII. In some embodiments, the disclosure provides two or more bacterial strains, wherein the bacteria are BaiCD– strains and BaiCD+ strains and belong to Clostridium clusters IV, XIVa, or XVII. In some embodiments, the disclosure provides two or more bacterial strains, wherein the bacteria are BaiCD– strains and BaiCD+ strains and belong to Clostridium clusters XIVa or XVII. In some embodiments, the disclosure provides two or more bacterial strains, wherein the bacteria are BaiCD– strains and BaiCD+ strains and belong to Clostridium clusters IV or XIVa.

TABLE C

| Composition C |
|---|
| SEQ_12 - VE202-26 - Clostridium_scindens (XIVa)* |
| SEQ_03 - 5 - Clostridium_hathewayi (XIVa)* |
| SEQ_05 - 10 - Blautia_hansenii (XIVa)* |
| SEQ_01 - 71 - Blautia_wexlerae (XIVa)* |
| SEQ_07 - 59 - Blautia_producta/Blautia_coccoides (XIVa)* |
| SEQ_18 - 148 - Dorea_longicatena (XIVa) |
| SEQ_21 - 189 - Clostridium_innocuum (XVII) |
| SEQ_10 - 211 - Flavonifractor_plautii (IV) |
| SEQ_14 - VE202-13 - Anaerotruncus_colihominis (IV) |
| SEQ_16 - VE202-16 - Clostridium_symbiosum) (XIVa) |

*= BaiCD+

In one aspect, the disclosure provides Composition D (See e.g., FIG. 1, Table D). As shown in FIG. 1, Composition D contains bacteria that have the following 16S rDNA sequences: SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions with two or more purified bacterial strains that have 16S rDNA sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include three or more purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include at least ten purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides a composition that consists of ten purified bacterial strains comprising 16S rDNA sequences with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively. In some embodiments, the disclosure provides a composition that consists essentially of ten purified bacterial strains comprising 16S rDNA sequences with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively In some embodiments, the disclosure provides compositions that include two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include three or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include at least ten more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides a composition that consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively. In some embodiments, the disclosure provides a composition that consists essentially of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively.

The bacterial strains in Composition D are related to the following bacteria: *Clostridium scindens, Clostridium hathewayi, Blautia hansenii, Blautia wexlerae, Anaerotruncus colihominis, Dorea longicatena, Clostridium innocuum, Flavonifractor plautii, Lachnospiraceae bacterium 7_1_58FAA, Subdoligranulum, Turicibacter sanguinis,* and *Lactobacillus* mucosae. In some embodiments, the disclosure provides compositions with two or more bacterial strains of species selected from the group consisting of *Clostridium scindens, Clostridium hathewayi, Blautia hansenii, Blautia wexlerae, Anaerotruncus colihominis, Dorea longicatena, Clostridium innocuum, Erysipelotrichaceae_bacterium_21-3, Flavonifractor plautii, Lachnospiraceae bacterium 7_1_58FAA, Turicibacter sanguinis,* and *Lactobacillus* mucosae. In some embodiments, the disclosure provides compositions that include two or more purified bacterial strains comprise 16S rDNA sequences having at least 97% homology with nucleic acid sequences selected from the group consisting of SEQ ID NO:87, SEQ ID NO:90, SEQ ID NO:91, SEQ ID NO:93, SEQ ID NO:94, SEQ ID NO:95, SEQ ID NO:97, SEQ ID NO:98, SEQ ID NO:99, and SEQ ID NO:105.

In some embodiments, the compositions disclosed herein do not include *Flavinofractor plautii, Subdoligranulum* or *Lachnospiraceae bacterium* 7_1_58FAA. In some embodiments, the composition comprises two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:2, and SEQ ID NO:6, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:87, SEQ ID NO:90, SEQ ID NO:91, SEQ ID NO:94, SEQ ID NO:95, SEQ ID NO:97, SEQ ID NO:98, SEQ ID NO:99, and SEQ ID NO:105, wherein the composition does not include a bacterial strain comprising a 16S rDNA sequence having at least 97% homology with a nucleic acid sequence of SEQ ID NO:93.

The strains of Composition D include both BaiCD+ strains and Bai CD− strains. In some embodiments, the disclosure provides compositions comprising two or more bacteria, wherein one or more bacteria are BaiCD+ strains and one or more bacteria are BaiCD− strains. In some embodiments of the one or more bacteria that are BaiCD+ strains are selected from bacterial strains comprising 16S rDNA sequences having at least 97% homology with nucleic acid sequences selected from the group consisting of SEQ ID NO:12, SEQ ID NO:3, SEQ ID NO:5, and SEQ ID NO:1. In some embodiments the one or more bacteria that are BaiCD− strains are selected from bacterial strains comprising 16S rDNA sequences having at least 97% homology with nucleic acid sequences selected from the group consisting of SEQ ID NO:18, SEQ ID NO:21, SEQ ID NO:10, and SEQ ID NO:14. In some embodiments of the one or more bacteria that are BaiCD+ strains are selected from the bacterial species *Clostridium scindens, Clostridium hathewayi, Blautia hansenii,* and *Blautia wexlerae*. In some embodiments of the one or more bacteria that are BaiCD− strains are selected from the bacterial species *Dorea longicatena, Clostridium innocuum, Flavonifractor plautii,* and *Anaerotruncus colihominis*. The Clostridial strains of Composition D are classified as belonging to *Clostridium* clusters IV, XIVa, and XVII. In some embodiments, the disclosure provides two or more bacterial strains, wherein the bacteria are BaiCD− strains and BaiCD+ strains and belong to *Clostridium* clusters IV, XIVa, or XVII. In some embodiments, the disclosure provides two or more bacterial strains, wherein the bacteria are BaiCD− strains and BaiCD+ strains and belong to *Clostridium* clusters XIVa or XVII. In some embodiments, the disclosure provides two or more bacterial strains, wherein the bacteria are BaiCD− strains and BaiCD+ strains and belong to *Clostridium* clusters IV or XIVa.

Composition D includes the non-*Clostridium* strains *Turicibacter sanguinis* and *Lactobacillus* mucosae. In some embodiments, the disclosure provides compositions comprising two or more bacteria, wherein the composition includes both *Clostridium* strains and non-*Clostridium* strains. In some embodiments, the non-*clostridium* strains are the members of the genus *Lactobacillus*. Members of the genus *Lactobacillus* include, without limitation *L. acetotolerans, L. acidifarinae, L. acidipiscis, L. acidophilus, L.* agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii subsp. bulgaricus, L. delbrueckii subsp. delbrueckii, L. delbrueckii subsp. lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hilgardii, L. homohiochii, L. iners, L. ingluviei, L. intestinalis, L. jensenii, L. johnsonii, L. kalixensis, L. kefiranofaciens, L. kefiri, L. kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae, and L. zymae. In some embodiments, the non-clostridium strain is Lactobacillus mucosae. In some embodiments, the non-clostridium strain is Lactobacillus mucosae. In some embodiments, the Lactobacillus mucosae has a 16S rDNA sequence comprising SEQ ID NO:2. In some embodiments, the Lactobacillus mucosae has a 16S rDNA sequence having at least 97% homology with a nucleic acid comprising SEQ ID NO:2. In some embodiments, the Lactobacillus mucosae has a 16S rDNA sequence having at least 97% homology with a nucleic acid comprising SEQ ID NO:91.

In some embodiments, the disclosure provides compositions comprising two or more bacteria, wherein the composition includes both Clostridium strains and non-Clostridium strains. In some embodiments, the non-clostridium strains are members of the genus Turicibacter. In some embodiments, the non-clostridium strain is Turicibacter sanguinis. In some embodiments, the Turicibacter sanguinis has a 16S rDNA sequence comprising SEQ ID NO:6. In some embodiments, the Turicibacter sanguinis has a 16S rDNA sequence having at least 97% homology with a nucleic acid comprising SEQ ID NO:6. In some embodiments, the Turicibacter sanguinis has a 16S rDNA sequence having at least 97% homology with a nucleic acid comprising SEQ ID NO:90.

In some embodiments, the disclosure provides compositions comprising two or more bacteria, wherein the composition includes both Clostridium strains and non-Clostridium strains. In some embodiments, the non-Clostridium strains are Lactobacillus mucosae and Turicibacter sanguinis.

In some embodiments, the disclosure provides compositions comprising two or more bacteria, wherein the composition does not include Lactobacillus. In some embodiments, the disclosure provides compositions comprising two or more bacteria, wherein the composition does not include Turicibacter. In some embodiments, the disclosure provides compositions comprising two or more bacteria, wherein the composition does not include Lactobacillus or Turicibacter. In some embodiments, the disclosure provides compositions comprising two or more bacteria, wherein the composition only includes clostridia strains. In some embodiments, the disclosure provides compositions comprising two or more bacteria, wherein the composition only includes clostridia strains belonging to Clostridium cluster IV, XIVa or XVII strains. In some embodiments, the disclosure provides compositions comprising two or more bacteria, wherein the composition does not include Clostridium cluster XI strains.

In some embodiments, the disclosure provides compositions comprising two or more purified bacterial strains selected from the group consisting of: Clostridium scindens, Pseudoflavonifractor capillosus, and Blautia hansenii. In some embodiments, the compositions disclosed herein do not include Clostridium scindens, Pseudoflavonifractor capillosus, or Blautia hansenii.

TABLE D

| Composition D |
|---|
| SEQ_12 - VE202-26 - Clostridium_scindens (XIVa)* |
| SEQ_03 - 5 - Clostridium_hathewayi (XIVa)* |
| SEQ_05 - 10 - Blautia_hansenii (XIVa)* |
| SEQ_01 - 71 - Blautia_wexlerae (XIVa)* |
| SEQ_14 - VE202-13 - Anaerotruncus_colihominis (IV) |
| SEQ_18 - 148 - Dorea_longicatena (XIVa) |
| SEQ_21 - 189 - Clostridium_innocuum (XVII) |
| SEQ_10 - 211 - Flavonifractor_plautii (IV |
| SEQ_02 - 102 - Turicibacter_sanguinis (non-Clostridium) |
| SEQ_06 - 40 - Lactobacillus_mucosae (non-Clostridium) |

*= BaiCD+

In one aspect, the disclosure provides Composition F (See e.g., FIGS. 13 and 14, and Tables F1 and F2). As shown in FIG. 13, Composition F contains bacteria that have the following 16S rDNA sequences: SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

In some embodiments, the disclosure provides compositions with two or more purified bacterial strains that have 16S rDNA sequences selected from the group consisting of SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

In some embodiments, the compositions include two or more purified bacterial strains comprising 16S rDNA sequences having at least 97% homology with nucleic acid sequences selected from the group consisting of SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

The bacterial strains in Composition F are related to the following bacteria: *Dorea longicatena, Ruminococcus obeum, Megasphaera elsdenii, Acidaminococcus fermentans, Acidaminococcus intestine, Megasphaera elsdenii, Ruminococcus faecis, Bacteroides cellulosilyticus, Anaerostipes hadrus, Ruminococcus obeum, Flavonifractor plautii, Eubacterium rectale, Flavonifractor plautii, Megasphaera elsdenii, Eubacterium rectale, Ruminococcus champanellensis, Ruminococcus albus, Ruminococcus champanellensis, Ruminococcus faecis, Bifidobacterium bifidum, Anaerostipes hadrus, Anaerostipes hadrus, Anaerostipes hadrus, Eubacterium rectale, Ruminococcus faecis, Blautia luti, Ruminococcus faecis, Anaerostipes hadrus, Anaerostipes hadrus, Ruminococcus faecis, Eubacterium rectale, Eubacterium rectale, Anaerostipes hadrus, Ruminococcus faecis, Ruminococcus faecis, Dorea longicatena, Roseburia faecis, Blautia luti, Fusicatenibacter saccharivorans, Fusicatenibacter saccharivorans, Roseburia faecis, Megasphaera elsdenii, Eubacterium rectale, Eubacterium rectale, Roseburia faecis, Blautia faecis, Fusicatenibacter saccharivorans*, and *Dorea formicigenerans*.

In some embodiments, the disclosure provides compositions with two or more bacterial strains of species selected from the group consisting of *Dorea longicatena, Ruminococcus obeum, Megasphaera elsdenii, Acidaminococcus fermentans, Acidaminococcus intestine, Megasphaera elsdenii, Ruminococcus faecis, Bacteroides cellulosilyticus, Anaerostipes hadrus, Ruminococcus obeum, Flavonifractor plautii, Eubacterium rectale, Flavonifractor plautii, Megasphaera elsdenii, Eubacterium rectale, Ruminococcus champanellensis, Ruminococcus albus, Ruminococcus champanellensis, Ruminococcus faecis, Bifidobacterium bifidum, Anaerostipes hadrus, Anaerostipes hadrus, Anaerostipes hadrus, Eubacterium rectale, Ruminococcus faecis, Blautia luti, Ruminococcus faecis, Anaerostipes hadrus, Anaerostipes hadrus, Ruminococcus faecis, Eubacterium rectale, Eubacterium rectale, Anaerostipes hadrus, Ruminococcus faecis, Ruminococcus faecis, Dorea longicatena, Roseburia faecis, Blautia luti, Fusicatenibacter saccharivorans, Fusicatenibacter saccharivorans, Roseburia faecis, Megasphaera elsdenii, Eubacterium rectale, Eubacterium rectale, Roseburia faecis, Blautia faecis, Fusicatenibacter saccharivorans*, and *Dorea formicigenerans*.

In some embodiments, the disclosure provides compositions that include two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:100, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, and SEQ ID NO:120. It should be appreciated that multiple strains of the compositions disclosed herein can have the same related bacterial species. For instance, Composition F includes 12 strains that have *Eubacterium rectale* as the closest related species.

In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster IX. In some embodiments, at least one of the bacterial strains of the composition belongs to *Clostridium* cluster IV. In some embodiments, at least one of the bacterial strains of the composition belongs to *Clostridium* cluster XIVa and at least one of the bacterial strains belongs to *Clostridium* cluster IX. In some embodiments, at least one of the bacterial strains of the composition belongs to *Clostridium* cluster IV and at least one of the bacterial strains belongs to *Clostridium* cluster IX. In some embodiments, at least one of the bacterial strains of the composition belongs to *Clostridium* cluster IV, at least one of the bacterial strains belongs to *Clostridium* cluster XIVa, and at least one of the bacterial strains belongs to *Clostridium* cluster IX. In some embodiments, the compositions provided herein do not include bacterial strains belonging to *Clostridium* cluster XVIII. In some embodiments, the compositions provided herein do not include bacterial strains belonging to *Clostridium* cluster XVI or XVIII.

Composition F includes non-*clostridium* bacterial strains. In some embodiments, the disclosure provides compositions comprising two or more bacteria, wherein the composition includes both *Clostridium* strains and non-*clostridium* strains. In some embodiments, the non-*clostridium* strains are the members of the genus *Bacteroides*. In some embodiments, the non-*clostridium* strain is *Bacteroides* cellulosilyticus. In some embodiments, the non-*clostridium* strains are the members of the genus *Bifidobacterium*. In some embodiments, the non-*clostridium* strain is *Bifidobacterium bifidum*. In some embodiments, the disclosure provides compositions comprising two or more bacteria, wherein the composition includes both *Clostridium* strains and non-*Clostridium* strains, and wherein the non-*Clostridium* strains are *Bacteroides* cellulosilyticus and *Bifidobacterium bifidum*.

In some embodiments, the disclosure provides compositions comprising two or more bacteria, wherein the composition does not include *Bacteroides*. In some embodiments, the disclosure provides compositions comprising two or more bacteria, wherein the composition does not include *Bifidobacterium*. In some embodiments, the disclosure provides compositions comprising two or more bacteria, wherein the composition does not include *Bacteroides* and does not include *Bifidobacterium*. In some embodiments, the disclosure provides compositions comprising two or more bacteria, wherein the composition does not include non-*Clostridium* strains. In some embodiments, the disclosure provides compositions comprising two or more bacteria, wherein the composition only includes *clostridia* strains belonging to *Clostridium* cluster IV, XIVa or XVII strains. In some embodiments, the disclosure provides compositions comprising two or more bacteria, wherein the composition does not include *Clostridium* cluster XI strains.

TABLE F1

| | Composition F | |
|---|---|---|
| SEQ_NO | StrainID | Genus_species |
| SEQ_24 | YK96 | *Dorea_longicatena* |
| SEQ_25 | YK101 | *Ruminococcus_obeum* |
| SEQ_26 | YK110 | *Megasphaera_elsdenii* |
| SEQ_27 | YK149 | *Acidaminococcus_fermentans/ Acidaminococcus_intestini* |
| SEQ_28 | YK154 | *Megasphaera_elsdenii* |
| SEQ_29 | YK36 | *Ruminococcus_faecis* |
| SEQ_30 | YK95 | *Bacteroides_cellulosilyticus* |
| SEQ_31 | YK32 | *Anaerostipes_hadrus* |
| SEQ_32 | YK64 | *Ruminococcus_obeum* |
| SEQ_33 | YK73 | *Flavonifractor_plautii* |
| SEQ_34 | YK87 | *Eubacterium_rectale* |
| SEQ_35 | YK105 | *Flavonifractor_plautii* |
| SEQ_36 | YK153 | *Megasphaera_elsdenii* |
| SEQ_37 | YK163 | *Eubacterium_rectale* |
| SEQ_38 | YK191 | *Ruminococcus_champanellensis/ Ruminococcus_albus* |
| SEQ_39 | YK99 | *Ruminococcus_champanellensis* |
| SEQ_40 | YK55 | *Ruminococcus_faecis* |
| SEQ_41 | YK75 | *Bifidobacterium_bifidum* |
| SEQ_42 | YK90 | *Anaerostipes_hadrus* |
| SEQ_43 | YK30 | *Anaerostipes_hadrus* |
| SEQ_44 | YK31 | *Anaerostipes_hadrus* |
| SEQ_45 | YK12 | *Eubacterium_rectale* |
| SEQ_46 | YK27 | *Ruminococcus_faecis* |
| SEQ_47 | YK28 | *Blautia_luti* |
| SEQ_48 | YK29 | *Ruminococcus_faecis* |
| SEQ_49 | YK33 | *Anaerostipes_hadrus* |
| SEQ_50 | YK34 | *Anaerostipes_hadrus* |
| SEQ_51 | YK35 | *Ruminococcus_faecis* |
| SEQ_52 | YK51 | *Eubacterium_rectale* |
| SEQ_53 | YK52 | *Eubacterium_rectale* |
| SEQ_54 | YK54 | *Anaerostipes_hadrus* |
| SEQ_55 | YK56 | *Ruminococcus_faecis* |
| SEQ_56 | YK57 | *Ruminococcus_faecis* |
| SEQ_57 | YK58 | *Dorea_longicatena* |
| SEQ_58 | YK65 | *Roseburia_faecis* |
| SEQ_59 | YK67 | *Blautia_luti* |
| SEQ_60 | YK69 | *Fusicatenibacter_saccharivorans* |
| SEQ_61 | YK70 | *Fusicatenibacter_saccharivorans* |
| SEQ_62 | YK71 | *Roseburia_faecis* |
| SEQ_63 | YK74 | *Megasphaera_elsdenii* |
| SEQ_64 | YK88 | *Eubacterium_rectale* |
| SEQ_65 | YK89 | *Eubacterium_rectale* |
| SEQ_66 | YK97 | *Roseburia_faecis* |
| SEQ_67 | YK98 | *Blautia_faecis* |
| SEQ_68 | YK139 | *Fusicatenibacter_saccharivorans* |
| SEQ_69 | YK141 | *Dorea_formicigenerans* |
| SEQ_70 | YK142 | *Ruminococcus_faecis* |
| SEQ_71 | YK152 | *Blautia_hansenii* |
| SEQ_72 | YK155 | *Blautia_hansenii* |
| SEQ_73 | YK157 | *Eubacterium_rectale* |
| SEQ_74 | YK160 | *Roseburia_faecis* |
| SEQ_75 | YK166 | *Eubacterium_rectale* |
| SEQ_76 | YK168 | *Eubacterium_rectale* |
| SEQ_77 | YK169 | *Eubacterium_rectale* |
| SEQ_78 | YK171 | *Eubacterium_rectale* |
| SEQ_79 | YK192 | *Roseburia_faecis* |

TABLE F2

| | Composition F, strain groupings | |
|---|---|---|
| Cluster | Composition F | *SCFAs |
| XIVa | *Eubacterium rectale* 12 | A, B, L |
| | *Ruminococcus faecis* 8 | A, L |
| | *Ruminococcus obeum* 2 | A, L |
| | *Blautia faecis* 1 | A, L |
| | *Blautia hansenii* 2 | A, L |
| | *Blautia luti* 2 | A, L |
| | *Anaerostipes hadrus* 7 | B |
| | *Roseburia faecis* 5 | A, B |
| | *Fusicatenibacter saccharivorans* 3 | A, L |
| | *Dorea formicigenerans* 1 | A |
| | *Dorea longicatena* 2 | A |
| IV | *Flavonifractor_plautii* 2 | A, B |
| | *Ruminococcus champanellensis* 2 | A |
| IX | *Acidaminococcus fermentans* 1 | A, B, P |
| | *Megasphaera elsdeni* 4 | P |
| other | *Bacteroides cellulosilyticus* 1 | A, S |
| | *Bifiidobacterium Bifidum* | L, A |

*Short chain fatty acid legend: A, acetate; B, Butyrate; L, lactate; P, propionate; S, succinate In one aspect, the disclosure provides Composition G (See e.g., FIG. 19; Table G). As shown in FIG. 19, Composition G contains bacteria that have the following 16S rDNA sequences: SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

In some embodiments, the disclosure provides compositions with two or more purified bacterial strains that have 16S rDNA sequences selected from the group consisting of SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

In some embodiments, the compositions include two or more purified bacterial strains comprising 16S rDNA sequences having at least 97% homology with nucleic acid sequences selected from the group consisting of SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

The bacterial strains in Composition G are related to the following bacteria: *Acidaminococcus fermentans, Acidaminococcus intestine, Anaerostipes hadrus, Blautia faecis, Blautia hansenii, Dorea formicigenerans, Dorea longicatena, Eubacterium rectale, Flavonifractor plautii, Fusicatenibacter saccharivorans, Megasphaera elsdenii, Roseburia faecis, Ruminococcus champanellensis, Ruminococcus albus, Ruminococcus faecis*, and *Ruminococcus obeum*.

In some embodiments, the disclosure provides compositions with two or more bacterial strains of species selected from the group consisting of *Acidaminococcus fermentans, Acidaminococcus intestine, Anaerostipes hadrus, Blautia faecis, Blautia hansenii, Dorea formicigenerans, Dorea longicatena, Eubacterium rectale, Flavonifractor plautii, Fusicatenibacter saccharivorans, Megasphaera elsdenii, Roseburia faecis, Ruminococcus champanellensis, Ruminococcus albus, Ruminococcus faecis,* and *Ruminococcus obeum.*

In some embodiments, the disclosure provides compositions that include two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, and SEQ ID NO:119.

TABLE G

Composition G

| | | |
|---|---|---|
| SEQ_27 | YK149 | *Acidaminococcus_fermentans/ Acidaminococcus_intesti* |
| SEQ_43 | YK90 | *Anaerostipes_hadrus* |
| SEQ_44 | YK30 | *Anaerostipes_hadrus* |
| SEQ_51 | YK34 | *Anaerostipes_hadrus* |
| SEQ_55 | YK54 | *Anaerostipes_hadrus* |
| SEQ_68 | YK98 | *Blautia_faecis* |
| SEQ_72 | YK152 | *Blautia_hansenii* |
| SEQ_70 | YK141 | *Dorea_formicigenerans* |
| SEQ_24 | YK96 | *Dorea_longicatena* |
| SEQ_34 | YK87 | *Eubacterium_rectale* |
| SEQ_37 | YK163 | *Eubacterium_rectale* |
| SEQ_46 | YK12 | *Eubacterium_rectale* |
| SEQ_76 | YK166 | *Eubacterium_rectale* |
| SEQ_77 | YK168 | *Eubacterium_rectale* |
| SEQ_35 | YK105 | *Flavonifractor_plautii* |
| SEQ_62 | YK70 | *Fusicatenibacter_saccharivorans* |
| SEQ_26 | YK110 | *Megasphaera_elsdenii* |
| SEQ_63 | YK71 | *Roseburia_faecis* |
| SEQ_67 | YK97 | *Roseburia_faecis* |
| SEQ_40 | YK99 | *Ruminococcus_champanellensis* |
| SEQ_38 | YK191 | *Ruminococcus_champanellensis/ Ruminococcus_albus* |
| SEQ_47 | YK27 | *Ruminococcus_faecis* |
| SEQ_56 | YK56 | *Ruminococcus_faecis* |
| SEQ_25 | YK101 | *Ruminococcus_obeum* |
| SEQ_32 | YK64 | *Ruminococcus_obeum* |

Figure 26:
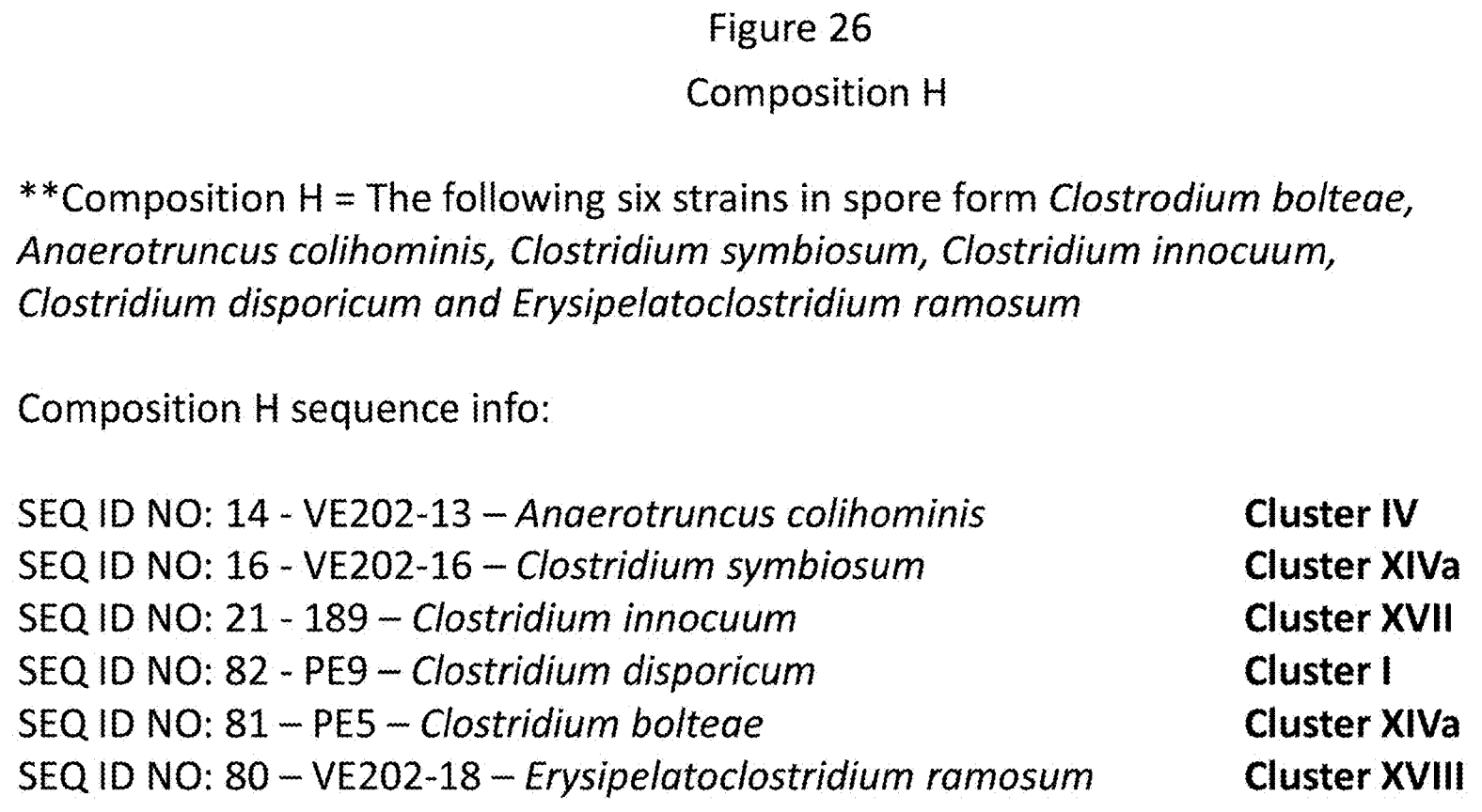

In one aspect, the disclosure provides Composition H (See e.g., FIG. 26, Table H). As shown in FIG. 26, Composition H contains bacteria that have the following 16S rDNA sequences: SEQ ID NO:14, SEQ ID NO:16, SEQ ID NO:21, SEQ ID NO:82, SEQ ID NO:81, and SEQ ID NO:80. In some embodiments, the disclosure provides compositions with two or more purified bacterial strains that have 16S rDNA sequences selected from the group consisting of SEQ ID NO:14, SEQ ID NO:16, SEQ ID NO:21, SEQ ID NO:82, SEQ ID NO:81, and SEQ ID NO:80.

In some embodiments, the compositions include two or more purified bacterial strains comprising 16S rDNA sequences having at least 97% homology with nucleic acid sequences selected from the group consisting of SEQ ID NO:14, SEQ ID NO:16, SEQ ID NO:21, SEQ ID NO:82, SEQ ID NO:81, and SEQ ID NO:80. In some embodiments, the compositions include four or more purified bacterial strains comprising 16S rDNA sequences having at least 97% homology with nucleic acid sequences selected from the group consisting of SEQ ID NO:14, SEQ ID NO:16, SEQ ID NO:21, SEQ ID NO:82, SEQ ID NO:81, and SEQ ID NO:80.

The bacterial strains in Composition H are related to the following bacteria: *Anaerotruncus colihominis, Clostridium symbiosum, Clostridium innocuum, Erysipelotrichaceae*_bacterium_21-3, *Clostridium disporicum, Clostridium bolteae,* and *Erysipelatoclostridium ramosum.* In some embodiments, the disclosure provides compositions with two or more bacterial strains selected from the group consisting of *Anaerotruncus colihominis, Clostridium symbiosum, Clostridium innocuum, Erysipelotrichaceae_bacterium_*21-3, *Clostridium disporicum, Clostridium bolteae,* and *Erysipelatoclostridium ramosum.*

In some embodiments, the disclosure provides compositions that include two or more purified bacterial strains comprise 16S rDNA sequences having at least 97% homology with nucleic acid sequences selected from the group consisting of SEQ ID NO:86, SEQ ID NO:95, SEQ ID NO:98, SEQ ID NO:110, SEQ ID NO:122, and SEQ ID NO:123.

Composition H includes bacteria from *Clostridium* cluster I, IV, XIVa, XVII and XVIII. In some embodiments, the disclosure provides compositions that include two or more purified bacterial strains from *Clostridium* cluster I, IV, XIVa, XVII and XVIII. In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster XVII. In some embodiments, at least one of the bacterial strains of the composition belongs to *Clostridium* cluster I. In some embodiments, at least one of the bacterial strains of the composition belongs to *Clostridium* cluster XVIII. In some embodiments, at least one of the bacterial strains of the composition belongs to *Clostridium* cluster XIVa and at least one of the bacterial strains belongs to *Clostridium* cluster IV. In some embodiments, at least one of the bacterial strains of the composition belongs to *Clostridium* cluster XIVa and at least one of the bacterial strains belongs to *Clostridium* cluster XVII.

TABLE H

Composition H

| SEQ ID NO | Strain | Closest species | Cluster |
|---|---|---|---|
| SEQ ID NO: 14 | VE202-13 | *Anaerotruncus colihominis* | Cluster IV |
| SEQ ID NO: 16 | VE202-16 | *Clostridium symbiosum* WAL-14163 | Cluster XIVa |
| SEQ ID NO: 21 | 189 | *Clostridium innocuum* | Cluster XVII |
| SEQ ID NO: 82 | PE9 | *Clostridium disporicum* | Cluster I |
| SEQ ID NO: 81 | PE5 | *Clostridium bolteae* | Cluster XIVa |
| SEQ ID NO: 80 | VE202-18 | *Erysipelatoclostridium ramosum* | Cluster XVIII |

In some embodiments, the disclosure provides compositions comprising two or more bacteria, wherein the composition does not include bacteria from *Clostridium* cluster I. In some embodiments, the disclosure provides compositions comprising two or more bacteria, wherein the composition does not include bacteria from *Clostridium* cluster XVIII. In some embodiments, the disclosure provides compositions comprising two or more bacteria, wherein the composition does not include bacteria from *Clostridium* cluster I and does not include bacteria from *Clostridium* cluster XVIII.

In some embodiments, the disclosure provides compositions comprising two or more bacteria, wherein all the bacteria are anaerobic bacteria. In some embodiments, the disclosure provides compositions comprising two or more bacteria, wherein all the bacteria are obligate anaerobic bacteria.

In some embodiments, the disclosure provides compositions comprising two or more bacteria (e.g., purified bacterial strains), wherein the composition does not include *Clostridium scindens*. In some embodiments, the disclosure provides compositions comprising two or more bacteria, wherein the composition does not include *Flavonifractor plautii*. In some embodiments, the disclosure provides compositions comprising two or more bacteria, wherein the composition does not include Parabacteroides. In some embodiments, the disclosure provides compositions comprising two or more bacteria, wherein the composition does not include *Lactobacillus*. In some embodiments, the disclosure provides compositions comprising two or more bacteria, wherein the composition does not include *Colinsella*. In some embodiments, the disclosure provides compositions comprising two or more bacteria, wherein the composition does not include *Dialister*. In some embodiments, the disclosure provides compositions comprising two or more bacteria, wherein the composition does not include *Raoultella*. In some embodiments, the disclosure provides compositions comprising two or more bacteria, wherein the composition does not include *Streptococcus*. In some embodiments, the disclosure provides compositions comprising two or more bacteria, wherein the composition does not include *Staphylococcus*. In some embodiments, the disclosure provides compositions comprising two or more bacteria, wherein the composition does not include *Microbacterium*. In some embodiments, the disclosure provides compositions comprising two or more bacteria, wherein the composition does not include *Proteobacteria*. In some embodiments, the disclosure provides compositions comprising two or more bacteria, wherein the composition does not include *Peptostreptococcaceae*. In some embodiments, the disclosure provides compositions comprising two or more bacteria, wherein the composition does not include *Oscillospiraceae*.

In one aspect, the disclosure provides bacterial strains with 16S rDNA sequences that have homology to a nucleic acid sequence of any one of the sequences of the bacterial strains or species described herein. In some embodiments, the bacterial strain has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8% or 99.9% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* (1970) 48:443, by the search for similarity method of Pearson and Lipman. *Proc. Natl. Acad. Sci. USA* (1998) 85:2444, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res*. (1977) 25:3389-3402, and Altschul et al., *J. Mol. Biol*. (1990) 215:403-410, respectively.

In one aspect, the disclosure provides compositions comprising multiple purified bacterial strains (e.g., Compositions A-J). For instance, FIGS. 1, 13, 19, and 26 present several example compositions comprising multiple bacterial strains. In one aspect, the 16S rDNA sequences of purified bacterial strains of the compositions were compared to 16S rDNA sequences of known bacterial species/strains in a bacterial genome database to identify the closest known related bacterial species to the bacterial strains disclosed herein (See e.g., Table 1). It should be appreciated that multiple bacterial strains of the compositions disclosed herein may have the same closest related bacterial species. In one aspect, the disclosure provides compositions comprising one or more bacterial strains or species with 16S rDNA sequences that have homology to a nucleic acid sequence of any one of the sequences provided by SEQ ID NOs:1-83 and 124-159. In some embodiments, the species with 16S rDNA sequences with homology to a nucleic acid sequence of any one of the closest related species to any of the strains described herein, correspond to bacterial strains with 16S rDNA sequences provided by SEQ ID NOs:84-123.

In some embodiments, the compositions disclosed herein provide at least one of the bacterial strains (e.g., purified bacterial strains) described herein. In some embodiments, the compositions that comprise at least one bacterial strain, comprise at least one bacterial strain with a 16S rDNA sequence selected from any one of SEQ ID NOs:1-122 and 124-159. In some embodiments, the compositions that comprise at least one bacterial strain, comprise at least one bacterial strain with a 97% homology to 16S rDNA sequence selected from any one of SEQ ID NOs:1-122 and 124-159.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more bacterial strains (e.g., purified bacterial strains).

It should be appreciated the compositions and methods provided herein can be distinguished from compositions and methods associated with the treatment of *C. difficile* infection that are available. For instance, it has been proposed that non-toxigenic *C. difficile* strains, i.e., strains that do not produce *C. difficile* toxins, may be used to treat *C. difficile* infection (See, e.g., U.S. Pat. No. 6,635,260). The compositions disclosed herein can be distinguished at least because the compositions described herein do not comprise non-toxigenic strains of *C. difficile*. Thus, in some embodiments, the compositions herein do not include comprise non-toxigenic strains of *C. difficile*. *C. difficile* belongs to *Clostridium* cluster XI. In some embodiments, the compositions herein do not include bacterial strains belonging to *Clostridium* cluster XI.

It is also considered in the art that bacterial strains expressing a bile inducible 7α/β-dehydroxylation operon can be used in the treatment of *C. difficile* (see, e.g., Buffie et al. *Nature* (2015) 517:205-208). The catalysis of bile acid 7a dihydroxylation is mediated by a stereo-specific NAD (H)-dependent 3-oxo-$\Delta^4$-cholenoic acid oxidoreductase encoded by the gene baiCD. In some embodiments, the compositions provided herein do not mediate bile acid 7-alpha-dehydroxylation.

In contrast to the findings in the art, in some embodiments, as shown herein, combinations of bacterial strains that do not encode baiCD (or a homolog thereof), or encode a baiCD that comprises one or more mutations that result in a non-functional BaiCD protein ("baiCD–"), are more effective at treating *C. difficile* infection and/or reducing or inhibiting production of Toxin B by *C. difficile* than combinations of bacterial strains that have a functional BaiCD protein ("baiCD+"). Thus, in some embodiments, the compositions of bacterial strains provided herein are baiCD– (i.e., the combination of the bacteria has no effective baiCD+ function). In some embodiments, all of bacterial strains in the compositions provided herein are baiCD–. In some embodiments, the majority (i.e., 50% or greater) of the bacterial strains in the compositions are baiCD–. In some embodiments, the majority (i.e., 50% or greater) of the bacterial strains in the compositions are baiCD– and the composition has no effective BaiCD function. In some embodiments, the minority (i.e., 50% or less) of the bacterial strains in the compositions are baiCD– and the composition has no effective BaiCD function. In some embodiments, bacterial strains for the compositions are selected based on the absence (or presence) of a baiCD gene or a predicted baiCD gene. In some embodiments, bacterial strains may be modified (e.g., genetically engineered) to prevent or reduce expression of a baiCD gene and/or to reduce or eliminate NAD(H)-dependent 3-oxo-$\Delta^4$-cholenoic acid oxidoreductase activity of BaiCD protein. The NAD(H)-dependent 3-oxo-$\Delta^4$-cholenoic acid oxidoreductase activity of a bacterial strain may be assessed by methods such as measuring the amount of 7α-dehydroxylated bile acid. In some embodiments, the compositions described herein comprise bacterial strains without the baiCD operon (baiCD–) or baiCD function.

In some embodiments, the compositions described herein do not include *Clostridium scindens*. In some embodiments, the compositions described herein do not include *Barnesiella intestihominis*. In some embodiments, the compositions described herein do not include *Blautia hansenii*. In some embodiments, the compositions described herein do not include *Pseudoflavinofractor capillosus*. In some embodiments, the compositions described herein do not include *Clostridium scindens. Barnesiella intestihominis, Blautia hansenii* or *Pseudoflavinofractor capillosus*.

In some embodiments, the compositions provided herein do not include *Colinsella aerofaciens*. In some embodiments, the compositions provided herein do not include *Acetovibrio ethanolgignens*. In some embodiments, the compositions provided herein do not bacterial strains belonging to *Clostridum* cluster I. In some embodiments, the compositions provided herein do not include *Clostridium butyricum*. In some embodiments, the compositions provided herein do not include *Clostridium disporicum*. In some embodiments, the compositions provided herein do not include strains belonging to *Clostridum* cluster XI. In some embodiments, the compositions provided herein do not include *Clostridium glycolicum*. In some embodiments, the compositions provided herein do not include *Faecalibacterium prausnitzii*. In some embodiments, the compositions provided herein do not include *Turicibacter sanguinis*. In some embodiments, the compositions provided herein do not include *Eubacterium rectale*. In some embodiments, the compositions provided herein do not include *Eubacterium ventriosum*. In some embodiments, the compositions provided herein do not include *Ruminococcus obeum*. In some embodiments, the compositions provided herein do not include *Pseudobutyrivibrio*. In some embodiments, the compositions provided herein do not include *Christensenellaceae*. In some embodiments, the compositions do not comprise gram-negative bacteria. In some embodiments, the compositions do not comprise *E. coli*. In some embodiments, the compositions do not comprise fungi, such as *Monilla* species.

In some embodiments of the compositions provided herein, the compositions do not include bacterial strains that are resistant to one or more antibiotics. It should be appreciated that it may be desirable to have a mechanism to remove the bacterial compositions provided herein from the body of the subject after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. As used herein, an "antibiotic that is efficacious in a human" refers to an antibiotic that has been used to successfully treat bacterial infections in a human.

In some embodiments, the compositions described herein comprise spore forming and non-spore forming bacterial strains. In some embodiments, the compositions described herein comprise spore forming bacterial strains. In some embodiments, the compositions described herein comprise only spore forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (As discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

In some embodiments, the disclosure provides compositions wherein the compositions comprise bacterial strains that are spore forming bacterial strains. In some embodiments, the disclosure provides compositions wherein the compositions comprise bacterial strains that are non-spore forming bacterial strains. In some embodiments, the disclosure provides compositions wherein the compositions comprise bacterial strains that are spore forming bacterial strains and bacterial strains that are non-spore forming bacterial strains. In some embodiments, the disclosure provides compositions, wherein the compositions comprise a mixture of bacterial strains wherein at least 10% of the bacterial strains are spore forming bacterial strains, at least 20% of the bacterial strains are spore forming bacterial strains, at least 30% of the bacterial strains are spore forming bacterial strains, at least 40% of the bacterial strains are spore forming bacterial strains, at least 50% of the bacterial strains are spore forming bacterial strains, at least 60% of the bacterial strains are spore forming bacterial strains, at least 70% of the bacterial strains are spore forming bacterial strains, at least 80% of the bacterial strains are spore forming bacterial strains, at least 90% of the bacterial strains are spore forming bacterial strains bacteria up to 100% spore forming bacterial strains. Whether a bacterial strain is a spore forming strain can be determined for instance by evaluating the genome of the bacterial strain for the presence of sporulation genes. However, it should be appreciated that not all bacteria that are predicted to encode spore forming genes can be made to sporulate. In addition, whether a bacterial strain is a spore forming strain can be determined by exposing the bacterial strain to stress conditions, e.g., heat or exposure to chemicals (e.g., ethanol or chloroform), that are known to induce sporulation.

It should be appreciated that spore forming bacteria can be in spore form or in vegetative form. In some embodiments of the compositions provided herein, the spore forming bacteria are in spore form. In some embodiments of the compositions provided herein, the spore forming bacteria are in vegetative form. In some embodiments of the compositions provided herein, the spore forming bacteria are both present in spore form and in vegetative form. In some embodiments, the disclosure provides compositions, wherein the compositions comprise spore forming bacteria at least 10% of the spore forming bacteria are in spore format, at least 20% of the spore forming bacteria are in spore format, at least 30% of the spore forming bacteria are in spore format, at least 40% of the spore forming bacteria are in spore format, at least 50% of the spore forming bacteria are in spore format, at least 60% of the spore forming bacteria are in spore format, at least 70% of the spore forming bacteria are in spore format, at least 80% of the spore forming bacteria are in spore format, at least 90% of the spore forming bacteria are in spore format, up to 100% in spore format.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

Methods of inducing sporulation of spore-forming bacterial strains are well known in the art (See e.g., Paredes-Sabja et al., *Trends Microbial.* (2011) 19(2):85-94). Generally, bacterial strains that are spore-formers can be made to go into spore form by stressing the bacterial strains. Non-limiting examples of stresses that can induce sporulation are an increase in temperature, change in the nutrients available and/or exposure to chemicals (e.g., ethanol or chloroform). It should be noted that bacteria that are non-spore formers, for instance because they are missing sporulation genes, cannot be made to sporulate by stress. To prepare compositions in which all the bacterial strains are in the spore form, the composition or bacterial cultures used to prepare the composition may be subjected to treatment to kill any bacteria not in spore form (e.g., in vegetative form), for example by exposing the composition to heat and are chemically breaking down the non-spore bacteria. The bacteria in spore format can subsequently be separated from the non-spore bacteria for instance by filtration.

The amount of spores can be quantified using techniques know in the art. These techniques include phase contrast microscopy for enumerating spores using a hemocytometer. In addition, the viability of spores can be determined by plating the spores and growing the spores. For instance, spores can be plated in appropriate media and incubated in the anaerobic chamber for a period of time (e.g., 48-96 hrs.). Viability can subsequently be determined by quantifying the colony forming units which correspond to spores that germinated. For instance, spores can be plated on TCCFA plates (Taurocholate, cycloserine, cefoxintin, fructose agar plates), in which taurocholate helps the spores to germinate. In addition, spores can be quantified using the dipicolinic assay (DPA assay). DPA is an agent that allows for spore selection and is a clear indicator of endospores. When complexed with terbium, bright green luminescence is observed.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals.

As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected.

As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In some embodiments, the bacterial strains of the compositions provided herein are obligate anaerobes. In some embodiments, the bacterial strains of the compositions provided herein are facultative anaerobes.

Aspects of the present disclosure are related to methods for treating a pathogenic infection in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject. In some embodiments, the subject is a pig.

In some embodiments, the subject is a carrier of a pathogenic organism and is suffering from the effects of the infection (e.g., diarrhea caused by *C. difficile* toxins). In some embodiments the subject is an asymptomatic carrier of a pathogen. In some embodiments, the subject is a carrier of *C. difficile*. In some embodiments the subject is an asymptomatic *C. difficile* carrier. In some embodiments, the subject has experienced recurrent or chronic pathogenic infections. In some embodiments, the subject is suffering from a first occurrence of a particular pathogenic infection. In some embodiments, the subject has been treated with antibiotics which resulted in the recurrence of the pathogenic infection. In some embodiments, the subject has been treated with antibiotics which resulted in a first occurrence of a pathogenic infection. In some embodiments, the subject is to undergo a procedure that puts the subject at a higher risk of infection. In some embodiments, the compositions provided herein are administered to a subject to lower the risk of becoming infected by a pathogen.

In some embodiments, the compositions provided herein are administered to a subject if the subject has a dysbiosis (e.g., has as microbiome associated with a disease state). In some embodiments, treatment with the compositions provided herein results in the change in the microbiome of the subject. In some embodiments, treatment with the compositions provided herein removes the dysbiosis in the subject resulting in a healthy microbiome. In some embodiments, treatment with the compositions provided herein removes the dysbiosis in the subject resulting in microbiome refractory or less susceptible to infection by a pathogen.

As used herein, the term "pathogen" in regard to a pathogenic infection refers to a microorganism (e.g., a bacterium) that causes a disease or a disease state in a subject. In some embodiments, the disease or disease state of the subject may include symptoms such as colitis, diarrhea, watery diarrhea, abdominal cramping, fever, blood or pus in the stool, nausea, dehydration, loss of appetite, chills, weight loss, and/or kidney failure. In some embodiments, the pathogenic infection may be diagnosed, for example, by detecting a pathogen (or protein or nucleic acid associated with a pathogen) in a fecal sample collected from the subject. In some embodiments, the pathogenic infection may be diagnosed, for example, by comparing the microbiota of a fecal sample of the subject with the microbiota in a fecal sample of a healthy subject.

In some embodiments, the pathogenic infection is *C. difficile*; *Clostridium perfringens*; *Clostridium botulinum*;

*Clostridium tributrycum; Clostridium sporogenes; Escherichia coli; Pseudomonas aeruginosa*, such as Multidrug Resistant *Pseudomonas aeruginosa*; Vancomycin Resistant Enterococci (VRE); Carbapenem Resistant Enterobacteriaceae (CRE); *Neisseria gonorrheae; Acinetobacter*; Multidrug Resistant *Acinetobacter; Campylobacter*; Multi-drug resistant *Campylobacter; Candida*; Fluconazole-resistant *Candida*; Extended spectrum beta-lactamese (ESBL) producing Enterobacteriaceae; *Salmonella, Salmonella Typhimurium*, Drug resistant non-typhoid *Salmonella* spp.; Drug resistant *Salmonella Typhi*; Drug resistant *Shigella; Staphylococcus aureus*, such as Methicillin Resistant *S. aureus* or vancomycin resistant *S. aureus*; Drug resistant *Streptococcus pneumoniae*; Drug resistant Tuberculosis; Erythromycin Resistant Group A *Streptococcus*; Clindamycin resistant Group B *Streptococcus*, and any combinations thereof. In some embodiments, the pathogenic infection is *C. difficile*. In some embodiments, the *C. difficile* is an antibiotic-resistant *C. difficile*, e.g., fluoroquinolone resistant *C. difficile*. In some embodiments, the pathogenic infection is vancomycin-resistant Enterococci.

Additional non-limiting examples of pathogens responsible for pathogenic infection that can be treated according to the methods provided herein are *Leishmania, Staphylococcus epidermis, Staphylococcus saprophyticus, Streptococcus pyogenes, Streptococcus pneumoniae, Streptococcus agalactiae, Enterococcus faecalis, Corynebacterium diptheriae, Bacillus anthracis, Listeria monocytogenes, Clostridium perfringens, Clostridium tetanus, Clostridium botulinum, Clostridium difficile, Neisseria meningitidis, Neisseria gonorrhoeae, Escherichia coli, Salmonella typhimurium, Salmonella cholerasuis, Salmonella enterica, Salmonella enteriditis, Yersinia pestis, Yersinia pseudotuberculosis, Yersinia enterocolitica, Vibrio cholerae, Campylobacter jejuni, Campylobacter fetus, Helicobacter pylori, Pseudomonas aeruginosa, Pseudomonas mallei, Haemophilus influenzae, Bordetella pertussis, Mycoplasma pneumoniae, Ureaplasma urealyticum, Legionella pneumophila, Treponema pallidum, Leptospira interrogans, Borrelia burgdorferi, Mycobacterium tuberculosis, Mycobacterium leprae, Chlamydia psittaci, Chlamydia trachomatis, Chlamydia pneumoniae, Rickettsia ricketsii, Rickettsia akari, Rickettsia prowazekii, Brucella abortus, Brucella melitens, Brucella suis*, and *Francisella tularensis*. In general, any bacterium that is capable of inducing a disease in a subject and/or that is not present in healthy individual is considered a pathogen herein. It should be appreciated that a subject may carry multiple pathogens and/or have multiple pathogenic infections.

Any of the compositions described herein may be administered to a subject in a therapeutically effective amount or a dose of a therapeutically effective amount to treat or prevent a pathogenic infection (e.g., one or more pathogenic infections). The terms "treat" or "treatment" refer to reducing or alleviating one or more of the symptoms associated with a pathogenic infection, reducing the amount of bacterial toxin produced by the pathogenic infection, and/or reducing the bacterial load of the pathogenic infection. The terms "prevent" or "prevention" encompass prophylactic administration and may reduce the incidence or likelihood of pathogenic infection or a recurrent or chronic pathogenic infection. For instance, in some embodiments, administration of the compositions provided herein result in a healthy microbiome that is refractory to pathogenic infection, thereby preventing the pathogenic infection.

As used herein, a "therapeutically effective amount" of composition, such as a pharmaceutical composition, is any amount that results in a desired response or outcome in a subject, such as those described herein, including but not limited to prevention of infection, an immune response or an enhanced immune response to the pathogenic infection, prevention or reduction of symptoms associated with pathogenic infection, and/or a reduction or inhibition of toxin production by the pathogenic infection. It should be appreciated that the term effective amount may be expressed in number of bacteria or bacterial spores to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to enhance survival of the subject, reduce the bacterial burden of the pathogenic infection in the subject, and/or reduce or inhibit toxin production by the pathogenic infection. In some embodiments, the therapeutically effective amount is an amount sufficient to reduce the bacterial burden of the pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the bacterial burden in a subject with a pathogenic infection that has not received any of the compositions described herein, or as compared to a fecal sample from the same subject that was collected prior to administration of any of the compositions.

In some embodiments, the compositions provided herein inhibit the production of a bacterial toxin, e.g., *C. difficile* Toxin B. In some embodiments, the therapeutically effective amount is an amount sufficient to reduce or inhibit the amount of bacterial toxin (e.g., *C. difficile* Toxin B) produced by pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of the bacterial toxin in a subject with a pathogenic infection that has not received any of the compositions described herein or as compared to a fecal sample from the same subject that was collected prior to administration of any of the compositions.

In some embodiments, the compositions provided herein induce the proliferation and/or accumulation of regulatory T cells in the subject. As will be evident to one of ordinary skill in the art, regulatory T cells, also referred to as "Tregs," are a subset of T lymphocytes that are generally thought to suppress an abnormal or excessive immune response and play a role in immune tolerance. Regulatory T cells may be identified based expression of the markers Foxp3 and CD4 (Foxp3+CD4+). The term regulatory T cells may also include Foxp3-negative regulatory T cells that are IL-10-producing CD4-positive T cells.

In some embodiments, the therapeutically effective amount is an amount sufficient to induce the proliferation and/or accumulation of Tregs in the subject (or in a sample obtained from a subject) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of Tregs in a subject (e.g., a subject with a pathogenic infection) that has not received any of the compositions described herein or as compared to a fecal sample from the same subject that was collected prior to administration of any of the compositions.

As used herein, the phrase "induces proliferation and/or accumulation of regulatory T cells" refers to an effect of inducing the differentiation of immature T cells into regulatory T cells, which differentiation leads to the proliferation and/or the accumulation of regulatory T cells. Further, the meaning of "induces proliferation and/or accumulation of regulatory T cells" includes in vivo effects, in vitro effects, and ex vivo effects. In some embodiments, the proliferation and/or accumulation of regulatory T cells may be assessed by detecting and/or quantifying the number of cells that express markers of regulatory T cells (e.g., Foxp3 and CD4), for example by flow cytometry. In some embodiments, the proliferation and/or accumulation of regulatory T cells may be assessed by determining the activity of the regulatory T cells, such as the production of cytokines (e.g., IL-10).

In some embodiments, the therapeutically effective amount is an amount sufficient to recolonize or repopulate the gastrointestinal tract of the subject with non-pathogenic bacteria. In some embodiments, the therapeutically effective amount is an amount sufficient to graft one or more of the bacterial strains of the composition in the gastrointestinal tract of the subject. In some embodiments, a fecal sample is obtained from the subject to assess the bacterial burden of the pathogenic infection and/or evaluate the efficacy of administration of the bacterial compositions described herein. In some embodiments, the microbiota of the subject (e.g., the identity and abundance of strains and/or species of the microbiota) may be assessed to determine a disease state of the subject and/or assess progress of the treatment. In some embodiments, the microbiota of the subject having a pathogenic infection is compared to the microbiota of a healthy subject, such as a subject that is not experiencing or has not experienced the pathogenic infection. In some embodiments, the microbiota of the subject having a pathogenic infection is compared to the microbiota of the same subject from a fecal sample obtained from the subject prior to the pathogenic infection.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. No. 3,261,761; U.S. Pat. No. 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the invention can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, *AAPS PharmSciTech*, (2016) 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., *Int J Pharm* 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions of the present invention, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^4$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^4$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^4$ and $10^{-3}$, between $10^{-7}$ and $10^4$, between $10^{-6}$ and $10^4$, between $10^{-5}$ and $10^4$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^4$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^4$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^4$ and $10^{-3}$, between $10^{-7}$ and $10^4$, between $10^{-6}$ and $10^4$, between $10^{-5}$ and $10^4$, between $10^{-7}$ and $10^{-5}$, between $10^{-6}$ and $10^{-5}$, or between $10^{-7}$ and $10^{-6}$ grams of all of the bacteria combined per dosage amount.

Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soybean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein. In some embodiments, the person has not been administered and antibiotic to treat the pathogenic infection. In some embodiments, the compositions provided herein comprise the first treatment of the pathogenic infection.

In some embodiments, the subject may be administered one or more doses of an antibiotic prior to or concurrently with a bacterial composition. Generally, the first line of defense in the treatment of a pathogenic infection is the administration of an antibiotic. In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

Table 1 below provides sequence identifier numbers (SEQ ID NOs) used in the compositions of the experiments disclosed herein, along with the accompanying strain identification number (Strain ID). The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 01 | 71 | Blautia wexlerae | SEQ_94 | 96.62 | 207 | NR_044054 |
| SEQ ID NO: 02 | 102 | Turicibacter_sanguinis | SEQ_91 | 97.81 | 183 | NR_028816 |
| SEQ ID NO: 03 | 5 | Clostridium_hathewayi | SEQ_105 | 92.42 | 198 | NR_036928 |
| SEQ ID NO: 04 | 7 | Blautia_hansenii | SEQ_99 | 96.62 | 207 | NR_104687 |
| SEQ ID NO: 05 | 10 | Blautia_hansenii | SEQ_99 | 98.06 | 206 | NR_104687 |
| SEQ ID NO: 06 | 40 | Lactobacillus_mucosae | SEQ_90 | 87.57 | 185 | NR_024994 |
| SEQ ID NO: 07 | 59 | Blautia_producta | SEQ_106 | 98.54 | 206 | NR_113270 |
| SEQ ID NO: 07 | 59 | Blautia_coccoides | SEQ_103 | 98.54 | 206 | NR_104700 |
| SEQ ID NO: 08 | 79 | Blautia_hansenii | SEQ_99 | 100 | 194 | NR_104687 |
| SEQ ID NO: 09 | VE202-21 | Eubacterium_contortum | SEQ_109 | 94.59 | 296 | NR_117147 |
| SEQ ID NO: 09 | VE202-21 | Eubacterium_fissicatena | SEQ_108 | 94.59 | 296 | NR_117142 |
| SEQ ID NO: 10 | 211 | Flavonifractor_plautii | SEQ_93 | 98.49 | 199 | NR_043142 |
| SEQ ID NO: 11 | VE202-9 | Anaerostipes_caccae | SEQ_88 | 99.5 | 399 | NR_028915 |
| SEQ ID NO: 12 | VE202-26 | Clostridium_scindens | SEQ_87 | 95.76 | 354 | NR_028785 |
| SEQ ID NO: 13 | 136 | Marvinbryantia_formatexigens | SEQ_89 | 94.66 | 131 | NR_042152 |
| SEQ ID NO: 14 | VE202-13 | Anaerotruncus_colihominis | SEQ_95 | 99.34 | 1365 | NR_027558 |
| SEQ ID NO: 15 | VE202-14 | Eubacterium_fissicatena | SEQ_102 | 93.33 | 1530 | NR_117563 |
| SEQ ID NO: 16 | VE202-16 | Clostridium_symbiosum | SEQ_122 | 98.43 | 1469 | NR_118730 |
| SEQ ID NO: 17 | VE202-7 | Clostridium_bolteae | SEQ_110 | 99.86 | 1390 | NR_113410 |
| SEQ ID NO: 18 | 148 | Dorea_longicatena | SEQ_97 | 99.7 | 1318 | NR_028883 |
| SEQ ID NO: 19 | 16 | Blautia_producta | SEQ_106 | 98.33 | 1493 | NR_113270 |
| SEQ ID NO: 20 | 170 | Dorea_longicatena | SEQ_97 | 99.7 | 1318 | NR_028883 |
| SEQ ID NO: 21 | 189 | Clostridium_innocuum | SEQ_98 | 98.64 | 1476 | NR_029164 |
| SEQ ID NO: 22 | 169 | Dorea_longicatena | SEQ_97 | 99.58 | 475 | NR_028883 |
| SEQ ID NO: 23 | VE202-29 | Eisenbergiella_tayi | SEQ_121 | 100 | 354 | NR_118643 |

TABLE 1-continued

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 24 | YK96 | Dorea_longicatena | SEQ_97 | 99.48 | 191 | NR_028883 |
| SEQ ID NO: 25 | YK101 | Ruminococcus_obeum | SEQ_85 | 96.81 | 188 | NR_118692 |
| SEQ ID NO: 26 | YK110 | Megasphaera_elsdenii | SEQ_119 | 96.62 | 207 | NR_102980 |
| SEQ ID NO: 27 | YK149 | Acidaminococcus_fermentans | SEQ_115 | 99.48 | 192 | NR_074928 |
| SEQ ID NO: 27 | YK149 | Acidaminococcus_intestini | SEQ_112 | 99.48 | 192 | NR_074306 |
| SEQ ID NO: 28 | YK154 | Megasphaera_elsdenii | SEQ_119 | 96.12 | 206 | NR_102980 |
| SEQ ID NO: 29 | YK36 | Ruminococcus_faecis | SEQ_96 | 99.29 | 425 | NR_116747 |
| SEQ ID NO: 30 | YK95 | Bacteroides_cellulosilyticus | SEQ_100 | 99.54 | 437 | NR_112933 |
| SEQ ID NO: 31 | YK32 | Anaerostipes_hadrus | SEQ_107 | 98.8 | 415 | NR_104799 |
| SEQ ID NO: 32 | YK64 | Ruminococcus_obeum | SEQ_84 | 99.04 | 415 | NR_119185 |
| SEQ ID NO: 33 | YK73 | Flavonifractor_plautii | SEQ_93 | 98.56 | 418 | NR_043142 |
| SEQ ID NO: 34 | YK87 | Eubacterium_rectale | SEQ_114 | 99.52 | 416 | NR_074634 |
| SEQ ID NO: 35 | YK105 | Flavonifractor_plautii | SEQ_93 | 99.26 | 407 | NR_043142 |
| SEQ ID NO: 36 | YK153 | Megasphaera_elsdenii | SEQ_119 | 96.04 | 429 | NR_102980 |
| SEQ ID NO: 37 | YK163 | Eubacterium_rectale | SEQ_114 | 99.76 | 415 | NR_074634 |
| SEQ ID NO: 38 | YK191 | Ruminococcus_champanellensis | SEQ_117 | 94.47 | 416 | NR_102884 |
| SEQ ID NO: 38 | YK191 | Ruminococcus_albus | SEQ_113 | 94.47 | 416 | NR_074399 |
| SEQ ID NO: 39 | YK99 | Ruminococcus_champanellensis | SEQ_117 | 97.28 | 184 | NR_102884 |
| SEQ ID NO: 40 | YK55 | Ruminococcus_faecis | SEQ_96 | 99.02 | 408 | NR_116747 |
| SEQ ID NO: 41 | YK75 | Bifidobacterium_bifidum | SEQ_118 | 99.45 | 183 | NR_102971 |
| SEQ ID NO: 42 | YK90 | Anaerostipes_hadrus | SEQ_107 | 98.97 | 194 | NR_104799 |
| SEQ ID NO: 43 | YK30 | Anaerostipes_hadrus | SEQ_107 | 99.48 | 191 | NR_104799 |
| SEQ ID NO: 44 | YK31 | Anaerostipes_hadrus | SEQ_107 | 98.97 | 194 | NR_104799 |
| SEQ ID NO: 45 | YK12 | Eubacterium_rectale | SEQ_114 | 99.27 | 412 | NR_074634 |
| SEQ ID NO: 46 | YK27 | Ruminococcus_faecis | SEQ_96 | 99.51 | 412 | NR_116747 |
| SEQ ID NO: 47 | YK28 | Blautia_luti | SEQ_111 | 99.5 | 400 | NR_041960 |
| SEQ ID NO: 48 | YK29 | Ruminococcus_faecis | SEQ_96 | 99.03 | 413 | NR_116747 |
| SEQ ID NO: 49 | YK33 | Anaerostipes_hadrus | SEQ_107 | 99.27 | 413 | NR_104799 |
| SEQ ID NO: 50 | YK34 | Anaerostipes_hadrus | SEQ_107 | 99.51 | 410 | NR_104799 |
| SEQ ID NO: 51 | YK35 | Ruminococcus_faecis | SEQ_96 | 99.51 | 409 | NR_116747 |
| SEQ ID NO: 52 | YK51 | Eubacterium_rectale | SEQ_114 | 99.27 | 413 | NR_074634 |
| SEQ ID NO: 53 | YK52 | Eubacterium_rectale | SEQ_114 | 99.03 | 413 | NR_074634 |
| SEQ ID NO: 54 | YK54 | Anaerostipes_hadrus | SEQ_107 | 85.82 | 409 | NR_104799 |
| SEQ ID NO: 55 | YK56 | Ruminococcus_faecis | SEQ_96 | 99.03 | 413 | NR_116747 |
| SEQ ID NO: 56 | YK57 | Ruminococcus_faecis | SEQ_96 | 98.79 | 413 | NR_116747 |

TABLE 1-continued

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 57 | YK58 | Dorea_longicatena | SEQ_97 | 98.8 | 417 | NR_028883 |
| SEQ ID NO: 58 | YK65 | Roseburia_faecis | SEQ_92 | 99.27 | 413 | NR_042832 |
| SEQ ID NO: 59 | YK67 | Blautia_luti | SEQ_111 | 98.57 | 419 | NR_041960 |
| SEQ ID NO: 60 | YK69 | Fusicatenibacter_saccharivorans | SEQ_116 | 99.27 | 413 | NR_114326 |
| SEQ ID NO: 61 | YK70 | Fusicatenibacter_saccharivorans | SEQ_116 | 98.79 | 414 | NR_114326 |
| SEQ ID NO: 62 | YK71 | Roseburia_faecis | SEQ_92 | 99.28 | 414 | NR_042832 |
| SEQ ID NO: 63 | YK74 | Megasphaera_elsdenii | SEQ_119 | 96.06 | 431 | NR_102980 |
| SEQ ID NO: 64 | YK88 | Eubacterium_rectale | SEQ_114 | 99.28 | 415 | NR_074634 |
| SEQ ID NO: 65 | YK89 | Eubacterium_rectale | SEQ_114 | 99.27 | 413 | NR_074634 |
| SEQ ID NO: 66 | YK97 | Roseburia_faecis | SEQ_92 | 99.28 | 414 | NR_042832 |
| SEQ ID NO: 67 | YK98 | Blautia_faecis | SEQ_104 | 98.02 | 405 | NR_109014 |
| SEQ ID NO: 68 | YK139 | Fusicatenibacter_saccharivorans | SEQ_116 | 99.03 | 412 | NR_114326 |
| SEQ ID NO: 69 | YK141 | Dorea_formicigenerans | SEQ_120 | 98.51 | 402 | NR_044645 |
| SEQ ID NO: 70 | YK142 | Ruminococcus_faecis | SEQ_96 | 98.79 | 413 | NR_116747 |
| SEQ ID NO: 71 | YK152 | Blautia_hansenii | SEQ_99 | 99.5 | 401 | NR_104687 |
| SEQ ID NO: 72 | YK155 | Blautia_hansenii | SEQ_99 | 98.79 | 413 | NR_104687 |
| SEQ ID NO: 73 | YK157 | Eubacterium_rectale | SEQ_114 | 99.27 | 413 | NR_074634 |
| SEQ ID NO: 74 | YK160 | Roseburia_faecis | SEQ_92 | 99.03 | 414 | NR_042832 |
| SEQ ID NO: 75 | YK166 | Eubacterium_rectale | SEQ_114 | 99.27 | 409 | NR_074634 |
| SEQ ID NO: 76 | YK168 | Eubacterium_rectale | SEQ_114 | 99.27 | 413 | NR_074634 |
| SEQ ID NO: 77 | YK169 | Eubacterium_rectale | SEQ_114 | 99.28 | 416 | NR_074634 |
| SEQ ID NO: 78 | YK171 | Eubacterium_rectale | SEQ_114 | 97.87 | 188 | NR_074634 |
| SEQ ID NO: 79 | YK192 | Roseburia_faecis | SEQ_92 | 99.03 | 414 | NR_042832 |
| SEQ ID NO: 80 | VE202-18 | Erysipelatoclostridium_ramosum | SEQ_123 | 100 | 1485 | NR_113243 |
| SEQ ID NO: 81 | PE5 | Clostridium_bolteae | SEQ_110 | 100 | 1385 | NR_113410 |
| SEQ ID NO: 82 | PE9 | Clostridium_disporicum | SEQ_86 | 99.21 | 382 | NR_026491 |
| SEQ ID NO: 83 | 211-B | Bacteroides_ovatus | SEQ_101 | 95.64 | 436 | NR_112940 |

TABLE 2

Bacterial species with a high degree of homology based on whole genome analysis:

| Strain | Whole genome homology |
|---|---|
| SEQ_10 - 211 | Lachnospiraceae bacterium 7_1_58FAA Subdoligranulum Flavinofractor plautii |
| SEQ_14 - VE202-13 | Anaerotruncus_colihominis |
| SEQ_15 - VE202-14 | Eubacterium_fissicatena Ruminococcus torques |
| SEQ_16 - VE202-16 | Clostridium_symbiosum |
| SEQ_17 - VE202-7 | Clostridium_bolteae |
| SEQ_22 - 169/SEQ_20-170 | Dorea_longicatena |
| SEQ_19 - 16 | Blautia_producta |
| SEQ_21 - 189 | Clostridium_innocuum Erysipelotrichaceae_bacterium_21_3 |

TABLE 3

Bacterial species with highest degree of homology based on whole genome analysis

| Composition B strain number | Strain identifier | SEQ ID # of 16S region as determined by Sanger sequencing | Closest species based on Sanger sequencing of 16S region | SEQ ID # of 16S regions as determined by WGS | *Consensus SEQ ID # of 16S region as determined by WGS | Closest species based on Concensus SEQ ID # of 16S region as compared with 16S database | Closest species based on WGS compared versus WG databases | Additional closely related sequences | Clostridium cluster |
|---|---|---|---|---|---|---|---|---|---|
| 1 | VE202-7 | 17 | Clostridium bolteae | 124, 125, 126, 127, 128 | 124 | Clostridium bolteae | Clostridium bolteae 90A9 | | XIVa |
| 2 | VE202-13 | 14 | Anaerotruncus colihominis | 129, 130, 131 | 129 | Anaerotruncus colihominis | Anaerotruncus colihominis DSM 17241 | | IV |
| 3 | VE202-14 | 15 | Eubacterium fissicatena | 132, 133, 134, 135, 136 | 132 | Dracourtella massiliensis | Dracourtella massiliensis GD1 | Ruminococcus torques; Sellimonas intestinalis | XIVa |
| 4 | VE202-16 | 16 | Clostridium symbiosum | 137, 138, 139, 140 | 137 | Clostridium symbiosum | Clostridium symbiosum WAL-14163 | | XIVa |
| 5 | strain #16 | 19 | Blautia producta | 141, 142, 143, 144, 145 | 141 | Blautia producta | Clostridium bacterium UC5.1-1D4 | Blautia product ATCC 27340 | XIVa |
| 6 | strain #170 | 20 | Dorea longicatena | 146, 147, 148, 149, 150, 151 | 146 | Dorea longicatena | Dorea longicatena CAG:42 | | XIVa |
| 7 | strain #189 | 21 | Clostridium innocuum | 152, 153, 154, 155, 156 | 152 | Clostridium innocuum | Erysipelotrichaceae bacterium 21_3 | | XVII |
| 8 | strain #211 | 10 | Flavinofractor plautii | 157, 158, 159 | 157 | Flavinofractor plautii | Clostridium orbiscindens 1_3_50AFAA | Subdolinogranulum | IV |

^WGS refers to Whole Genome Sequencing performed on a PacBio Biosciences platform (Menlo Park, CA).
*Consensus sequence is defined as the 16S sequence that has the most overlap with all other identified 16S sequences.

In some embodiments, in any of the compositions described herein, Clostridum bolteae can be replaced with Clostridium bolteae 90A9. In some embodiments, in any of the compositions described herein, Anaerotruncus colihominis can be replaced with Anaerotruncus colihominis DSM 17241. In some embodiments, in any of the compositions described herein, Eubacterium fissicatena can be replaced with Sellimonas instestinalis, Drancourtella massiliensis or Drancourtella massiliensis GP1. In some embodiments, in any of the compositions described herein, Clostridium symbiosum can be replaced with Clostridium symbiosum WAL-14163. In some embodiments, in any of the compositions described herein, Blautia producta can be replaced with Clostridium bacterium CD5.1-1D4 or Blautia product ATCC27340. In some embodiments, in any of the compositions described herein, Dorea longicatena can be replaced with Dorea longicatena CAG:42. In some embodiments, in any of the compositions described herein, Clostridium innocuum can be replaced with Erysipelotrichaceae_bacterium_21_3. In some embodiments, in any of the compositions described herein, Flavonifractor plautii can be replaced with Clostridium orbiscindens 1_3_50AFAA.

Aspects described herein provide pharmaceutical composition comprising a purified bacterial mixture consisting of bacterial strains comprising 16S rDNA sequences of at least 95% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 97% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 98% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 99% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21.

In some aspects, at least a portion of the bacteria of the pharmaceutical composition are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture consisting of bacterial strains comprising 16S rDNA sequences of at least 95% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 97% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 98% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 99% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising bacterial strains comprising 16S rDNA sequences of at least 95% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 97% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 98% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 99% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising bacterial strains comprising 16S rDNA sequences of at least 95% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 97% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 98% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 99% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture consisting of the following bacterial strains: *Clostridium bolteae, Anaerostruncus colihominis, Sellimonas intestinalis, Clostridium symbiosum, Blautia producta, Dorea Longicatena, Erysipelotrichaceae bacterium*, and *Clostridium orbiscindens*.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising the following bacterial strains: *Clostridium bolteae, Anaerostruncus colihominis, Sellimonas intestinalis, Clostridium symbiosum, Blautia producta, Dorea Longicatena, Erysipelotrichaceae bacterium*, and *Clostridium orbiscindens*.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide methods of treating an infectious disease in a subject, the method comprising administering the pharmaceutical composition of any of the aspects described herein to the subject in an amount sufficient to treat the infectious disease. In some aspects, the infectious disease is *Clostridium difficile* infection.

The nucleic acid sequences of the 16S rDNA, or portion thereof, for the bacterial strains described herein are provided below:

```
> SEQ ID NO: 01|71|
GCCCGGAGCAGTTGATGTGAAGGATGGGTCACCTGTGGACTGCATTGGAACTGTCATACTTGAGTGCCGGAGGGTAA

GCGGAATTCCTAGTGTAGCGGTGAAATGCGTAGATATTAGGAGGAACACCAGTGGCGAAGGCGGCTTACTGGACGGT

AACTGACGTTGAGGCTCGAAAGCGTGGGGAGCAAACAGGATTAGATACCCTGGTAA
```

-continued

> SEQ ID NO: 02|102|
CTAACCGTGGAGGTCATTGGAAACTGGTCAACTTGAGTGCAGAAGAGGGAAGTGGAATTCCATGTGTAGCGGTGAAA

TGCGTAGAGATATGGAGGAACACCAGTGGCGAAGGCGGCTTCCTGGTCTGTAACTGACACTGAGGCGCGAAAGCGTG

GGGGGCAAACAGGATTAGATCCCCCGGTAA

> SEQ ID NO: 03|5|
ATGAAAGCCGGGGCTCAACCCCGGTACTGCTTTGGAAACTGTTTGACTTGAGTGCTTGAGAGGTAAGTGGAATTCCT

AGTGTAGCGGGAAATGTTTAGATATTAGGAGGACACCAGTGGCGAAGGCGGCTTACTGGACTGTAACTGACGTTGTG

GCTCGATTTGTGGGGAGCAAACAGGATTATATCCCCTGGTAA

> SEQ ID NO: 04|7|
CGGAAGGTCTGATGTGAAGGTTGGGGCTTACCCCGGACTGCATTGGAAACTGTTTTTCTAGAGTGCCCGAGAGGTAA

GCGGAATTCCTAGTGTAGCGGTGAAATGCTTTAGATATTAGGAGGAACACCAGTGGCGAAGGCGGCTTACTGGACGG

TAACTGACGTTGAGGCTCGAAAGCGTGGGGAGCAAACAGGATTAGATACCCTGGTAA

> SEQ ID NO: 05|10|
CGATGTCTGAGTGAAGGCTGGGGCTTACCCCAGGACTGCATTGGAACTGTTTTTCTAGAGTGCCGGAGAGGTAAGCG

GAATTCCTAGTGTAGCGGTGAAATGCGTAGATATTAGGAGGAACACCAGTGGCGAAGGCGGCTTACTGGACGGTAAC

TGACGTTGAGGCTCGAAAGCGTGGGGAGCAAACAGGATTAGATACCCTGGTAA

> SEQ ID NO: 06|40|
TTAACCAAGAAGTGCATTGGAACTGTCAGACTTGGGGGAAAAAAAGACAGTGCAACTCCATGTGTAGCGGTGGAATG

CTCCATATATATGGAAGAACACCAGTGGCGAAGGCGGCTGTCTGGTCTGCAACTGACGCTGAGGCTCGAATTCATGG

GTAAGAAAGTATTAGTCCCTTGTAA

> SEQ ID NO: 07|59|
ACCCGCTTGGTCTGAGGTGAGGCTGGGGCTTAACCCCAGGACTGCATTGGAAACTGTTGTTCTAGAGTGCCGGAGAG

GTAAGCGGAATTCCTAGTGTAGCGGTGAAATGCGTAGATATTAGGAGGAACACCAGTGGCGAAGGCGGCTTACTGGA

CGGTAACTGACGTTGAGGCTCGAAAGCGTGGGGAGCAAACAGGATTAGATACCCTGGTAA

> SEQ ID NO: 08|79|
TAGGCTGGGGCTTAACCCCAGGACTGCATTGGAAACTGTTTTTCTAGAGTGCCGGAGAGGTAAGCGGAATTCCTAGT

GTAGCGGTGAAATGCGTAGATATTAGGAGGAACACCAGTGGCGAAGGCGGCTTACTGGACGGTAACTGACGTTGAGG

CTCGAAAGCGTGGGGAGCAAACAGGATTAGATACCCTGGTAA

> SEQ ID NO: 09|VE202-21|
TTGCATTGGACACTATGTCAGCTGAGTGTCGGAGAGGTAAGTGGAATTCCTAGTGTAGCGGTGAAATGCGTAGATAT

TAGGAGGAACACCAGTGGCGAAGGCGGCTTACTGCACGTTTTCTGACGTTGAGGCTCGAAATCGTGGGGAGCAAACA

AAATAGATACCCTGGTAGTCCACGCCGTAAACGATGCATACTAGGTGTCGGGTGGCAAAGCCATTCGGTGCCGCAG

CAAACGCAATAAGTATGCCACCTGGGGAGTACGTTCGCAAGAATGAAACTCAAATAAATTGACGGA

> SEQ ID NO: 10|211|
CCCGTCGTAGATGTGAACTGGGGGCTCACCTCCAGCCTGCATTTGAAACTGTAGTTCTTGAGTGCTGGAGAGGCAAT

CGGAATTCCGTGTGTAGCGGTGAAATGCGTAGATATACGGAGGAACACCAGTGGCGAAGGCGGATTGCTGGACAGTA

ACTGACGCTGAGGCGCGAAAGCGTGGGGAGCAAACAGGATTAGATACCCTCATAA

> SEQ ID NO: 11|VE202-9|
ACCTGATGCAGCGACGCCGCGTGAGTGAAGAAGTATTTCGGTATGTAAAGCTCTATCAGCAGGGAAGAAAAAAGACG

GTACCTGACTAAGAAGCCCCGGCTAACTACGTGCCAGCAGCCGCGGTAATACGTAGGGGGCAAGCGTTATCCGGAAT

TACTGGGTGTAAAGGGTGCGTAGGTGGCATGGTAAGTCAGAAGTGAAAGCCCGGGGCTTAACCCCGGGACTGCTTTT

GAAACTGTCATGCTGGAGTGCAGGAGAGGTAAGCGGAATTCCTAGTGTAGCGGTGAAATGCGTAGATATTAGGAGGA

ACACCAGTGGCGAAGGCGGCTTACTGGACTGTCACTGACACTGATGCACGAAAGCGTGGGGAGCAAACAGGATTAGA

TACCCTGGAAGTCCAT

> SEQ ID NO: 12|VE202-26|
ATGGGAGCGTAGATGGCGACTGGGCCATATGTGACAGCCCTGGTCTCAACCCCTTAACTGCATTTGGAACTGAGTGG

CTGGAGTGTCGGAGAGGCAGGCGGAATTCCTAGTGTAGCGGTGAAATGCGTAGATATTAGGAGGAACACCAGTGGCG

AAGGCGGCCTGCTGGACGATGACTGACGTTGAGGCTCGAAAGCGTGGGGAGCAAACAGGATTAGATACCCTGGTAGT

CCACGCCGTAAACGATGACTACTAGGTGTCGGGTGGCAAGGACATTCGGTGCCGCAGCAAACGCAATAAGTAGTCCA

CCTGGGGAGTACGTTCGCAAGAATGAAACTCAAAGGAAATTGACGGA

> SEQ ID NO: 13|136|
CGCAGCGGAGTGTATCCTAGGCTCACCTGGCTGCTTTCGAACTGGTTTTCTAGATCGTGTAGAGGGGGAGATTCCTG

GTGTAGCGTGAAATGCGTAGATATCTGGAGGAACACCAGTGGCGAAGGCGGCCTCCTGGACGGCAACTGACGTTGAG

GCTCGAAAGTGTGGGGAGCAAACAGGATTAGATACCCTGGTAA

> SEQ ID NO: 14|VE202-13|
TCAAAGAGTTTGATCCTGGCTCAGGACGAACGCTGGCGGCGCGCCTAACACATGCAAGTCGAACGGAGCTTACGTTT

TGAAGTTTTCGGATGGACGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGCACATGCCCCTGCAACCAAAGGAGCAATCC

GCTGAAAGATGGGCTCGCGTCCGATTAGCCAGTTGGCGGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGATATTGCACA

ATGGGCGAAAGCCTGATGCAGCGACGCCGCGTGAGGGAAGACGGTCTTCGGATTGTAAACCTCTGTCTTTGGGGAAG

AAAATGACGGTACCCAAAGAGGAAGCTCCGGCTAACTACGTGCCAGCAGCCGCGGTAATACGTAGGGAGCAAGCGTT

GTCCGGAATTACTGGGTGTAAAGGGAGCGTAGGCGGGATGGCAAGTAGAATGTTAAATCCATCGGCTCAACCGGTGG

CTGCGTTCTAAACTGCCGTTCTTGAGTGAAGTAGAGGCAGGCGGAATTCCTAGTGTAGCGGTGAAATGCGTAGATAT

TAGGAGGAACACCAGTGGCGAAGGCGGCCTGCTGGGCTTTAACTGACGCTGAGGCTCGAAAGCGTGGGGAGCAAACA

GGATTAGATACCCTGGTAGTCCACGCCGTAAACGATGATTACTAGGTGTGGGGGACTGACCCCTTCCGTGCCGCAG

TTAACACAATAAGTAATCCACCTGGGGAGTACGGCCGCAAGGTTGAAACTCAAAGGAATTGACGGGGCCCGCACAA

GCAGTGGAGTATGTGGTTTAATTCGAAGCAACGCGAAGAACCTTACCAGGTCTTGACATCGGATGCATAGCCTAGAG

ATAGGTGAAGCCCTTCGGGGCATCCAGACAGGTGGTGCATGGTTGTCGTCAGCTCGTGTCGTGAGATGTTGGGTTAA

GTCCCGCAACGAGCGCAACCCTTATTATTAGTTGCTACGCAAGAGCACTCTAATGAGACTGCCGTTGACAAAACGGA

GGAAGGTGGGGATGACGTCAAATCATCATGCCCCTTATGACCTGGGCTACACACGTACTACAATGGCACTAAAACAG

AGGGCGGCGACACCGCGAGGTGAAGCGAATCCCGAAAAAGTGTCTCAGTTCAGATTGCAGGCTGCAACCCGCCTGCA

TGAAGTCGGAATTGCTAGTAATCGCGGATCAGCATGCCGCGGTGAATACGTTCCCGGGCCTTGTACACACCGCCCGT

CACACCATGGGAGTCGGTAACACCCGAAGCCAGTAGCCTAACCGCAAGGGGGCGCTGTCGAAGGTGGGATTGATGA

CTGGGGTGAAGTCGTAACAAGGTAGCCGTATCGGAAGGTGCGGCTGGATCACCTCCTTT

> SEQ ID NO: 15|VE202-14|
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

-continued

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

> SEQ ID NO: 16|VE202-16|
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

> SEQ ID NO: 17|VE202-7|
ATGAGAGTTTGATCCTGGCTCAGGATGAACGCTGGCGGCGTGCCTAACACATGCAAGTCGAACGAAGCAATTAAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

-continued

```
GATTAGATACCCTGGTAGTCCACGCCGTAAACGATGAATGCTAGGTGTTGGGGGGCAAAGCCCTTCGGTGCCGTCGC
AAACGCAGTAAGCATTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCAAGTCTTGACATCCTCTTGACCGGCGTGTAA
CGGCGCCTTCCCTTCGGGGCAAGAGACAGGTGGTGCATGGTTGTCGTCAGCTCGTGTCGTGAGATGTTGGGTTAA
GTCCCGCAACGAGCGCAACCCTTATCCTTAGTAGCCAGCAGGTAAAGCTGGGCACTCTAGGGAGACTGCCAGGGATA
ACCTGGAGGAAGGTGGGGATGACGTCAAATCATCATGCCCCTTATGATTTGGGCTACACACGTGCTACAATGGCGTA
AACAAAGGGAAGCAAGACAGTGATGTGGAGCAAATCCCAAAAATAACGTCCCAGTTCGGACTGTAGTCTGCAACCCG
ACTACACGAAGCTGGAATCGCTAGTAATCGCGAATCAGAATGTCGCGGTGAATACGTTCCCGGGTCTTGTACACACC
GCCCGTCACACCATGGGAGTCAGCAACGCCCGAAGTCAGTGACCCAACTCGCAAGAGAGGGAGCTGCCGAAGGCGGG
GCAGGTAACTGGGGTGAAGTCGTAACAAGGTAGCCGTATCGGAAGGTGCGGCTGGATCACCTCCTTT
```

> SEQ ID NO: 18|148|
```
AACGAGAGTTTGATCCTGGCTCAGGATGAACGCTGGCGGCGTGCTTAACACATGCAAGTCGAGCGAAGCACTTTGGA
AGATTCTTCGGATGAAGACTTTTGTGACTGAGCGGCGGACGGGTGAGTAACGCGTGGGTAACCTGCCTCATACAGGG
GGATAACAGTTAGAAATGACTGCTAATACCGCATAAGACCACGGTACCGCATGGTACAGTGGTAAAAACTCCGGTGG
TATGAGATGGACCCGCGTCTGATTAGGTAGTTGGTGGGGTAACGGCCTACCAAGCCGACGATCAGTAGCCGACCTGA
GAGGGTGACCGGCCACATTGGGACTGAGACACGGCCCAGACTCCTACGGGAGGCAGCAGTGGGGAATATTGCACAAT
GGAGGAAACTCTGATGCAGCGACGCCGCGTGAAGGATGAAGTATTTCGGTATGTAAACTTCTATCAGCAGGGAAGAA
AATGACGGTACCTGACTAAGAAGCCCCGGCTAACTACGTGCCAGCAGCCGCGGTAATACGTAGGGGGCAAGCGTTAT
CCGGATTTACTGGGTGTAAAGGGAGCGTAGACGGCACGGCAAGCCAGATGTGAAAGCCCGGGGCTCAACCCCGGGAC
TGCATTTGGAACTGCTGAGCTAGAGTGTCGGAGAGGCAAGTGGAATTCCTAGTGTAGCGGTGAAATGCGTAGATATT
AGGAGGAACACCAGTGGCGAAGGCGGCTTGCTGGACGATGACTGACGTTGAGGCTCGAAAGCGTGGGGAGCAAACAG
GATTAGATACCCTGGTAGTCCACGCCGTAAACGATGACTGCTAGGTGTCGGGTGGCAAAGCCATTCGGTGCCGCAGC
TAACGCAATAAGCAGTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCTGATCTTGACATCCCGATGACCGCTTCGTAA
TGGAAGCTTTTCTTCGGAACATCGGTGACAGGTGGTGCATGGTTGTCGTCAGCTCGTGTCGTGAGATGTTGGGTTAA
GTCCCGCAACGAGCGCAACCCCTATCTTCAGTAGCCAGCAGGTTAAGCTGGGCACTCTGGAGAGACTGCCAGGGATA
ACCTGGAGGAAGGTGGGGATGACGTCAAATCATCATGCCCCTTATGACCAGGGCTACACACGTGCTACAATGGCGTA
AACAAAGAGAAGCGAACTCGCGAGGGTAAGCAAATCTCAAAAATAACGTCTCAGTTCGGATTGTAGTCTGCAACTCG
ACTACATGAAGCTGGAATCGCTAGTAATCGCAGATCAGAATGCTGCGGTGAATACGTTCCCGGGTCTTGTACACACC
GCCCGTCACACCATGGGAGTCAGTAACGCCCGAAGTCAGTGACCCAACCGTAAGGAGGGAGCTGCCGAAGGTGGGAC
CGATAACTGGGGTGAAGTCGTAACAAGGTAGCCGTATCGGAAGGTGCGGCTGGATCACCTCCTTT
```

> SEQ ID NO: 19|16|
```
ATCAGAGAGTTTGATCCTGGCTCAGGATGAACGCTGGCGGCGTGCTTAACACATGCAAGTCGAGCGAAGCACTTAAG
TGGATCTCTTCGGATTGAAACTTATTTGACTGAGCGGCGGACGGGTGAGTAACGCGTGGGTAACCTGCCTCATACAG
GGGGATAACAGTTAGAAATGGCTGCTAATACCGCATAAGCGCACAGGACCGCATGGTCTGGTGTGAAAAACTCCGGT
GGTATGAGATGGACCCGCGTCTGATTAGCTAGTTGGAGGGGTAACGGCCCACCAAGGCGACGATCAGTAGCCGGCCT
GAGAGGGTGAACGGCCACATTGGGACTGAGACACGGCCCAGACTCCTACGGGAGGCAGCAGTGGGGAATATTGCACA
ATGGGGGAAACCCTGATGCAGCGACGCCGCGTGAAGGAAGAAGTATCTCGGTATGTAAACTTCTATCAGCAGGGAAG
AAAATGACGGTACCTGACTAAGAAGCCCCGGCTAACTACGTGCCAGCAGCCGCGGTAATACGTAGGGGGCAAGCGTT
ATCCGGATTTACTGGGTGTAAAGGGAGCGTAGACGGAAGAGCAAGTCTGATGTGAAAGGCTGGGGCTTAACCCCAGG
ACTGCATTGGAAACTGTTTTTCTAGAGTGCCGGAGAGGTAAGCGGAATTCCTAGTGTAGCGGTGAAATGCGTAGATA
TTAGGAGGAACACCAGTGGCGAAGGCGGCTTACTGGACGGTAACTGACGTTGAGGCTCGAAAGCGTGGGGAGCAAAC
```

-continued

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

> SEQ ID NO: 20|170|
AACGAGAGTTTGATCCTGGCTCAGGATGAACGCTGGCGGCGTGCTTAACACATGCAAGTCGAGCGAAGCACTTTGGA

AGATTCTTCGGATGATTTCCTTTGTGACTGAGCGGCGGACGGGTGAGTAACGCGTGGGTAACCTGCCTCATACAGGG

GGATAACAGTTAGAAATGACTGCTAATACCGCATAAGACCACGGTACCGCATGGTACAGTGGTAAAAACTCCGGTGG

TATGAGATGGACCCGCGTCTGATTAGGTAGTTGGTGGGGTAACGGCCTACCAAGCCGACGATCAGTAGCCGACCTGA

GAGGGTGACCGGCCACATTGGGACTGAGACACGGCCCAGACTCCTACGGGAGGCAGCAGTGGGGAATATTGCACAAT

GGAGGAAACTCTGATGCAGCGACGCCGCGTGAAGGATGAAGTATTTCGGTATGTAAACTTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCACGGCAAGCCAGATGTGAAAGCCCGGGGCTCAACCCCGGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGCTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAAGCGAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

> SEQ ID NO: 21|189|
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

> SEQ ID NO: 22|169|
AGTAACGCGTGGGTAACCTGCCTCATACAGGGGGATAACAGTTAGAAATGACTGCTAATACCGCATAAGACCACGGT

ACCGCATGGTACAGTGGTAAAAACTCCGGTGGTATGAGATGGACCCGCGTCTGATTAGGTAGTTGGTGGGGTAACGG

CCTACCAAGCCGACGATCAGTAGCCGACCTGAGAGGGTGACCGGCCACATTGGGACTGAGACACGGCCCAGACTCCT

ACGGGAGGCAGCAGTGGGGAATATTGCACAATGGAGGAAACTCTGATGCAGCGACGCCGCGTGAAGGATGAAGTATT

TCGGTATGTAAACTTCTATCAGCAGGGAAGAAAATGACGGTACCTGACTAAGAAGCCCCGGCTAACTACGTGCCAGC

AGCCGCGGTAATACGTAGGGGGCAAGCGTTATCCGGATTTACTGGGTGTAAAGGGAGCGTAGACGGCACGGCAAGCC

AGATGTGAAAGCCC

> SEQ ID NO: 23|VE202-29|
CAGGCTGGAGTGCAGGAGAGGTAAGCGGAATTCCTAGTGTAGCGGTGAAATGCGTAGATATTAGGAGGAACACCAGT

GGCGAAGGCGGCTTACTGGACTGTAACTGACGTTGAGGCTCGAAAGCGTGGGGAGCAAACAGGATTAGATACCCTGG

TAGTCCACGCGGTAAACGATGATTGCTAGGTGTAGGTGGGTATGGACCCATCGGTGCCGCAGCTAACGCAATAAGCA

ATCCACCTGGGGAGTACGTTCGCAAGAATGAAACTCAAAGGAATTGACGGGGACCCGCACAAGCGGTGGAGCATGTG

GTTTAATTCGAAGCAACGCGAAGAACCTTACCAAGTCTTGACATCC

> SEQ ID NO: 24|YK96|
CCGGGGCTCACCCCGGGACTGCATTTGGAACTGCTGAGCTAGAGTGTCGGAGAGGCAAGTGGAATTCCTAGTGTAGC

GGTGAAATGCGTAGATATTAGGAGGAACACCAGTGGCGAAGGCGGCTTGCTGGACGATGACTGACGTTGAGGCTCGA

AAGCGTGGGGAGCAAACAGGATTAGATACCCTGGTA

> SEQ ID NO: 25|YK101|
AGGGTCAACCCCTGGACTGCATTGGAAACTGTCAGGCTGGAGTGCCGGAGAGGTAAGCGGAATTCCTAGTGTAGCGG

TGAAATGCGTAGATATTAGGAGGAACACCAGTGGCGAAGGCGGCTTACTGGACGGTAACTGACGTTGATGCTCGAAA

GCGTGGGGAGCAAACAGGATTAGATAACCTGGTAAA

> SEQ ID NO: 26|YK110|
GGGAAGTCGGTCTTAAGTGCGGGGCTTAACCCCGTGAGGGGACCGAAACTGTGAAGCTCGAGTGTCGGAGAGGAAAG

CGGAATTCCTAGTGTAGCGGTGAAATGCGTAGATATTAGGAGGAACACCAGTGGCGAAAGCGGCTTTCTGGACGACA

ACTGACGCTGAGGCGCGAAAGCCAGGGGAGCAAACGGGATTAGATACCCCAGTAA

> SEQ ID NO: 27|YK149|
TAGTCTGAGTGATGCGGGGCTTAACCCCGTATGGCGTTGGATACTGGAAGTCTTGAGTGCAGGAGAGGAAAGGGGAA

TTCCCAGTGTAGCGGTGAAATGCGTAGATATTGGGAGGAACACCAGTGGCGAAGGCGCCTTTCTGGACTGTGTCTGA

CGCTGAGATGCGAAAGCCAGGGTAGCAAACGGGATTAGATACCACGGTA

> SEQ ID NO: 28|YK154|
GATAGTCGGTCTTAAGTGCGGGGCTTACCCCGTGAGGGGACCGAAACTGTGAAGCTCGAGTGTCGGAGAGGAAAGCG

GAATTCCTAGTGTAGCGGTGAAATGCGTAGATATTAGGAGGAACACCAGTGGCGAAAGCGGCTTTCTGGACGACAAC

TGACGCTGAGGCGCGAAAGCCAGGGGAGCAAACGGGATTAGATACCACGGTAA

> SEQ ID NO: 29|YK36|
CGTTTGCTCCACGCTTTCGAGCCTCACGTCAGTTACCGTCCAGTAAGCCGCCTTCGCCACTGGTGTTCCTCCTAATA

TCTACGCATTTCACCGCTACACTAGGAATTCCGCTTACCTCTCCGGTACTCTAGATTGACAGTTTCCAATGCAGTCC

CGGGGTTGAGCCCCGGGTTTTCACATCAGACTTGCCACTCCGTCTACGCTCCCTTTACACCCAGTAAATCCGGATAA

CGCTTGCACCATACGTATTACCGCGGCTGCTGGCACGTATTTAGCCGGTGCTTCTTAGTCAGGTACCGTCATTTTCT

TCCCTGCTGATAGAGCTTTACATACCGAAATACTTCATCGCTCACGCGGCGTCGCTGCATCAGGGTTTCCCCCATTG

TGCAATATTCCCCACTGCTGCCTCCCGTAGGAGTTTGGA

> SEQ ID NO: 30|YK95|
TGTCACACTTTCGAGCATCAGCGTCAGTTACAGTCCAGTAAGCTGCCTTCGCAATCGGAGTTCTTCGTGATATCTAA

GCATTTCACCGCTACACCACGAATTCCGCCTACCTCTACTGCACTCAAGACGACCAGTATCAACTGCAATTTTACGG

TTGAGCCGCAAACTTTCACAGCTGACTTAATAGTCCGCCTACGCTCCCTTTAAACCCAATAAATCCGGATAACGCTT

GGATCCTCCGTATTACCGCGGCTGCTGGCACGGAGTTAGCCGATCCTTATTCGTATGGTACATACAAAAAGCCACAC

GTGGCTCACTTTATTCCCATATAAAAGAAGTTTACAACCCATAGGGCAGTCATCCTTCACGCTACTTGGCTGGTTCA

GACTCTCGTCCATTGACCAATATTCCTCACTGCTGCCTCCCGTAGGTAGTTTGGAA

> SEQ ID NO: 31|YK32|
CCGTTGTCACGCTTTCGTGCTCAGTGTCAGTTTCAGTCCAGTAAGCCGCCTTCGCCACTGATGTTCCTCCTAATATC

TACGCATTTCACCGCTACACTAGGAATTCCGCTTACCTCTCCTGCACTCCAGTCTGACAGTTTCAAAAGCAGTCCCA

GAGTTAAGCCCTGGGTTTTCACTTCTGACTTGCCATACCACCTACGCACCCTTTACACCCAGTAATTCCGGATAACG

CTTGCCCCCTACGTATTACCGCGGCTGCTGGCACGTAGTTAGCCGGGGCTTCTTAGTCAGGTACCGTCATTTTCTTC

CCTGCTGATAGAGCTTTACATACCGAAATACTTCTTCACTCACGCGGCGTCGCTGCATCAGGGTTCCCCCCATTGTG

CAATATTCCCCACTGCTGCCTCCCGTGGAAGTTTGGA

> SEQ ID NO: 32|YK64|
GCGAATGTCACGCATTCGAGCCTCACGTCAGTTACCGTCCAGTAAGCCGCCTTCGCCACTGGTGTTCCTCCTAATAT

CTACGCATTTCACCGCTACACTAGGAATTCCGCTTACCTCTCCGGCACTCAAGACTAACAGTTTCCAATGCAGTCCA

GGGGTTGAGCCCCCGCCTTTCACATCAGACTTGCCAGTCCGTCTACGCTCCCTTTACACCCAGTAAATCCGGATAAC

GCTTGCCCCCTACGTATTACCGCGGCTGCTGGCACGTAGTTAGCCGGGGCTTCTTAGTCAGGTACCGTCACTATCTT

CCCTGCTGATAGAAGTTTACATACCGAGATACTTCTTCCTTCACGCGGCGTCGCTGCATCAGGGTTTCCCCCATTGT

GCAATATTCCCCACTGCTGCCTCCCGTGGGAGTTTGGAA

> SEQ ID NO: 33|YK73|
TGCTCACGCTTTCGCGCTCAGCGTCAGTTACTGTCCAGCAATCCGCCTTCGCCACTGGTGTTCCTCCGTATATCTAC

GCATTTCACCGCTACACACGGAATTCCGATTGCCTCTCCAGCACTCAAGAACTACAGTTTCAAATGCAGGCTGGAGG

TTGAGCCCCCAGTTTTCACATCTGACTTGCAATCCCGCCTACACGCCCTTTACACCCAGTAAATCCGGATAACGCTT

GCCACCTACGTATTACCGCGGCTGCTGGCACGTAGTTAGCCGTGGCTTATTCGTCAGGTACCGTCATTTGTTTCGTC

CCTGACAAAAGAAGTTTACAACCCGAAAGCCTTCTTCCTTCACGCGGCGTTGCTGGGTCAGGCTTGCGCCCATTGCC

CAATATTCCCCACTGCTGCCTCCCGTGGTAGTTTGGA

> SEQ ID NO: 34|YK87|
TGTCCACGCTTTCGAGCTCAGCGTCAGTTATCGTCCAGTAAGCCGCCTTCGCCACTGGTGTTCCTCCTAATATCTAC

GCATTTCACCGCTACACTAGGAATTCCGCTTACCCCTCCGACACTCTAGTACGACAGTTTCCAATGCAGTACCGGGG

TTGAGCCCCGGGCTTTCACATCAGACTTGCCGCACCGCCTGCGCTCCCTTTACACCCAGTAAATCCGGATAACGCTT

GCACCATACGTATTACCGCGGCTGCTGGCACGTATTTAGCCGGTGCTTCTTAGTCAGGTACCGTCATTATCTTCCCT

-continued

GCTGATAGAGCTTTACATACCGAAATACTTCTTCGCTCACGCGGCGTCGCTGCATCAGGCTTTCGCCCATTGTGCAA

TATTCCCCACTGCTGACTCCCGTAGGAGTTTGGA

> SEQ ID NO: 35|YK105|
CGTTTCTCCACGCTTCGCGCTCAGCGTCAGTTACTGTCCAGCAATCCGCCTTCGCCACTGGTGTTCCTCCGTATATC

TACGCATTTCACCGCTACACACGGAATTCCGATTGCCTCTCCAGCACTCAAGAACTACAGTTTCAAATGCAGGCTGG

AGGTTGAGCCCCCAGTTTTCACATCTGACTTGCAATCCCGCCTACACGCCCTTTACACCCAGTAAATCCGGATAACG

CTTGCCACCTACGTATTACCGCGGCTGCTGGCACGTAGTTAGCCGTGGCTTATTCGTCAGGTACCGTCATTTGTTTC

GTCCCCGACAAAAGAAGTTTACAACCCGAAAGCCTTCTTCCTTCACGCGGCGTTGCTGGGTCAGGCTTGCGCCCATT

GCCCAATATTCCCCACTGCTGCCTCCCTGGGAAGTTTGG

> SEQ ID NO: 36|YK153|
ATGTCCTGACTTCGCGCCTCAGCGTCAGTTGTCGTCCAGAAAGCCGCTTTCGCCACTGGTGTTCCTCCTAATATCTA

CGCATTTCACCGCTACACTAGGAATTCCGCTTTCCTCTCCGACACTCGAGCTTCACAGTTTCGGTCCCCTCACGGGG

TTAAGCCCCGCACTTTTAAGACCGACTTGCGATGCCGCCTGCGCGCCCTTTACGCCCAATAATTCCGGACAACGCTT

GCCACCTACGTATTACCGCGGCTGCTGGCACGTAGTTAGCCGTGGCTTTCTCTTACGGTACCGTCAGGGATAACGGG

TATTGACCGCTATCCTGTTCGTCCCATATAACAGAACTTTACAACCCGAAGGCCGTCATCGTTCACGCGGCGTTGCT

CCGTCAGACTTTCGTCCATTGCGGAAGATTCCCCACTGCTGCCTCCCTGGGAAGTTTGGA

> SEQ ID NO: 37|YK163|
GTTTGCTCACGCTTTCGAGCTCAGCGTCAGTTATCGTCCAGTAAGCCGCCTTCGCCACTGGTGTTCCTCCTAATATC

TACGCATTTCACCGCTACACTAGGAATTCCGCTTACCCCTCCGACACTCTAGTACGACAGTTTCCAATGCAGTACCG

GGGTTGAGCCCCGGGCTTTCACATCAGACTTGCCGCACCGCCTGCGCTCCCTTTACACCCAGTAAATCCGGATAACG

CTTGCACCATACGTATTACCGCGGCTGCTGGCACGTATTTAGCCGGTGCTTCTTAGTCAGGTACCGTCATTATCTTC

CCTGCTGATAGAGCTTTACATACCGAAATACTTCTTCGCTCACGCGGCGTCGCTGCATCAGGCTTTCGCCCATTGTG

CAATATTCCCCACTGCTGCCTCCCGTAGGAGTTTGG

> SEQ ID NO: 38|YK191|
CGTTGCTCACGCATTCGAGCCTCAGCGTCAGTTAAGCCCAGTAAGCCGCCTTCGCCACTGATGTTCCTCCTAATATC

TACGCATTTCACCGCTACACTAGGAATTCCGCTTACCTCTACTTCACTCAAGAACCACAGTTTCAAATGCAGTTTAT

GGGTTAAGCCCATAGTTTTCACATCTGACTTGCGATCCCGCCTACGCTCCCTTTACACCCAGTAATTCCGGACAACG

CTCGCTCCCTACGTATTACCGCGGCTGCTGGCACGTAGTTAGCCGGAGCTTCCTCCTCAGGTACCGTCTTTTTTCGT

CCCTGAAGACAGAGGTTTACAATCCTAAAACCTTCTTCCCTCACGCGGCATCGCTGCATCAGAGTTTCCTCCATTGT

GCAATATTCCCCACTGCTGCCTCCCGTAGGAGTTTGGAA

> SEQ ID NO: 39|YK99|
TGGGCTTACCCATAAACTGCATTTGAAACTGTGGTTCTTGAGTGAAGTAGAGGTAAGCGGAATTCCTAGTGTAGCGG

TGAAATGCGTAGATATTAGGAGGAACATCAGTGGCGAAGGCGGCTTACTGGGCTTTAACTGACGCTGAGGCTCGAAA

GCGTGGGGAGCAAACAGGATTAGATACCCAAGTAA

> SEQ ID NO: 40|YK55|
GTCAGCATCGAGCTCACGTCAGTTACCGTCCAGTAAGCCGCCTTCGCCACTGGTGTTCCTCCTAATATCTACGCATT

TCACCGCTACACTAGGAATTCCGCTTACCTCTCCGGTACTCTAGATTGACAGTTTCCAATGCAGTCCCGGGGTTGAG

CCCCGGGTTTTCACATCAGACTTGCCACTCCGTCTACGCTCCCTTTACACCCAGTAAATCCGGATAACGCTTGCACC

ATACGTATTACCGCGGCTGCTGGCACGTATTTAGCCGGTGCTTCTTAGTCAGGTACCGTCATTTTCTTCCCTGCTGA

TAGAGCTTTACATACCGAAATACTTCATCGCTCACGCGGCGTCGCTGCATCAGGGTTTCCCCCATTGTGCAATATTC

CCCACTGCTGCCTCCCGAGGGAGTTTGGA

> SEQ ID NO: 41|YK75|
TCATCGCTTACGGTGGATCTGCGCCGGGTACGGGCGGGCTGGAGTGCGGTAGGGGAGACTGGAATTCCCGGTGTAAC

GGTGGAATGTGTAGATATCGGGAAGAACACCGATGGCGAAGGCAGGTCTCTGGGCCGTCACTGACGCTGAGGAGCGA

AAGCGTGGGGAGCGAACAGGATTAGATACAACGGTAA

> SEQ ID NO: 42|YK90|
TGAACCCAGGGCTTAACTCTGGGACTGCTTTTGAACTGTCAGACTGGAGTGCAGGAGAGGTAAGCGGAATTCCTAGT

GTAGCGGTGAAATGCGTAGATATTAGGAGGAACATCAGTGGCGAAGGCGGCTTACTGGACTGAAACTGACACTGAGG

CACGAAAGCGTGGGGAGCAAACAGGATTAGATACCATGGTAA

> SEQ ID NO: 43|YK30|
ACCAGGGCTTAACTCTGGGACTGCTTTTGAACTGTCAGACTGGAGTGCAGGAGAGGTAAGCGGAATTCCTAGTGTAG

CGGTGAAATGCGTAGATATTAGGAGGAACATCAGTGGCGAAGGCGGCTTACTGGACTGAAACTGACACTGAGGCACG

AAAGCGTGGGGAGCAAACAGGATTAGATACCCTGGTAA

> SEQ ID NO: 44|YK31|
GAACCCAGGGCTTAACTCTGGGACTGCTTTTGAACTGTCAGACTGGAGTGCAGGAGAGGTAAGCGGAATTCCTAGTG

TAGCGGTGAAATGCGTAGATATTAGGAGGAACATCAGTGGCGAAGGCGGCTTACTGGACTGAAACTGACACTGAGGC

ACGAAAGCGTGGGGAGCAAACAGGATTAGATACCCCGGTAA

> SEQ ID NO: 45|YK12|
GAGTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAGGGAGTTTGGA

> SEQ ID NO: 46|YK27|
TGTCAGCTTTCGAGCTCACGTCAGTTACCGTCCAGTAAGCCGCCTTCGCCACTGGTGTTCCTCCTAATATCTACGCA

TTTCACCGCTACACTAGGAATTCCGCTTACCTCTCCGGTACTCTAGATTGACAGTTTCCAATGCAGTCCCGGGGTTG

AGCCCCGGGTTTTCACATCAGACTTGCCACTCCGTCTACGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTTTCTTCCCTGCT

GATAGAGCTTTACATACCGAAATACTTCATCGCTCACGCGGCGTCGCTGCATCAGGGTTTCCCCCATTGTGCAATAT

TCCCCACTGCTGCCTCCCGTAGGAGTTTGGA

> SEQ ID NO: 47|YK28|
CACGTCAGTTACCGTCCAGTAAGCCGCCTTCGCCACTGGTGTTCCTCCTAATATCTACGCATTTCACCGCTACACTA

GGAATTCCGCTTACCTCTCCGGCACTCAAGACGGGCAGTTTCCAATGCAGTCCCGGGGTTGAGCCCCAGCCTTTCAC

ATCAGACTTGTCCATCCGTCTACGCTCCCTTTACACCCAGTAAATCCGGATAACGCTTGCCCCCTACGTATTACCGC

GGCTGCTGGCACGTAGTTAGCCGGGGCTTCTTAGTCAGGTACCGTCATTTTCTTCCCTGCTGATAGAAGTTTACATA

CCGAGATACTTCTTCCTTCACGCGGCGTCGCTGCATCAGGGTTTCCCCCATTGTGCAATATTCCCCACTGCTGCCTC

CCGTAGGAGTTTGGG

> SEQ ID NO: 48|YK29|
GTCAGCTTTCGAGCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCCCGTGGGGAGTTTGGA

> SEQ ID NO: 49|YK33|
GATGCTCAGCTTTCGTGCTCAGTGTCAGTTTCAGTCCAGTAAGCCGCCTTCGCCACTGATGTTCCTCCTAATATCTA

CGCATTTCACCGCTACACTAGGAATTCCGCTTACCTCTCCTGCACTCCAGTCTGACAGTTTCAAAAGCAGTCCCAGA

GTTAAGCCCTGGGTTTTCACTTCTGACTTGCCATACCACCTACGCACCCTTTACACCCAGTAATTCCGGATAACGCT

TGCCCCCTACGTATTACCGCGGCTGCTGGCACGTAGTTAGCCGGGGCTTCTTAGTCAGGTACCGTCATTTTCTTCCC

TGCTGATAGAGCTTTACATACCGAGATACTTCTTCACTCACGCGGCGTCGCTGCATCAGGGTTTCCCCCATTGTGCA

ATATTCCCCACTGCTGCCTCCCGAAGGAAGTTTGGA

> SEQ ID NO: 50|YK34|70A_009_YK34_A1_A02
GTGTCAGCTTCGTGCTCAGTGTCAGTTTCAGTCCAGTAAGCCGCCTTCGCCACTGATGTTCCTCCTAATATCTACGC

ATTTCACCGCTACACTAGGAATTCCGCTTACCTCTCCTGCACTCCAGTCTGACAGTTTCAAAAGCAGTCCCAGAGTT

AAGCCCTGGGTTTTCACTTCTGACTTGCCATACCACCTACGCACCCTTTACACCCAGTAATTCCGGATAACGCTTGC

CCCCTACGTATTACCGCGGCTGCTGGCACGTAGTTAGCCGGGGCTTCTTAGTCAGGTACCGTCATTTTCTTCCCTGC

TGATAGAGCTTTACATACCGAGATACTTCTTCACTCACGCGGCGTCGCTGCATCAGGGTTTCCCCCATTGTGCAATA

TTCCCCACTGCTGCCTCCCGTAGGGAGTTTGGA

> SEQ ID NO: 51|YK35|
GTCAGCTTCGAGCCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCGCGTAGGAGTTTGGA

> SEQ ID NO: 52|YK51|
TGTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTGCCTCCCGAAGGGAGTTTGGA

> SEQ ID NO: 53|YK52|
TTCAGCTTTCGAGCTCAGCGTCAGTTATCGTCCAGTAAGCCGCCTTCGCCACTGGTGTTCCTCCTAATATCTACGCA

TTTCACCGCTACACTAGGAATTCCGCTTACCCCTCCGACACTCTAGTACGACAGTTTCCAATGCAGTACCGGGGTTG

AGCCCCGGGCTTTCACATCAGACTTGCCGCGCACCGCCTGCGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTATCTTCCCTGCT

GATAGAGCTTTACATACCGAAATACTTCTTCGCTCACGCGGCGTCGCTGCATCAGGCTTTCGCCCATTGTGCAATAT

TCCCCACTGCTGCCTCCCGAGGGGAGTTTGG

> SEQ ID NO: 54|YK54|
TTCGGTCTGCTTTCCCCTTCTCGCGCCTCAGTGTCAGTTTCTGTCTAGTAAGCCGCCTTCGCCACTGATGTTCCTCC

TAATATCTACGCACTTCACCGCTCCACAATGAATTCCGCTTACCCCTCCCGCGCTCTAGTCTGACAGTTTTAAAAAA

ACTCCCCGAGAGAAACCCTGGGTTTTTTCTTCTGACATGCGATATCCCACCCCCACCCTTTATACACCCAAAAATCG

GATAAAAGGTGCGACCTACGTATTATACCGGCTGCTGGGGCGTAGATAGCCGGGGGTTCTTATACAGGGACCGTCAT

TTTCTTTCCCGCTGATACAGCTTTACATACCGAAATACTTCTTTCTCACGCGGCGTCGCTGCATCAGGGTTTCCCCC

ATTGTGCAATATTCCCCACTGCTGCCTCCCGAAGGGGAAGTTGGGGGAAA

> SEQ ID NO: 55|YK56|
GTTCAGCTTTCGAGCCTCACGTCAGTTACCGTCCAGTAAGCCGCCTTCGCCACTGGTGTTCCTCCTAATATCTACGC

ATTTCACCGCTACACTAGGAATTCCGCTTACCTCTCCGGTACTCTAGATTGACAGTTTCCAATGCAGTCCCGGGGTT

GAGCCCCGGGTTTTCACATCAGACTTGCCACTCCGTCTACGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTTTCTTCCCTGC

TGATAGAGCTTTACATACCGAAATACTTCATCGCTCACGCGGCGTCGCTGCATCAGGGTTTCCCCCATTGTGCAATA

TTCCCCACTGCTGCCTCCCGAGGGAGTTTGGA

> SEQ ID NO: 56|YK57|
GTCAGCTTTCGAGCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCCCGAGGGGAGTTTGGA

> SEQ ID NO: 57|YK58|
TCTCACGCTTTCGAGCTCACGTCAGTCATCGTCCAGCAAGCCGCCTTCGCCACTGGTGTTCCTCCTAATATCTACGC

ATTTCACCGCTACACTAGGAATTCCACTTGCCTCTCCGACACTCTAGCTCAGCAGTTCCAAATGCAGTCCCGGGGTT

GAGCCCCGGGCTTTCACATCTGGCTTGCCGTGCCGTCTACGCTCCCTTTACACCCAGTAAATCCGGATAACGCTTGC

CCCCTACGTATTACCGCGGCTGCTGGCACGTAGTTAGCCGGGGCTTCTTAGTCAGGTACCGTCATTTTCTTCCCTGC

TGATAGAAGTTTACATACCGAAATACTTCATCCTTCACGCGGCGTCGCTGCATCAGAGTTTCCTCCATTGTGCAATA

TTCCCCACTGCTGCCTCCCGTAGGGAGTTTGG

> SEQ ID NO: 58|YK65|
GTCAGCTTTCGAGCTCAGCGTCAGTTATCGTCCAGTAAGCCGCCTTCGCCACTGGTGTTCCTCCTAATATCTACGCA

TTTCACCGCTACACTAGGAATTCCACTTACCCCTCCGACACTCTAGTACGACAGTTTCCAATGCAGTACCGGGGTTG

AGCCCCGGGCTTTCACATCAGACTTGCCGCACCGCCTGCGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTCTTCTTCCCTGC

TGATAGAGCTTTACATACCGAAATACTTCTTCGCTCACGCGGCGTCGCTGCATCAGGGTTTCCCCCATTGTGCAATA

TTCCCCACTGCTGCCTCCCGAGGGAGTTTGGA

> SEQ ID NO: 59|YK67|
AGCCCGCTTTCGAGCCTCACGTCAGTTACCGTCCAGTAAGCCGCCTTCGCCACTGGTGTTCCTCCTAATATCTACG

CATTTCACCGCTACACTAGGAATTCCGCTTACCTCTCCGGCACTCAAGACGGGCAGTTTCCAATGCAGTCCCGGGGT

TGAGCCCCAGCCTTTCACATCAGACTTGTCCATCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTTTCTTCCCTG

CTGATAGAAGTTTACATACCGAGATACTTCTTCCTTCACGCGGCGTCGCTGCATCAGGGTTTCCCCCATTGTGCAAT

ATTCCCCACTGCTGCCTCCCGAAGGAAGTTTGGA

> SEQ ID NO: 60|YK69|
TGCTCAGCTTTCGAGCCTCACGTCAGTTACCGTCCAGTAAGCCGCCTTCGCCACTGGTGTTCTTCCTAATATCTACG

CATTTCACCGCTACACTAGGAATTCCGCTTACCTCTCCGGCACTCGAGCCAGACAGTTTCCAATGCAGTCCCAGGGT

TAAGCCCTGGGTTTTCACATCAGACTTGCCTTGCCGTCTACGCTCCCTTTACACCCAGTAAATCCGGATAACGCTTG

CCCCTACGTATTACCGCGGCTGCTGGCACGTAGTTAGCCGGGGCTTCTTAGTCAGGTACCGTCATTATCTTCCCTG

CTGATAGAGCTTTACATACCGAAATACTTCTTCGCTCACGCGGCGTCGCTGCATCAGGGTTTCCCCCATTGTGCAAT

ATTCCCCACTGCTGCCTCCCGAAGGGAGTTTGGA

-continued

> SEQ ID NO: 61|YK70|
GTTGCTCAGCTTTCGAGCTCACGTCAGTTACCGTCCAGTAAGCCGCCTTCGCCACTGGTGTTCTTCCTAATATCTAC

GCATTTCACCGCTACACTAGGAATTCCGCTTACCTCTCCGGCACTCGAGCCAGACAGTTTCCAATGCAGTCCCAGGG

TTAAGCCCTGGGTTTTCACATCAGACTTGCCTTGCCGTCTACGCTCCCTTTACACCCAGTAAATCCGGATAACGCTT

GCCCCCTACGTATTACCGCGGCTGCTGGCACGTAGTTAGCCGGGGCTTCTTAGTCAGGTACCGTCATTATCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGAAAGTTTGGA

> SEQ ID NO: 62|YK71|
TGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCACTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTCTTCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGGAGTTTGGA

> SEQ ID NO: 63|YK74|
GATGCCCTGGCTTCGCGCTCAGCGTCAGTTGTCGTCCAGAAAGCCGCTTTCGCCACTGGTGTTCCTCCTAATATCTA

CGCATTTCACCGCTACACTAGGAATTCCGCTTTCCTCTCCGACACTCGAGCTTCACAGTTTCGGTCCCCTCACGGGG

TTAAGCCCCGCACTTTTAAGACCGACTTGCGATGCCGCCTGCGCGCCCTTTACGCCCAATAATTCCGGACAACGCTT

GCCACCTACGTATTACCGCGGCTGCTGGCACGTAGTTAGCCGTGGCTTTCTCTTACGGTACCGTCAGGGATAACGGG

TATTGACCGCTATCCTGTTCGTCCCATATAACAGAACTTTACAACCCGAAGGCCGTCATCGTTCACGCGGCGTTGCT

CCGTCAGACTTTCGTCCATTGCGGAAGATTCCCCACTGCTGCCTCCCGGGGGAGTTTGGA

> SEQ ID NO: 64|YK88|
GTCCCGCTTTCGAGCCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAAGGGAAGTTTGG

> SEQ ID NO: 65|YK89|
TGTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTGCCTCCCGAAGGGAGTTTGGA

> SEQ ID NO: 66|YK97|
TGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCACTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTCTTCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGGAGTTTGGA

-continued

> SEQ ID NO: 67|YK98|
ATTCAGCTTTCGAGCTCACGTCAGTTACCGTCCAGTAAGCCGCCTTCGCCACTGGTGTTCCTCCTAATATCTACGCA

TTTCACCGCTACACTAGGAATTCCGCTTACCCCTCCGGCACTCAAGCATACCAGTTTCCAATGCAGTCCAGGGGTTA

AGCCCCTGCCTTTCACATCAGACTTGATACGCCGTCTACGCTCCCTTTACACCCAGTAAATCCGGATAACGCTCGCC

CCCTACGTATTACCGCGGCTGCTGGCACGTAGTTAGCCGGGGCTTCTTAGTCAGGTACCGTCATTATCTTCCCTGCT

GATAGAAGTTTACATACCGAGATACTTCTTCCTTCACGCGGCGTCGCTGCATCAGGGTTTCCCCCATTGTGCAATAT

TCCCCACTGCTGCCTCCCGAGGGAAGTTTGGA

> SEQ ID NO: 68|YK139|
GTGTCAGCTTTCGAGCTCACGTCAGTTACCGTCCAGTAAGCCGCCTTCGCCACTGGTGTTCTTCCTAATATCTACGC

ATTTCACCGCTACACTAGGAATTCCGCTTACCTCTCCGGCACTCGAGCCAGACAGTTTCCAATGCAGTCCCAGGGTT

AAGCCCTGGGTTTTCACATCAGACTTGCCTTGCCGTCTACGCTCCCTTTACACCCAGTAAATCCGGATAACGCTTGC

CCCCTACGTATTACCGCGGCTGCTGGCACGTAGTTAGCCGGGGCTTCTTAGTCAGGTACCGTCATTATCTTCCCTGC

TGATAGAGCTTTACATACCGAAATACTTCTTCGCTCACGCGGCGTCGCTGCATCAGGGTTTCCCCCATTGTGCAATA

TTCCCCACTGCTGCCTCCCGAGGGAGTTTGG

> SEQ ID NO: 69|YK141|
GCCAGCTTCGAGCCTCACGTCAGTCATCGTCCAGTAAGCCGCCTTCGCCACTGGTGTTCCTCCTAATATCTACGCAT

TTCACCGCTACACTAGGAATTCCACTTACCTCTCCGACACTCTAGCTGCACAGTTTCCAAAGCAGTCCACAGGTTGA

GCCCATGCCTTTCACTTCAGACTTGCACAGCCGTCTACGCTCCCTTTACACCCAGTAAATCCGGATAACGCTTGCCC

CCTACGTATTACCGCGGCTGCTGGCACGTAGTTAGCCGGGGCTTCTTAGTCAGGTACCGTCATTTTCTTCCCTGCTG

ATAGAAGTTTACATACCGAAATACTTCATCCTTCACGCGGCGTCGCTGCATCAGGCTTTCGCCCATTGTGCAATATT

CCCCACTGCTGCCTCCCGAGGGAAGTTTGGA

> SEQ ID NO: 70|YK142|
TGATCAGCTTTCGAGCTCACGTCAGTTACCGTCCAGTAAGCCGCCTTCGCCACTGGTGTTCCTCCTAATATCTACGC

ATTTCACCGCTACACTAGGAATTCCGCTTACCTCTCCGGTACTCTAGATTGACAGTTTCCAATGCAGTCCCGGGGTT

GAGCCCCGGGTTTTCACATCAGACTTGCCACTCCGTCTACGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTTTCTTCCCTGC

TGATAGAGCTTTACATACCGAAATACTTCATCGCTCACGCGGCGTCGCTGCATCAGGGTTTCCCCCATTGTGCAATA

TTCCCCACTGCTGCCTCCCGGGGGAGTTTGGA

> SEQ ID NO: 71|YK152|
GATGATCAGCTTTCGAGCTCACGTCAGTTACCGTCCAGTAAGCCGCCTTCGCCACTGGTGTTCCTCCTAATATCTAC

GCATTTCACCGCTACACTAGGAATTCCGCTTACCTCTCCGGCACTCTAGAAAAACAGTTTCCAATGCAGTCCTGGGG

TTAAGCCCCAGCCTTTCACATCAGACTTGCTCTTCCGTCTACGCTCCCTTTACACCCAGTAAATCCGGATAACGCTT

GCCCCCTACGTATTACCGCGGCTGCTGGCACGTAGTTAGCCGGGGCTTCTTAGTCAGGTACCGTCATTTTCTTCCCT

GCTGATAGAAGTTTACATACCGAGATACTTCTTCCTTCACGCGGCGTCGCTGCATCAGGGTTTCCCCCATTGTGCAA

TATTCCCCACTGCTGCCTCCCGGGGGAAGTTTGGA

> SEQ ID NO: 72|YK155|
TTGATCAGCTTTCGAGCTCACGTCAGTTACCGTCCAGTAAGCCGCCTTCGCCACTGGTGTTCCTCCTAATATCTACG

CATTTCACCGCTACACTAGGAATTCCGCTTACCTCTCCGGCACTCTAGAAAAACAGTTTCCAATGCAGTCCTGGGGT

TAAGCCCCAGCCTTTCACATCAGACTTGCTCTTCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTTTCTTCCCTG

CTGATAGAAGTTTACATACCGAGATACTTCTTCCTTCACGCGGCGTCGCTGCATCAGGGTTTCCCCCATTGTGCAAT

ATTCCCCACTGCTGCCTCCCGAAGGGAGTTTGG

-continued

> SEQ ID NO: 73|YK157|
GTATTTCAGCTTTCGAGCTCAGCGTCAGTTATCGTCCAGTAAGCCGCCTTCGCCACTGGTGTTCCTCCTAATATCTA

CGCATTTCACCGCTACACTAGGAATTCCGCTTACCCCTCCGACACTCTAGTACGACAGTTTCCAATGCAGTACCGGG

GTTGAGCCCCGGGCTTTCACATCAGACTTGCCGCACCGCCTGCGCTCCCTTTACACCCAGTAAATCCGGATAACGCT

TGCACCATACGTATTACCGCGGCTGCTGGCACGTATTTAGCCGGTGCTTCTTAGTCAGGTACCGTCATTATCTTCCC

TGCTGATAGAGCTTTACATACCGAAATACTTCTTCGCTCACGCGGCGTCGCTGCATCAGGCTTTCGCCCATTGTGCA

ATATTCCCCACTGCTGCCTCCCGAAGGGAGTTTGGA

> SEQ ID NO: 74|YK160|
GCTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCACTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTCTTCTTCCCTG

CTGATAGAGCTTTACATACCGAAATACTTCTTCGCTCACGCGGCGTCGCTGCATCAGGGTTTCCCCCATTGTGCAAT

ATTCCCCACTGCTGCCTCCCGAGGGGAGTTTGGA

> SEQ ID NO: 75|YK166|
TTTCAGCTTCGAGCCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTAGCTCCCGAAGGAGTTTGGA

> SEQ ID NO: 76|YK168|
AGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAAGGGAGTTTGGA

> SEQ ID NO: 77|YK169|
GTCCAGCTTTCGAGCCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAGGGAGTTTGGA

> SEQ ID NO: 78|YK171|
TGAGCCGGGCTCACCCCGGTACTGCATTGGAACTGTCGTACTAGAGTGTCGGAGGGGTAAGCGGAATTCCTAGTGTA

GCGGTGAAATGCGTAGATATTAGGAGGAACACCAGTGGCGAAGGCGGCTTACTGGACGATAACTGACGCTGAGGCTC

GAAAGCGTGGGGAGCAAACAGGATTAGATACACCGGTAA

> SEQ ID NO: 79|YK192|
CACGATGTCAGCTTTCGAGCTCAGCGTCAGTTATCGTCCAGTAAGCCGCCTTCGCCACTGGTGTTCCTCCTAATATC

TACGCATTTCACCGCTACACTAGGAATTCCACTTACCCCTCCGACACTCTAGTACGACAGTTTCCAATGCAGTACCG

GGGTTGAGCCCCGGGCTTTCACATCAGACTTGCCGCACCGCCTGCGCTCCCTTTACACCCAGTAAATCCGGATAACG

CTTGCACCATACGTATTACCGCGGCTGCTGGCACGTATTTAGCCGGTGCTTCTTAGTCAGGTACCGTCATTCTTCTT

-continued

CCCTGCTGATAGAGCTTTACATACCGAAATACTTCTTCGCTCACGCGGCGTCGCTGCATCAGGGTTTCCCCCATTGT

GCAATATTCCCCACTGCTGCCTCCCGAGGGGAGTTTGGA

> SEQ ID NO: 80|VE202-18|
ATGGAGAGTTTGATCCTGGCTCAGGATGAACGCTGGCGGCGTGCCTAATACATGCAAGTCGAACGCGAGCACTTGTG

CTCGAGTGGCGAACGGGTGAGTAATACATAAGTAACCTGCCCTAGACAGGGGGATAACTATTGGAAACGATAGCTAA

GACCGCATAGGTACGGACACTGCATGGTGACCGTATTAAAAGTGCCTCAAAGCACTGGTAGAGGATGGACTTATGG

CGCATTAGCTGGTTGGCGGGGTAACGGCCCACCAAGGCGACGATGCGTAGCCGACCTGAGAGGGTGACCGGCCACAC

TGGGACTGAGACACGGCCCAGACTCCTACGGGAGGCAGCAGTAGGGAATTTTCGGCAATGGGGGAAACCCTGACCGA

GCAACGCCGCGTGAAGGAAGAAGGTTTTCGGATTGTAAACTTCTGTTATAAAGGAAGAACGGCGGCTACAGGAAAT

GGTAGCCGAGTGACGGTACTTTATTAGAAAGCCACGGCTAACTACGTGCCAGCAGCCGCGGTAATACGTAGGTGGCA

AGCGTTATCCGGAATTATTGGGCGTAAAGAGGGAGCAGGCGGCAGCAAGGGTCTGTGGTGAAAGCCTGAAGCTTAAC

TTCAGTAAGCCATAGAAACCAGGCAGCTAGAGTGCAGGAGAGGATCGTGGAATTCCATGTGTAGCGGTGAAATGCG

TAGATATATGGAGGAACACCAGTGGCGAAGGCGACGATCTGGCCTGCAACTGACGCTCAGTCCCGAAAGCGTGGGGA

GCAAATAGGATTAGATACCCTAGTAGTCCACGCCGTAAACGATGAGTACTAAGTGTTGGATGTCAAAGTTCAGTGCT

GCAGTTAACGCAATAAGTACTCCGCCTGAGTAGTACGTTCGCAAGAATGAAACTCAAAGGAATTGACGGGGGCCCG

CACAAGCGGTGGAGCATGTGGTTTAATTCGAAGCAACGCGAAGAACCTTACCAGGTCTTGACATACTCATAAAGGCT

CCAGAGATGGAGAGATAGCTATATGAGATACAGGTGGTGCATGGTTGTCGTCAGCTCGTGTCGTGAGATGTTGGGTT

AAGTCCCGCAACGAGCGCAACCCTTATCGTTAGTTACCATCATTAAGTTGGGGACTCTAGCGAGACTGCCAGTGAC

AAGCTGGAGGAAGGCGGGGATGACGTCAAATCATCATGCCCCTTATGACCTGGGCTACACACGTGCTACAATGGATG

GTGCAGAGGGAAGCGAAGCCGCGAGGTGAAGCAAAACCCATAAAACCATTCTCAGTTCGGATTGTAGTCTGCAACTC

GACTACATGAAGTTGGAATCGCTAGTAATCGCGAATCAGCATGTCGCGGTGAATACGTTCTCGGGCCTTGTACACA

CCGCCCGTCACACCACGAGAGTTGATAACACCCGAAGCCGGTGGCCTAACCGCAAGGAAGGAGCTGTCTAAGGTGGG

ATTGATGATTGGGGTGAAGTCGTAACAAGGTATCCCTACGGGAACGTGGGGATGGATCACCTCCTTT

> SEQ ID NO: 81|PE5|
ATGAGAGTTTGATCCTGGCTCAGGATGAACGCTGGCGGCGTGCCTAACACATGCAAGTCGAACGAAGCAATTGAAGG

AAGTTTTCGGATGGAATTCGATTGACTGAGTGGCGGACGGGTGAGTAACGCGTGGATAACCTGCCTCACACTGGGGG

ATAACAGTTAGAAATGACTGCTAATACCGCATAAGCGCACAGTACCGCATGGTACAGTGTGAAAAACTCCGGTGGT

GTGAGATGGATCCGCGTCTGATTAGCCAGTTGGCGGGGTAACGGCCCACCAAAGCGACGATCAGTAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATAT

TAGGAGGAACACCAGTGGCGAAGGCGGCTTACTGGACGATAACTGACGTTGAGGCTCGAAAGCGTGGGGAGCAAACA

GGATTAGATACCCTGGTAGTCCACGCCGTAAACGATGAATGCTAGGTGTTGGGGGCAAAGCCCTTCGGTGCCGTCG

CAAACGCAGTAAGCATTCCACCTGGGGAGTACGTTCGCAAGAATGAAACTCAAAGGAATTGACGGGACCCGCACA

AGCGGTGGAGCATGTGGTTTAATTCGAAGCAACGCGAAGAACCTTACCAAGTCTTGACATCCTCTTGACCGGCGTGT

AACGGCGCCTTCCCTTCGGGGCAAGAGAGACAGGTGGTGCATGGTTGTCGTCAGCTCGTGTCGTGAGATGTTGGGTT

AAGTCCCGCAACGAGCGCAACCCTTATCCTTAGTAGCCAGCAGGTAAAGCTGGGCACTCTAGGGAGACTGCCAGGG

ATAACCTGGAGGAAGGTGGGGATGACGTCAAATCATCATGCCCCTTATGATTTGGGCTACACACGTGCTACAATGGC

GTAAACAAAGGGAAGCAAGACAGTGATGTGGAGCAAATCCCAAAAATAACGTCCCAGTTCGGACTGTAGTCTGCAAC

CCGACTACACGAAGCTGGAATCGCTAGTAATCGCGAATCAGAATGTCGCGGTGAATACGTTCCCGGGTCTTGTACA

CACCGCCCGTCACACCATGGGAGTCAGCAACGCCCGAAGTCAGTGACCCAACTCGCAAGAGAGGGAGCTGCCGAAGG

CGGGGCAGGTAACTGGGGTGAAGTCGTAACAAGGTAGCCGTATCGGAAGGTGCGGCTGGATCACCTCCTTT

> SEQ ID NO: 82|PE9|
AATTCGACGTTGTCCGGATTACTGGGCGTAAAGGGAGCGTAGGCGGACTTTTAAGTGAGATGTGAAATACCCGGCT

CAACTTGGGTGCTGCATTTCAAACTGGAAGTCTAGAGTGCAGGAGAGGAGAATGGAATTCCTAGTGTAGCGGTGAAA

TGCGTAGAGATTAGGAAGAACACCAGTGGCGAAGGCGATTCTCTGGACTGTAACTGACGCTGAGGCTCGAAAGCGTG

GGGAGCAAACAGGATTAGATACCCTGGTAGTCCACGCCGTAAACGATGAATACTAGGTGTAGGGGTTGTCATGACCT

CTGTGCCGCCGCTAACGCATTAAGTATTCCGCCTGGGGAGTACGGTCGCAAGATTAAAACTCAAAGAAATTGACGGA

> SEQ ID NO: 83|211-B|
ACGAGCGTATCGGATTATTGGGTTTAAGGGAGCGTAGGTGGATTGTTAAGTCAGTTGTGAAAGTTTGCGGCTCAACC

GTAAAATTGCAGTTGAAACTGGCAGTCTTGAGTACAGTAGAGGTGGGCGGAATTCGTGGTGTAGCGGTGAAATGCTT

AGATATCACGAAGAACTCCGATTGCGAAGGCAGCTCACTAGACTGTCACTGACACTGATGCTCGAAAGTGTGGGTAT

CAAACAGGATTAGATACCCTGGTAGTCCACACAGTAAACGATGAATACTCGCTGTTTGCGATATACAGTAAGCGGCC

AAGCGAAAGCATTAAGTATTCCACCTGGGGAGTACGCCGGCAACGGTGAAACTCAAAGAAATTGACGGAAGCCCGCC

CAGGGGGGAAAAACATGGGGTTTAGTTGGATGATACGGGGAGGAACCTC

> SEQ ID NO: 84|NR_119185.1|Ruminococcus obeum 16S ribosomal RNA gene, complete
sequence
GGCGGCGTGCTTAACACATGCAAGTCGAACGGGAAACCTTTCATTGAAGCTTCGGCAGATTTGGNNTGTTTCTAGTG

GCGGACGGGTGAGTAACGCGTGGGTAACCTGCCTTATACAGGGGATAACAACCAGAAATGGTTGCTAATACCGCAT

AAGCGCACAGGACCGCATGGTCTGGTGTGAAAAACTCCGGTGGTATAAGATGGACCCGCGTTGGATTAGCTAGTTGG

CAGGGTAACGGCCTACCAAGGCGACGATCCATAGCCGGCCTGAGAGGGTGAACGGCCACATTGGGACTGAGACACGG

CCCAGACTCCTACGGGAGGCAGCAGTGGGGAATATTGCACAATGGGGGAAACCCTGATGCAGCGACGCCGCGTGAAG

GAAGAAGTATCTCGGTATGTAAACTTCTATCAGCAGGGAAGATAGTGACGGTACCTGACTAAGAAGCCCCGGCTAAC

TACGTGCCAGCAGCCGCGGTAATACGTAGGGGGCAAGCGTTATCCGGATTTACTGGGTGTAAAGGGAGCGTAGACGG

ACTGGCAAGTCTGATGTGAAAGGCGGGGGCTCAACCCCTGGACTGCATTGGAAACTGTTAGTCTTGAGTGCCGGAGA

GGTAAGCGGAATTCCTAGTGTAGCGGTGAAATGCGTAGATATTAGGAGGAACACCAGTGGCGAAGGCGGCTTACTGG

ACGGTAACTGACGTTGAGGCTCGAAAGCGTGGGGAGCAAACAGGATTAGATACCCTGGTAGTCCACGCCGTAAACGA

TGATTACTAGGTGTTGGGGAGCAAAGCTCTTCGGTGCCGCCGCAAACGCATTAAGTATTCCACCTGGGGAGTACGTT

CGCAAGAATGAAACTCAAAGGAATTGACGGGACCCGCACAAGCGGTGGAGCATGTGGTTTAATTCGAAGCAACGCG

AAGAACCTTACCAAGTCTTGACATCCCTCTGACCGNCCCTTAACCGGATCTTTCCTTCGGGACAGGGGAGACAGGTG

GTGCATGGTTGTCGTCAGCTCGTGTCGTGAGATGTTGGGTTAAGTCCCGCAACGAGCGCAACCCCTATCCCCAGTAG

CCAGCAGTCCGGCTGGGCACTCTGAGGAGACTGCCAGGGATAACCTGGAGGAAGGCGGGGATGACGTCAAATCATCA

TGCCCCTTATGATTTGGGCTACACACGTGCTACAATGGCGTAAACAAAGGGAAGCAAGCCTGCGAAGGTAAGCAAAT

CCCAAAAATAACGTCCCAGTTCGGACTGCAGTCTGCAACTCGACTGCACGAAGCTGGAATCGCTAGTAATCGCGGAT

CAGAATGCCGCGGTGAATACGTTCCCGGGTCTTGTACACACCGCCCGTCACACCATGGGAGTCAGTAACGCCCGAAG

TCAGTGACCTAACTGCAAAGAAGGAGCTGCCGAAGGCGGGACCGATGACTGGGGTGAAGTCGTAACAAGGT

> SEQ ID NO: 85|NR_118692.1|Ruminococcus obeum strain ATCC 29174 16S ribosomal RNA
gene, complete sequence
GGCGTGCTTAACACATGCAAGTCGAACGGGAAACTTTTCATTGAAGCTTCGGCAGATTTGGTCTGTTTCTAGTGGCG

GACGGGTGAGTAACGCGTGGGTAACCTGCCTTATACAGGGGATAACAACCAGAAATGGTTGCTAATACCGCATAAG

CGCACAGGACCGCATGGTCTGGTGTGAAAAACTCCGGTGGTATAAGATGGACCCGCGTTGGATTAGCTAGTTGGCAG

GGTAACGGCCTACCAAGGCGACGATCCATAGCCGGCCTGAGAGGGTGAACGGCCACATTGGGACTGAGACACGCCCC

AGACTCCTCGGGAGGCAGCAGTGGGGAATATTGCACAATGGGGGAAACCCTGATGCAGCGACGCCGCGTGAAGGAAG

```
AAGTATCTCGGTATGTAAACTTCTATCAGCAGGGAAGATAGTGACGGTACCTGACTAAGAAGCCCCGKCTAACTACG

TGCCAGCAGCCGCGGTAATACGTAGGGGGCAAGCGTTATCCGGATTTACTGGGTGTAAAGGGAGCGTAGACGGACTG

GCAAGTCTGATGTGAAAGGCGGGGGCTCAACCCCTGGACTGCATTGGAAACTGTTAGTCTTGAGTGCCGGAGAGGTA

AGCGGAATTCCTAGTGTAGCGGTGAAATGCGTAGATATTAGGAGGAACACCAGTGGCGAAGGCGGCTTACTGGACGG

TAACTGACGTTGAGGCTCGAAAGCGTGGGGAGCAAACAGGATTAGATACCCTGGTAGTCCACGCCGCAAACGATGAA

TACTAGGTGTTGGGGAGCAAAGCTCTTCGGTGCCGCCGCAAACGCATTAAGTATTCCACCTGGGGAGTACGTTCGCA

AGAATGAAACTCAAAGGAATTGACGGGGACCCGCACAAGCGGTGGAGCATGTGGTTTAATTCGAAGCAACGCGAAGA

ACCTTACCAAGTCTTGACATCCCTCTGACCGTCCCTTAACCGGATCTTTCCTTCGGGACAGGGGAGACAGGTGGTGC

ATGGTTGTCGTCAGCTCGTGTCGTGAGATGTTGGGTTAAGTCCCGCAACGAGCGCAACCCCTATCCCCAGTAGCCAG

CAGTNCGGCTGGGCACTCTGAGGAGACTGCCAGGGATAACCTGGAGGAAGGCGGGGATGACGTCAAATCATCATGCC

CCTTATGATTTGGGCTACACACGTGCTACAATGGCGTAAACAAAGGGAAGCNAGCCTKCGRAGGTAAGCAAATCCCA

NAAATAACGTCCCAGTTCGGACTGCAGTCTGCAACTCGACTGCACGAAGCTGGAATCGCTAGTAATCGCGGATCAGA

ATGCCGCGGTGAATACGTTCCCGGGTCTTGTACACACCGCCCGTCACACCATGGGAGTCAGTAACGCCCGAAGTCAG

TGACCTAACTGC

> SEQ ID NO: 86|NR_026491.1|Clostridium disporicum strain DS1 16S ribosomal RNA gene,
partial sequence
GCTCAGGACGAACGCTGGCGGCGTGCCTAACACATGCAAGTCGAGCGAGTTGATTCTCTTCGGAGATGAAGCTAGCG

GCGGACGGGTGAGTAACACGTGGGCAACCTGCCTCATAGAGGGGAATAGCCTCCCGAAAGGGAGATTAATACCGCAT

AAGATTGTAGCTTCGCATGAAGTAGCAATTAAAGGAGCAATCCGCTATGAGATGGGCCCGCGGCGCATTAGCTAGTT

GGTGAGGTAACGGCTCACCAAGGCGACGATGCGTAGCCGACCTGAGAGGGTGATCGGCCACATTGGGACTGAGACAC

GGCCCAGACTCCTACGGGAGGCAGCAGTGGGGAATATTGCACAATGGGGGAAACCCTGATGCAGCAACGCCGCGTGA

GTGATGACGGCCTTCGGGTTGTAAAGCTCTGTCTTCAGGGACGATAATGACGGTACCTGAGGAGGAAGCCACGGCTA

ACTACGTGCCAGCAGCCGCGGTAATACGTAGGTGGCGAGCGTTGTCCGGATTTACTGGGCGTAAAGGGAGCGTAGGC

GGACTTTTAAGTGAGATGTGAAATACCCGGGCTCAACTTGGGTGCTGCATTTCAAACTGGAAGTCTAGAGTGCAGGA

GAGGAGAATGGAATTCCTAGTGTAGCGGTGAAATGCGTAGAGATTAGGAAGAACACCAGTGGCGAAGGCGATTCTCT

GGACTGTAACTGACGCTGAGGCTCGAAAGCGTGGGGAGCAAACAGGATTAGATACCCTGGTAGTCCACGCCGTAAAC

GATGAATACTAGGTGTAGGGGTTGTCATGACCTCTGTGCCGCCGCTAACGCATTAAGTATTCCGCCTGGGGAGTACG

GTCGCAAGATTAAAACTCAAAGGAATTGACGGGGCCCGCACAAGCAGCGGAGCATGTGGTTTAATTCGAAGCAACG

CGAAGAACCTTACCTAGACTTGACATCTCCTGAATTACCCGTAACTGGGGAAGCCACTTCGGTGGCAGGAAGACAGG

TGGTGCATGGTTGTCGTCAGCTCGTGTCGTGAGATGTTGGGTTAAGTCCCGCAACGAGCGCAACCCTTATTGTTAGT

TGCTACCATTTAGTTGAGCACTCTAGCGAGACTGCCCGGGTTAACCGGGAGGAAGGTGGGGATGACGTCAAATCATC

ATGCCCCTTATGTCTAGGGCTACACACGTGCTACAATGGCAAGTACAAAGAGAAGCAAGACCGCGAGGTGGAGCAAA

ACTCAAAAACTTGTCTCAGTTCGGATTGTAGGCTGAAACTCGCCTACATGAAGCTGGAGTTGCTAGTAATCGCGAAT

CAGCATGTCGCGGTGAATACGTTCCCGGGCCTTGTACACACCGCCCGTCACACCATGAGAGTTGGCAATACCCAACG

TACGTGATCTAACCCGCAAGGGAGGAAGCGTCCTAAGGTAGGGTCAGCGATTGGGGTGAAGTCGTAACAAGGTAGCC

GTAGGAGAA

> SEQ ID NO: 87|NR_028785.1|Clostridium scindens strain ATCC 35704 16S ribosomal RNA
gene, complete sequence
GAGAGTTTGATCCTGGCTCAGGATGAACGCTGGCGGCGTGCCTAACACATGCAAGTCGAACGAAGCGCCTGGCCCCG

ACTTCTTCGGAACGAGGAGCCTTGCGACTGAGTGGCGGACGGGTGAGTAACGCGTGGGCAACCTGCCTTGCACTGGG

GGATAACAGCCAGAAATGGCTGCTAATACCGCATAAGACCGAAGCGCCGCATGGCGCGGCGGCCAAAGCCCCGGCGG

TGCAAGATGGGCCCGCGTCTGATTAGGTAGTTGGCGGGGTAACGGCCCACCAAGCCGACGATCAGTAGCCGACCTGA

GAGGGTGACCGGCCACATTGGGACTGAGACACGGCCCAGACTCCTACGGGAGGCAGCAGTGGGGAATATTGCACAAT
```

-continued

```
GGGGGAAACCCTGATGCAGCGACGCCGCGTGAAGGATGAAGTATTTCGGTATGTAAACTTCTATCAGCAGGGAAGAA

GATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGATGCAAGCCAGATGTGAAAGCCCGGGGCTCAACCCCGGGAC

TGCATTTGGAACTGCGTGGCTGGAGTGTCGGAGAGGCAGGCGGAATTCCTAGTGTAGCGGTGAAATGCGTAGATATT

AGGAGGAACACCAGTGGCGAAGGCGGCCTGCTGGACGATGACTGACGTTGAGGCTCGAAAGCGTGGGGAGCAAACAG

GATTAGATACCCTGGTAGTCCACGCCGTAAACGATGACTACTAGGTGTCGGGTGGCAAGGCCATTCGGTGCCGCAGC

AAACGCAATAAGTAGTCCACCTGGGGAGTACGTTCGCAAGAATGAAACTCAAAGGAATTGACGGGACCCGCACAAG

CGGTGGAGCATGTGGTTTAATTCGAAGCAACGCGAAGAACCTTACCTGATCTTGACATCCCGATGCCAAAGCGCGTA

ACGCGCTCTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCATTTTGGATGGGCACTCTGGAGAGACTGCCAGGGAGAA

CCTGGAGGAAGGTGGGGATGACGTCAAATCATCATGCCCCTTATGACCAGGGCTACACACGTGCTACAATGGCGTAA

ACAAAGGGAGGCGAACCCGCGAGGGTGGGCAAATCCCAAAAATAACGTCTCAGTTCGGATTGTAGTCTGCAACTCGA

CTACATGAAGTTGGAATCGCTAGTAATCGCGAATCAGAATGTCGCGGTGAATACGTTCCCGGGTCTTGTACACACCG

CCCGTCACACCATGGGAGTCAGTAACGCCCGAAGCCGGTGACCCAACCCGTAAGGGAGGGAGCCGTCGAAGGTGGGA

CCGATAACTGGGGTGAAGTCGTAACAAGGTAGCCGTATCGGAAGGTGCGGCTGGATCACCTCCTTC

> SEQ ID NO: 88|NR_028915.1|Anaerostipes caccae strain L1-92 16S ribosomal RNA gene,
partial sequence
GCGCTTAATACATGTCAAGTCGAACGAAGCATTTAGGATTGAAGTTTTCGGATGGATTTCCTATATGACTGAGTGGC

GGACGGGTGAGTAACGCGTGGGAACCTGCCCTATACAGGGGGATAACAGCTGGAAACGGCTGCTAATACCGCATAA

GCGCACAGAATCGCATGATTCAGTGTGAAAAGCCCTGGCAGTATAGGATGGTCCCGCGTCTGATTAGCTGGTTGGTG

AGGTAACGGCTCACCAAGGCGACGATCAGTAGCCGGCTTGAGAGAGTGAACGGCCACATTGGGACTGAGACACGGCC

CAAACTCCTACGGGAGGCAGCAGTGGGGAATATTGCACAATGGGGGTAAACCCTGATGCAGCGACGCCGCGTGAGTG

AAGAAGTATTTCGGTATGTAAAGCTCTATCAGCAGGGAAGAAAACAGACGGTACCTGACTAAGAAGCCCCGGCTAAC

TACGTGCCAGCAGCCGCGGTAATACGTAGGGGGCAAGCGTTATCCGGAATTACTGGGTGTAAAGGGTGCGTAGGTGG

CATGGTAAGTCAGAAGTGAAAGCCCGGGGCTTAACCCCGGGACTGCTTTTGAAACTGTCATGCTGGAGTGCAGGAGA

GGTAAGCGGAATTCCTAGTGTAGCGGTGAAATGCGTAGATATTAGGAGGAACACCAGTGGCGAAGGCGGCTTACTGG

ACTGTCACTGACACTGATGCACGAAAGCGTGGGGAGCAAACAGGATTAGATACCCTGGTAGTCCACGCCGTAAACGA

TGAATACTAGGTGTCGGGGCCGTAGAGGCTTCGGTGCCGCAGCAAACGCAGTAAGTATTCCACCTGGGGAGTACGTT

CGCAAGAATGAAACTCAAAGGAATTGACGGGACCCGCACAAGCGGTGGAGCATGTGGTTTAATTCGAAGCAACGCG

AAGAACCTTACCTGGTCTTGACATCCCAATGACCGAACCTTAACCGGTTTTTCTTTCGAGACATTGGAGACAGGTG

GTGCATGGTTGTCGTCAGCTCGTGTCGTGAGATGTTGGGTTAAGTCCCGCAACGAGCGCAACCCCTATCTTTAGTAG

CCAGCATTTAAGGTGGGCACTCTAGAGAGACTGCCAGGGATAACCTGGAGGAAGGTGGGGACGACGTCAAATCATCA

TGCCCCTTATGGCCAGGGCTACACACGTGCTACAATGGCGTAAACAAAGGGAAGCGAAGTCGTGAGGCGAAGCAAAT

CCCAGAAATAACGTCTCAGTTCGGATTGTAGTCTGCAACTCGACTACATGAAGCTGGAATCGCTAGTAATCGTGAAT

CAGAATGTCACGGTGAATACGTTCCCGGGTCTTGTACACACCGCCCGTCACACCATGGGAGTCAGTAACGCCCGAAG

TCAGTGACCCAACCGCAAGGAGGGAGCTGCCGAAGGTGGGACCGATAACTGGGGTGAAGTCGTAACAAGG

> SEQ ID NO: 89|NR_042152.1|Marvinbryantia formatexigens strain I-52 16S ribosomal RNA
gene, partial sequence >gi|636558750|ref|NR_114807.1|Marvinbryantia formatexigens strain I-
52 16S ribosomal RNA gene, complete sequence
TGGCGGCGTGCTTAACACATGCAAGTCGAGCGAAGCATTTTAAATGAAGTTTTCGGACGGAATTTAAATGACTGAG

CGGCGGACGGGTGAGTAACGCGTGGATAACCTGCCTTATACAGGGGGATAACAGCCAGAAATGGCTGCTAATACCGC

ATAAGCGCACGGTACCGCATGGTACAGTGTGAAAAACTCCGGTGGTATAAGATGGGTCCGCGTTGGATTAGGCAGTT

GGCGGGGTAAAGGCCCACCAAACCGACGATCCATAGCCGGCCTGAGAGGGTGGACGGCCACATTGGGACTGAGACAC
```

```
GGCCCAGACTCCTACGGGAGGCAGCAGTGGGGAATATTGCACAATGGGGGAAACCCTGATGCAGCGACGCCGCGTGG

GTGAAGAAGTATTTCGGTATGTAAAGCCCTATCAGCAGGGAAGAAAATGACGGTACCTGACCAAGAAGCCCCGGCTA

ACTACGTGCCAGCAGCCGCGGTAATACGTAGGGGGCAAGCGTTATCCGGATTTACTGGGTGTAAAGGGAGCGTAGAC

GGCCATGCAAGTCTGGTGTGAAAGGCGGGGGCTCAACCCCCGGACTGCATTGGAAACTGTATGGCTTGAGTGCCGGA

GAGGTAAGCGGAATTCCTGGTGTAGCGGTGAAATGCGTAGATATCAGGAGGAACACCAGTGGCGAAGGCGGCTTACT

GGACGGTAACTGACGTTGAGGCTCGAAAGCGTGGGGAGCAAACAGGATTAGATACCCTGGTAGTCCACGCCGTAAAC

GATGAATACCAGGTGTCGGGGGACACGGTCCTTCGGTGCCGCAGCAAACGCACTAAGTATTCCACCTGGGGAGTACG

TTCGCAAGAATGAAACTCAAAGGAATTGACGGGGACCCGCACAAGCGGTGGAGCATGTGGTTTAATTCGAAGCAACG

CGAAGAACCTTACCAGGTCTTGACATCCGGACGACCGGACAGTAACGTGTCCTTCCCTTCGGGGCGTCCGAGACAGG

TGGTGCATGGTTGTCGTCAGCTCGTGTCGTGAGATGTTGGGTTAAGTCCCGCAACGAGCGCAACCCCTGTTCCCAGT

AGCCAGCATTCAGGATGGGCACTCTGGGGAGACTGCCAGGGATAACCTGGAGGAAGGCGGGGATGACGTCAAATCAT

CATGCCCCTTATGATCTGGGCTACACACGTGCTACAATGGCGTGAACAGAGGGAAGCGAACCCGCGAGGGGGAGCAA

ATCCCAGAAATAACGTCCCAGTTCGGATTGTAGTCTGCAACCCGGCTACATGAAGCTGGAATCGCTAGTAATCGCGG

ATCAGCATGCCGCGGTGAATACGTTCCCGGGTCTTGTACACACCGCCCGTCACACCATGGGAGTCGGAAATGCCCGA

AGTCAGTGACCCAACCGGAAGGAGGGAGCTGCCGAAGGCGGGGCCGGTAACTGGGGTGAAGTCGTAACAA

> SEQ ID NO: 90|NR_024994.1|Lactobacillus mucosae strain S32 16S ribosomal RNA gene,
complete sequence
AGAGTTTGATCCTGGCTCAGGATGAACGCCGGCGGTGTGCCTAATACATGCAAGTCGAACGCGTTGGCCCAACTGAT

TGAACGTGCTTGCACGGACTTGACGTTGGTTTACCAGCGAGTGGCGGACGGGTGAGTAACACGTAGGTAACCTGCCC

CAAAGCGGGGGATAACATTTGGAAACAGATGCTAATACCGCATAACAATTTGAATCGCATGATTCAAATTTAAAAGA

TGGCTTCGGCTATCACTTTGGGATGGACCTGCGGCGCATTAGCTTGTTGGTAGGGTAACGGCCTACCAAGGCTGTGA

TGCGTAGCCGAGTTGAGAGACTGATCGGCCACAATGGAACTGAGACACGGTCCATACTCCTACGGGAGGCAGCAGTA

GGGAATCTTCCACAATGGGCGCAAGCCTGATGGAGCAACACCGCGTGAGTGAAGAAGGGTTTCGGCTCGTAAAGCTC

TGTTGTTAGAGAAGAACGTGCGTGAGAGCAACTGTTCACGCAGTGACGGTATCTAACCAGAAAGTCACGGCTAACTA

CGTGCCAGCAGCCGCGGTAATACGTAGGTGGCAAGCGTTATCCGGATTTATTGGGCGTAAAGCGAGCGCAGGCGGTT

TGATAAGTCTGATGTGAAAGCCTTTGGCTTAACCAAAGAAGTGCATCGGAAACTGTCAGACTTGAGTGCAGAAGAGG

ACAGTGGAACTCCATGTGTAGCGGTGGAATGCGTAGATATATGGAAGAACACCAGTGGCGAAGGCGGCTGTCTGGTC

TGCAACTGACGCTGAGGCTCGAAAGCATGGGTAGCGAACAGGATTAGATACCCTGGTAGTCCATGCCGTAAACGATG

AGTGCTAGGTGTTGGAGGGTTTCCGCCCTTCAGTGCCGCAGCTAACGCATTAAGCACTCCGCCTGGGGAGTACGACC

GCAAGGTTGAAACTCAAAGGAATTGACGGGGGCCCGCACAAGCGGTGGAGCATGTGGTTTAATTCGAAGCTACGCGA

AGAACCTTACCAGGTCTTGACATCTTGCGCCAACCCTAGAGATAGGGCGTTTCCTTCGGGAACGCAATGACAGGTGG

TGCATGGTCGTCGTCAGCTCGTGTCGTGAGATGTTGGGTTAAGTCCCGCAACGAGCGCAACCCTTGTTACTAGTTGC

CAGCATTCAGTTGGGCACTCTAGTGAGACTGCCGGTGACAAACCGGAGGAAGGTGGGGACGACGTCAGATCATCATG

CCCCTTATGACCTGGGCTACACACGTGCTACAATGGACGGTACAACGAGTCGCGAACTCGCGAGGGCAAGCTAATCT

CTTAAAACCGTTCTCAGTTCGGACTGCAGGCTGCAACTCGCCTGCACGAAGTCGGAATCGCTAGTAATCGCGGATCA

GCATGCCGCGGTGAATACGTTCCCGGGCCTTGTACACACCGCCCGTCACACCATGAGAGTTTGCAACACCCAAAGTC

GGTGGGGTAACCCTTCGGGGAGCTAGCCGCCTAAGGTGGGGCAGATGATTAGGGTGAAGTCGTAACAAGGTAGCCGT

AGGAGAACCTGCGGCTGGATCACCTCCT

> SEQ ID NO: 91|NR_028816.1|Turicibacter sanguinis strain MOL361 16S ribosomal RNA
gene, complete sequence
AGAGTTTGATCATGGCTCAGGATGAACGCTGGCGGCGTGCCTAATACATGCAAGTCGAGCGAACCACTTCGGTGGTG AGCGGCGAACGGGTGAGTAACACGTAGGTTATCTGCCCATCAGACGGGGACAACGATTGGAAACGATCGCTAATACC
```

```
GGATAGGACGAAAGTTTAAAGGTGCTTCGGCACCACTGATGGATGAGCCTGCGGCGCATTAGCTAGTTGGTAGGGTA

AAGGCCTACCAAGGCGACGATGCGTAGCCGACCTGAGAGGGTGAACGGCCACACTGGGACTGAGACACGGCCCAGAC

TCCTACGGGAGGCAGCAGTAGGGAATCTTCGGCAATGGGCGAAAGCCTGACCGAGCAACGCCGCGTGAATGATGAAG

GCCTTCGGGTTGTAAAATTCTGTTATAAGGGAAGAATGGCTCTAGTAGGAAATGGCTAGAGTGTGACGGTACCTTAT

GAGAAAGCCACGGCTAACTACGTGCCAGCAGCCGCGGTAATACGTAGGTGGCGAGCGTTATCCGGAATTATTGGGCG

TAAAGAGCGCGCAGGTGGTTGATTAAGTCTGATGTGAAAGCCCACGGCTTAACCGTGGAGGGTCATTGGAAACTGGT

CAACTTGAGTGCAGAAGAGGGAAGTGGAATTCCATGTGTAGCGGTGAAATGCGTAGAGATATGGAGGAACACCAGTG

GCGAAGGCGGCTTCCTGGTCTGTAACTGACACTGAGGCGCGAAAGCGTGGGGAGCAAACAGGATTAGATACCCTGGT

AGTCCACGCCGTAAACGATGAGTGCTAAGTGTTGGGGGTCGAACCTCAGTGCTGAAGTTAACGCATTAAGCACTCCG

CCTGGGGAGTACGGTCGCAAGACTGAAACTCAAAGGAATTGACGGGGACCCGCACAAGCGGTGGAGCATGTGGTTTA

ATTCGAAGCAACGCGAAGAACCTTACCAGGTCTTGACATACCAGTGACCGTCCTAGAGATAGGATTTTCCCTTCGGG

GACAATGGATACAGGTGGTGCATGGTTGTCGTCAGCTCGTGTCGTGAGATGTTGGGTTAAGTCCCGCAACGAGCGCA

ACCCCTGTCGTTAGTTGCCAGCATTCAGTTGGGGACTCTAACGAGACTGCCAGTGACAAACTGGAGGAAGGTGGGGA

TGACGTCAAATCATCATGCCCCTTATGACCTGGGCTACACACGTGCTACAATGGTTGGTACAAAGAGAAGCGAAGCG

GTGACGTGGAGCAAACCTCATAAAGCCAATCTCAGTTCGGATTGTAGGCTGCAACTCGCCTACATGAAGTTGGAATC

GCTAGTAATCGCGAATCAGCATGTCGCGGTGAATACGTTCCCGGGTCTTGTACACACCGCCCGTCACACCACGAGAG

TTTACAACACCCGAAGTCAGTGGCCTAACCGCAAGGAGGGAGCTGCCTAAGGTGGGGTAGATGATTGGGGTGAAGTC

GTAACAAGGTATCCCTACCGGAAGGTGGGGTTGGATCACCTCCTT

> SEQ ID NO: 92|NR_042832.1|Roseburia faecis strain M72/1 16S ribosomal RNA gene, partial
sequence
GATGAACGCTGGCGGCGTGCTTAACACATGCAAGTCGAACGAAGCACTCTATTTGATTTTCTTCGGAAATGAAGATT

TTGTGACTGAGTGGCGGACGGGTGAGTAACGCGTGGGTAACCTGCCTCATACAGGGGGATAACAGTTGGAAACGACT

GCTAATACCGCATAAGCGCACAGGATCGCATGATCCGGTGTGAAAAACTCCGGTGGTATGAGATGGACCCGCGTCTG

ATTAGCCAGTTGGCAGGGTAACGGCCTACCAAAGCGACGATCAGTAGCCGACCTGAGAGGGTGACCGGCCACATTGG

GACTGAGACACGGCCCAAACTCCTACGGGAGGCAGCAGTGGGGAATATTGCACAATGGGGGAAACCCTGATGCAGCG

ACGCCGCGTGAGCGAAGAAGTATTTCGGTATGTAAAGCTCTATCAGCAGGGAAGAAGAATGACGGTACCTGACTAAG

AAGCACCGGCTAAATACGTGCCAGCAGCCGCGGTAATACGTATGGTGCAAGCGTTATCCGGATTTACTGGGTGTAAA

GGGAGCGCAGGCGGTGCGGCAAGTCTGATGTGAAAGCCCGGGGCTCAACCCCGGTACTGCATTGGAAACTGTCGTAC

TAGAGTGTCGGAGGGGTAAGTGGAATTCCTAGTGTAGCGGTGAAATGCGTAGATATTAGGAGGAACACCAGTGGCGA

AGGCGGCTTACTGGACGATAACTGACGCTGAGGCTCGAAAGCGTGGGGAGCAAACAGGATTAGATACCCTGGTAGTC

CACGCCGTAAACGATGAATACTAGGTGTCGGGAGCATTGCTCTTCGGTGCCGCAGCAAACGCAATAAGTATTCCAC

CTGGGGAGTACGTTCGCAAGAATGAAACTCAAAGGAATTGACGGGGACCCGCACAAGCGGTGGAGCATGTGGTTTAA

TTCGAAGCAACGCGAAGAACCTTACCAAGTCTTGACATCCCGATGACAGAGTATGTAATGTACYTTCTCTTCGGAGC

ATCGGTGACAGGTGGTGCATGGTTGTCGTCAGCTCGTGTCGTGAGATGTTGGGTTAAGTCCCGCAACGAGCGCAACC

CCTGTCCTTAGTAGCCAGCGGTTCGGCCGGGCACTCTAGGGAGACTGCCAGGGATAACCTGGAGGAAGGCGGGGATG

ACGTCAAATCATCATGCCCCTTATGACTTGGGCTACACACGTGCTACAATGGCGTAAACAAAGGGAAGCGGAGCCGT

GAGGCCGAGCAAATCTCAAAAATAACGTCTCAGTTCGGACTGTAGTCTGCAACCCGACTACACGAAGCTGGAATCGC

TAGTAATCGCAGATCAGAATGCTGCGGTGAATACGTTCCCGGGTCTTGTACACACCGCCCGTCACACCATGGGAGTT

GGAAATGCCCGAAGTCAGTGACCCAACCGCAAGGAGGGAGCTGCCGAAGGCAGGTTCGATAACTGGGGTG

> SEQ ID NO: 93|NR_043142.1|Flavonifractor plautii strain Prevot S1 16S ribosomal RNA
gene, partial sequence
CGCTGGCGGCGTGCTTAACACATGCAAGTCGAACGGGGTGCTCATGACGGAGGATTCGTCCAATGGATTGAGTTACC TAGTGGCGGACGGGTGAGTAACGCGTGAGGAACCTGCCTTGGAGAGGGGAATAACACTCCGAAAGGAGTGCTAATAC
```

CGCATGAAGCAGTTGGGTCGCATGGCTCTGACTGCCAAAGATTTATCGCTCTGAGATGGCCTCGCGTCTGATTAGCT
AGTAGGCGGGGTAACGGCCCACCTAGGCGACGATCAGTAGCCGGACTGAGAGGTTGACCGGCCACATTGGGACTGAG
ACACGGCCCAGACTCCTACGGGAGGCAGCAGTGGGGAATATTGGGCAATGGGCGCAAGCCTGACCCAGCAACGCCGC
GTGAAGGAAGAAGGCTTTCGGGTTGTAAACTTCTTTTGTCGGGGACGAAACAAATGACGGTACCCGACGAATAAGCC
ACGGCTAACTACGTGCCAGCAGCCGCGGTAATACGTAGGTGGCAAGCGTTATCCGGATTTACTGGGTGTAAAGGGCG
TGTAGGCGGGATTGCAAGTCAGATGTGAAAACTGGGGGCTCAACCTCCAGCCTGCATTTGAAACTGTAGTTCTTGAG
TGCTGGAGAGGCAATCGGAATTCCGTGTGTAGCGGTGAAATGCGTAGATATACGGAGGAACACCAGTGGCGAAGGCG
GATTGCTGGACAGTAACTGACGCTGAGGCGCGAAAGCGTGGGGAGCAAACAGGATTAGATACCCTGGTAGTCCACGC
CGTAAACGATGGATACTAGGTGTGGGGGGTCTGACCCCCTCCGTGCCGCAGTTAACACAATAAGTATCCCACCTGGG
GAGTACGATCGCAAGGTTGAAACTCAAAGGAATTGACGGGGGCCCGCACAAGCGGTGGAGTATGTGGTTTAATTCGA
AGCAACGCGAAGAACCTTACCAGGGCTTGACATCCCACTAACGAGGCAGAGATGCGTTAGGTGCCCTTCGGGGAAAG
TGGAGACAGGTGGTGCATGGTTGTCGTCAGCTCGTGTCGTGAGATGTTGGGTTAAGTCCCGCAACGAGCGCAACCCT
TATTGTTAGTTGCTACGCAAGAGCACTCTAGCGAGACTGCCGTTGACAAAACGGAGGAAGGTGGGGACGACGTCAAA
TCATCATGCCCCTTATGTCCTGGGCCACACACGTACTACAATGGTGGTTAACAGAGGGAGGCAATACCGCGAGGTGG
AGCAAATCCCTAAAAGCCATCCCAGTTCGGATTGCAGGCTGAAACCCGCCTGTATGAAGTTGGAATCGCTAGTAATC
GCGGATCAGCATGCCGCGGTGAATACGTTCCCGGGCCTTGTACACACCGCCCGTCACACCATGAGAGTCGGGAACAC
CCGAAGTCCGTAGCCTAACCGCAAGGAGGGCGCGGCCGAAGGTGGGTTCGATAATTGGGGTGAAGTCGTAACAAGGT
AG

> SEQ ID NO: 94|NR_044054.1|*Blautia wexlerae* strain DSM 19850 16S ribosomal RNA gene, partial sequence
CAAGTCGAACGGGAATTANTTTATTGAAACTTCGGTCGATTTAATTTAATTCTAGTGGCGGACGGGTGAGTAACGCG
TGGGTAACCTGCCTTATACAGGGGGATAACAGTCAGAAATGGCTGCTAATACCGCATAAGCGCACAGAGCTGCATGG
CTCAGTGTGAAAAACTCCGGTGGTATAAGATGGACCCGCGTTGGATTAGCTTGTTGGTGGGGTAACGGCCCACCAAG
GCGACGATCCATAGCCGGCCTGAGAGGGTGAACGGCCACATTGGGACTGAGACACGGCCCAGACTCCTACGGGAGGC
AGCAGTGGGGAATATTGCACAATGGGGGAAACCCTGATGCAGCGACGCCGCGTGAAGGAAGAAGTATCTCGGTATGT
AAACTTCTATCAGCAGGGAAGATAGTGACGGTACCTGACTAAGAAGCCCCGGCTAACTACGTGCCAGCAGCCGCGGT
AATACGTAGGGGGCAAGCGTTATCCGGATTTACTGGGTGTAAAGGGAGCGTAGACGGTGTGGCAAGTCTGATGTGAA
AGGCATGGGCTCAACCTGTGGACTGCATTGGAAACTGTCATACTTGAGTGCCGGAGGGGTAAGCGGAATTCCTAGTG
TAGCGGTGAAATGCGTAGATATTAGGAGGAACACCAGTGGCGAAGGCGGCTTACTGGACGGTAACTGACGTTGAGGC
TCGAAAGCGTGGGGAGCAAACAGGATTAGATACCCTGGTAGTCCACGCCGTAAACGATGAATAACTAGGTGTCGGGT
GGCAAAGCCATTCGGTGCCGTCGCAAACGCAGTAAGTATTCCACCTGGGGAGTACGTTCGCAAGAATGAAACTCAAA
GGAATTGACGGGACCCGCACAAGCGGTGGAGCATGTGGTTTAATTCGAAGCAACGCGAAGAACCTTACCAAGTCTT
GACATCCGCCTGACCGATCCTTAACCGGATCTTTCCTTCGGGACAGGCGAGACAGGTGGTGCATGGTTGTCGTCAGC
TCGTGTCGTGAGATGTTGGGTTAAGTCCCGCAACGAGCGCAACCCCTATCCTCAGTAGCCAGCATTTAAGGTGGGCA
CTCTGGGGAGACTGCCAGGGATAACCTGGAGGAAGGCGGGGATGACGTCAAATCATCATGCCCCTTATGATTTGGGC
TACACACGTGCTACAATGGCGTAAACAAAGGGAAGCGAGATTGTGAGATGGAGCAAATCCCAAAAATAACGTCCCAG
TTCGGACTGTAGTCTGCAACCCGACTACACGAAGCTGGAATCGCTAGTAATCGCGGATCAGAATGCCGCGGTGAATA
CGTTCCCGGGTCTTGTACACACCGCCCGTCACACCATGGGAGTCAGTAACGCCCGAAGTCAGTGACCTAACTGCAAA
GAAGGAGCTGCCGAAGGCGGGACCGATGACTGGGGTGAAGTCGTAACAAGGT > SEQ ID NO: 95|NR_027558.1|*Anaerotruncus colihominis* strain WAL 14565 16S ribosomal
RNA gene, partial sequence
AACGGAGCTTACGTTTTGAAGTTTTCGGATGGATGAATGTAAGCTTAGTGGCGGACGGGTGAGTAACACGTGAGCAA

CCTGCCTTTCAGAGGGGGATAACAGCCGGAAACGGCTGCTAATACCGCATGATGTTGCGGGGGCACATGCCCCTGCA

ACCAAAGGAGCAATCCGCTGAAAGATGGGCTCGCGTCCGATTAGCCAGTTGGCGGGGTAACGGCCCACCAAAGCGAC

GATCGGTAGCCGGACTGAGAGGTTGAACGGCCACATTGGGACTGAGACACGGCCCAGACTCCTACGGGAGGCAGCAG

TGGGGGATATTGCACAATGGGCGAAAGCCTGATGCAGCGACGCCGCGTGAGGGAAGACGGTCTTCGGATTGTAAACC

TCTGTCTTTGGGGAAGAAAATGACGGTACCCAAAGAGGAAGCTCCGGCTAACTACGTGCCAGCAGCCGCGGTAATAC

GTAGGGAGCAAGCGTTGTCCGGAATTACTGGGTGTAAAGGGAGCGTAGGCGGGATGGCAAGTAGAATGTTAAATCCA

TCGGCTCAACCGGTGGCTGCGTTCTAAACTGCCGTTCTTGAGTGAAGTAGAGGCAGGCGGAATTCCTAGTGTAGCGG

TGAAATGCGTAGATATTAGGAGGAACACCAGTGGCGAAGGCGGCCTGCTGGGCTTTAACTGACGCTGAGGCTCGAAA

GCGTGGGGAGCAAACAGGATTAGATACCCTGGTAGTCCACGCCGTAAACGATGATTACTAGGTGTGGGGGGACTGAC

CCCTTCCGTGCCGCAGTTAACACAATAAGTAATCCACCTGGGGAGTACGGCCGCAAGGTTGAAACTCAAAGGAATTG

ACGGGGGCCCGCACAAGCAGTGGAGTATGTGGTTTAATTCGAAGCAACGCGAAGAACCTTACCAGGTCTTGACATCG

GCGTAATAGCCTAGAGAGTAGGTGAAGCCCTTCGGGGCATCCAGACAGGTGGTGCATGGTTGTCGTCAGCTCGTGTC

GTGAGATGTTGGGTTAAGTCCCGCAACGAGCGCAACCCTTATTATTAGTTGCTACGCAAGAGCACTCTAATGAGACT

GCCGTTGACAAAACGGAGGAAGGTGGGGATGACGTCAAATCATCATGCCCCTTATGACCTGGGCTACACACGTACTA

CAATGGCACTAAAACAGAGGGCGGCGACACCGCGAGGTGAAGCGAATCCCAGAAAAAGTGTCTCAGTTCAGATTGCA

GGCTGCAACCCGCCTGCATGAAGTCGGAATTGCTAGTAATCGCGGATCAGCATGCCGCGGTGAATACGTTCCCGGGC

CTTGTACACACCGCCCGTCACACCATGGGAGTCCGGGTAACACCCGAAGCCAGTAG

> SEQ ID NO: 96|NR_116747.1|*Ruminococcus faecis* strain Eg2 16S ribosomal RNA gene,
partial sequence
ATGCAAGTCGAACGAAGCACCTTGATTTGATTCTTCGGATGAAGATCTTGGTGACTGAGTGGCGGACGGGTGAGTAA

CGCGTGGGTAACCTGCCTCATACAGGGGGATAACAGTTAGAAATGACTGCTAATACCGCATAAGACCACAGCACCGC

ATGGTGCAGGGGTAAAAACTCCGGTGGTATGAGATGGACCCGCGTCTGATTAGGTAGTTGGTGGGGTAACGGCCTAC

CAAGCCGACGATCAGTAGCCGACCTGAGAGGGTGACCGGCCACATTGGGACTGAGACACGGCCCAAACTCCTACGGG

AGGCAGCAGTGGGGAATATTGCACAATGGGGGAAACCCTGATGCAGCGACGCCGCGTGAGCGATGAAGTATTTCGGT

ATGTAAAGCTCTATCAGCAGGGAAGAAAATGACGGTACCTGACTAAGAAGCACCGGCTAAATACGTGCCAGCAGCCG

CGGTAATACGTATGGTGCAAGCGTTATCCGGATTTACTGGGTGTAAAGGGAGCGTAGACGGAGTGGCAAGTCTGATG

TGAAAACCCGGGGCTCAACCCCGGGACTGCATTGGAAACTGTCAATCTAGAGTACCGGAGAGGTAAGCGGAATTCCT

AGTGTAGCGGTGAAATGCGTAGATATTAGGAGGAACACCAGTGGCGAAGGCGGCTTACTGGACGGTAACTGACGTTG

AGGCTCGAAAGCGTGGGGAGCAAACAGGATTAGATACCCTGGTAGTCCACGCCGTAAACGATGACTACTAGGTGTCG

GGCAGCAAAGCTGTTCGGTGCCGCAGCAAACGCAATAAGTAGTCCACCTGGGGAGTACGTTCGCAAGAATGAAACTC

AAAGGAATTGACGGGACCCGCACAAGCGGTGGAGCATGTGGTTTAATTCGAAGCAACGCGAAGAACCTTACCTGCT

CTTGACATCTCCCTGACCGGCAAGTAATGTTGCCTTTCCTTCGGGACAGGGATGACAGGTGGTGCATGGTTGTCGTC

AGCTCGTGTCGTGAGATGTTGGGTTAAGTCCCGCAACGAGCGCAACCCCTATCTTTAGTAGCCAGCGGTTTGGCCGG

GCACTCTAGAGAGACTGCCAGGGATAACCTGGAGGAAGGTGGGGATGACGTCAAATCATCATGCCCCTTATGAGCAG

GGCTACACACGTGCTACAATGGCGTAAACAAAGGGAGGCAGAACCGCGAGGTCGAGCAAATCCCAAAAATAACGTCT

CAGTTCGGATTGTAGTCTGCAACTCGACTACATGAAGCTGGAATCGCTAGTAATCGCGAATCAGAATGTCGCGGTGA

ATACGTTCCCGGGTCTTGTACACACCGCCCGTCACACCATGGGAGTCAGTAACGCCCGAAGTCAGTGACCCAACCGT

AAGGAGGAGCTGCCGAAG

-continued

> SEQ ID NO: 97|NR_028883.1|Dorea longicatena strain 111-35 16S ribosomal RNA gene, partial sequence
TAACGCGTGGGTAACCTGCCTCATACAGGGGGATAACAGTTAGAAATGACTGCTAATACCGCATAAGACCACGTACC

GCATGGTACAGTGGTAAAAACTCCGGTGGTATGAGATGGACCCGCGTCTGATTAGGTAGTTGGTGGGGTAACGGCCT

ACCAAGCCGACGATCAGTAGCCGACCTGAGAGGGTGACCGGCCACATTGGGACTGAGACACGGCCCAGACTCCTACG

GGAGGCAGCAGTGGGGAATATTGCACAATGGAGGAAACTCTGATGCAGCGACGCCGCGTGAAGGATGAAGTATTTCG

GTATGTAAACTTCTATCAGCAGGGAAGAAAATGACGGTACCTGACTAAGAAGCCCCGGCTAACTACGTGCCAGCAGC

CGCGGTAATACGTAGGGGGCAAGCGTTATCCGGATTTACTGGGTGTAAAGGGAGCGTAGACGGCACGGCAAGCCAGA

TGTGAAAAGCCCGGGGCTCAACCCCGGGACTGCATTTGGAACTGCTGAGCTAGAGTGTCGGAGAGGCAAGTGGAATT

CCTAGTGTAGCGGTGAAATGCGTAGATATTAGGAGGAACACCAGTGGCGAAGGCGGCTTGCTGGACGATGACTGACG

TTGAGGCTCGAAAGCGTGGGGAGCAAACAGGATTAGATACCCTGGTAGTCCACGCCGTAAACGATGACTGCTAGGTG

TCGGGTGGCAAAGCCATTCGGTGCCGCAGCTAACGCAATAAGCAGTCCACCTGGGGAGTACGTTCGCAAGAATGAAA

CTCAAAGGAATTGACGGGGACCCGCACAAGCGGTGGAGCATGTGGTTTAATTCGAAGCAACGCGAAGAACCTTACCT

GATCTTGACATCCCGATGACCGCTTCGTAATGGAAGTTTTTCTTCGGAACATCGGTGACAGGTGGTGCATGGTTGTC

GTCAGCTCGTGTCGTGAGATGTTGGGTTAAGTCCCGCAACGAGCGCAACCCCTATCTTCAGTAGCCAGCAGGTTAAG

CTGGGCACTCTGGAGAGACTGCCAGGGATAACCTGGAGGAAGGTGGGGATGACGTCAAATCATCATGCCCCTTATGA

CCAGGGCTACACACGTGCTACAATGGCGTAAACAAAGAGAAGCGAACTCGCGAGGGTAAGCAAATCTCAAAAATAAC

GTCTCAGTTCGGATTGTAGTCTGCAACTCGACTACATGAAGCTGGAATCGCTAGTAATCGCAGATCAGAATGCTGCG

GTGAATACGTTCCCGGGTCTTGTACACACCGCCCGTCACACCATGGGAGTCATAACGCCCGAAGTCAGTGACCCAAC

CGTAAGG

> SEQ ID NO: 98|NR_029164.1|Clostridium innocuum strain B-3 16S ribosomal RNA gene, partial sequence
ATGGAGAGTTTGATCCTGGCTCAGGATGAACGCTGGCGGCATGCCTAATACATGCAAGTCGAACGAAGTCTTCAGGA

AGCTTGCTTCCAAAAAGACTTAGTGGCGAACGGGTGAGTAACACGTAGGTAACCTGCCCATGTGTCCGGGATAACTG

CTGGAAACGGTAGCTAAAACCGGATAGGTATACGGAGCGCATGCTCTGTATATTAAAGCGCCCTTCAAGGCGTGAAC

ATGGATGGACCTGCGACGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGYAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGAA

ATTCAGTGCTGCAGTTAACGCAATAAGTTCTCCGCCTGGGGAGTATGCACGCAAGTTNGAAACTCAAAGGAATTGAC

GGGGGCCCGCACAAGCGNTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGACCACAAAGAGCAGCGACTTGGTGACAAGAAGCGAATCTCATAAAGATCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGA

-continued

> SEQ ID NO: 99|NR_104687.1|Blautia hansenii strain JCM 14655 16S ribosomal RNA gene, partial sequence
AGAGTTTGATCCTGGCTCAGGATGAACGCTGGCGGCGTGCTTAACACATGCAAGTCGAGCGAAGCACTTATCATTGA

CTCTTCGGAAGATTTGATATTTGACTGAGCGGCGGACGGGTGAGTAACGCGTGGGTAACCTGCCTCATACAGGGGAA

TAACAGTTAGAAATGGCTGCTAATGCCGCATAAGCGCACAGGACCGCATGGTCTGGTGTGAAAAACTGAGGTGGTAT

GAGATGGACCCGCGTCTGATTAGGTAGTTGGTGGGGTAACGGCCTACCAAGCCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTTTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGGTGCAAAGCAGTTCGGTGCCGCAGCAAA

CGCAATAAGTATTCCACCTGGGGAGTACGTTCGCAAGAATGAAACTCAAAGGAATTGACGGGGACCCGCACAAGCGG

TGGAGCATGTGGTTTAATTCGAAGCAACGCGAAGAACCTTACCAAGTCTTGACATCTGCCTGACCGTTCCTTAACCG

GAGCTTTCCTTCGGGACAGGCAAGACAGGTGGTGCATGGTTGTCGTCAGCTCGTGTCGTGAGATGTTGGGTTAAGTC

CCGCAACGAGCGCAACCCCTATCCTTAGTAGCCAGCAGTCCGGCTGGGCACTCTAGGGAGACTGCCGGGGATAACCC

GGAGGAAGGCGGGGACGACGTCAAATCATCATGCCCCTTATGATTTGGGCTACACACGTGCTACAATGGCGTAAACA

AAGGGAAGCGAAGCGGTGACGCTTAGCAAATCTCAAAAATAACGTCCCAGTTCGGACTGCAGTCTGCAACTCGACTG

CACGAAGCTGGAATCGCTAGTAATCGCGAATCAGAATGTCGCGGTGAATACGTTCCCGGGTCTTGTACACACCGCCC

GTCACACCATGGGAGTCAGTAACGCCCGAAGTCAGTGACCCAACCTTATGGAGGGAGCTGCCGAAGGCGGGACCGAT

AACTGGGGTGAAGTCGTAACAAGGTAACC

> SEQ ID NO: 100|NR_ 112933.1|Bacteroides cellulosilyticus strain JCM 15632 16S ribosomal RNA gene, partial sequence
AGAGTTTGATCCTGGCTCAGGATGAACGCTAGCTACAGGCTTAACACATGCAAGTCGAGGGGCAGCATGACCTAGCA

ATAGGTTGATGGCGACCGGCGCACGGGTGAGTAACACGTATCCAACCTACCGGTTATTCCGGGATAGCCTTTCGAAA

GAAAGATTAATACCGGATAGTATAACGAGAAGGCATCTTTTTGTTATTAAAGAATTTCGATAACCGATGGGGATGCG

TTCCATTAGTTTGTTGGCGGGGTAACGGCCCACCAAGACATCGATGGATAGGGGTTCTGAGAGGAAGGTCCCCCACA

TTGGAACTGAGACACGGTCCAAACTCCTACGGGAGGCAGCAGTGAGGAATATTGGTCAATGGACGAGAGTCTGAACC

AGCCAAGTAGCGTGAAGGATGACTGCCCTATGGGTTGTAAACTTCTTTTATATGGGAATAAAGTGAGCCACGTGTGG

CTTTTTGTATGTACCATACGAATAAGGATCGGCTAACTCCGTGCCAGCAGCCGCGGTAATACGGAGGATCCGAGCGT

TATCCGGATTTATTGGGTTTAAAGGGAGCGTAGGCGGACTATTAAGTCAGCTGTGAAAGTTTGCGGCTCAACCGTAA

AATTGCAGTTGATACTGGTCGTCTTGAGTGCAGTAGAGGTAGGCGGAATTCGTGGTGTAGCGGTGAAATGCTTAGAT

ATCACGAAGAACTCCGATTGCGAAGGCAGCTTACTGGACTGTAACTGACGCTGATGCTCGAAAGTGTGGGTATCAAA

CAGGATTAGATACCCTGGTAGTCCACACAGTAAACGATGAATACTCGCTGTTTGCGATATACAGCAAGCGGCCAAGC

GAAAGCATTAAGTATTCCACCTGGGGAGTACGCCGGCAACGGTGAAACTCAAAGGAATTGACGGGGCCCGCACAAG

CGGAGGAACATGTGGTTTAATTCGATGATACGCGAGGAACCTTACCCGGGCTTAAATTGCATCTGAATAATTTGGAA

ACAGATTAGCCGCAAGGCAGATGTGAAGGTGCTGCATGGTTGTCGTCAGCTCGTGCCGTGAGGTGTCGGCTTAAGTG

CCATAACGAGCGCAACCCTTATCTTTAGTTACTAACAGGTCATGCTGAGGACTCTAGAGAGACTGCCGTCGTAAGAT

GTGAGGAAGGTGGGGATGACGTCAAATCAGCACGGCCCTTACGTCCGGGGCTACACACGTGTTACAATGGGGGGTAC

AGAAGGCAGCTACACAGCGATGTGATGCTAATCCCAAAAGCCTCTCTCAGTTCGGATTGGAGTCTGCAACCCGACTC

```
CATGAAGCTGGATTCGCTAGTAATCGCGCATCAGCCACGGCGCGGTGAATACGTTCCCGGGCCTTGTACACACCGCC

CGTCAAGCCATGAAAGCCGGGGGTACCTGAAGTCCGTAACCGCAAGGAGCGGCCTAGGGTAAAACTGGTAATTGGGG

CTAAGTCGTA
```

> SEQ ID NO: 101|NR_112940.1|*Bacteroides ovatus* strain JCM 5824 16S ribosomal RNA gene, partial sequence

```
GGCTCAGGATGAACGCTAGCTACAGGCTTAACACATGCAAGTCGAGGGGCAGCATTTTAGTTTGCTTGCAAACTGAA

GATGGCGACCGGCGCACGGGTGAGTAACACGTATCCAACCTGCCGATAACTCCGGAATAGCCTTTCGAAAGAAAGAT

TAATACCGGATAGCATACGAATATCGCATGATATTTTTATTAAAGAATTTCGGTTATCGATGGGGATGCGTTCCATT

AGTTTGTTGGCGGGGTAACGGCCCACCAAGACTACGATGGATAGGGGTTCTGAGAGGAAGGTCCCCCACATTGGAAC

TGAGACACGGTCCAAACTCCTACGGGAGGCAGCAGTGAGGAATATTGGTCAATGGGCGAGAGCCTGAACCAGCCAAG

TAGCGTGAAGGATGAAGGCTCTATGGGTCGTAAACTTCTTTTATATGGGAATAAAGTTTTCCACGTGTGGAATTTTG

TATGTACCATATGAATAAGGATCGGCTAACTCCGTGCCAGCAGCCGCGGTAATACGGAGGATCCGAGCGTTATCCGG

ATTTATTGGGTTTAAAGGGAGCGTAGGTGGATTGTTAAGTCAGTTGTGAAAGTTTGCGGCTCAACCGTAAAATTGCA

GTTGAAACTGGCAGTCTTGAGTACAGTAGAGGTGGGCGGAATTCGTGGTGTAGCGGTGAAATGCTTAGATATCACGA

AGAACTCCGATTGCGAAGGCAGCTCACTAGACTGTTACTGACACTGATGCTCGAAAGTGTGGGTATCAAACAGGATT

AGATACCCTGGTAGTCCACACAGTAAACGATGAATACTCGCTGTTTGCGATATACAGTAAGCGGCCAAGCGAAAGCA

TTAAGTATTCCACCTGGGGAGTACGCCGGCAACGGTGAAACTCAAAGGAATTGACGGGGGCCCGCACAAGCGGAGGA

ACATGTGGTTTAATTCGATGATACGCGAGGAACCTTACCCGGGCTTAAATTGCAACAGAATATATTGGAAACAGTAT

AGCCGTAAGGCTGTTGTGAAGGTGCTGCATGGTTGTCGTCAGCTCGTGCCGTGAGGTGTCGGCTTAAGTGCCATAAC

GAGCGCAACCCTTATCTTTAGTTACTAACAGGTTATGCTGAGGACTCTAGAGAGACTGCCGTCGTAAGATGTGAGGA

AGGTGGGGATGACGTCAAATCAGCACGGCCCTTACGTCCGGGGCTACACACGTGTTACAATGGGGGGTACAGAAGGC

AGCTACCTGGCGACAGGATGCTAATCCCAAAAACCTCTCTCAGTTCGGATCGAAGTCTGCAACCCGACTTCGTGAAG

CTGGATTCGCTAGTAATCGCGCATCAGCCATGGCGCGGTGAATACGTTCCCGGGCCTTGTACACACCGCCCGTCAAG

CCATGAAAGCCGGGGGTACCTGAAGTACGTAACCGCAAGGAGCGTCCTAGGGTAAAACTGGTAATTGGGGCTA
```

> SEQ ID NO: 102|NR_117563.1|*Eubacterium fissicatena* 16S ribosomal RNA gene, partial sequence

```
TAGAGTTTGATCCTGGCTCAGGATGAACGCTGGCGGCGTGCTTAACACATGCAAGTCGAGCGAAGCGCTTTACTTAG

ATTTCTTCGGATTGAAGAGTTTTGCGACTGAGCGGCGGACGGGTGAGTAACGCGTGGGTAACCTGCCTCATACAGGG

GGATAACAGTTAGAAATGACTGCTAATACCGCATAAGACCACAGTACCGCATGGTACAGTGGGAAAAACTCCGGTGG

TATGAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGGGAAACCCTGATGCAGCGACGCCGCGTGAAGGATGAAGTATTTCGGTATGTAAACTTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTTATGTAAGTCTGATGTGAAAACCCGGGGCTCAACCCCGGGAC

TGCATTGGAAACTATGTAACTAGAGTGTCGGAGAGGTAAGTGGAATTCCTAGTGTAGCGGTGAAATGCGTAGATATT

AGGAGGAACACCAGTGGCGAAGGCGGCTTACTGGACGATCACTGACGTTGAGGCTCGAAAGCGTGGGGAGCAAACAG

GATTAGATACCCTGGTAGTCCACGCCGTAAACGATGAATACTAGGTGTCGGGTGGCAAAGCCATTCGGTGCCGCAGC

AAACGCAATAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGCTCTTGACATCCCACTGACCGGCGTGTAA

TGGCGCCTTCCCTTCGGGGCAGTGGAGACAGGTGGTGCATGGTTGTCGTCAGCTCGTGTCGTGAGATGTTGGGTTAA

GTCCCGCAACGAGCGCAACCCTTATCTTTAGTAGCCAGCGGTTTGGCCGGGCACTCTAGAGAGACTGCCAGGGATAA

CCTGGAGGAAGGTGGGGATGACGTCAAATCATCATGCCCCTTATGAGCAGGGCTACACACGTGCTACAATGGCGTAA

ACAAAGGGAGGCAATACCGCGAGGTTGAGCAAATCCCAAAAATAACGTCTCAGTTCGGATTGTAGTCTGCAACTCGA
```

> SEQ ID NO: 103|NR_104700.1|Blautia coccoides strain JCM 1395 16S ribosomal RNA gene, partial sequence AGAGTTTGATCCTGGCTCAGGATGAACGCTGGCGGCGTGCTTAACACATGCAAGTCGAGCGAAGCGCTAAGACAGAT
TTCTTCGGATTGAAGTCTTTGTGACTGAGCGGCGGACGGGTGAGTAACGCGTGGGTAACCTGCCTCATACAGGGGGA
TAACAGTTAGAAATGACTGCTAATACCGCATAAGCGCACAGGACCGCATGGTCTGGTGTGAAAAACTCCGGTGGTAT
GAGATGGACCCGCGTCTGATTAGCTAGTTGGAGGGGTAACGGCCCACCAAGGCGACGATCAGTAGCCGGCCTGAGAG
GGTGAACGGCCACATTGGGACTGAGACACGGCCCAGACTCCTACGGGAGGCAGCAGTGGGGAATATTGCACAATGGG
GGAAACCCTGATGCAGCGACGCCGCGTGAAGGAAGAAGTATCTCGGTATGTAAACTTCTATCAGCAGGGAAGAAAT
GACGGTACCTGACTAAGAAGCCCCGGCTAACTACGTGCCAGCAGCCGCGGTAATACGTAGGGGGCAAGCGTTATCCG
GATTTACTGGGTGTAAAGGGAGCGTAGACGGAAGAGCAAGTCTGATGTGAAAGGCTGGGGCTTAACCCCAGGACTGC
ATTGGAAACTGTTGTTCTAGAGTGCCGGAGAGGTAAGCGGAATTCCTAGTGTAGCGGTGAAATGCGTAGATATTAGG
AGGAACACCAGTGGCGAAGGCGGCTTACTGGACGGTAACTGACGTTGAGGCTCGAAAGCGTGGGGAGCAAACAGGAT
TAGATACCCTGGTAGTCCACGCCGTAAACGATGAATACTAGGTGTCGGGTGGCAAAGCCATTCGGTGCCGCAGCAAA
CGCAATAAGTATTCCACCTGGGGAGTACGTTCGCAAGAATGAAACTCAAAGGAATTGACGGGGACCCGCACAAGCGG
TGGAGCATGTGGTTTAATTCGAAGCAACGCGAAGAACCTTACCAAGTCTTGACATCCCTCTGACCGTCCCGTAACGG
GGGCTTCCCTTCGGGGCAGAGGAGACAGGTGGTGCATGGTTGTCGTCAGCTCGTGTCGTGAGATGTTGGGTTAAGTC
CCGCAACGAGCGCAACCCTTATCCTTAGTAGCCAGCACATGATGGTGGGCACTCTAGGGAGACTGCCGGGGATAACC
CGGAGGAAGGCGGGGACGACGTCAAATCATCATGCCCCTTATGATTTGGGCTACACACGTGCTACAATGGCGTAAAC
AAAGGGAAGCGAGACAGCGATGTTGAGCGAATCCCAAAAATAACGTCCCAGTTCGGACTGCAGTCTGCAACTCGACT
GCACGAAGCTGGAATCGCTAGTAATCGCGGATCAGAATGCCGCGGTGAATACGTTCCCGGGTCTTGTACACACCGCC
CGTCACACCATGGGAGTCAGTAACGCCCGAAGTCAGTGACCTAACCGAAAGGAAGGAGCTGCCGAAGGCGGGACCGA
TAACTGGGGTGAAGTCGTAACAAGGTAACC > SEQ ID NO: 104|NR_109014.1|Blautia faecis strain M25 16S ribosomal RNA gene, partial sequence ATAACAGCCAGAAATGACTGCTAATACCGCATAAGCGCACAGAACCGCATGGTTCGGTGTGAAAAACTCCGGTGGTA
TAAGATGGACCCGCGTTGGATTAGCTAGTTGGCAGGGCAGCGGCCTACCAAGGCGACGATCCATAGCCGGCCTGAGA
GGGTGAACGGCCACATTGGGACTGAGACACGGCCCAGACTCCTACGGGAGGCAGCAGTGGGGAATATTGCACAATGG
GGGAAACCCTGATGCAGCGACGCCGCGTGAAGGAAGAAGTATCTCGGTATGTAAACTTCTATCAGCAGGGAAGATAA
TGACGGTACCTGACTAAGAAGCCCCGGCTAACTACGTGCCAGCAGCCGCGGTAATACGTAGGGGGCAAGCGTTATCC
GGATTTACTGGGTGTAAAGGGAGCGTAGACGGCGCAGCAAGTCTGATGTGAAAGGCAGGGGCTTAACCCCTGGACTG
CATTGGAAACTGCTGTGCTTGAGTGCCGGAGGGGTAAGCGGAATTCCTAGTGTAGCGGTGAAATGCGTAGATATTAG
GAGGAACACCAGTGGCGAAGGCGGCTTACTGGACGGTAACTGACGTTGAGGCTCGAAAGCGTGGGGAGCAAACAGGA
TTAGATACCCTGGTAGTCCACGCCGTAAACGATGAATACTAGGTGTCAGGGAGCACAGCTCTTTGGTGCCGCCGCAA
ACGCATTAAGTATTCCACCTGGGGAGTACGTTCGCAAGAATGAAACTCAAAGGAATTGACGGGACCCGCACAAGCG
GTGGAGCATGTGGTTTAATTCGAAGCAACGCGAAGAACCTTACCAAATCTTGACATCCCTCTGACCGGGACTTAACC
GTCCCTTTCCTTCGGGACAGGGGAGACAGGTGGTGCATGGTTGTCGTCAGCTCGTGTCGTGAGATGTTGGGTTAAGT
CCCGCAACGAGCGCAACCCCTATCCTTAGTAGCCAGCACGCARTGGTGGGCACTCTGAGGAGACTGCCAGGGATAAC
CTGGAGGAAGGCGGGGATGACGTCAAATCATCATGCCCCTTATGATTTGGGCTACACACGTGCTACAATGGCGTAAA
CAAAGGGAAGCGAACCCGCGAGGGTGGGCAAATCTCAAAAATAACGTCCCAGTTCGGACTGCAGTCTGCAACTCGAC -continued

TGCACGAAGCTGGAATCGCTAGTAATCGCGGATCAGAATGCCGCGGTGAATACGTTCCCGGGTCTTGTACACACCGC

CCGTCACACCATGGGAGTCAGTAACGCCCG

> SEQ ID NO: 105|NR_036928.1|*Clostridium hathewayi* strain 1313 16S ribosomal RNA gene, partial sequence

CTCAGGATGAACGCTGGCGGCGTGCTTAACACATGCAAGTCGAGCGAAGCGGTTTCAATGAAGTTTTCGGATGGATT

TGAAATTGACTTAGCGGCGGACGGGTGAGTAACGCGTGGGTAACCTGCCTTACACTGGGGGATAACAGTTAGAAATG

ACTGCTAATACCGCATAAGCGCACAGGGCCGCATGGNCTGGTGTGAAAAACTCCGGNGGTGTAAGATGGACCCGCGT

CTGATTAGGTAGTTGGNGGGGTAACGGCCCACCAAGCCGACGATCAGTAGCCGACCTGAGAGGGTGACCGGCCACAT

TGGGACTGAGACACGGCCCAAACTCCTACGGGAGGCAGCAGTGGGGAATATTGGACAATGGGCGAAAGCCTGATCCA

GCGACGCCGCGTGAGTGAAGAAGTATTTCGGTATGTAAAGCTCTATCAGCAGGGAAGAAAATGACGGTACCTGACTA

AGAAGCCCCGGCTAACTACGTGCCAGCAGCCGCGGTAATACGTAGGGGGCAAGCGTTATCCGGATTTACTGGGTGTA

AAGGGAGCGTAGACGGTTTAGCAAGTCTGAAGTGAAAGCCCGGGGCTCAACCCCGGTACTGCTTTGGAAACTGTTAG

ACTTGAGTGCAGGAGAGGTAAGTGGAATTCCTAGTGTAGCGGTGAAATGCGTAGATATTAGGAGGAACACCAGTGGC

GAAGGCGGCTTACTGGACTGTAACTGACGTTGAGGCTCGAAAGCGTGGGGAGCAAACAGGATTAGATACCCTGGTAG

TCCACGCCGTAAACGATGAATACTAGGTGTCGGGGGCAAAGCCCTTCGGTGCCGCCGCAAACGCAATAAGTATTCC

ACCTGGGGAGTACGTTCGCAAGAATGAAACTCAAAGGAATTGACGGGGACCCGCACAAGCGGTGGAGCATGTGGTTT

AATTCGAAGCAACGCGAAGAACCTTACCAAGTCTTGACATCCCACTGAAAACACNTTAACCGTGATCCCTCTTCGGA

GCAGTGGAGACAGGTGGTGCATGGTTGTCGTCAGCTCGTGTCGTGAGATGTTGGGTTAAGTCCCGCAACGAGCGCAA

CCCTTATCCTTAGTAGCCAGCGAGTAGAGTCGGGCACTCTGGGGAGACTGCCAGGGATAACCTGGAGGAAGGTGGGG

ATGACGTCAAATCATCATGCCCCTTATGATTTGGGCTACACACGTGCTACAATGGCGTAAACAAAGGGAGGCAAAGG

AGCGATCTGGAGCAAACCCCAAAAATAACGTCTCAGTTCGGATTGCAGGCTGCAACTCGCCTGCATGAAGCTGGAAT

CGCTAGTAATCGCGAATCAGAATGTCGCGGTGAATACGTTCCCGGGTCTTGTACACACCGCCCGTCACACCATGGGA

GTTGGTAACGCCCGAAGTCAGTGACCCAACCGAAAGGAGGGAGCT

> SEQ ID NO: 106|NR_113270.1|*Blautia producta* strain JCM 1471 16S ribosomal RNA gene, partial sequence

AGAGTTTGATCCTGGCTCAGGATGAACGCTGGCGGCGTGCTTAACACATGCAAGTCGAGCGAAGCACTAAGACGGAT

TTCTTCGGATTGAAGTCTTTGTGACTGAGCGGCGGACGGGTGAGTAACGCGTGGGTAACCTGCCTCATACAGGGGGA

TAACAGTTAGAAATGACTGCTAATACCGCATAAGCGCACAGGACCGCATGGTCTGGTGTGAAAAACTCCGGTGGTAT

GAGATGGACCCGCGTCTGATTAGCTAGTTGGAGGGGTAACGGCCCACCAAGGCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTGTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGTGGCAAAGCCATTCGGTGCCGCAGCAAA

CGCAATAAGTATTCCACCTGGGGAGTACGTTCGCAAGAATGAAACTCAAAGGAATTGACGGGACCCGCACAAGCGG

TGGAGCATGTGGTTTAATTCGAAGCAACGCGAAGAACCTTACCAAGTCTTGACATCCCTCTGACCGTCCCGTAACGG

GGACTTCCCTTCGGGGCAGAGGAGACAGGTGGTGCATGGTTGTCGTCAGCTCGTGTCGTGAGATGTTGGGTTAAGTC

CCGCAACGAGCGCAACCCTTATCCTTAGTAGCCAGCACATGATGGTGGGCACTCTAGGGAGACTGCCGGGGATAACC

CGGAGGAAGGCGGGGACGACGTCAAATCATCATGCCCCTTATGATTTGGGCTACACACGTGCTACAATGGCGTAAAC

AAAGGGAAGCGAGACAGCGATGTTGAGCGAATCCCAAAAATAACGTCCCAGTTCGGACTGCAGTCTGCAACTCGACT

GCACGAAGCTGGAATCGCTAGTAATCGCGGATCAGAATGCCGCGGTGAATACGTTCCCGGGTCTTGTACACACCGCC

CGTCACACCATGGGAGTCAGTAACGCCCGAAGTCAGTGACCTAACCGAAAGGAAGGAGCTGCCGAAGGCGGGACCGA

TAACTGGGGTGAAGTCGTAACAAGGTAACC

> SEQ ID NO: 107|NR_104799.1|*Anaerostipes hadrus* strain DSM 3319 16S ribosomal RNA gene, partial sequence
TGGCTCAGGATGAACGCTGGCGGCGTGCTTAACACATGCAAGTCGAACGAAGCTGCTTAACTGATCTTCTTCGGAAT

TGACGTTTTGTAGACTGAGTGGCGGACGGGTGAGTAACGCGTGGGCAACCTGCCCTGTACAGGGGGATAACAGTCAG

AAATGACTGCTAATACCGCATAAGACCACAGCACCGCATGGTGCAGGGGTAAAAACTCCGGTGGTACAGGATGGACC

CGCGTCTGATTAGCTGGTTGGTGAGGTAACGGCTCACCAAGGCGACGATCAGTAGCCGGCTTGAGAGAGTGAACGGC

CACATTGGGACTGAGACACGGCCCAAACTCCTACGGGAGGCAGCAGTGGGGAATATTGCACAATGGGGGAAACCCTG

ATGCAGCGACGCCGCGTGAGTGAAGAAGTATCTCGGTATGTAAAGCTCTATCAGCAGGGAAGAAAATGACGGTACCT

GACTAAGAAGCCCCGGCTAACTACGTGCCAGCAGCCGCGGTAATACGTAGGGGGCAAGCGTTATCCGGAATTACTGG

GTGTAAAGGGTGCGTAGGTGGTATGGCAAGTCAGAAGTGAAAACCCAGGGCTTAACTCTGGGACTGCTTTTGAAACT

GTCAGACTGGAGTGCAGGAGAGGTAAGCGGAATTCCTAGTGTAGCGGTGAAATGCGTAGATATTAGGAGGAACATCA

GTGGCGAAGGCGGCTTACTGGACTGAAACTGACACTGAGGCACGAAAGCGTGGGGAGCAAACAGGATTAGATACCCT

GGTAGTCCACGCCGTAAACGATGAATACTAGGTGTCGGGGCCGTAGAGGCTTCGGTGCCGCAGCCAACGCAGTAAGT

ATTCCACCTGGGGAGTACGTTCGCAAGAATGAAACTCAAAGGAATTGACGGGACCCGCACAAGCGGTGGAGCATGT

GGTTTAATTCGAAGCAACGCGAAGAACCTTACCTGGTCTTGACATCCTTCTGACCGGTCCTTAACCGGACCTTTCCT

TCGGGACAGGAGAGACAGGTGGTGCATGGTTGTCGTCAGCTCGTGTCGTGAGATGTTGGGTTAAGTCCCGCAACGAG

CGCAACCCCTATCTTTAGTAGCCAGCATTTCAGGTGGGCACTCTAGAGAGACTGCCAGGGATAACCTGGAGGAAGGT

GGGGACGACGTCAAATCATCATGCCCCTTATGACCAGGGCTACACACGTGCTACAATGGCGTAAACAGAGGGAAGCA

GCCTCGTGAGAGTGAGCAAATCCCAAAAATAACGTCTCAGTTCGGATTGTAGTCTGCAACTCGACTACATGAAGCTG

GAATCGCTAGTAATCGCGAATCAGAATGTCGCGGTGAATACGTTCCCGGGTCTTGTACACACCGCCCGTCACACCAT

GGGAGTCAGTAACGCCCGAAGTCAGTGACCCAACCGTAAGGAGGGAGCTGCCGAAGGCGGGACCGATAACTGGGGTG

AAGTCGTAACAAGGTAGCCGTATCGGAAGGTGCGGCTGGATCACCTCCTTTC

> SEQ ID NO: 108|NR_117142.1|*Eubacterium fissicatena* strain DSM 3598 16S ribosomal RNA gene, partial sequence
GTTTGATCCTGGCTCAGGATGAACGCTGGCGGCGTGCTTAACACATGCAAGTCGAGCGAAGCGCTTTACTTAGATTT

CTTCGGATTGAAGAGTTTTGCGACTGAGCGGCGGACGGGTGAGTAACGCGTGGGTAACCTGCCTCATACAGGGGGAT

AACAGTTAGAAATGACTGCTAATACCGCATAAGACCACAGTACCGCATGGTACAGTGGGAAAAACTCCGGTGGTATG

AGATGGACCCGCGTCTGATTAGCTAGTTGGTAAGGTAACGGCTTACCAAGGCAACGATCAGTAGCCGACCTGAGAGG

GTGACCGGCCACATTGGGACTGAGACACGGCCCAAACTCCTACGGGAGGCAGCAGTGGGGAATATTGCACAATGGG

GAAACCCTGATGCAGCGACGCCGCGTGAAGGATGAAGTATTTCGGTATGTAAACTTCTATCAGCAGGGAAGAAAATG

ACGGTACCTGACTAAGAAGCCCCGGCTAACTACGTGCCAGCAGCCGCGGTAATACGTAGGGGCAAGCGTTATCCGG

ATTTACTGGGTGTAAAGGGAGCGTAGACGGTTATGTAAGTCTGATGTGAAAACCCGGGGCTCAACCCCGGGACTGCA

TTGGAAACTATGTAACTAGAGTGTCGGAGAGGTAAGTGGAATTCCTAGTGTAGCGGTGAAATGCGTAGATATTAGGA

GGAACACCAGTGGCGAAGGCGGCTTACTGGACGATCACTGACGTTGAGGCTCGAAAGCGTGGGGAGCAAACAGGATT

AGATACCCTGGTAGTCCACGCCGTAAACGATGAATACTAGGTGTCGGGTGGCAAAGCCATTCGGTGCCGCAGCAAAC

GCAATAAGTATTCCACCTGGGGAGTACGTTCGCAAGAATGAAACTCAAAGGAATTGACGGGACCCGCACAAGCGGT

GGAGCATGTGGTTTAATTCGAAGCAACGCGAAGAACCTTACCTGCTCTTGACATCCCACTGACCGGCGTGTAATGGC

GCCTTCCCTTCGGGGCAGTGGAGACAGGTGGTGCATGGTTGTCGTCAGCTCGTGTCGTGAGATGTTGGGTTAAGTCC

CGCAACGAGCGCAACCCTTATCTTTAGTAGCCAGCGGTTTGGCCGGGCACTCTAGAGAGACTGCCAGGGATAACCTG

GAGGAAGGTGGGGATGACGTCAAATCATCATGCCCCTTATGAGCAGGGCTACACACGTGCTACAATGGCGTAAACAA

AGGGAGGCAATACCGCGAGGTTGAGCAAATCCCAAAAATAACGTCTCAGTTCGGATTGTAGTCTGCAACTCGACTAC

ATGAAGCTGGAATCGCTAGTAATCGCGAATCAGAATGTCGCGGTGAATACGTTCCCGGGTCTTGTACACACCGCCCG

TCACACCATGGGAGTTGGTAACGCCCGAAGTCAGTGACCCAACCGTAAGGAGGGAGCTGCCGAAGGCGGGATCGATA

ACTGGGGTGAAGTCGTAACAAGGTAGCCGTATCGGAAGGTGCGGCTGGATCACCTCCTTT

> SEQ ID NO: 109|NR_117147.1|*Eubacterium contortum* strain DSM 3982 16S ribosomal RNA gene, partial sequence
TTTGATCCTGGCTCAGGATGAACGCTGGCGACGTGCTTAACACATGCAAGTCGAGCGAAGCACTTTACTTTGATTTC

TTCGGAATGAAAGGTTTTGTGACTGAGCGGCGGACGGGTGAGTAACGCGTGGGTAACCTGCCTCATACAGGGGGATA

ACAGTTAGAAATGACTGCTAATACCGCATAAGACCACAGTACCGCATGGTACAGTGGGAAAAACTCCGGTGGTATGA

GATGGACCCGCGTCTGATTAGCTAGTTGGTAAGGTAACGGCTTACCAAGGCGACGATCAGTAGCCGACCTGAGAGGG

TGACCGGCCACATTGGGACTGAGACACGGCCCAAACTCCTACGGGAGGCAGCAGTGGGGAATATTGCACAATGGGGG

AAACCCTGATGCAGCGACGCCGCGTGAAGGATGAAGTATTTCGGTATGTAAACTTCTATCAGCAGGGAAGAAAATGA

CGGTACCTGACTAAGAAGCCCCGGCTAACTACGTGCCAGCAGCCGCGGTAATACGTAGGGGGCAAGCGTTATCCGGA

TTTACTGGGTGTAAAGGGAGCGTAGACGGTTATGTAAGTCTGATGTGAAAACCCGGGGCTCAACCCCGGGACTGCAT

TGGAAACTATGTAACTAGAGTGTCGGAGAGGTAAGTGGAATTCCTAGTGTAGCGGTGAAATGCGTAGATATTAGGAG

GAACACCAGTGGCGAAGGCGGCTTACTGGACGATGACTGACGTTGAGGCTCGAAAGCGTGGGGAGCAAACAGGATTA

GATACCCTGGTAGTCCACGCCGTAAACGATGAATACTAGGTGTCGGGTGGCAAAGCCATTCGGTGCCGCAGCAAACG

CAATAAGTATTCCACCTGGGGAGTACGTTCGCAAGAATGAAACTCAAAGGAATTGACGGGGACCCGCACAAGCGGTG

GAGCATGTGGTTTAATTCGAAGCAACGCGAAGAACCTTACCTGCTCTTGACATCCCCCTGACCGGCGTGTAATGGTG

CCTTTCCTTCGGGACAGGGGAGACAGGTGGTGCATGGTTGTCGTCAGCTCGTGTCGTGAGATGTTGGGTTAAGTCCC

GCAACGAGCGCAACCCTTATCTTTAGTAGCCAGCGGTTTGGCCGGGCACTCTAGAGAGACTGCCAGGGATAACCTGG

AGGAAGGTGGGGATGACGTCAAATCATCATGCCCCTTATGAGCAGGGCTACACACGTGCTACAATGGCGTAAACAAA

GGGAGGCGAAGCCGTGAGGTGGAGCAAATCCCAAAAATAACGTCTCAGTTCGGATTGTAGTCTGCAACTCGACTACA

TGAAGCTGGAATCGCTAGTAATCGCGAATCAGAATGTCGCGGTGAATACGTTCCCGGGTCTTGTACACACCGCCCGT

CACACCATGGGAGTTGGTAACGCCCGAAGTCAGTGACCCAACCGCAAGGAGGGAGCTGCCGAGGGTGGGACCGATAA

CTGGGGTGAAGTCGTAACAAGGTAGCCGTATCGGAAGGTGCGGCTGGATCACCTCCTTTCT

> SEQ ID NO: 110|NR_113410.1|*Clostridium bolteae* strain JCM 12243 16S ribosomal RNA gene, partial sequence
TTTTAATTGACTGAGTGGCGGACGGGTGAGTAACGCGTGGATAACCTGCCTCACACTGGGGGATAACAGTTAGAAAT

GACTGCTAATACCGCATAAGCGCACAGTACCGCATGGTACAGTGTGAAAAACTCCGGTGGTGTGAGATGGATCCGCG

TCTGATTAGCCAGTTGGCGGGGTAACGGCCCACCAAAGCGACGATCAGTAGCCGACCTGAGAGGGTGACCGGCCACA

TTGGGACTGAGACACGGCCCAAACTCCTACGGGAGGCAGCAGTGGGGAATATTGCACAATGGGCGAAAGCCTGATGC

AGCGACGCCGCGTGAGTGAAGAAGTATTTCGGTATGTAAAGCTCTATCAGCAGGGAAGAAAATGACGGTACCTGACT

AAGAAGCCCCGGCTAACTACGTGCCAGCAGCCGCGGTAATACGTAGGGGGCAAGCGTTATCCGGATTTACTGGGTGT

AAAGGGAGCGTAGACGGCGAAGCAAGTCTGAAGTGAAAACCCAGGGCTCAACCCTGGGACTGCTTTGGAAACTGTTT

TGCTAGAGTGTCGGAGAGGTAAGTGGAATTCCTAGTGTAGCGGTGAAATGCGTAGATATTAGGAGGAACACCAGTGG

CGAAGGCGGCTTACTGGACGATAACTGACGTTGAGGCTCGAAAGCGTGGGGAGCAAACAGGATTAGATACCCTGGTA

GTCCACGCCGTAAACGATGAATGCTAGGTGTTGGGGGCAAAGCCCTTCGGTGCCGTCGCAAACGCAGTAAGCATTC

CACCTGGGGAGTACGTTCGCAAGAATGAAACTCAAAGGAATTGACGGGGACCCGCACAAGCGGTGGAGCATGTGGTT

TAATTCGAAGCAACGCGAAGAACCTTACCAAGTCTTGACATCCTCTTGACCGGCGTGTAACGGCGCCTTCCCTTCGG

GGCAAGAGAGACAGGTGGTGCATGGTTGTCGTCAGCTCGTGTCGTGAGATGTTGGGTTAAGTCCCGCAACGAGCGCA

ACCCTTATCCTTAGTAGCCAGCAGGTAAAGCTGGGCACTCTAGGGAGACTGCCAGGGATAACCTGGAGGAAGGTGGG

GATGACGTCAAATCATCATGCCCCTTATGATTTGGGCTACACACGTGCTACAATGGCGTAAACAAAGGGAAGCAAGA

CAGTGATGTGGAGCAAATCCCAAAAATAACGTCCCAGTTCGGACTGTAGTCTGCAACCCGACTACACGAAGCTGGAA

TCGCTAGTAATCGCGAATCAGAATGTCGCGGTGAATACGTTCCCGGGTCTTGTACACACCGCCCGTCACACCATGGG

AGTCAGCAACGCCCGAAGTCAGTGACCCAACTCGCAAGAGAGGGAGCTGCCGAAGGCGGGGCAGGTAACTGGGGTGA

AGTC

> SEQ ID NO: 111|NR_041960.1|*Blautia luti* strain BInIX 16S ribosomal RNA gene, complete sequence
GTGGGTAACCTGCCTTATACAGGGGGATAACAGTCAGAAATGACTGCTAATACCGCATAAGCGCACAGAGCTGCATG

GCTCCGGTGTGAAAAACTCCGGTGGTATAAGATGGACCCGCGTTGGATTAGCTAGTTGGTGAGGTAACGGCCCACCA

AGGCGACGATCCATAGCCGGCCTGAGAGGGTGAACGGCCACATTGGGACTGAGACACGGCCCAGACTCCTACGGGAG

GCAGCAGTGGGGAATATTGCACAATGGGGGAAACCCTGATGCAGCGACGCCGCGTGAAGGAAGAAGTATCTCGGTAT

GTAAACTTCTATCAGCAGGGAAGAAAATGACGGTACCTGACTAAGAAGCCCCGGCTAACTACGTGCCAGCAGCCGCG

GTAATACGTAGGGGGCAAGCGTTATCCGGATTTACTGGGTGTAAAGGGAGCGTAGACGGCATGGACAAGTCTGATGT

GAAAGGCTGGGGCTCAACCCCGGGACTGCATTGGAAACTGCCCGTCTTGAGTGCCGGAGAGGTAAGCGGAATTCCTA

GTGTAGCGGTGAAATGCGTAGATATTAGGAGGAACACCAGTGGCGAAGGCGGCTTACTGGACGGTAACTGACGTTGA

GGCTCGAAAGCGTGGGGAGCAAACAGGATTAGATACCCTGGTAGTCCACGCGGTAAACGATGAATCCTAGGTGTCGG

GGAGCAAANNNNTTCGGTGCCGCCGCAAACGCATTAAGCATTCCACCTGGGGAGTACGTTCGCAAGAATGAAACTCA

AAGGAATTGACGGGACCCGCACAAGCGGTGGAGCATGTGGTTTAATTCGAAGCAACGCGAAGAACCTTACCAAGTC

TTGACATCCCTCTGACCGAGTATGTATGGTACTTTTCCTTCGGGAGAGAGAGGAGACAGGTGGTGCATGGTTGTCGT

CAGCTCGTGTCGTGAGATGTTGGGTTAAGTCCCGCAACGAGCGCAACCCCTATCCCCAGTAGCCAGCGGTTCGGCCG

GGCACTCTGAGGAGACTGCCAGGGATAACCTGGAGGAAGGCGGGGATGACGTCAAATCATCATGCCCCTTATGATTT

GGGCTACACACGTGCTACAATGGCGTAAACAAAGGGAAGCAAGCCTGCGAGGGTGGGCAAATCCCAAAAATAACGTC

CCAGTTCGGACTGTAGTCTGCAACCCGACTACACGAAGCTGGAATCGCTAGTAATCGCGGATCAGAATGCCGCGGTG

AATACGTTCCCGGGTCTTGTACACACCGCCCGTCACACCATGGGAGTCAGTAACGCCCGAAGTCAGTGACCTAACT

> SEQ ID NO: 112|NR_074306.1|*Acidaminococcus intestini* RyC-MR95 strain RyC-MR95 16S ribosomal RNA, complete sequence
CTGGCGGCGTGCTTAACACATGCAAGTCGAACGGAGAACTTATTTCGGTAAGTTCTTAGTGGCGAACGGGTGAGTAA

CGCGTGGGCAACCTGCCCTCCAGTTGGGGACAACATTCCGAAAGGGATGCTAATACCGAATGTCCTCCCTCCTCCGC

ATGGAGGAGGGAGGAAAGATGGCCTCTGCTTGCAAGCTATCGCTGGAAGATGGGCCCGCGTCTGATTAGCTAGTTGG

TGGGGTAACGGCTCACCAAGGCGATGATCAGTAGCCGGTCTGAGAGGATGAACGGCCACATTGGGACTGAGACACGG

CCCAAACTCCTACGGGAGGCAGCAGTGGGGAATCTTCCGCAATGGACGAAAGTCTGACGGAGCAACGCCGCGTGAGT

GATGAAGGTCTTCGGATTGTAAAACTCTGTTGTTAGGGACGAAAGCACCGTGTTCGAACAGGTCATGGTGTTGACGG

TACCTAACGAGGAAGCCACGGCTAACTACGTGCCAGCAGCCGCGGTAATACGTAGGTGGCAAGCGTTGTCCGGAATT

ATTGGGCGTAAAGAGCATGTAGGCGGCTTTTAAGTCTGACGTGAAAATGCGGGGCTTAACCCCGTATGGCGTTGGA

TACTGGAAGTCTTGAGTGCAGGAGAGGAAAGGGGAATTCCCAGTGTAGCGGTGAAATGCGTAGATATTGGGAGGAAC

ACCAGTGGCGAAGGCGCCTTTCTGGACTGTGTCTGACGCTGAGATGCGAAAGCCAGGGTAGCAAACGGGATTAGATA

CCCCGGTAGTCCTGGCCGTAAACGATGGATACTAGGTGTAGGAGGTATCGACCCCTTCTGTGCCGGAGTTAACGCAA

TAAGTATCCCGCCTGGGGACTACGATCGCAAGATTGAAACTCAAAGGAATTGACGGGGCCCGCACAAGCGGTGGAG

TATGTGGTTTAATTCGACGCAACGCGAAGAACCTTACCAAGGCTTGACATTGAGTGAAAGACCTAGAGATAGGTCCC

TCCCTTCGGGGACACGAAAACAGGTGGTGCATGGCTGTCGTCAGCTCGTGTCGTGAGATGTTGGGTTAAGTCCCGCA

ACGAGCGCAACCCCTATCCTATGTTACCAGCGCGTAAAGGCGGGGACTCATAGGAGACTGCCAGGGATAACTTGGAG

GAAGGCGGGGATGACGTCAAGTCATCATGCCCCTTATGTCTTGGGCTACACACGTACTACAATGGTCGGCAACAAAG

GGCAGCGAAACCGCGAGGTGGAGCAAATCCCAGAAACCCGACCCCAGTTCGGATCGTAGGCTGCAACCCGCCTACGT

```
GAAGTTGGAATCGCTAGTAATCGCAGGTCAGCATACTGCGGTGAATACGTTCCCGGGCCTTGTACACACCGCCCGTC

ACACCACGAAAGTTGGTAACACCCGAAGCCGGTGAGATAACCTTTTAGGAGTCAGCTGTCTAAGGTGGGGCCGATGA

TTGGGGTGAAGTCGTAACAAGGTAGC
```

> SEQ ID NO: 113|NR_074399.1|*Ruminococcus albus* strain 7 16S ribosomal RNA gene, complete sequence

```
AGAGTTTGATCCTGGCTCAGGACGAACGCTGGCGGCACGCTTAACACATGCAAGTCGAACGAGCGAAAGAGTGCTTG

CACTCTCTAGCTAGTGGCGGACGGGTGAGTAACACGTGAGCAATCTGCCTTTCGGAGAGGGATACCAATTGGAAACG

ATTGTTAATACCTCATAACATAACGAAGCCGCATGACTTTGTTATCAAATGAATTTCGCCGAAAGATGAGCTCGCGT

CTGATTAGGTAGTTGGTGAGGTAACGGCCCACCAAGCCGACGATCAGTAGCCGGACTGAGAGGTTGAACGGCCACAT

TGGGACTGAGACACGGCCCAGACTCCTACGGGAGGCAGCAGTGGGGAATATTGCACAATGGGCGAAAGCCTGATGCA

GCGATGCCGCGTGAGGGAAGAAGGTTTTAGGATTGTAAACCTCTGTCTTTGGGGACGATAATGACGGTACCCAAGGA

GGAAGCTCCGGCTAACTACGTGCCAGCAGCCGCGGTAATACGTAGGGAGCGAGCGTTGTCCGGAATTACTGGGTGTA

AAGGGAGCGTAGGCGGATTGCAAGTCAGGTGTGAAATTTAGGGGCTTAACCCCTGAACTGCACTTGAAACTGTAGT

TCTTGAGTGAAGTAGAGGTAAGCGGAATTCCTAGTGTAGCGGTGAAATGCGTAGATATTAGGAGGAACATCAGTGGC

GAAGGCGGCTTACTGGGCTTTAACTGACGCTGAGGCTCGAAAGCGTGGGGAGCAAACAGGATTAGATACCCTGGTAG

TCCACGCCGTAAACGATGATTACTAGGTGTGGGGGGACTGACCCCTTCCGTGCCGCAGTTAACACAATAAGTAATCC

ACCTGGGGAGTACGGCCGCAAGGCTGAAACTCAAAGGAATTGACGGGGACCCGCACAAGCAGTGGAGTATGTGGTTT

AATTCGAAGCAACGCGAAGAACCTTACCAGGTCTTGACATCGTACGCATAGCATAGAGATATGTGAAATCCCTTCGG

GGACGTATAGACAGGTGGTGCATGGTTGTCGTCAGCTCGTGTCGTGAGATGTTGGGTTAAGTCCCGCAACGAGCGC

AACCCTTACTGTTAGTTGCTACGCAAGAGCACTCTAGCAGGACTGCCGTTGACAAAACGGAGGAAGGTGGGGATGAC

GTCAAATCATCATGCCCCTTATGACCTGGGCTACACACGTACTACAATGGCTGTTAACAGAGGGAAGCAAAACAGTG

ATGTGGAGCAAAACCCTAAAAGCAGTCTTAGTTCGGATTGTAGGCTGCAACCCGCCTACATGAAGTCGGAATTGCTA

GTAATCGCGGATCAGCATGCCGCGGTGAATACGTTCCCGGGCCTTGTACACACCGCCCGTCACGCCATGGGAGTCGG

TAACACCCGAAGCCTGTGTTCTAACCGCAAGGAGGAAGCAGTCGAAGGTGGGATTGATGACTGGGGTGAAGTCGTAA

CAAGGTAGCCGTATCGGAAGGTGCGGCTGGATCACCT
```

> SEQ ID NO: 114|NR_074634.1|*Eubacterium rectale* strain ATCC 33656 16S ribosomal RNA gene, complete sequence

```
AGAGTTTGATCCTGGCTCAGGATGAACGCTGGCGGCGTGCTTAACACATGCAAGTCGAACGAAGCACTTTATTTGAT

TTCCTTCGGGACTGATTATTTTGTGACTGAGTGGCGGACGGGTGAGTAACGCGTGGGTAACCTGCCTTGTCAGGGGG

GATAACAGTTGGAAACGGCTGCTAATACCGCATAAGCGCACGGCATCGCATGATGCAGTGTGAAAAACTCCGGTGGT

ATAAGATGGACCCGCGTTGGATTAGCTAGTTGGTGAGGTAACGGCCCACCAAGGCGACGATCCATAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGCGAAGAAGTATTTCGGTATGTAAAGCTCTATCAGCAGGGAAGATA

ATGACGGTACCTGACTAAGAAGCACCGGCTAAATACGTGCCAGCAGCCGCGGTAATACGTATGGTGCAAGCGTTATC

CGGATTTACTGGGTGTAAAGGGAGCGCAGGCGGTGCGGCAAGTCTGATGTGAAAGCCCGGGGCTCAACCCCGGTACT

GCATTGGAAACTGTCGTACTAGAGTGTCGGAGGGGTAAGCGGAATTCCTAGTGTAGCGGTGAAATGCGTAGATATTA

GGAGGAACACCAGTGGCGAAGGCGGCTTACTGGACGATAACTGACGCTGAGGCTCGAAAGCGTGGGGAGCAAACAGG

ATTAGATACCCTGGTAGTCCACGCCGTAAACGATGAATACTAGGTGTTGGGAAGCATTGCTTCTCGGTGCCGTCGCA

AACGCAGTAAGTATTCCACCTGGGGAGTACGTTCGCAAGAATGAAACTCAAAGGAATTGACGGGACCCGCACAAGC

GGTGGAGCATGTGGTTTAATTCGAAGCAACGCGAAGAACCTTACCAAGTCTTGACATCCTTCTGACCGGTACTTAAC

CGTACCTTCTCTTCGGAGCAGGAGTGACAGGTGGTGCATGGTTGTCGTCAGCTCGTGTCGTGAGATGTTGGGTTAAG

TCCCGCAACGAGCGCAACCCTTATCTTTAGTAGCCAGCGGTTCGGCCGGGCACTCTAGAGAGACTGCCAGGGATAAC

CTGGAGGAAGGCGGGGATGACGTCAAATCATCATGCCCCTTATGACTTGGGCTACACACGTGCTACAATGGCGTAAA
```

CAAAGGGAAGCAAAGCTGTGAAGCCGAGCAAATCTCAAAAATAACGTCTCAGTTCGGACTGTAGTCTGCAACCCGAC

TACACGAAGCTGGAATCGCTAGTAATCGCAGATCAGAATGCTGCGGTGAATACGTTCCCGGGTCTTGTACACACCGC

CCGTCACACCATGGGAGTTGGGAATGCCCGAAGCCAGTGACCTAACCGAAAGGAAGGAGCTGTCGAAGGCAGGCTCG

ATAACTGGGGTGAAGTCGTAACAAGGTAGCCGTATCGGAAGGTGCGGCTGGATCACCT

> SEQ ID NO: 115|NR_074928.1|*Acidaminococcus fermentans* strain DSM 20731 16S
ribosomal RNA gene, complete sequence
AGAGTTTGATCCTGGCTCAGGACGAACGCTGGCGGCGTGCTTAACACATGCAAGTCGAACGGAGAACTTTCTTCGGA

ATGTTCTTAGTGGCGAACGGGTGAGTAACGCGTAGGCAACCTGCCCTCTGGTTGGGGACAACATTCCGAAAGGGATG

CTAATACCGAATGAGATCCTCTTTCCGCATGGAGAGAGGATGAAAGATGGCCTCTACTTGTAAGCTATCGCCAGAAG

ATGGGCCTGCGTCTGATTAGCTAGTAGGTGAGGTAACGGCTCACCTAGGCGATGATCAGTAGCCGGTCTGAGAGGAT

GAACGGCCACATTGGGACTGAGACACGGCCCAAACTCCTACGGGAGGCAGCAGTGGGGAATCTTCCGCAATGGACGA

AAGTCTGACGGAGCAACGCCGCGTGAGTGATGAAGGCCTTCGGGTTGTAAAACTCTGTTGTCAGGGACGAAAGCACC

GATCTATAATACATTTTGGTGTTGACGGTACCTGACGAGGAAGCCACGGCTAACTACGTGCCAGCAGCCGCGGTAAT

ACGTAGGTGGCAAGCGTTGTCCGGAATTATTGGGCGTAAAGAGCATGTAGGCGGGCTTTTAAGTCCGACGTGAAAAT

GCGGGGCTTAACCCCGTATGGCGTTGGATACTGGAAGTCTTGAGTGCAGGAGAGGAAAGGGGAATTCCCAGTGTAGC

GGTGAAATGCGTAGATATTGGGAGGAACACCAGTGGCGAAGGCGCCTTTCTGGACTGTGTCTGACGCTGAGATGCGA

AAGCCAGGGTAGCAAACGGGATTAGATACCCCGGTAGTCCTGGCCGTAAACGATGGGTACTAGGTGTAGGAGGTATC

GACCCCTTCTGTGCCGGAGTTAACGCAATAAGTACCCCGCCTGGGGACTACGATCGCAAGATTGAAACTCAAAGGAA

TTGACGGGGCCCGCACAAGCGGTGGAGTATGTGGTTTAATTCGACGCAACGCGAAGAACCTTACCAAGGCTTGACA

TTGAGTGAAAGACCCAGAGATGGGTCCCCTTCTTCGGAAGCACGAAAACAGGTGGTGCATGGCTGTCGTCAGCTCGT

GTCGTGAGATGTTGGGTTAAGTCCCGCAACGAGCGCAACCCTTATCCTATGTTACCAGCACGTAATGGTGGGGACTC

ATAGGAGACTGCCAGGGATAACCTGGAGGAAGGCGGGGATGACGTCAAGTCATCATGCCCCTTATGTCTTGGGCTAC

ACACGTACTACAATGGTCGGCAACAAAGGGCAGCGAAGCCGCGAGGCGGAGCCAATCCCAGAAACCCGACCCCAGTT

CGGATCGCAGGCTGCAACCCGCCTGCGTGAAGTTGGAATCGCTAGTAATCGCAGGTCAGCATACTGCGGTGAATACG

TTCCCGGGCCTTGTACACACCGCCCGTCACACCACGAAAGTTGGTAACACCCGAAGCCGGTGAGATAACCTTTTAGG

AGTCAGCTGTCTAAGGTGGGGCCGATGATTGGGGTGAAGTCGTAACAAGGTAGCCGTTCGAGAACGAGCGGCTGGAT

CACCT

> SEQ ID NO: 116|NR_114326.1|*Fusicatenibacter saccharivorans* strain HT03-11 16S ribosomal
RNA gene, partial sequence
TGGCTCAGGATGAACGCTGGCGGCGTGCTTAACACATGCAAGTCGAGCGAAGCAGTTAAGAAGATTYTTCGGATGAT

TCTTGACTGACTGAGCGGCGGACGGGTGAGTAACGCGTGGGTGACCTGCCCCATACCGGGGGATAACAGCTGGAAAC

GGCTGCTAATACCGCATAAGCGCACAGAGCTGCATGGCTCGGTGTGAAAAACTCCGGTGGTATGGGATGGGCCCGCG

TCTGATTAGGCAGTTGGCGGGGTAACGGCCCACCAAACCGACGATCAGTAGCCGGCCTGAGAGGGCGACCGGCCACA

TTGGGACTGAGACACGGCCCAAACTCCTACGGGAGGCAGCAGTGGGGAATATTGCACAATGGGGGAAACCCTGATGC

AGCGACGCCGCGTGAGCGAAGAAGTATTTCGGTATGTAAAGCTCTATCAGCAGGGAAGATAATGACGGTACCTGACT

AAGAAGCCCCGGCTAACTACGTGCCAGCAGCCGCGGTAATACGTAGGGGGCAAGCGTTATCCGGATTTACTGGGTGT

AAAGGGAGCGTAGACGGCAAGGCAAGTCTGATGTGAAAACCCAGGGCTTAACCCTGGGACTGCATTGGAAACTGTCT

GGCTCGAGTGCCGGAGAGGTAAGCGGAATTCCTAGTGTAGCGGTGAAATGCGTAGATATTAGGAAGAACACCAGTGG

CGAAGGCGGCTTACTGGACGGTAACTGACGTTGAGGCTCGAAAGCGTGGGGAGCAAACAGGATTAGATACCCTGGTA

GTCCACGCCGTAAACGATGAATGCTAGGTGTTGGGGAGCAAAGCTCTTCGGTGCCGCCGCAAACGCATTAAGCATTC

CACCTGGGGAGTACGTTCGCAAGAATGAAACTCAAAGGAATTGACGGGACCCGCACAAGCGGTGGAGCATGTGGTT

TAATTCGAAGCAACGCGAAGAACCTTACCAGGTCTTGACATCCCGATGACCGGCCCGTAACGGGGCCTTCTCTTCGG

AGCATTGGAGACAGGTGGTGCATGGTTGTCGTCAGCTCGTGTCGTGAGATGTTGGGTTAAGTCCCGCAACGAGCGCA

ACCCTTATCCTCAGTAGCCAGCAGGTAAAGCTGGGCACTCTGTGGAGACTGCCAGGGATAACCTGGAGGAAGGTGGG

GATGACGTCAAATCATCATGCCCCTTATGATCTGGGCTACACACGTGCTACAATGGCGTAAACAAAGGGAGGCAAAG

CCGCGAGGTGGAGCAAATCCCAAAAATAACGTCTCAGTTCGGACTGCAGTCTGCAACTCGACTGCACGAAGCTGGAA

TCGCTAGTAATCGCGAATCAGAATGTCGCGGTGAATACGTTCCCGGGTCTTGTACACACCGCCCGTCACACCATGGG

AGTTGGTAACGCCCGAAGTCAGTGACCCAACCTTTTA

> SEQ ID NO: 117|NR_102884.1|*Ruminococcus champanellensis* strain 18P13 16S ribosomal RNA gene, complete sequence
AGAGTTTGATCCTGGCTCAGGACGAACGCTGGCGGCACGCCTAACACATGCAAGTCGAACGGAGATAAAGACTTCGG

TTTTTATCTTAGTGGCGGACGGGTGAGTAACACGTGAGCAACCTGCCTCTGAGAGAGGGATAGCTTCTGGAAACGGA

TGGTAATACCTCATAACATAGCGGTACCGCATGATACTGCTATCAAAGATTTATCGCTCAGAGATGGGCTCGCGTCT

GATTAGCTAGATGGTGAGGTAACGGCTCACCATGGCGACGATCAGTAGCCGGACTGAGAGGTTGAACGGCCACATTG

GGACTGAGACACGGCCCAGACTCCTACGGGAGGCAGCAGTGGGGAATATTGCACAATGGGCGCAAGCCTGATGCAGC

GATGCCGCGTGGAGGAAGAAGGTTTTCGGATTGTAAACTCCTGTCTTAAGGGACGATAATGACGGTACCTTAGGAGG

AAGCTCCGGCTAACTACGTGCCAGCAGCCGCGGTAATACGTAGGGAGCGAGCGTTGTCCGGAATTACTGGGTGTAAA

GGGAGCGTAGGCGGATTGCAAGTCAGATGTGAAAACTATGGGCTTAACCCATAGACTGCATTTGAAACTGTAGTTC

TTGAGTGAAGTAGAGGTAAGCGGAATTCCTAGTGTAGCGGTGAAATGCGTAGATATTAGGAGGAACATCGGTGGCGA

AGGCGGCTTACTGGGCTTTTACTGACGCTGAGGCTCGAAAGCGTGGGGAGCAAACAGGATTAGATACCCTGGTAGTC

CACGCTGTAAACGATGATTACTAGGTGTGGGGGGACTGACCCCTTCCGTGCCGCAGTTAACACAATAAGTAATCCAC

CTGGGGAGTACGGCCGCAAGGTTGAAACTCAAAGGAATTGACGGGGGCCCGCACAAGCAGTGGAGTATGTGGTTTAA

TTCGAAGCAACGCGAAAAACCTTACCAGGTCTTGACATCGAGTGAATGATCTAGAGATAGATCAGTCCTTCGGGACA

CAAAGACAGGTGGTGCATGGTTGTCGTCAGCTCGTGTCGTGAGATGTTGGGTTAAGTCCCGCAACGAGCGCAACCCT

TACCTTTAGTTGCTACGCAAGAGCACTCTAGAGGGACTGCCGTTGACAAAACGGAGGAAGGTGGGGATGACGTCAAA

TCATCATGCCCCTTATGACCTGGGCTACACACGTACTACAATGGCAATGAACAGAGGGAAGCAATACAGTGATGTGG

AGCAAATCCCCAAAAATTGTCCCAGTTCAGATTGTAGGCTGCAACTCGCCTACATGAAGTCGGAATTGCTAGTAATC

GCAGATCAGCATGCTGCGGTGAATACGTTCCCGGGCCTTGTACACACCGCCCGTCACACCATGGGAGTCGGTAACAC

CCGAAGCCAGTAGCCTAACCGCAAGGAGGGCGCTGTCGAAGGTGGGATTGATGACTGGGGTGAAGTCGTAACAAGGT

AGCCGTATCGGAAGGTGCGGCTGGATCACCT

> SEQ ID NO: 118|NR_102971.1|*Bifidobacterium bifidum* S17 strain S17 16S ribosomal RNA, complete sequence
TTTTTGTGGAGGGTTCGATTCTGGCTCAGGATGAACGCTGGCGGCGTGCTTAACACATGCAAGTCGAACGGGATCCA

TCGGGCTTTGCTTGGTGGTGAGAGTGGCGAACGGGTGAGTAATGCGTGACCGACCTGCCCCATGCTCCGGAATAGCT

CCTGGAAACGGGTGGTAATGCCGGATGTTCCACATGATCGCATGTGATTGTGGGAAAGATTCTATCGGCGTGGGATG

GGGTCGCGTCCTATCAGCTTGTTGGTGAGGTAACGGCTCACCAAGGCTTCGACGGGTAGCCGGCCTGAGAGGGCGAC

CGGCCACATTGGGACTGAGATACGGCCCAGACTCCTACGGGAGGCAGCAGTGGGGAATATTGCACAATGGGCGCAAG

CCTGATGCAGCGACGCCGCGTGAGGGATGGAGGCCTTCGGGTTGTAAACCTCTTTTGTTTGGGAGCAAGCCTTCGGG

TGAGTGTACCTTTCGAATAAGCGCCGGCTAACTACGTGCCAGCAGCCGCGGTAATACGTAGGGCGCAAGCGTTATCC

GGATTTATTGGGCGTAAAGGGCTCGTAGGCGGTCGTCGCGTCCGGTGTGAAAGTCCATCGCTTAACGGTGGATCTG

CGCCGGGTACGGGCGGCTGGAGTGCGGTAGGGGAGACTGGAATTCCCGGTGTAACGGTGGAATGTGTAGATATCGG

GAAGAACACCGATGGCGAAGGCAGGTCTCTGGGCCGTCACTGACGCTGAGGAGCGAAAGCGTGGGGAGCGAACAGGA

TTAGATACCCTGGTAGTCCACGCCGTAAACGGTGGACGCTGGATGTGGGGCACGTTCCACGTGTTCCGTGTCGGAGC

TAACGCGTTAAGCGTCCCGCCTGGGGAGTACGGCCGCAAGGCTAAAACTCAAAGAAATTGACGGGGGCCCGCACAAG

CGGCGGAGCATGCGGATTAATTCGATGCAACGCGAAGAACCTTACCTGGGCTTGACATGTTCCCGACGACGCCAGAG

ATGGCGTTTCCCTTCGGGGCGGGTTCACAGGTGGTGCATGGTCGTCGTCAGCTCGTGTCGTGAGATGTTGGGTTAAG

TCCCGCAACGAGCGCAACCCTCGCCCCGTGTTGCCAGCACGTTATGGTGGGAACTCACGGGGACCGCCGGGGTTAA

CTCGGAGGAAGGTGGGGATGACGTCAGATCATCATGCCCCTTACGTCCAGGGCTTCACGCATGCTACAATGGCCGGT

ACAGCGGGATGCGACATGGCGACATGGAGCGGATCCCTGAAAACCGGTCTCAGTTCGGATCGGAGCCTGCAACCCGG

CTCCGTGAAGGCGGAGTCGCTAGTAATCGCGGATCAGCAACGCCGCGGTGAATGCGTTCCCGGGCCTTGTACACACC

GCCCGTCAAGTCATGAAAGTGGGCAGCACCCGAAGCCGGTGGCCTAACCCCTTGTGGGATGGAGCCGTCTAAGGTGA

GGCTCGTGATTGGGACTAAGTCGTAACAAGGTAGCCGTACCGGAAGGTGCGGCTGGATCACCTCCTTTCT

> SEQ ID NO: 119|NR_102980.1|*Megasphaera elsdenii* strain DSM 20460 16S ribosomal RNA gene, complete sequence
AGAGTTTGATCCTGGCTCAGGACGAACGCTGGCGGCGTGCTTAACACATGCAAGTCGAACGAGAAGAGATGAGAAGC

TTGCTTCTTATCAATTCGAGTGGCAAACGGGTGAGTAACGCGTAAGCAACCTGCCCTTCAGATGGGGACAACAGCTG

GAAACGGCTGCTAATACCGAATACGTTCTTTTTGTCGCATGGCAGAGGGAAGAAAGGGAGGCTCTTCGGAGCTTTCG

CTGAAGGAGGGGCTTGCGTCTGATTAGCTAGTTGGAGGGGTAACGGCCCACCAAGGCGACGATCAGTAGCCGGTCTG

AGAGGATGAACGGCCACATTGGGACTGAGACACGGCCCAGACTCCTACGGGAGGCAGCAGTGGGGAATCTTCCGCAA

TGGACGAAAGTCTGACGGAGCAACGCCGCGTGAACGATGACGGCCTTCGGGTTGTAAAGTTCTGTTATACGGGACGA

ATGGCGTAGCGGTCAATACCCGTTACGAGTGACGGTACCGTAAGAGAAAGCCACGGCTAACTACGTGCCAGCAGCCG

CGGTAATACGTAGGTGGCAAGCGTTGTCCGGAATTATTGGGCGTAAAGGGCGCGCAGGCGGCGTCGTAAGTCGGTCT

TAAAAGTGCGGGGCTTAACCCCGTGAGGGGACCGAAACTGCGATGCTAGAGTATCGGAGAGGAAAGCGGAATTCCTA

GTGTAGCGGTGAAATGCGTAGATATTAGGAGGAACACCAGTGGCGAAAGCGGCTTTCTGGACGACAACTGACGCTGA

GGCGCGAAAGCCAGGGGAGCAAACGGGATTAGATACCCCGGTAGTCCTGGCCGTAAACGATGGATACTAGGTGTAGG

AGGTATCGACCCCTTCTGTGCCGGAGTTAACGCAATAAGTATCCCGCCTGGGGAGTACGGCCGCAAGGCTGAAACTC

AAAGGAATTGACGGGGGCCCGCACAAGCGGTGGAGTATGTGGTTTAATTCGACGCAACGCGAAGAACCTTACCAAGC

CTTGACATTGATTGCTATGGATAGAGATATCCAGTTCCTCTTCGGAGGACAAGAAAACAGGTGGTGCACGGCTGTCG

TCAGCTCGTGTCGTGAGATGTTGGGTTAAGTCCCGCAACGAGCGCAACCCCTATCTTCTGTTACCAGCGGTTCGGCC

GGGGACTCAGGAGAGACTGCCGCAGACAATGCGGAGGAAGGCGGGGATGACGTCAAGTCATCATGCCCCTTATGGCT

TGGGCTACACACGTACTACAATGGCTCTTAATAGAGGGAAGCGAAGGAGCGATCCGGAGCAAACCCCAAAAACAGAG

TCCCAGTTCGGATTGCAGGCTGCAACTCGCCTGCATGAAGCAGGAATCGCTAGTAATCGCAGGTCAGCATACTGCGG

TGAATACGTTCCCGGGCCTTGTACACACCGCCCGTCACACCACGAAAGTCATTCACACCCGAAGCCGGTGAGGTAAC

CTTTTGGAGCCAGCCGTCGAAGGTGGGGGCGATGATTGGGGTGAAGTCGTAACAAGGTAGCCGTATCGGAAGGTGCG

GCTGGATCACCT

> SEQ ID NO: 120|NR_044645.2|*Dorea formicigenerans* strain ATCC 27755 16S ribosomal RNA gene, complete sequence
TTAAACGAGAGTTTGATCCTGGCTCAGGATGAACGCTGGCGGCGTGCTTAACACATGCAAGTCGAGCGAAGCACATA

AGTTTGATTCTTCGGATGAAGACTTTTGTGACTGAGCGGCGGACGNNNGAGTAACGCGTGGGTAACCTGCCTCATAC

AGGGGGATAACAGYTAGAAATGGCTGCTAATACCGCATAAGACCACAGTACTGCATGGTACAGTGNNNAAAACTCCG

GTGGTATGAGATGGACCCGCGTCTGATTAGGTAGTTGGTGAGGTAACGGCCCACCNAGCCGACGATCAGTAGCCGAC

CTGAGAGGGTGACCGGCCACATTGGGACTGAGACACGGCCNNGACTCCTACGGGAGGCAGCAGTGGGGAATATTGCA

CAATGGGCGAAAGCCTGATGCAGCGACGCCGCGTGAAGGATGAAGTATTTCGGTATGTAAACTTCTATCAGCAGGGA

AGAAAATGACGGTACCTGACTAAGAAGCCCCGGCTAACTACGTGCCAGCAGCCGNGGTAATACGTAGGGGGNNAGCG

TTATCCGGATTTACTGGGTGTAAAGGGAGCGTAGACGGCTGTGCAAGTCTGAAGTGAAAGGCATGGGCTCAACCTGT

GGACTGCTTTGGAAACTGTGCAGCTAGAGTGTCGGAGAGGTAAGTGGAATTCCTAGTGTAGCGGTGAAATGCGTAGA

TATTAGGAGGAACACCAGTGGCGAAGGCGGCNTACTGGACGATGACTGACGTTGAGGCTCGAAAGCGTGGGGAGCAA

-continued

ACAGGATTAGATACCCTGGTAGTCCACGCCGTAAACGATGACTGCTAGGTGTCGGGTAGCAAAGCTATTCGGTGCCG

CAGCTAACGCAATAAGCAGTCCACCTGGGGAGTACGTTCGCAAGAATGAAACTCAAAGGAATTGACGGGGNCCNGCA

CAAGCGGTGGAGCATGTGGTTTAATTCGAANNAACGCGAAGAACCTTACCTGATCTTGACATCCCGATGACCGCTTC

GTAATGGAAGYTTTTCTTCGGAACATCGGTGACAGGTGGTGCATGGTTGTCGTCAGCTCGTGTCGTGAGATGTTGGG

TTAAGTCCCGCAACGAGCGCAACCCTTATCTTCAGTAGCCAGCATTTAGGATGGGCACTCTGGAGAGACTGCCAGGG

ATAACCTGGAGGAAGGTGGGGATGACGTNNAATCATCATGCCCCTTATGACCAGGGCTACACACGTGCTACAATGGC

GTAAACAGAGGGAGGCAGAGCCGCGAGGCCGAGCAAATCTCAAAAATAACGTCTCAGTTCGGATTGTAGTCTGCAAC

TCGACTACATGAAGCTGGAATCGCTAGTAATCGCAGATCAGAATGCTGCGGTGAATACGTTCCCGGGTCTTGTACAC

ACCGCCCGTCACACCATGGGAGTCAGTAACGCCCGAAGTCAGTGACCCAACCGAAAGGAGGGAGCTGCCGAAGGTGG

GACCGATAACTGGGGT

> SEQ ID NO: 121|NR_118643.1|Eisenbergiella tayi strain B086562 16S ribosomal RNA gene, partial sequence
GGTATAACTTAGTGGCGGACGGGTGAGTAACGCGTGGGAAACCTGCCCTGTACCGGGGGATAACACTTAGAAATAGG

TGCTAATACCGCATAAGCGCACGGAACCGCATGGTTCCGTGTGAAAAACTCCGGTGGTACAGGATGGTCCCGCGTCT

GATTAGCCAGTTGGCAGGGTAACGGCCTACCAAAGCGACGATCAGTAGCCGGCCTGAGAGGGTGAACGGCCACATTG

GGACTGAGACACGGCCCAAACTCCTACGGGAGGCAGCAGTGGGGAATATTGCACAATGGGGGAAACCCTGATGCAGC

GACGCCGCGTGAGTGAAGAAGTATTTCGGTATGTAAAGCTCTATCAGCAGGGAAGAAAATGACGGTACCTGACTAAG

AAGCCCCGGCTAACTACGTGCCAGCAGCCGCGGTAATACGTAGGGGGCAAGCGTTATCCGGATTTACTGGGTGTAAA

GGGAGCGTAGACGGCATGGCAAGCCAGATGTGAAAACCCAGGGCTCAACCTTGGGATTGCATTTGGAACTGCCAGGC

TGGAGTGCAGGAGAGGTAAGCGGAATTCCTAGTGTAGCGGTGAAATGCGTAGATATTAGGAGGAACACCAGTGGCGA

AGGCGGCTTACTGGACTGTAACTGACGTTGAGGCTCGAAAGCGTGGGGAGCAAACAGGATTAGATACCCTGGTAGTC

CACGCGGTAAACGATGATTGCTAGGTGTAGGTGGGTATGGACCCATCGGTGCCGCAGCTAACGCAATAAGCAATCCA

CCTGGGGAGTACGTTCGCAAGAATGAAACTCAAAGGAATTGACGGGACCCGCACAAGCGGTGGAGCATGTGGTTTA

ATTCGAAGCAACGCGAAGAACCTTACCAAGTCTTGACATCCCAATGACGCACCTGTAAAGAGGTGTTCCCTTCGGGG

CATTGGAGACAGGTGGTGCATGGTTGTCGTCAGCTCGTGTCGTGAGATGTTGGGTTAAGTCCCGCAACGAGCGCAAC

CCTTATTCTTAGTAGCCAGCAGGTAAAGCTGGGCACTCTAAGGAGACTGCCGGGGATAACCCGGAGGAAGGCGGGGA

TGACGTCAAATCATCATGCCCCTTATGATTTGGGCTACACACGTGCTACAATGGCGTAAACAAAGGGAAGCGAGACA

GTGATGTGGAGCAAATCYCAGAAATAACGTCTCAGTTCGGATTGTAGTCTGCAACTCGACTACATGAAGCTGGAATC

GCTAGTAATCGCGAATCAGCATGTCGCGGTGAATACGTTCCCGGGTCTTGTACACACCGCCCGTCACACCATGGGAG

TTGGAAATGCCCGAAGTCTGTGACCTAACCGAAAGGGAGGAGCAGCCGAAGGCAGGTCTGATAACTGGGGTGAAGTC

GTAA

> SEQ ID NO: 122|NR_118730.1|Clostridium symbiosum strain ATCC 14940 16S ribosomal RNA gene, partial sequence
AAACATGAGAGTTTGATCCTGGCTCAGGATGAACGCTGGCGGCGTGCCTAACACATGCAAGTCGAACGAAGCGATTT

AACGGAAGTTTTCGGATGGAAGTTGAATTGACTGAGTGGCGGACGGGTGAGTAACGCGTGGGTAACCTGCCTTGTAC

TGGGGGACAACAGTTAGAAATGACTGCTAATACCGCATAAGCGCACAGTATTGCATGATACAGTGTGAAAAACTCCG

GTGGTACAAGATGGACCCGCGTCTGATTAGCTAGTTGGTAAGGTAACGGCTTACCAAGGCGACGATCAGTAGCCGAC

CTGAGAGGGTGACCGGCCACATTGGGACTGAGACACGGCCNNAACTCCTACGGGAGGCAGCAGTGGGGAATATTGCA

CAATGGGCGAAAGCCTGATGCAGCGACGCCGCGTGAGTGAAGAAGTATTTCGGTATGTAAAGCTCTATCAGCAGGGA

AGAAAATGACGGTACCTGACTAAGAAGCCCCGGCTAACTACGTGCCAGCAGCCGCGGTAATACGTAGGGGGNNAGCG

TTATCCGGATTTACTGGGTGTAAAGGGAGCGTAGACGGTAAAGCAAGTCTGAAGTGAAAGCCCGCGNCTCAACTGCG

GNNCTGCTTTGGAAACTGTTTAACTGGAGTGTCGGAGAGGTAAGTGGAATTCCTAGTGTAGCGGTGAAATGCGTAGA

TATTAGGAGGAACACNAGTGGCGAAGGCGACTTACTGGACGATAACTGACGTTGAGGCTCGAAAGCGTGGGGAGCAA

-continued

ACAGGATTAGATACCCTGGTAGTCCACGCCGTAAACGATGAATACTAGGTGTTGGGGAGCAAAGCTCTTCGGTGCCG

TCGCAAACGCAGTAAGTATTCCACCTGGGGAGTACGTTCGCAAGAATGAAACTCAAAGGAATTGACGGGGACCNGCA

CAAGCGGTGGAGCATGTGGTTTAATTCGAANNAACGCGAAGAACCTTACCAGGTCTTGACATCGACTCGACGGGGGA

GTAACGTCCCNNTNCCTTCGGGGCGGAGAAGACAGGTGGTGCATGGTTGTCGTCAGCTCGTGTCGTGAGATGTTGGG

TTNAGTCCCGCAACGAGCGCAACCCTTATTCTAAGTAGCCAGCGGTTCGGCCGGGAACTCTTGGGAGACTGCCAGGG

ATAACCTGGAGGAAGGTGGGGATGACGTCNAATCATCATGCCCCTTATGATCTGGGCTACACACGTGCTACAATGGC

GTAAACANAGAGAAGCAAGACCGCGAGGTGGAGCAAATCTCAAAAATAACGTCTCAGTTCGGACTGCAGGCTGCAAC

TCGCCTGCACGAAGCTGGAATCGCTAGTAATCGCGAATCAGAATGTCGCGGTGAATACGTTCCCGGGTCTTGTACAC

ACCGNNCGTCACACCATGGGAGTCAGTAACGCCCGAAGTCAGTGACCCAACCGCAAGGAGGGAGCTGCCGAAGGCGG

GACCGANAACNNGGG

> SEQ ID NO: 123|NR_113243.1|*Erysipelatoclostridium ramosum* strain JCM 1298 16S
ribosomal RNA gene, partial sequence
AGAGTTTGATCCTGGCTCAGGATGAACGCTGGCGGCGTGCCTAATACATGCAAGTCGAACGCGAGCACTTGTGCTCG

AGTGGCGAACGGGTGAGTAATACATAAGTAACCTGCCCTAGACAGGGGGATAACTATTGGAAACGATAGCTAAGACC

GCATAGGTACGGACACTGCATGGTGACCGTATTAAAAGTGCCTCAAAGCACTGGTAGAGGATGGACTTATGGCGCAT

TAGCTGGTTGGCGGGGTAACGGCCCACCAAGGCGACGATGCGTAGCCGACCTGAGAGGGTGACCGGCCACACTGGGA

CTGAGACACGGCCCAGACTCCTACGGGAGGCAGCAGTAGGGAATTTTCGGCAATGGGGGAAACCCTGACCGAGCAAC

GCCGCGTGAAGGAAGAAGGTTTTCGGATTGTAAACTTCTGTTATAAAGGAAGAACGGCGGCTACAGGAAATGGTAGC

CGAGTGACGGTACTTTATTAGAAAGCCACGGCTAACTACGTGCCAGCAGCCGCGGTAATACGTAGGTGGCAAGCGTT

ATCCGGAATTATTGGGCGTAAAGAGGGAGCAGGCGGCAGCAAGGGTCTGTGGTGAAAGCCTGAAGCTTAACTTCAGT

AAGCCATAGAAACCAGGCAGCTAGAGTGCAGGAGAGGATCGTGGAATTCCATGTGTAGCGGTGAAATGCGTAGATAT

ATGGAGGAACACCAGTGGCGAAGGCGACGATCTGGCCTGCAACTGACGCTCAGTCCCGAAAGCGTGGGGAGCAAATA

GGATTAGATACCCTAGTAGTCCACGCCGTAAACGATGAGTACTAAGTGTTGGATGTCAAAGTTCAGTGCTGCAGTTA

ACGCAATAAGTACTCCGCCTGAGTAGTACGTTCGCAAGAATGAAACTCAAAGGAATTGACGGGGCCCGCACAAGCG

GTGGAGCATGTGGTTTAATTCGAAGCAACGCGAAGAACCTTACCAGGTCTTGACATACTCATAAAGGCTCCAGAGAT

GGAGAGATAGCTATATGAGATACAGGTGGTGCATGGTTGTCGTCAGCTCGTGTCGTGAGATGTTGGGTTAAGTCCCG

CAACGAGCGCAACCCTTATCGTTAGTTACCATCATTAAGTTGGGGACTCTAGCGAGACTGCCAGTGACAAGCTGGAG

GAAGGCGGGGATGACGTCAAATCATCATGCCCCTTATGACCTGGGCTACACACGTGCTACAATGGATGGTGCAGAGG

GAAGCGAAGCCGCGAGGTGAAGCAAAACCCATAAAACCATTCTCAGTTCGGATTGTAGTCTGCAACTCGACTACATG

AAGTTGGAATCGCTAGTAATCGCGAATCAGCATGTCGCGGTGAATACGTTCTCGGGCCTTGTACACACCGCCCGTCA

CACCACGAGAGTTGATAACACCCGAAGCCGGTGGCCTAACCGCAAGGAAGGAGCTGTCTAAGGTGGGATTGATGATT

GGGGTGAAGTCGTAACAAGGTAACC

>SEQ ID NO: 124 |PROKKA_00507 16S ribosomal RNA gene | VE202-7
ATGAGAGTTTGATCCTGGCTCAGGATGAACGCTGGCGGCGTGCCTAACACATGCAAGTCGAACGAAGCAATTAAAGG

AAGTTTTCGGATGGAATTTGATTGACTGAGTGGCGGACGGGTGAGTAACGCGTGGATAACCTGCCTCACACTGGGGG

ATAACAGTTAGAAATGACTGCTAATACCGCATAAGCGCACAGTACCGCATGGTACGGTGTGAAAAACTCCGGTGGTG

TGAGATGGATCCGCGTCTGATTAGCCAGTTGGCGGGGTAACGGCCCACCAAAGCGACGATCAGTAGCCGACCTGAGA

GGGTGACCGGCCACATTGGGACTGAGACACGGCCCAAACTCCTACGGGAGGCAGCAGTGGGGAATATTGCACAATGG

GCGAAAGCCTGATGCAGCGACGCCGCGTGAGTGAAGAAGTATTTCGGTATGTAAAGCTCTATCAGCAGGGAAGAAAA

TGACGGTACCTGACTAAGAAGCCCCGGCTAACTACGTGCCAGCAGCCGCGGTAATACGTAGGGGGCAAGCGTTATCC

GGATTCACTGGGTGTAAAGGGAGCGTAGACGGCGAAGCAAGTCTGAAGTGAAAACCCAGGGCTCAACCCTGGGACTG

CTTTGGAAACTGTTTTGCTAGAGTGTCGGAGAGGTAAGTGGAATTCCTAGTGTAGCGGTGAAATGCGTAGATATTAG

GAGGAACACCAGTGGCGAAGGCGGCTTACTGGACGATAACTGACGTTGAGGCTCGAAAGCGTGGGGAGCAAACAGGA
TTAGATACCCTGGTAGTCCACGCCGTAAACGATGAATGCTAGGTGTTGGGGGGCAAAGCCCTTCGGTGCCGTCGCAA
ACGCAGTAAGCATTCCACCTGGGGAGTACGTTCGCAAGAATGAAACTCAAAGGAATTGACGGGGACCCGCACAAGCG
GTGGAGCATGTGGTTTAATTCGAAGCAACGCGAAGAACCTTACCAAGTCTTGACATCCTCTTGACCGGCGTGTAACG
GCGCCTTCCCTTCGGGGCAAGAGAGACAGGTGGTGCATGGTTGTCGTCAGCTCGTGTCGTGAGATGTTGGGTTAAGT
CCCGCAACGAGCGCAACCCTTATCCTTAGTAGCCAGCAGGTAGAGCTGGGCACTCTAGGGAGACTGCCAGGGATAAC
CTGGAGGAAGGTGGGGATGACGTCAAATCATCATGCCCCTTATGATTTGGGCTACACACGTGCTACAATGGCGTAAA
CAAAGGGAAGCAAGACAGTGATGTGGAGCAAATCCCAAAAATAACGTCCCAGTTCGGACTGTAGTCTGCAACCCGAC
TACACGAAGCTGGAATCGCTAGTAATCGCGAATCAGAATGTCGCGGTGAATACGTTCCCGGGTCTTGTACACACCGC
CCGTCACACCATGGGAGTCAGCAACGCCCGAAGTCAGTGACCCAACTCGCAAGAGGGGAGCTGCCGAAGGCGGGGC
AGGTAACTGGGGTGAAGTCGTAACAAGGTAGCCGTATCGGAAGGTGCGGCTGGATCACCTCCTTT
>SEQ ID NO: 125 |PROKKA_00709 16S ribosomal RNA gene | VE202-7
ATGAGAGTTTGATCCTGGCTCAGGATGAACGCTGGCGGCGTGCCTAACACATGCAAGTCGAACGAAGCAATTAAAAT
GAAGTTTTCGGATGGATTTTTGATTGACTGAGTGGCGGACGGGTGAGTAACGCGTGGATAACCTGCCTCACACTGGG
GGATAACAGTTAGAAATGACTGCTAATACCGCATAAGCGCACAGTACCGCATGGTACGGTGTGAAAAACTCCGGTGG
TGTGGGATGGATCCGCGTCTGATTAGCCAGTTGGCGGGGTAACGGCCCACCAAAGCGACGATCAGTAGCCGACCTGA
GAGGGTGACCGGCCACATTGGGACTGAGACACGGCCCAAACTCCTACGGGAGGCAGCAGTGGGGAATATTGCACAAT
GGGCGAAAGCCTGATGCAGCGACGCCGCGTGAGTGAAGAAGTATTTCGGTATGTAAAGCTCTATCAGCAGGGAAGAA
AATGACGGTACCTGACTAAGAAGCCCCGGCTAACTACGTGCCAGCAGCCGCGGTAATACGTAGGGGGCAAGCGTTAT
CCGGATTTACTGGGTGTAAAGGGAGCGTAGACGGCGAAGCAAGTCTGAAGTGAAAACCCAGGGCTCAACCCTGGGAC
TGCTTTGGAAACTGTTTTGCTAGAGTGTCGGAGAGGTAAGTGGAATTCCTAGTGTAGCGGTGAAATGCGTAGATATT
AGGAGGAACACCAGTGGCGAAGGCGGCTTACTGGACGATAACTGACGTTGAGGCTCGAAAGCGTGGGGAGCAAACAG
GATTAGATACCCTGGTAGTCCACGCCGTAAACGATGAATGCTAGGTGTTGGGGGGCAAAGCCCTTCGGTGCCGTCGC
AAACGCAGTAAGCATTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCAAGTCTTGACATCCTCTTGACCGGCGTGTAA
CGGCGCCTTCCCTTCGGGGCAAGAGAGACAGGTGGTGCATGGTTGTCGTCAGCTCGTGTCGTGAGATGTTGGGTTAA
GTCCCGCAACGAGCGCAACCCTTATCCTTAGTAGCCAGCAGGTAAAGCTGGGCACTCTAGGGAGACTGCCAGGGATA
ACCTGGAGGAAGGTGGGGATGACGTCAAATCATCATGCCCCTTATGATTTGGGCTACACACGTGCTACAATGGCGTA
AACAAAGGGAAGCAAGACAGTGATGTGGAGCAAATCCCAAAAATAACGTCCCAGTTCGGACTGTAGTCTGCAACCCG
ACTACACGAAGCTGGAATCGCTAGTAATCGCGAATCAGAATGTCGCGGTGAATACGTTCCCGGGTCTTGTACACACC
GCCCGTCACACCATGGGAGTCAGCAACGCCCGAAGTCAGTGACCCAACTCGCAAGAGAGGGAGCTGCCGAAGGCGGG
GCAGGTAACTGGGGTGAAGTCGTAACAAGGTAGCCGTATCGGAAGGTGCGGCTGGATCACCTCCTTT
>SEQ ID NO: 126 |PROKKA_01766 16S ribosomal RNA gene | VE202-7
ATGAGAGTTTGATCCTGGCTCAGGATGAACGCTGGCGGCGTGCCTAACACATGCAAGTCGAACGAAGCAATTAAAAT
GAAGTTTTCGGATGGATTTTTGATTGACTGAGTGGCGGACGGGTGAGTAACGCGTGGATAACCTGCCTCACACTGGG
GGATAACAGTTAGAAATGACTGCTAATACCGCATAAGCGCACAGTACCGCATGGTACGGTGTGAAAAACTCCGGTGG
TGTGAGATGGATCCGCGTCTGATTAGCCAGTTGGCGGGGTAACGGCCCACCAAAGCGACGATCAGTAGCCGACCTGA
GAGGGTGACCGGCCACATTGGGACTGAGACACGGCCCAAACTCCTACGGGAGGCAGCAGTGGGGAATATTGCACAAT
GGGCGAAAGCCTGATGCAGCGACGCCGCGTGAGTGAAGAAGTATTTCGGTATGTAAAGCTCTATCAGCAGGGAAGAA
ATGACGGTACCTGACTAAGAAGCCCCGGCTAACTACGTGCCAGCAGCCGCGGTAATACGTAGGGGGCAAGCGTTATC
CGGATTTACTGGGTGTAAAGGGAGCGTAGACGGCGAAGCAAGTCTGAAGTGAAAACCCAGGGCTCAACCCTGGGACT -continued

GCTTTGGAAACTGTTTTGCTAGAGTGTCGGAGAGGTAAGTGGAATTCCTAGTGTAGCGGTGAAATGCGTAGATATTA

GGAGGAACACCAGTGGCGAAGGCGGCTTACTGGACGATAACTGACGTTGAGGCTCGAAAGCGTGGGGAGCAAACAGG

ATTAGATACCCTGGTAGTCCACGCCGTAAACGATGAATGCTAGGTGTTGGGGGCAAAGCCCTTCGGTGCCGTCGCAA

ACGCAGTAAGCATTCCACCTGGGGAGTACGTTCGCAAGAATGAAACTCAAAGGAATTGACGGGGACCCGCACAAGCG

GTGGAGCATGTGGTTTAATTCGAAGCAACGCGAAGAACCTTACCAAGTCTTGACATCCTCTTGACCGGCGTGTAACG

GCGCCTTCCCTTCGGGGCAAGAGAGACAGGTGGTGCATGGTTGTCGTCAGCTCGTGTCGTGAGATGTTGGGTTAAGT

CCCGCAACGAGCGCAACCCTTATCCTTAGTAGCCAGCAGGTAAAGCTGGGCACTCTAGGGAGACTGCCAGGGATAAC

CTGGAGGAAGGTGGGGATGACGTCAAATCATCATGCCCCTTATGATTTGGGCTACACACGTGCTACAATGGCGTAAA

CAAAGGGAAGCAAGACAGTGATGTGGAGCAAATCCCAAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 127 |PROKKA_01779 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

GATTAGATACCCTGGTAGTCCACGCCGTAAACGATGAATGCTAGGTGTTGGGGGCAAAGCCCTTCGGTGCCGTCGCA

AACGCAGTAAGCATTCCACCTGGGGAGTACGTTCGCAAGAATGAAACTCAAAGGAATTGACGGGGACCCGCACAAGC

GGTGGAGCATGTGGTTTAATTCGAAGCAACGCGAAGAACCTTACCAAGTCTTGACATCCTCTTGACCGGCGTGTAAC

GGCGCCTTCCCTTCGGGGCAGGAGAGACAGGTGGTGCATGGTTGTCGTCAGCTCGTGTCGTGAGATGTTGGGTTAAG

TCCCGCAACGAGCGCAACCCTTATCCTTAGTAGCCAGCAGGTAGAGCTGGGCACTCTAGGGAGACTGCCAGGGATAA

CCTGGAGGAAGGTGGGGATGACGTCAAATCATCATGCCCCTTATGATTTGGGCTACACACGTGCTACAATGGCGTAA

ACAAAGGGAAGCAAGACAGTGATGTGGAGCAAATCCCAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 128 |PROKKA_05926 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTAATTGACTGAGTGGCGGACGGGTGAGTAACGCGTGGATAACCTGCCTCACACTGGG

GATAACAGTTAGAAATGACTGCTAATACCGCATAAGCGCACAGTACCGCATGGTACGGTGTGAAAAACTCCGGTGGT

GTGAGATGGATCCGCGTCTGATTAGCCAGTTGGCGGGGTAACGGCCCACCAAAGCGACGATCAGTAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGTGAAGAAGTATTTCGGTATGTAAAGCTCTATCAGCAGGGAAGAAA

ATGACGGTACCTGACTAAGAAGCCCCGGCTAACTACGTGCCAGCAGCCGCGGTAATACGTAGGGGGCAAGCGTTATC

CGGATTTACTGGGTGTAAAGGGAGCGTAGACGGCGAAGCAAGTCTGAAGTGAAAACCCAGGGCTCAACCCTGGGACT

-continued

GCTTTGGAAACTGTTTTGCTAGAGTGTCGGAGAGGTAAGTGGAATTCCTAGTGTAGCGGTGAAATGCGTAGATATTA
GGAGGAACACCAGTGGCGAAGGCGGCTTACTGGACGATAACTGACGTTGAGGCTCGAAAGCGTGGGGAGCAAACAGG
ATTAGATACCCTGGTAGTCCACGCCGTAAACGATGAATGCTAGGTGTTGGGGGGCAAAGCCCTTCGGTGCCGTCGCA
AACGCAGTAAGCATTCCACCTGGGGAGTACGTTCGCAAGAATGAAACTCAAAGGAATTGACGGGACCCGCACAAGC
GGTGGAGCATGTGGTTTAATTCGAAGCAACGCGAAGAACCTTACCAAGTCTTGACATCCTCTTGACCGGCGTGTAAC
GGCGCCTTCCCTTCGGGGCAAGAGAGACAGGTGGTGCATGGTTGTCGTCAGCTCGTGTCGTGAGATGTTGGGTTAAG
TCCCGCAACGAGCGCAACCCTTATCCTTAGTAGCCAGCAGGTAAAGCTGGGCACTCTAGGGAGACTGCCAGGGATAA
CCTGGAGGAAGGTGGGGATGACGTCAAATCATCATGCCCCTTATGATTTGGGCTACACACGTGCTACAATGGCGTAA
ACAAAGGGAAGCAAGACAGTGATGTGGAGCAAATCCCAAAATAACGTCCCAGTTCGGACTGTAGTCTGCAACCCGAC
TACACGAAGCTGGAATCGCTAGTAATCGCGAATCAGAATGTCGCGGTGAATACGTTCCCGGGTCTTGTACACACCGC
CCGTCACACCATGGGAGTCAGCAACGCCCGAAGTCAGTGACCCAACTCGCAAGAGAGGGAGCTGCCGAAGGCGGGC
AGGTAACTGGGGTGAAGTCGTAACAAGGTAGCCGTATCGGAAGGTGCGGCTGGATCACCTCCTTT

>SEQ ID NO: 129 | PROKKA_01784 16S ribosomal RNA gene
TCAAAGAGTTTGATCCTGGCTCAGGACGAACGCTGGCGGCGCGCCTAACACATGCAAGTCGAACGGAGCTTACGTTT
TGAAGTTTTCGGATGGATGAATGTAAGCTTAGTGGCGGACGGGTGAGTAACACGTGAGCAACCTGCCTTTCAGAGGG
GGATAACAGCCGGAAACGGCTGCTAATACCGCATGATGTTGCGGGGCACATGCCCCTGCAACCAAAGGAGCAATCC
GCTGAAAGATGGGCTCGCGTCCGATTAGCCAGTTGGCGGGGTAACGGCCCACCAAAGCGACGATCGGTAGCCGGACT
GAGAGGTTGAACGGCCACATTGGGACTGAGACACGGCCCAGACTCCTACGGGAGGCAGCAGTGGGGGATATTGCACA
ATGGGCGAAAGCCTGATGCAGCGACGCCGCGTGAGGGAAGACGGTCTTCGGATTGTAAACCTCTGTCTTTGGGGAAG
AAAATGACGGTACCCAAAGAGGAAGCTCCGGCTAACTACGTGCCAGCAGCCGCGGTAATACGTAGGGAGCAAGCGTT
GTCCGGAATTACTGGGTGTAAAGGGAGCGTAGGCGGGATGGCAAGTAGAATGTTAAATCCATCGGCTCAACCGGTGG
CTGCGTTCTAAACTGCCGTTCTTGAGTGAAGTAGAGGCAGGCGGAATTCCTAGTGTAGCGGTGAAATGCGTAGATAT
TAGGAGGAACACCAGTGGCGAAGGCGGCCTGCTGGGCTTTAACTGACGCTGAGGCTCGAAAGCGTGGGGAGCAAACA
GGATTAGATACCCTGGTAGTCCACGCCGTAAACGATGATTACTAGGTGTGGGGGACTGACCCCTTCCGTGCCGCAG
TTAACACAATAAGTAATCCACCTGGGGAGTACGGCCGCAAGGTTGAAACTCAAAGGAATTGACGGGGCCCGCACAA
GCAGTGGAGTATGTGGTTTAATTCGAAGCAACGCGAAGAACCTTACCAGGTCTTGACATCGGATGCATAGCCTAGAG
ATAGGTGAAGCCCTTCGGGGCATCCAGACAGGTGGTGCATGGTTGTCGTCAGCTCGTGTCGTGAGATGTTGGGTTAA
GTCCCGCAACGAGCGCAACCCTTATTATTAGTTGCTACGCAAGAGCACTCTAATGAGACTGCCGTTGACAAAACGGA
GGAAGGTGGGGATGACGTCAAATCATCATGCCCCTTATGACCTGGGCTACACACGTACTACAATGGCACTAAAACAG
AGGGCGGCGACACCGCGAGGTGAAGCGAATCCCGAAAAAGTGTCTCAGTTCAGATTGCAGGCTGCAACCCGCCTGCA
TGAAGTCGGAATTGCTAGTAATCGCGGATCAGCATGCCGCGGTGAATACGTTCCCGGGCCTTGTACACACCGCCCGT
CACACCATGGGAGTCGGTAACACCCGAAGCCAGTAGCCTAACCGCAAGGGGGCGCTGTCGAAGGTGGGATTGATGA
CTGGGGTGAAGTCGTAACAAGGTAGCCGTATCGGAAGGTGCGGCTGGATCACCTCCTTT >SEQ ID NO: 130 | PROKKA_01864 16S ribosomal RNA gene
TCAAAGAGTTTGATCCTGGCTCAGGACGAACGCTGGCGGCGCGCCTAACACATGCAAGTCGAACGGAGCTTACGTTT
TGAAGTTTTCGGATGGACGAATGTAAGCTTAGTGGCGGACGGGTGAGTAACACGTGAGCAACCTGCCTTTCAGAGGG
GATAACAGCCGGAAACGGCTGCTAATACCGCATGATGTTGCGGGGCACATGCCCCTGCAACCAAAGGAGCAATCCG
CTGAAAGATGGGCTCGCGTCCGATTAGCCAGTTGGCGGGGTAACGGCCCACCAAAGCGACGATCGGTAGCCGGACTG
AGAGGTTGAACGGCCACATTGGGACTGAGACACGGCCCAGACTCCTACGGGAGGCAGCAGTGGGGGATATTGCACAA
TGGGCGAAAGCCTGATGCAGCGACGCCGCGTGAGGGAAGACGGTCTTCGGATTGTAAACCTCTGTCTTTGGGGAAGA
AAATGACGGTACCCAAAGAGGAAGCTCCGGCTAACTACGTGCCAGCAGCCGCGGTAATACGTAGGGAGCAAGCGTTG -continued

TCCGGAATTACTGGGTGTAAAGGGAGCGTAGGCGGGATGGCAAGTAGAATGTTAAATCCATCGGCTCAACCGGTGGC

TGCGTTCTAAACTGCCGTTCTTGAGTGAAGTAGAGGCAGGCGGAATTCCTAGTGTAGCGGTGAAATGCGTAGATATT

AGGAGGAACACCAGTGGCGAAGGCGGCCTGCTGGGCTTTAACTGACGCTGAGGCTCGAAAGCGTGGGGAGCAAACAG

GATTAGATACCCTGGTAGTCCACGCCGTAAACGATGATTACTAGGTGTGGGGGGACTGACCCCTTCCGTGCCGCAGT

TAACACAATAAGTAATCCACCTGGGGAGTACGGCCGCAAGGTTGAAACTCAAAGGAATTGACGGGGGCCCGCACAAG

CAGTGGAGTATGTGGTTTAATTCGAAGCAACGCGAAGAACCTTACCAGGTCTTGACATCGGATGCATAGCCTAGAGA

TAGGTGAAGCCCTTCGGGGCATCCAGACAGGTGGTGCATGGTTGTCGTCAGCTCGTGTCGTGAGATGTTGGGTTAAG

TCCCGCAACGAGCGCAACCCTTATTATTAGTTGCTACGCAAGAGCACTCTAATGAGACTGCCGTTGACAAAACGGAG

GAAGGTGGGGATGACGTCAAATCATCATGCCCCTTATGACCTGGGCTACACACGTACTACAATGGCACTAAAACAGA

GGGCGGCGACACCGCGAGGTGAAGCGAATCCCGAAAAAGTGTCTCAGTTCAGATTGCAGGCTGCAACCCGCCTGCAT

GAAGTCGGAATTGCTAGTAATCGCGGATCAGCATGCCGCGGTGAATACGTTCCCGGGCCTTGTACACACCGCCCGTC

ACACCATGGGAGTCGGTAACACCCGAAGCCAGTAGCCTAACCGCAAGGGGGCGCTGTCGAAGGTGGGATTGATGAC

TGGGGTGAAGTCGTAACAAGGTAGCCGTATCGGAAGGTGCGGCTGGATCACCTCCTTT

>SEQ ID NO: 131 | PROKKA_02671 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGATGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGCACATGCCCCTGCAACCAAAGGAGCAATCC

GCTGAAAGATGGGCTCGCGTCCGATTAGCCAGTTGGCGGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGGATATTGCACA

ATGGGCGAAAGCCTGATGCAGCGACGCCGCGTGAGGGAAGACGGTCTTCGGATTGTAAACCTCTGTCTTTGGGGAAG

AAAATGACGGTACCCAAAGAGGAAGCTCCGGCTAACTACGTGCCAGCAGCCGCGGTAATACGTAGGGAGCAAGCGTT

GTCCGGAATTACTGGGTGTAAAGGGAGCGTAGGCGGGATGGCAAGTAGAATGTTAAATCCATCGGCTCAACCGGTGG

CTGCGTTCTAAACTGCCGTTCTTGAGTGAAGTAGAGGCAGGCGGAATTCCTAGTGTAGCGGTGAAATGCGTAGATAT

TAGGAGGAACACCAGTGGCGAAGGCGGCCTGCTGGGCTTTAACTGACGCTGAGGCTCGAAAGCGTGGGGAGCAAACA

GGATTAGATACCCTGGTAGTCCACGCCGTAAACGATGATTACTAGGTGTGGGGGGACTGACCCCTTCCGTGCCGCAG

TTAACACAATAAGTAATCCACCTGGGGAGTACGGCCGCAAGGTTGAAACTCAAAGGAATTGACGGGGGCCCGCACAA

GCAGTGGAGTATGTGGTTTAATTCGAAGCAACGCGAAGAACCTTACCAGGTCTTGACATCGGATGCATAGCCTAGAG

ATAGGTGAAGCCCTTCGGGGCATCCAGACAGGTGGTGCATGGTTGTCGTCAGCTCGTGTCGTGAGATGTTGGGTTAA

GTCCCGCAACGAGCGCAACCCTTATTATTAGTTGCTACGCAAGAGCACTCTAATGAGACTGCCGTTGACAAAACGGA

GGAAGGTGGGGATGACGTCAAATCATCATGCCCCTTATGACCTGGGCTACACACGTACTACAATGGCACTAAAACAG

AGGGCGGCGACACCGCGAGGTGAAGCGAATCCCGAAAAAGTGTCTCAGTTCAGATTGCAGGCTGCAACCCGCCTGCA

TGAAGTCGGAATTGCTAGTAATCGCGGATCAGCATGCCGCGGTGAATACGTTCCCGGGCCTTGTACACACCGCCCGT

CACACCATGGGAGTCGGTAACACCCGAAGCCAGTAGCCTAACCGCAAGGGGGCGCTGTCGAAGGTGGGATTGATGA

CTGGGGTGAAGTCGTAACAAGGTAGCCGTATCGGAAGGTGCGGCTGGATCACCTCCTTT

>SEQ ID NO: 132 | PROKKA_00690 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AAATGACGGTACCTGAGTAAGAAGCACCGGCTAAATACGTGCCAGCAGCCGCGGTAATACGTATGGTGCAAGCGTTA

-continued

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCGTCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 133 | PROKKA_00991 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGAAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 134 | PROKKA_01948 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

-continued

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 135 | PROKKA_02310 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGAAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 136 | PROKKA_02993 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA
TCCGGATTTACTGGGTGTAAAGGGAGCGTAGACGGATAGGCAAGTCTGGAGTGAAAACCCAGGGCTCAACCCTGGGA
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA
GGATTAGATACCCTGGTAGTCCACGCCGTAAACGATGACTACTAGGTGTCGGTGTGCAAAGCACATCGGTGCCGCAG
CAAACGCAATAAGTAGTCCACCTGGGGAGTACGTTCGCAAGAATGAAACTCAAAGGAATTGACGGGACCCGCACAA
GCGGTGGAGCATGTGGTTTAATTCGAAGCAACGCGAAGAACCTTACCTGGTCTTGACATCCGGATGACGGGCGAGTA
ATGTCGCCGTCCCTTCGGGGCATCCGAGACAGGTGGTGCATGGTTGTCGTCAGCTCGTGTCGTGAGATGTTGGGTTA
AGTCCCGCAACGAGCGCAACCCTTATCTTCAGTAGCCAGCATATAAGGTGGGCACTCTGGAGAGACTGCCAGGGAGA
ACCTGGAGGAAGGTGGGGATGACGTCAAATCATCATGCCCCTTATGGCCAGGGCTACACACGTGCTACAATGGCGTA
AACAAAGGGAAGCGAGAGGGTGACCTGGAGCGAATCCCAAAAATAACGTCTCAGTTCGGATTGTAGTCTGCAACTCG
ACTACATGAAGCTGGAATCGCTAGTAATCGCGGATCAGCATGCCGCGGTGAATACGTTCCCGGGTCTTGTACACACC
GCCCGTCACACCATGGGAGTCAGTAACGCCCGAAGCCAGTGACCCAACCTTAGAGGAGGGAGCTGTCGAAGGCGGGA
CGGATAACTGGGGTGAAGTCGTAACAAGGTAGCCGTATCGGAAGGTGCGGCTGGATCACCTCCTTT

>SEQ ID NO: 137 | PROKKA_00436 16S ribosomal RNA gene
ATGAGAGTTTGATCCTAGCTCAGGATGAACGCTGGCGGCGTGCCTAACACATGCAAGTCGAACGAAGCAATTTAACG
GAAGTTTTCGGATGGAAGTTGAATTGACTGAGTGGCGGACGGGTGAGTAACGCGTGGGTAACCTGCCTTGTACTGGG
GGACAACAGTTAGAAATGACTGCTAATACCGCATAAGCGCACAGTATCGCATGATACAGTGTGAAAAACTCCGGTGG
TACAAGATGGACCCGCGTCTGATTAGCTAGTTGGTAAGGTAACGGCTTACCAAGGCGACGATCAGTAGCCGACCTGA
GAGGGTGACCGGCCACATTGGGACTGAGACACGGCCCAAACTCCTACGGGAGGCAGCAGTGGGGAATATTGCACAAT
GGGCGAAAGCCTGATGCAGCGACGCCGCGTGAGTGAAGAAGTATTTCGGTATGTAAAGCTCTATCAGCAGGGAAGAA
AATGACGGTACCTGACTAAGAAGCCCCGGCTAACTACGTGCCAGCAGCCGCGGTAATACGTAGGGGGCAAGCGTTAT
CCGGATTTACTGGGTGTAAAGGGAGCGTAGACGGTAAAGCAAGTCTGAAGTGAAAGCCCGCGGCTCAACTGCGGGAC
TGCTTTGGAAACTGTTTAACTGGAGTGTCGGAGAGGTAAGTGGAATTCCTAGTGTAGCGGTGAAATGCGTAGATATT
AGGAGGAACACCAGTGGCGAAGGCGACTTACTGGACGATAACTGACGTTGAGGCTCGAAAGCGTGGGGAGCAAACAG
GATTAGATACCCTGGTAGTCCACGCCGTAAACGATGAATACTAGGTGTTGGGGAGCAAAGCTCTTCGGTGCCGTCGC
AAACGCAGTAAGTATTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCAGGTCTTGACATCGATCCGACGGGGAGTAA
CGTCCCCTTCCCTTCGGGGCGGAGAAGACAGGTGGTGCATGGTTGTCGTCAGCTCGTGTCGTGAGATGTTGGGTTAA
GTCCCGCAACGAGCGCAACCCTTATTCTAAGTAGCCAGCGGTTCGGCCGGGAACTCTTGGGAGACTGCCAGGGATAA
CCTGGAGGAAGGTGGGGATGACGTCAAATCATCATGCCCCTTATGATCTGGGCTACACACGTGCTACAATGGCGTAA
ACAAAGAGAAGCAAGACCGCGAGGTGGAGCAAATCTCAAAAATAACGTCTCAGTTCGGACTGCAGGCTGCAACTCGC
CTGCACGAAGCTGGAATCGCTAGTAATCGCGAATCAGAATGTCGCGGTGAATACGTTCCCGGGTCTTGTACACACCG
CCCGTCACACCATGGGAGTCAGTAACGCCCGAAGTCAGTGACCCAACCGCAAGGAGGGAGCTGCCGAAGGCGGGACC
GATAACTGGGGTGAAGTCGTAACAAGGTAGCCGTATCGGAAGGTGCGGCTGGATCACCTCCTTT >SEQ ID NO: 138 | PROKKA_00685 16S ribosomal RNA gene
ATGAGAGTTTGATCCTGGCTCAGGATGAACGCTGGCGGCGTGCCTAACACATGCAAGTCGAACGAAGCGATTTAACG
GAAATTTTCGGATGGAAGTTGAATTGACTGAGTGGCGGACGGGTGAGTAACGCGTGGGTAACCTGCCTTGTACTGGG
GGACAACAGTTAGAAATGACTGCTAATACCGCATAAGCGCACAGTATCGCATGATACAGTGTGAAAAACTCCGGTGG
TACAAGATGGACCCGCGTCTGATTAGCTAGTTGGTAAGGTAACGGCTTACCAAGGCGACGATCAGTAGCCGACCTGA
GAGGGTGACCGGCCACATTGGGACTGAGACACGGCCCAAACTCCTACGGGAGGCAGCAGTGGGGAATATTGCACAAT

```
GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 139 | PROKKA_01171 16S ribosomal RNA gene
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 140 | PROKKA_05969 16S ribosomal RNA gene
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGGATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT
```

```
GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 141 | PROKKA_00279 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTTTAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 142 | PROKKA_01221 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT
```

-continued

GAGAGGGTGAACGGCCACATTGGGACTGAGACACGGCCCAGACTCCTACGGGAGGCAGCAGTGGGGAATATTGCACA
ATGGGGGAAACCCTGATGCAGCGACGCCGCGTGAAGGAAGAAGTATCTCGGTATGTAAACTTCTATCAGCAGGGAAG
AAAATGACGGTACCTGACTAAGAAGCCCCGGCTAACTACGTGCCAGCAGCCGCGGTAATACGTAGGGGGCAAGCGTT
ATCCGGATTTACTGGGTGTAAAGGGAGCGTAGACGGAAGAGCAAGTCTGATGTGAAAGGCTGGGGCTTAACCCCAGG
ACTGCATTGGAAACTGTTTTTCTAGAGTGCCGGAGAGGTAAGTGGAATTCCTAGTGTAGCGGTGAAATGCGTAGATA
TTAGGAGGAACACCAGTGGCGAAGGCGGCTTACTGGACGGTAACTGACGTTGAGGCTCGAAAGCGTGGGGAGCAAAC
AGGATTAGATACCCTGGTAGTCCACGCCGTAAACGATGAATACTAGGTGTCGGGTGGCAAAGCCATTCGGTGCCGCA
GCAAACGCAATAAGTATTCCACCTGGGGAGTACGTTCGCAAGAATGAAACTCAAAGGAATTGACGGGGACCCGCACA
AGCGGTGGAGCATGTGGTTTAATTCGAAGCAACGCGAAGAACCTTACCAAGTCTTGACATCCCTCTGACCGGCCCGT
AACGGGCCTTCCCTTCGGGGCAGAGGAGACAGGTGGTGCATGGTTGTCGTCAGCTCGTGTCGTGAGATGTTGGGTT
AAGTCCCGCAACGAGCGCAACCCCTATCCTTAGTAGCCAGCAGGTGAAGCTGGGCACTCTAGGGAGACTGCCGGGGA
TAACCCGGAGGAAGGCGGGGACGACGTCAAATCATCATGCCCCTTATGATTTGGGCTACACACGTGCTACAATGGCG
TAAACAAAGGGAAGCGGGACAGCGATGTTGAGCAAATCCCAAAAATAACGTCCCAGTTCGGACTGCAGTCTGCAACT
CGACTGCACGAAGCTGGAATCGCTAGTAATCGCGAATCAGAATGTCGCGGTGAATACGTTCCCGGGTCTTGTACACA
CCGCCCGTCACACCATGGGAGTCAGTAACGCCCGAAGTCAGTGACCCAACCTTACAGGAGGGAGCTGCCGAAGGCGG
GACCGATAACTGGGGTGAAGTCGTAACAAGGTAGCCGTATCGGAAGGTGCGGCTGGATCACCTCCTTT

>SEQ ID NO: 143 | PROKKA_02318 16S ribosomal RNA gene
ATCAGAGAGTTTGATCCTGGCTCAGGATGAACGCTGGCGGCGTGCTTAACACATGCAAGTCGAGCGAAGCACTTAAG
TGGATCTCTTCGGATTGAAGCTTATTTGACTGAGCGGCGGACGGGTGAGTAACGCGTGGGTAACCTGCCTCATACAG
GGGGATAACAGTTAGAAATGGCTGCTAATACCGCATAAGCGCACAGGACCGCATGGTCTGGTGTGAAAAACTCCGGT
GGTATGAGATGGACCCGCGTCTGATTAGCTAGTTGGAGGGGTAACGGCCCACCAAGGCGACGATCAGTAGCCGGCCT
GAGAGGGTGAACGGCCACATTGGGACTGAGACACGGCCCAGACTCCTACGGGAGGCAGCAGTGGGGAATATTGCACA
ATGGGGGAAACCCTGATGCAGCGACGCCGCGTGAAGGAAGAAGTATCTCGGTATGTAAACTTCTATCAGCAGGGAAG
AAAATGACGGTACCTGACTAAGAAGCCCCGGCTAACTACGTGCCAGCAGCCGCGGTAATACGTAGGGGGCAAGCGTT
ATCCGGATTTACTGGGTGTAAAGGGAGCGTAGACGGAAGAGCAAGTCTGATGTGAAAGGCTGGGGCTTAACCCCAGG
ACTGCATTGGAAACTGTTTTTCTAGAGTGCCGGAGAGGTAAGCGGAATTCCTAGTGTAGCGGTGAAATGCGTAGATA
TTAGGAGGAACACCAGTGGCGAAGGCGGCTTACTGGACGGTAACTGACGTTGAGGCTCGAAAGCGTGGGGAGCAAAC
AGGATTAGATACCCTGGTAGTCCACGCCGTAAACGATGAATACTAGGTGTCGGGTGGCAAAGCCATTCGGTGCCGCA
GCAAACGCAATAAGTATTCCACCTGGGGAGTACGTTCGCAAGAATGAAACTCAAAGGAATTGACGGGGACCCGCACA
AGCGGTGGAGCATGTGGTTTAATTCGAAGCAACGCGAAGAACCTTACCAAGTCTTGACATCCCTCTGACCGGCCCGT
AACGGGCCTTCCCTTCGGGGCAGAGGAGACAGGTGGTGCATGGTTGTCGTCAGCTCGTGTCGTGAGATGTTGGGTT
AAGTCCCGCAACGAGCGCAACCCCTATCCTTAGTAGCCAGCAGGTGAAGCTGGGCACTCTAGGGAGACTGCCGGGGA
TAACCCGGAGGAAGGCGGGGACGACGTCAAATCATCATGCCCCTTATGATTTGGGCTACACACGTGCTACAATGGCG
TAAACAAAGGGAAGCGAGACAGCGATGTTGAGCAAATCCCAAAAATAACGTCCCAGTTCGGACTGCAGTCTGCAACT
CGACTGCACGAAGCTGGAATCGCTAGTAATCGCGAATCAGAATGTCGCGGTGAATACGTTCCCGGGTCTTGTACACA
CCGCCCGTCACACCATGGGAGTCAGTAACGCCCGAAGTCAGTGACCCAACCTTACAGGAGGGAGCTGCCGAAGGCGG
GACCGATAACTGGGGTGAAGTCGTAACAAGGTAGCCGTATCGGAAGGTGCGGCTGGATCACCTCCTTT >SEQ ID NO: 144 | PROKKA_02336 16S ribosomal RNA gene
ATCAGAGAGTTTGATCCTGGCTCAGGATGAACGCTGGCGGCGTGCTTAACACATGCAAGTCGAGCGAAGCACTTAAG
CGGATCTCTTCGGATTGAAACTTATTTGACTGAGCGGCGGACGGGTGAGTAACGCGTGGGTAACCTGCCTCATACAG
GGGGATAACAGTTAGAAATGGCTGCTAATACCGCATAAGCGCACAGGACCGCATGGTCTGGTGTGAAAAACTCCGGT
GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 145 | PROKKA_04947 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACATCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCTAGTTCGGACTGCAGTCTGCAACT

CGACTGCACGAAGCTGGAATCGCTAGTAATCGCGAATCAGAATGTCGCGGTAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 146 | PROKKA_00208 16S ribosomal RNA gene
AACGAGAGTTTGATCCTGGCTCAGGATGAACGCTGGCGGCGTGCTTAACACATGCAAGTCGAGCGAAGCACTTAAGT

TGATTCTTCGGATGAAGACTTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

-continued

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACCGCTTCGTA

ATGGAAGTTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 147 | PROKKA_00340 16S ribosomal RNA gene
AACGAGAGTTTGATCCTGGCTCAGGATGAACGCTGGCGGCGTGCTTAACACATGCAAGTCGAGCGAAGCACTTTGGA

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGCTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAAGCGAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 148 | PROKKA_01031 16S ribosomal RNA gene
AACGAGAGTTTGATCCTGGCTCAGGATGAACGCTGGCGGCGTGCTTAACACATGCAAGTCGAGCGAAGCACTTAAGT

TTGATTCTTCGGATGAAGACTTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGATCTTGACATCCCGATGACCGCTTCGTA

ATGGAAGCTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 149 | PROKKA_01840 16S ribosomal RNA gene
AACGAGAGTTTGATCCTGGCTCAGGATGAACGCTGGCGGCGTGCTTAACACATGCAAGTCGAGCGAAGCACTTTGGA

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGATCTTGACATCCCGATGACCGCTTCGTA

ATGGAAGCTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 150 | PROKKA_02944 16S ribosomal RNA gene
AACGAGAGTTTGATCCTGGCTCAGGATGAACGCTGGCGGCGTGCTTAACACATGCAAGTCGAGCGAAGCGCTTAAGT

TTGATTCTTCGGATGAAGACTTTTGTGACTGAGCGGCGGACGGGTGAGTAACGCGTGGGTAACCTGCCTCATACAGG

-continued

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGCTCAACCCCGGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGTTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAGGCAAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 151 | PROKKA_04036 16S ribosomal RNA gene
AACGAGAGTTTGATCCTGGCTCAGGATGAACGCTGGCGGCGTGCTTAACACATGCAAGTCGAGCGAAGCGCTTTGGG

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTTTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGATCTTGACATCCCGATGACTGCTTCGTA

ATGGAAGTTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 152 | PROKKA_00437 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

```
CTGGAAACGGTAGCTAAAACCGGATAGGTATACAGAGCGCATGCTCAGTATATTAAAGCGCCCATCAAGGCGTGAAC
ATGGATGGACCTGCGGCGCATTAGCTAGTTGGTGAGGTAACGGCTCACCAAGGCGATGATGCGTAGCCGGCCTGAGA
GGGTAAACGGCCACATTGGGACTGAGACACGGCCCAAACTCCTACGGGAGGCAGCAGTAGGGAATTTTCGTCAATGG
GGGAAACCCTGAACGAGCAATGCCGCGTGAGTGAAGAAGGTCTTCGGATCGTAAAGCTCTGTTGTAAGTGAAGAACG
GCTCATAGAGGAAATGCTATGGGAGTGACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCGTAGGTGGCGTACTAAGTCTGTAGTAAA
AGGCAATGGCTCAACCATTGTAAGCTATGGAAACTGGTATGCTGGAGTGCAGAAGAGGGCGATGGAATTCCATGTGT
AGCGGTAAAATGCGTAGATATATGGAGGAACACCAGTGGCGAAGGCGGTCGCCTGGTCTGTAACTGACACTGAGGCA
CGAAAGCGTGGGGAGCAAATAGGATTAGATACCCTAGTAGTCCACGCCGTAAACGATGAGAACTAAGTGTTGGAGGA
ATTCAGTGCTGCAGTTAACGCAATAAGTTCTCCGCCTGGGGAGTATGCACGCAAGTGTGAAACTCAAAGGAATTGAC
GGGGGCCCGCACAAGCGGTGGAGTATGTGGTTTAATTCGAAGCAACGCGAAGAACCTTACCAGGCCTTGACATGGAA
ACAAATACCCTAGAGATAGGGGGATAATTATGGATCACACAGGTGGTGCATGGTTGTCGTCAGCTCGTGTCGTGAGA
TGTTGGGTTAAGTCCCGCAACGAGCGCAACCCTTGTCGCATGTTACCAGCATCAAGTTGGGGACTCATGCGAGACTG
CCGGTGACAAACCGGAGGAAGGTGGGGATGACGTCAAATCATCATGCCCCTTATGGCCTGGGCTACACACGTACTAC
AATGGCGGCCACAAAGAGCAGCGACACAGTGATGTGAAGCGAATCTCATAAAGGTCGTCTCAGTTCGGATTGAAGTC
TGCAACTCGACTTCATGAAGTCGGAATCGCTAGTAATCGCAGATCAGCATGCTGCGGTGAATACGTTCTCGGGCCTT
GTACACACCGCCCGTCAAACCATGGGAGTCAGTAATACCCGAAGCCGGTGGCATAACCGTAAGGAGTGAGCCGTCGA
AGGTAGGACCGATGACTGGGGTTAAGTCGTAACAAGGTATCCCTACGGGAACGTGGGGATGGATCACCTCCTTT

>SEQ ID NO: 153 | PROKKA_00896 16S ribosomal RNA gene
ATGGAGAGTTTGATCCTGGCTCAGGATGAACGCTGGCGGCATGCCTAATACATGCAAGTCGAACGAAGTTTCGAGGA
AGCTTGCTTCCAAAGAGACTTAGTGGCGAACGGGTGAGTAACACGTAGGTAACCTGCCCATGTGTCCGGGATAACTG
CTGGAAACGGTAGCTAAAACCGGATAGGTATACAGAGCGCATGCTCAGTATATTAAAGCGCCCATCAAGGCGTGAAC
ATGGATGGACCTGCGGCGCATTAGCTAGTTGGTGAGGTAACGGCTCACCAAGGCGATGATGCGTAGCCGGCCTGAGA
GGGTAAACGGCCACATTGGGACTGAGACACGGCCCAAACTCCTACGGGAGGCAGCAGTAGGGAATTTTCGTCAATGG
GGGAAACCCTGAACGAGCAATGCCGCGTGAGTGAAGAAGGTCTTCGGATCGTAAAGCTCTGTTGTAAGTGAAGAACG
GCTCATAGAGGAAATGCTATGGGAGTGACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCGTAGGTGGCGTACTAAGTCTGTAGTAAA
AGGCAATGGCTCAACCATTGTAAGCTATGGAAACTGGTATGCTGGAGTGCAGAAGAGGGCGATGGAATTCCATGTGT
AGCGGTAAAATGCGTAGATATATGGAGGAACACCAGTGGCGAAGGCGGTCGCCTGGTCTGTAACTGACACTGAGGCA
CGAAAGCGTGGGGAGCAAATAGGATTAGATACCCTAGTAGTCCACGCCGTAAACGATGAGAACTAAGTGTTGGAGGA
ATTCAGTGCTGCAGTTAACGCAATAAGTTCTCCGCCTGGGGAGTATGCACGCAAGTGTGAAACTCAAAGGAATTGAC
GGGGGCCCGCACAAGCGGTGGAGTATGTGGTTTAATTCGAAGCAACGCGAAGAACCTTACCAGGCCTTGACATGGAA
ACAAATACCCTAGAGATAGGGGGATAATTATGGATCACACAGGTGGTGCATGGTTGTCGTCAGCTCGTGTCGTGAGA
TGTTGGGTTAAGTCCCGCAACGAGCGCAACCCTTGTCGCATGTTACCAGCATCAAGTTGGGGACTCATGCGAGACTG
CCGGTGACAAACCGGAGGAAGGTGGGGATGACGTCAAATCATCATGCCCCTTATGGCCTGGGCTACACACGTACTAC
AATGGCGGCCACAAAGAGCAGCGACACAGTGATGTGAAGCGAATCTCATAAAGGTCGTCTCAGTTCGGATTGAAGTC
TGCAACTCGACTTCATGAAGTCGGAATCGCTAGTAATCGCAGATCAGCATGCTGCGGTGAATACGTTCTCGGGCCTT
GTACACACCGCCCGTCAAACCATGGGAGTCAGTAATACCCGAAGCCGGTGGCATAACCGTAAGGAGTGAGCCGTCGA
AGGTAGGACCGATGACTGGGGTTAAGTCGTAACAAGGTATCCCTACGGGAACGTGGGGATGGATCACCTCCTTT
```

>SEQ ID NO: 154 | PROKKA_02845 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCTCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 155 | PROKKA_04164 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGACCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGCAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 156 | PROKKA_04921 16S ribosomal RNA gene
ATGGAGAGTTTGATCCTGGCTCAGGATGAACGCTGGCGGCATGCCTAATACATGCAAGTCGAACGAAGTTTCGAGGA
AGCTTGCTTCCAAAGAGACTTAGTGGCGAACGGGTGAGTAACACGTAGGTAACCTGCCCATGTGTCCGGGATAACTG
CTGGAAACGGTAGCTAAAACCGGATAGGTATACAGAGCGCATGCTCAGTATATTAAAGCGCCCATCAAGGCGTGAAC
ATGGATGGACCTGCGGCGCATTAGCTAGTTGGTGAGGTAACGGCCCACCAAGGCGATGATGCGTAGCCGGCCTGAGA
GGGTAAACGGCCACATTGGGACTGAGACACGGCCCAAACTCCTACGGGAGGCAGCAGTAGGGAATTTTCGTCAATGG
GGGAAACCCTGAACGAGCAATGCCGCGTGAGTGAAGAAGGTCTTCGGATCGTAAAGCTCTGTTGTAAGTGAAGAACG
GCTCATAGAGGAAATGCTATGGGAGTGACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCGTAGGTGGCGTACTAAGTCTGTAGTAAA
AGGCAATGGCTCAACCATTGTAAGCTATGGAAACTGGTATGCTGGAGTGCAGAAGAGGGCGATGGAATTCCATGTGT
AGCGGTAAAATGCGTAGATATATGGAGGAACACCAGTGGCGAAGGCGGTCGCCTGGTCTGTAACTGACACTGAGGCA
CGAAAGCGTGGGGAGCAAATAGGATTAGATACCCTAGTAGTCCACGCCGTAAACGATGAGAACTAAGTGTTGGAGGA
ATTCAGTGCTGCAGTTAACGCAATAAGTTCTCCGCCTGGGGAGTATGCACGCAAGTGTGAAACTCAAAGGAATTGAC
GGGGGCCCGCACAAGCGGTGGAGTATGTGGTTTAATTCGAAGCAACGCGAAGAACCTTACCAGGCCTTGACATGGAA
ACAAATACCCTAGAGATAGGGGGATAATTATGGATCACACAGGTGGTGCATGGTTGTCGTCAGCTCGTGTCGTGAGA
TGTTGGGTTAAGTCCCGCAACGAGCGCAACCCTTGTCGCATGTTACCAGCATCAAGTTGGGGACTCATGCGAGACTG
CCGGTGACAAACCGGAGGAAGGTGGGGATGACGTCAAATCATCATGCCCCTTATGGCCTGGGCTACACACGTACTAC
AATGGCGGCCACAAAGAGCAGCGACACAGTGATGTGAAGCGAATCTCATAAAGGTCGTCTCAGTTCGGATTGAAGTC
TGCAACTCGACTTCATGAAGTCGGAATCGCTAGTAATCGCAGATCAGCATGCTGCGGTGAATACGTTCTCGGGCCTT
GTACACACCGCCCGTCAAACCATGGGAGTCAGTAATACCCGAAGCCGGTGGCATAACCGTAAGGAGTGAGCCGTCGA
AGGTAGGACCGATGACTGGGGTTAAGTCGTAACAAGGTATCCCTACGGGAACGTGGGGATGGATCACCTCCTTT >SEQ ID NO: 157 | PROKKA_00199 16S ribosomal RNA gene
TATTGAGAGTTTGATCCTGGCTCAGGATGAACGCTGGCGGCGTGCTTAACACATGCAAGTCGAACGGGGTGCTCATG
ACGGAGGATTCGTCCAACGGATTGAGTTACCTAGTGGCGGACGGGTGAGTAACGCGTGAGGAACCTGCCTTGGAGAG
GGGAATAACACTCCGAAAGGAGTGCTAATACCGCATGATGCAGTTGGGTCGCATGGCTCTGACTGCCAAAGATTTAT
CGCTCTGAGATGGCCTCGCGTCTGATTAGCTAGTAGGCGGGTAACGGCCCACCTAGGCGACGATCAGTAGCCGGAC
TGAGAGGTTGACCGGCCACATTGGGACTGAGACACGGCCCAGACTCCTACGGGAGGCAGCAGTGGGGAATATTGGGC
AATGGGCGCAAGCCTGACCCAGCAACGCCGCGTGAAGGAAGAAGGCTTTCGGGTTGTAAACTTCTTTTGTCGGGGAC
GAAACAAATGACGGTACCCGACGAATAAGCCACGGCTAACTACGTGCCAGCAGCCGCGGTAATACGTAGGTGGCAAG
CGTTATCCGGATTTACTGGGTGTAAAGGGCGTGTAGGCGGGATTGCAAGTCAGATGTGAAAACTGGGGGCTCAACCT
CCAGCCTGCATTTGAAACTGTAGTTCTTGAGTGCTGGAGAGGCAATCGGAATTCCGTGTGTAGCGGTGAAATGCGTA
GATATACGGAGGAACACCAGTGGCGAAGGCGGATTGCTGGACAGTAACTGACGCTGAGGCGCGAAAGCGTGGGGAGC
AAACAGGATTAGATACCCTGGTAGTCCACGCCGTAAACGATGGATACTAGGTGTGGGGGTCTGACCCCCTCCGTGCC
GCAGTTAACACAATAAGTATCCCACCTGGGGAGTACGATCGCAAGGTTGAAACTCAAAGGAATTGACGGGGGCCCGC
ACAAGCGGTGGAGTATGTGGTTTAATTCGAAGCAACGCGAAGAACCTTACCAGGGCTTGACATCCCACTAACGAAGC
AGAGATGCATTAGGTGCCCTTCGGGGAAAGTGGAGACAGGTGGTGCATGGTTGTCGTCAGCTCGTGTCGTGAGATGT
TGGGTTAAGTCCCGCAACGAGCGCAACCCTTATTGTTAGTTGCTACGCAAGAGCACTCTAGCGAGACTGCCGTTGAC
AAAACGGAGGAAGGTGGGGACGACGTCAAATCATCATGCCCCTTATGTCCTGGGCCACACACGTACTACAATGGTGG
TTAACAGAGGGAGGCAATACCGCGAGGTGGAGCAAATCCCTAAAAGCCATCCCAGTTCGGATTGCAGGCTGAAACCC

GCCTGTATGAAGTTGGAATCGCTAGTAATCGCGGATCAGCATGCCGCGGTGAATACGTTCCCGGGCCTTGTACACAC

CGCCCGTCACACCATGAGAGTCGGGAACACCCGAAGTCCGTAGCCTAACCGCAAGGAGGGCGCGGCCGAAGGTGGGT

TCGATAATTGGGGTGAAGTCGTAACAAGGTAGCCGTATCGGAAGGTGCGGCTGGATCACCTCCTTT

>SEQ ID NO: 158 | PROKKA_00208 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATGATGCAGTTGGGTCGCATGGCTCTGACTGCCAAAGATTTAT

CGCTCTGAGATGGCCTCGCGTCTGATTAGCTAGTAGGCGGGGTAACGGCCCACCTAGGCGACGATCAGTAGCCGGAC

TGAGAGGTTGACCGGCCACATTGGGACTGAGACACGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCGGGGAC

GAAACAAATGACGGTACCCGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

GATATACGGAGGAACACCAGTGGCGAAGGCGGATTGCTGGACAGTAACTGACGCTGAGGCGCGAAAGCGTGGGGAGC

AAACAGGATTAGATACCCTGGTAGTCCACGCCGTAAACGATGGATACTAGGTGTGGGGGGTCTGACCCCCTCCGTGC

CGCAGTTAACACAATAAGTATCCCACCTGGGGAGTACGATCGCAAGGTTGAAACTCAAAGGAATTGACGGGGCCCG

CACAAGCGGTGGAGTATGTGGTTTAATTCGAAGCAACGCGAAGAACCTTACCAGGGCTTGACATCCCACTAACGAAG

CAGAGATGCATTAGGTGCCCTTCGGGGAAAGTGGAGACAGGTGGTGCATGGTTGTCGTCAGCTCGTGTCGTGAGATG

TTGGGTTAAGTCCCGCAACGAGCGCAACCCTTATTGTTAGTTGCTACGCAAGAGCACTCTAGCGAGACTGCCGTTGA

CAAAACGGAGGAAGGTGGGGACGACGTCAAATCATCATGCCCCTTATGTCCTGGGCCACACACGTACTACAATGGTG

GTTAACAGAGGGAGGCAATACCGCGAGGTGGAGCAAATCCCTAAAAGCCATCCCAGTTCGGATTGCAGGCTGAAACC

CGCCTGTATGAAGTTGGAATCGCTAGTAATCGCGGATCAGCATGCCGCGGTGAATACGTTCCCGGGCCTTGTACACA

CCGCCCGTCACACCATGAGAGTCGGGAACACCCGAAGTCCGTAGCCTAACCGCAAGGAGGGCGCGGCCGAAGGTGGG

TTCGATAATTGGGGTGAAGTCGTAACAAGGTAGCCGTATCGGAAGGTGCGGCTGGATCACCTCCTTT

>SEQ ID NO: 159 | PROKKA_04460 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATAATGCAGTTGGGTCGCATGGCTCTGACTGCCAAAGATTTAT

CGCTCTGAGATGGCCTCGCGTCTGATTAGCTAGTAGGCGGGGTAACGGCCCACCTAGGCGACGATCAGTAGCCGGAC

TGAGAGGTTGACCGGCCACATTGGGACTGAGACACGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCAGGGAC

GAAACAAATGACGGTACCTGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

GATATACGGAGGAACACCAGTGGCGAAGGCGGATTGCTGGACAGTAACTGACGCTGAGGCGCGAAAGCGTGGGGAGC

AAACAGGATTAGATACCCTGGTAGTCCACGCCGTAAACGATGGATACTAGGTGTGGGGGGTCTGACCCCTCCGTGCC

GCAGTTAACACAATAAGTATCCCACCTGGGGAGTACGATCGCAAGGTTGAAACTCAAAGGAATTGACGGGGCCCGC

ACAAGCGGTGGAGTATGTGGTTTAATTCGAAGCAACGCGAAGAACCTTACCAGGGCTTGACATCCCACTAACGAAGC

AGAGATGCATTAGGTGCCCTTCGGGGAAAGTGGAGACAGGTGGTGCATGGTTGTCGTCAGCTCGTGTCGTGAGATGT

TGGGTTAAGTCCCGCAACGAGCGCAACCCTTATTGTTAGTTGCTACGCAAGAGCACTCTAGCGAGACTGCCGTTGAC

AAAACGGAGGAAGGTGGGGACGACGTCAAATCATCATGCCCCTTATGTCCTGGGCCACACACGTACTACAATGGTGG

TTAACAGAGGGAGGCAATACCGCGAGGTGGAGCAAATCCCTAAAAGCCATCCCAGTTCGGATTGCAGGCTGAAACCC

-continued

```
GCCTGTATGAAGTTGGAATCGCTAGTAATCGCGGATCAGCATGCCGCGGTGAATACGTTCCCGGGCCTTGTACACAC

CGCCCGTCACACCATGAGAGTCGGGAACACCCGAAGTCCGTAGCCTAACCGCAAGGAGGGCGCGGCCGAAGGTGGGT

TCGATAATTGGGGTGAAGTCGTAACAAGGTAGCCGTATCGGAAGGTGCGGCTGGATCACCTCCTTT
```

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Mouse Model of C. difficile Infection

Mouse Husbandry

Experiments were performed using C57BL/6J female mice purchased from Jackson Laboratories (Bar Harbor, Me.) and housed in ventilated sterile cages. All animals were maintained in a specific-pathogen-free facility. Animals were acclimated to the vivarium for at least 3 days prior to study (i.e., commencing antibiotic courses). For experiments involving C. difficile infection, mice were administered 10-10$^4$ C. difficile VPI 10463 spores in 200 µl PBS by oral gavage. Experiments were performed in compliance with institutional guidelines and approved by the institution's Institutional Animal Care and Use Committee. Sterile food and drinking water were provided to the animals Live Biotherapeutic Product (LBP) Preparation Individual bacterial strains were isolated from fecal material obtained from healthy donors. The individual strains were struck out from 15% glycerol freezer stocks onto EG (Eggerth Gagnon) agar plates containing 5% horse blood in an anaerobic chamber and incubated for 24-48 hours at 37° C. Colonies were inoculated into pre-reduced liquid Peptone Yeast Glucose (PYG) media and grown for 24-48 hours until dense (static in the anaerobic chamber). Optical density ($OD_{600}$) of the cultures was assessed and live biotherapeutic product (LBP) cocktails were prepared inside an anaerobic chamber adjusting inputs based upon $OD_{600}$ for equal CFU ratio cocktails in PBS (sterile, pre-treated).

C. difficile Colony Forming Unit (CFU) Determination

Fecal pellets were collected, transported to an anaerobic chamber (<2 hours), and manually homogenized in 500 µl, of pre-reduced PBS using a pipette tip and through repeated pipetting. Serial dilutions of fecal homogenates were prepared in pre-reduced PBS, 100 µl, of which was spread onto cycloserine-cefoxitin-fructose agar with sodium taurocholate (TCCFA) plates, and incubated anaerobically at 37° C. C. difficile CFUs were enumerated at 48 hours.

Murine Susceptibility to C. difficile Infection

Groups of mice were evaluated for susceptibility to C. difficile using three antibiotic regimen protocols: (1) an antibiotic cocktail, (2) clindamycin administration, or (3) cefoperazone administration (FIGS. 2 and 3). The antibiotic cocktail consisted of kanamycin (0.4 mg/ml), gentamicin (0.035 mg/ml), colistin (0.056 mg/ml), metronidazole (0.215 mg/ml), vancomycin (0.045 mg/ml) in the drinking water from day −10 to day −3, followed by a single intraperitoneal clindamycin injection (200 µg/mouse). The clindamycin administration involved a single intraperitoneal injection of clindamycin (200 µg/mouse) on day −1. The notation of days is relative to day 0, the day of C. difficile infection.

Figure 4E:
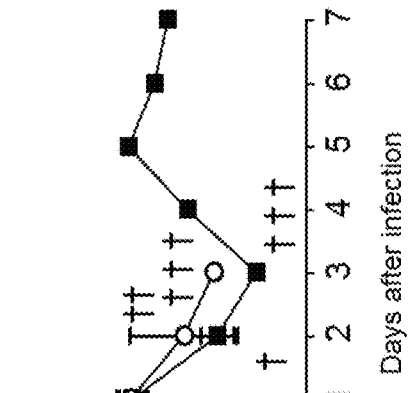
Figure 4F:
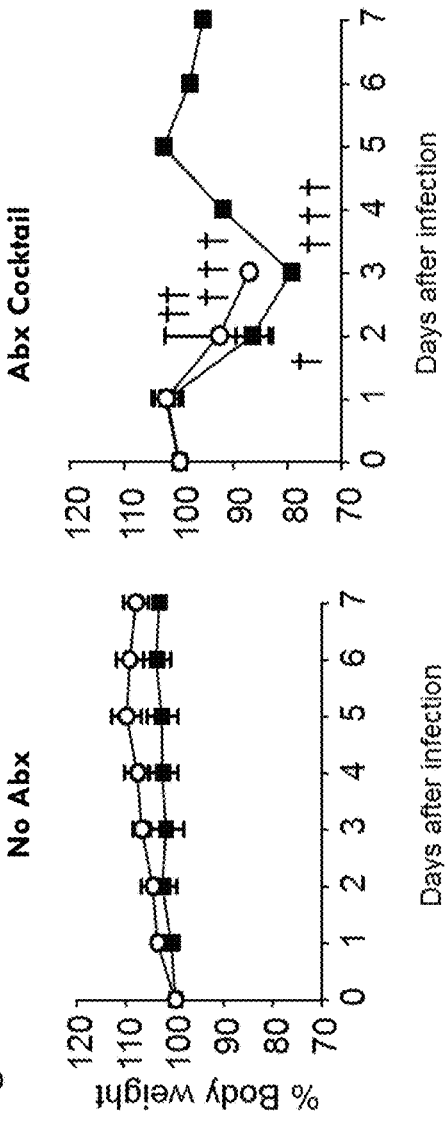
Figure 4G:
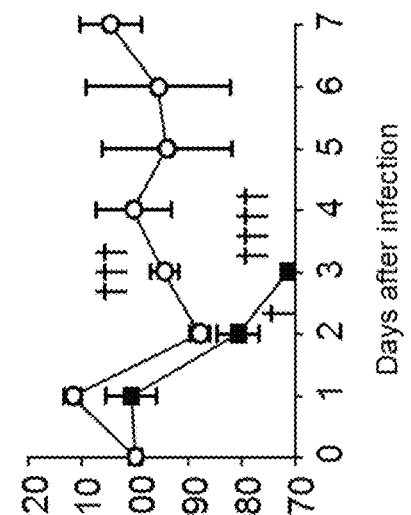
Figure 4H:
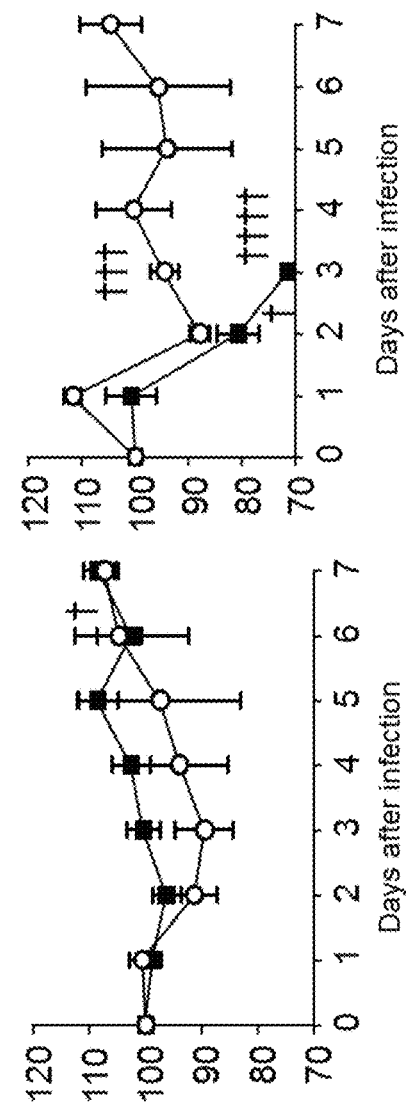
Figure 4I:
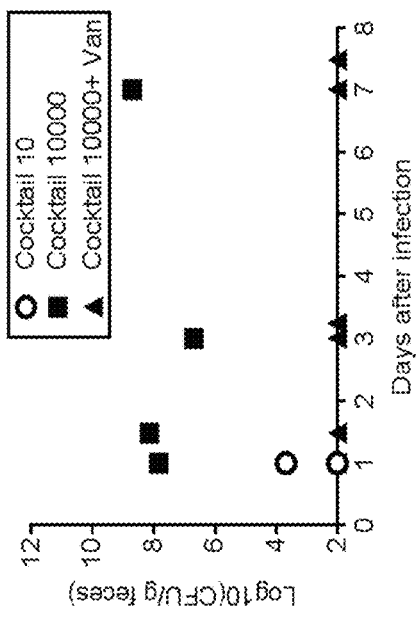
Figure 4J:
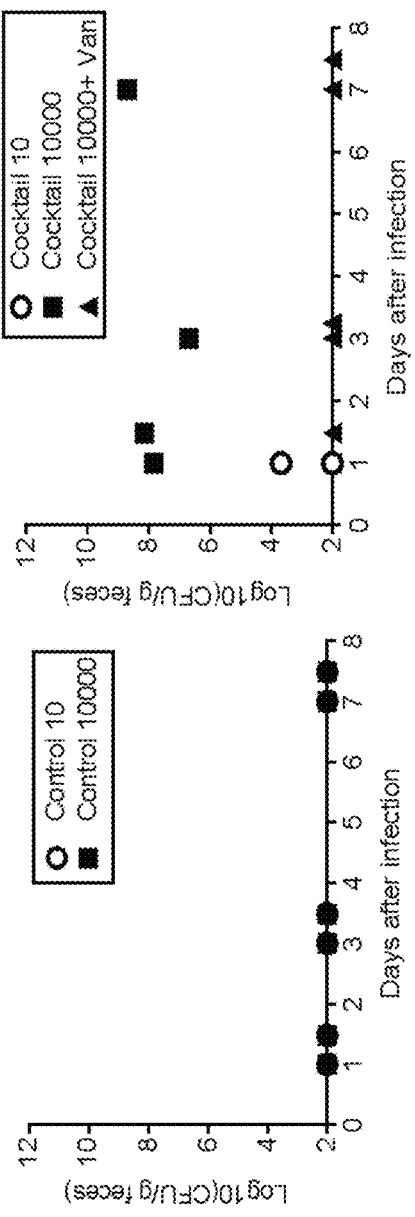
Figure 4L:
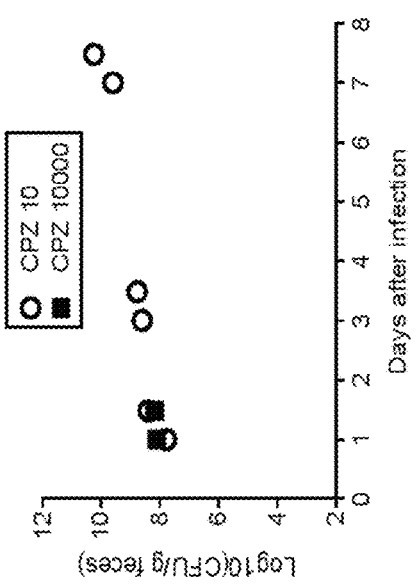
Figure 4K:
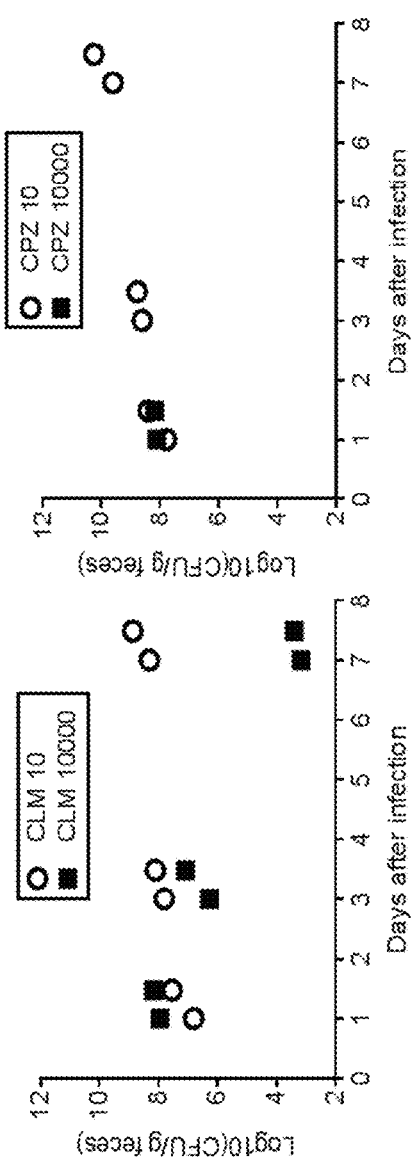

Mice were treated with the indicated antibiotic regimen as described above and then infected with either 10 or 10$^4$ C. difficile spores by oral gavage on day 0 (FIGS. 2 and 3). An additional experimental arm was added to the antibiotic treatment model in which mice were treated with vancomycin after C. difficile infection (FIG. 4J; black triangles).

Mice were monitored daily following infection for mortality/survival (FIGS. 4A-4D) and weight (FIGS. 4E-4H). Fecal pellets were also collected daily and used for C. difficile CFU enumeration, presented as CFU/gram feces (FIGS. 4I-4L).

The groups of mice that received cefoperazone treatment had a significant change in weight (FIG. 4H) and substantial C. difficile bacterial load in the fecal pellets (FIG. 4L), even following administration with 10 C. difficile spores. These results indicated that the cefoperazone pre-treatment regimen provided a good model for C. difficile infection and for evaluating protection and/or treatment of C. difficile infection. In the absence of antibiotic treatment prior to infection, C. difficile infection was not established (FIG. 4I) and all mice survived (FIG. 4A) without significant change in body weight (FIG. 4E).

Example 2: Live Biotherapeutic Product (LBP) Preparations Protect Against *C. difficile* Infection The following LBP compositions were evaluated for their capacity to protect and/or treat *C. difficile* infection:
Composition A,
Composition B,
Composition C,
Composition D,
Composition E (See e.g., Narushima et al., Gut Microbes (2014) 5(3) 333-339), and
Composition I: a mixture of *Clostridium scindens, Pseudoflavonifractor capillosus* and *Blautia hansenii* (FIG. 5).

In general, LBP cocktails were mixed in PYG media, and each mouse was administered a dose by oral gavage in 250 µL pre-reduced PBS (media-free). For composition E, bacteria were mixed in equal volumes (not equal ratios/CFUs) and administered in a 250 µL dose. Each LBP of Compositions A-D contained $10^8$ CFUs total in a 250 µL dose, comprised of $10^7$ CFU of each of the bacterial strains (FIG. 1), for a total of $10^8$ CFU administered to each animal. Composition I contained a total of $10^6$ CFUs in a 250 µL dose (approximately 333,000 of each of the 3 bacteria mixed).

Figure 6:
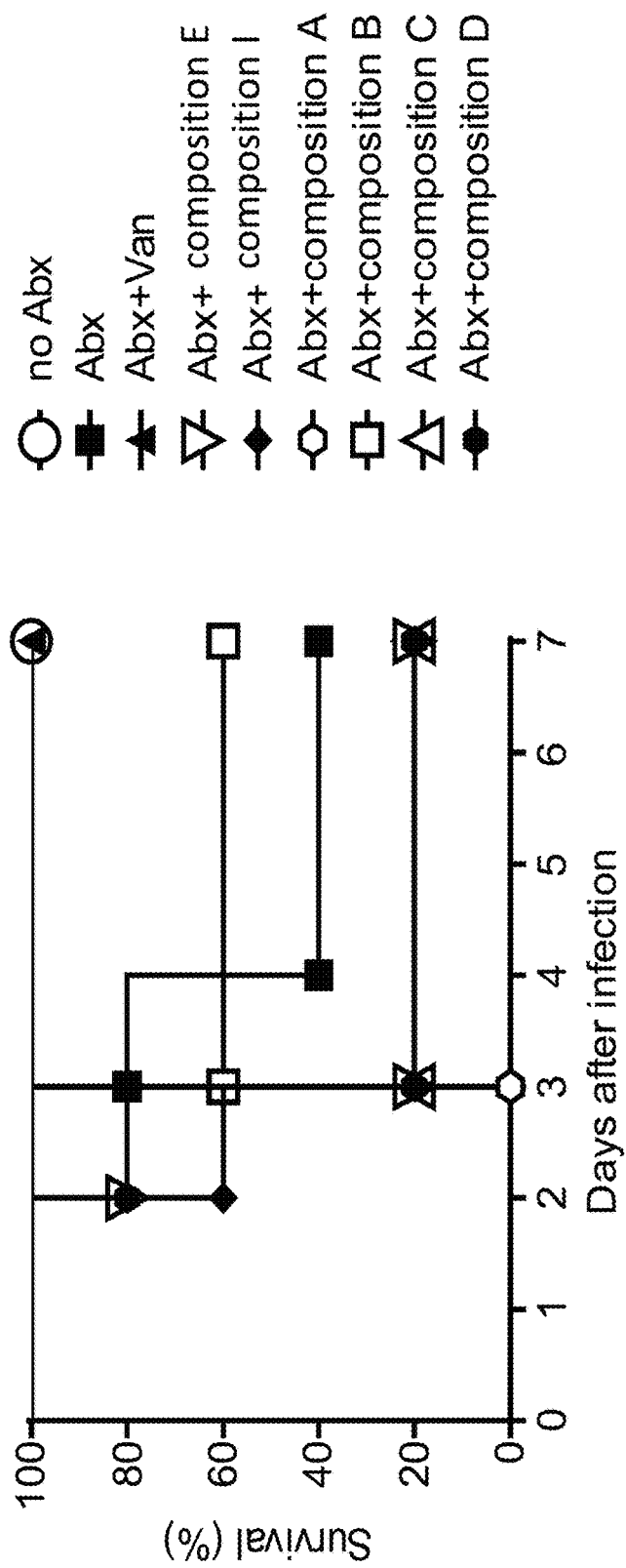
FIG. 6 shows survival of mice over time post infection with *C. difficile* spores, according to the experimental conditions shown in FIG. 5. Mice losing >20% body weight of baseline were included in mortality numbers in survival curves.
Figure 7A:
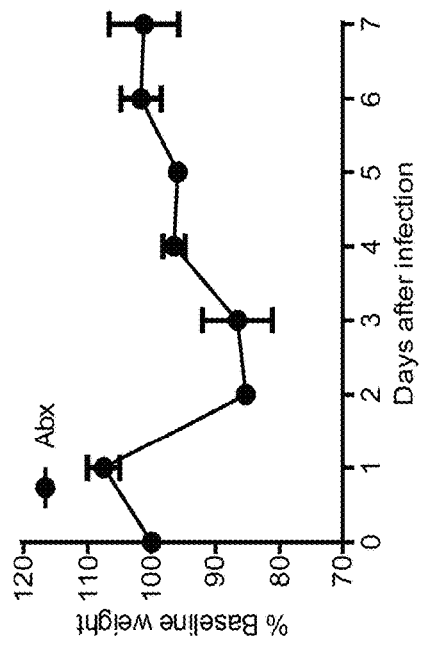
FIGS. 7A-7I show weight of the mice at various times post infection with *C. difficile* spores. Groups of mice received cefoperazone (Abx) treatment followed by the indicated composition, or no cefoperazone (no Abx), then were administered *C. difficile* spores.
Figure 7B:
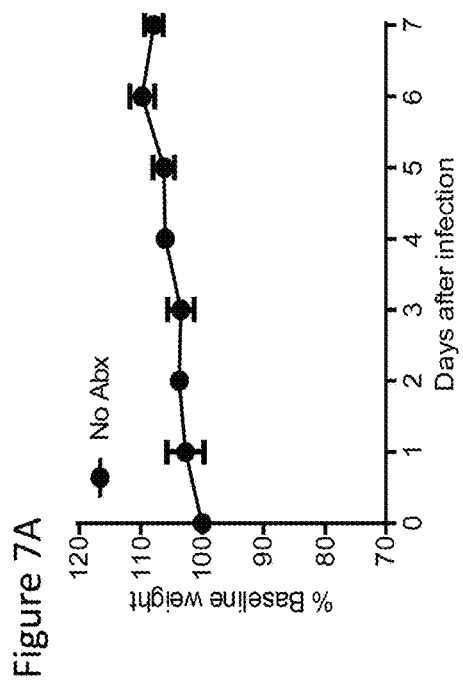
Figure 7C:
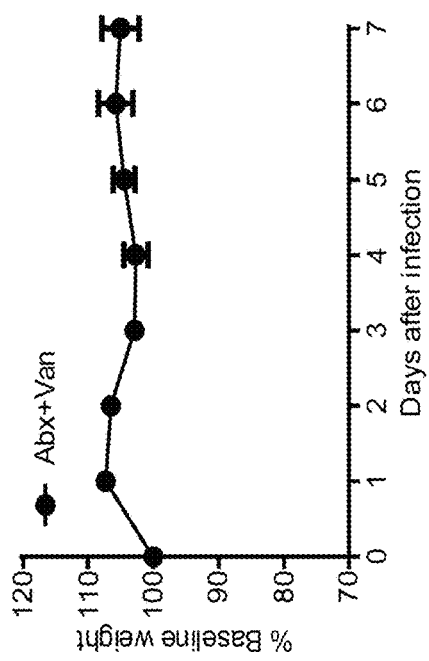
Figure 7E:
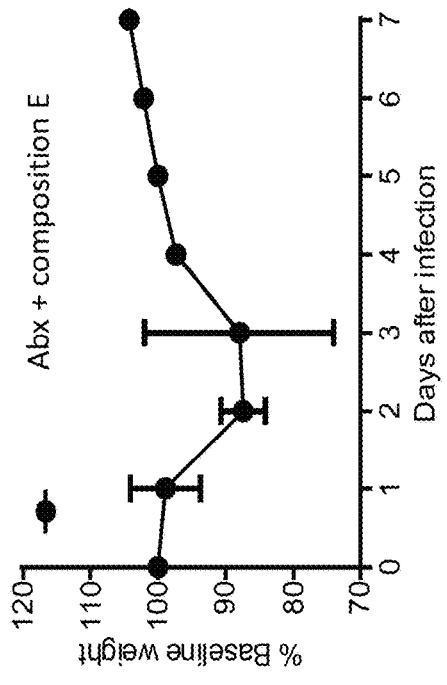
Figure 7D:
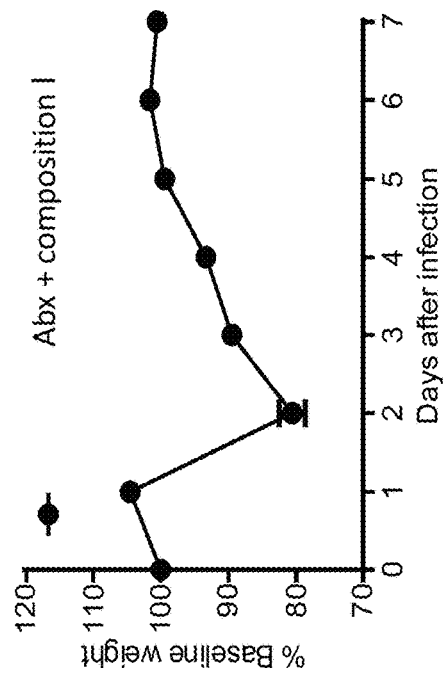
Figure 7F:
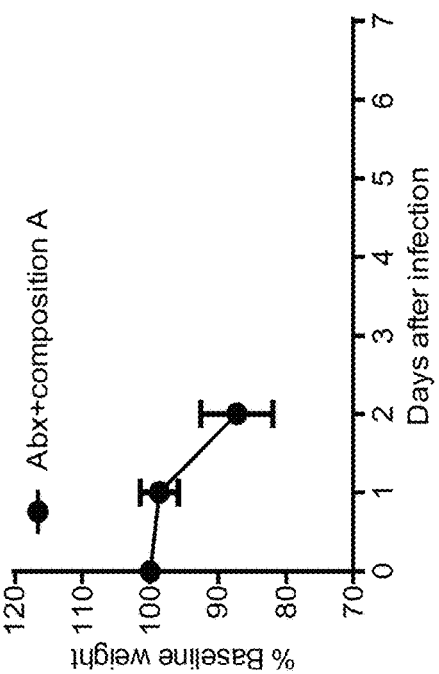
Figure 7H:
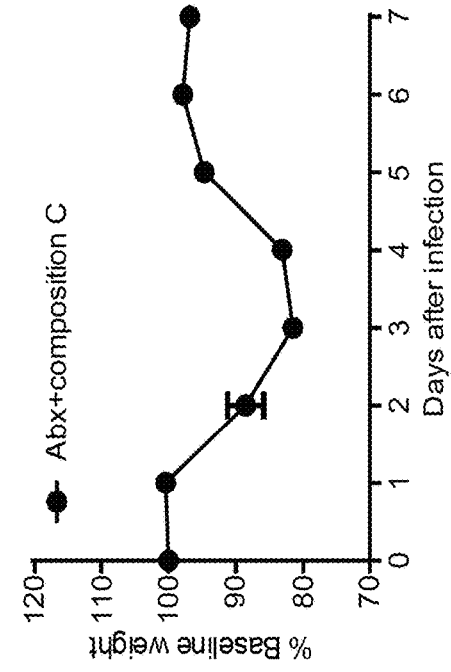
Figure 7G:
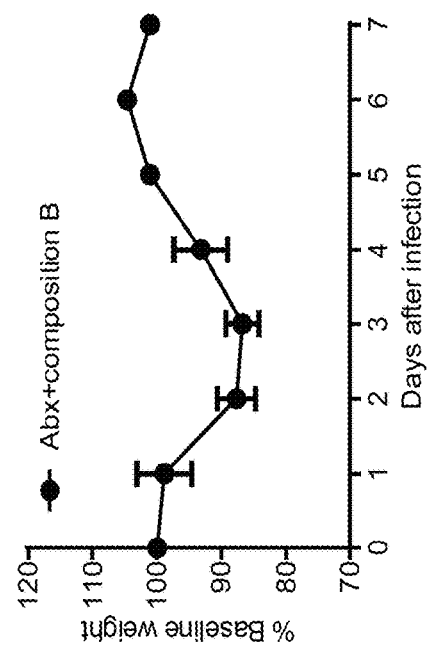
Figure 7I:
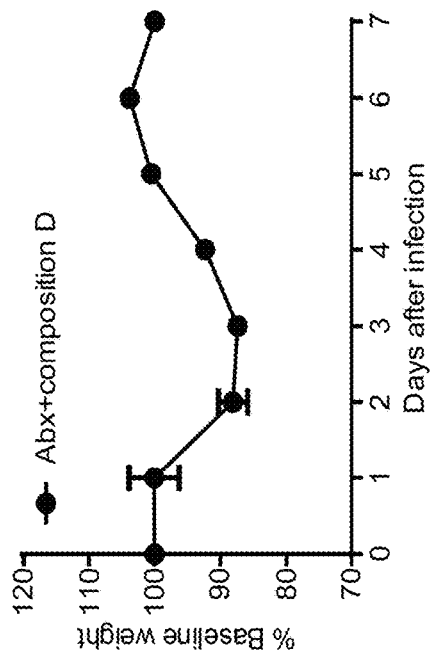
Figure 8B:
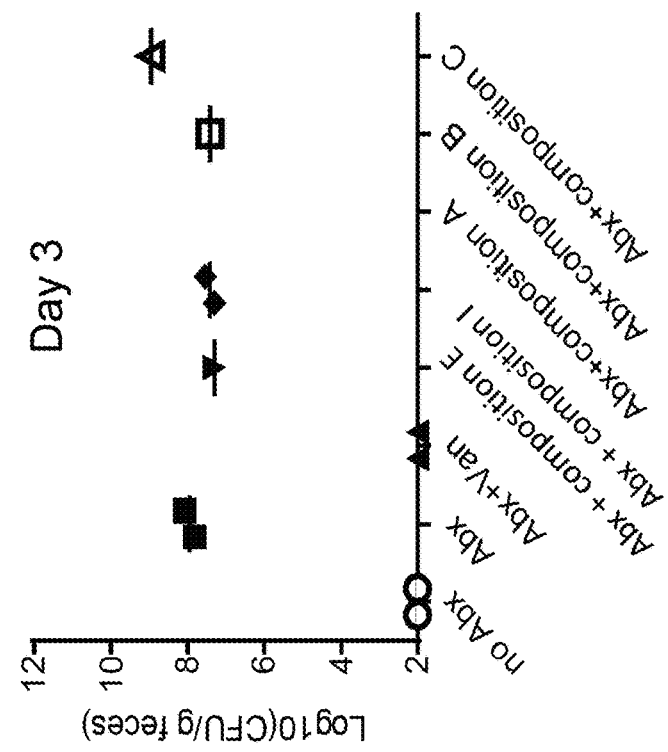
Figure 8A:
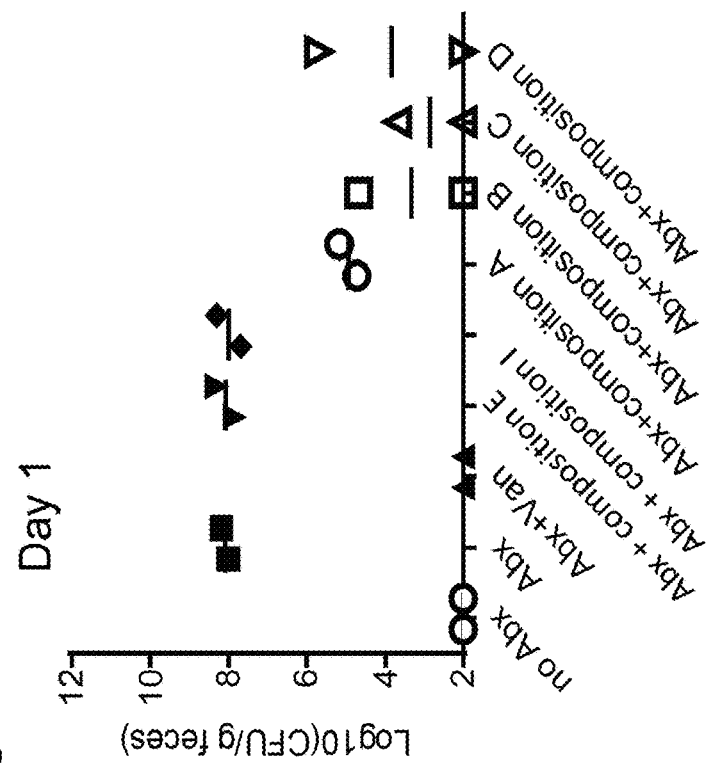

Groups of mice were subjected to cefoperazone treatment, as described in Example 1, and were administered the indicated composition by oral gavage 2 days after the cessation of cefoperazone treatment. Twenty-four hours later, the mice were subjected to infection with $10^4$ *C. difficile* spores (FIG. 5). Mice evaluated for survival/mortality (FIG. 6), weight (FIGS. 7A-7I, and *C. difficile* CFUs (FIGS. 8A-8C). The results show that administration of Composition B prior to *C. difficile* infection is an effective protection and/or treatment against *C. difficile* infection.

Figure 10:
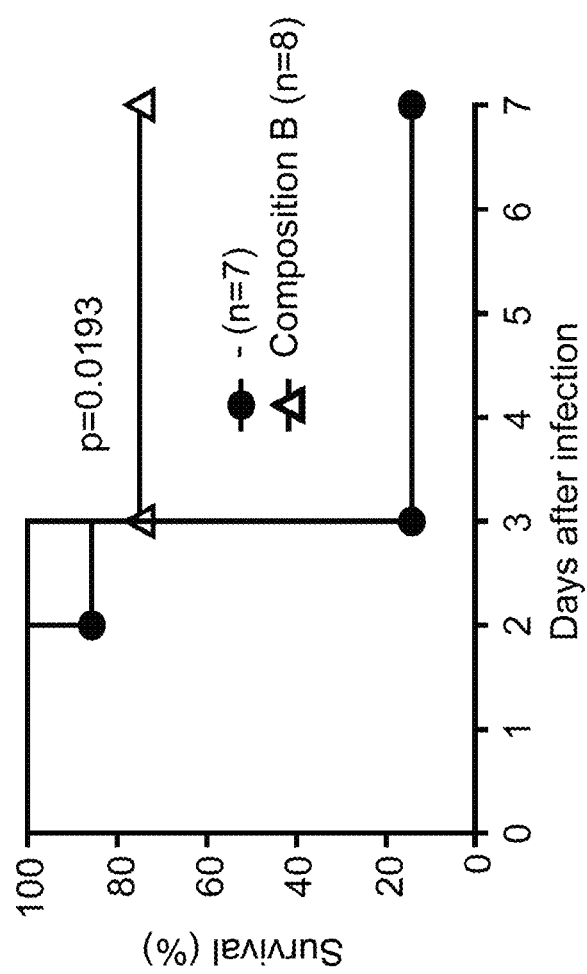
FIG. 10 shows survival of the mice over time post infection with *C. difficile* spores, according to the experimental conditions shown in FIG. 9. Mice losing >20% body weight of baseline were included in mortality numbers in survival curves.
Figure 11:
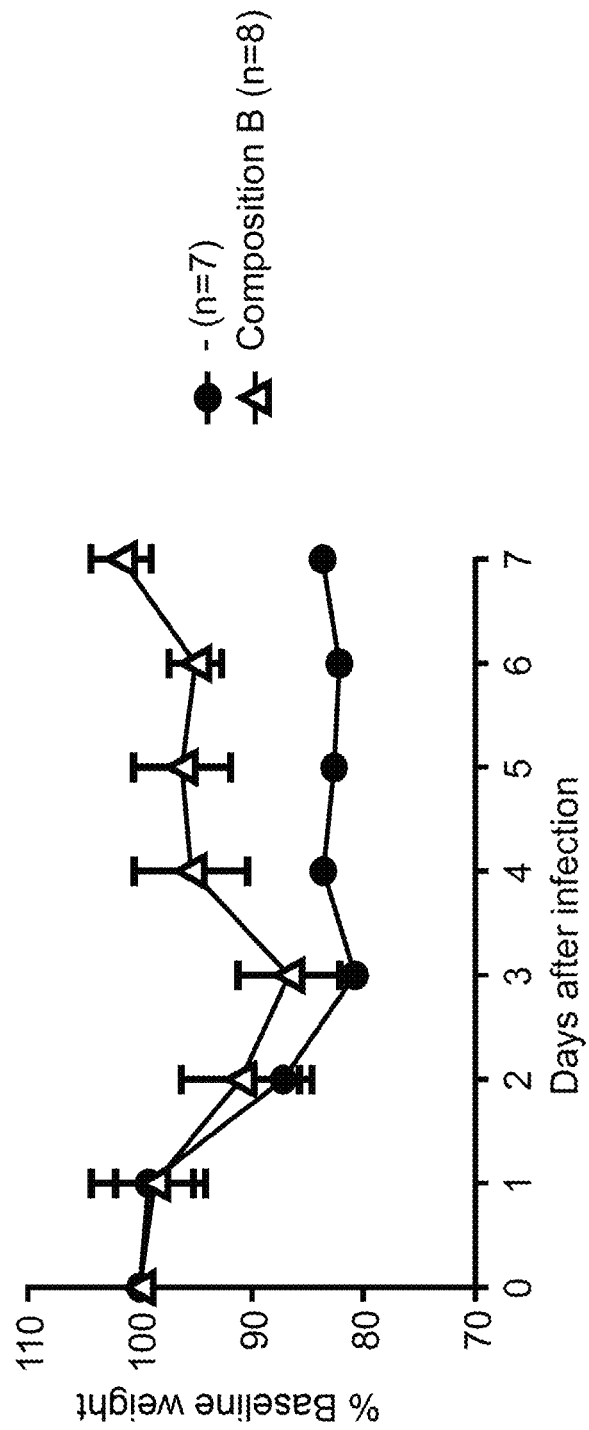
FIG. 11 shows weight of the mice at various times post infection with *C. difficile* spores.
Figure 12:
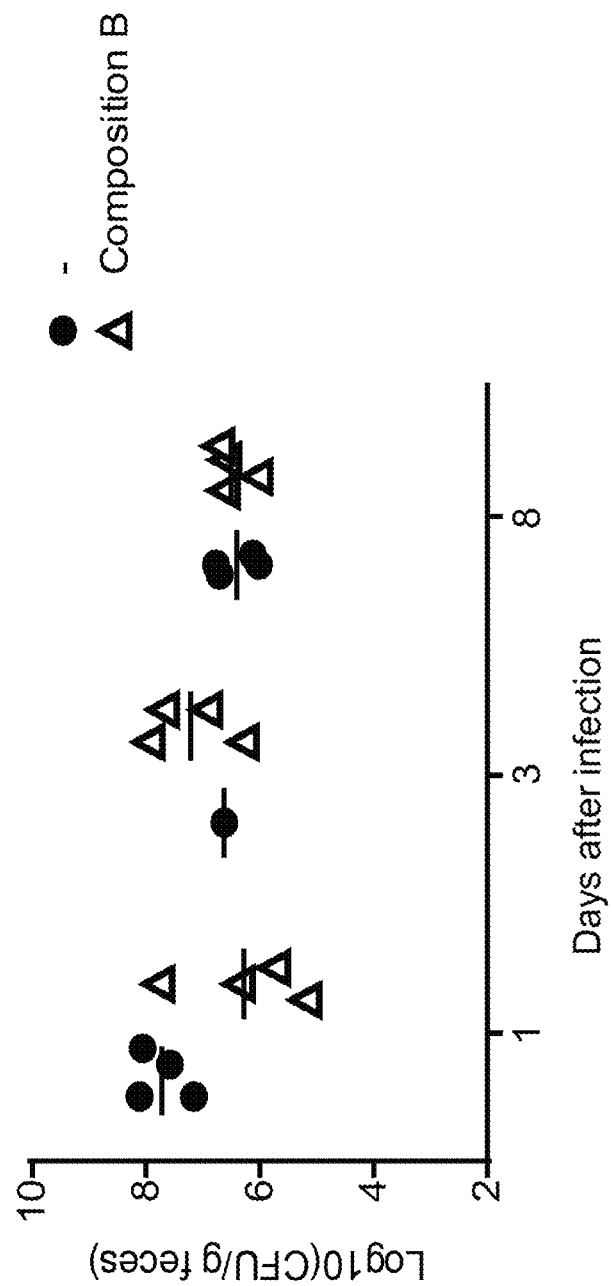
FIG. 12 shows the *C. difficile* burden in colony forming units (CFUs) in fecal pellets collected from mice 1, 3, and 8 days post infection with *C. difficile*.

Example 3: Composition B Protects Against and/or Treats *C. difficile* Infection Groups of 10-12 week old mice were used in the *C. difficile* mouse model (FIG. 9). Mice were subjected to cefoperazone treatment as described in Example 1. One group of mice was then administered Composition B ($10^8$ CFU per mouse) administered by oral gavage, as described in Examples 1 and 2, 2 days after the cessation of cefoperazone treatment. The other group of mice did not receive a live biotherapeutic product after cefoperazone treatment (control). Twenty-four hours later, the mice were subjected to *C. difficile* infection ($10^4$ *C. difficile* spores) and then evaluated for survival/mortality (FIG. 10), weight (FIG. 11), and *C. difficile* burden (CFUs per gram feces; FIG. 12). These results confirm the results of Example 2 that demonstrate treatment with Composition B prior to *C. difficile* infection is an effective protection and/or treatment against *C. difficile* infection.

Example 4: LBP Composition F Protects Against and/or Treat *C. difficile* Infection FIG. 13 shows the strains of live biotherapeutic product (LBP) Composition F. The genus-species classification indicates the closest species based on the sequence of the isolated strain. FIG. 14 shows the classification by *Clostridium* cluster of the strains in Composition F.

Figure 16:
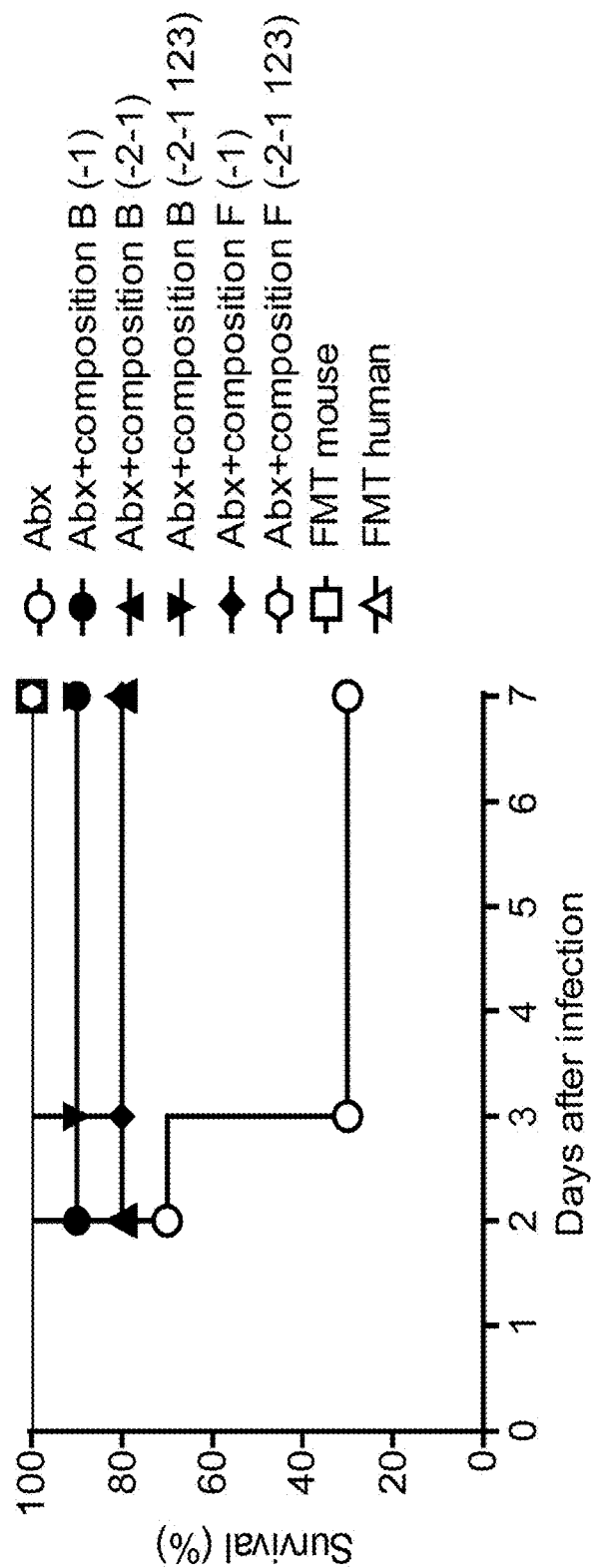
FIG. 16 shows survival of the mice over time post infection with *C. difficile* spores, according to the experimental conditions shown in FIG. 15. Mice losing >20% body weight of baseline were included in mortality numbers in survival curves.
Figure 17A:
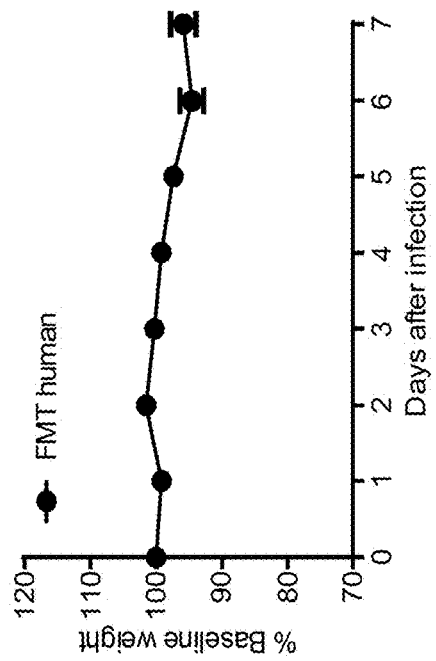
FIGS. 17A-17H show weight of the mice at various times post infection with *C. difficile* spores. Groups of mice received cefoperazone (Abx) treatment followed by the indicated composition, then were administered *C. difficile* spores.
Figure 17B:
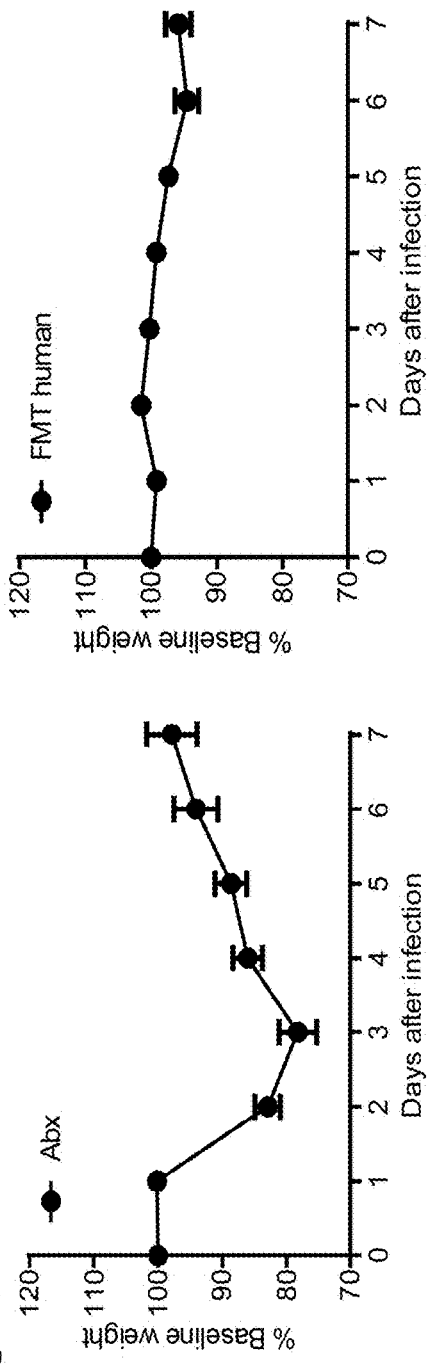
Figure 17C:
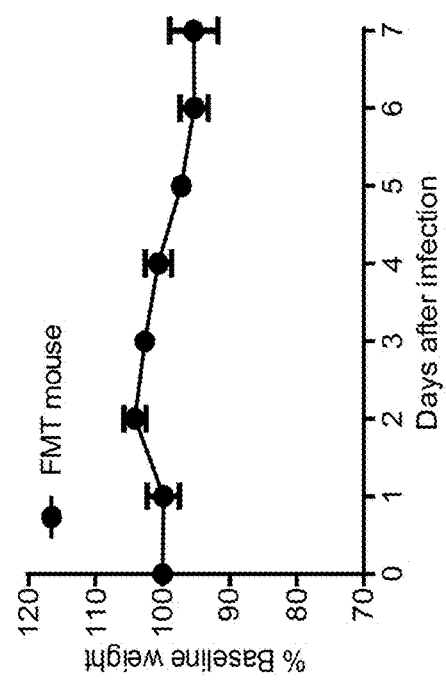
Figure 17E:
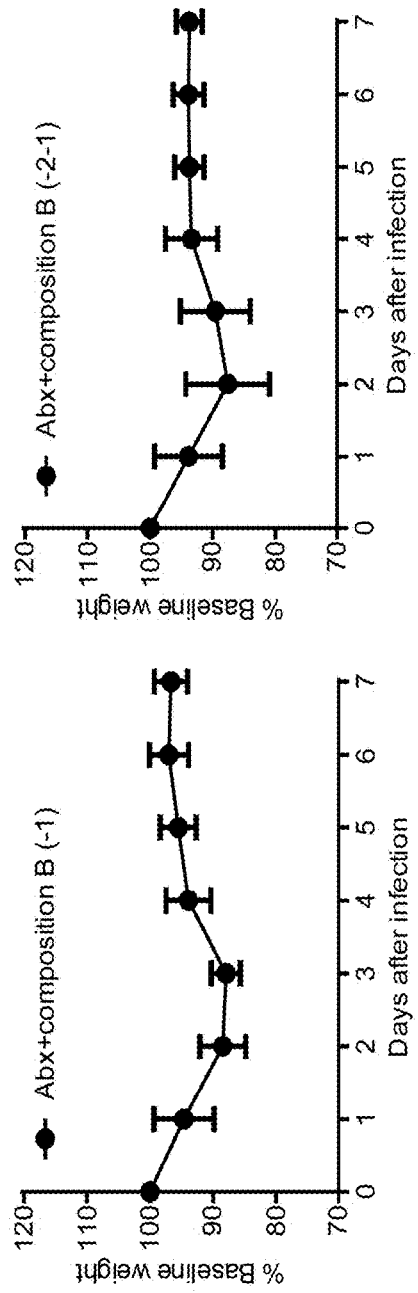
Figure 17F:
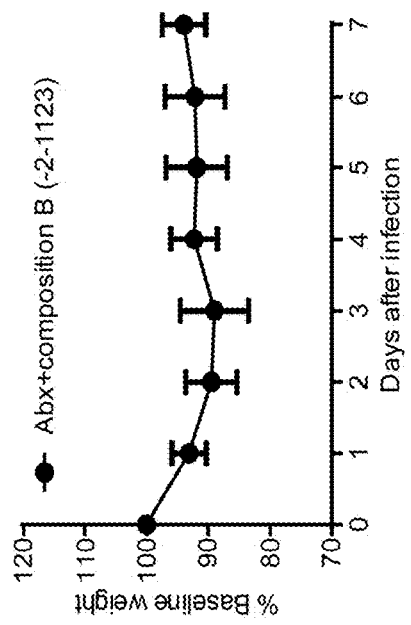
Figure 17D:
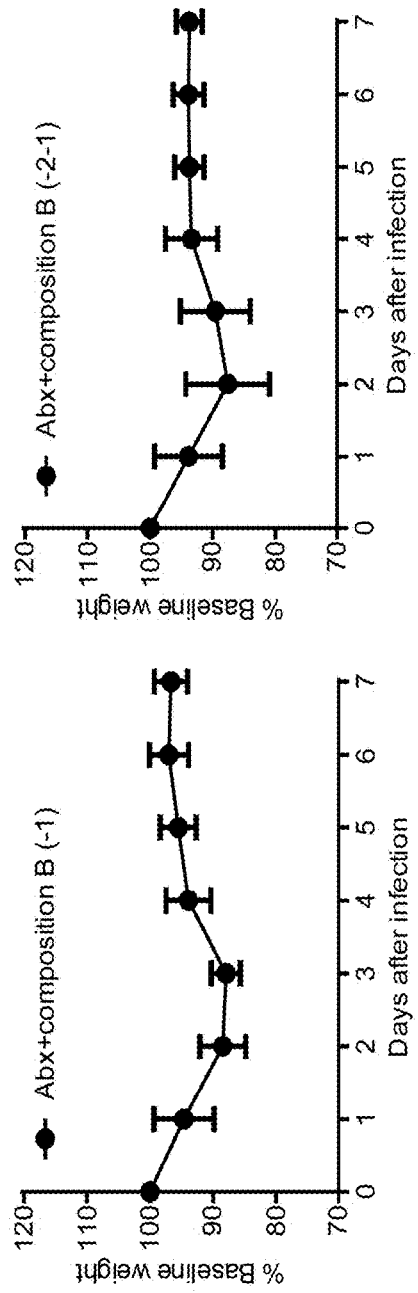
Figure 17H:
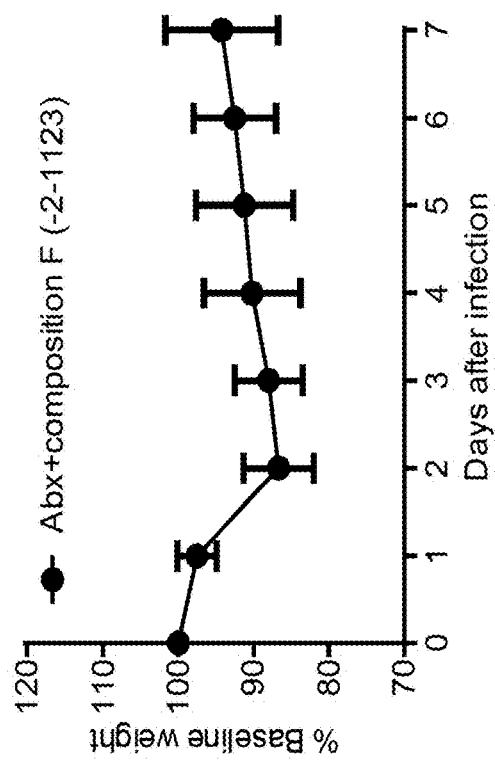
Figure 17G:
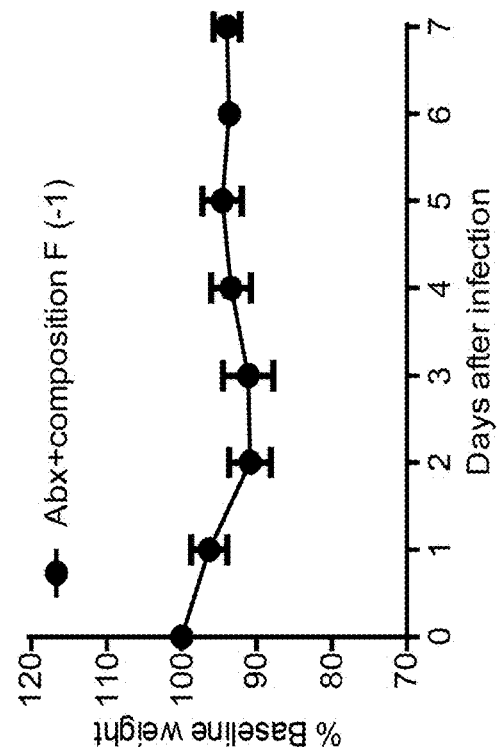
Figure 22B:
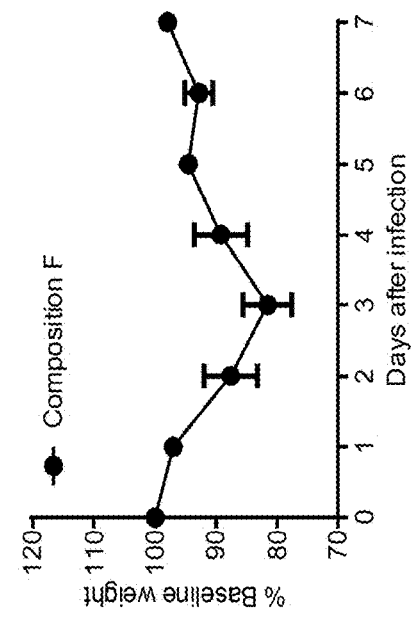
FIGS. 22A-22J show weight of the mice at various times post infection with *C. difficile* spores.
Figure 22A:
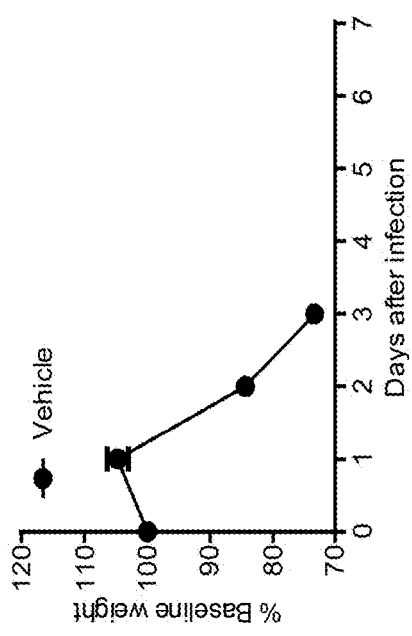
Figure 22C:
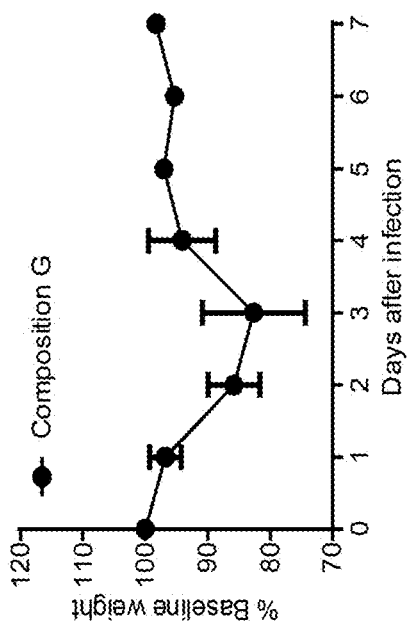
Figure 22E:
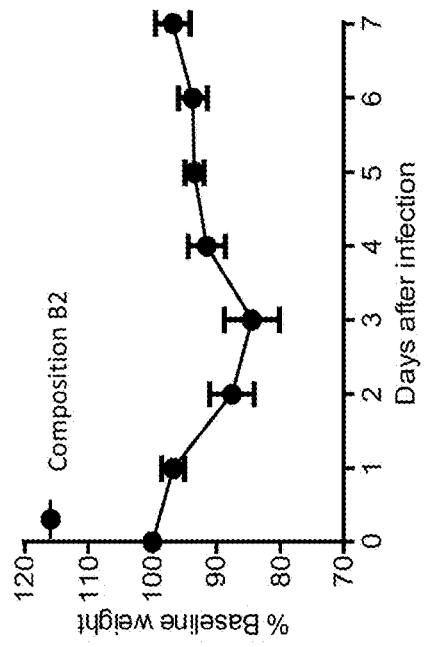
Figure 22G:
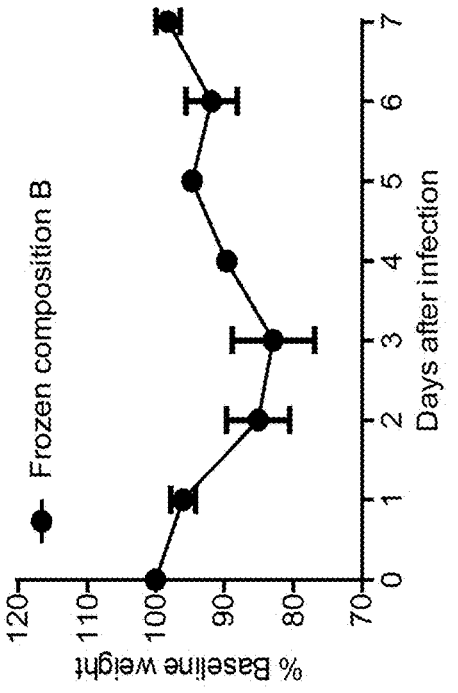
Figure 22D:
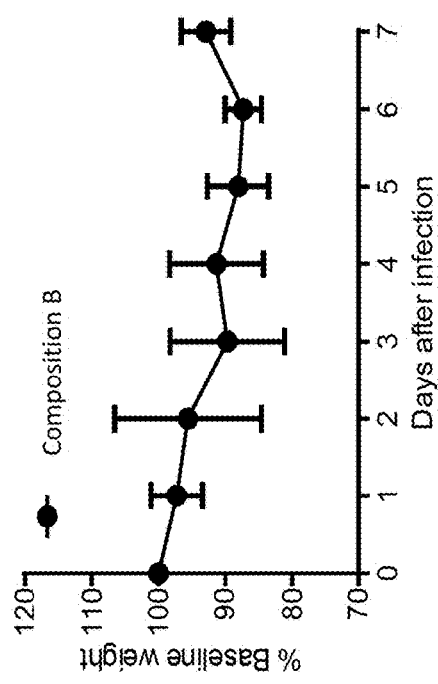
Figure 22F:
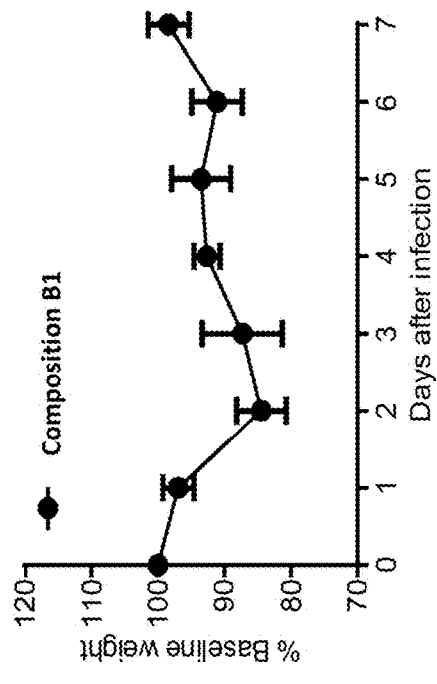
Figure 22I:
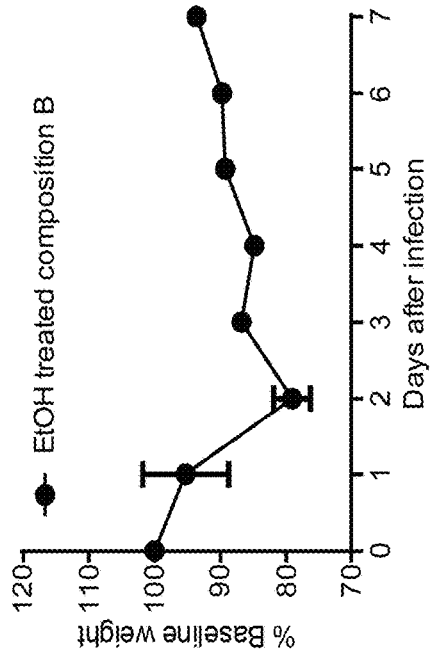
Figure 22H:
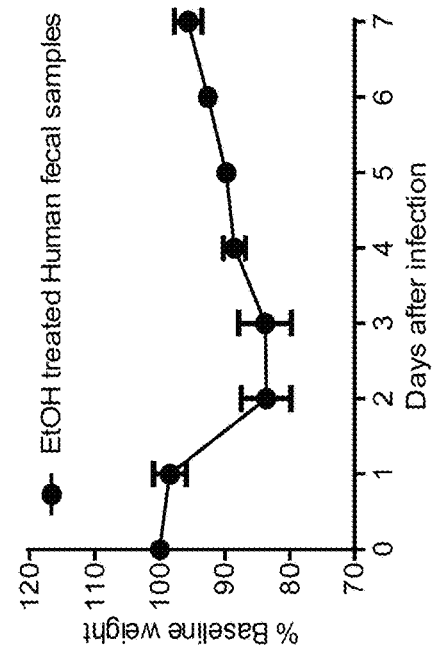
Figure 22J:
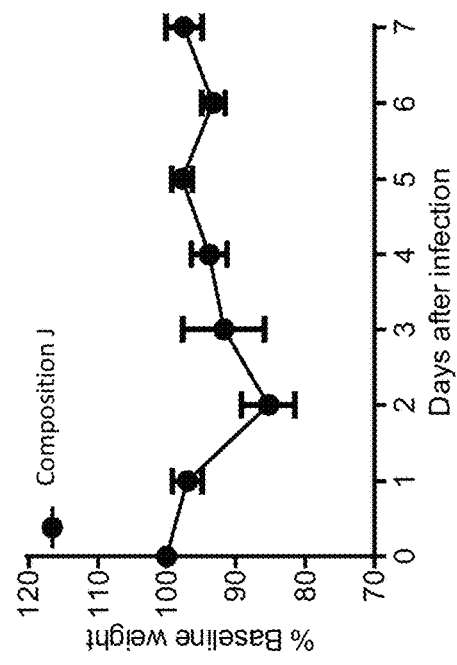

Groups of mice were administered cefoperazone, as described in the Examples above, then administered LBPs or fecal matter transplant (FMT) from mice or human (FIG. 15). Composition B was administered to the indicated groups on day −1; days −2 and −1; or on days −2, −1, 1, 2, and 3, relative to infection with $10^4$ *C. difficile* spores. Composition F was administered to the indicated groups on day −1 or on days −2, −1, 1, 2, and 3, relative to administration of *C. difficile* spores. Additional groups received FMT from mice or from humans (200 µL of a 10% fecal sample s per mouse). Mice were then evaluated for survival/mortality (FIG. 16), weight (FIGS. 17A-17H), and *C. difficile* burden (CFU/gram feces) on days 1, 3, 8 and 17 after infection (FIGS. 18A and 18B). The data demonstrate that Composition B, Composition F, and FMT protect against and/or treat *C. difficile* infection.

Example 5: LBP Compositions Protect Against and/or Treat *C. difficile* Infection FIG. 19 shows the strains of LBP Composition G. The genus-species notation indicates the closest species based on the sequence of the isolated strain. Composition G includes a subset of the strains of Composition F. Groups of mice were administered cefoperazone, as described in the Examples above, then administered the LBP:
Composition B;
Composition B-1 (Composition B with *Bacteroides* added);
Composition B-2 (Composition B from which *Flavonifractor plautii* was removed and *Bacteroides* added);
Composition F;
Composition G;
Human fecal samples subjected to ethanol treatment;
Composition B subjected to ethanol treatment;
Composition B that had been frozen; or
Composition J: *Clostridium innocuum, Clostridium bolteae* and *Clostridium symbiosum* subjected to ethanol treatment;
(See also FIG. 20).

The *Bacteroides* strain used in Composition B-1 and B-2 was *Bacteroides ovatus* (strain identifier 211-B; SEQ ID NO: 83).

Figure 23:
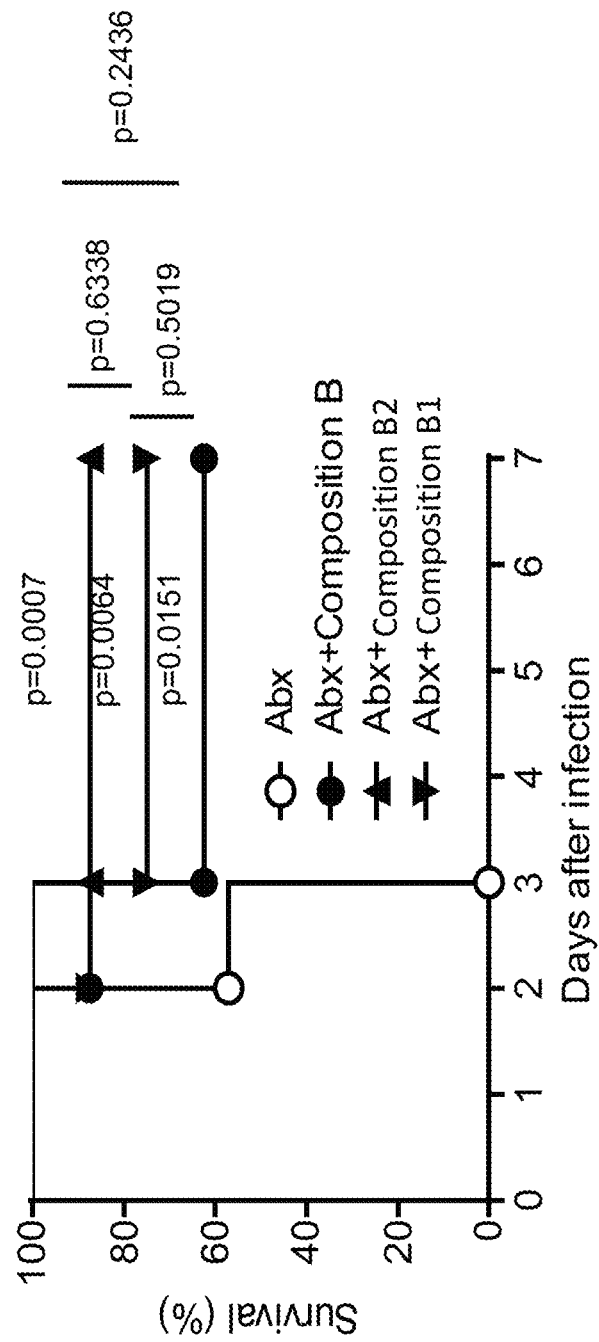
FIG. 23 shows the load of *C. difficile* in colony forming units (CFUs) in fecal pellets at various times post infection with *C. difficile*.
Figure 24:
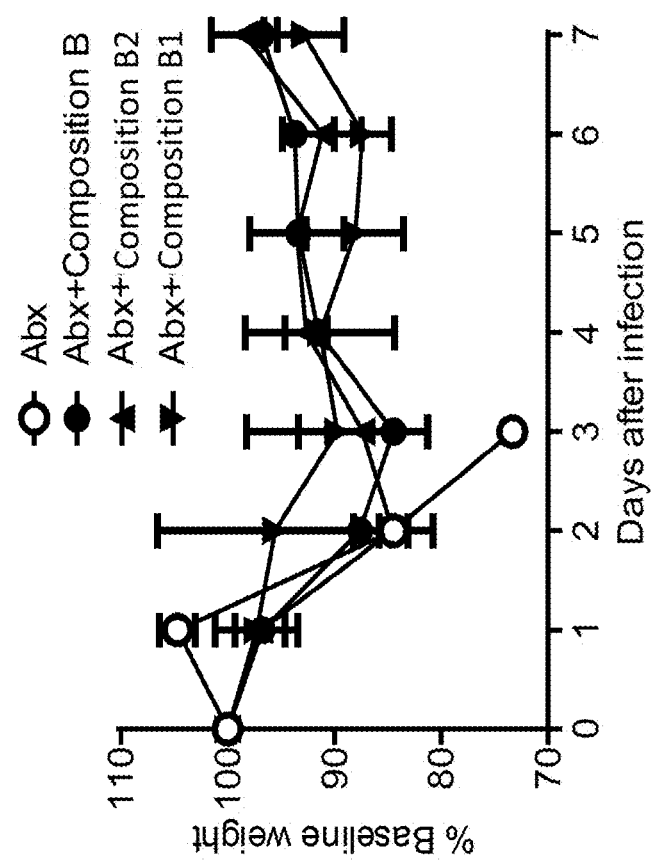
FIG. 24 shows weight of the indicated groups of mice at various times post infection with *C. difficile* spores.

Mice were challenged with *C. difficile* VPI 10463 spores ($10^4$) and monitored daily (Day 0 to Day 7 post *C. difficile* infection) for survival/mortality (FIGS. 21 and 23) and change in weight (FIGS. 22A-22J and 24). These data show that the compositions protect against and/or treat *C. difficile* infection.

Example 6: LBP Compositions Protect Against and/or Treat *C. difficile* Infection Groups of mice were subjected to cefoperazone treatment, as described above, then administered human fecal matter transplant, Composition B, Composition B+4 spores, or Composition H (FIG. 25). "Composition B+4 spores" refers to Composition B plus the following four strains in spore form: *Clostridium bolteae, Anaerotruncus colihominis, Clostridium symbiosum* and *Clostridium innocuum*. Composition H contains the following six strains in spore form: *Clostridium bolteae, Anaerotruncus colihominis, Clostridium symbiosum, Clostridium innocuum, Clostridium disporicum* and *Erysipelatoclostridium ramosum* (FIG. 26).

Figure 28A:
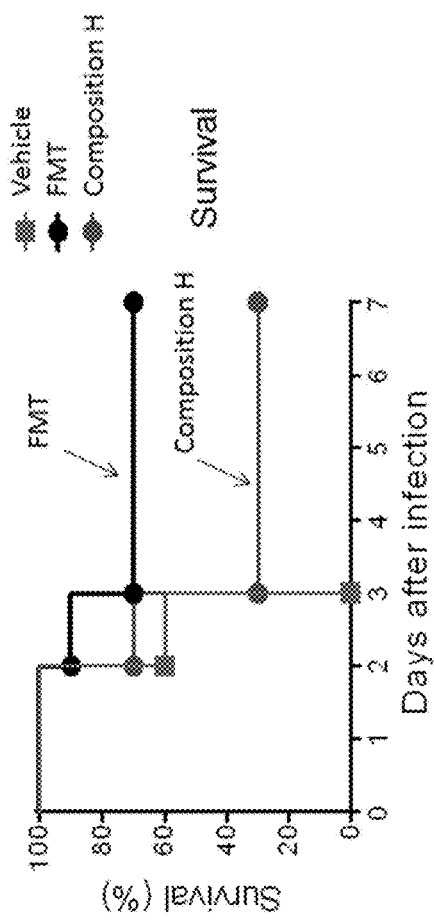
FIGS. 28A and 28B show results from the experimental conditions shown in FIG. 25.
Figure 28B:
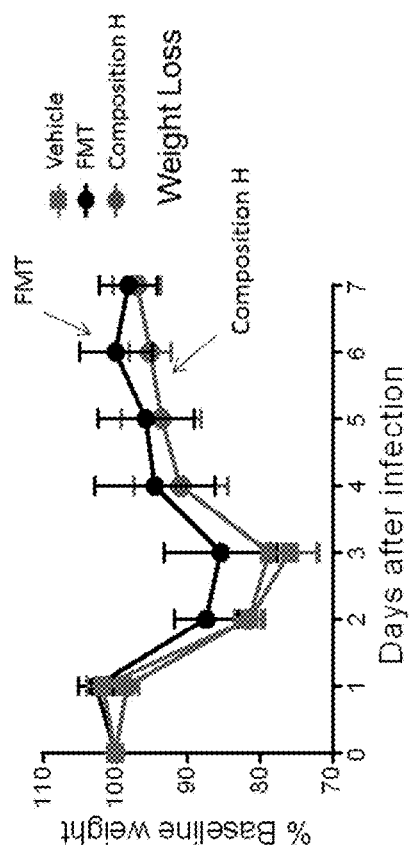
Figures 29A, 29B, 29C:
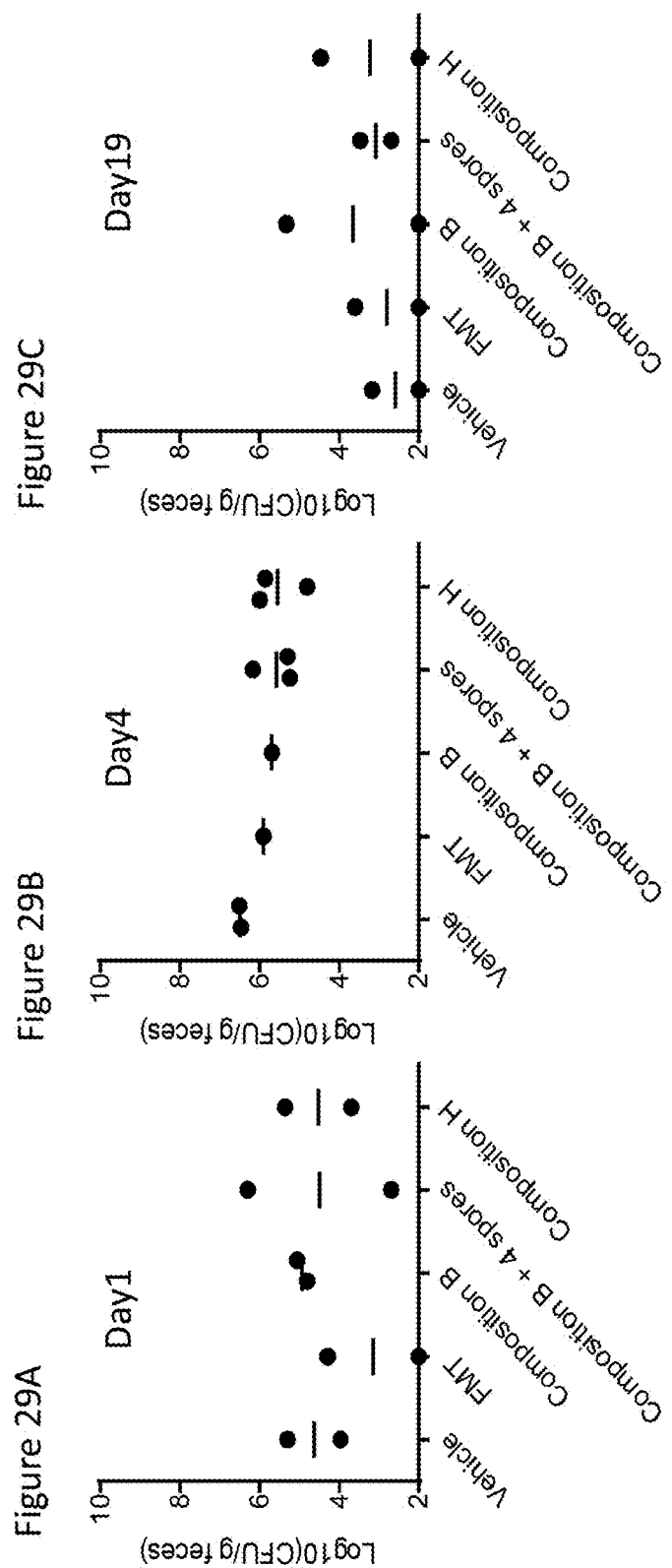
FIG. 29A shows survival/mortality of mice that received the indicated treatment prior to *C. difficile* infection.
FIG. 29B shows the weight over time of mice that received the indicated treatment prior to *C. difficile* infection.
FIG. 29C shows *C. difficile* burden at 19 days post *C. difficile* infection.

Mice were then challenged with *C. difficile* infection with $10^4$ *C. difficile* VPI 10463 spores and monitored for survival/mortality (FIGS. 27A and 28A), weight (FIGS. 27B and 28B). Mice that lost more than 20% body weight relative to baseline were included in mortality numbers in survival curves. The *C. difficile* burden was assessed by CFU in fecal pellets on days 1, 4 and 19 after infection (FIGS. 29A-29C).

These data indicate that Composition B as well as other compositions can improve survival in the cefoperazone-induced *C. difficile* mouse model and protect against and/or treat *C. difficile* infection.

Example 7: *C. difficile* Toxin Experiment

Vero cells, epithelial cells derived from African Green Monkey kidney epithelium, are sensitive to a variety of bacterial toxins, including *C. difficile* Toxin B. Exposure of cells to *C. difficile* Toxin B results in inhibition of the function of Rho, Rac, and Cdc42 leading to a decline in F-actin, a change in cell morphology (e.g., cell rounding), and eventually apoptosis.

To determine whether administration of bacterial compositions described herein has an effect on the production or activity of *C. difficile* Toxin B, a cellular assay was performed. Briefly, groups of mice were treated with cefoperazone, as described above, and administered human fecal matter transplant (FMT) ("4-3"); Composition B ("5-3"); Composition B plus four strains in spore form: *Clostridium bolteae*, *Anaerotruncus colihominis*, *Clostridium symbiosum* and *Clostridium innocuum* ("7-4"), or no treatment. Each of the groups of mice were then exposed to *C. difficile* infection with $10^4$ *C. difficile* spores. The groups of mice that did not receive a treatment after cefoperazone administration and prior to *C. difficile* infection are referred to as "2-1 (Cdiff)" and "2-4 (Cdiff)." An additional group of mice was not exposed to *C. difficile* as indicated by "N3 (Healthy)".

Figure 30:
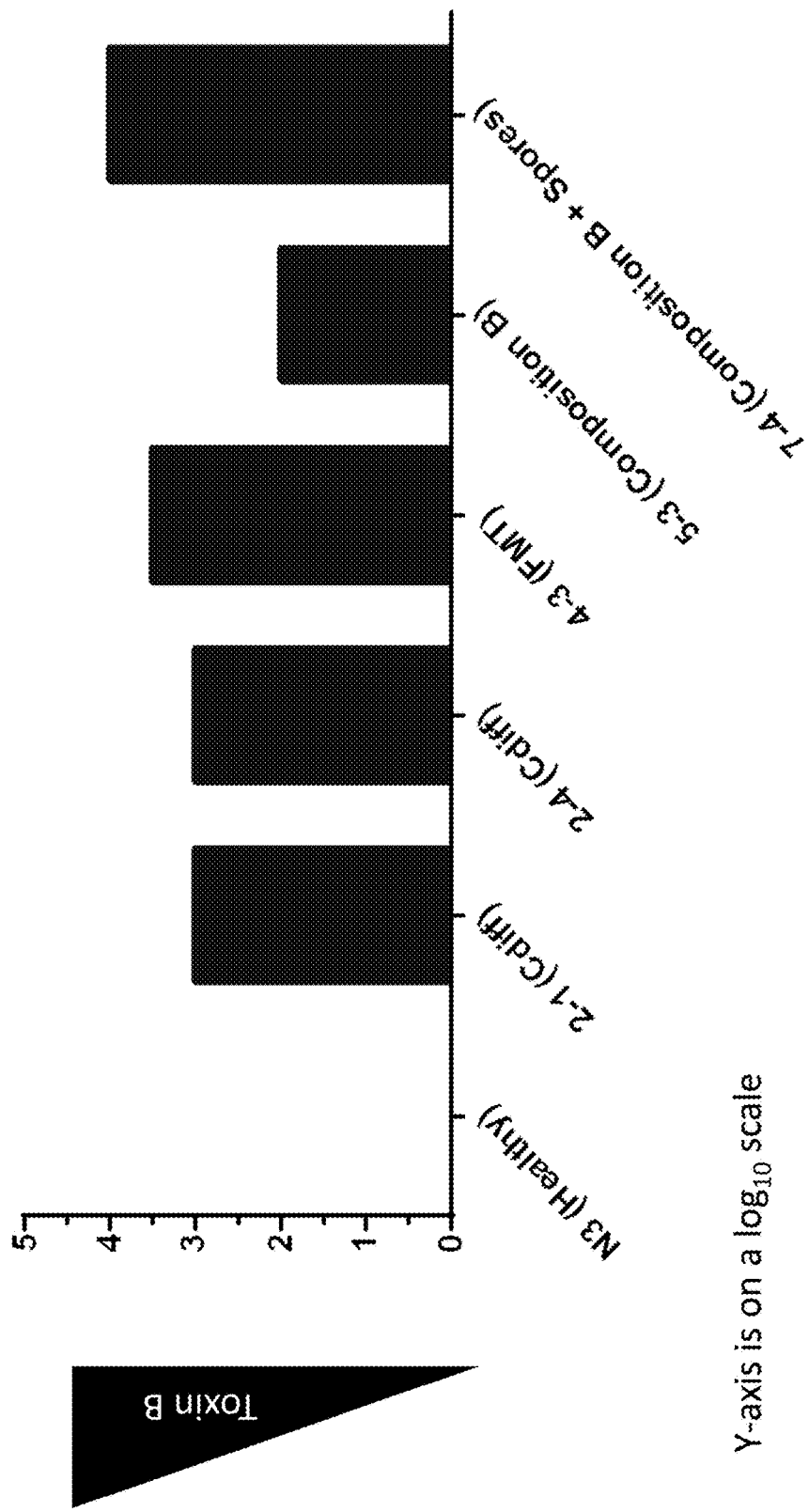
FIG. 30 shows that Composition B reduced the amount of *C. difficile* Toxin B compared to no treatment controls: "2-1 (Cdiff)" and "2-4 (Cdiff)" and FMT. In addition, Composition B reduced the amount of *C. difficile* Toxin B compared to Composition B with additional spores.

Fecal pellets were collected from each of the groups of mice, weighed, and homogenized in PBS and normalized to a fixed concentration (~25 mg/mL). The samples were centrifuged to prepare a clarified supernatant, which was then diluted in 10-fold serial dilutions to produce a range from 1:10 to $1:10^{-6}$ dilutions of clarified pellet supernatant. Vero cell cultures were exposed to the diluted samples for approximately 18 hours, then visualized by phase contract microscopy to assess morphological changes (i.e., cell rounding) associated with *C. difficile* toxin exposure. The cells were scored based on the highest concentration of supernatant that did not yield a change in morphology (FIG. 30). The samples from mice that had been treated with Composition B prior to *C. difficile* infection had reduced amounts of *C. difficile* Toxin B, as compared to samples from control mice that did not receive a treatment after cefoperazone administration and prior to *C. difficile* infection ("2-1 (Cdiff)" and "2-4 (Cdiff)") as well as compared to samples from mice that received FMT. Notably, the samples from mice that had been treated with Composition B also had reduced amounts of *C. difficile* Toxin B, as compared to samples from mice that had been treated with Composition B with additional spores.

Example 8: In Vitro Competition Between Compositions B and *C. difficile*

Composition B was assessed for its ability to suppress *Clostridium difficile* growth by an in vitro mixed culture competition assay. From glycerol freezer stocks, individual strains of Composition B, *C. difficile* (Cdiff), *Clostridium bifermentans*, and *Bacteroides* thetaiotaomicron were struck out onto Eggerth-Gagnon agar plates with horse blood (EG+HB). Single colonies of each of the strains were subsequently inoculated into brain heart infusion (BHI) liquid media and allowed to grow in pure culture for 24-48 hours. Turbid cultures were sub-cultured then grown to exponential phase and finally diluted and combined to prepare a mixed culture with an optical density ($OD_{600}$) of 0.1. Exponential phase Cdiff culture was added to the mixed culture at a final concentration with an OD of 0.1. After the cultures were combined and incubated for 2-3 hours, samples were collected, serially diluted, and plated on Taurocholate-Cycloserine-Cefoxitin-Fructose Agar (TC-CFA) plates to select for Cdiff growth. After 48-72 hours, the colony forming units (CFUs) of Cdiff in each competition experiment were determined by manual colony counting.

EG+HB agar plates were prepared according to standard procedures and reduced in an anaerobic environment for at least 6-8 hours prior to use. Liquid BHI medium was obtained from BD Biosciences (Catalog #211059, San Jose, Calif.), prepared according to the manufacturer's instructions, and reduced in an anaerobic environment for at least 18-24 hours prior to use. TCCFA plates were prepared according to standard procedures and reduced in an anaerobic environment for at least 6-8 hours prior to use. *Clostridium difficile* strain used in the experiments: American Type Culture Collection (ATCC) 43255.

TABLE 4

| Composition B strains Composition B |
|---|
| VE202-7 |
| VE202-13 |
| VE202-14 |
| VE202-16 |
| Strain #16 |
| Strain #170 |
| Strain #189 |
| Strain #211 |

Strains were struck out onto EG+HB agar plates from frozen glycerol stocks inside an anaerobic chamber for 48-72 hours. Single colonies were inoculated into 10 mL of BHI media and grown 24-48 hours at 37° C. in the anaerobic chamber. Turbid cultures were then diluted to an OD of 0.1 and grown for 2-3 hours at 37° C. in the anaerobic chamber. Exponential phase cultures were diluted and combined at equivalent ODs. For the competition assay, each of the strains of Combination B (Table 4) were combined in equal parts, based on $OD_{600}$, to reach a final consortium $OD_{600}$ of 0.1. *C. bifermentans* and *B. thetaiotaomicron* were setup to compete with Cdiff individually at an OD of 0.1. The OD600 for Cdiff in each of the mixed culture competition experiments was 0.1. After combination, the cultures were incubated for 2-3 hours at 37° C. in the anaerobic chamber, then prepared for enumerations on Cdiff selective plates.

TCCFA plates are selective for Cdiff growth, and none of the Combination B strains, nor either of the control strains (*C. bifermentans* and *B. thetaiotaomicron*), grow on these plates. Inside an anaerobic chamber, a 100 µL sample of each competition culture was collected and serially diluted 1:10 to reach a final dilution of $1 \times 10^{-6}$. Plates for CFU enumeration were prepared by spreading 100 µL of each of the $1 \times 10^{-4}$ through $1 \times 10^{-6}$ dilutions on TCCFA plates using sterile spreading loops. CFU plates were incubated for 48-72 hours at 37° C. in the anaerobic chamber. CFU enumeration was completed by manually counting colonies.

Figure 31:
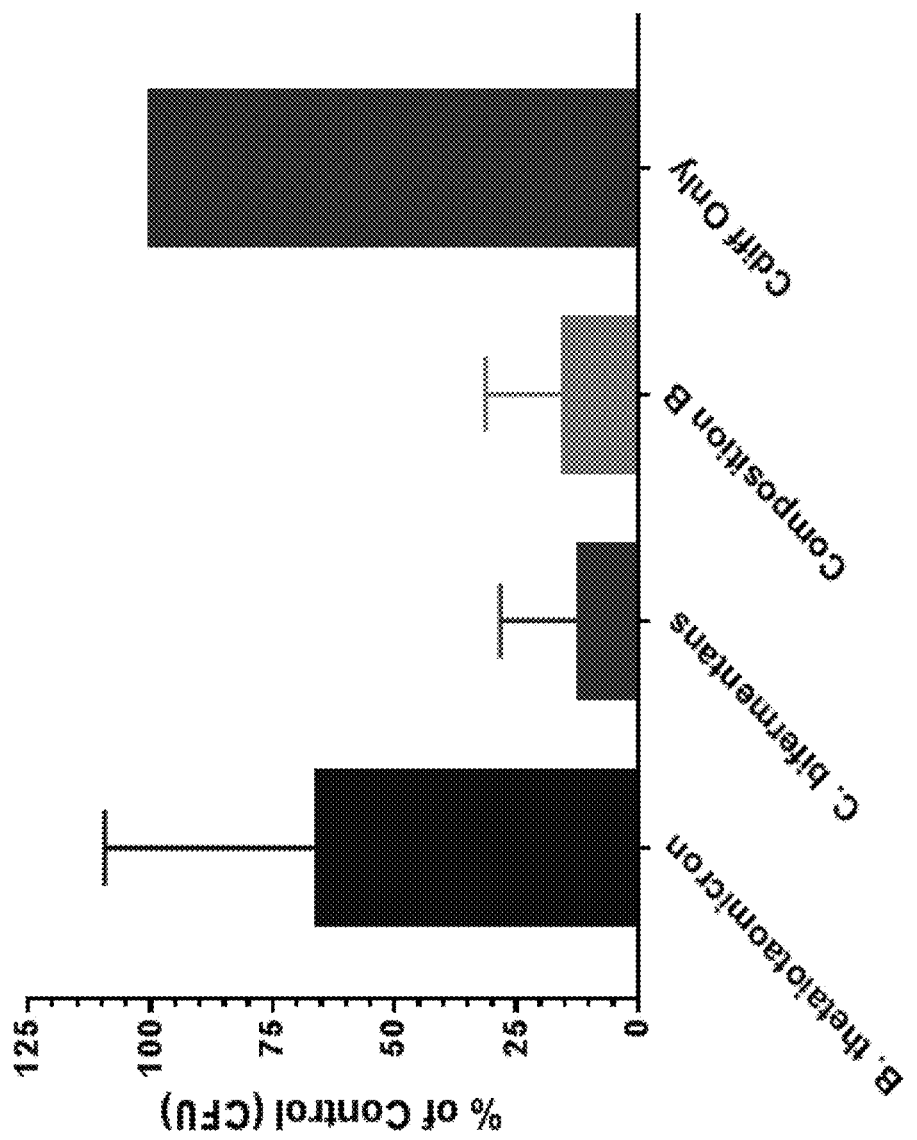
FIG. 31 shows Composition B reduced *C. difficile* growth in in vitro competition experiments. Cultures of *C. difficile* were incubated in the presence of *B. thetaiotaomicron*, *C. bifermentans*, or Composition B, or in the absence of a competing strain(s) (*C. diff* only). The quantity of *C. difficile* is presented as the percentage of the control (*C. diff* only).

To determine the effect of competition, the ratio of CFUs determined for the competition samples and Cdiff alone was calculated and expressed as a percentage. Inhibition of Cdiff growth by the Composition B cocktail was compared to the responses of *B. thetaiotaomicron* (negative control) and *C. bifermentans* (positive control). The results are shown in Table 5 and FIG. 31.

TABLE 5

Summary Results for In Vitro Competition

| Experiment Number | No Competing Strain(s) | Competition with B. thetaiotaomicron | Competition with C. bifermentans | Competition with Composition B |
|---|---|---|---|---|
| n = 1 | 100 |  |  | 33.8 |
| n = 2 | 100 | 9.90 | 0.1 | 0.5 |
| n = 3 | 100 | 115 | 39.5 | 33.1 |
| n = 4 | 100 | 41.3 | 0.7 | 0.7 |
| n = 5 | 100 | 105 | 14.1 | 20.9 |
| n = 6 | 100 | 57.4 | 4.1 | 1.6 |
| Mean | 100 | 65.6 | 11.7 | 15.1 |
| Std. Dev. | 0 | 43.8 | 16.5 | 16.2 |
| Total N | 6 | 5 | 5 | 6 |

Data is expressed as Cdiff CFU as a percentage of control. Each n is representative of a single biological replicate, independent of other measurements.

In in vitro competition, Composition B inhibited Cdiff growth to 15.1±16.2% of control (absence of competing strain(s)). This result is consistent with the inhibition observed by the positive control, C. bifermentans, of 11.7±16.5% of control. B. thetaiotaomicron, a negative control, yielded a negligible effect on Cdiff growth at 65.6±43.8% of control. Given the variability inherent in the assessment of CFU, inhibition of growth to <25% of control is considered to be significant inhibition and both the positive control and Composition B cocktail meet this threshold of activity. The Composition B consortium attenuated Cdiff growth in vitro comparable to the direct competition observed by C. bifermentans. Direct competition with B. thetaiotaomicron did not significantly inhibit Cdiff growth.

Example 9: Determination of In Vitro Short-Chain Fatty Acid Production

Each strain of Composition B was assessed for individual short-chain fatty acid (SCFA) production in vitro. Composition B strains were grown in pure cultures inside an anaerobic chamber. Spent supernatant from liquid media cultures was harvested by centrifugation, filter sterilized, and then stored at <−70° C. Frozen clarified supernatant specimens were analyzed for short-chain fatty acids (SCFAs).

EG+HB agar plates (Eggerth-Gagnon agar plates with horse blood) were prepared according to standard methods and reduced in an anaerobic environment for at least 6-8 hours prior to use. Liquid PYG medium (pre-formulated, pre-reduced) was obtained from Anaerobe Systems (Catalog#AS-822; Morgan Hill, Calif.).

Strains were struck out onto EG+HB agar plates from frozen 15% glycerol stocks inside an anaerobic chamber for 48-72 hours. Single colonies were inoculated into 7 mL PYG media and grown 24-48 hours at 37° C. in the anaerobic chamber. Unless otherwise noted, when the optical density (OD) was >0.2, samples were collected for CFU enumeration and filtration. Inside an anaerobic chamber, a 100 μL sample of turbid culture was collected and serially diluted 1:10 to reach a final dilution of $1\times10^{-6}$. Plates for CFU enumeration were prepared by spreading 100 μL/dilution for the $1\times10^{-4}$ through $1\times10^{-6}$ dilutions on EG+HB agar plates using sterile glass beads. CFU plates were incubated for 48-72 hours in the anaerobic chamber. CFU enumeration was completed using the EasyCount 2 (bioMérieux SA, Marcy-l'Étoile, France). Immediately after samples of turbid cultures were collected for CFU enumeration, the remaining turbid cultures were centrifuged at approximately 1000 RCF for 10 minutes to pellet cellular debris. The clarified supernatants were transferred to a 0.2 μm plate filter and vacuum filtered to remove any remaining particulates prior to bioanalysis. In the event of blockage in the filter plate, clarified supernatants were manually filtered using 0.2 μm syringe filters. Filtered supernatants were aliquoted and stored at <−70° C. prior to bioanalysis of SCFAs.

To facilitate easier comparisons between samples, raw SCFA data (μg/mL) was normalized by the $\log_{10}$ of corresponding determined/estimated CFU for the culture. The results are depicted in Table 6 and Table 7 below.

TABLE 6

Enumerated CFUs for Composition B Strains

| Sample ID | OD600 | Enumerated CFU (CFU/mL) |
|---|---|---|
| VE202-7 | >2 | 6.11E+08 |
| VE202-13 | 0.8 | 4.00E+08 |
| VE202-14 | >2 | 1.60E+09 |
| VE202-16 | 1.92 | 1.28E+09 |
| #16 | 1.97 | 1.69E+08 |
| #170 | 1.8 | 1.08E+08 |
| #189 | 1.03 | 1.74E+09 |
| #211 | 0.35 | 3.71E+08 |

TABLE 7

SFCAs produced by individual Composition B strains

| | Normalized (μg/Log(CFU/mL) * mL) | | | | | | | |
|---|---|---|---|---|---|---|---|---|
| Sample ID | Acetate | Propionate | Iso-butyrate | Butyrate | 2-Methyl-butyrate | Iso-valerate | Valerate | Hexanoate |
| VE202-7 | 123.7 | 0.077 | 0.102 | 0.208 | 0.015 | 0.056 | BLOQ | 0.031 |
| VE202-13 | 30.1 | 0.545 | 0.116 | 34.452 | 0.288 | 0.188 | 0.097 | 0.034 |

TABLE 7-continued

SFCAs produced by individual Composition B strains

Normalized (μg/Log(CFU/mL) * mL)

| Sample ID | Acetate | Propionate | Iso-butyrate | Butyrate | 2-Methyl-butyrate | Iso-valerate | Valerate | Hexanoate |
|---|---|---|---|---|---|---|---|---|
| VE202-14 | 110.5 | 0.054 | 0.022 | 0.248 | 0.011 | 0.014 | BLOQ | 0.009 |
| VE202-16 | 313.2 | 0.000 | 0.000 | 0.280 | 0.004 | 0.000 | BLOQ | 0.009 |
| #16 | 104.0 | 0.005 | 0.000 | 50.988 | 0.014 | 0.033 | BLOQ | 0.009 |
| #170 | 87.1 | 0.055 | 0.025 | 0.215 | 0.011 | 0.039 | BLOQ | 0.016 |
| #189 | 0.0 | BLOQ | 0.000 | 35.751 | 0.005 | 0.019 | 0.359 | 0.587 |
| #211 | 57.6 | 5.289 | 0.000 | 78.227 | 0.028 | 0.050 | 0.053 | 0.095 |

Seven strains of Composition B were found to produce significant quantities (>1 μg/Log(CFU/mL) * mL) of the 2-carbon SCFA, acetate. One strain, (#211), produced substantial quantities of the 3-carbon SCFA, propionate. Four strains of Composition B produced substantial quantities of the 4-carbon SCFA, butyrate. Trace quantities (<1 μg/Log(CFU/mL) * mL) of other SCFAs were also produced by the Composition B strains.

Example 10: Composition B Induces Regulatory T Cells (Tress)

Each of the bacterial strains of Composition B were grown to log phase, combined to a total dose of ~$10^8$ cfu per mouse. Germ-free mice were inoculated with Composition B or a negative control by oral gavage and sacrificed following four weeks of colonization. Lamina propria leukocytes were isolated from colonic tissue of individual mice by standard procedures and assessed by flow cytometry. The regulatory T cell content was evaluated as the percentage of Foxp3-positive cells among CD4+ T cells.

Figure 32:
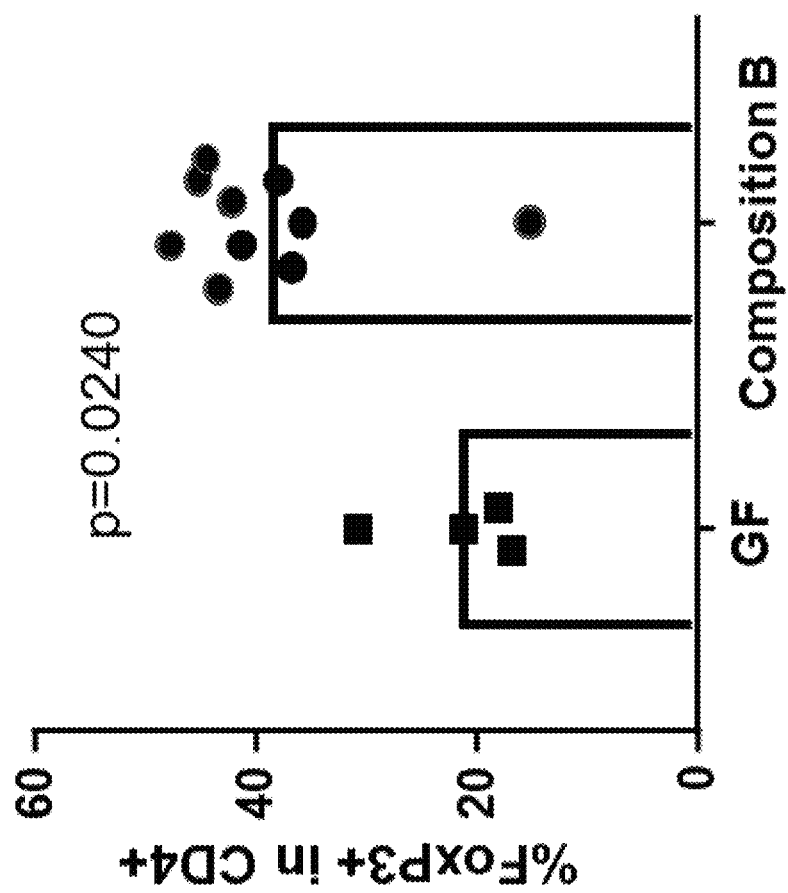
FIG. 32 shows that inoculation with Composition B induced the percentage of FoxP3+CD4+ cells (regulatory T cells) in the intestine of germ-free mice as compared to control mice ("GF").

As shown in FIG. 32, mice that were inoculated with Composition B were found to have significantly more regulatory T cells as compared to mice that were inoculated with the control.

What is claimed is:

1. A pharmaceutical composition comprising a purified bacterial mixture consisting of bacterial strains comprising 16S rDNA sequences of at least 97% sequence identity to SEQ ID NO:10, SEQ ID NO:14, SEQ ID NO:15, SEQ ID NO:16, SEQ ID NO:17, SEQ ID NO:19, SEQ ID NO:20, and SEQ ID NO:21; wherein the bacterial strains are lyophilized.

2. The pharmaceutical composition of claim 1, wherein one or more of the bacterial strains are spore-formers.

3. The pharmaceutical composition of claim 1, wherein the bacterial strains originate from more than one human donor.

4. The pharmaceutical composition of claim 1, further comprising a pharmaceutically acceptable excipient.

5. The pharmaceutical composition of claim 1, wherein the pharmaceutical composition is formulated for oral administration.

6. The pharmaceutical composition of claim 1, wherein the pharmaceutical composition is in the form of a capsule.

7. The pharmaceutical composition of claim 1, wherein the pharmaceutical composition is formulated for delivery to the colon.

8. The pharmaceutical composition of claim 1, wherein the pharmaceutical composition further comprises one or more enteric polymers.

* * * * *